United States Patent
Argiriadi et al.

(10) Patent No.: US 10,508,113 B2
(45) Date of Patent: Dec. 17, 2019

(54) INHIBITORS OF TYROSINE KINASE 2 MEDIATED SIGNALING

(71) Applicant: AbbVie Inc., North Chicago, IL (US)

(72) Inventors: Maria A. Argiriadi, Southboro, MA (US); Eric C. Breinlinger, Charlton, MA (US); Ellen Yulin Tsai Chien, San Mateo, CA (US); Marlon D. Cowart, Round Lake Beach, IL (US); Kristine E. Frank, Grayslake, IL (US); Michael M. Friedman, Kennebunkport, ME (US); David J. Hardee, Vernon Hills, IL (US); J. Martin Herold, Holliston, MA (US); Huaqing Liu, Buffalo Grove, IL (US); Wei Qiu, Gurnee, IL (US); Marc J. Scanio, Libertyville, IL (US); Michael R. Schrimpf, Grayslake, IL (US); Thomas R. Vargo, Stow, MA (US); Stacy A. Van Epps, Ashland, MA (US); Matthew P. Webster, Kenosha, WI (US); Andrew J. Little, Brighton, MA (US); Matthew H. Katcher, Evanston, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 16/299,485

(22) Filed: Mar. 12, 2019

(65) Prior Publication Data

US 2019/0276450 A1     Sep. 12, 2019

Related U.S. Application Data

(60) Provisional application No. 62/641,728, filed on Mar. 12, 2018.

(51) Int. Cl.
   *C07D 405/14*     (2006.01)
   *C07D 471/04*     (2006.01)

(52) U.S. Cl.
   CPC .................. *C07D 471/04* (2013.01)

(58) Field of Classification Search
   CPC .................. C07D 405/14; C07D 471/04
   See application file for complete search history.

(56) References Cited

U.S. PATENT DOCUMENTS

| | | |
|---|---|---|
| 8,334,291 B2 | 12/2012 | Schirok et al. |
| 9,085,578 B2 | 7/2015 | Nagamiya et al. |
| 2005/0215612 A1 | 9/2005 | Kuo et al. |
| 2012/0258958 A1 | 10/2012 | Salituro et al. |
| 2016/0046597 A1 | 2/2016 | Schnute et al. |
| 2018/0127420 A1 | 5/2018 | Zhang et al. |
| 2018/0312508 A1 | 11/2018 | Deng et al. |

FOREIGN PATENT DOCUMENTS

| | | |
|---|---|---|
| CN | 105712998 A | 6/2016 |
| JP | 2013234180 A | 11/2013 |
| JP | 2014024838 A | 2/2014 |
| WO | 2001023389 A2 | 4/2001 |
| WO | 2003082274 A1 | 10/2003 |
| WO | 2005040073 A2 | 5/2005 |
| WO | 2005040111 A3 | 5/2005 |
| WO | 2005123672 A2 | 12/2005 |
| WO | 2006058120 A1 | 6/2006 |
| WO | 2007019126 A3 | 2/2007 |
| WO | 2007070398 A1 | 6/2007 |
| WO | 2007084557 A2 | 7/2007 |
| WO | 2007103308 A2 | 9/2007 |
| WO | 2008048981 A3 | 4/2008 |
| WO | 2008104077 A1 | 9/2008 |
| WO | 2008153858 A1 | 12/2008 |
| WO | 2009000832 A2 | 12/2008 |

(Continued)

OTHER PUBLICATIONS

Abraham C., et al., "IL-23 and Autoimmunity: New Insights into the Pathogenesis of Inflammatory Bowel Disease", Annu. Rev. Med., 2009, vol. 60, pp. 97-110.

Alabdulaali M., "The role of JAK2 abnormalities in hematologic neoplasms", Hematology Reviews, 2009, vol. 1:e10, pp. 56-61.

Argiriadi M., et al., "Enabling structure-based drug design of Tyk2 through co-crystallization with a stabilizing aminoindazole inhibitor", BMC Structural Biology, 2012, vol. 12, No. 22, pp. 1-11.

Boudeau J., et al., "Emerging roles of pseudokinases", TRENDS in Cell Biology, 2006, vol. 16, No. 9, pp. 443-452.

(Continued)

*Primary Examiner* — Brenda L Coleman

(57) ABSTRACT

Disclosed herein are compounds of Formula (I), and pharmaceutically acceptable salts thereof, wherein $R_1$, R2, $R_3$, $R_{4a}$, $R_{4b}$, $X^1$, $X^2$, $X^3$, $X^4$, $X^5$, nad n are as defined herein, pharmaeceutical compositions 2C $X^5$, and n are as defined herein, pharmaceutical compositions comprising same, and methods of preparation and use.

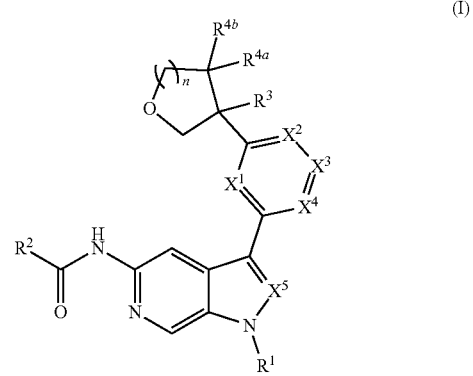

30 Claims, No Drawings

(56) References Cited

FOREIGN PATENT DOCUMENTS

| | | |
|---|---|---|
| WO | 2009011912 A8 | 1/2009 |
| WO | 2009054941 A1 | 4/2009 |
| WO | 2009062258 A1 | 5/2009 |
| WO | 2009075830 A1 | 6/2009 |
| WO | 2009100130 A1 | 8/2009 |
| WO | 2009152133 A1 | 12/2009 |
| WO | 2009155156 A1 | 12/2009 |
| WO | 2010051781 A1 | 5/2010 |
| WO | 2010078900 A2 | 7/2010 |
| WO | 2010090764 A1 | 8/2010 |
| WO | 2010100144 A1 | 9/2010 |
| WO | 2010109005 A1 | 9/2010 |
| WO | 2011068881 A1 | 6/2011 |
| WO | 2011068899 A1 | 6/2011 |
| WO | 2011079231 A1 | 6/2011 |
| WO | 2011113798 A2 | 9/2011 |
| WO | 2011113802 A2 | 9/2011 |
| WO | 2012000970 A1 | 1/2012 |
| WO | 2012022045 A1 | 2/2012 |
| WO | 2012022265 A1 | 2/2012 |
| WO | 2012030894 A1 | 3/2012 |
| WO | 2012030924 A1 | 3/2012 |
| WO | 2012066061 A1 | 5/2012 |
| WO | 2012078777 A1 | 6/2012 |
| WO | 2012106995 A1 | 8/2012 |
| WO | 2012126181 A1 | 9/2012 |
| WO | 2013024002 A1 | 2/2013 |
| WO | 2013038189 A1 | 3/2013 |
| WO | 2013041539 A1 | 3/2013 |
| WO | 2013078254 A1 | 5/2013 |
| WO | 2013132270 A1 | 9/2013 |
| WO | 2014026327 A1 | 2/2014 |
| WO | 2014028589 A2 | 2/2014 |
| WO | 2014047662 A3 | 3/2014 |
| WO | 2014074660 A1 | 5/2014 |
| WO | 2014074661 A1 | 5/2014 |
| WO | 2014074670 A1 | 5/2014 |
| WO | 2014130693 A1 | 8/2014 |
| WO | 2014165143 A1 | 10/2014 |
| WO | 2014200682 A1 | 12/2014 |
| WO | 2015015378 A3 | 2/2015 |
| WO | 2015026683 A1 | 2/2015 |
| WO | 2015069310 A1 | 5/2015 |
| WO | 2015089143 A1 | 6/2015 |
| WO | 2015091584 A1 | 6/2015 |
| WO | 2015131080 A1 | 9/2015 |
| WO | 2016138352 A1 | 9/2016 |
| WO | 2016169504 A1 | 10/2016 |
| WO | 2016173477 A1 | 11/2016 |
| WO | 2017040757 A1 | 3/2017 |
| WO | 2017087590 A1 | 5/2017 |
| WO | 2017093727 A1 | 6/2017 |
| WO | 2017133665 A1 | 8/2017 |
| WO | 2017133667 A1 | 8/2017 |
| WO | 2017133670 A1 | 8/2017 |
| WO | 2017136870 A1 | 8/2017 |
| WO | 2017136871 A9 | 8/2017 |
| WO | 2017144995 A1 | 8/2017 |
| WO | 2018067432 A1 | 4/2018 |
| WO | 2018071794 A1 | 4/2018 |
| WO | 2018075937 A1 | 4/2018 |
| WO | 2018081488 A1 | 5/2018 |
| WO | 2018093968 A1 | 5/2018 |
| WO | 2018111787 A1 | 6/2018 |
| WO | 2018165240 A1 | 9/2018 |
| WO | 2018234354 A1 | 12/2018 |
| WO | 2019023468 A1 | 1/2019 |

OTHER PUBLICATIONS

Catlett I., et al., "A First-In-Human, Study of BMS-986165, a Selective, Potent, Allosteric Small Molecule Inhibitor of Tyrosine Kinase 2", Scientific Abstracts, SAT0226, Jun. 17, 2017, 1 page.

Duan J., et al., "Discovery of pyrrolo[1,2-b]pyridazine-3-carboxamides as Janus kinase (JAK) inhibitors", Bioorg. & Med. Chem. Lett., 2014, vol. 24, pp. 5721-5726.

Duffin K., et al., "Genetic variations associated with psoriasis and psoriatic arthritis found by genome-wide association", Dermatologic Therapy, 2010, vol. 23, pp. 101-113.

Fensome A., et al., "Dual Inhibition of TYK2 and JAK1 for the Treatment of Autoimmune Diseases: Discovery of ((S)-2,2-Difluorocyclopropyl)((1R,5S) -3-(2-((1-methyl-1H-pyrazol-4-yl)amino)pyrimidin-4-yl)-3,8-diazabicyclo[3.2.1]octan-8-yl)methanone (PF-06700841)", J. Med. Chem., 2018, vol. 61, pp. 8597-8612.

Filla S., et al., "Novel Potent 5-$HT_{1F}$ Receptor Agonists: Structure-Activity Studies of a Series of Substituted N-[3-(1-Methyl-4-piperidinyl)-1H-pyrrolo[3,2-b]pyridin-5-yl]amides", J. Med. Chem., 2003, vol. 46, pp. 3060-3071.

Gillooly K., et al., "BMS-986165 Is a Highly Potent and Selective Allosteric Inhibitor of Tyk2, Blocks IL-12, IL-23 and Type I Interferon Signaling and Provides for Robust Efficacy in Preclinical Models of Systemic Lupus Erythematosus and Inflammatory Bowel Disease", ACR/ARHP Annual Meeting, Oct. 19, 2016, Abstract No. 11L, 2 pages.

He X., et al., "Selective Tyk2 inhibitors as potential therapeutic agents: a patent review (2015-2018)", Expert Opinion on Therapeutic Patents, 2019, vol. 29, No. 2, pp. 137-149.

Hong K., et al., "IL-12, Independently of IFN-γ, Plays a Crucial Role in the Pathogenesis of a Murine Psoriasis-Like Skin Disorder", J. Immunol., 1999, vol. 162, pp. 7480-7491.

Hu H., et al., "Discovery of 3,5-substituted 6-azaindazoles as potent pan-Pim inhibitors", Bioorg. & Med. Chem. Lett., 2015, vol. 25, pp. 5258-5264.

Hue S., et al., "Interleukin-23 drives innate and T cell-mediated intestinal inflammation", J. Exp. Med., 2006, vol. 203, No. 11, pp. 2473-2483.

Jakša S., et al., "The Synthesis and Hybridization Studies of Oligodeoxyribonucleotides Containing the 2'-Deoxyguanosine Modification, 8-Aza-3-deaza-2'-deoxyguanosine", Croatica Chemica Acta, 2002, vol. 76, No. 1, pp. 175-187.

Jang W., et al., "Discovery of Tyk2 inhibitors via the virtual site-directed fragment-based drug design", Bioorg. & Med. Chem. Lett., 2015, vol. 25, pp. 3947-3952.

Lee E., et al., "Increased Expression of Interleukin 23 p19 and p40 in Lesional Skin of Patients with Psoriasis Vulgaris", J. Exp. Med., 2004, vol. 199, No. 1, pp. 125-130.

Liang J., et al., "Lead identification of novel and selective TYK2 inhibitors", European Journal of Medicinal Chemistry, 2013, vol. 67, pp. 175-187.

Liang, J., et al., "Lead Optimization of a 4-Aminopyridine Benzamide Scaffold To Identify Potent, Selective, and Orally Bioavailable TYK2 Inhibitors", J. Med. Chem., 2013, vol. 56, pp. 4521-4536.

Liang Y., et al., "Therapeutic potential of tyrosine kinase 2 in autoimmunity", Expert Opin. Ther. Targets, 2014, vol. 18, No. 5, pp. 571-580.

Liu C., et al., "6-((2-Oxo-1-substituted-1,2-dihydropyridin-3-yl)amino)imidazo[1,2-b]pyridazine derivatives as potent, selective, and orally active Tyk2 JH2 inhibitors", 254th American Society National Meeting (ACS), Aug. 20, 2017, Editorial Abstract, 2 pages.

Liu C., et al., "Identification of Imidazo[1,2-b]pyridazine Derivatives as Potent, Selective, and Orally Active Tyk2 JH2 Inhibitors", ACS Med. Chem. Lett., 2019, vol. 10, pp. 383-388.

Menet C., "Toward selective TYK2 inhibitors as therapeutic agents for the treatment of inflammatory disease", Pharm. Pat. Anal., 2014, vol. 3, No. 4, pp. 449-466.

Miao W., et al., "Potent and Selective Tyk2 Inhibitor Highly Efficacious in Rodent Models of Inflammatory Bowel Disease and Psoriasis", ACR/ARHP Annual Meeting, Sep. 28, 2016, Abstract No. 1911, 2 pages.

Mortezavi M., et al., "IL12/IL23 Inhibition in the Treatment of Psoriatic Arthritis", Curr. Treat. Options in Rheum., 2015, vol. 1, pp. 197-209.

(56) References Cited

OTHER PUBLICATIONS

Moslin R., et al, "Identification of imidazo[1,2-b]pyridazine TYK2 pseudokinase ligands as potent and selective allosteric inhibitors of TYK2 signalling", Med. Chem. Commun., 2017, vol. 8, No. 4, pp. 700-712.

Norman P., "Selective JAK1 inhibitor and selective Tyk2 inhibitor patents", Expert Opin. Ther. Patents, 2012, vol. 22, No. 10, pp. 1233-1249.

Norman P., "Evaluation of WO2013125543, WO2013146963 and EP2634185: the first Tyk2 inhibitors from Takeda and Sareum", Expert Opin. Ther. Patents, 2014, vol. 24, No. 3, pp. 361-368.

Papp K., et al., "Risankisumab versus Ustekinumab for Moderate-to-Severe Plaque Psoriasis", N. Engl. J. Med., 2017, vol. 376, No. 16, pp. 1551-1560.

Papp K., et al., "Phase 2 Trial of Selective Tyrosine Kinase 2 Inhibition in Psoriasis", N. Engl. J. Med., 2018, vol. 379, No. 14, pp. 1313-1321.

Piskin G., et al., "Clinical improvement in chronic plaque-type psoriasis lesions after narrow-band UVB therapy is accompanied by a decrease in the expression of IFN-γ inducers—IL-12, IL-18 and IL-23", Experimental Dermatology, 2004, vol. 13, pp. 764-772.

Piskin G., et al., "In Vitro and In Situ Expression of IL-23 by Keratinocytes in Healthy Skin and Psoriasis Lesions: Enhanced Expression in Psoriatic Skin", J. Immunol., 2006, vol. 176, pp. 1908-1915.

Rashid F., et al., (2017), "New Non-anti-TNF-α Biological Therapies for the Treatment of Inflammatory Bowel Disease." In: Mamula P., Grossman A., Baldassano R., Kelse J., (eds), Pediatric Inflammatory Bowel Disease, Springer, Cham., Chapter 35, pp. 425-450.

Settesoldi A., et al., "Ustekinumab: moving the target from psoriasis to Crohn's disease", Expert Rev. Gastroenterol. Hepatol., 2014, vol. 8, No. 1, pp. 5-13.

Sohn S., et al., "A Restricted Role for TYK2 Catalytic Activity in Human Cytokine Responses Revealed by Novel TYK2-Selective Inhibitors", J. Immunol., 2013, vol. 191, pp. 2205-2216.

Tite T., et al., "Design and synthesis of new C-nucleosides as potential adenosine deaminase inhibitors", Tetrahedron, 2010, vol. 66, pp. 9620-9628.

Yen D., et al., "IL-23 is essential for T cell-mediated colitis and promotes inflammation via IL-17 and IL-6", J. Clin. Invest., 2006, vol. 116, No. 5, pp. 1310-1316.

Yogo T., et al., "Structure-Based Design and Synthesis of 3-Amino-1,5-dihydro-4H-pyrazolopyridin-4-one Derivatives as Tyrosine Kinase 2 Inhibitors", J. Med. Chem., 2016, vol. 59, pp. 733-749.

Yogo T., "Structure-Based Design, Synthesis, and Dermal Application of Novel Tyrosine Kinase 2 (TYK2) Inhibitors", $12^{th}$ Annual Drug Discovery Chemistry, Kinase Inhibitor Chemistry, Apr. 26, 2017, Slide Presentation, 28 pages.

Statement of the circumstances regarding accelerated examination for Japanese Patent Application No. 2019-44439, filed Apr. 1, 2019 with the Commissioner of the Japanese Patent Office, 12 pages.

International Search Report and Written Opinion for PCT/US2019/021824, dated Jun. 26, 2019, 17 pages.

Liu Y., et al., "The Discovery of Orally Bioavailable Tyrosine Threonine Kinase (TTK) Inhibitors: 3-(4-(heterocyclyl)phenyl)-1H-indazole-5-carboxamides as Anticancer Agents", Journal of Medicinal Chemistry, 2015, vol. 58, pp. 3366-3392.

Extended European Search Report for EP 19 16 2206, dated Jul. 30, 2019, 6 pages.

INHIBITORS OF TYROSINE KINASE 2 MEDIATED SIGNALING

RELATED APPLICATIONS

The present application claims priority to U.S. Provisional Application No. 62/641,728, filed Mar. 12, 2018, the entire contents of which are hereby incorporated herein by reference.

BACKGROUND

The Janus kinase (Jak) family is composed of four phosphotransferases, Jak1, Jak2, Jak3 and Tyrosine kinase 2 (Tyk2), each of which associates with a distinct set of cytokine receptors, mediating a cascade of autophosphorylation and subsequent activation of Signal Transducer and Activation of Transcription (STAT) proteins. Activated STATs dissociate from the cytokine receptor and translocate to the cell nucleus to regulate transcription of selected STAT-dependent pro-inflammatory genes. Disruption or dysregulation of the Jak-STAT pathways, such as through genetic mutations or increased localized concentrations of inflammatory cytokines, is a key driver of various pathologies.

Significant evidence exists for the role of inflammatory cytokines, interleukin (IL)-12 and IL- 23, in inflammatory and autoimmune diseases. IL-23 shares a p40 subunit with IL-12 but each has a unique p19 subunit. It has been demonstrated that mice deficient in either p40, p19, IL-12, or IL-23 are protected from disease in models of inflammatory bowel disease (IBD) and psoriasis. See, e.g., Hue et al., *J. Exp. Med.* (2006) 203:2473-2483 (IBD); Hong et al., *J. Immunol.* (1999) 162:7480-7491 (psoriasis). Dysregulated expression of IL-12 and/or IL-23 has been found in patients suffering from psoriasis and inflammatory bowel disease. See, e.g., Lee et al., *J. Exp. Med.* (2004) 199:125-130 (psoriasis); Piskin et al., *J. Immunol.* (2006) 176:1908-1915 (psoriasis); Piskin et al., *Ex. Dermatol.* (2004) 13:764-772 (psoriasis); Duffin et al., *Dermatol. Ther.* (2010) 23:101-113 (psoriasis); Abraham and Cho, *Annu. Rev. Med.* (2009) 60:97-110 (IBD); and Yen et al., *J. Clin. Invest.* (2006) 116:1310-1316 (IBD). The anti IL- 12/23 p40 monoclonal antibody, ustekinumab (Stelara®), has been found efficacious in the treatment of psoriasis and Crohn's disease (CD). See, e.g., Mortezavi et al.,*Curr. Treat. Options in Rheum.* (2015) 1:197-209 (psoriasis); Settesoldi et al., *Expert Rev. Gastroenterol. Hepatol.* (2014) 8:5-13 (CD); Rashid F., Lichtenstein G.R. "New Non-anti-TNF-α Biological Therapies for the Treatment of Inflammatory Bowel Disease." *Pediatric Inflammatory Bowel Disease.* Ed. Mamula P., Grossman A., Baldassano R., Kelsen J., Markowitz J.; Cham: Springer International Publishing AG, 2017. pp 425-450 (CD). Risankisumab, an anti-IL-23 p19 monoclonal antibody, has also been found efficacious in the treatment of psoriasis and Crohn's disease. See, e.g., Papp et al., *N. Engl. J. Med.* (2017) 376:1551-1560 (psoriasis); Rashid supra (CD).

Since the IL-12/23 signaling pathways are mediated by Jak2/Tyk2 heterodimer via phosphorylation of STAT3/4, developing Jak2 and Tyk2 inhibitors is of high interest to the scientific and medical community. See, e.g., Liang et al., *J. Med. Chem.* (2013) 56:4521-4536. Blockade of Jak2 activity, however, is viewed as problematic since Jak2 also regulates the erythropoietin signaling pathway, and its inhibition is associated with unwanted hematologic toxicities such as anemia, neutropenia, and thrombocytopenia. See, e.g., Liang supra; Alabdulaali, *Hematology Reviews* (2009) 1:e10 56-61. Given the high degree of sequence homology between the Jak family kinase members, development of selective Tyk2 inhibitors, sparing Jak2 inhibition, presents a significant challenge. See e.g., Liang supra.

SUMMARY

Described herein are compounds of Formula (I), and pharmaceutically acceptable salts thereof:

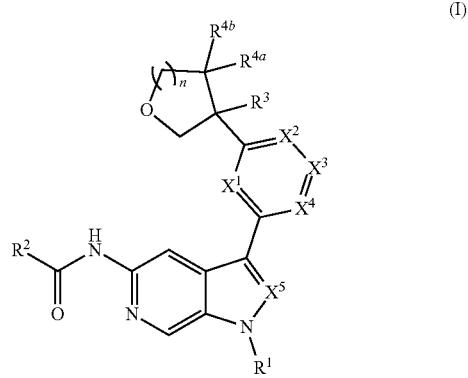

(I)

wherein $R^1$, $R^2$, $R^3$, $R^4$, $R^{4b}$, $X^1$, $X^2$, $X^3$, $X^4$, $X^5$, and n are as defined herein; and pharmaceutical compositions comprising same. Compounds of Formula (I) may potently and selectively inhibit Tyk2, with half maximal effective concentration ($EC_{50}$) (as measured by the Tyk2 (Tyk2/Jak2 PSTAT4 T-Blast) alpha screen assay and Jak2 (PTATS UT7) alpha screen assay, described herein) of less than 4μM, and with a 10-fold to over 1000-fold selectivity for Tyk2 over Jak2. See, e.g.,Examples, Table C.

Further described are methods of treating a disease comprising administering to a subject in need thereof an effective amount of a compound of Formula (I), or pharmaceutically acceptable salt thereof, wherein the disease is inflammatory bowel disease (e.g., Crohn's disease, ulcerative colitis) or psoriasis.

Further described are methods of preparing compounds of Formula (I), or salts thereof. For example, a compound of Formula (I), or salt thereof, may be prepared by reacting a compound of Formula (D), or salt thereof:

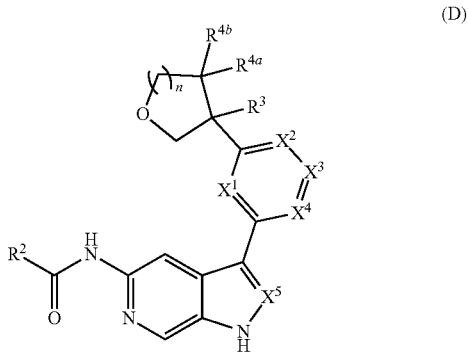

(D)

with a compound of formula $R^1$-$LG^3$, wherein $LG^3$ is a leaving group.

Alternatively, a compound of Formula (I), or salt thereof, may be prepared from palladium or copper catalyzed coupling of a compound of Formula (H), or salt thereof:

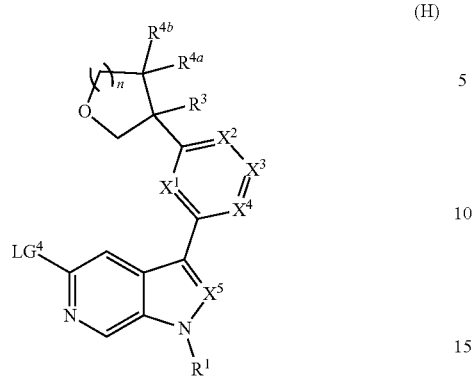
(H)
with a compound of Formula R²C(=O)NH₂, or salt thereof, wherein LG⁴ is a leaving group.
Further described are compounds of the below formula:
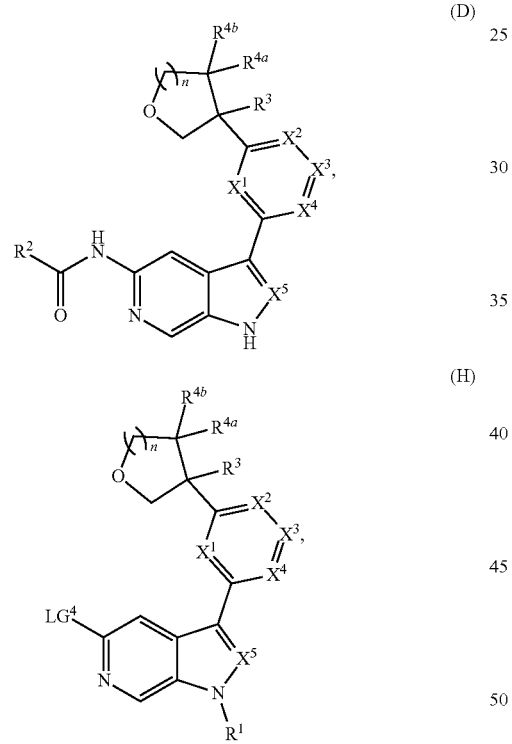
(D)
(H)
(C)
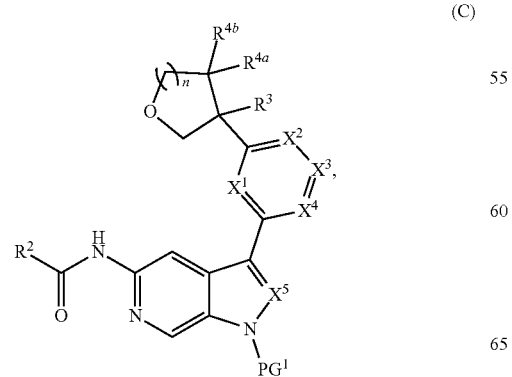
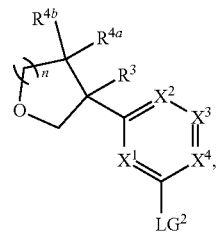
(B)
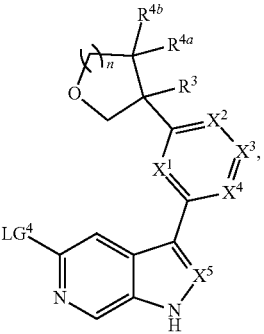
(G)
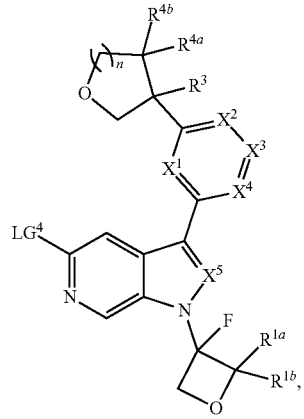
(I-iv)
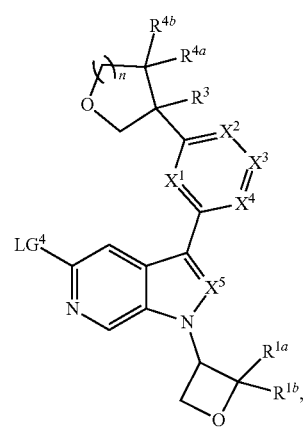
(I-v)

-continued

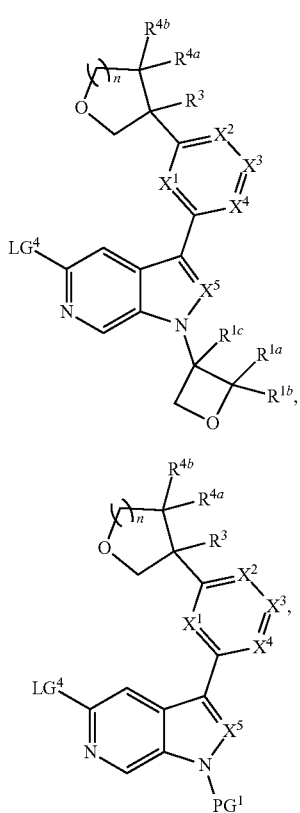

and salts thereof, wherein n, $X_1$, $X^2$, $X^3$, $X^4$, $X^5$, $R_1$, $R^2$, $R^3$, $R^{4a}$, $R^{4b}$, $LG^2$, $LG^4$, $R^{1a}$, $R^{1b}R^{1c}$, and $PG^1$ are as defined herein.

DEFINITIONS

Definitions of specific functional groups and chemical terms are described in more detail below. The chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein may comprise one or more asymmetric centers, and thus may exist in various stereoisomeric forms, e.g., enantiomers and/or diastereomers and/or geometric (cis/trans or E/Z) isomers in a composition. For example, compositions may comprise a mixture of stereoisomers, including racemic (equal) mixtures, non-racemic (scalemic) mixtures that are enriched in one or more stereoisomer, or may comprise an individual stereoisomer in substantially pure (>99%) form. As used herein, "enriched" refers to a composition which comprises greater than (>) 50% of one stereoisomer over the sum total of other stereoisomer(s) which may be present in the composition. In certain embodiments, a composition may comprise >60%, >65%, >70%, >75%, >80%, >85%, >90%, >91%, >92%, >93%, >94%, >95%, >96%, >97%, >98%, >99%, >99.5%, or >99.9% of one stereoisomer over the sum total of other stereoisomer(s) which may be present in the composition; or may comprise less than (<) 0.1%, <0.5%, <1%, <2%, <3%, <4%, <5%, <6%, <7%, <8%, <9%, <10%, <15%, <20%, <25%, <30%, <35%, <40%, <45%, or <50% of one stereoisomer over the sum total of other stereoisomer(s) which may be present in the composition. For simplicity, calculating enriched amounts of any of the stereoisomer(s), if provided as pharmaceutically acceptable salt(s) in a composition, are based on the hypothetical amount of free base form.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}$F with $^{18}$F, replacement of a carbon by a $^{13}$C- or $^{14}$C-enriched carbon, and/or replacement of an oxygen atom with $^{18}$O, are within the scope of the disclosure.

When a range of values is listed, it is intended to encompass each value and sub-range within the range. For example, "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a monovalent radical of a straight-chain or branched saturated hydrocarbon group having from 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$).

"Haloalkyl" is an alkyl group wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 6 carbon atoms ("$C_{1-6}$haloalkyl"). In some embodiments, the haloalkyl moiety has 1 to 5 carbon atoms ("$C_{1-5}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. Examples of haloalkyl groups include -CF$_3$, -CHF$_2$, -CFH$_2$, -CF$_2$CF$_3$, -CH$_2$CF$_3$, -CF$_2$CF$_2$CF$_3$, -CCl$_3$, -CFCl$_2$, and -CF$_2$Cl.

"Carbocyclyl" or "carbocyclic" refers to a monovalent radical of a monocyclic, non-aromatic, 3- to 6- membered ring system having from 3 to 6 ring carbon atoms ("$C_{3-6}$ carbocyclyl") and zero ring heteroatoms. In some embodiments, a carbocyclyl group has 3 to 4 ring carbon atoms ("$C_{3-4}$ carbocyclyl") . In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), and cyclohexadienyl ($C_6$).

"Heterocyclyl" or "heterocyclic" refers to a monovalent radical of a monocyclic, non-aromatic, 4- to 6-membered ring system having ring carbon atoms and 1 to 3 ring heteroatoms, wherein each heteroatom is independently selected from nitrogen, oxygen, and sulfur ("4- to 6-membered heterocyclyl"). Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, and dihydropyrrolyl. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinanyl.

As used herein, "unsubstituted or substituted $C_{3-6}$carbocyclyl$C_{1-3}$alkyl" and "unsubstituted or substituted 4- to 6-membered heterocyclyl$C_{1-3}$alkyl" refer to an unsubstituted or substituted $C_{3-6}$carbocyclyl or unsubstituted or substituted 4- to 6-membered heterocyclyl attached to an unsubstituted $C_{1-3}$alkyl group, and wherein the point of attachment to the parent molecule is on the unsubstituted $C_{1-3}$alkyl group.

As used herein, appending an "-ene" as a suffix designates a divalent radical, containing two points of attachment. For example, appending "-ene" to "alkyl" (to provide "alkylene") designates that group as a divalent alkyl group, and the two points of attachment may be anywhere and at any carbon of the alkyl group, which may be straight-chained or branched. Exemplary straight-chained alkylene groups include -$CH_2$- ($C_1$ alkylene), -$CH_2CH_2$- ($C_2$ alkylene), -$CH_2CH_2CH_2$- ($C_3$ alkylene), and the like. Exemplary branched alkylene groups include -CH($CH_3$)- ($C_2$ alkylene), -CH($CH_2CH_3$)- ($C_3$ alkylene), - $CH_2$CH($CH_3$)- ($C_3$ alkylene), -CH($CH_3$)$CH_2$- ($C_3$ alkylene), -$C(CH_3)_2$- ($C_3$ alkylene), and the like.

"Halo" or "halogen" refers to fluorine (fluoro, -F), chlorine (chloro, -Cl), bromine (bromo, -Br), or iodine (iodo, -I).

"Salt" refers to any and all salts, and is produced from the ionic complexation of a basic compound with an inorganic or organic acid, or an acidic compound with an inorganic or organic base, to provide a compound which is electronically neutral. "Pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. See also Berge et al., *J. Pharmaceutical Sciences* (1977) 66:1-19. A "free base" of a compound is the neutral and complexation-free (e.g., salt-free) form of the compound. In certain embodiments, a compound of Formula (I) may be a salt (e.g., a pharmaceutically acceptable salt). In certain embodiments, e.g., in the absence of reference to a pharmaceutically acceptable salt, a compound of Formula (I) may be present as the free base form.

A "leaving group" refers to a molecular fragment that departs with a pair of electrons in heterolytic bond cleavage wherein the molecular fragment is an anion or neutral molecule. A "leaving group" also refers to a molecular fragment which departs via a cross-coupling reaction. Exemplary leaving groups which depart with a pair of electrons in heterolytic bond cleavage include, but are not limited to, halo (e.g., chloro, bromo, iodo) and activated hydroxyl groups, such as a trifluoromethanesulfonyl activated hydroxyl group (-OTf) 4-toluenesulfonyl activated hydroxyl group (- OTs), methanesulfonyl activated hydroxyl group (-OMs), benzenesulfonyl activated hydroxyl group (-OBs), or -OS($O)_2OCH_3$. Exemplary leaving groups which depart via a cross-coupling reaction, include, but are not limited to, boronic acids or boronic esters (e.g., a dioxoborolane group, e.g., tetramethyl dioxoborolane), trialkyl stannanes (e.g., (R')$_3$Sn-, wherein R' is $C_{1-3}$alkyl), and halo (e.g., chloro, bromo, iodo).

Amino protecting groups are described in detail in *Protecting Groups in Organic Synthesis*, T. W. Greene and P. G. M. Wuts, 3rd edition, John Wiley & Sons, 1999. Exemplary amino protecting groups include, but are not limited to, (i) amide R-(C=O)- groups, such as formyl, acetyl, chloroacetyl, trichloroacetyl, trifluoroacetyl, phenylacetyl, and 3-phenylpropanoyl; (ii) carbamate RO-(C=O)- groups, wherein R is methyl, ethyl, 9-fluorenylmethyl (Fmoc), 4-methoxyphenacyl (Phenoc), 2,2,2- trichloroethyl (Troc), 2-trimethylsilylethyl (Teoc), 2-phenylethyl (hZ), 1,1-dimethyl-2,2-dibromoethyl (DB-t-Boc), 1,1-dimethyl-2,2,2-trichloroethyl (TCBoc), 1-methyl-1-(4-biphenylyl)ethyl (Bpoc), 1- (3,5-di-t-butylphenyl)-1-methylethyl (t-Bumeoc), 2-(2'- and 4'-pyridyl)ethyl (Pyoc), t-butyl (Boc), 1- adamantyl (Adoc), vinyl (Voc), allyl (Alloc), and benzyl (Cbz); (iii) sulfonamide R-($SO_2$)- groups, wherein R is toluene, benzene, methyl, trifluoromethyl, and 2-nitrobenene; and (iv) alkyl R-$CH_2$- groups, wherein R is benzene, toluene, paramethoxybenzene (PMB), or 2-(trimethylsilyl)ethoxy (SEM).

A "subject" refers to a mammal, and includes, but is not limited to, humans (i.e., a male or female of any age group, e.g., a pediatric subject (e.g., infant, child, adolescent) or adult subject (e.g., young adult, middle-aged adult or senior adult)) and/or other non-human mammals, for example, primates (e.g., cynomolgus monkeys, rhesus monkeys), cats, and/or dogs.

"Treat," "treating" and "treatment" refers to an action that occurs while a subject is suffering from the disease, and which reduces the severity of the disease, or retards or slows the progression of the disease or associated symptoms.

An "effective amount" of a compound, or a pharmaceutically acceptable salt thereof, is an amount, alone or in combination with other therapies, which provides a therapeutic benefit in the treatment of a disease from which the subject suffers, or to delay or minimize one or more symptoms associated with the disease from which the subject suffers.

"Inhibition", "inhibiting", "inhibit" and "inhibitor", and the like, refer to the ability of a compound to reduce, slow, halt, or prevent activity of a particular in vivo or in vitro biological process (e.g., inhibition of Tyk2, IL-12, and/or IL-23 activity) in a cell relative to vehicle.

DETAILED DESCRIPTION

Described herein are compounds of Formula (I), pharmaceutically acceptable salts thereof, and pharmaceutical compositions comprising same:

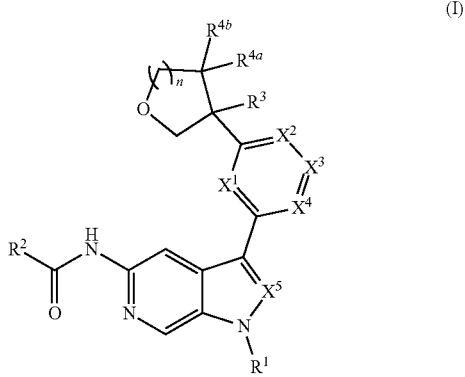

(I)

wherein:

$R^1$ is hydrogen, or $R^1$ is unsubstituted or substituted $C_{1-6}$alkyl, unsubstituted or substituted $C_{3-6}$carbocyclyl, or unsubstituted or substituted 4- to 6-membered heterocyclyl;

$R^2$ is -NH$_2$, -NHR$^{2a}$, -OR$^{2a}$, unsubstituted or substituted $C_{1-6}$alkyl, or unsubstituted or substituted $C_3$carbocyclyl, and $R^{2a}$ is unsubstituted or substituted $C_{1-6}$alkyl or unsubstituted or substituted $C_3$carbocyclyl;

$R^3$ is hydrogen, -(C$_{1-3}$alkylene)$_m$-OR$^{3a}$, -(C$_{1-3}$alkylene)$_m$-N(R$^{3a}$)$_2$, $C_{1-3}$alkyl, or $C_{1-3}$haloalkyl, wherein m is 0 or 1, and each instance of $R^{3a}$ is independently hydrogen, $C_{1-3}$alkyl, or $C_{1-3}$haloalkyl;

n is 0 or 1, and each instance of $R^{4a}$ and $R^{4b}$ is independently hydrogen, halogen, $C_{1-3}$alkyl, or $C_{1-3}$haloalkyl, or $R^{4a}$ and $R^{4b}$ are joined to form an oxo (=O) group; or n is 1, $R^4a$ is hydrogen, $C_{1-3}$alkyl, or $C_{1-3}$haloalkyl, and $R^{4b}$ is -OH, -OR$^{4c}$, or -OC(=O)R$^{4d}$, wherein each instance of R$^4$c and R$^{4d}$ is independently unsubstituted or substituted $C_{1-3}$alkyl;

$X^3$ is N or CR$^5$, wherein R$^5$ is hydrogen, -CN, -OR$^{5a}$, -NHR$^{5a}$, or unsubstituted or substituted $C_{1-6}$alkyl, and R$^{5a}$ is unsubstituted or substituted $C_{1-6}$alkyl, unsubstituted or substituted $C_{3-6}$carbocyclyl, unsubstituted or substituted $C_{3-6}$carbocyclylC$_{1-3}$alkyl, unsubstituted or substituted 4- to 6-membered heterocyclyl, or unsubstituted or substituted 4- to 6-membered heterocyclylC$_{1-3}$alkyl;

each instance of $X^1$, $X^2$, $X^4$, and $X^5$ is independently N or CH, provided no more than two of $X^2$, $X^3$, and $X^4$ is N; and each instance of substituted is independent substitution with 1, 2, or 3 substituents selected from the group consisting of halogen, -CN, -OH, $C_{1-3}$alkyl, $C_{1-3}$haloalkyl, -OC$_{1-3}$alkyl, and -OC$_{1-3}$haloalkyl.

Compounds of Formula (I) may potently and selectively inhibit Tyk2, with half maximal effective concentration (EC$_{50}$) (as measured by the Tyk2 (Tyk2/Jak2 PSTAT4 T-Blast) alpha screen assay and Jak2 (PTAT5 UT7) alpha screen assay, described herein) of less than 4µM, and with a 10-fold to over 1000-fold selectivity for Tyk2 over Jak2. See, e.g., Examples, Table C. In certain embodiments, a compound of Formula (I), or pharmaceutically acceptable salt thereof, has an EC$_{50}$ against Tyk2 of less than 3.5 µM, of less than 2 µM, of less than 1 µM, of less than 0.5 µM, of less than 0.1 µM, of less than 0.05 µM, or of less than 0.01 µM, as measured by the Tyk2 (Tyk2/Jak2 PSTAT4 T-Blast) alpha screen assay and Jak2 (PTAT5 UT7) alpha screen assay, described herein. In certain embodiments, a compound of Formula (I), or pharmaceutically acceptable salt thereof, has a >10-fold, >20-fold, >30-fold, >40- fold, >50-fold, >60-fold, >70-fold, >80-fold, >90-fold, >100-fold, >150-fold, >200-fold, >300-fold, >400-fold, >500-fold, >600-fold, >700-fold, >800-fold, >900-fold, >1,000-fold, or >2,000-fold selectivity for Tyk2 over Jak2.

In certain further embodiments, a compound of Formula (I) may potently and selectively inhibit Tyk2, with a 10-fold to over 1000-fold selectivity for Tyk2 over Jak1 (as measured by the Jak1 (PTAT3 TF1) alpha screen assay, described herein). See, e.g., Examples, Table C. In certain embodiments, a compound of Formula (I), or pharmaceutically acceptable salt thereof, has a >10-fold, >20-fold, >30- fold, >40-fold, >50-fold, >60-fold, >70-fold, >80-fold, >90-fold, >100-fold, >150-fold, >200-fold, >300-fold, >400-fold, >500-fold, >600-fold, >700-fold, >800-fold, >900-fold, >1,000-fold, or >2,000-fold selectivity for Tyk2 over Jak1.

Compounds of Formula (I) may further comprise one or more stereocenters. In certain embodiments, the compound comprises a stereocenter on the carbon to which group R$^3$ is attached. For example, in certain embodiments, the compound is a stereoisomer of Formula (I-a), or a pharmaceutically acceptable salt thereof. In certain embodiments, the compound is a stereoisomer of Formula (I-b), or a pharmaceutically acceptable salt thereof.

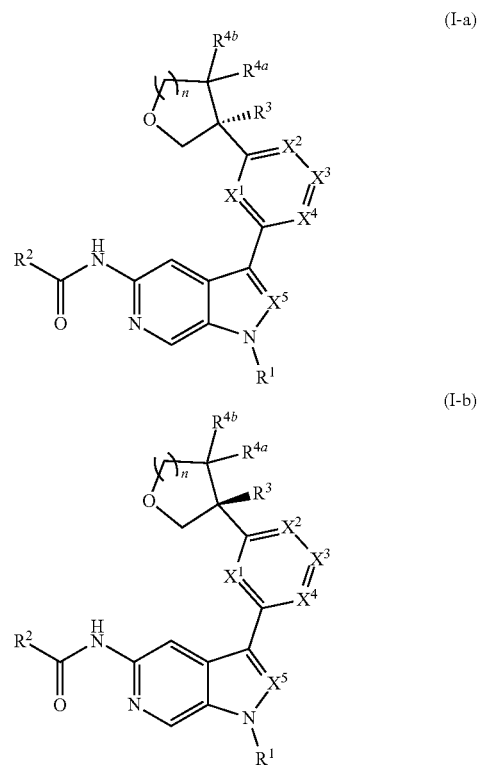

In certain preferred embodiments, the compound of Formula (I) is a stereoisomer of Formula (I-a). Without wishing to be bound by any particular theory, it is believed that the observed improved activity of stereoisomers of Formula (I-a) over their mirror images (of Formula (I-b)) is via maximized positive non-covalent interactions within the Tyk2 pseudokinase binding domain.

(i) Groups $R^1$ and $R^2$

As generally described herein, $R^1$ is hydrogen, or $R^1$ is unsubstituted or substituted $C_{1-6}$alkyl, unsubstituted or substituted $C_{3-6}$carbocyclyl, or unsubstituted or substituted 4- to 6-membered heterocyclyl, wherein each instance of substituted is independent substitution with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl.

In certain embodiments, $R^1$ is hydrogen.

In certain embodiments, $R^1$ is unsubstituted or substituted $C_{1-6}$alkyl, unsubstituted or substituted $C_{3-6}$carbocyclyl, or unsubstituted or substituted 4- to 6-membered heterocyclyl, wherein each instance of substituted is independent substitution with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl.

In certain embodiments, $R^1$ is an unsubstituted $C_{1-6}$alkyl, or $C_{1-6}$alkyl substituted with 1, 2, or 3 substituents selected from the group consisting of halogen, -CN, -OH, -$OC_{1-3}$alkyl, and -$OC_{1-3}$haloalkyl. In certain embodiments, $R^1$ is unsubstituted $C_{1-3}$alkyl, or $C_{1-3}$alkyl substituted with 1, 2, or 3 substituents selected from the group consisting of halogen, -CN, -OH, -$OC_{1-3}$alkyl, and -$OC_{1-3}$haloalkyl. In certain embodiments, $R^1$ is unsubstituted $C_{1-2}$alkyl, or $C_{1-2}$alkyl substituted with 1, 2, or 3 substituents selected from the group consisting of halogen, -CN, -OH, -$OC_{1-3}$alkyl, and -$OC_{1-3}$haloalkyl. In certain embodiments, any of the aforementioned $R^1$ groups is unsubstituted or substituted with 1, 2, or 3 halogen atoms. In certain embodiments, $R^1$ is -$CH_3$, -$CH_2F$, -$CHF_2$, or -$CF_3$.

In certain embodiments, $R^1$ is an unsubstituted $C_{3-6}$carbocyclyl, or $C_{3-6}$carbocyclyl substituted with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl. In certain embodiments, $R^1$ is unsubstituted $C_3$carbocyclyl, or $C_3$carbocyclyl substituted with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl. In certain embodiments, $R^1$ is unsubstituted $C_4$carbocyclyl, or $C_4$carbocyclyl substituted with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl. In certain embodiments, any of the aforementioned $R^1$ groups is unsubstituted or substituted with 1, 2, or 3 halogen, -CN, -$CH_3$, -$CH_2F$, -$CHF_2$, or -$CF_3$ groups. In certain embodiments, $R^1$ is $C_{3-4}$carbocyclyl substituted with 1, 2, or 3 halogen substituents, or 1 -CN substituent. In certain embodiments, $R^1$ is:

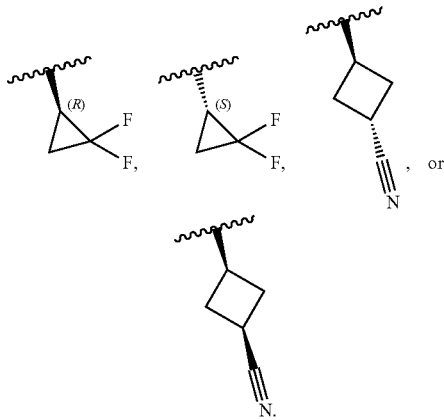

In certain embodiments, $R^1$ is an unsubstituted 4- to 6-membered heterocyclyl, or 4- to 6- membered heterocyclyl substituted with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl. In certain embodiments, $R^1$ is unsubstituted 4- to 5-membered heterocyclyl, or 4- to 5-membered heterocyclyl substituted with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl. In certain embodiments, $R^1$ is unsubstituted 4- to 5-membered heterocyclyl containing 1 or 2 ring heteroatoms independently selected from the group consisting of oxygen and nitrogen, or is a 4- to 5-membered heterocyclyl containing 1 or 2 ring heteroatoms independently selected from the group consisting of oxygen and nitrogen and which is substituted with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl. In certain embodiments, $R^1$ is unsubstituted oxetanyl, or $R^1$ is oxetanyl substituted with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl. In certain embodiments, $R^1$ is unsubstituted tetrahydrofuranyl, or $R^1$ is tetrahydrofuranyl substituted with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl. In certain embodiments, any of the aforementioned $R^1$ groups is unsubstituted or substituted with 1, 2, or 3 halogen, -CN, -$CH_3$, -$CH_2F$, -$CHF_2$, or -$CF_3$ groups. In certain embodiments, $R^1$ is:

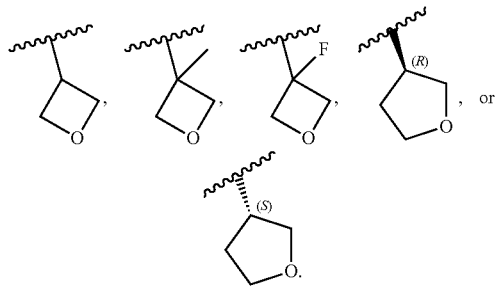

As generally described herein, $R^2$ is -$NH_2$, -$NHR^{2a}$, -$OR^{2a}$, unsubstituted or substituted $C_{1-6}$alkyl, or unsubstituted or substituted $C_3$carbocyclyl, and $R^{2a}$ is unsubstituted or substituted $C_{1-6}$alkyl or unsubstituted or substituted $C_3$carbocyclyl; and wherein each instance of substituted is independent substitution with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl.

In certain embodiments, $R^2$ is -$NH_2$, -$NHR^{2a}$, or -$OR^{2a}$, wherein $R^{2a}$ is $C_{1-6}$alkyl, or $C_{1-6}$alkyl substituted with 1, 2, or 3 substituents selected from the group consisting of halogen, -CN, -OH, -$OC_{1-3}$alkyl, and -$OC_{1-3}$haloalkyl. In certain embodiments, $R^2$ is -$NH_2$, -$NHR^{2a}$, or -$OR^{2a}$ wherein $R^{2a}$ is $C_{1-3}$alkyl, or $C_{1-3}$alkyl substituted with 1, 2, or 3 substituents selected from the group consisting of halogen, -CN, -OH, -$OC_{1-3}$alkyl, and -$OC_{1-3}$haloalkyl. In certain embodiments, $R^2$ is -$NH_2$, -$NHR^{2a}$, or -$OR^{2a}$ wherein $R^{2a}$ is $C_{1-2}$alkyl, or $C_{1-2}$alkyl substituted with 1, 2, or 3 substituents selected from the group consisting of halogen, -CN, -OH, -$OC_{1-3}$alkyl, and -$OC_{1-3}$haloalkyl. In certain embodiments, $R^2$ is -$NH_2$, -$NHR^2a$, or -$OR^{2a}$ wherein $R^{2a}$ is $C_1$alkyl, or $C_1$alkyl substituted with 1, 2, or 3 substituents selected from the group consisting of halogen, -CN, -OH, -OC$_{1-3}$alkyl, and -OC$_{1-3}$haloalkyl. In certain embodiments, R$^2$ is -NH$_2$, -NHCH$_3$, or -OCH$_3$.

In certain embodiments, R$^2$ is C$_{1-6}$alkyl, or C$_{1-6}$alkyl substituted with 1, 2, or 3 substituents selected from the group consisting of halogen, -CN, -OH, -OC$_{1-3}$alkyl, and -OC$_{1-3}$haloalkyl. In certain embodiments, R$^2$ is C$_{1-3}$alkyl, or C$_{1-3}$alkyl substituted with 1, 2, or 3 substituents selected from the group consisting of halogen, -CN, -OH, -OC$_{1-3}$alkyl, and -OC$_{1-3}$haloalkyl. In certain embodiments, R$^2$ is C$_{1-2}$alkyl, or C$_{1-2}$alkyl substituted with 1, 2, or 3 substituents selected from the group consisting of halogen, -CN, -OH, -OC$_{1-3}$alkyl, and -OC$_{1-3}$haloalkyl. In certain embodiments, R$^2$ is C$_1$alkyl, or C$_1$alkyl substituted with 1, 2, or 3 substituents selected from the group consisting of halogen, -CN, -OH, -OC$_{1-3}$alkyl, and -OC$_{1-3}$haloalkyl. In certain embodiments, R$^2$ is -CH$_3$ or -CH$_2$OH.

In certain embodiments, R$^2$ is unsubstituted C$_3$carbocyclyl, or C$_3$carbocyclyl substituted with 1, 2, or 3 halogen substituents.

In certain embodiments, R$^2$ is -NH$_2$, -NHR$^{2a}$, unsubstituted or substituted C$_{1-3}$alkyl, and R$^{2a}$ is unsubstituted or substituted C$_{1-3}$alkyl.

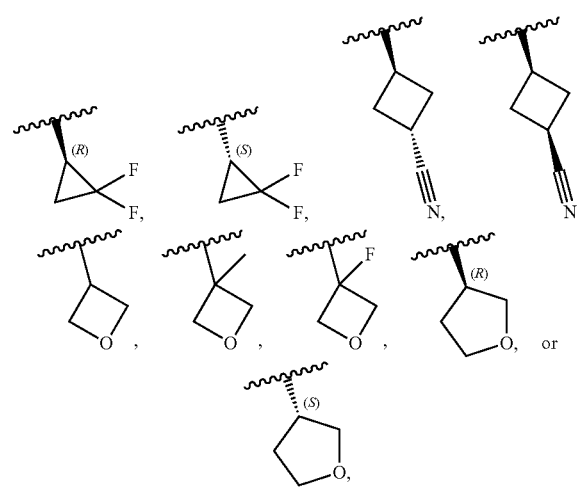

In certain embodiments, R$^1$ is -CH$_3$, -CH$_2$F, -CHF$_2$, -CF$_3$, and R$^2$ -NH$_2$, -NHCH$_3$, -OCH$_3$, -CH$_3$, or -CH$_2$OH.

(ii) Groups R$^3$, R$^{4a}$, R$^{4b}$, m, and n

As generally described herein, R$^3$ is hydrogen, -(C$_{1-3}$alkylene)$_m$-OR$^{3a}$, -(C$_{1-3}$alkylene)$_m$- N(R$^{3a}$)$_2$, C$_{1-3}$alkyl, or C$_{1-3}$haloalkyl, wherein m is 0 or 1, and each instance of R$^{3a}$ is independently hydrogen, C$_{1-3}$alkyl, or C$_{1-3}$haloalkyl.

In certain embodiments, R$^3$ is hydrogen.

In certain embodiments, R$^3$ is -(C$_{1-3}$alkylene)$_m$-OR$^{3a}$, -(C$_{1-3}$alkylene)$_m$-N(R$^{3a}$)$_2$, C$_{1-3}$alkyl, or C$_{1-3}$haloalkyl.

In certain embodiments, R$^3$ is C$_{1-3}$alkyl or C$_{1-3}$haloalkyl. In certain embodiments, R$^3$ is C$_{1-2}$alkyl or C$_{1-2}$haloalkyl. In certain embodiments, R$^3$ is C$_1$alkyl or C$_1$haloalkyl. In certain embodiments, R$^3$ is C$_2$alkyl or C$_2$haloalkyl. In certain embodiments, R$^3$ is -CH$_3$ or -CH$_2$CH$_3$.

In certain embodiments, wherein m is 0 and R$^3$ is -(C$_{1-3}$alkylene)$_m$-OR$^{3a}$ or -(C$_{1-3}$alkylene)$_m$- N(R$^{3a}$)$_2$, R$^3$ may also be depicted as -OR$^{3a}$ or -N(R$^{3a}$)$_2$, wherein each instance of R$^{3a}$ is independently hydrogen, C$_{1-3}$alkyl, or C$_{1-3}$haloalkyl. In certain embodiments, R$^3$ is -OR$^{3a}$. In certain embodiments, each instance of R$^{3a}$ is hydrogen. In certain embodiments, at least one R$^{3a}$ is C$_{1-3}$alky or C$_{1-3}$haloalkyl. In certain embodiments, at least one R$^{3a}$ is C$_1$alkyl or C$_1$haloalkyl. In certain embodiments, R$^{3a}$ is hydrogen or -CH$_3$. In certain embodiments, R$^3$ is -OH or -OCH$_3$.

In certain embodiments, wherein m is 1 and R$^3$ is -(C$_{1-3}$alkylene)$_m$-OR$^{3a}$, -(C$_{1-3}$alkylene)$_m$- N(R$^{3a}$)$_2$, each instance of R$^{3a}$ is independently hydrogen, C$_{1-3}$alkyl, or C$_{1-3}$haloalkyl. In certain embodiments, R$^3$ is -(C$_{1-2}$alkylene)$_m$-OR$^{3a}$ or -(C$_{1-2}$alkylene)$_m$-N(R$^3$a)$_2$, wherein m is 1. In certain embodiments, R$^3$ is -(C$_1$alkylene)$_m$-OR$^{3a}$ or -(C$_1$alkylene)$_m$-N(R$^3$a)$_2$, wherein m is 1. In certain embodiments R$^3$ is -(C$_1$alkylene)$_m$-OR$^{3a}$, -(C$_2$alkylene)$_m$-OR$^{3a}$, or -(C$_3$alkylene)$_m$-OR$^3$a, wherein m is 1. In certain embodiments R$^3$ is -(C$_1$alkylene)$_m$-N(R$^{3a}$)$_2$, -(C$_2$alkylene)$_m$-N (R$^{3a}$)$_2$, or -(C$_3$alkylene)$_m$- N(R$^3$a)$_2$, wherein m is 1. In certain embodiments R$^3$ is -(C$_1$alkylene)$_m$-OR$^3$a or -(C$_1$alkylene)$_m$-N(R$^3$a)$_2$, wherein m is 1. In certain embodiments, at least one instance of R$^{3a}$ is C$_{1-3}$alkyl or C$_{1-3}$haloalkyl. In certain embodiments, at least one instance of R$^{3a}$ is C$_1$alkyl or C$_1$haloalkyl. In certain embodiments, at least one instance of R$^{3a}$ is -CH$_3$. In certain embodiments, at least one instance of R$^{3a}$ is hydrogen. In certain embodiments, each instance of R$^{3a}$ is hydrogen. In certain embodiments, R$^3$ is -CH(OH)CH$_3$, -CH$_2$OH, or -CH$_2$NH$_2$.

As generally described herein, n is 0 or 1, and each instance of R$^{4a}$ and R$^{4b}$ is independently hydrogen, halogen, C$_{1-3}$alkyl, or C$_{1-3}$haloalkyl, or R$^{4a}$ and R$^{4b}$ are joined to form an oxo (=O) group; or n is 1, R$^{4a}$ is hydrogen, C$_{1-3}$alkyl, or C$_{1-3}$haloalkyl, and R$^{4b}$ is -OH, -OR$^{4c}$, or -OC(=O)R$^{4d}$, wherein each instance of R$^4$c and R$^{4d}$ is independently unsubstituted or substituted C$_{1-3}$alkyl.

In certain embodiments, n is 0; each instance of R$^{4a}$ and R$^{4b}$ is independently hydrogen, halogen, C$_{1-3}$alkyl, or C$_{1-3}$haloalkyl; or R$^{4a}$ and R$^{4b}$ are joined to form an oxo (=O) group. In certain embodiments, n is 0, and each instance of R$^{4a}$ and R$^{4b}$ is hydrogen. In certain embodiments, n is 0, and each instance of R$^{4a}$ and R$^{4b}$ is independently halogen (e.g., fluoro). In certain embodiments, n is 0, and each instance of R$^{4a}$ and R$^{4b}$ is independently C$_{1-3}$alkyl or C$_{1-3}$haloalkyl (e.g., -CH$_3$ or -CF$_3$). In certain embodiments, n is 0, R$^{4a}$ is hydrogen and R$^{4b}$ is halogen (e.g., fluoro), C$_{1-3}$alkyl, or C$_{1-3}$haloalkyl (e.g., -CH$_3$ or -CF$_3$). In certain embodiments, n is 0, and R$^{4a}$ and R$^{4b}$ are joined to form an oxo (=O) group.

In certain embodiments, n is 1; each instance of R$^{4a}$ and R$^{4b}$ is independently hydrogen, halogen, C$_{1-3}$alkyl, or C$_{1-3}$haloalkyl; or R$^{4a}$ and R$^{4b}$ are joined to form an oxo (=O) group; or R$^{4a}$ is hydrogen, C$_{1-3}$alkyl, or C$_{1-3}$haloalkyl, and R$^{4b}$ is -OH, -OR$^{4c}$, or -OC(=O)R$^{4d}$, wherein each instance of R$^4$c and R$^{4d}$ is independently unsubstituted or substituted C$_{1-3}$alkyl. In certain embodiments, n is 1, and each instance of R$^{4a}$ and R$^{4b}$ is hydrogen. In certain embodiments, n is 1, and each instance of R$^{4a}$ and R$^{4b}$ is independently halogen (e.g., fluoro). In certain embodiments, n is 1, and each instance of R$^{4a}$ and R$^{4b}$ is independently C$_{1-3}$alkyl or C$_{1-3}$haloalkyl (e.g., -CH$_3$ or -CF$_3$). In certain embodiments, n is 1, R$^{4a}$ is hydrogen and R$^{4b}$ is halogen (e.g., fluoro), C$_{1-3}$alkyl, or C$_{1-3}$haloalkyl (e.g., -CH$_3$ or -CF$_3$). In certain embodiments, n is 1, and R$^{4a}$ and R$^{4b}$ are joined to form an oxo (=O) group. In certain embodiments, n is 1, R$^{4a}$ is hydrogen, C$_{1-3}$alkyl, or C$_{1-3}$haloalkyl, and R$^{4b}$ is -OH, -OR$^4$c, or -OC(=O)R$^{4d}$, wherein each instance of R$^4$c and R$^{4d}$ is independently unsubstituted or substituted C$_{1-3}$alkyl. In certain embodiments, n is 1, R$^{4a}$ is hydrogen, and R$^{4b}$ is -OH, -OR$^{4c}$, or -OC(=O)R$^{4d}$, wherein each R$^{4c}$ and R$^{4d}$ is unsubstituted or substituted C$_{1-3}$alkyl. In certain embodiments, n is 1, R$^{4a}$ is C$_{1-3}$alkyl or C$_{1-3}$haloalkyl, and R$^{4b}$ is -OH, -OR$^{4c}$, or -OC(=O)R$^{4d}$, wherein each instance of R$^{4c}$ and R$^{4d}$ is independently unsubstituted or substituted C$_{1-3}$alkyl.

In certain embodiments, n is 0 or 1, and each instance of R$^{4a}$ and R$^{4b}$ is hydrogen. In certain embodiments, n is 0 or 1, R$^{4a}$ is hydrogen, and R$^{4b}$ is halogen (e.g., fluoro). In certain embodiments, n is 0 or 1, and each instance of R$^{4a}$ and R$^{4b}$ is halogen (e.g., fluoro). In certain embodiments, n is 0 or 1, and each instance of R$^{4a}$ and R$^{4b}$ is C$_{1-3}$alkyl or C$_{1-3}$haloalkyl (e.g., -CH$_3$). In certain embodiments, n is 1, R$^{4a}$ is hydrogen, C$_{1-3}$alkyl, or C$_{1-3}$haloalkyl (e.g., -CH$_3$), and R$^{4b}$ is -OH, -OR$^{4c}$, or -OC(=O)R$^{4d}$.

In certain embodiments, R$^3$ is hydrogen, -OH, -OCH$_3$, -CH(OH)CH$_3$, -CH$_2$OH, -CH$_2$NH$_2$, -CH$_3$, or -CH$_2$CH$_3$, each instance of R$^{4a}$ and R$^{4b}$ is hydrogen, and n is 0 or 1.

(iii) Groups X$^1$, X$^2$, X$^3$, X$^4$, X$^5$, and R$^5$

As generally described herein, each instance of X$^1$, X$^2$, X$^4$, and X$^5$ is independently N or CH, and X$^3$ is N or CR$^5$; R$^5$ is hydrogen, -CN, -OR$^{5a}$, -NHR$^{5a}$, or unsubstituted or substituted C$_{1-6}$alkyl; R$^{5a}$ is unsubstituted or substituted C$_{1-6}$alkyl, unsubstituted or substituted C$_{3-6}$carbocyclyl, unsubstituted or substituted C$_{3-6}$carbocyclylC$_{1-3}$alkyl, unsubstituted or substituted 4- to 6-membered heterocyclyl, or unsubstituted or substituted 4- to 6-membered heterocyclylC$_{1-3}$alkyl; each instance of substituted is independent substitution with 1, 2, or 3 substituents selected from the group consisting of halogen, -CN, -OH, C$_{1-3}$alkyl, C$_{1-3}$haloalkyl, -OC$_{1-3}$alkyl, and -OC$_{1-3}$haloalkyl; provided no more than two of X$^2$, X$^3$, and X$^4$ is N.

In certain embodiments, X$^1$ is N. In certain embodiments, X$^1$ is CH.

In certain embodiments, X$^2$ is N. In certain embodiments, X$^2$ is CH.

In certain embodiments, X$^3$ is N. In certain embodiments, X$^3$ is CR$^5$.

In certain embodiments, X$^4$ is N. In certain embodiments, X$^4$ is CH.

In certain embodiments, X$^5$ is N. In certain embodiments, X$^5$ is CH.

As generally described herein, no more than two of X$^2$, X$^3$, and X$^4$ is N, i.e., none of X$^2$, X$^3$, and X$^4$ is N, or one or two of X$^2$, X$^3$, and X$^4$ is N. In certain embodiments, wherein none of X$^2$, X$^3$, and X$^4$ is N, then X$^2$ is CH, X$^3$ is CR$^5$, and X$^4$ is CH. In certain embodiments, wherein one of X$^2$, X$^3$, and X$^4$ is N, then (i) X$^2$ is CH, X$^3$ is CR$^5$, and X$^4$ is N, or (ii) X$^2$ is CH, X$^3$ is N, and X$^4$ is CH. In certain embodiments, wherein two of X$^2$, X$^3$, and X$^4$ is N, then X$^2$ is CH, X$^3$ is N, and X$^4$ is N.

In certain embodiments, only one of X$^1$, X$^2$, X$^3$, X$^4$, and X$^5$, is N, e.g., in certain embodiments, X$^1$ is N, X$^2$ is CH, X$^3$ is CR$^5$, X$^4$ is CH, and X$^5$ is CH. In certain embodiments, only two of X$^1$, X$^2$, X$^3$, X$^4$, and X$^5$ is N, e.g., in certain embodiments: (i) X$^1$ is N, X$^3$ is N, and X$^2$, X$^4$, and X$^5$ are not N; or (ii) X$^1$ is N, X$^4$ is N, and X$^2$, X$^3$, and X$^5$ are not N. In certain embodiments, only three of X$^1$, X$^2$, X$^3$, X$^4$, and X$_5$ is N, provided no more than two of X$^2$, X$^3$, and X$^4$ is N, e.g., in certain embodiments: (i) X$^1$ is N, X$^4$ is N, X$^5$ is N, and X$^2$ and X$^3$ are not N; or (ii) X$^1$ is N, X$^3$ is N, X$^5$ is N, and X$^2$ and X$^4$ are not N. In certain embodiments, X$^1$ is N, X$^2$ is CH, X$^3$ is N or CR$^5$, X$^4$ is CH or N, and X$^5$ is CH or N.

In certain embodiments, X$^3$ is CR$^5$ and R$^5$ is hydrogen.

In certain embodiments, X$^3$ is CR$^5$ and R$^5$ is -CN, -OR$^5$, -NHR$^{5a}$, or unsubstituted or substituted C$_{1-6}$alkyl; R$^{ya}$ is unsubstituted or substituted C$_{1-6}$alkyl, unsubstituted or substituted C$_{3-6}$carbocyclyl, unsubstituted or substituted C$_{3-6}$carbocyclylC$_{1-3}$alkyl, unsubstituted or substituted 4- to 6-membered heterocyclyl, or unsubstituted or substituted 4- to 6-membered heterocyclylC$_{1-3}$alkyl; each instance of substituted is independent substitution with 1, 2, or 3 substituents selected from the group consisting of halogen, -CN, -OH, C$_{1-3}$alkyl, C$_{1-3}$haloalkyl, -OC$_{1-3}$alkyl, and -OC$_{1-3}$haloalkyl.

In certain embodiments, X$^3$ is CR$^5$ and R$^5$ is -CN.

In certain embodiments, X$^3$ is CR$^5$ and R$^5$ is -OR$^{5a}$ or -NHR$^{5a}$, wherein R$^{5a}$ is unsubstituted or substituted C$_{1-6}$alkyl, unsubstituted or substituted C$_{3-6}$carbocyclyl, unsubstituted or substituted C$_{3-6}$carbocyclylC$_{1-3}$alkyl, unsubstituted or substituted 4- to 6-membered heterocyclyl, or unsubstituted or substituted 4- to 6-membered heterocyclylC$_{1-3}$alkyl; and each instance of substituted is independent substitution with 1, 2, or 3 substituents selected from the group consisting of halogen, -CN, -OH, C$_{1-3}$alkyl, C$_{1-3}$haloalkyl, -OC$_{1-3}$alkyl, and -OC$_{1-3}$haloalkyl.

In certain embodiments, X$^3$ is CR$^5$ and R$^5$ is -OR$^{5a}$ or -NHR$^{5a}$, wherein R$_{5a}$ unsubstituted C$_{1-6}$alkyl, or C$_{1-6}$alkyl independently substituted with 1, 2, or 3 substituents selected from the group consisting of halogen, -CN, -OH, -OC$_{1-3}$alkyl, and -OC$_{1-3}$haloalkyl. In certain embodiments, X$^3$ is CR$^5$ and R$^5$ is -OR$^{5a}$ or -NHR$^{5a}$, wherein R$^{5a}$ is unsubstituted C$_{1-4}$alkyl, or C$_{1-4}$alkyl independently substituted with 1, 2, or 3 substituents selected from the group consisting of halogen, -CN, -OH, -OC$_{1-3}$alkyl, and -OC$_{1-3}$haloalkyl. In any of the aforementioned embodiments, a substituted R$^{5a}$ group is independently substituted with one -OH or -CN group. In certain embodiments, X$^3$ is CR$^5$ and R$^5$ is -OR$^{5a}$ or -NHR$^{5a}$, wherein R$^{5a}$ is selected from the group consisting of -CH$_3$, -CH$_2$CH$_3$, -CH(CH$_3$)$_2$, -CH$_2$CH$_2$OH, -CH$_2$CH$_2$OCH$_3$, -CHF$_2$, -CH$_2$CN,

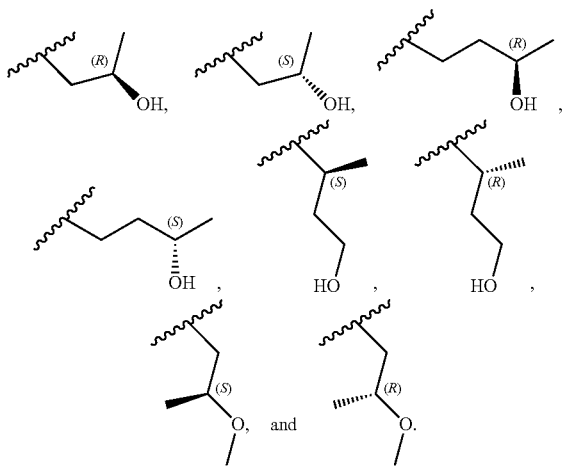

In certain embodiments, X$^3$ is CR$^5$ and R$^5$ is -OR$^{5a}$ or -NHR$^{5a}$, wherein R$^{5a}$ is unsubstituted or substituted C$_{3-6}$carbocyclyl or unsubstituted or substituted C$_{3-6}$carbocyclyl C$_{1-3}$alkyl, and wherein the substituted C$_{3-6}$carbocyclyl is independently substituted with 1, 2, or 3 substituents selected from the group consisting of halogen, -CN, -OH, C$_{1-3}$alkyl, C$_{1-3}$haloalkyl, -OC$_{1-3}$alkyl, and -OC$_{1-3}$haloalkyl. In certain embodiments, X$^3$ is CR$^5$ and R$^5$ is -OR$^{5a}$ or -NHR$^{5a}$, wherein R$^{ya}$ is unsubstituted or substituted C$_{3-4}$carbocyclyl or unsubstituted or substituted C$_{3-4}$carbocyclyl C$_{1-3}$alkyl, wherein the substituted C$_{3-4}$carbocyclyl group is independently substituted with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl. In certain embodiments, $X^3$ is $CR^5$ and $R^5$ is -$OR^{5a}$ or -$NHR^{5a}$, wherein $R^{5a}$ is:

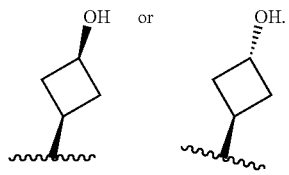 [SMILES: *[C@H]1C[C@@H](O)C1 ; *[C@H]1C[C@H](O)C1]

In certain embodiments, $X^3$ is $CR^5$ and $R^5$ is -$OR^{5s}$ or -$NHR^{5a}$, wherein $R^{5a}$ is unsubstituted or substituted 4- to 6-membered heterocyclyl or unsubstituted or substituted 4- to 6-membered heterocyclyl$C_{1-3}$alkyl, wherein the substituted 4- to 6-membered heterocyclyl group is independently substituted with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl. In certain embodiments, $X^3$ is $CR^5$ and $R^5$ is - $OR^{5a}$ or -$NHR^{5a}$, wherein $R^{5a}$ is unsubstituted or substituted 4- to 5-membered heterocyclyl or unsubstituted or substituted 4- to 5-membered heterocyclyl$C_{1-3}$alkyl, wherein the substituted 4- to 5- membered heterocyclyl group is independently substituted with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl. In certain embodiments, $X^3$ is $CR^5$ and $R^5$ is -$OR^{5a}$ or -$NHR^{5a}$, wherein $^{Rya}$ is unsubstituted or substituted 4- membered heterocyclyl or unsubstituted or substituted 4-membered heterocyclyl$C_{1-3}$alkyl, wherein the substituted 4-membered heterocyclyl group is independently substituted with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl. In certain embodiments, the 4-membered heterocyclyl is an oxetanyl ring. In certain embodiments, $X^3$ is $CR^5$ and $R^5$ is -$OR^{5a}$ or -$NHR^{5a}$, wherein $R^{5a}$ is:

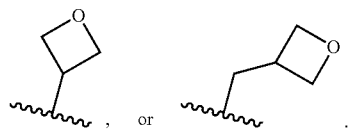 [SMILES: *C1COC1 ; *CC1COC1 ; "," ; "."]

In certain embodiments, $X^3$ is $CR^5$ and $R^5$ is unsubstituted $C_{1-6}$alkyl or $C_{1-6}$alkyl substituted with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl. In certain embodiments, $X^3$ is $CR^5$ and $R^5$ is unsubstituted $C_{1-6}$alkyl or $C_{1-6}$alkyl substituted with 1, 2, or 3 substituents independently selected from the group consisting of halogen, -CN, -OH, -$OC_{1-3}$alkyl, and -$OC_{1-3}$haloalkyl. In certain embodiments, $X^3$ is $CR^5$ and $R^5$ is unsubstituted $C_{1-6}$alkyl. In certain embodiments, $X^3$ is $CR^5$ and $R^5$ is unsubstituted $C_{1-3}$alkyl. In certain embodiments, $X^3$ is $CR^5$ and $R^5$ is unsubstituted $C_{1-2}$alkyl. In certain embodiments, $X^3$ is $CR^5$ and $R^5$ is $C_{1-6}$alkyl substituted with 1, 2, or 3 substituents independently selected from the group consisting of halogen, -CN, -OH, -$OC_{1-3}$alkyl, and -$OC_{1-3}$haloalkyl. In certain embodiments, $X^3$ is $CR^5$ and $R^5$ is $C_{1-3}$alkyl substituted with 1, 2, or 3 substituents independently selected from the group consisting of halogen, -CN, -OH, -$OC_{1-3}$alkyl, and -$OC_{1-3}$haloalkyl. In certain embodiments, $X^3$ is $CR^5$ and $R^5$ is $C_{1-3}$alkyl substituted with 1 substituent selected from the group consisting of -OH, -$OC_{1-3}$alkyl, and -$OC_{1-3}$haloalkyl. In certain such embodiments, $R^5$ is $C_{1-3}$alkyl substituted with 1 substituent that is -$OC_{1-3}$alkyl. In certain embodiments, $X^3$ is $CR^5$ and $R^5$ is $C_{1-2}$alkyl substituted with 1, 2, or 3 substituents independently selected from the group consisting of halogen, -CN, -OH, -$OC_{1-3}$alkyl, and -$OC_{1-3}$haloalkyl. In certain embodiments, $R^5$ is $C_1$alkyl substituted with 1 substituent selected from the group consisting of -OH, -$OC_{1-3}$alkyl and -$OC_{1-3}$haloalkyl. In certain embodiments, $R^5$ is -$CH_3$. In certain embodiments, $R^5$ is -$CH_2F$, -$CHF_2$, -$CF_3$, or -$CH_2OCH_3$.

In certain embodiments, $X^1$ is N; $X^2$ is CH; $X^4$ is CH or N; $X^5$ is CH or N; $X^3$ is N or $CR^5$, and $R^5$ is selected from the group consisting of hydrogen, -CN, -$CH_3$, -$CH_2F$, -$CF_3$, -$CH_2OCH_3$, - $OCH_3$, -$OCH_2CH_3$, -$OCH(CH_3)_2$, -$OCH_2CH_2OH$, -$OCH_2CH_2OCH_3$, -$OCHF_2$, -$OCH_2CN$,

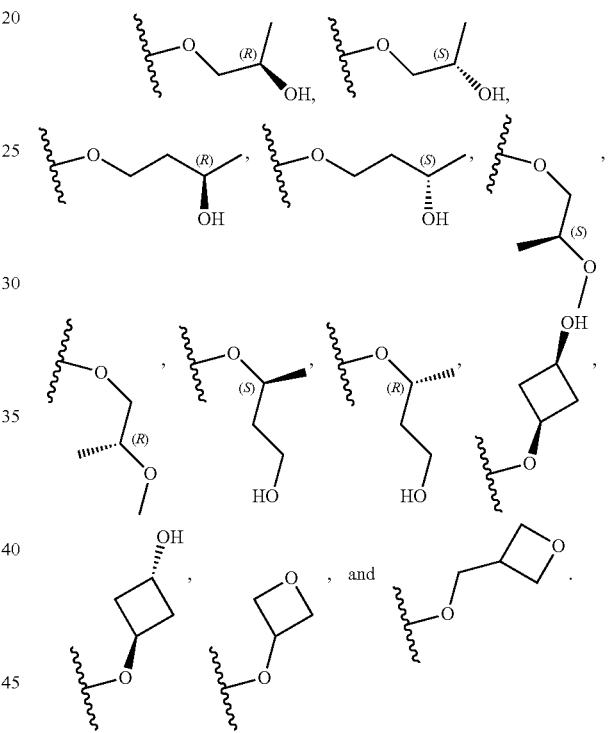

(iv) Various Combinations of Certain Embodiments

In certain embodiments of Formula (I), $X^1$ is N; $X^2$, $X^4$, and $X^5$ are each CH; $X^3$ is N or $CR^5$; $R^1$ is unsubstituted or substituted $C_{1-3}$alkyl, unsubstituted or substituted $C_{3-4}$carbocyclyl, or unsubstituted or substituted 4- to 5-membered heterocyclyl; $R^2$ is -$NH_2$, -$NHR^{2a}$, unsubstituted or substituted $C_{1-3}$alkyl, and $R^{5a}$ is unsubstituted or substituted $C_{1-3}$alkyl; $R^3$ is -$(C_{1-3}$alkylene$)_m$-$OR^{3a}$, -$(C_{1-3}$alkylene$)_m$-N$(R^{3a})_2$, $C_{1-3}$alkyl, or $C_{1-3}$haloalkyl, wherein each instance of $R^{3a}$ is independently hydrogen, $C_{1-3}$alkyl, or $C_{1-3}$haloalkyl; m is 0 or 1; n is 0 or 1; each instance of $R^{4a}$ and $R^{4b}$ is hydrogen; $R^5$ is hydrogen, -CN, -$OR^{5a}$, -$NHR^{5a}$, or unsubstituted or substituted $C_{1-6}$alkyl, wherein $R^{5a}$ is unsubstituted or substituted $C_{1-6}$alkyl, unsubstituted or substituted $C_{3-6}$carbocyclyl, unsubstituted or substituted $C_{3-6}$carbocyclyl$C_{1-3}$alkyl, unsubstituted or substituted 4- to 6-membered heterocyclyl, or unsubstituted or substituted 4- to 6- membered heterocyclyl$C_{1-3}$alkyl; and wherein each instance of substituted is independent substitution with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl.

In certain embodiments of Formula (I), $X^1$ is N; $X^2$, $X^4$, and $X^5$ are each CH; $X^3$ is N or $CR^5$; $R^1$ is unsubstituted or substituted $C_{1-3}$alkyl; $R^2$ is -$NH_2$, -$NHCH_3$, -$CH_3$, or -$CH_2OH$; $R^3$ is -($C_{1-3}$alkylene)$_m$-$OR^{3a}$, $C_{1-3}$alkyl, or $C_{1-3}$haloalkyl; m is 0 or 1; n is 0 or 1; $R^{4a}$ and $R^{4b}$ are each hydrogen; and wherein each instance of substituted is independent substitution with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl. In certain embodiments, $R^5$ is hydrogen. In certain embodiments, $R^5$ is -CN. In certain embodiments, $R^5$ is -$OR^{5a}$. In certain embodiments, $R^5$ is -$NHR^{5a}$. In certain embodiments, $R^5$ is unsubstituted or substituted $C_{1-6}$alkyl. In certain embodiments, the compound is a stereoisomer of Formula (I-a), or pharmaceutically acceptable salt thereof.

In certain embodiments of Formula (I), $X^1$ is N; $X^2$, $X^4$, and $X^5$ are each CH; $X^3$ is N or $CR^5$; $R^1$ is unsubstituted or substituted $C_{3-4}$carbocyclyl; $R^2$ is -$NH_2$, -$NHCH_3$, -$CH_3$, or -$CH_2OH$; $R^3$ is -($C_{1-3}$alkylene)$_m$-$OR^{3a}$, $C_{1-3}$alkyl, or $C_{1-3}$haloalkyl; m is 0 or 1; n is 0 or 1; $R^{4a}$ and $R^{4b}$ are each hydrogen; and wherein each instance of substituted is independent substitution with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl. In certain embodiments, $R^5$ is hydrogen. In certain embodiments, $R^5$ is -CN. In certain embodiments, $R^5$ is -$OR^{5a}$. In certain embodiments, $R^5$ is -$NHR^{5a}$. In certain embodiments, $R^5$ is unsubstituted or substituted $C_{1-6}$alkyl. In certain embodiments, the compound is a stereoisomer of Formula (I-a), or pharmaceutically acceptable salt thereof.

In certain embodiments of Formula (I), $X^1$ is N; $X^2$, $X^4$, and $X^5$ are each CH; $X^3$ is N or $CR^5$; $R^1$ is unsubstituted or substituted 4- to 5-membered heterocyclyl; $R^2$ is -$NH_2$, -$NHCH_3$, -$CH_3$, or -$CH_2OH$; $R^3$ is -($C_{1-3}$alkylene)$_m$-$OR^{3a}$, $C_{1-3}$alkyl, or $C_{1-3}$haloalkyl; m is 0 or 1; n is 0 or 1; $R^{4a}$ and $R^{4b}$ are each hydrogen; and wherein each instance of substituted is independent substitution with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl. In certain embodiments, $R^5$ is hydrogen. In certain embodiments, $R^5$ is -CN. In certain embodiments, $R^5$ is -$OR^{5a}$. In certain embodiments, $R^5$ is -$NHR^{5a}$. In certain embodiments, $R^5$ is unsubstituted or substituted $C_{1-6}$alkyl. In certain embodiments, the compound is a stereoisomer of Formula (I-a), or pharmaceutically acceptable salt thereof.

In certain embodiments, of Formula (I), $X^1$ is N; $X^2$, $X^4$, and $X^5$ are each CH; $X^3$ is $CR^5$; $R^1$ is unsubstituted $C_{1-3}$alkyl, or unsubstituted or substituted 4-membered heterocyclyl, wherein substituted is independent substitution with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl; $R^2$ is -$CH_3$; $R^3$ is -($C_{1-3}$alkylene)$_m$- $OR^{3a}$ wherein m is 0 or 1; n is 1; $R^{4a}$ and $R^{4b}$ are each hydrogen; and $R^5$ is $C_1$alkyl substituted with 1 substituent selected from the group consisting of -OH, -$OC_{1-3}$alkyl or -$OC_{1-3}$haloalkyl. In certain embodiments, the compound is a stereoisomer of Formula (I-a), or pharmaceutically acceptable salt thereof In certain embodiments, of Formula (I), $X^1$ is N; $X^2$, $X^4$, and $X^5$ are each CH; $X^3$ is $CR^5$; $R^1$ is unsubstituted $C_{1-3}$alkyl; $R^2$ is -$CH_3$; $R^3$ is -($C_{1-3}$alkylene)$_m$-$OR^{3a}$ wherein m is 0; n is 1; $R^{4a}$ and $R^{4b}$ are each hydrogen; and $R^5$ is $C_1$alkyl substituted with 1 substituent selected from the group consisting of - OH, -$OC_{1-3}$alkyl or -$OC_{1-3}$haloalkyl. In certain embodiments, the compound is a stereoisomer of Formula (I-a), or pharmaceutically acceptable salt thereof.

In certain embodiments, of Formula (I), $X^1$ is N; $X^2$, $X^4$, and $X^5$ are each CH; $X^3$ is $CR^5$; $R^1$ is unsubstituted or substituted 4-membered heterocyclyl, wherein substituted is independent substitution with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl; $R^2$ is -$CH_3$; $R^3$ is -($C_{1-3}$alkylene)$_m$-$OR^{3a}$ wherein m is 0; n is 1; $R^{4a}$ and $R^{4b}$ are each hydrogen; and $R^5$ is $C_1$alkyl substituted with 1 substituent selected from the group consisting of -OH, -$OC_{1-3}$alkyl or -$OC_{1-3}$haloalkyl. In certain embodiments, the compound is a stereoisomer of Formula (I-a), or pharmaceutically acceptable salt thereof.

In certain embodiments, of Formula (I), $X^1$ is N; $X^2$, $X^4$, and $X^5$ are each CH; $X^3$ is $CR^5$; $R^1$ is unsubstituted $C_{1-3}$alkyl; $R^2$ is -$CH_3$; $R^3$ is -($C_{1-3}$alkylene)$_m$-$OR^{3a}$ wherein m is 0; n is 1; $R^{4a}$ and $R^{4b}$ are each hydrogen; and $R^5$ is -$OR^{5a}$ wherein Rya is $C_{1-6}$alkyl substituted with 1 substituent selected from the group consisting of -OH, -$OC_{1-3}$alkyl or -$OC_{1-3}$haloalkyl. In certain embodiments, the compound is a stereoisomer of Formula (I-a), or pharmaceutically acceptable salt thereof.

In certain embodiments, of Formula (I), $X^1$ is N; $X^2$, $X^4$, and $X^5$ are each CH; $X^3$ is $CR^5$; $R^1$ is unsubstituted $C_{1-3}$alkyl; $R^2$ is -$CH_3$; $R^3$ is -($C_{1-3}$alkylene)$_m$-$OR^{3a}$ wherein m is 1; n is 1; $R^{4a}$ and $R^{4b}$ are each hydrogen; and $R^5$ is $C_1$alkyl substituted with 1 substituent selected from the group consisting of - OH, -$OC_{1-3}$alkyl or -$OC_{1-3}$haloalkyl. In certain embodiments, the compound is a stereoisomer of Formula (I-a), or pharmaceutically acceptable salt thereof.

In certain embodiments, of Formula (I), $X^1$ is N; $X^2$, $X^4$, and $X^5$ are each CH; $X^3$ is $CR^5$; $R^1$ is unsubstituted or substituted 4-membered heterocyclyl, wherein substituted is independent substitution with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl; $R^2$ is -$CH_3$; $R^3$ is -($C_{1-3}$alkylene)$_m$-$OR^{3a}$ wherein m is 1; n is 1; $R^{4a}$ and $R^{4b}$ are each hydrogen; $R^5$ is $C_1$alkyl substituted with 1 substituent selected from the group consisting of -OH, -$OC_{1-3}$alkyl or -$OC_{1-3}$haloalkyl. In certain embodiments, the compound is a stereoisomer of Formula (I-a), or pharmaceutically acceptable salt thereof.

In certain embodiments, of Formula (I), $X^1$ is N; $X^2$, $X^4$, and $X^5$ are each CH; $X^3$ is $CR^5$; $R^1$ is unsubstituted $C_{1-3}$alkyl; $R^2$ is -$CH_3$; $R^3$ is -($C_{1-3}$alkylene)$_m$-$OR^{3a}$ wherein m is 1; n is 1; $R^{4a}$ and $R^{4b}$ are each hydrogen; and $R^5$ is -$OR^{5a}$ wherein $R^{5a}$ is $C_{1-6}$alkyl substituted with 1 substituent selected from the group consisting of -OH, -$OC_{1-3}$alkyl or -$OC_{1-3}$haloalkyl. In certain embodiments, the compound is a stereoisomer of Formula (I-a), or pharmaceutically acceptable salt thereof.

In certain embodiments of Formula (I), $X^1$ is N; $X^2$, $X^4$, and $X^5$ are each CH; $X^3$ is $CR^5$; $R^1$ is unsubstituted $C_{1-3}$alkyl; $R^2$ is -$CH_3$; $R^3$ is -($C_{1-3}$alkylene)$_m$-$OR^{3a}$ wherein m is 0; $R^{4a}$ and $R^{4b}$ are each hydrogen; $R^5$ is -$OR^{5a}$ wherein $R^{5a}$ is $C_{3-6}$carbocyclyl substituted with 1 substituent selected from the group consisting of -OH, -$OC_{1-3}$alkyl and -$OC_{1-3}$haloalkyl; and n is 1.

In certain embodiments of Formula (I), $X^1$ is N; $X^2$, $X^4$, and $X^5$ are each CH; $X^3$ is $CR^5$; $R^1$ is unsubstituted $C_{1-3}$alkyl; $R^2$ is -$CH_3$; $R^3$ is -($C_{1-3}$alkylene)$_m$-$OR^{3a}$ wherein m is 1; $R^{4a}$ a and $R^{4b}$ are each hydrogen; $R^5$ is -$OR^{5a}$ wherein $R^{5a}$ is $C_{3-6}$carbocyclyl substituted with 1 substituent selected from the group consisting of -OH, -$OC_{1-3}$alkyl and -$OC_{1-3}$haloalkyl; and n is 1.

In other embodiments of Formula (I), (I-a), or (I-b), wherein $X^1$ is N, $X^2$, $X^4$, and $X^5$ are each CH, and $X^3$ is $CR^5$, provided is a compound of Formula (II), (II-a), or (II-b):

(II)

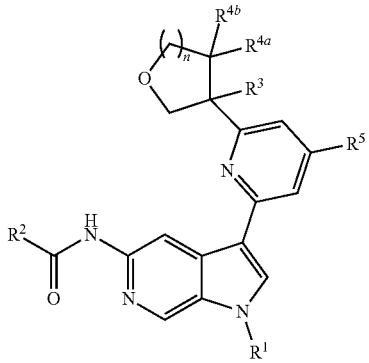

(II-a)

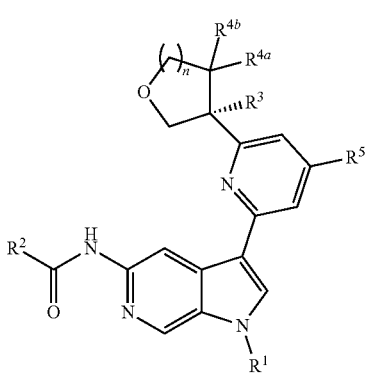

(II-b)

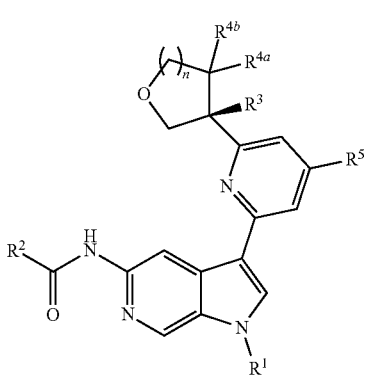

or a pharmaceutically acceptable salt thereof. In certain embodiments, the compound is of Formula (II-a), or a pharmaceutically acceptable salt thereof.

In certain embodiments of Formula (II-a), $R^1$ is unsubstituted or substituted $C_{1-3}$alkyl, unsubstituted or substituted $C_{3-4}$carbocyclyl, or unsubstituted or substituted 4- to 5-membered heterocyclyl, wherein each instance of substituted is independent substitution with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl. In certain embodiments of Formula (II-a), $R^1$ is -$CH_3$, -$CH_2F$, -$CHF_2$, -$CF_3$,

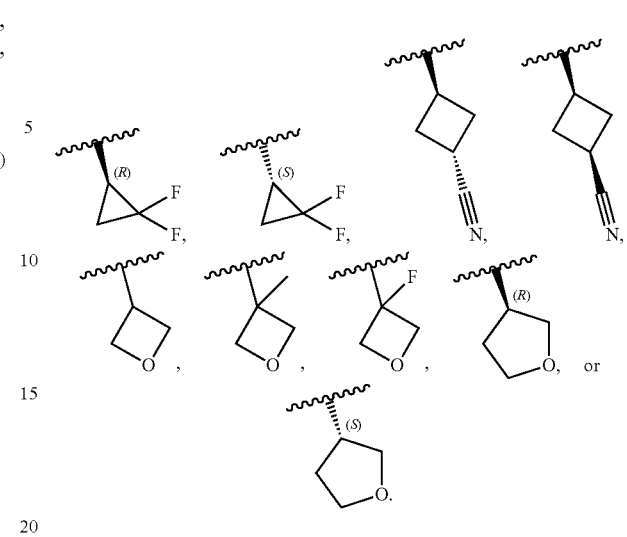

In certain embodiments of Formula (II-a), $R^2$ is -$NH_2$, -$NHR^{2a}$, unsubstituted or substituted $C_{1-3}$alkyl, and $R^{2a}$ is unsubstituted or substituted $C_{1-3}$alkyl, wherein each instance of substituted is independent substitution with 1, 2, or 3 substituents selected from the group consisting of halogen, -CN, -OH, -$OC_{1-3}$alkyl, and -$OC_{1-3}$haloalkyl. In certain embodiments of Formula (II-a), $R^2$ is -$NH_2$, - $NHCH_3$, -$OCH_3$, -$CH_3$, or -$CH_2OH$.

In certain embodiments of Formula (II-a), $R^3$ is -($C_{1-3}$alkylene)$_m$-$OR^{3a}$, -($C_{1-3}$alkylene)$_m$- $N(R^{3a})_2$, $C_{1-3}$alkyl, or $C_{1-3}$haloalkyl, wherein each instance of $R^{3a}$ is independently hydrogen, $C_{1-3}$alkyl, or $C_{1-3}$haloalkyl; and m is 0 or 1. In certain embodiments of Formula (II-a), $R^3$ is -OH, -$OCH_3$, - CH(OH)$CH_3$, -$CH_2OH$, -$CH_2NH_2$, -$CH_3$, or -$CH_2CH_3$.

In certain embodiments of Formula (II-a), n is 1.

In certain embodiments of Formula (II-a), each instance of $R^{4a}$ and $R^{4b}$ is hydrogen.

In certain embodiments of Formula (II-a), $R^5$ is hydrogen, -CN, -$OR^{5a}$, -$NHR^{5a}$, or unsubstituted or substituted $C_{1-6}$alkyl, and $R^{5a}$ is unsubstituted or substituted $C_{1-6}$alkyl, unsubstituted or substituted $C_{3-6}$carbocyclyl, unsubstituted or substituted $C_{3-6}$carbocyclyl$C_{1-3}$alkyl, unsubstituted or substituted 4- to 6-membered heterocyclyl, or unsubstituted or substituted 4- to 6-membered heterocyclyl$C_{1-3}$alkyl, wherein each instance of substituted is independent substitution with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl. In certain embodiments of Formula (II-a), $R^5$ is hydrogen, -CN, -$CH_3$, - $CH_2F$, -$CHF_2$, -$CF_3$, -$CH_2OCH_3$, -$OCH_3$, -$OCH_2CH_3$, -$OCH(CH_3)_2$, -$OCH_2CH_2OH$, -$OCH_2CH_2OCH_3$,- $OCHF_2$, -$OCH_2CN$,

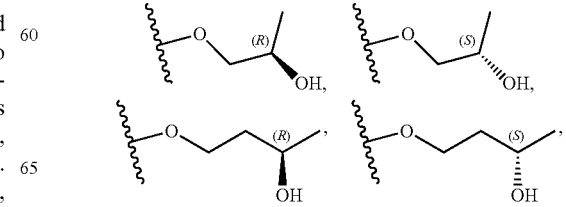

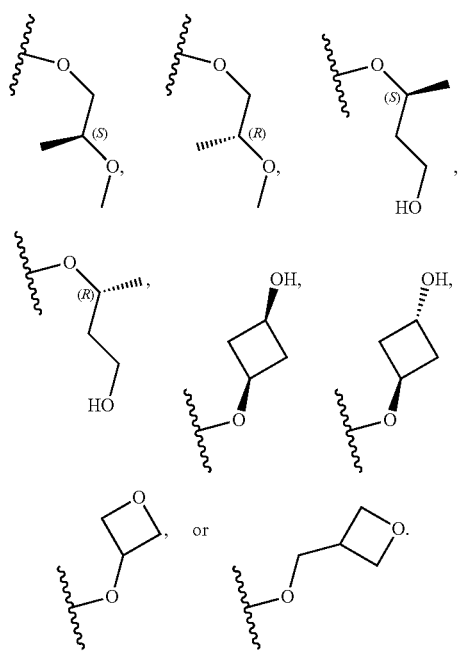

In certain embodiments of Formula (II-a), $R^1$ is unsubstituted or substituted $C_{1-3}$alkyl, unsubstituted or substituted $C_{3-4}$carbocyclyl, or unsubstituted or substituted 4- to 5-membered heterocyclyl; $R^2$ is $-NH_2$, $-NHR^{2a}$, unsubstituted or substituted $C_{1-3}$alkyl, and $R^{2a}$ is unsubstituted or substituted $C_{1-3}$alkyl; $R^3$ is $-(C_{1-3}$alkylene$)_m$-$OR^{3a}$, $-(C_{1-3}$alkylene$)_m$-$N(R^{3a})_2$, $C_{1-3}$alkyl, or $C_{1-3}$haloalkyl, wherein each instance of $R^{3a}$ is independently hydrogen, $C_{1-3}$alkyl, or $C_{1-3}$haloalkyl; m is 0 or 1; n is 1; each instance of $R^{4a}$ and $R^{4b}$ is hydrogen; $R^5$ is hydrogen, -CN, $-OR^{5a}$, $-NHR^{5a}$, or unsubstituted or substituted $C_{1-6}$alkyl; $R^{5a}$ is unsubstituted or substituted $C_{1-6}$alkyl, unsubstituted or substituted $C_{3-6}$carbocyclyl, unsubstituted or substituted $C_{3-6}$carbocyclyl$C_{1-3}$alkyl, unsubstituted or substituted 4- to 6-membered heterocyclyl, or unsubstituted or substituted 4- to 6-membered heterocyclyl$C_{1-3}$alkyl; and wherein each instance of substituted is independent substitution with 1, 2, or 3 substituents selected from the group consisting of halogen, -CN, -OH, $C_{1-3}$alkyl, $C_{1-3}$haloalkyl, $-OC_{1-3}$alkyl, and $-OC_{1-3}$haloalkyl.

In certain embodiments of Formula (II-a), $R^1$ is $-CH_3$, $-CH_2F$, $-CHF_2$, $-CF_3$,

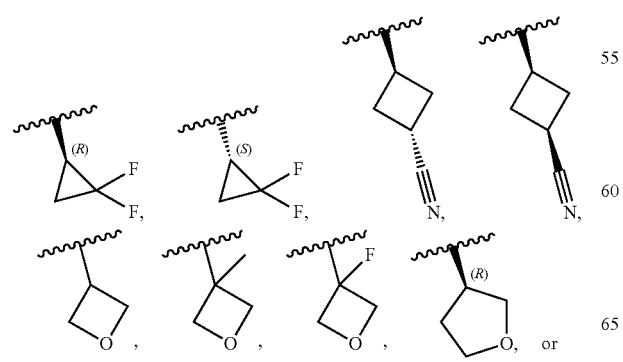

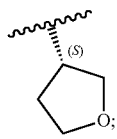

$R^2$ $-NH_2$, $-NHCH_3$, $-OCH_3$, $-CH_3$, or $-CH_2OH$; $R^3$ is -OH, $-OCH_3$, $-CH(OH)CH_3$, $-CH_2OH$, $-CH_2NH_2$, $-CH_3$, or $-CH_2CH_3$; each instance of $R^{4a}$ and $R^{4b}$ is hydrogen; $R^5$ is hydrogen, -CN, $-CH_3$, $-CH_2F$, $-CHF_2$, $-CF_3$, $-CH_2OCH_3$, $-OCH_3$, $-OCH_2CH_3$, $-OCH(CH_3)_2$, $-OCH_2CH_2OH$, $-OCH_2CH_2OCH_3$, $-OCHF_2$, $-OCH_2CN$, and n is 1.

In yet other embodiments of Formula (II), (II-a), or (II-b), wherein $R^3$ is $-(C_{1-3}$alkylene$)_m$- $OR^{3a}$, provided is a compound of Formula (III), (III-a), or (III-b):

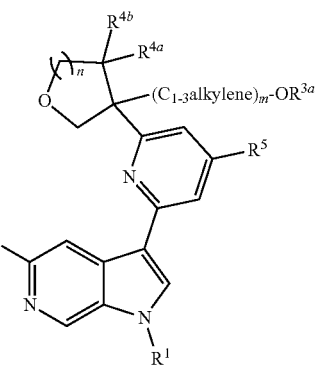

(III)

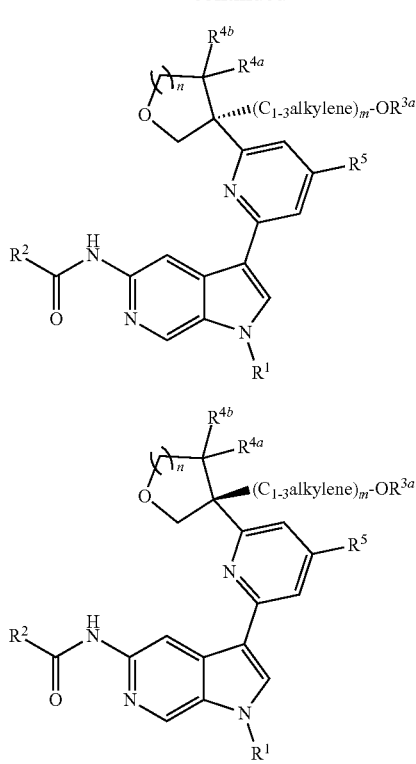

or a pharmaceutically acceptable salt thereof. In certain embodiments, the compound is of Formula (III-a), or a pharmaceutically acceptable salt thereof.

In certain embodiments of Formula (III-a), $R^1$ is unsubstituted or substituted $C_{1-3}$alkyl, unsubstituted or substituted $C_{3-4}$carbocyclyl, or unsubstituted or substituted 4- to 5-membered heterocyclyl, wherein each instance of substituted is independent substitution with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl. In certain embodiments of Formula (III-a), $R^1$ is -$CH_3$, -$CH_2F$, -$CHF_2$, -$CF_3$, In certain embodiments of Formula (III-a), $R^2$ is -$NH_2$, -$NHR^{2a}$, unsubstituted or substituted $C_{1-3}$alkyl, and $R^{2a}$ is unsubstituted or substituted $C_{1-3}$alkyl, wherein each instance of substituted is independent substitution with 1, 2, or 3 substituents selected from the group consisting of halogen, -CN, -OH, -$OC_{1-3}$alkyl, and -$OC_{1-3}$haloalkyl. In certain embodiments of Formula (II-a), $R^2$ is -$NH_2$, -$NHCH_3$, -$OCH_3$, -$CH_3$, or -$CH_2OH$.

In certain embodiments of Formula (III-a), $R^{3a}$ is hydrogen. In certain embodiments of Formula (III-a), $R^{3a}$ is hydrogen and m is 0. In certain embodiments of Formula (III-a), $R^{3a}$ is hydrogen and m is 1. In certain embodiments of Formula (III-a), $R^{3a}$ is $C_{1-3}$alkyl. In certain embodiments of Formula (III-a), $R^{3a}$ is $C_{1-3}$alkyl and m is 0. In certain embodiments of Formula (III-a), $R^{3a}$ is $C_{1-3}$alkyl and m is 1. In certain embodiments of Formula (III-a), $R^{3a}$ is $C_{1-3}$haloalkyl. In certain embodiments of Formula (III-a), $R^{3a}$ is $C_{1-3}$haloalkyl and m is 0. In certain embodiments of Formula (III-a), $R^{3a}$ is $C_{1-3}$haloalkyl and m is 1. In certain embodiments of Formula (III-a), $R^{3a}$ is hydrogen or -$CH_3$.

In certain embodiments of Formula (III-a), n is 1.

In certain embodiments of Formula (III-a), each instance of $R^{4a}$ and $R^{4b}$ is hydrogen.

In certain embodiments of Formula (III-a), $R^5$ is hydrogen, -CN, -$OR^{5a}$, -$NHR^{5a}$, or unsubstituted or substituted $C_{1-6}$alkyl, and $R^{5a}$ is unsubstituted or substituted $C_{1-6}$alkyl, unsubstituted or substituted $C_{3-6}$carbocyclyl, unsubstituted or substituted $C_{3-6}$carbocyclyl$C_{1-3}$alkyl, unsubstituted or substituted 4- to 6-membered heterocyclyl, or unsubstituted or substituted 4- to 6-membered heterocyclyl$C_{1-3}$alkyl, wherein each instance of substituted is independent substitution with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl. In certain embodiments of Formula (III-a), $R^5$ is hydrogen, -CN, -$CH_3$, -$CH_2F$, -$CHF_2$, -$CF_3$, -$CH_2OCH_3$, -$OCH_3$, -$OCH_2CH_3$, -$OCH(CH_3)_2$, -$OCH_2CH_2OH$, -$OCH_2CH_2OCH_3$,

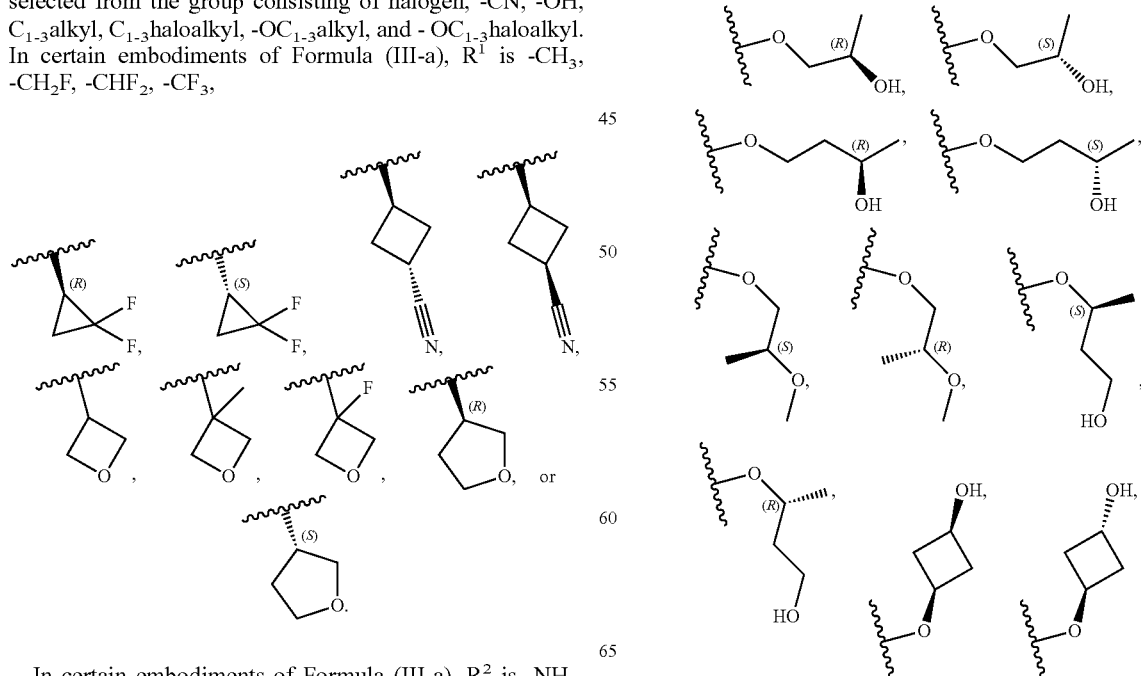

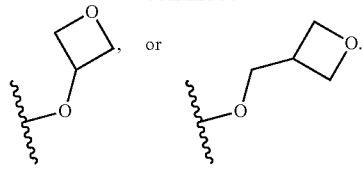 or

-OCHF$_2$, -OCH$_2$CN,

In certain embodiments of Formula (III-a), R$^1$ is unsubstituted or substituted C$_{1-3}$alkyl, unsubstituted or substituted C$_{3-4}$carbocyclyl, or unsubstituted or substituted 4- to 5-membered heterocyclyl; R$^2$ is -NH$_2$, -NHR$^{2a}$, unsubstituted or substituted C$_{1-3}$alkyl, and R$^{2a}$ is unsubstituted or substituted C$_{1-3}$alkyl; R$^{3a}$ is independently hydrogen, C$_{1-3}$alkyl, or C$_{1-3}$haloalkyl; m is 0 or 1; n is 1; each instance of R$^{4a}$ and R$^{4b}$ is hydrogen; R$^5$ is hydrogen, -CN, -OR$^{5a}$, -NHR$^{5a}$, or unsubstituted or substituted C$_{1-6}$alkyl; R$^{5a}$ is unsubstituted or substituted C$_{1-6}$alkyl, unsubstituted or substituted C$_{3-6}$carbocyclyl, unsubstituted or substituted C$_{3-6}$carbocyclylC$_{1-3}$alkyl, unsubstituted or substituted 4- to 6-membered heterocyclyl, or unsubstituted or substituted 4- to 6-membered heterocyclylC$_{1-3}$alkyl; and wherein each instance of substituted is independent substitution with 1, 2, or 3 substituents selected from the group consisting of halogen, -CN, -OH, C$_{1-3}$alkyl, C$_{1-3}$haloalkyl, -OC$_{1-3}$alkyl, and -OC$_{1-3}$haloalkyl.

In certain embodiments of Formula (III-a), R$^1$ is -CH$_3$, -CH$_2$F, -CHF$_2$, -CF$_3$,

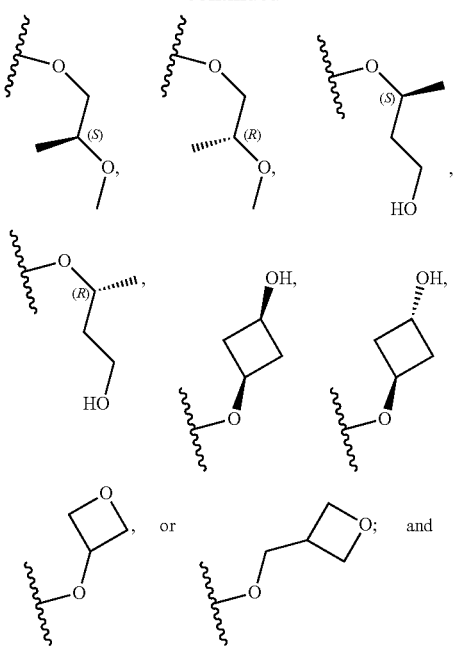

R$^2$ -NH$_2$, -NHCH$_3$, -OCH$_3$, -CH$_3$, or -CH$_2$OH; R$^{3a}$ is hydrogen or -CH$_3$; m is 0 or 1; each instance of R$^{4a}$ and R$^{4b}$ is hydrogen; R$^5$ is hydrogen, -CN, -CH$_3$, -CH$_2$F, -CHF$_2$, -CF$_3$, -CH$_2$OCH$_3$, -OCH$_3$, -OCH$_2$CH$_3$, -OCH(CH$_3$)$_2$, -OCH$_2$CH$_2$OH, -OCH$_2$CH$_2$OCH$_3$, -OCHF$_2$, -OCH$_2$CN,

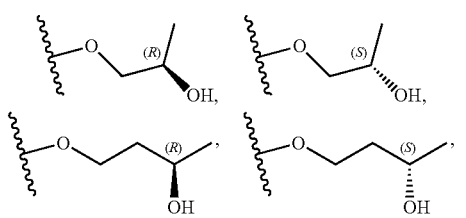

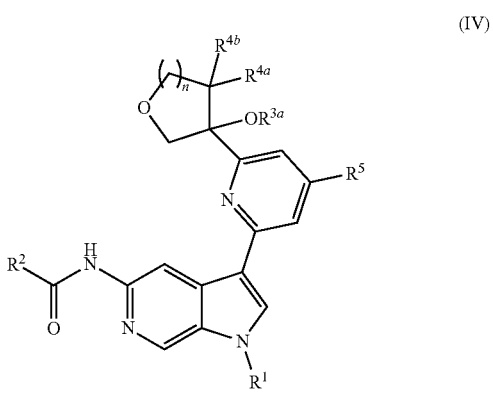

n is 1.

In other embodiments of Formula (II), (II-a), or (II-b), wherein R$^3$ is -COR$^{3a}$ (wherein m is 0), provided is a compound of Formula (IV), (IV-a), or (IV-b):

-continued

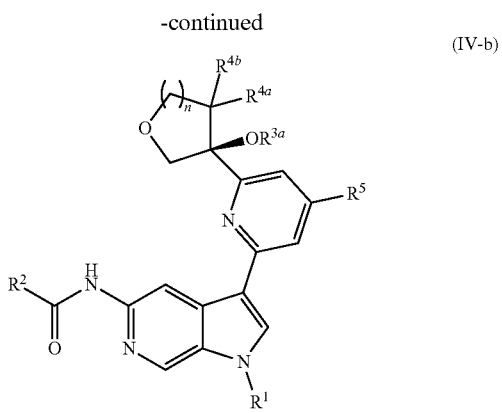
(IV-b)

or a pharmaceutically acceptable salt thereof. In certain embodiments, the compound is of Formula (IV-a), or a pharmaceutically acceptable salt thereof.

In certain embodiments of Formula (IV-a), $R^1$ is unsubstituted or substituted $C_{1-3}$alkyl, unsubstituted or substituted $C_{3-4}$carbocyclyl, or unsubstituted or substituted 4- to 5-membered heterocyclyl, wherein each instance of substituted is independent substitution with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl. In certain embodiments of Formula (IV-a), $R^1$ is -$CH_3$, -$CH_2F$, -$CHF_2$, -$CF_3$,

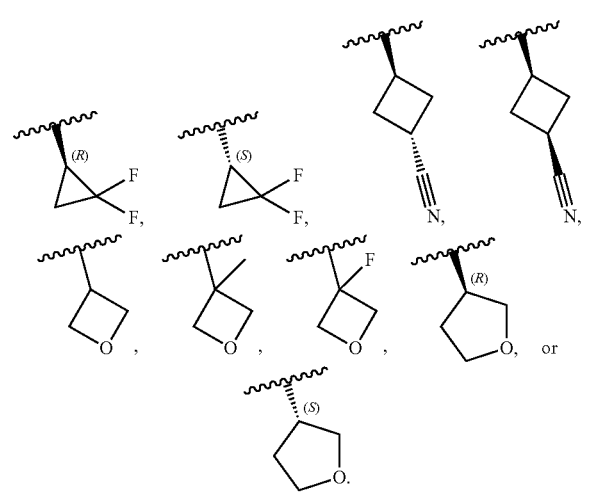

In certain embodiments of Formula (IV-a), $R^2$ is -$NH_2$, -$NHR^{2a}$, unsubstituted or substituted $C_{1-3}$alkyl, and $R^{ea}$ is unsubstituted or substituted $C_{1-3}$alkyl, wherein each instance of substituted is independent substitution with 1, 2, or 3 substituents selected from the group consisting of halogen, -CN, -OH, -$OC_{1-3}$alkyl, and -$OC_{1-3}$haloalkyl. In certain embodiments of Formula (IV-a), $R^2$ is -$NH_2$, - $NHCH_3$, -$OCH_3$, -$CH_3$, or -$CH_2OH$.

In certain embodiments of Formula (IV-a), $R^{3a}$ is hydrogen. In certain embodiments of Formula (IV-a), $R^{3a}$ is $C_{1-3}$alkyl. In certain embodiments of Formula (IV-a), $R^{3a}$ is $C_{1-3}$haloalkyl. In certain embodiments of Formula (IV-a), $R^{3a}$ is hydrogen or -$CH_3$.

In certain embodiments of Formula (IV-a), n is 1.

In certain embodiments of Formula (IV-a), each instance of $R^{4a}$ and $R^{4b}$ is hydrogen.

In certain embodiments of Formula (IV-a), $R^5$ is hydrogen, -CN, -$OR^{5a}$, -$NHR^{5a}$, or unsubstituted or substituted $C_{1-6}$alkyl, and $R^{5a}$ is unsubstituted or substituted $C_{1-6}$alkyl, unsubstituted or substituted $C_{3-6}$carbocyclyl, unsubstituted or substituted $C_{3-6}$carbocyclyl$C_{1-3}$alkyl, unsubstituted or substituted 4- to 6-membered heterocyclyl, or unsubstituted or substituted 4- to 6-membered heterocyclyl$C_{1-3}$alkyl, wherein each instance of substituted is independent substitution with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl. In certain embodiments of Formula (IV-a), $R^5$ is hydrogen, -CN, -$CH_3$, - $CH_2F$, -$CHF_2$, -$CF_3$, -$CH_2OCH_3$, -$OCH_3$, -$OCH_2CH_3$, -$OCH(CH_3)_2$, -$OCH_2CH_2OH$, -$OCH_2CH_2OCH_3$,

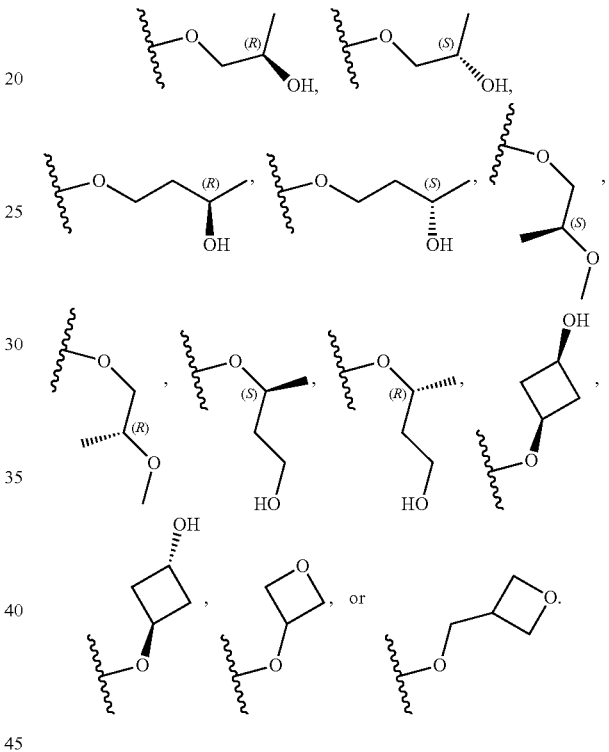

-$OCHF_2$, -$OCH_2CN$,

In certain embodiments of Formula (IV-a), $R^1$ is unsubstituted or substituted $C_{1-3}$alkyl, unsubstituted or substituted $C_{3-4}$carbocyclyl, or unsubstituted or substituted 4- to 5-membered heterocyclyl; $R^2$ is -$NH_2$, -$NHR^{2a}$, unsubstituted or substituted $C_{1-3}$alkyl, and $R^{2a}$ is unsubstituted or substituted $C_{1-3}$alkyl; $R^{3a}$ is independently hydrogen, $C_{1-3}$alkyl, or $C_{1-3}$haloalkyl; n is 1; each instance of $R^{4a}$ and $R^{4b}$ is hydrogen; $R^5$ is hydrogen, -CN, -$OR^{5a}$, -$NHR^{5a}$, or unsubstituted or substituted $C_{1-6}$alkyl; $R^{5a}$ is unsubstituted or substituted $C_{1-6}$alkyl, unsubstituted or substituted $C_{3-6}$carbocyclyl, unsubstituted or substituted $C_{3-6}$carbocyclyl$C_{1-3}$alkyl, unsubstituted or substituted 4- to 6-membered heterocyclyl, or unsubstituted or substituted 4- to 6-membered heterocyclyl$C_{1-3}$alkyl; and wherein each instance of substituted is independent substitution with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl.

In certain embodiments of Formula (IV-a), $R^1$ is -$CH_3$, -$CH_2F$, -$CHF_2$, -$CF_3$,

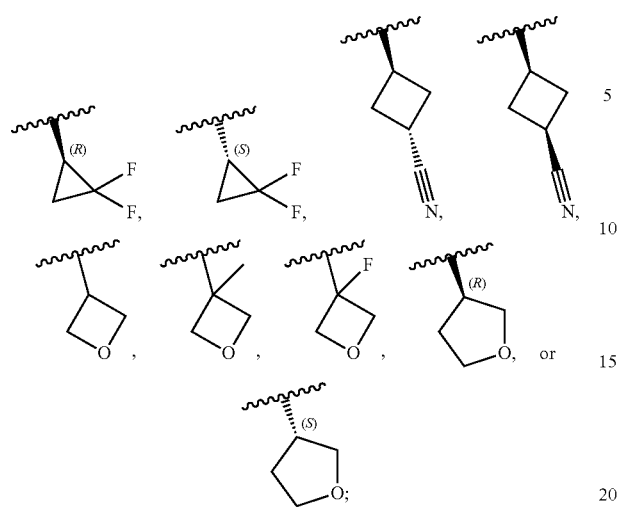
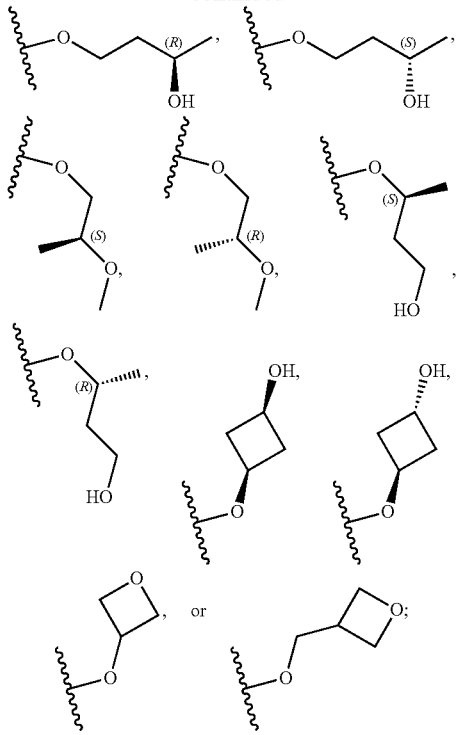
R² -NH₂, -NHCH₃, -OCH₃, -CH₃, or -CH₂OH; R³ᵃ is hydrogen or -CH₃; each instance of R⁴ᵃ and R⁴ᵇ is hydrogen; R⁵ is hydrogen, -CN, - CH₃, -CH₂F, -CHF₂, -CF₃, -CH₂OCH₃, -OCH₃, -OCH₂CH₃, -OCH(CH₃)₂, -OCH₂CH₂OH, - OCH₂CH₂OCH₃, -OCHF₂, -OCH₂CN,
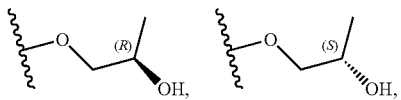
and n is 1.
Exemplary compounds of Formula (I) include, but are not limited to, the compounds listed in Tables A1, A2, and B1, and pharmaceutically acceptable salts thereof:

TABLE A1

Exemplary compounds wherein R[1] is not hydrogen

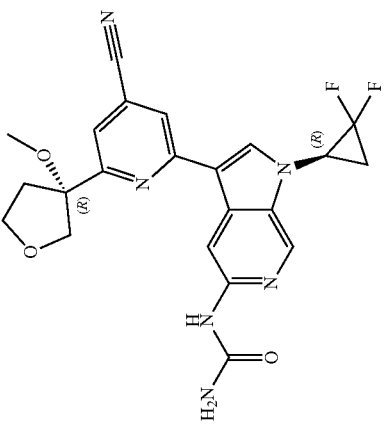

(1)
(R)-1-(3-(6-(3-methoxytetrahydrofuran-3-yl)pyridin-2-yl)-1-methyl-1H-pyrrolo[2,3-c]pyridin-5-yl)urea

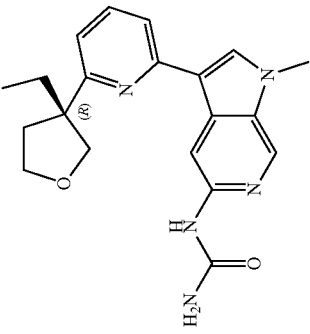

(3.3)
(R)-1-(3-(6-(3-ethyltetrahydrofuran-3-yl)pyridin-2-yl)-1-methyl-1H-pyrrolo[2,3-c]pyridin-5-yl)urea

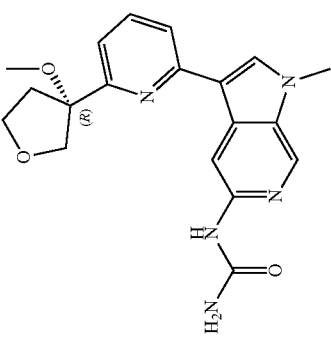

(12a.3)
1-(3-(4-cyano-6-((R)-3-methoxytetrahydrofuran-3-yl)pyridin-2-yl)-1-((R)-2,2-difluorocyclopropyl)-1H-pyrrolo[2,3-c]pyridin-5-yl)urea

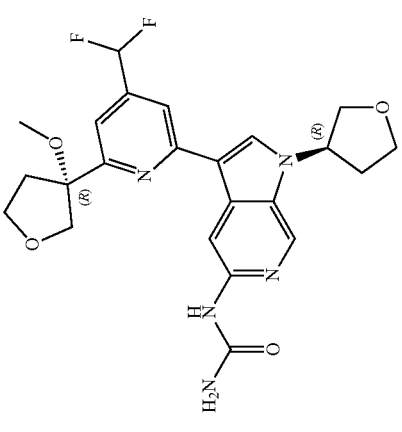

(1a)
(S)-1-(3-(6-(3-methoxytetrahydrofuran-3-yl)pyridin-2-yl)-1-methyl-1H-pyrrolo[2,3-c]pyridin-5-yl)urea

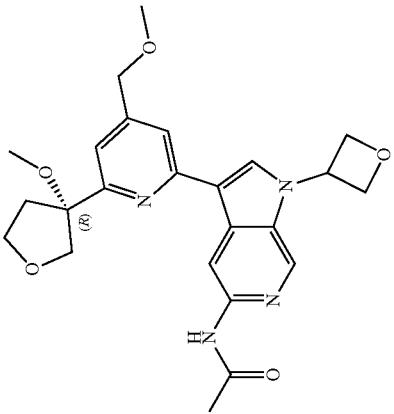

(4)
(R)-N-(3-(4-(methoxymethyl)-6-(3-methoxytetrahydrofuran-3-yl)pyridin-2-yl)-1-(oxetan-3-yl)-1H-pyrrolo[2,3-c]pyridin-5-yl)acetamide

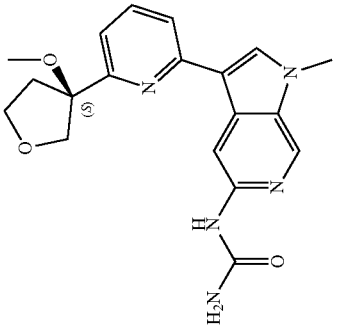

(12b.2)
1-(3-(4-(difluoromethyl)-6-((R)-3-methoxytetrahydrofuran-3-yl)pyridin-2-yl)-1-((R)-tetrahydrofuran-3-yl)-1H-pyrrolo[2,3-c]pyridin-5-yl)urea TABLE A1-continued Exemplary compounds wherein R¹ is not hydrogen (12b.3)
1-(3-(4-(difluoromethyl)-6-((R)-3-methoxytetrahydrofuran-3-yl)pyridin-2-yl)-1-((S)-tetrahydrofuran-3-yl)-1H-pyrrolo[2,3-c]pyridin-5-yl)urea (12b.4)
(R)-1-(3-(4-(difluoromethyl)-6-(3-methoxytetrahydrofuran-3-yl)pyridin-2-yl)-1-(oxetan-3-yl)-1H-pyrrolo[2,3-c]pyridin-5-yl)urea (4.2)
(S)-N-(3-(4-(difluoromethyl)-6-(3-methoxytetrahydrofuran-3-yl)pyridin-2-yl)-1-(oxetan-3-yl)-1H-pyrrolo[2,3-c]pyridin-5-yl)acetamide (4.3)
(R)-N-(3-(4-(difluoromethyl)-6-(3-methoxytetrahydrofuran-3-yl)pyridin-2-yl)-1-(oxetan-3-yl)-1H-pyrrolo[2,3-c]pyridin-5-yl)acetamide (1.2)
1-(1-((R)-2,2-difluorocyclopropyl)-3-(6-((R)-3-methoxytetrahydrofuran-3-yl)pyridin-2-yl)-1H-pyrrolo[2,3-c]pyridin-5-yl)urea (1.3)
1-(1-((S)-2,2-difluorocyclopropyl)-3-(6-((R)-3-methoxytetrahydrofuran-3-yl)pyridin-2-yl)-1H-pyrrolo[2,3-c]pyridin-5-yl)urea TABLE A1-continued Exemplary compounds wherein R¹ is not hydrogen

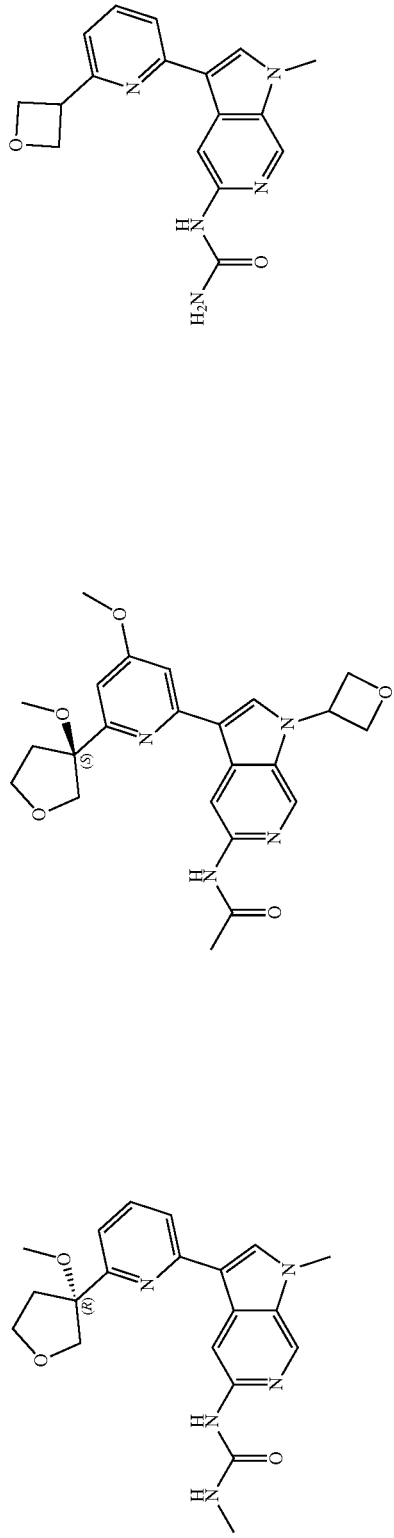

(1a.2) (R)-1-(3-(6-(3-methoxytetrahydrofuran-3-yl)pyridin-2-yl)-1-methyl-1H-pyrrolo[2,3-c]pyridin-5-yl)-3-methylurea (4.4) (S)-N-(3-(4-methoxy-6-(3-methoxytetrahydrofuran-3-yl)pyridin-2-yl)-1-(oxetan-3-yl)-1H-pyrrolo[2,3-c]pyridin-5-yl)acetamide

(13) 1-(1-methyl-3-(6-(oxetan-3-yl)pyridin-2-yl)-1H-pyrrolo[2,3-c]pyridin-5-yl)urea

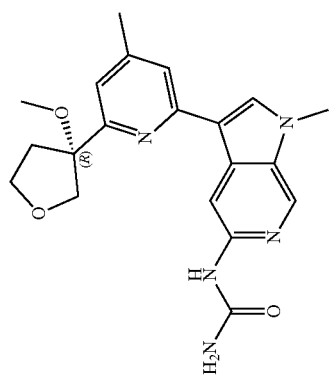

(1b.2) (R)-1-(3-(6-(3-methoxytetrahydrofuran-3-yl)-4-methylpyridin-2-yl)-1-methyl-1H-pyrrolo[2,3-c]pyridin-5-yl)urea (5) (R)-N-(3-(4-methoxy-6-(3-methoxytetrahydrofuran-3-yl)pyridin-2-yl)-1-(oxetan-3-yl)-1H-pyrrolo[2,3-c]pyridin-5-yl)acetamide

(14) 1-(3-(6-(3-hydroxyoxetan-3-yl)pyridin-2-yl)-1-methyl-1H-pyrrolo[2,3-c]pyridin-5-yl)urea TABLE A1-continued Exemplary compounds wherein R¹ is not hydrogen

| (1b.3) (S)-1-(3-(6-(3-methoxytetrahydrofuran-3-yl)pyridin-2-yl)-1-methyl-1H-pyrrolo[2,3-c]pyridin-5-yl)-4-methylpyridin-2-yl)-1-methyl-1H-pyrrolo[2,3-c]pyridin-5-yl)urea | (5.2) N-(3-(4-methoxy-6-((R)-3-methoxytetrahydrofuran-3-yl)pyridin-2-yl)-1-((R)-tetrahydrofuran-3-yl)-1H-pyrrolo[2,3-c]pyridin-5-yl)acetamide | (14.2) N-(3-(6-(3-hydroxyoxetan-3-yl)-4-methoxypyridin-2-yl)-1-methyl-1H-pyrrolo[2,3-c]pyridin-5-yl)acetamide |
| --- | --- | --- |
| (1b.4) 1-(3-(6-(3-methoxyoxetan-3-yl)pyridin-2-yl)-1-methyl-1H-pyrrolo[2,3-c]pyridin-5-yl)urea | (5.3) N-(3-(4-methoxy-6-((S)-3-methoxytetrahydrofuran-3-yl)pyridin-2-yl)-1-((R)-tetrahydrofuran-3-yl)-1H-pyrrolo[2,3-c]pyridin-5-yl)acetamide | (14.3) N-(3-(6-(3-hydroxyoxetan-3-yl)-4-isopropoxypyridin-2-yl)-1-methyl-1H-pyrrolo[2,3-c]pyridin-5-yl)acetamide |

TABLE A1-continued

Exemplary compounds wherein R¹ is not hydrogen (2) (R)-N-(3-(4-(methoxymethyl)-6-(3-methoxytetrahydrofuran-3-yl)pyridin-2-yl)-1-methyl-1H-pyrrolo[2,3-c]pyridin-5-yl)acetamide (6) (R)-N-(3-(6-(3-methoxytetrahydrofuran-3-yl)-4-(oxetan-3-ylmethoxy)pyridin-2-yl)-1-methyl-1H-pyrrolo[2,3-c]pyridin-5-yl)acetamide (14.4) N-(3-(4-(((S)-4-hydroxybutan-2-yl)oxy)-6-((R)-3-methoxytetrahydrofuran-3-yl)pyridin-2-yl)-1-methyl-1H-pyrrolo[2,3-c]pyridin-5-yl)acetamide (2.2) (R)-N-(3-(6-(3-methoxytetrahydrofuran-3-yl)-4-methylpyridin-2-yl)-1-methyl-1H-pyrrolo[2,3-c]pyridin-5-yl)acetamide (6.2) (S)-N-(3-(6-(3-methoxytetrahydrofuran-3-yl)-4-(oxetan-3-ylmethoxy)pyridin-2-yl)-1-methyl-1H-pyrrolo[2,3-c]pyridin-5-yl)acetamide (14.5) N-(3-(4-((S)-2-hydroxypropoxy)-6-((R)-3-methoxytetrahydrofuran-3-yl)pyridin-2-yl)-1-methyl-1H-pyrrolo[2,3-c]pyridin-5-yl)acetamide TABLE A1-continued Exemplary compounds wherein R¹ is not hydrogen

| | | |
|---|---|---|
| (2.3a) (R)-N-(3-(6-(3-ethyltetrahydrofuran-3-yl)pyridin-2-yl)-1-methyl-1H-pyrrolo[2,3-c]pyridin-5-yl)acetamide | (6.3) (R)-N-(3-(4-(cyanomethoxy)-6-(3-methoxytetrahydrofuran-3-yl)pyridin-2-yl)-1-methyl-1H-pyrrolo[2,3-c]pyridin-5-yl)acetamide | (14.6) N-(3-(4-((R)-2-hydroxypropoxy)-6-((R)-3-methoxytetrahydrofuran-3-yl)pyridin-2-yl)-1-methyl-1H-pyrrolo[2,3-c]pyridin-5-yl)acetamide |
| (2.4) (S)-N-(3-(4-(methoxymethyl)-6-(3-methoxytetrahydrofuran-3-yl)pyridin-2-yl)-1-methyl-1H-pyrrolo[2,3-c]pyridin-5-yl)acetamide | (7) N-(3-(4-((R)-3-hydroxybutoxy)-6-((R)-3-methoxytetrahydrofuran-3-yl)pyridin-2-yl)-1-methyl-1H-pyrrolo[2,3-c]pyridin-5-yl)acetamide | (15) (R)-1-(3-(6-(3-hydroxyoxetan-3-yl)pyridin-2-yl)-1-(tetrahydrofuran-3-yl)-1H-pyrrolo[2,3-c]pyridin-5-yl)urea |

TABLE A1-continued

Exemplary compounds wherein R¹ is not hydrogen

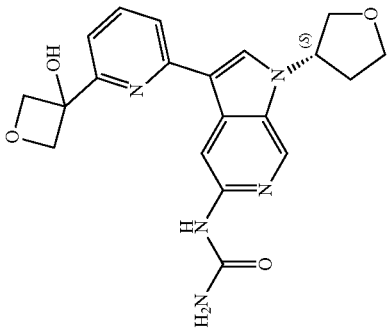

(2.5)
(S)-N-(3-(4-cyano-6-(3-methoxytetrahydrofuran-3-yl)pyridin-2-yl)-1-methyl-1H-pyrrolo[2,3-c]pyridin-5-yl)acetamide

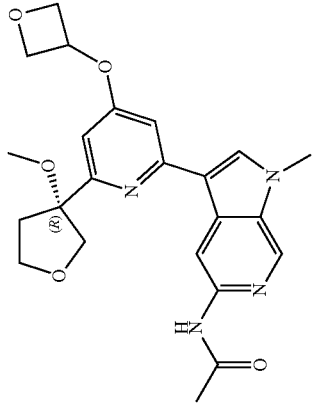

(8)
(R)-N-(3-(6-(3-methoxytetrahydrofuran-3-yl)-4-(oxetan-3-yloxy)pyridin-2-yl)-1-methyl-1H-pyrrolo[2,3-c]pyridin-5-yl)acetamide

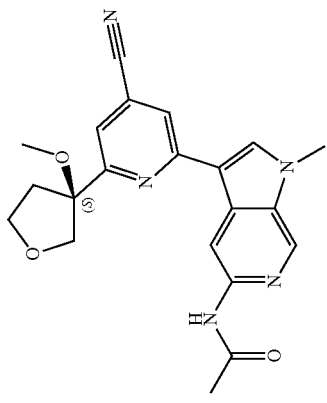

(15.2)
(S)-1-(3-(6-(3-hydroxyoxetan-3-yl)pyridin-2-yl)-1-(tetrahydrofuran-3-yl)-1H-pyrrolo[2,3-c]pyridin-5-yl)urea

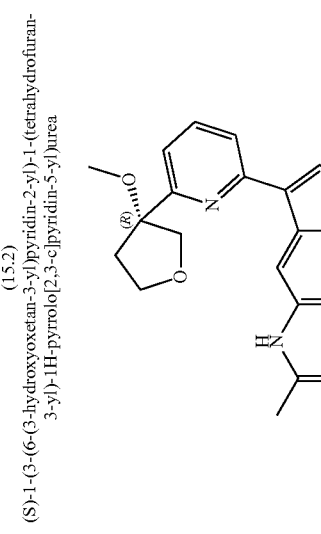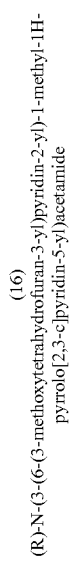

(2.6)
(R)-N-(3-(4-cyano-6-(3-methoxytetrahydrofuran-3-yl)pyridin-2-yl)-1-methyl-1H-pyrrolo[2,3-c]pyridin-5-yl)acetamide

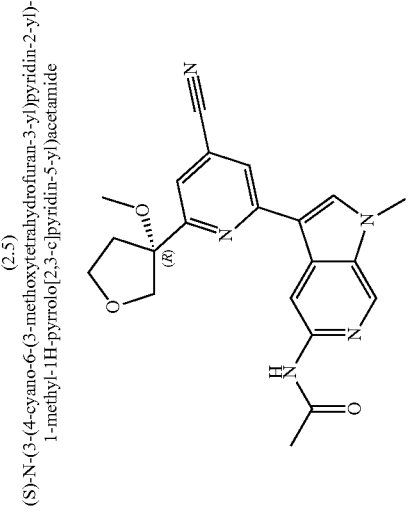

(9)
N-(3-(4-((S)-3-hydroxybutoxy)-6-((R)-3-methoxytetrahydrofuran-3-yl)pyridin-2-yl)-1-methyl-1H-pyrrolo[2,3-c]pyridin-5-yl)acetamide

(16)
(R)-N-(3-(6-(3-methoxytetrahydrofuran-3-yl)pyridin-2-yl)-1-methyl-1H-pyrrolo[2,3-c]pyridin-5-yl)acetamide TABLE A1-continued Exemplary compounds wherein R¹ is not hydrogen

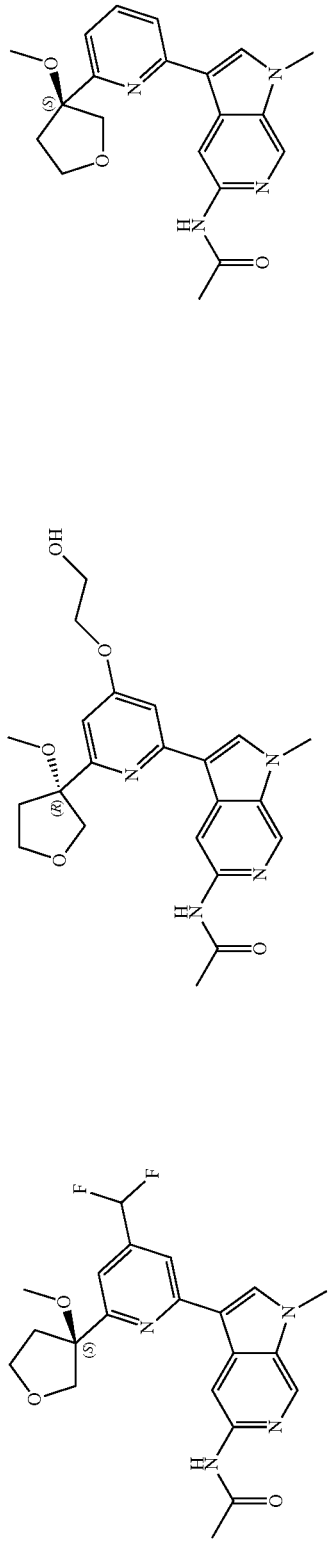

(2.7) (S)-N-(3-(4-(difluoromethyl)-6-(3-methoxytetrahydrofuran-3-yl)pyridin-2-yl)-1-methyl-1H-pyrrolo[2,3-c]pyridin-5-yl)acetamide (2.8) (R)-N-(3-(4-(difluoromethyl)-6-(3-methoxytetrahydrofuran-3-yl)pyridin-2-yl)-1-methyl-1H-pyrrolo[2,3-c]pyridin-5-yl)acetamide

(10) (R)-N-(3-(4-(2-hydroxyethoxy)-6-(3-methoxytetrahydrofuran-3-yl)pyridin-2-yl)-1-methyl-1H-pyrrolo[2,3-c]pyridin-5-yl)acetamide

(11) N-(3-(4-((trans-3-hydroxycyclobutoxy)-6-((R)-3-methoxytetrahydrofuran-3-yl)pyridin-2-yl)-1-methyl-1H-pyrrolo[2,3-c]pyridin-5-yl)acetamide (16a) (S)-N-(3-(6-(3-methoxytetrahydrofuran-3-yl)pyridin-2-yl)-1-methyl-1H-pyrrolo[2,3-c]pyridin-5-yl)acetamide

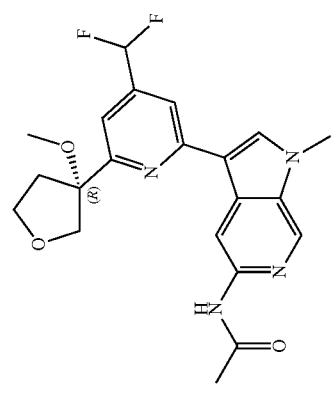

(17) N-(1-((trans)-3-cyanocyclobutyl)-3-(6-((R)-3-methoxytetrahydrofuran-3-yl)pyridin-2-yl)-1H-pyrrolo[2,3-c]pyridin-5-yl)acetamide TABLE A1-continued Exemplary compounds wherein R¹ is not hydrogen

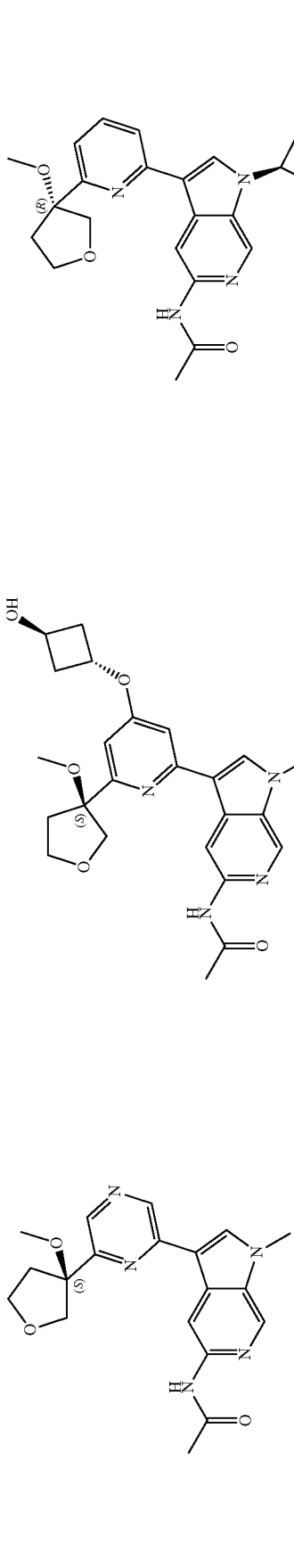

(2.9) (S)-N-(3-(6-(3-methoxytetrahydrofuran-3-yl)pyrazin-2-yl)-1-methyl-1H-pyrrolo[2,3-c]pyridin-5-yl)acetamide

(11a) N-(3-(4-((trans)-3-hydroxycyclobutoxy)-6-((S)-3-methoxytetrahydrofuran-3-yl)pyridin-2-yl)-1-methyl-1H-pyrrolo[2,3-c]pyridin-5-yl)acetamide

(17a) N-(1-((cis)-3-cyanocyclobutyl)-3-(6-((R)-3-methoxytetrahydrofuran-3-yl)pyridin-2-yl)pyrrolo[2,3-c]pyridin-5-yl)acetamide

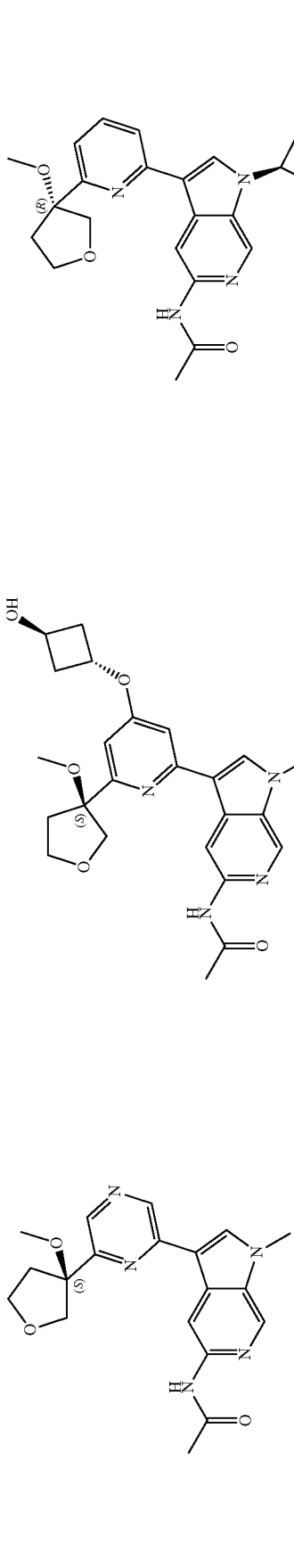

(2.10) (R)-N-(3-(6-(3-methoxytetrahydrofuran-3-yl)pyrazin-2-yl)-1-methyl-1H-pyrrolo[2,3-c]pyridin-5-yl)acetamide

(11.2) N-(3-(4-((cis)-3-hydroxycyclobutoxy)-6-((R)-3-methoxytetrahydrofuran-3-yl)pyridin-2-yl)-1-methyl-1H-pyrrolo[2,3-c]pyridin-5-yl)acetamide

(17.2) N-(1-((trans)-3-cyanocyclobutyl)-3-(4-(difluoromethyl)-6-((R)-3-methoxytetrahydrofuran-3-yl)pyridin-2-yl)-1H-pyrrolo[2,3-c]pyridin-5-yl)acetamide TABLE A1-continued Exemplary compounds wherein R[1] is not hydrogen

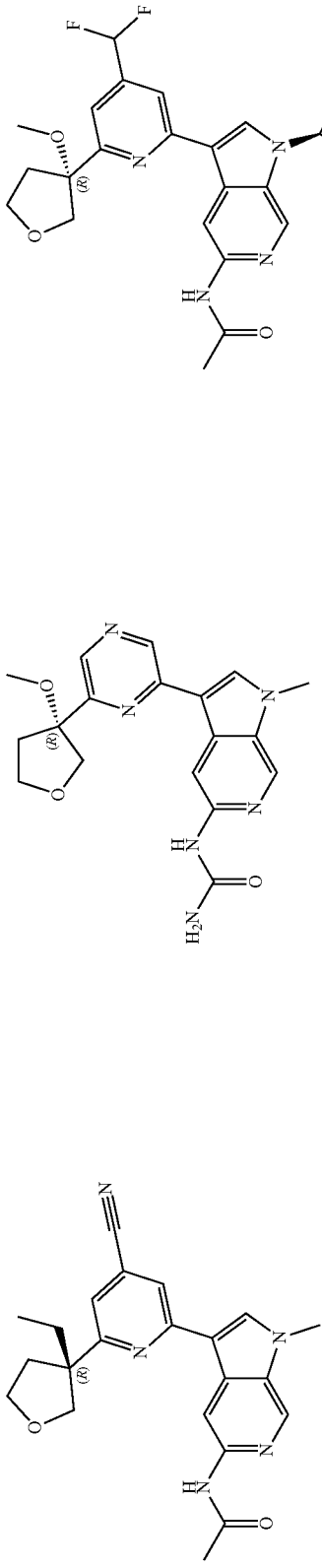

(2.11) (R)-N-(3-(4-cyano-6-(3-ethyltetrahydrofuran-3-yl)pyridin-2-yl)-1-methyl-1H-pyrrolo[2,3-c]pyridin-5-yl)acetamide

(12) (R)-1-(3-(6-(3-methoxytetrahydrofuran-3-yl)pyrazin-2-yl)-1-methyl-1H-pyrrolo[2,3-c]pyridin-5-yl)urea (17.3) N-(1-((cis)-3-cyanocyclobutyl)-3-(4-(difluoromethyl)-6-((R)-3-methoxy-tetrahydrofuran-3-yl)pyridin-2-yl)-1H-pyrrolo[2,3-c]pyridin-5-yl)acetamide

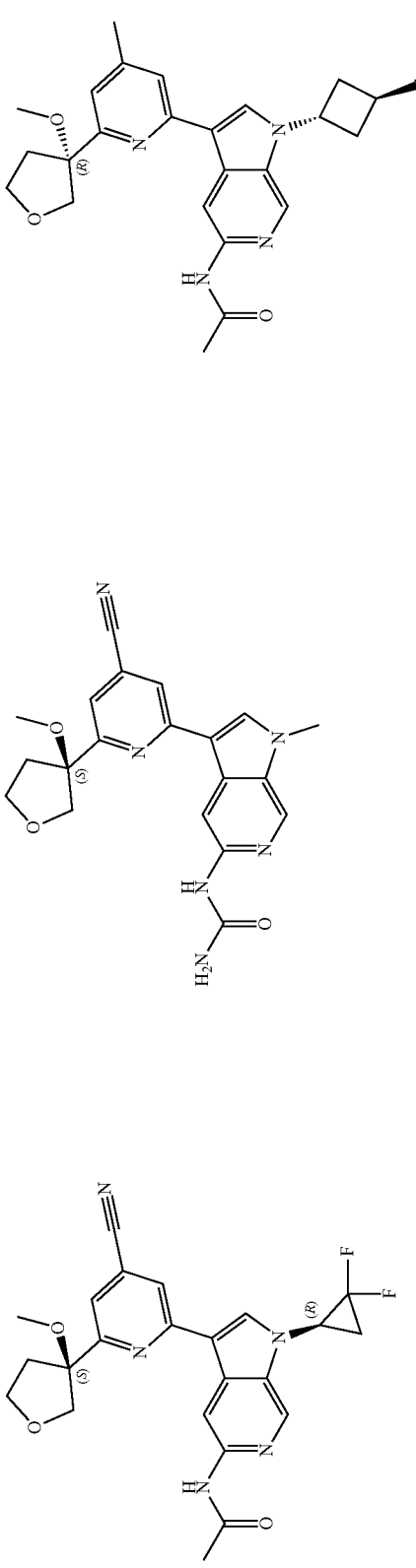

(2a.2) N-(3-(4-cyano-6-((S)-3-methoxytetrahydrofuran-3-yl)pyridin-2-yl)-1-((R)-2,2-difluorocyclopropyl)-1H-pyrrolo[2,3-c]pyridin-5-yl)acetamide (12.2) (S)-1-(3-(4-cyano-6-(3-methoxytetrahydrofuran-3-yl)pyridin-2-yl)-1-methyl-1H-pyrrolo[2,3-c]pyridin-5-yl)urea (17.4) N-(1-((trans)-3-cyanocyclobutyl)-3-(6-((R)-3-methoxytetrahydrofuran-3-yl)-4-methylpyridin-2-yl)-1H-pyrrolo[2,3-c]pyridin-5-yl)acetamide TABLE A1-continued Exemplary compounds wherein R¹ is not hydrogen

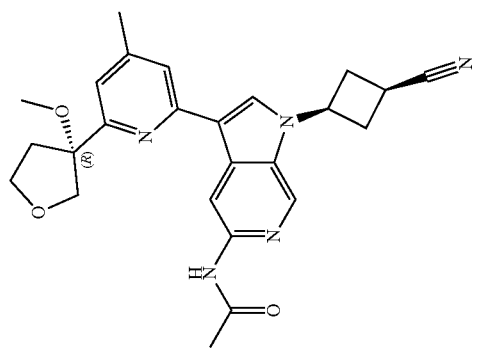

(17.5)
N-(1-((cis)-3-cyanocyclobutyl)-3-(6-((R)-3-methoxytetrahydrofuran-3-yl)-4-methylpyridin-2-yl)-1H-pyrrolo[2,3-c]pyridin-5-yl)acetamide

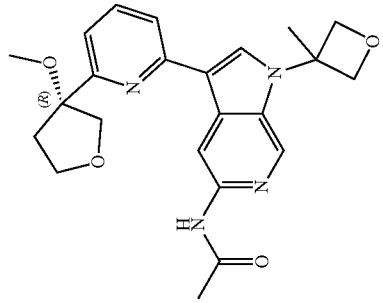

(18)
(R)-N-(3-(6-(3-methoxytetrahydrofuran-3-yl)pyridin-2-yl)-1-(3-methyloxetan-3-yl)-1H-pyrrolo[2,3-c]pyridin-5-yl)acetamide

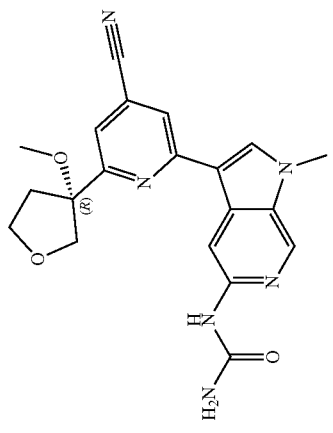

(12.3)
(R)-1-(3-(4-cyano-6-(3-methoxytetrahydrofuran-3-yl)pyridin-2-yl)-1-methyl-1H-pyrrolo[2,3-c]pyridin-5-yl)urea

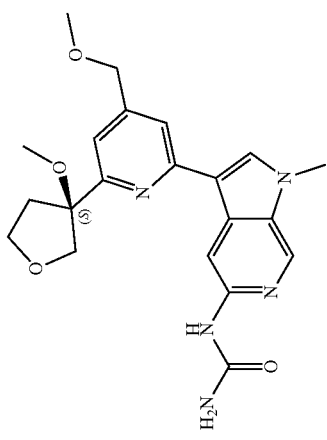

(12.4)
(S)-1-(3-(4-(methoxymethyl)-6-(3-methoxytetrahydrofuran-3-yl)pyridin-2-yl)-1-methyl-1H-pyrrolo[2,3-c]pyridin-5-yl)urea

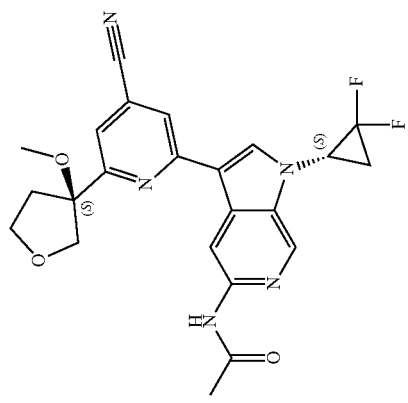

(2a.4)
N-(3-(4-cyano-6-((S)-3-methoxytetrahydrofuran-3-yl)pyridin-2-yl)-1-((S)-2,2-difluorocyclopropyl)-1H-pyrrolo[2,3-c]pyridin-5-yl)acetamide

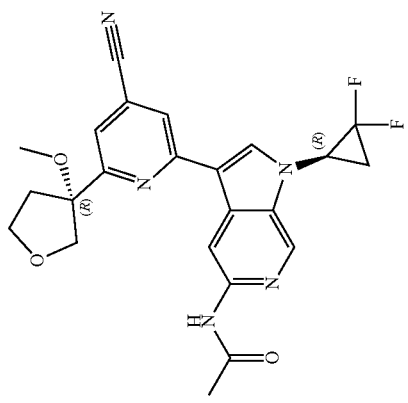

(2a.3)
N-(3-(4-cyano-6-((R)-3-methoxytetrahydrofuran-3-yl)pyridin-2-yl)-1-((R)-2,2-difluorocyclopropyl)-1H-pyrrolo[2,3-c]pyridin-5-yl)acetamide TABLE A1-continued Exemplary compounds wherein R[1] is not hydrogen

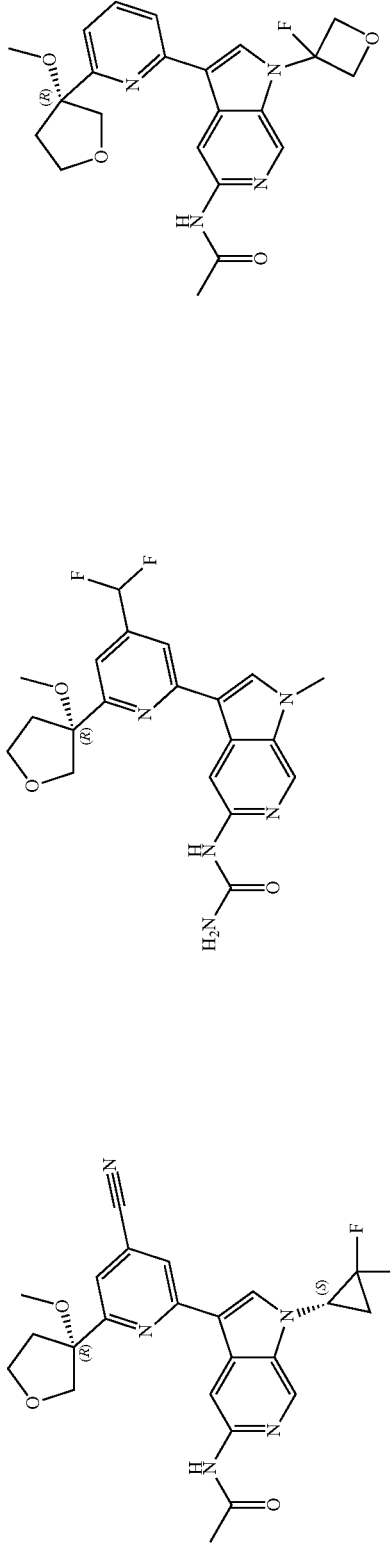

(2a.5) N-(3-(4-cyano-6-((R)-3-methoxytetrahydrofuran-3-yl)pyridin-2-yl)-1-(((S)-2,2-difluorocyclopropyl)-1H-pyrrolo[2,3-c]pyridin-5-yl)acetamide (12.5) (R)-1-(3-(4-(difluoromethyl)-6-(3-methoxytetrahydrofuran-3-yl)pyridin-2-yl)-1-methyl-1H-pyrrolo[2,3-c]pyridin-5-yl)urea (18a) (R)-N-(1-(3-fluorooxetan-3-yl)-3-(6-(3-methoxytetrahydrofuran-3-yl)pyridin-2-yl)-1H-pyrrolo[2,3-c]pyridin-5-yl)acetamide

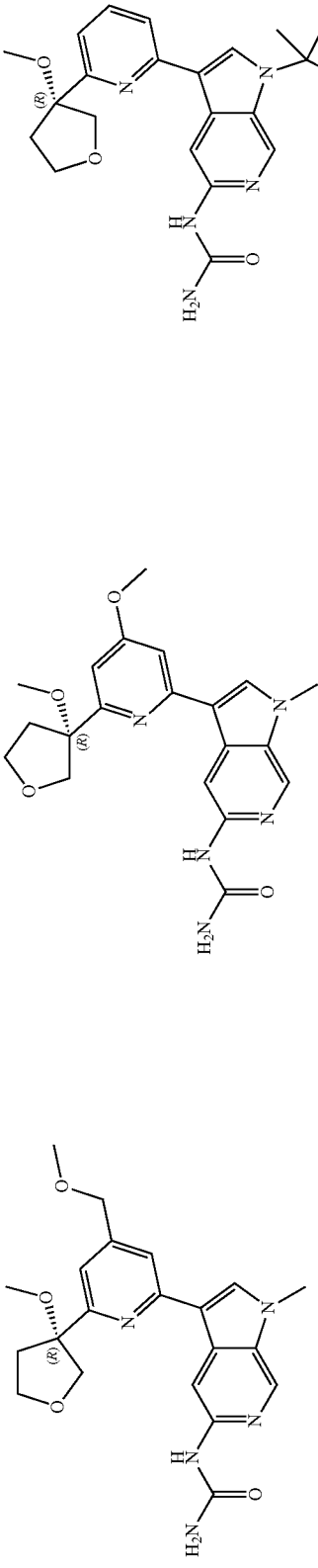

(3) (R)-1-(3-(4-(methoxymethyl)-6-(3-methoxytetrahydrofuran-3-yl)pyridin-2-yl)-1-methyl-1H-pyrrolo[2,3-c]pyridin-5-yl)urea (12.6) (R)-1-(3-(4-methoxy-6-(3-methoxytetrahydrofuran-3-yl)pyridin-2-yl)-1-methyl-1H-pyrrolo[2,3-c]pyridin-5-yl)urea

(19) (R)-1-(3-(6-(3-methoxytetrahydrofuran-3-yl)pyridin-2-yl)-1-(3-methyloxetan-3-yl)-1H-pyrrolo[2,3-c]pyridin-5-yl)urea

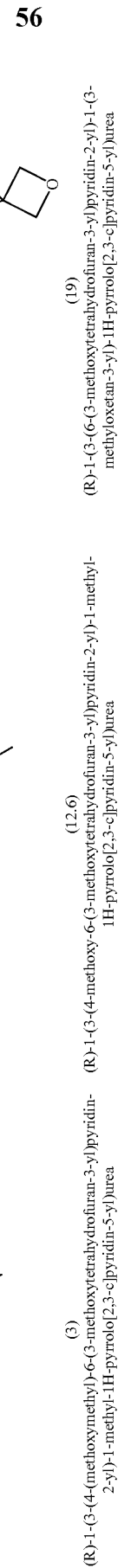

TABLE A1-continued

Exemplary compounds wherein R¹ is not hydrogen

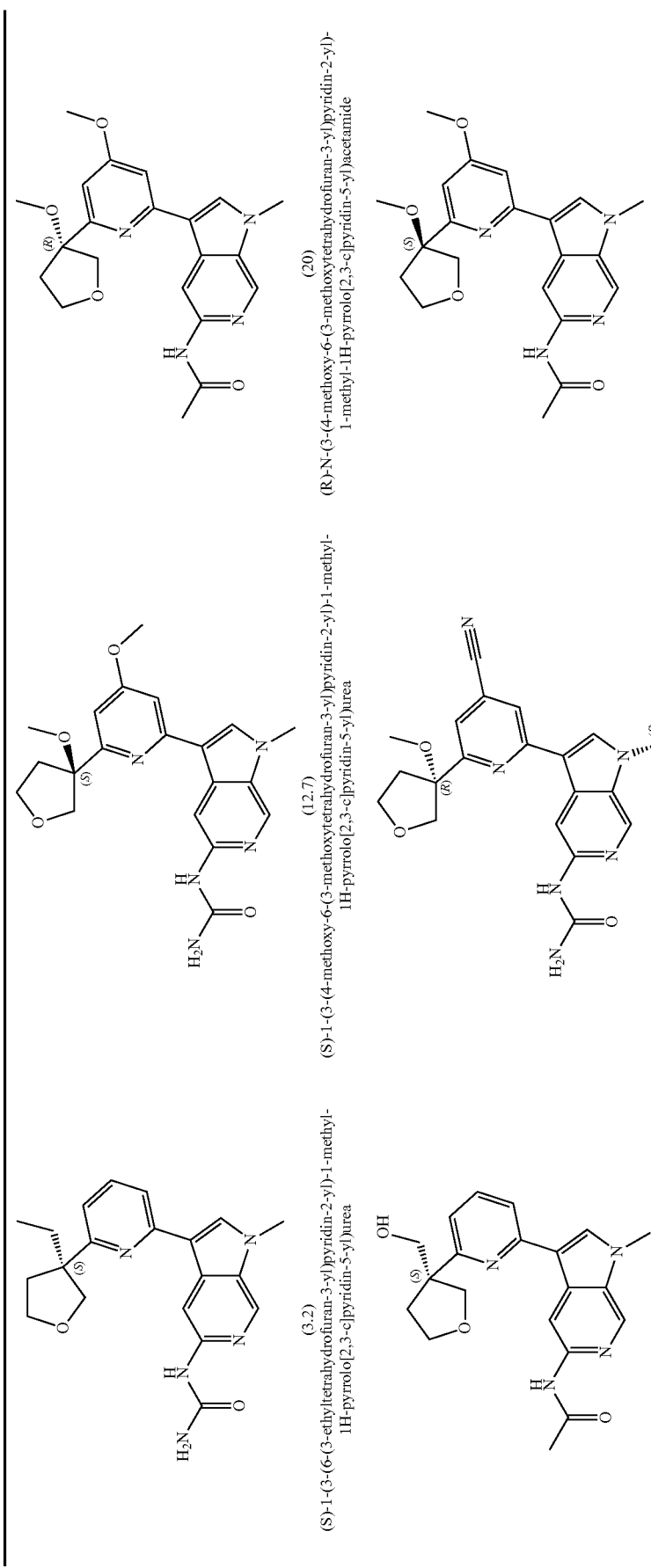

(3.2)
(S)-1-(3-(6-(3-ethyltetrahydrofuran-3-yl)pyridin-2-yl)-1-methyl-1H-pyrrolo[2,3-c]pyridin-5-yl)urea (12.7)
(S)-1-(3-(4-methoxy-6-(3-methoxytetrahydrofuran-3-yl)pyridin-2-yl)-1-methyl-1H-pyrrolo[2,3-c]pyridin-5-yl)urea

(20)
(R)-N-(3-(4-methoxy-6-(3-methoxytetrahydrofuran-3-yl)pyridin-2-yl)-1-methyl-1H-pyrrolo[2,3-c]pyridin-5-yl)acetamide

(21)
(S)-N-(3-(6-(3-(hydroxymethyl)tetrahydrofuran-3-yl)pyridin-2-yl)-1-methyl-1H-pyrrolo[2,3-c]pyridin-5-yl)acetamide (12a.2)
1-(3-(4-cyano-6-((R)-3-methoxytetrahydrofuran-3-yl)pyridin-2-yl)-1-((S)-2,2-difluorocyclopropyl)-1H-pyrrolo[2,3-c]pyridin-5-yl)urea (20a)
(S)-N-(3-(4-methoxy-6-(3-methoxytetrahydrofuran-3-yl)pyridin-2-yl)-1-methyl-1H-pyrrolo[2,3-c]pyridin-5-yl)acetamide TABLE A1-continued Exemplary compounds wherein R¹ is not hydrogen

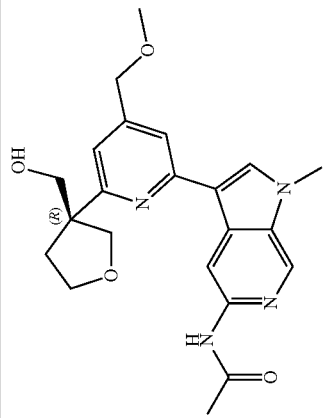

(22a)
(R)-N-(3-(6-(3-(hydroxymethyl)tetrahydrofuran-3-yl)-4-(methoxymethyl)pyridin-2-yl)-1-methyl-1H-pyrrolo[2,3-c]pyridin-5-yl)acetamide

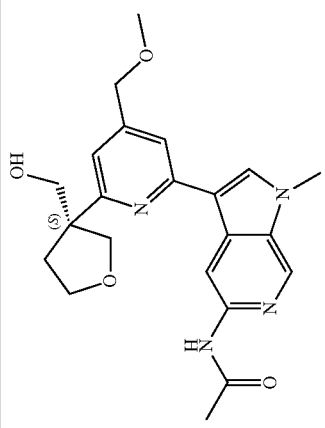

(22)
(S)-N-(3-(6-(3-(hydroxymethyl)tetrahydrofuran-3-yl)-4-(methoxymethyl)pyridin-2-yl)-1-methyl-1H-pyrrolo[2,3-c]pyridin-5-yl)acetamide

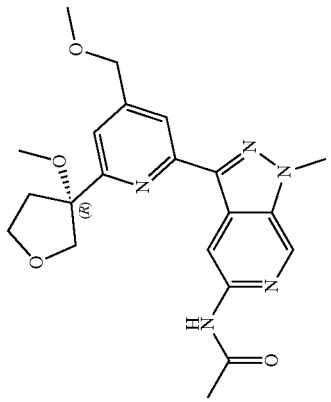

(23)
(R)-N-(3-(4-(methoxymethyl)-6-(3-methoxytetrahydrofuran-3-yl)pyridin-2-yl)-1-methyl-1H-pyrazolo[3,4-c]pyridin-5-yl)acetamide

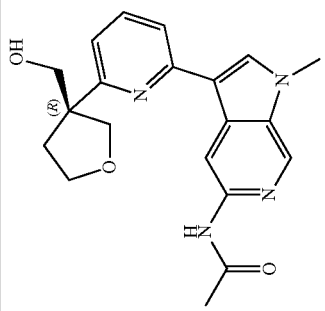

(21a)
(R)-N-(3-(6-(3-(hydroxymethyl)tetrahydrofuran-3-yl)pyridin-2-yl)-1-methyl-1H-pyrrolo[2,3-c]pyridin-5-yl)acetamide

TABLE A2

Exemplary compounds wherein R¹ is not hydrogen (1b.5) (S)-1-(1-methyl-3-(6-(3-methyltetrahydrofuran-3-yl)pyrazin-2-yl)-1H-pyrrolo[2,3-c]pyridin-5-yl)urea (1b.6) (R)-1-(1-methyl-3-(6-(3-methyltetrahydrofuran-3-yl)pyrazin-2-yl)-1H-pyrrolo[2,3-c]pyridin-5-yl)urea (2.3) (S)-N-(3-(6-(3-ethyltetrahydrofuran-3-yl)pyridin-2-yl)-1-methyl-1H-pyrrolo[2,3-c]pyridin-5-yl)acetamide (22.2) (R)-N-(3-(4-(difluoromethoxy)-6-(3-methoxytetrahydrofuran-3-yl)pyridin-2-yl)-1-methyl-1H-pyrrolo[2,3-c]pyridin-5-yl)acetamide (22.3) N-(3-(6-((R)-3-((S)-1-hydroxyethyl)tetrahydrofuran-3-yl)-4-(methoxymethyl)pyridin-2-yl)-1-methyl-1H-pyrrolo[2,3-c]pyridin-5-yl)acetamide (22.4) N-(3-(6-((R)-3-((R)-1-hydroxyethyl)tetrahydrofuran-3-yl)-4-(methoxymethyl)pyridin-2-yl)-1-methyl-1H-pyrrolo[2,3-c]pyridin-5-yl)acetamide TABLE A2-continued Exemplary compounds wherein R¹ is not hydrogen

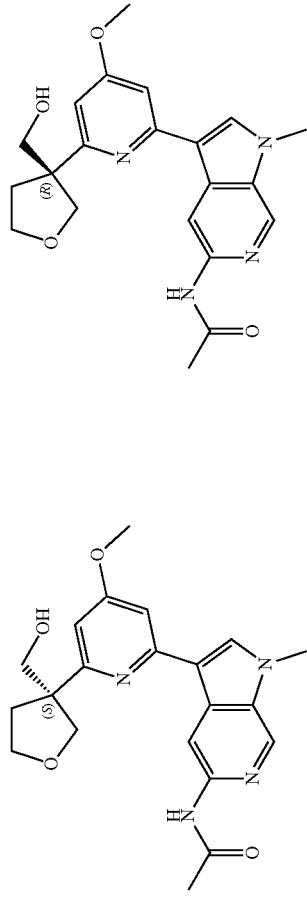

(22.5)
(S)-N-(3-(4-(difluoromethyl)-6-(3-(hydroxymethyl)tetrahydrofuran-3-yl)pyridin-2-yl)-1-methyl-1H-pyrrolo[2,3-c]pyridin-5-yl)acetamide

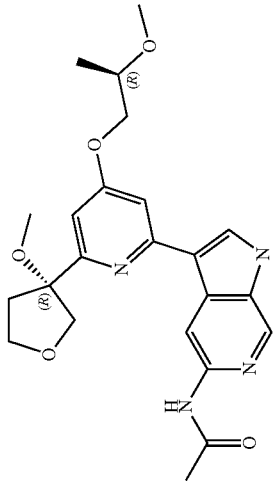

(22.6)
(S)-N-(3-(6-(3-(hydroxymethyl)tetrahydrofuran-3-yl)-4-methoxypyridin-2-yl)-1-methyl-1H-pyrrolo[2,3-c]pyridin-5-yl)acetamide

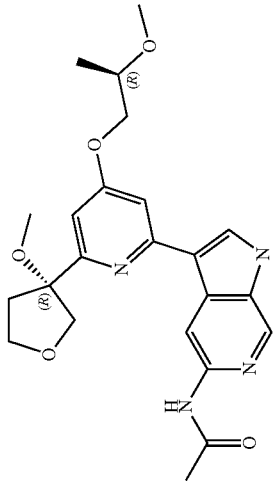

(22.7)
(R)-N-(3-(6-(3-(hydroxymethyl)tetrahydrofuran-3-yl)-4-methoxypyridin-2-yl)-1-methyl-1H-pyrrolo[2,3-c]pyridin-5-yl)acetamide

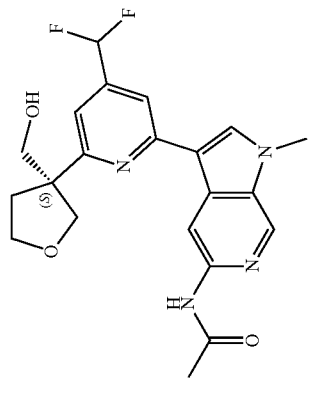

(22.8)
(S)-N-(3-(6-(3-(hydroxymethyl)tetrahydrofuran-3-yl)-4-(2-methoxyethoxy)pyridin-2-yl)-1-methyl-1H-pyrrolo[2,3-c]pyridin-5-yl)acetamide

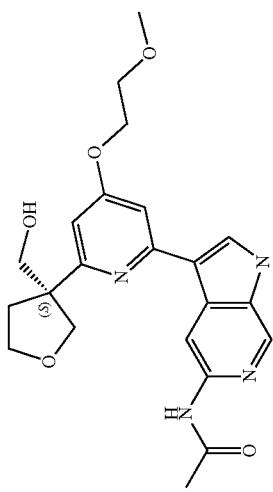

(22.9)
(R)-N-(3-(6-(3-(hydroxymethyl)tetrahydrofuran-3-yl)-4-(2-methoxy-ethoxy)pyridin-2-yl)-1-methyl-1H-pyrrolo[2,3-c]pyridin-5-yl)acetamide

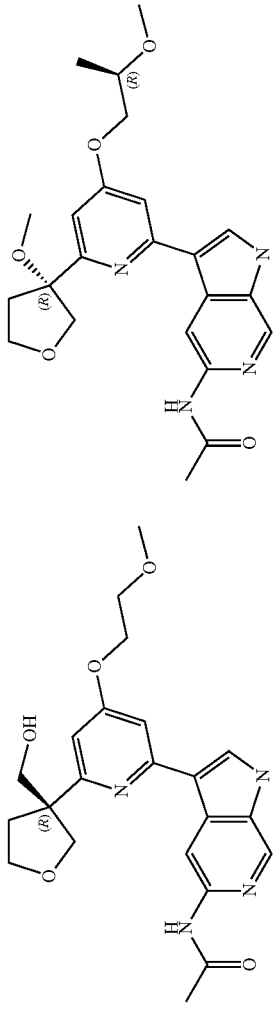

(22.10)
N-(3-(4-((R)-2-methoxypropoxy)-6-((R)-3-methoxytetrahydrofuran-3-yl)pyridin-2-yl)-1-methyl-1H-pyrrolo[2,3-c]pyridin-5-yl)pyridin-2-yl)acetamide TABLE A2-continued Exemplary compounds wherein R¹ is not hydrogen

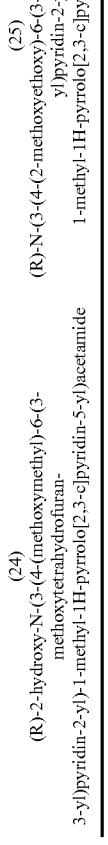

(24)
(R)-2-hydroxy-N-(3-(4-(methoxymethyl)-6-(3-methoxytetrahydrofuran-3-yl)pyridin-2-yl)-1-methyl-1H-pyrrolo[2,3-c]pyridin-5-yl)acetamide

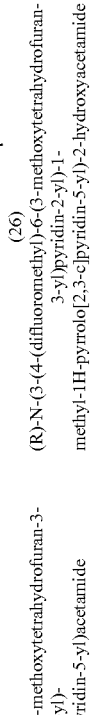

(25)
(R)-N-(3-(4-(2-methoxyethoxy)-6-(3-methoxytetrahydrofuran-3-yl)pyridin-2-yl)-1-methyl-1H-pyrrolo[2,3-c]pyridin-5-yl)acetamide

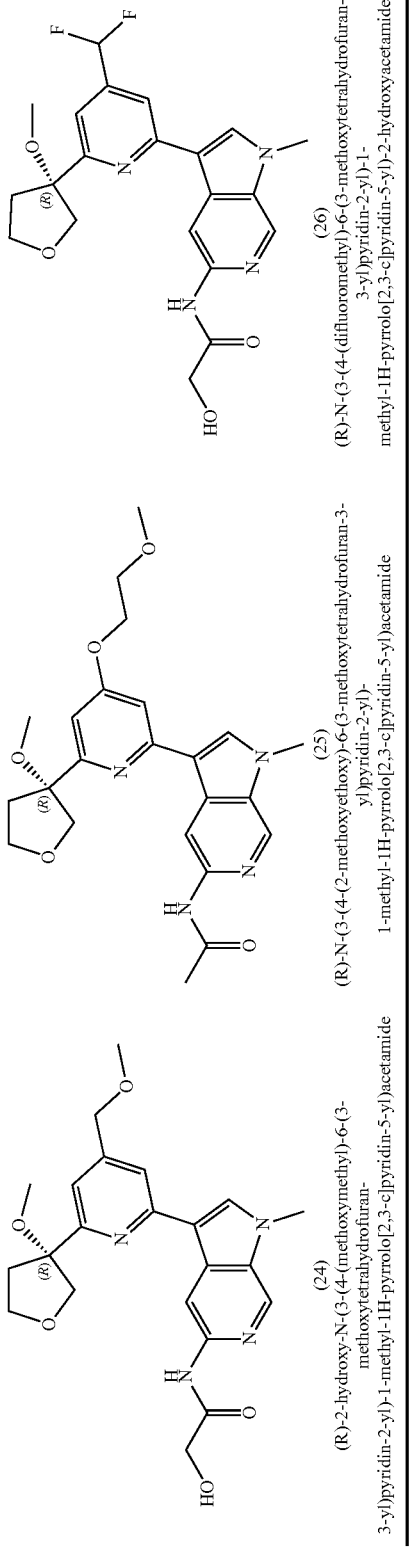

(26)
(R)-N-(3-(4-(difluoromethyl)-6-(3-methoxytetrahydrofuran-3-yl)pyridin-2-yl)-1-methyl-1H-pyrrolo[2,3-c]pyridin-5-yl)-2-hydroxyacetamide

TABLE B1

Exemplary compounds wherein R¹ is hydrogen (1-NH) 1-(3-(6-(3-methoxytetrahydrofuran-3-yl)pyridin-2-yl)-1H-pyrrolo[2,3-c]pyridin-5-yl)urea (2-NH) (R)-N-(3-(4-(methoxymethyl)-6-(3-methoxytetrahydrofuran-3-yl)pyridin-2-yl)-1H-pyrrolo[2,3-c]pyridin-5-yl)acetamide (5-NH) (R)-N-(3-(4-methoxy-6-(3-methoxytetrahydrofuran-3-yl)pyridin-2-yl)-1H-pyrrolo[2,3-c]pyridin-5-yl)acetamide (6-NH) (R)-N-(3-(6-(3-methoxytetrahydrofuran-3-yl)-4-(oxetan-3-ylmethoxy)pyridin-2-yl)-1H-pyrrolo[2,3-c]pyridin-5-yl)acetamide (7-NH) N-(3-(4-((R)-3-hydroxybutoxy)-6-((R)-3-methoxytetrahydrofuran-3-yl)pyridin-2-yl)-1H-pyrrolo[2,3-c]pyridin-5-yl)acetamide (8-NH) (R)-N-(3-(6-(3-methoxytetrahydrofuran-3-yl)-4-(oxetan-3-yloxy)pyridin-2-yl)-1H-pyrrolo[2,3-c]pyridin-5-yl)acetamide TABLE B1-continued Exemplary compounds wherein R¹ is hydrogen (9-NH) N-(3-(4-((S)-3-hydroxybutoxy)-6-((R)-3-methoxytetrahydrofuran-3-yl)pyridin-2-yl)-1H-pyrrolo[2,3-c]pyridin-5-yl)acetamide (10-NH) (R)-N-(3-(4-(2-hydroxyethoxy)-6-(3-methoxytetrahydrofuran-3-yl)pyridin-2-yl)-1H-pyrrolo[2,3-c]pyridin-5-yl)acetamide (12-NH) (R)-1-(3-(6-(3-methoxytetrahydrofuran-3-yl)pyrazin-2-yl)-1H-pyrrolo[2,3-c]pyridin-5-yl)urea (13-NH) 1-(3-(6-(oxetan-3-yl)pyridin-2-yl)-1H-pyrrolo[2,3-c]pyridin-5-yl)urea (16-NH) N-(3-(6-(3-methoxytetrahydrofuran-3-yl)pyridin-2-yl)-1H-pyrrolo[2,3-c]pyridin-5-yl)acetamide (17-NH) (R)-N-(3-(6-(3-methoxytetrahydrofuran-3-yl)pyridin-2-yl)-1H-pyrrolo[2,3-c]pyridin-5-yl)acetamide (21-NH) N-(3-(6-(3-(hydroxymethyl)tetrahydrofuran-3-yl)pyridin-2-yl)-1H-pyrrolo[2,3-c]pyridin-5-yl)acetamide (23-NH) (R)-N-(3-(4-(methoxymethyl)-6-(3-methoxytetrahydrofuran-3-yl)pyridin-2-yl)-1H-pyrazolo[3,4-c]pyridin-5-yl)acetamide In certain embodiments, a composition comprises a compound, or pharmaceutically acceptable salt thereof, of Table A1, A2, or Table B1, in an enriched amount, i.e., >50%, >60%, >65%, >70%, >75%, >80%, >85%, >90%, >91%, >92%, >93%, >94%, >95%, >96%, >97%, >98%, >99%, >99.5%, or >99.9%, of the compound, or pharmaceutically acceptable salt thereof, of Table A1 or Table B1, over the sum total of other stereoisomer(s) present in the composition; and/or wherein the composition comprises <0.1%, <0.5%, <1%, <2%, <3%, <4%, <5%, <6%, <7%, <8%, <9%, <10%, <15%, <20%, <25%, <30%, <35%, <40%, <45%, or <50% of other stereoisomer(s) present in the composition.

In certain embodiments, the compound, or pharmaceutically acceptable salt thereof, is selected from the compounds listed in Tables A1 or A2.

In certain embodiments of Table A1 or A2, wherein n is 1, $R^3$ is -$OR^{3a}$ (wherein m is 0), and the compound is a stereoisomer of Formula (I-a), the compound of Formula (I) is selected from the group consisting of Ex #1, #1.2, #1.3, #1a.2, #1b.2, #2, #2.2, #2.6, #2.8, #2.10, #2a.3, #2a.5, #3, #4, #4.3, #5, #5.2, #6, #6.3, #7, #8, #9, #10, #11, #11.2, #12, #12.3, #12.5, #12.6, #12a.2, #12a.3, #12b.2, #12b.3, #12b.4, #14.4, #14.5, #14.6, #16, #17, #17a, #17.2, #17.3, #17.4, #17.5, #18, #18a, #19, #20, #23, #22.2, #22.10, #24, #25, #26, and pharmaceutically acceptable salts thereof In certain embodiments, the compound of Formula (I) is selected from the group consisting of Ex #1, #2, #3, #4, #5, #6, #7, #8, #9, #10, #11, #12, #14.6, #16, #17, #18, #19, #20, #24, #25, #26, and pharmaceutically acceptable salts thereof In certain embodiments of Table Al or A2, wherein n is 1 and $R^3$ is $C_{1-3}$alkyl, the compound of Formula (I) is selected from the group consisting of Ex #3.2, #3.3, #2.3, #2.3a, #2.11, #1b.5, #1b.6, and pharmaceutically acceptable salts thereof. In certain embodiments, wherein n is 1, $R^3$ is $C_{1-3}$alkyl, and the compound is a stereoisomer of Formula (I-a), the compound of Formula (I) is Ex #1b.5, #2.3, or #3.2, or a pharmaceutically acceptable salt thereof.

In certain embodiments of Table Al or A2, wherein n is 1, $R^3$ is -$(C_{1-3}$alkylene$)_m$-$OR^{3a}$, and m is 1, the compound of Formula (I) is selected from the group consisting of Ex #21, #21a, #22, #22a, #22.3, #22.4, #22.5, #22.6, #22.7, #22.8, #22.9, and pharmaceutically acceptable salts thereof. In certain embodiments, wherein n is 1, $R^3$ is -$(C_{1-3}$alkylene$)_m$-$OR^{3a}$, m is 1, and the compound is a stereoisomer of Formula (I-a), the compound of Formula (I) is Ex #21, #22, #22.3, #22.4, #22.5, #22.6, #22.8, or a pharmaceutically acceptable salt thereof.

In certain embodiments of Table Al or A2, wherein n is 0, the compound of Formula (I) is selected from the group consisting of Ex #1b.4, #13, #14, #14.2, #14.3, #15, #15.2, and pharmaceutically acceptable salts thereof. In certain embodiments, the compound of Formula (I) is selected from the group consisting of Ex #13, #14, #15, and pharmaceutically acceptable salts thereof In certain embodiments of Table Al or A2, wherein n is 1, $R^3$ is -$(C_{1-3}$alkylene$)_m$-$OR^{3a}$ or $C_{1-3}$alkyl, m is 0 or 1, and the compound is a stereoisomer of Formula (I-a), the compound of Formula (I) is selected from the group consisting of Ex #1, #1.2, #1.3, #1a.2, #1b.2, #2, #2.2, #2.3, #2.6, #2.8, #2.10, #2a.3, #2a.5, #3, #4, #4.3, #5, #5.2, #6, #6.3, #7, #8, #9, #10, #11, #11.2, #12, #12.3, #12.5, #12.6, #12a.2, #12a.3, #12b.2, #12b.3, #12b.4, #14.4, #14.5, #14.6, #16, #17, #17a, #17.2, #17.3, #17.4, #17.5, #18, #18a, #19, #20, #21, #22, #23, #1b.5, #22.2, #22.3, #22.4, #22.5, #22.6, #22.8, #22.10, #24, #25, #26, and pharmaceutically acceptable salts thereof.

In certain embodiments, the compound of Formula (I) is selected from the group consisting of Ex #2, #4, #10, #11, #14.6, #22, and pharmaceutically acceptable salts thereof. In certain embodiments, the compound of Formula (I) is Ex #2, or a pharmaceutically acceptable salt thereof. In certain embodiments, the compound of Formula (I) is Ex #4, or a pharmaceutically acceptable salt thereof. In certain embodiments, the compound of Formula (I) is Ex #10, or a pharmaceutically acceptable salt thereof In certain embodiments, the compound of Formula (I) is Ex #11, or a pharmaceutically acceptable salt thereof. In certain embodiments, the compound of Formula (I) is Ex #14.6, or a pharmaceutically acceptable salt thereof. In certain embodiments, the compound of Formula (I) is Ex #22, or a pharmaceutically acceptable salt thereof.

(v) Pharmaceutical Compositions and Methods of Use

Further provided herein are pharmaceutical compositions comprising a compound of Formula (I), or a pharmaceutically acceptable salt thereof, and a pharmaceutically acceptable excipient. In certain embodiments, a compound of Formula (I), or a pharmaceutically acceptable salt thereof, is provided in an effective amount in the pharmaceutical composition.

Pharmaceutical compositions comprising compounds of Formula (I), or pharmaceutically acceptable salts thereof, may comprise a mixture of stereoisomers, including racemic (equal) mixtures, or non-racemic (scalemic) mixtures enriched in one or more stereoisomer. For example, in certain embodiments, the composition comprises a compound of Formula (I), or pharmaceutically acceptable salt thereof, in an enriched amount, i.e., >50%, >60%, >65%, >70%, >75%, >80%, >85%, >90%, >91%, >92%, >93%, >94%, >95%, >96%, >97%, >98%, >99%, >99.5%, or >99.9%, of stereoisomer (I-a) over the sum total of stereoisomers (I-a) and (I-b) in the composition; and/or wherein the composition comprises <0.1%, <0.5%, <1%, <2%, <3%, <4%, <5%, <6%, <7%, <8%, <9%, <10%, <15%, <20%, <25%, <30%, <35%, <40%, <45%, or <50% of stereoisomer (I-b) over the sum total of stereoisomers (I- a) and (I-b) in the composition. In certain embodiments, the composition comprises >95% of stereoisomer (I-a) over the sum total of stereoisomers (I-a) and (I-b) in the composition, and/or comprises <5% of stereoisomer (I-b) over the sum total of stereoisomers (I-a) and (I-b) in the composition. In other embodiments, the composition comprises a compound of Formula (I), or pharmaceutically acceptable salt thereof, in an enriched amount, i.e., >50%, >60%, >65%, >70%, >75%, >80%, >85%, >90%, >91%, >92%, >93%, >94%, >95%, >96%, >97%, >98%, >99%, >99.5%, or >99.9%, of stereoisomer (I-b) over the sum total of stereoisomers (I-a) and (I-b) in the composition; and/or wherein the composition comprises <0.1%, <0.5%, <1%, <2%, <3%, <4%, <5%, <6%, <7%, <8%, <9%, <10%, <15%, <20%, <25%, <30%, <35%, <40%, <45%, or <50% of stereoisomer (I-a) over the sum total of stereoisomers (I-a) and (I-b) in the composition. In certain embodiments, the composition comprises >95% of stereoisomer (I-b) over the sum total of stereoisomers (I-a) and (I-b) in the composition, and/or comprises <5% of stereoisomer (I-a) over the sum total of stereoisomers (I-a) and (I-b) in the composition.

In certain embodiments, the pharmaceutical composition comprises >90% of stereoisomer (I-a) over stereoisomer (I-b), or comprises <10% of stereoisomer (I-b). In certain embodiments, the composition comprises >91% of stereoisomer (I-a) over the sum total of stereoisomers (I-a) and (I-b) in the composition, or comprises <9% of stereoisomer (I-b) over the sum total of stereoisomers (I-a) and (I-b) in the composition. In certain embodiments, the composition comprises >92% of stereoisomer (I-a) over the sum total of stereoisomers (I-a) and (I-b) in the composition, or comprises <8% of stereoisomer (I-b) over the sum total of stereoisomers (I-a) and (I-b) in the composition. In certain embodiments, the composition comprises >93% of stereoisomer (I-a) over the sum total of stereoisomers (I-a) and (I-b) in the composition, or comprises <7% of stereoisomer (I-b) over the sum total of stereoisomers (I-a) and (I-b) in the composition. In certain embodiments, the composition comprises >94% of stereoisomer (I-a) over the sum total of stereoisomers (I-a) and (I-b) in the composition, or comprises <6% of stereoisomer (I-b) over the sum total of stereoisomers (I-a) and (I-b) in the composition. In certain embodiments, the composition comprises >95% of stereoisomer (I-a) over the sum total of stereoisomers (I-a) and (I-b) in the composition, or comprises <5% of stereoisomer (I-b) over the sum total of stereoisomers (I-a) and (I-b) in the composition. In certain embodiments, the composition comprises >96% of stereoisomer (I-a) over the sum total of stereoisomers (I-a) and (I-b) in the composition, or comprises <4% of stereoisomer (I-b) over the sum total of stereoisomers (I-a) and (I-b) in the composition. In certain embodiments, the composition comprises >97% of stereoisomer (I-a) over the sum total of stereoisomers (I-a) and (I-b) in the composition, or comprises <3% of stereoisomer (I-b) over the sum total of stereoisomers (I-a) and (I-b) in the composition. In certain embodiments, the composition comprises >98% of stereoisomer (I-a) over the sum total of stereoisomers (I-a) and (I-b) in the composition, or comprises <2% of stereoisomer (I-b) over the sum total of stereoisomers (I-a) and (I-b) in the composition. In certain embodiments, the composition comprises >99% of stereoisomer (I-a) over the sum total of stereoisomers (I-a) and (I-b) in the composition, or comprises <1% of stereoisomer (I-b) over the sum total of stereoisomers (I-a) and (I-b) in the composition. In certain embodiments, the composition comprises >99.5% of stereoisomer (I- a) over the sum total of stereoisomers (I-a) and (I-b) in the composition, or comprises <0.5% of stereoisomer (I-b) over the sum total of stereoisomers (I-a) and (I-b) in the composition. In certain embodiments, the composition comprises >99.9% of stereoisomer (I-a) over the sum total of stereoisomers (I-a) and (I-b) in the composition, or comprises <0.1% of stereoisomer (I-b) over the sum total of stereoisomers (I-a) and (I-b) in the composition.

Pharmaceutically acceptable excipients are well known to those skilled in the art, and include liquid vehicles such as water. Pharmaceutical compositions may be prepared by bringing the compound of Formula (I), or pharmaceutically acceptable salt thereof, into association with one or more pharmaceutically acceptable excipients, and then, if necessary and/or desirable, shaping and/or packaging the product into a desired single- or multi-dose unit.

Compounds of Formula (I), their pharmaceutically acceptable salts, and pharmaceutical compositions comprising same, may be administered to and useful for treatment of subjects suffering from inflammatory bowel disease (IBD) (e.g., Crohn's disease, ulcerative colitis) and/or psoriasis. Accordingly, provided are methods of treating a disease, comprising administering to a subject in need thereof an effective amount of a compound of Formula (I), or a pharmaceutically acceptable salt thereof, or a pharmaceutical composition thereof, to the subject, wherein the disease is inflammatory bowel disease (IBD) or psoriasis. Further provided are compounds of Formula (I), or pharmaceutically acceptable salts thereof, or compositions comprising same, for use in a medicament, e.g., for use in the treatment of inflammatory bowel disease (IBD) and/or psoriasis. In certain embodiments, the disease is Crohn's disease. In certain embodiments, the disease is ulcerative colitis. In certain embodiments, the disease is psoriasis. In certain embodiments, the effective amount is an amount effective in inhibiting Tyk2, IL-12, and/or IL-23 activity. In certain embodiments, the subject is a human subject.

(vi) Preparative Methods

Further provided herein are exemplary methods of preparing compounds of Formula (I), and salts thereof. See, e.g., Schemes 1-9 below, and the Examples.

In one aspect, as depicted in Schemes 1 and 2, provided is a method of preparing a compound of Formula (I), or salt thereof, comprising treating a compound of Formula (D), or salt thereof, which comprises a free NH moiety, with a functionalizing reagent (i.e., a reagent used to replace the hydrogen on the NH group with a non-hydrogen $R^1$ group) to provide a compound of Formula (I), wherein $R^1$ is unsubstituted or substituted $C_{1-6}$alkyl, unsubstituted or substituted $C_{3-6}$carbocyclyl, or unsubstituted or substituted 4- to 6-membered heterocyclyl.

For example, as depicted in Scheme 1, Step S3, in certain embodiments, the method comprises treating a compound of Formula (D), or salt thereof, with a compound of formula 1V-$LG^3$, or salt thereof, to provide a compound of Formula (I), wherein $LG^3$ is a leaving group, and $R^1$ is unsubstituted or substituted $C_{1-6}$alkyl, unsubstituted or substituted $C_{3-6}$carbocyclyl, or unsubstituted or substituted 4- to 6-membered heterocyclyl. See Scheme 1, Step S3. In certain embodiments, $LG^3$ is halo (e.g., chloro, bromo, iodo) or an activated hydroxyl group (e.g., -OTf, -OTs, -OMs, or -OBs). In certain embodiments, the method comprises treating a compound of Formula (D), or salt thereof, with a compound of formula $R^1$-$LG^3$, or salt thereof, wherein $R^1$ is -$CH_3$, an unsubstituted or substituted cyclopropyl, an unsubstituted or substituted cyclobutyl, an unsubstituted or substituted oxetanyl, an unsubstituted or substituted tetrahydrofuranyl, and $LG^3$ is halo (e.g., chloro, bromo, iodo) or an activated hydroxyl group (e.g., -OTf, -OTs, -OMs, or -OBs). In certain embodiments, the method comprises treating a compound of Formula (D), or salt thereof, with dimethyl sulfate, methyliodide, or methylbromide (in other words, a compound of formula $R^1$-$LG^3$, or salt thereof, wherein $R^1$ is -$CH_3$ and $LG^3$ is -OS(O)$_2$OCH$_3$, -Br, or -I) to provide a compound of Formula (I), or salt thereof, wherein $R^1$ is -$CH_3$. In certain embodiments, the method comprises treating a compound of Formula (D), or salt thereof, with 3-iodooxetane (in other words, a compound formula $R^1$-$LG^3$, or salt thereof, wherein $R^1$ is oxetanyl and $LG^3$ is iodo), to provide a compound of Formula (I), or salt thereof, wherein $R^1$ is 3-oxetanyl. In yet other embodiments of Scheme 1, Step S3, the method comprises treating a compound of Formula (D), or salt thereof, with formaldehyde under reductive amination conditions, to provide a compound of Formula (I), or salt thereof, wherein $R^1$ is -$CH_3$.

Scheme 1.

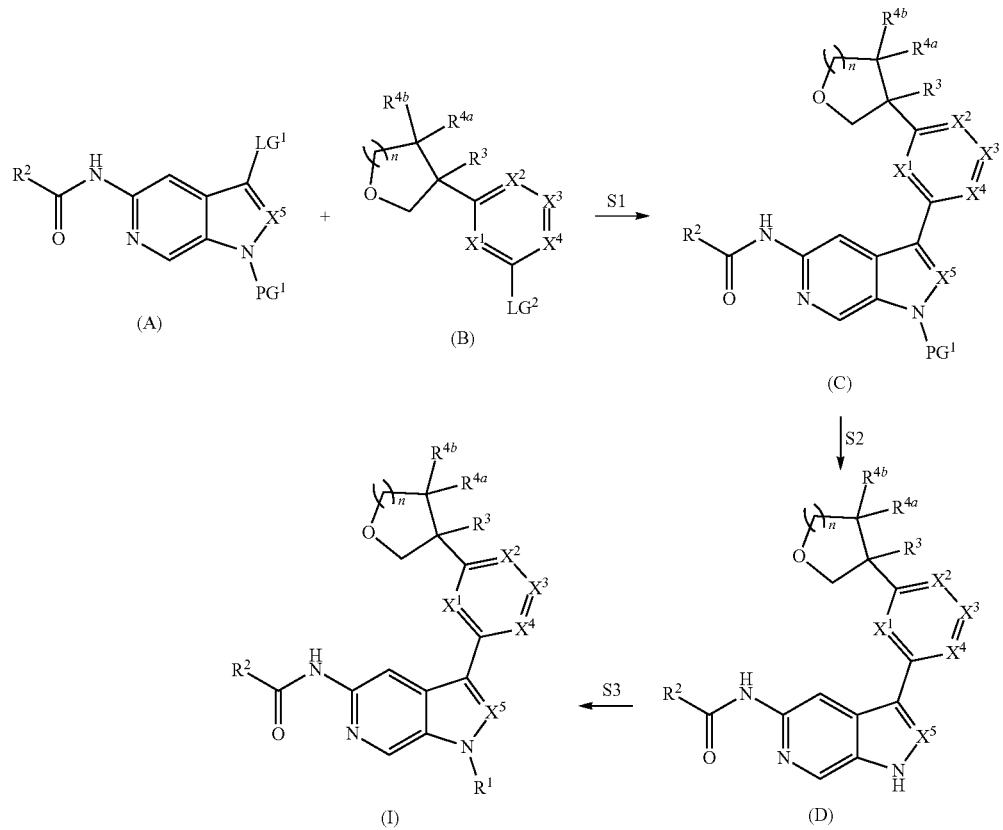

In yet other embodiments, compounds of Formula (I), and salts thereof, are synthesized from compounds of Formula (D), and salts thereof, following the procedure as shown in Scheme 2. For example, in certain embodiments, the method comprises treating a compound of Formula (D), or salt thereof, with an oxetan-3-one of Formula (X), wherein $R^{1a}$ and $R^{1b}$ may be the same or different, and are each independently hydrogen or -$CH_3$, followed by trapping of the in situ generated hemiaminal by fluorination (e.g., using a fluorinating reagent, such as bis(2-methoxyethyl)aminosulfur trifluoride, (diethylamino)sulfur trifluoride, or 1-(chloromethyl)-4-fluoro-1,4-diazoniabicyclo[2.2.2]octane ditetrafluoroborate) to provide a fluorinated compound of Formula (I-i), or salt thereof See, e.g., Scheme 2, Step S3-A.

In certain embodiments, the method further comprises treating the compound of Formula (I-i), or salt thereof, with a reducing agent to provide a compound of Formula (I-ii), or salt thereof. See, e.g., Scheme 2, Step S3-B. In certain alternative embodiments, the method further comprises replacing the fluorine of the compound of Formula (I-i), or salt thereof, with a group $R^{1c}$, wherein $R^{1c}$ is $C_{1-3}$alkyl, $C_{1-3}$haloalkyl, -$OC_{1-3}$alkyl, or -$OC_{1-3}$haloalkyl to provide a compound of Formula (I-iii), or salt thereof. See, e.g., Scheme 2, Step S3-C. In certain embodiments, the compound of Formula (I-i), or salt thereof is treated with $CH_3MgBr$, $CH_3CH_2MgBr$, or NaOH in $CH_3OH$, to provide a compound of Formula (I-iii), or salt thereof, wherein $R^{1c}$ is -$CH_3$, -$CH_2CH_3$, or -$OCH_3$.

Scheme 2.

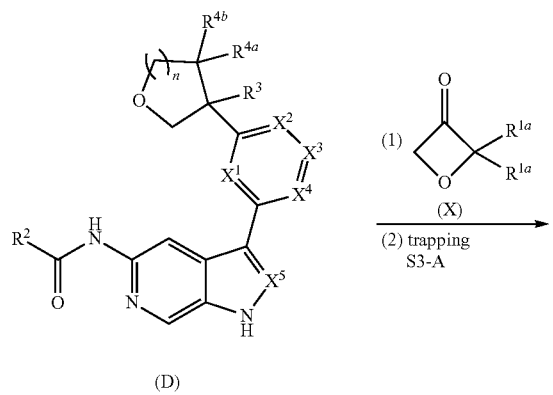

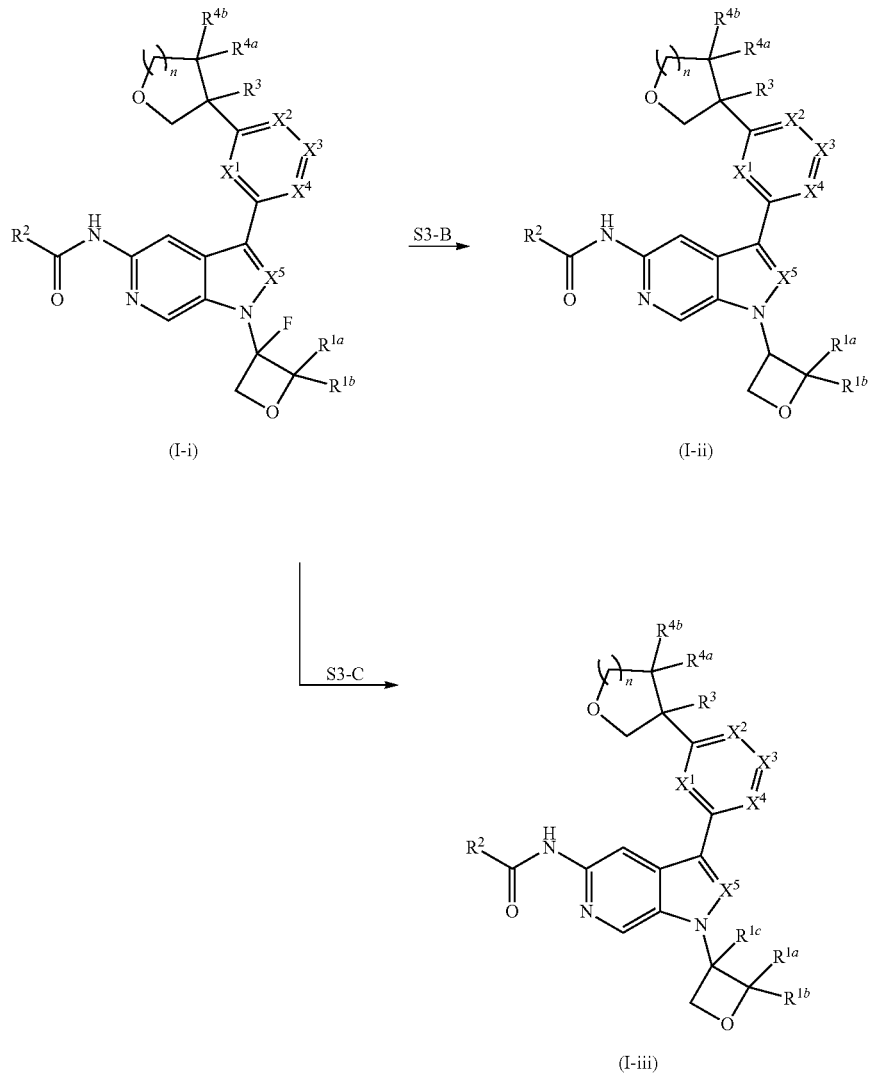

In certain embodiments, the compound of Formula (D), or salt thereof, is prepared from a compound of Formula (C), or salt thereof, by deprotection of an amino protecting group, $PG^1$. See Scheme 1, Step S2. In certain embodiments, $PG^1$ is -CH$_2$-phenyl, -S(=O)$_2$R$^G$ or -C(=O)OR$^G$ wherein R$^G$ is alkyl or phenyl, and wherein each instance of phenyl is unsubstituted or substituted by halogen, -C$_{1-3}$alkyl, -OC$_{1-3}$alkyl, or -NO$_2$. In certain embodiments, $PG^1$ is a t-Butoxycarbonyl (Boc) group, or a toluenesulfonyl (Ts) group, or a 2-nitrobenenesulfonyl (Ns) group, or a param-ethoxybenzyl (PMB) group.

In certain embodiments, the compound of Formula (C), or salt thereof, is prepared from the cross-coupling of a compound of Formula (A), or salt thereof with a compound of Formula (B), or salt thereof, wherein $LG^1$ and $LG^2$ are leaving groups, which may be the same or different. See Scheme 1, Step S1. In certain embodiments, $LG^1$ and $LG^2$ are each halogen groups (e.g., -Cl, -Br, -I), or one of $LG^1$ and $LG^2$ is a boronic acid or boronic ester (e.g., a dioxoborolane group, such as tetramethyldioxoborolane) and the other of $LG^1$ and $LG^2$ is a halogen group (e.g., -Cl, -Br, -I), and the cross-coupling reaction is facilitated using a palladium catalyst (e.g., PdCl$_2$(dppf)-DCM adduct; Pd$_2$(dba)$_3$).

Alternatively, in certain embodiments, a compound of Formula (I), or salt thereof, is prepared from coupling a compound of Formula (H), or salt thereof, wherein $LG^4$ is a leaving group (e.g., -Cl, - Br, -I) with a compound of Formula R$^2$C(=O)NH$_2$, in the presence of a palladium catalyst (e.g., Pd$_2$(dba)$_3$) or a copper catalyst (e.g. copper(I) iodide, such as wherein $LG^4$ is -I). See Scheme 3, Step S7. In certain embodiments, R$^2$ is -NH$_2$. In certain embodiments, $LG^4$ is -Br. In certain embodiments, $LG^4$ is -I.

Scheme 3.

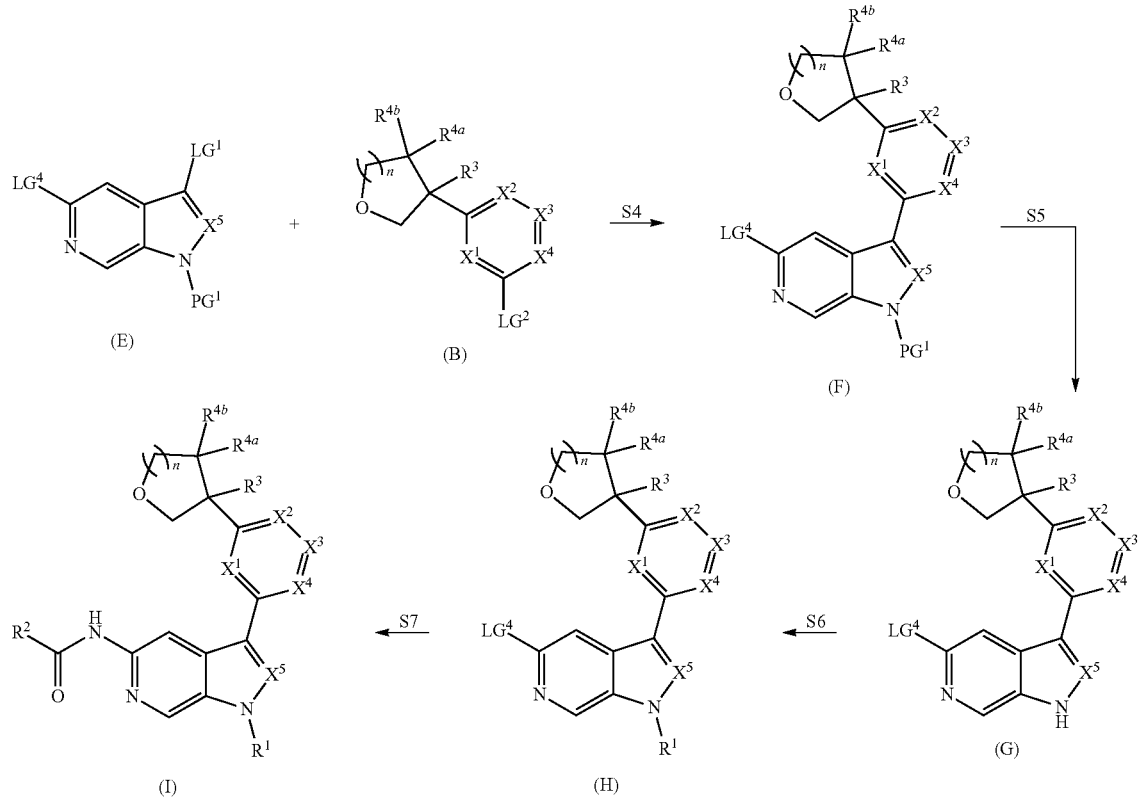

In certain embodiments, the compound of Formula (H), or salt thereof, is prepared by treating a compound of Formula (G), or salt thereof, with a compound of formula $R^1$-$LG^3$, or salt thereof, wherein $LG^3$ is a leaving group, and $R^1$ is unsubstituted or substituted $C_{1-6}$alkyl, unsubstituted or substituted $C_{3-6}$carbocyclyl, or unsubstituted or substituted 4- to 6-membered heterocyclyl, as described herein. See Scheme 3, Step S6. In certain embodiments, $LG^3$ is halo (e.g., chloro, bromo, iodo) or an activated hydroxyl group (e.g., -OTf, -OTs, -OMs, or -OBs). In certain embodiments, the method comprises treating a compound of Formula (G), or salt thereof, with a compound of formula $R^1$-$LG^3$, or salt thereof, wherein $R^1$ is -$CH_3$, an unsubstituted or substituted cyclopropyl, an unsubstituted or substituted cyclobutyl, an unsubstituted or substituted oxetanyl, or an unsubstituted or substituted tetrahydrofuranyl, and $LG^3$ is halo (e.g., chloro, bromo, iodo) or an activated hydroxyl group (e.g., -OTf, -OTs, -OMs, or -OBs). In other embodiments of Scheme 3, Step S6, the method comprises treating a compound of Formula (G), or salt thereof, with dimethyl sulfate, methyliodide, or methylbromide (in other words, a compound of formula $R^1$-$LG^3$, or salt thereof, wherein $R^1$ is -$CH_3$ and $LG^3$ is -OS(O)$_2$OCH$_3$, -Br, or -I) to provide a compound of Formula (H), or salt thereof, wherein $R^1$ is -$CH_3$. In certain embodiments, the method comprises treating a compound of Formula (G), or salt thereof, with 3-iodooxetane (in other words, a compound formula $R^1$-$LG^3$, or salt thereof, wherein $R^1$ is oxetanyl and $LG^3$ is iodo), to provide a compound of Formula (H), or salt thereof, wherein $R^1$ is 3-oxetanyl. In yet other embodiments of Scheme 1, Step S3, the method comprises treating a compound of Formula (G), or salt thereof, with formaldehyde under reductive amination conditions, to provide a compound of Formula (H), or salt thereof, wherein $R^1$ is -$CH_3$.

In yet other embodiments of Scheme 3, Step S6, and Scheme 4, the method comprises treating a compound of Formula (G), or salt thereof, with an oxetan-3-one of Formula (X), wherein $R^{1a}$ and $R^{1b}$ may be the same or different, and are each independently hydrogen or -$CH_3$, followed by trapping of the in situ generated hemiaminal by fluorination (e.g., using a fluorinating reagent, such as bis(2- methoxyethyl)aminosulfur trifluoride, (diethylamino)sulfur trifluoride, or 1-(chloromethyl)-4-fluoro- 1,4-diazoniabicyclo [2.2.2]octane ditetrafluoroborate) to provide a fluorinated compound of Formula (I- iv), or salt thereof. See, e.g., Scheme 4, Step S6-A. In certain embodiments, the method further comprises treating the compound of Formula (I-iv), or salt thereof, with a reducing agent to provide a compound of Formula (I-v), or salt thereof. See, e.g., Scheme 4, Step S6-B. In certain alternative embodiments, the method further comprises replacing the fluorine of the compound of Formula (I-iv), or salt thereof, with a group $R^{1c}$, wherein $R^{1c}$ is $C_{1-3}$alkyl, $C_{1-3}$haloalkyl, -O$C_{1-3}$alkyl, or -O$C_{1-3}$haloalkyl to provide a compound of Formula (I-vi), or salt thereof. See, e.g., Scheme 4, Step S6-C. In certain embodiments, the compound of Formula (I-iv), or salt thereof is treated with $CH_3MgBr$, $CH_3CH_2MgBr$, or NaOH in $CH_3OH$, to provide a compound of Formula (I-vi), or salt thereof, wherein $R^{1c}$ is -$CH_3$, -$CH_2CH_3$, or - $OCH_3$.

Scheme 4.

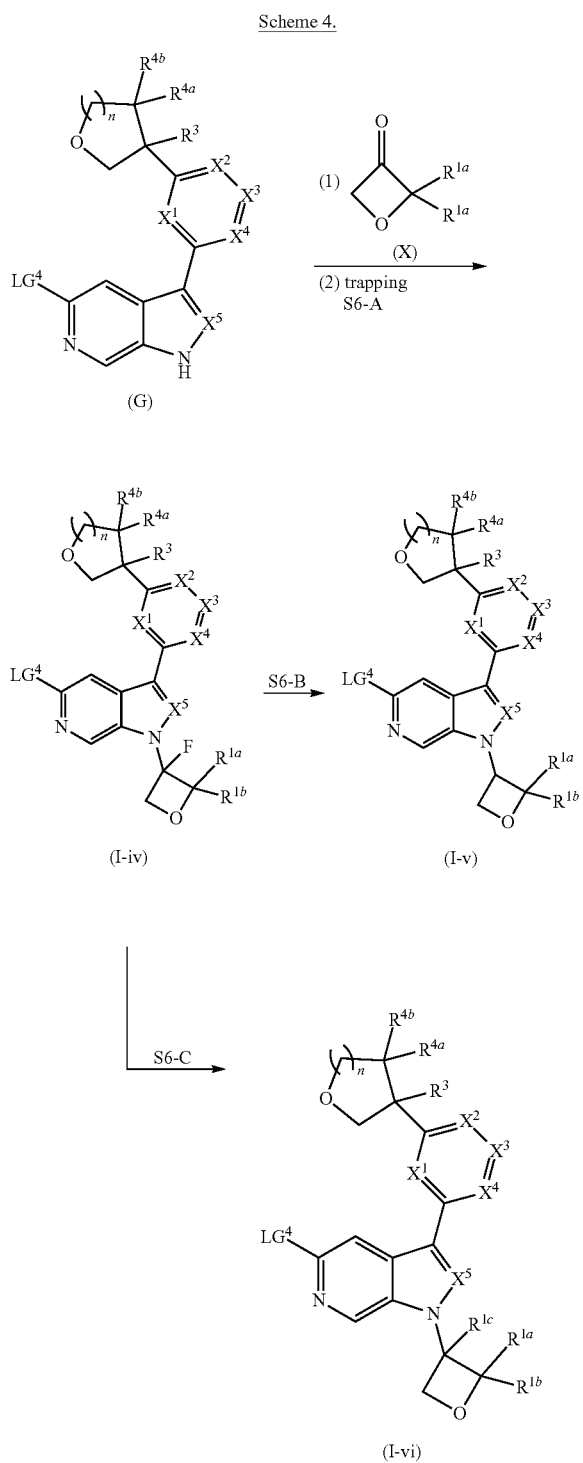

In certain embodiments, the compound of Formula (G), or salt thereof, is prepared from a compound of Formula (F), or salt thereof, by deprotection of an amino protecting group, $PG^1$. See Scheme 3, Step S5. In certain embodiments, $PG^1$ is -$CH_2$-phenyl, -S(=O)$_2R^G$ or -C(=O)O$R^G$ wherein $R^G$ is alkyl or phenyl, wherein each instance of phenyl is unsubstituted or substituted by halogen, -$C_{1-3}$alkyl, -O$C_{1-3}$alkyl, or -$NO_2$. In certain embodiments, $PG^1$ is a t-Butoxycarbonyl (Boc) group, a toluenesulfonyl (Ts) group, a 2-nitrobenenesulfonyl (Ns) group, or a paramethoxybenzyl (PMB) group.

In certain embodiments, the compound of Formula (F), or salt thereof, is prepared from the cross-coupling of a compound of Formula (E), or salt thereof with a compound of Formula (B), or salt thereof, wherein $LG^1$ and $LG^2$ are leaving groups, which may be the same or different. See Scheme 3, Step S4. In certain embodiments, $LG^1$ and $LG^2$ are each halogen groups (e.g., -Cl, -Br, -I) (wherein one $LG^1$ or $LG^2$ is first converted in situ to a boronic acid or ester), or one of $LG^1$ and $LG^2$ is a boronic acid or boronic ester (e.g., a dioxoborolane group, such as tetramethyldioxoborolane) and the other of $LG^1$ and $LG^2$ is a halogen group (e.g., -Cl, -Br, -I), and wherein the cross-coupling reaction is facilitated using a palladium catalyst (e.g., PdCl$_2$(dppf)-DCM adduct; Pd$_2$(dba)$_3$, Pd(OAc)$_2$, chloro(2- dicyclohexylphosphino-2',4',6'-triisopropyl-1,1'-biphenyl) [2-(2'-amino-1,1 '-biphenyl)]palladium (II) (XPhos-Pd-G2), or (2-dicyclohexylphosphino-2',4',6'-triisopropyl-1,1'-biphenyl) [2,-(2'-amino-1,1'- biphenyl)]palladium(II) methanesulfonate (XPhos-Pd-G3)).

In certain embodiments, compounds of Formula (B), and salts thereof, wherein m is 0 and $R^3$ is -O$R^{3a}$ or -N($R^{3a}$)$_2$, may be prepared following the method depicted in Scheme 5. For example, in certain embodiments, a compound of Formula (J), or salt thereof, may be coupled to a compound of Formula (K1) or (K2), or salt thereof, wherein $PG^2$ is hydrogen or an amino protecting group, and $LG^2$ and $LG^5$ are leaving groups which may be the same or different, to provide a compound of Formula (K1A) or (K2A), or salt thereof. See Scheme 5, Steps S8 and S10. In certain embodiments, $PG^2$ is hydrogen, -$CH_2$- phenyl, -S(=O)$_2R^G$ or -C(=O)O$R^G$ wherein $R^G$ is alkyl or phenyl, wherein each instance of phenyl is unsubstituted or substituted by halogen, -$C_{1-3}$alkyl, -O$C_{1-3}$alkyl, or -$NO_2$. In certain embodiments, $PG^2$ is hydrogen, a t-Butoxycarbonyl (Boc) group, a toluenesulfonyl (Ts) group, a 2-nitrobenenesulfonyl (Ns) group, or a paramethoxybenzyl (PMB) group. In certain embodiments, the compound of Formula (J), or salt thereof, is treated with a base (e.g., n-butyllithium, s-butyllithium, or t-butyllithium) in order to form a metalated (e.g., lithium) anion before treatment with a compound of Formula (K1) or (K2), or salt thereof, to provide a compound of Formula (B1A) or (B2A), or salt thereof. In certain further embodiments, the compound of Formula (B1A), or salt thereof, is treated with a compound of $R^{3a}LG^6$, or salt thereof, wherein $R^{3a}$ is $C_{1-3}$alkyl or $C_{1-3}$haloalkyl, and $LG^6$ is a leaving group, to provide an alkylated product of Formula (B1B), or salt thereof. See Scheme 5, Step S9. Alternatively, in certain further embodiments, the compound of Formula (B2A), or salt thereof, is treated with a compound of $R^{3a}LG^6$ or $R^{3b}$CHO, or salt thereof, wherein $R^{3a}$ is $C_{1-3}$alkyl or $C_{1-3}$haloalkyl, and $R^{3b}$ is $C_{1-2}$alkyl or $C_{1-2}$haloalkyl, to provide an alkylated product of Formula (B2B), or salt thereof wherein $R^{3a}$ is $C_{1-3}$alkyl or $C_{1-3}$haloalkyl (from reaction with $R^{3a}LG^6$), or -$CH_2$-$C_{1-2}$alkyl or -$CH_2$-$C_{1-2}$haloalkyl (from reaction with $R^{3b}$CHO), and the other $R^{3a}$ is hydrogen, or $C_{1-3}$alkyl or $C_{1-3}$haloalkyl (from additional reaction with $R^{3a}LG^6$). See Scheme 5, Step S11.

Scheme 5.

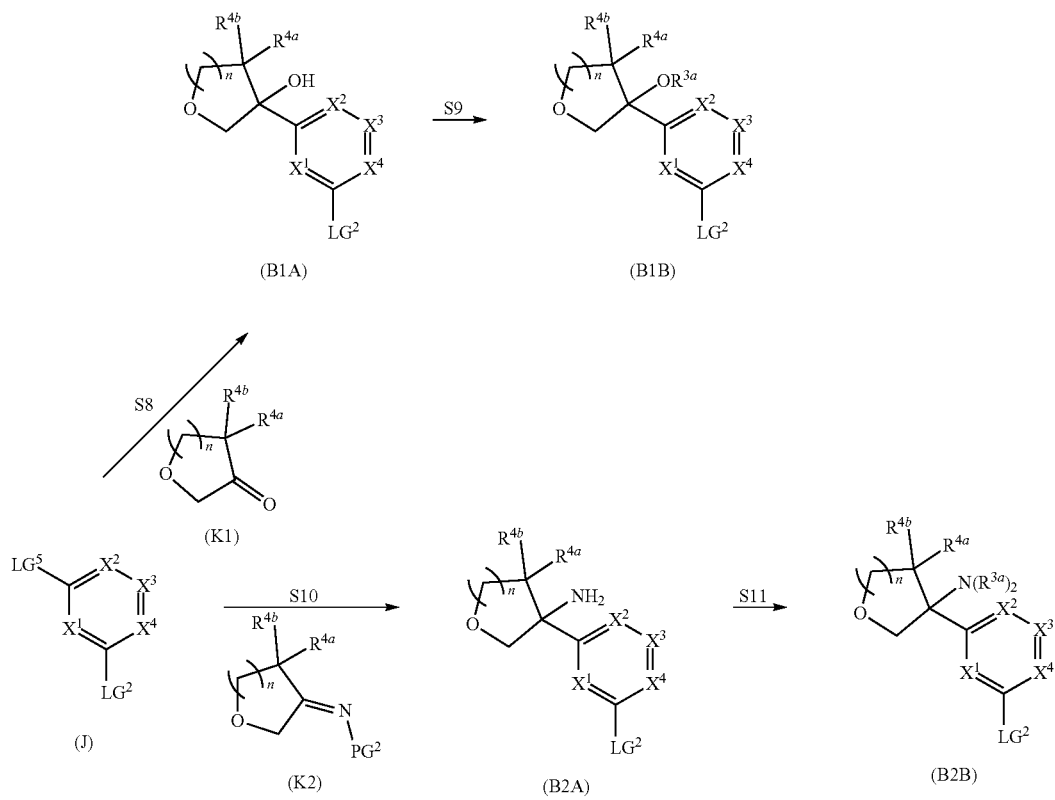

In certain embodiments, compounds of Formula (B), and salts thereof, wherein $R^3$ is -($C_{1-3}$alkylene)$_m$-OR$^{3a}$, -($C_{1-3}$alkylene)$_m$-N(R$^{3a}$)$_2$, $C_{1-3}$alkyl, or $C_{1-3}$haloalkyl, may be prepared following the method depicted in Scheme 6. For example, in certain embodiments, a compound of Formula (J), or salt thereof, may be coupled to a compound of Formula (K3), or salt thereof, using with a base (e.g., cesium carbonate, potassium phosphate, sodium carbonate) and a palladium catalyst (e.g., PdCl$_2$(dppf)-DCM adduct; Pd$_2$(dba)$_3$), wherein LG$^2$ and LG$^5$ are leaving groups, which may be the same or different, to provide a compound of Formula (B3A), or salt thereof. See Scheme 6, Step S12.

In certain embodiments, the compound of Formula (B3A), or salt thereof, is treated with an epoxidizing reagent (e.g., meta-chloroperoxybenzoic acid) to provide an epoxidized compound of Formula (B3B), or salt thereof. See Scheme 6, Step S13. In certain embodiments the epoxidized compound of Formula (B3B), or salt thereof, is treated with an acid (e.g., a Lewis acid such as scandium triflate or boron trifluoride etherate, or an inorganic acid such as sulfuric acid) to provide the rearranged product of Formula (B3C), or salt thereof. See Scheme 6, Step S14.

The aldehyde functional group of the compound of Formula (B3C), or salt thereof, may be synthetically manipulated to provide various compounds of Formula (B), and salts thereof. For example, the compound Formula (B3C), or salt thereof, may be reductively aminated with a compound of Formula NH(R$^{3a}$)$_2$, or salt thereof, to provide a compound of Formula (B3E), or salt thereof. See Scheme 6, Step S15. Alternatively, the aldehyde functional group may be reduced (e.g., using NaBH$_4$) to a -CH$_2$OH moiety, and optionally alkylated with a compound of R$^{3a}$LG$^6$, or salt thereof, wherein LG$^6$ is a leaving group, to provide a compound of Formula (B3D), or salt thereof, wherein R$^{3a}$ is hydrogen (from reduction) or R$^{3a}$ is $C_{1-3}$alkyl, or $C_{1-3}$haloalkyl (from subsequent optional alkylation). See Scheme 6, Step S16. Alternatively, the aldehyde functional group may be homologated to an olefin (e.g., upon treatment with trialkylsilylmethyl Grignard (e.g., (CH$_3$)$_3$SiCH$_2$MgCl, followed by treatment with a Lewis Acid; or upon treatment with a phosphonium ylide (e.g., CH$_2$PPh$_3$) via a Wittig homologation reaction) to provide a compound of Formula (B3F), or salt thereof. See Scheme 6, Step S17. The olefinic compound of Formula (B3F), or salt thereof, may then be reduced (e.g., using hydrogenation conditions, such as H$_2$ and Pd/C) to provide a compound of Formula (B3G), or salt thereof. See Scheme 6, Step S18. Alternatively, the aldehyde functional group may be treated with a nucleophilic (alkylating) agent, such as a methyl or ethyl Grignard reagent (e.g., CH$_3$MgBr, CH$_3$CH$_2$MgBr) to provide a compound of Formula (B3H), or salt thereof, wherein R' is $C_{1-2}$alkyl, and R$^{3a}$ is hydrogen or R$^{3a}$ is $C_{1-3}$alkyl, or $C_{1-3}$haloalkyl (from subsequent optional alkylation). See Scheme 6, Step S21.

Scheme 6.

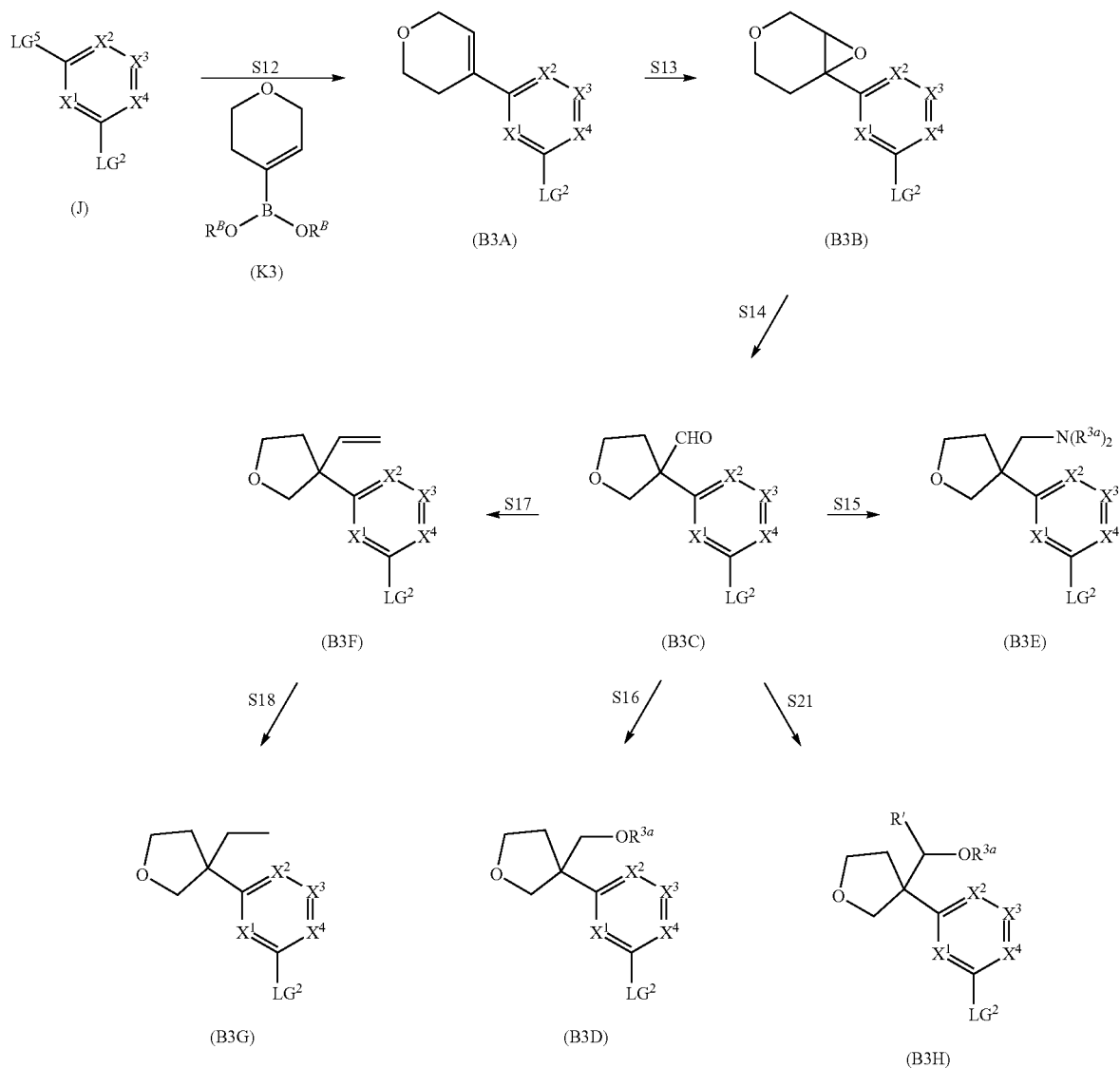

In certain embodiments, compounds of Formula (B), and salts thereof, wherein $R^3$ is hydrogen, may be prepared following the method depicted in Scheme 7. For example, in certain embodiments, a compound of Formula (J), or salt thereof, is coupled to a compound of Formula (K4), or salt thereof, wherein $LG^2$, $LG^5$, and $LG^7$ are leaving groups, which may be the same or different, to provide a compound of Formula (B4A), or salt thereof. In certain embodiments, one of $LG^5$ and $LG^7$ is a boronic acid or boronic ester (e.g., a dioxoborolane group, such as tetramethyldioxoborolane), the other of $LG^5$ and $LG^7$ is a halogen group (e.g., -Cl, -Br, -I), and $LG^2$ is a halogen group (e.g., -Cl, -Br, -I). In certain embodiments, $LG^5$ is a boronic acid or boronic ester (e.g., a dioxoborolane group, such as tetramethyldioxoborolane), and each of $LG^7$ and $LG^2$ are halogen groups, which may be the same or different.

Scheme 7.

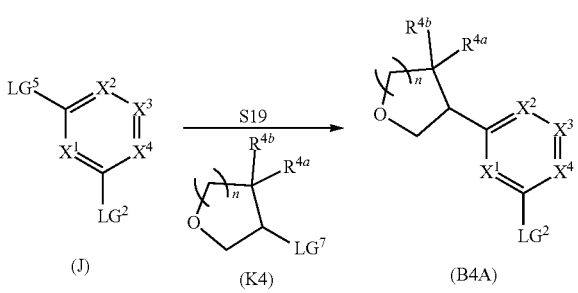

In certain embodiments, compounds of Formula (B), and salts thereof, wherein $R^3$ is $C_{1-3}$alkyl or $C_{1-3}$haloalkyl, may be prepared following the method depicted in Scheme 8. For example, in certain embodiments, a compound of Formula (L), or salt thereof, may be cyclized to the ether (such as using Mitzunobu conditions (e.g., PPh$_3$ and an azodicarboxylate, such as diethyl azodicarboxylate (DEAD) or diisopropyl azodicarboxylate (DIAD)), to provide a compound of Formula (B5), or salt thereof.

Scheme 8.

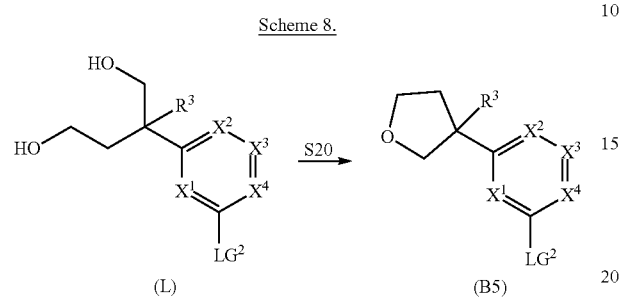

(L)    (B5)

In certain embodiments, compounds of Formula (B), and salts thereof, wherein X$^1$ is N and X$^3$ is CH, may be further synthetically manipulated to install a -OR$^{5a}$ group at X$^3$. For example, in certain embodiments, a compound of Formula (B-6A), or salt thereof, may be treated with an iridium or ruthenium dimer species (e.g., 1,5-cyclooctadiene methoxyiridium dimer or pentamethylcyclopentadienyl ruthenium dichloride dimer) and optionally a ligand (e.g., 4,4'-di-tert-butyl-2',2'-bipyridine) in combination with (R$^B$O)$_2$B-B(OR$^B$)$_2$ (e.g., bis(pinacolato)diboron) to provide a boronate ester of Formula (B-6B), or salt thereof, wherein each R$^B$ is C$_{1-3}$alkyl, or each R$^B$ is joined to form a 5- to 6-membered ring optionally substituted with 1, 2, 3, or 4 C$_{1-3}$alkyl groups. See Scheme 9, Step S22. In certain embodiments, the boronate ester of Formula (B-6B), or salt thereof, may be converted to a compound of Formula (B-6C), or salt thereof, upon treatment with an oxidizing reagent (e.g., potassium peroxomonosulfate), followed by subsequent alkylation (e.g., with a compound of formula R$^{5a}$LG$^8$, wherein LG$^8$ is a leaving group) to provide a compound of Formula (B-6D), or salt thereof. See Scheme 9, Steps S23-S24. In certain embodiments, LG$^8$ is halo (e.g., chloro, bromo, iodo) or an activated hydroxyl group (e.g., -OTf, -OTs, -OMs, or -OBs).

Scheme 9.

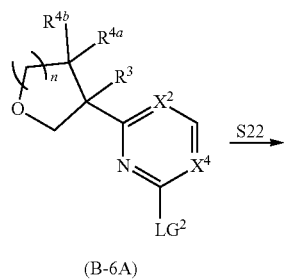

(B-6A)

-continued

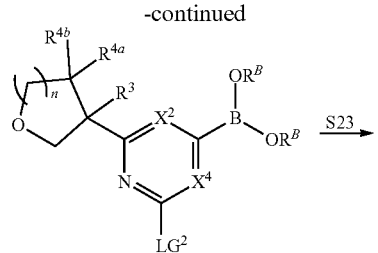

(B-6B)

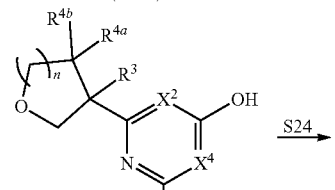

(B-6C)

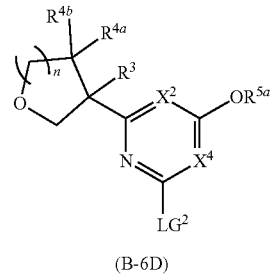

(B-6D)

(vii) Embodiments 1-125
Embodiments 1-125 are further provided herein.
Embodiment 1: a compound of Formula (I):

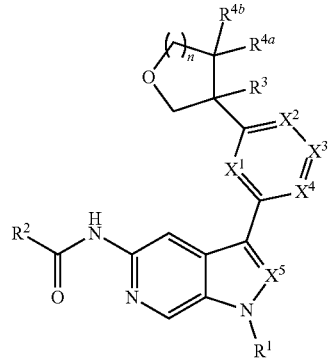

(I)

or a pharmaceutically acceptable salt thereof;
wherein:
R$^1$ is hydrogen, or R$^1$ is unsubstituted or substituted C$_{1-6}$alkyl, unsubstituted or substituted C$_{3-6}$carbocyclyl, or unsubstituted or substituted 4- to 6-membered heterocyclyl;
R$^2$ is -NH$_2$, -NHR$^{2a}$, -OR$^{2a}$, unsubstituted or substituted C$_{1-6}$alkyl, or unsubstituted or substituted C$_3$carbocyclyl, and $^{Rea}$ is unsubstituted or substituted C$_{1-6}$alkyl or unsubstituted or substituted C$_3$carbocyclyl;
R$^3$ is hydrogen, -(C$_{1-3}$alkylene)$_m$-OR$^{3a}$, -(C$_{1-3}$alkylene)$_m$-N(R$^{3a}$)$_2$, C$_{1-3}$alkyl, or C$_{1-3}$haloalkyl, wherein m is 0 or 1, and each instance of R$^{3a}$ is independently hydrogen, C$_{1-3}$alkyl, or C$_{1-3}$haloalkyl;

n is 0 or 1, and each instance of $R^{4a}$ and $R^{4b}$ is independently hydrogen, halogen, $C_{1-3}$alkyl, or $C_{1-3}$haloalkyl, or $R^{4a}$ and $R^{4b}$ are joined to form an oxo (=O) group; or n is 1, $R^{4a}$ is hydrogen, $C_{1-3}$alkyl, or $C_{1-3}$haloalkyl, and $R^{4b}$ is -OH, -$OR^{4c}$, or -OC(=O)$R^{4d}$, wherein each instance of $R^{4c}$ and $R^{4d}$ is independently unsubstituted or substituted $C_{1-3}$alkyl;

$X^3$ is N or $CR^5$, wherein $R^5$ is hydrogen, -CN, -$OR^{5a}$, -$NHR^{5a}$, or unsubstituted or substituted $C_{1-6}$alkyl, and $R^{5a}$ is unsubstituted or substituted $C_{1-6}$alkyl, unsubstituted or substituted $C_{3-6}$carbocyclyl, unsubstituted or substituted $C_{3-6}$carbocyclyl$C_{1-3}$alkyl, unsubstituted or substituted 4- to 6-membered heterocyclyl, or unsubstituted or substituted 4- to 6-membered heterocyclyl$C_{1-3}$alkyl;

each instance of $X^1$, $X^2$, $X^4$, and $X^5$ is independently N or CH, provided no more than two of $X^2$, $X^3$, and $X^4$ is N; and each instance of substituted is independent substitution with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl.

Embodiment 2: The compound of Embodiment 1, or a pharmaceutically acceptable salt thereof, wherein $R^1$ is unsubstituted or substituted $C_{1-6}$alkyl, unsubstituted or substituted $C_{3-6}$carbocyclyl, or unsubstituted or substituted 4- to 6-membered heterocyclyl.

Embodiment 3: The compound of Embodiment 2, or a pharmaceutically acceptable salt thereof, wherein $R^1$ is an unsubstituted $C_{1-6}$alkyl, or $C_{1-6}$alkyl substituted with 1, 2, or 3 substituents selected from the group consisting of halogen, -CN, -OH, -$OC_{1-3}$alkyl, and -$OC_{1-3}$haloalkyl.

Embodiment 4: The compound of Embodiment 3, or a pharmaceutically acceptable salt thereof, wherein $R^1$ is unsubstituted $C_{1-2}$alkyl, or $C_{1-2}$alkyl substituted with 1, 2, or 3 substituents selected from the group consisting of halogen, -CN, -OH, -$OC_{1-3}$alkyl, and -$OC_{1-3}$haloalkyl.

Embodiment 5: The compound of Embodiment 2, or a pharmaceutically acceptable salt thereof, wherein $R^1$ is unsubstituted or substituted $C_{3-6}$carbocyclyl.

Embodiment 6: The compound of Embodiment 5, or a pharmaceutically acceptable salt thereof, wherein $R^1$ is unsubstituted $C_3$carbocyclyl, or $C_3$carbocyclyl substituted with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl.

Embodiment 7: The compound of Embodiment 5, or a pharmaceutically acceptable salt thereof, wherein $R^1$ is unsubstituted $C_4$carbocyclyl, or $C_4$carbocyclyl substituted with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl.

Embodiment 8: The compound of Embodiment 5, or a pharmaceutically acceptable salt thereof, wherein $R^1$ is $C_{3-4}$carbocyclyl substituted with 1, 2, or 3 halogen substituents, or 1 -CN substituent.

Embodiment 9: The compound of Embodiment 2, or a pharmaceutically acceptable salt thereof, wherein $R^1$ is unsubstituted or substituted 4- to 6-membered heterocyclyl.

Embodiment 10: The compound of Embodiment 9, or a pharmaceutically acceptable salt thereof, wherein $R^1$ is unsubstituted 4- to 5-membered heterocyclyl containing 1 or 2 ring heteroatoms independently selected from the group consisting of oxygen and nitrogen, or 4- to 5-membered heterocyclyl containing 1 or 2 ring heteroatoms independently selected from the group consisting of oxygen and nitrogen and which is substituted with 1, 2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl.

Embodiment 11: The compound of Embodiment 10, or a pharmaceutically acceptable salt thereof, wherein $R^1$ is unsubstituted oxetanyl, or oxetanyl substituted with 1,2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl.

Embodiment 12: The compound of Embodiment 10, or a pharmaceutically acceptable salt thereof, wherein $R^1$ is unsubstituted tetrahydrofuranyl, or tetrahydrofuranyl substituted with 1,2, or 3 substituents selected from the group consisting of halogen, -CN, -OH, $C_{1-3}$alkyl, $C_{1-3}$haloalkyl, -$OC_{1-3}$alkyl, and -$OC_{1-3}$haloalkyl.

Embodiment 13: The compound of Embodiment 1, or a pharmaceutically acceptable salt thereof, wherein $R^1$ is -$CH_3$, -CHF, -$CF_3$,

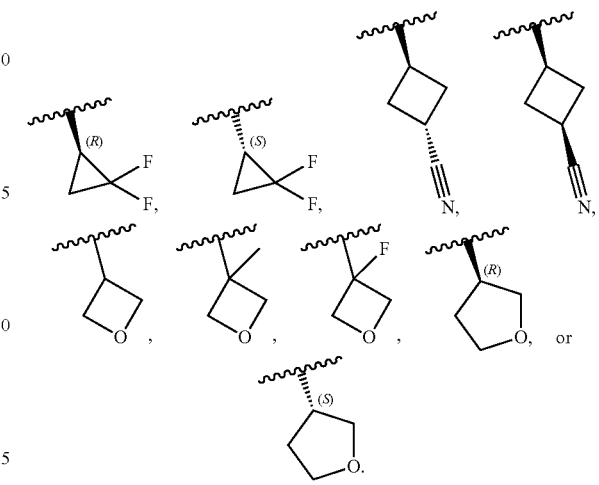

Embodiment 14: The compound of any one of Embodiments 1-13, or a pharmaceutically acceptable salt thereof, wherein $R^2$ is -$NH_2$, -$NHR^{2a}$, -$OR^{2a}$, or unsubstituted or substituted $C_{1-6}$alkyl, and $R^{2a}$ is unsubstituted or substituted $C_{1-6}$alkyl.

Embodiment 15: The compound of Embodiment 14, or a pharmaceutically acceptable salt thereof, wherein $R^2$ is -$NH_2$.

Embodiment 16: The compound of Embodiment 14, or a pharmaceutically acceptable salt thereof, wherein $R^2$ is unsubstituted or substituted $C_{1-6}$alkyl.

Embodiment 17: The compound of Embodiment 16, or a pharmaceutically acceptable salt thereof, wherein $R^2$ is unsubstituted or substituted $C_{1-3}$alkyl.

Embodiment 18: The compound of any one of Embodiments 1-13, or a pharmaceutically acceptable salt thereof, wherein $R^2$ is unsubstituted $C_3$carbocyclyl, or $C_3$carbocyclyl substituted with 1,2, or 3 halogen substituents.

Embodiment 19: The compound of any one of Embodiments 1-13, or a pharmaceutically acceptable salt thereof, wherein $R^2$ is -$NH_2$, -$NHCH_3$, -$OCH_3$, -$CH_3$, or -$CH_2OH$.

Embodiment 20: The compound of any one of Embodiments 1-19, or a pharmaceutically acceptable salt thereof, wherein n is 1.

Embodiment 21: The compound of any one of Embodiments 1-19, or a pharmaceutically acceptable salt thereof, wherein n is 0.

Embodiment 22: The compound of any one of Embodiments 1-21, or a pharmaceutically acceptable salt thereof, wherein $R^3$ is -$(C_{1-3}$alkylene$)_m$-OR$^{3a}$, -$(C_{1-3}$alkylene$)_m$-N$(R^{3a})_2$, $C_{1-3}$alkyl, or $C_{1-3}$haloalkyl.

Embodiment 23: The compound of Embodiment 22, or a pharmaceutically acceptable salt thereof, wherein $R^3$ is -$(C_{1-3}$alkylene$)_m$-OR$^{3a}$ or -$(C_{1-3}$alkylene$)_3$-N$(R^{3a})_2$.

Embodiment 24: The compound of Embodiment 22 or 23, or a pharmaceutically acceptable salt thereof, wherein $R^3$ is -$(C_{1-3}$alkylene$)_m$-OR$^{3a}$ or -$(C_{1-3}$alkylene$)_m$-N$(R^{3a})_2$ and m is 0.

Embodiment 25: The compound of Embodiment 22 or 23, or a pharmaceutically acceptable salt thereof, wherein $R^3$ is -$(C_{1-3}$alkylene$)_m$-OR$^{3a}$ or -$(C_{1-3}$alkylene$)_m$-N$(R^{3a})_2$ and m is 1.

Embodiment 26: The compound of Embodiment 22, or a pharmaceutically acceptable salt thereof, wherein $R^3$ is $C_{1-3}$alkyl or $C_{1-3}$haloalkyl.

Embodiment 27: The compound of any one of Embodiments 1-21, or a pharmaceutically acceptable salt thereof, wherein $R^3$ is hydrogen.

Embodiment 28: The compound of any one of Embodiments 1-21, or a pharmaceutically acceptable salt thereof, wherein $R^3$ is -OH, -OCH$_3$, -CH(OH)CH$_3$, -CH$_3$, -CH$_2$CH$_3$, -CH$_2$OH, or -CH$_2$NH$_2$.

Embodiment 29: The compound of any one of Embodiments 1-28, or a pharmaceutically acceptable salt thereof, wherein each instance of $R^{4a}$ and $R^{4ab}$ is hydrogen.

Embodiment 30: The compound of any one of Embodiments 1-29, or a pharmaceutically acceptable salt thereof, wherein $X^3$ is N.

Embodiment 31: The compound of any one of Embodiments 1-29, or a pharmaceutically acceptable salt thereof, wherein $X^3$ is CR$^5$.

Embodiment 32: The compound of Embodiment 31, or a pharmaceutically acceptable salt thereof, wherein $R^5$ is hydrogen.

Embodiment 33: The compound of Embodiment 31, or a pharmaceutically acceptable salt thereof, wherein $R^5$ is -CN.

Embodiment 34: The compound of Embodiment 31, or a pharmaceutically acceptable salt thereof, wherein $R^5$ is -OR$^{5a}$ or -NHR$^{5a}$, wherein $R^{5a}$ is unsubstituted $C_{1-6}$alkyl or $C_{1-6}$alkyl independently substituted with 1, 2, or 3 substituents selected from the group consisting of halogen, -CN, -OH, -OC$_{1-3}$alkyl, and -OC$_{1-3}$haloalkyl.

Embodiment 35: The compound of Embodiment 31, or a pharmaceutically acceptable salt thereof, wherein $R^5$ is -OR$^{5a}$ or -NHR$^{5a}$, wherein $R^{5a}$ is unsubstituted or substituted $C_{3-6}$carbocyclyl or unsubstituted or substituted $C_{3-6}$carbocyclylC$_{1-3}$alkyl, and wherein the substituted $C_{3-6}$carbocyclyl is independently substituted with 1, 2, or 3 substituents selected from the group consisting of halogen, -CN, -OH, $C_{1-3}$alkyl, $C_{1-3}$haloalkyl, -OC$_{1-3}$alkyl, and -OC$_{1-3}$haloalkyl.

Embodiment 36: The compound of Embodiment 31, or a pharmaceutically acceptable salt thereof, wherein $R^5$ is -OR$^{5a}$ or -NHR$^{5a}$, wherein $R^{5a}$ is unsubstituted or substituted 4- to 6-membered heterocyclyl or unsubstituted or substituted 4- to 6-membered heterocyclylC$_{1-3}$alkyl, wherein the substituted 4- to 6-membered heterocyclyl group is independently substituted with 1, 2, or 3 substituents selected from the group consisting of halogen, -CN, -OH, $C_{1-3}$alkyl, $C_{1-3}$haloalkyl, -OC$_{1-3}$alkyl, and -OC$_{1-3}$haloalkyl.

Embodiment 37: The compound of Embodiment 31, or a pharmaceutically acceptable salt thereof, wherein $R^5$ is hydrogen, -CN, -CH$_3$, -CH$_2$F, -CHF$_2$, -CF$_3$, -CH$_2$OCH$_3$, -OCH$_3$, -OCH$_2$CH$_3$, -OCH(CH$_3$)$_2$, -OCH$_2$CH$_2$OH, -OCH$_2$CH$_2$OCH$_3$, -OCHF$_2$, -OCH$_2$CN,

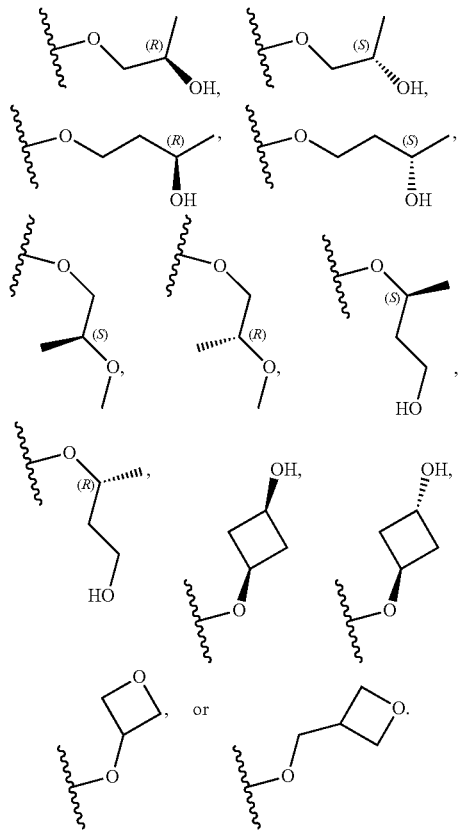

Embodiment 38: The compound of Embodiment 31, wherein $R^5$ is unsubstituted $C_{1-6}$alkyl or $C_{1-6}$alkyl substituted with 1, 2, or 3 substituents selected from the group consisting of halogen, -CN, -OH, $C_{1-3}$alkyl, $C_{1-3}$haloalkyl, -OC$_{1-3}$alkyl, and -OC$_{1-3}$haloalkyl.

Embodiment 39: The compound of Embodiment 38, wherein $R^5$ is $C_{1-3}$alkyl substituted with 1 substituent selected from the group consisting of -OH, -OC$_{1-3}$alkyl and -OC$_{1-3}$haloalkyl.

Embodiment 40: The compound of Embodiment 39, wherein $R^5$ is $C_{1-3}$alkyl substituted with 1 substituent that is -OC$_{1-3}$alkyl.

Embodiment 41: The compound of Embodiment 39, wherein $R^5$ is $C_1$alkyl substituted with 1 substituent selected from the group consisting of -OH, -OC$_{1-3}$alkyl and -OC$_{1-3}$haloalkyl.

Embodiment 42: The compound of any one of Embodiments 1-41, or a pharmaceutically acceptable salt thereof, wherein $X^1$ is N.

Embodiment 43: The compound of any one of Embodiments 1-42, or a pharmaceutically acceptable salt thereof, wherein $X^2$ is CH.

Embodiment 44: The compound of any one of Embodiments 1-43, or a pharmaceutically acceptable salt thereof, wherein $X^4$ is CH.

Embodiment 45: The compound of any one of Embodiments 1-44, or a pharmaceutically acceptable salt thereof, wherein $X^5$ is CH.

Embodiment 46: The compound of any one of Embodiments 1-29 and 31-41, or a pharmaceutically acceptable salt thereof, wherein $X^2$ is CH, $X^3$ is CR$^5$, and $X^4$ is CH.

Embodiment 47: The compound of any one of Embodiments 1-29, or a pharmaceutically acceptable salt thereof, wherein $X^1$ is N; $X^2$ is CH; $X^4$ is CH or N; $X^5$ is CH or N; and $X^3$ is N or $CR^5$.

Embodiment 48: The compound of Embodiment 47, or a pharmaceutically acceptable salt thereof, wherein $X^1$ is N; $X^2$ is CH; $X^4$ is CH; $X^5$ is CH; and $X^3$ is N or $CR^5$.

Embodiment 49: The compound of Embodiment 47, or a pharmaceutically acceptable salt thereof, wherein $X^1$ is N; $X^2$ is CH; $X^4$ is CH; $X^5$ is CH; and $X^3$ is $CR^5$.

Embodiment 50: The compound of Embodiment 1, or a pharmaceutically acceptable salt thereof, wherein:
$X^1$ is N; $X^2$, $X^4$, and $X^5$ are each CH; $X^3$ is N or $CR^5$; $R^1$ is unsubstituted or substituted $C_{1-3}$alkyl, unsubstituted or substituted $C_{3-4}$carbocyclyl, or unsubstituted or substituted 4- to 5-membered heterocyclyl;
$R^2$ is $-NH_2$, $-NHR^{2a}$, $-OR^{2a}$, unsubstituted or substituted $C_{1-3}$alkyl, and $R^{2a}$ is unsubstituted or substituted $C_{1-3}$alkyl;
$R^3$ is $-(C_{1-3}alkylene)_m-OR^{3a}$, $-(C_{1-3}alkylene)_m-N(R^{3a})_2$, $C_{1-3}$alkyl, or $C_{1-3}$haloalkyl, wherein each instance of $R^{3a}$ is independently hydrogen, $C_{1-3}$alkyl, or $C_{1-3}$haloalkyl; each instance of $R^{4a}$ and $R^{4b}$ is hydrogen;
$R^5$ is hydrogen, -CN, $-OR^{5a}$, $-NHR^{5a}$, or unsubstituted or substituted $C_{1-6}$alkyl, wherein $R^{5a}$ is unsubstituted or substituted $C_{1-6}$alkyl, unsubstituted or substituted $C_{3-6}$carbocyclyl, unsubstituted or substituted $C_{3-6}$carbocyclyl$C_{1-3}$alkyl, unsubstituted or substituted 4- to 6-membered heterocyclyl, or unsubstituted or substituted 4- to 6-membered heterocyclyl$C_{1-3}$alkyl;
m is 0 or 1; and n is 0 or 1; wherein substituted is independent substitution with 1, 2, or 3 substituents selected from the group consisting of halogen, -CN, -OH, $C_{1-3}$alkyl, $C_{1-3}$haloalkyl, $-OC_{1-3}$alkyl, and $-OC_{1-3}$haloalkyl.

Embodiment 51: The compound of Embodiment 50, or a pharmaceutically acceptable salt thereof, wherein:
$X^1$ is N;
$X^2$, $X^4$, and $X^5$ are each CH;
$X^3$ is N or $CR^5$;
$R^1$ is unsubstituted or substituted $C_{1-3}$alkyl, wherein substituted is independent substitution with 1, 2, or 3 substituents selected from the group consisting of halogen, -CN, -OH, $-OC_{1-3}$alkyl, and $-OC_{1-3}$haloalkyl;
$R^2$ is $-NH_2$, $-NHCH_3$, $-CH_3$, or $-CH_2OH$;
$R^3$ is $-(C_{1-3}alkylene)_m-OR^{3a}$, $C_{1-3}$alkyl, or $C_{1-3}$haloalkyl;
$R^{4a}$ and $R^{4b}$ are each hydrogen;
m is 0 or 1; and
n is 0 or 1.

Embodiment 52: The compound of Embodiment 50, or a pharmaceutically acceptable salt thereof, wherein:
$X^1$ is N;
$X^2$, $X^4$, and $X^5$ are each CH;
$X^3$ is N or $CR^5$;
$R^1$ is unsubstituted or substituted $C_{3-4}$carbocyclyl, wherein substituted is independent substitution with 1, 2, or 3 substituents selected from the group consisting of halogen, -CN, -OH, $C_{1-3}$alkyl, $C_{1-3}$haloalkyl, $-OC_{1-3}$alkyl, and $-OC_{1-3}$haloalkyl;
$R^2$ is $-NH_2$, $-NHCH_3$, $-CH_3$, or $-CH_2OH$;
$R^3$ is $-(C_{1-3}alkylene)_m-OR^{3a}$, $C_{1-3}$alkyl, or $C_{1-3}$haloalkyl;
$R^4a$ and $R^{4b}$ are each hydrogen;
m is 0 or 1; and
n is 0 or 1.

Embodiment 53: The compound of Embodiment 50, or a pharmaceutically acceptable salt thereof, wherein:
$X^1$ is N;
$X^2$, $X^4$, and $X^5$ are each CH;
$X^3$ is N or $CR^5$;
$R^1$ is unsubstituted or substituted 4- to 5-membered heterocyclyl, wherein substituted is independent substitution with 1, 2, or 3 substituents selected from the group consisting of halogen, -CN, -OH, $C_{1-3}$alkyl, $C_{1-3}$haloalkyl, $-OC_{1-3}$alkyl, and $-OC_{1-3}$haloalkyl;
$R^2$ is $-NH_2$, $-NHCH_3$, $-CH_3$, or $-CH_2OH$;
$R^3$ is $-(C_{1-3}alkylene)_m-OR^{3a}$, $C_{1-3}$alkyl, or $C_{1-3}$haloalkyl;
$R^4a$ and $R^{4b}$ are each hydrogen;
m is 0 or 1; and
n is 0 or 1.

Embodiment 54: The compound of Embodiment 50, or a pharmaceutically acceptable salt thereof, wherein:
$X^1$ is N;
$X^2$, $X^4$, and $X^5$ are each CH;
$X^3$ is $CR^5$;
$R^1$ is unsubstituted $C_{1-3}$alkyl, or unsubstituted or substituted 4-membered heterocyclyl, wherein substituted is independent substitution with 1, 2, or 3 substituents selected from the group consisting of halogen, -CN, -OH, $C_{1-3}$alkyl, $C_{1-3}$haloalkyl, $-OC_{1-3}$alkyl, and $-OC_{1-3}$haloalkyl;
$R^2$ is $-CH_3$;
$R^3$ is $-(C_{1-3}alkylene)_m-OR^{3a}$;
$R^{4a}$ and $R^{4b}$ are each hydrogen;
$R^5$ is $C_1$alkyl substituted with 1 substituent selected from the group consisting of -OH, $-OC_{1-3}$alkyl and $-OC_{1-3}$haloalkyl;
m is 0 or 1; and
n is 1.

Embodiment 55: The compound of Embodiment 50, or a pharmaceutically acceptable salt thereof, wherein:
$X^1$ is N;
$X^2$, $X^4$, and $X^5$ are each CH;
$X^3$ is $CR^5$;
$R^1$ is unsubstituted $C_{1-3}$alkyl;
$R^2$ is $-CH_3$;
$R^3$ is $-(C_{1-3}alkylene)_m-OR^{3a}$ wherein m is 0;
$R^{4a}$ and $R^{4b}$ are each hydrogen;
$R^5$ is $C_1$alkyl substituted with 1 substituent selected from the group consisting of -OH, $-OC_{1-3}$alkyl and $-OC_{1-3}$haloalkyl; and
n is 1.

Embodiment 56: The compound of Embodiment 1, or a pharmaceutically acceptable salt thereof, wherein:
$X^1$ is N;
$X^2$, $X^4$, and $X^5$ are CH;
$X^3$ is $CR^5$;
$R^1$ is unsubstituted or substituted 4-membered heterocyclyl, wherein substituted is independent substitution with 1, 2, or 3 substituents selected from the group consisting of halogen, -CN, -OH, $C_{1-3}$alkyl, $C_{1-3}$haloalkyl, $-OC_{1-3}$alkyl, and $-OC_{1-3}$haloalkyl;
$R^2$ is $-CH_3$;
$R^3$ is $-(C_{1-3}alkylene)_m-OR^{3a}$ wherein m is 0;
$R^{4a}$ and $R^{4b}$ are each hydrogen;
$R^5$ is $C_1$alkyl substituted with 1 substituent selected from the group consisting of -OH, $-OC_{1-3}$alkyl and $-OC_{1-3}$haloalkyl; and
n is 1.

Embodiment 57: The compound of Embodiment 1, or a pharmaceutically acceptable salt thereof, wherein
$X^1$ is N;
$X^2$, $X^4$, and $X^5$ are each CH;
$X^3$ is $CR^5$;
$R^1$ is unsubstituted $C_{1-3}$alkyl;
$R^2$ is $-CH_3$;
$R^3$ is $-(C_{1-3}alkylene)_m-OR^{3a}$ wherein m is 0;
$R^{4a}$ and $R^{4b}$ are each hydrogen;

$R^5$ is $-OR^{5a}$ wherein $R^{5a}$ is $C_{1-6}$alkyl substituted with 1 substituent selected from the group consisting of -OH, $-OC_{1-3}$alkyl and $-OC_{1-3}$haloalkyl; and
n is 1.

Embodiment 58: The compound of Embodiment 1, or a pharmaceutically acceptable salt thereof, wherein:
$X^1$ is N;
$X^2$, $X^4$, and $X^5$ are each CH;
$X^3$ is $CR^5$;
$R^1$ is unsubstituted $C_{1-3}$alkyl;
$R^2$ is $-CH_3$;
$R^3$ is $-(C_{1-3}$alkylene$)_m$-$OR^{3a}$ wherein m is 1;
$R^{4a}$ and $R^{4b}$ are each hydrogen;
$R^5$ is $C_1$alkyl substituted with 1 substituent selected from the group consisting of -OH, $-OC_{1-3}$alkyl and $-OC_{1-3}$haloalkyl; and
n is 1.

Embodiment 59: The compound of Embodiment 1, or a pharmaceutically acceptable salt thereof, wherein:
$X^1$ is N;
$X^2$, $X^4$, and $X^5$ are CH;
$X^3$ is $CR^5$;
$R^1$ is unsubstituted or substituted 4-membered heterocyclyl, wherein substituted is independent substitution with 1, 2, or 3 substituents selected from the group consisting of halogen, -CN, -OH, $C_{1-3}$alkyl, $C_{1-3}$haloalkyl, $-OC_{1-3}$alkyl, and $-OC_{1-3}$haloalkyl;
$R^2$ is $-CH_3$;
$R^3$ is $-(C_{1-3}$alkylene$)_m$-$OR^{3a}$ wherein m is 1;
$R^{4a}$ and $R^{4b}$ are each hydrogen;
$R^5$ is $C_1$alkyl substituted with 1 substituent selected from the group consisting of -OH, $-OC_{1-3}$alkyl and $-OC_{1-3}$haloalkyl; and
n is 1.

Embodiment 60: The compound of Embodiment 1, or a pharmaceutically acceptable salt thereof, wherein
$X^1$ is N;
$X^2$, $X^4$, and $X^5$ are each CH;
$X^3$ is $CR^5$;
$R^1$ is unsubstituted $C_{1-3}$alkyl;
$R^2$ is $-CH_3$;
$R^3$ is $-(C_{1-3}$alkylene$)_m$-$OR^{3a}$ wherein m is 1;
$R^{4a}$ and $R^{4b}$ are each hydrogen;
$R^5$ is $-OR^{5a}$ wherein $R^{5a}$ is $C_{1-6}$alkyl substituted with 1 substituent selected from the group consisting of -OH, $-OC_{1-3}$alkyl and $-OC_{1-3}$haloalkyl; and
n is 1.

Embodiment 61: The compound of Embodiment 1, or a pharmaceutically acceptable salt thereof, wherein:
$X^1$ is N;
$X^2$, $X^4$, and $X^5$ are each CH;
$X^3$ is $CR^5$;
$R^1$ is unsubstituted $C_{1-3}$alkyl;
$R^2$ is $-CH_3$;
$R^3$ is $-(C_{1-3}$alkylene$)_m$-$OR^{3a}$ wherein m is 0;
$R^{4a}$ and $R^{4b}$ are each hydrogen;
$R^5$ is $-OR^{5a}$ wherein $R^{5a}$ is $C_{3-6}$carbocyclyl substituted with 1 substituent selected from the group consisting of -OH, $-OC_{1-3}$alkyl and $-OC_{1-3}$haloalkyl; and
n is 1.

Embodiment 62: The compound of Embodiment 1, or a pharmaceutically acceptable salt thereof, wherein:
$X^1$ is N;
$X^2$, $X^4$, and $X^5$ are each CH;
$X^3$ is $CR^5$;
$R^1$ is unsubstituted $C_{1-3}$alkyl;
$R^2$ is $-CH_3$;
$R^3$ is $-(C_{1-3}$alkylene$)_m$-$OR^{3a}$ wherein m is 1;
$R^{4a}$ and $R^{4b}$ are each hydrogen;
$R^5$ is $-OR^{5a}$ wherein $R^{5a}$ is $C_{3-6}$carbocyclyl substituted with 1 substituent selected from the group consisting of -OH, $-OC_{1-3}$alkyl and $-OC_{1-3}$haloalkyl; and
n is 1.

Embodiment 63: The compound of any one of Embodiments 1-62, wherein the compound is of Formula (I-a):

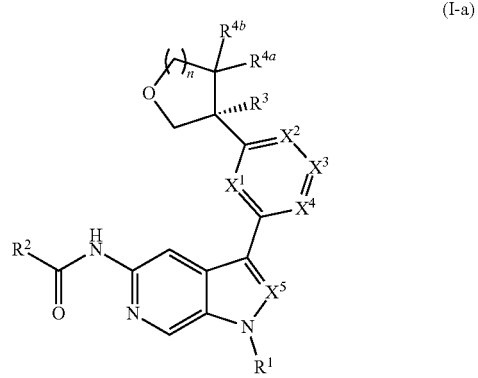

(I-a)

or a pharmaceutically acceptable salt thereof.

Embodiment 64: The compound of Embodiment 1, wherein the compound is of Formula (II-a):

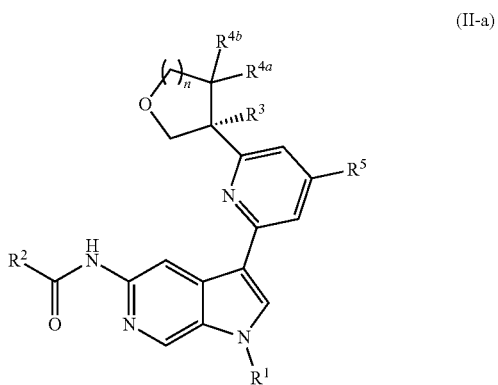

(II-a)

or a pharmaceutically acceptable salt thereof.

Embodiment 65: The compound of Embodiment 1, wherein the compound is of Formula (II-b):

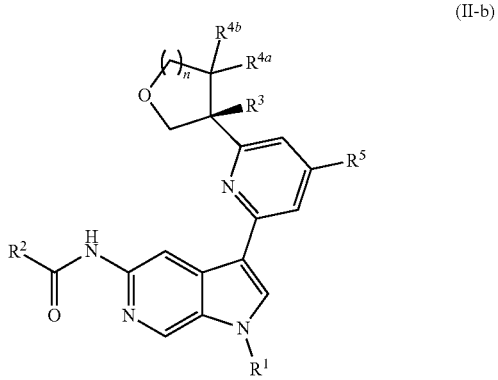

(II-b)

or a pharmaceutically acceptable salt thereof.

Embodiment 66: The compound of Embodiment 1, wherein the compound is of Formula (II-a):

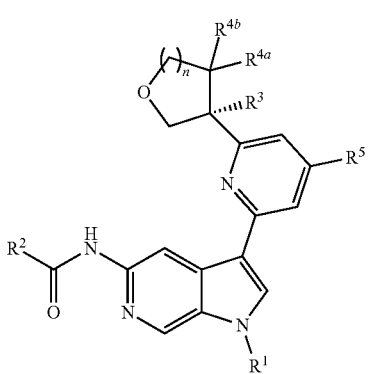

(II-a)

or a pharmaceutically acceptable salt thereof,
wherein:

$R^1$ is unsubstituted or substituted $C_{1-3}$alkyl, unsubstituted or substituted $C_{3-4}$carbocyclyl, or unsubstituted or substituted 4- to 5-membered heterocyclyl;

$R^2$ is $-NH_2$, $-NHR^{2a}$, unsubstituted or substituted $C_{1-3}$alkyl, and $R^{2a}$ is unsubstituted or substituted $C_{1-3}$alkyl;

$R^3$ is $-(C_{1-3}alkylene)_m-OR^{3a}$, $-(C_{1-3}alkylene)_m-N(R^{3a})_2$, $C_{1-3}$alkyl, or $C_{1-3}$haloalkyl, wherein m is 0 or 1, and each instance of $R^{3a}$ is independently hydrogen, $C_{1-3}$alkyl, or $C_{1-3}$haloalkyl;

each instance of $R^{4a}$ and $R^{4ab}$ is hydrogen;

$R^5$ is hydrogen, -CN, $-OR^{5a}$, $-NHR^{5a}$, or unsustituted or substituted $C_{1-6}$alkyl, wherein $R^{5a}$ is unsubstituted or substituted $C_{1-6}$alkyl, unsubstituted or substituted $C_{3-6}$carbocyclyl, unsubstituted or substituted $C_{3-6}$carbocyclyl$C_{1-3}$alkyl, unsubstituted or substituted 4- to 6-membered heterocyclyl, or unsubstituted or substituted 4- to 6-membered heterocyclyl$C_{1-3}$alkyl;

n is 0 or 1; and each instance of substituted is independent substitution with 1, 2, or 3 substituents selected from the group consisting of halogen, -CN, -OH, $C_{1-3}$alkyl, $C_{1-3}$haloalkyl, $-OC_{1-3}$alkyl, and $-OC_{1-3}$haloalkyl.

Embodiment 67: The compound of Embodiment 1, wherein the compound is of Formula (II-b):

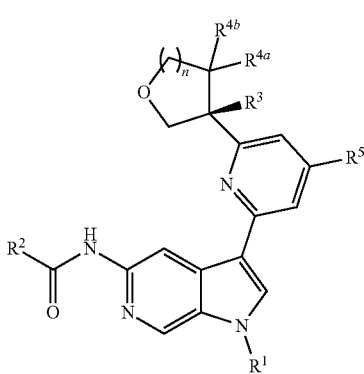

(II-b)

or a pharmaceutically acceptable salt thereof,
wherein:

$R^1$ is unsubstituted or substituted $C_{1-3}$alkyl, unsubstituted or substituted $C_{3-4}$carbocyclyl, or unsubstituted or substituted 4- to 5-membered heterocyclyl;

$R^2$ is $-NH_2$, $-NHR^{2a}$, unsubstituted or substituted $C_{1-3}$alkyl, and $R^{2a}$ is unsubstituted or substituted $C_{1-3}$alkyl;

$R^3$ is $-(C_{1-3}alkylene)_m-OR^{3a}$, $-(C_{1-3}alkylene)_m-N(R^{3a})_2$, $C_{1-3}$alkyl, or $C_{1-3}$haloalkyl, wherein m is 0 or 1, and each instance of $R^{3a}$ is independently hydrogen, $C_{1-3}$alkyl, or $C_{1-3}$haloalkyl;

each instance of $R^{4a}$ and $R^{4ab}$ is hydrogen;

$R^5$ is hydrogen, -CN, $-OR^{5a}$, $-NHR^{5a}$, or unsubstituted or substituted $C_{1-6}$alkyl, wherein $R^{5a}$ is unsubstituted or substituted $C_{1-6}$alkyl, unsubstituted or substituted $C_{3-6}$carbocyclyl, unsubstituted or substituted $C_{3-6}$carbocyclyl$C_{1-3}$alkyl, unsubstituted or substituted 4- to 6-membered heterocyclyl, or unsubstituted or substituted 4- to 6-membered heterocyclyl$C_{1-3}$alkyl;

n is 0 or 1; and each instance of substituted is independent substitution with 1, 2, or 3 substituents selected from the group consisting of halogen, -CN, -OH, $C_{1-3}$alkyl, $C_{1-3}$haloalkyl, $-OC_{1-3}$alkyl, and $-OC_{1-3}$haloalkyl.

Embodiment 68: The compound of Embodiments 64-67, or a pharmaceutically acceptable salt

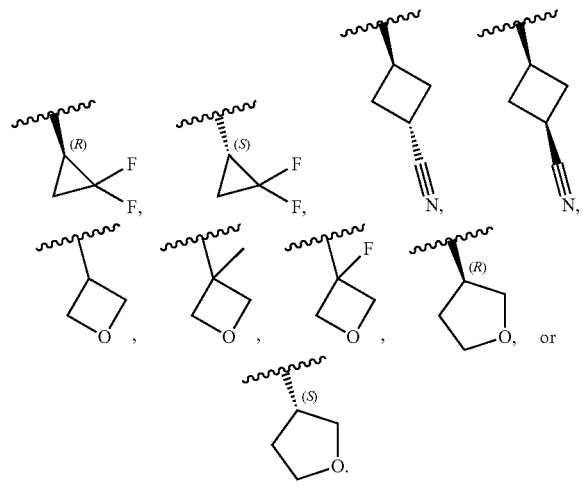

thereof, wherein $R^1$ is $-CH_3$, $-CH_2F$, $-CHF_2$, $-CF_3$,

Embodiment 69: The compound of any one of Embodiments 64-68, or a pharmaceutically acceptable salt thereof, wherein $R^2$ is $-NH_2$, $-NHCH_3$, $-OCH_3$, $-CH_3$, or $-CH_2OH$.

Embodiment 70: The compound of any one of Embodiments 64-69, or a pharmaceutically acceptable salt thereof, wherein $R^3$ is -OH, $-OCH_3$, $-CH_2OH$, $-CH_2NH_2$, -CH(OH)CH_3, $-CH_3$, or $CH_2CH_3$.

Embodiment 71: The compound of any one of Embodiments 64-70, or a pharmaceutically acceptable salt thereof, wherein each instance of $R^{4a}$ and $R^{4ab}$ is hydrogen.

Embodiment 72: The compound of any one of Embodiments 64-71, or a pharmaceutically acceptable salt thereof, wherein $R^5$ is hydrogen, -CN, $-CH_3$, $-CH_2F$, $-CHF_2$, $-CF_3$, $-CH_2OCH_3$, $-OCH_3$,

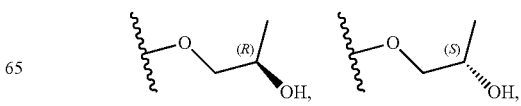

-continued

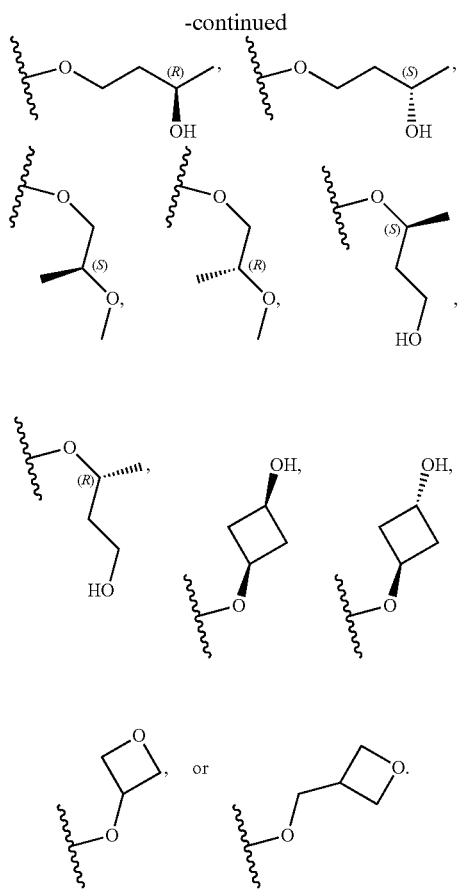

-OCH$_2$CH$_3$, -OCH(CH$_3$)$_2$, -OCH$_2$CH$_2$OH, -OCH$_2$CH$_2$OCH$_3$, -OCHF$_2$, -OCH$_2$CN,

Embodiment 73: The compound of any one of Embodiments 64-72, or a pharmaceutically acceptable salt thereof, wherein n is 1.

Embodiment 74: The compound of Embodiment 1, wherein the compound is of Formula (III-a):

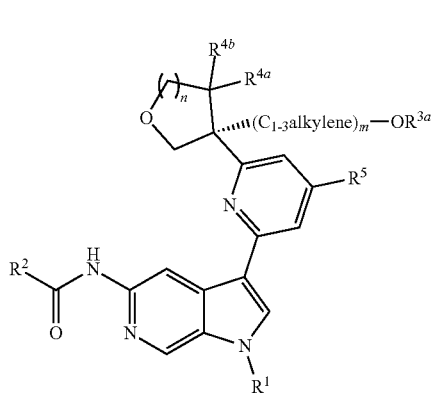

or a pharmaceutically acceptable salt thereof.

Embodiment 75: The compound of Embodiment 1, wherein the compound is of Formula (III-a):

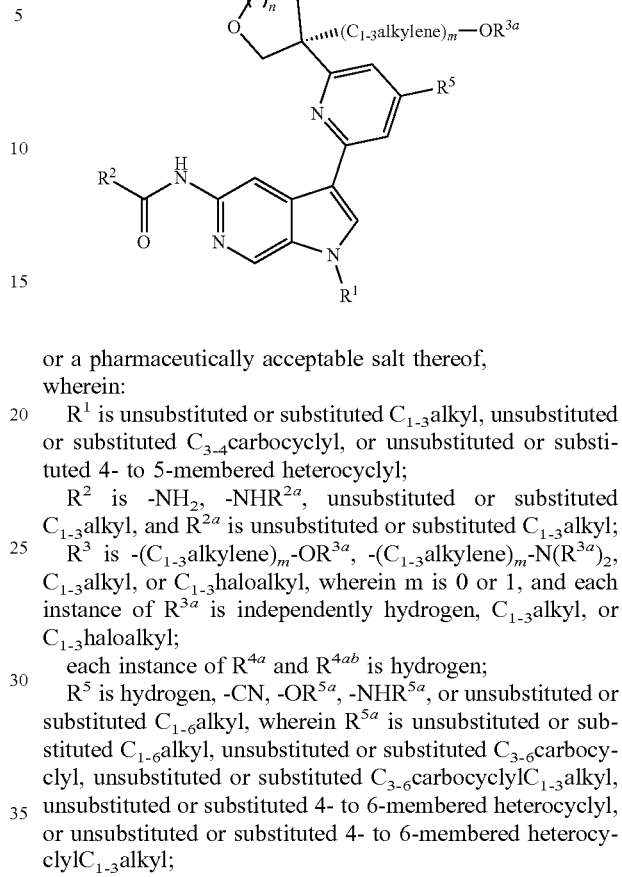

or a pharmaceutically acceptable salt thereof, wherein:

R$^1$ is unsubstituted or substituted C$_{1-3}$alkyl, unsubstituted or substituted C$_{3-4}$carbocyclyl, or unsubstituted or substituted 4- to 5-membered heterocyclyl;

R$^2$ is -NH$_2$, -NHR$^{2a}$, unsubstituted or substituted C$_{1-3}$alkyl, and R$^{2a}$ is unsubstituted or substituted C$_{1-3}$alkyl;

R$^3$ is -(C$_{1-3}$alkylene)$_m$-OR$^{3a}$, -(C$_{1-3}$alkylene)$_m$-N(R$^{3a}$)$_2$, C$_{1-3}$alkyl, or C$_{1-3}$haloalkyl, wherein m is 0 or 1, and each instance of R$^{3a}$ is independently hydrogen, C$_{1-3}$alkyl, or C$_{1-3}$haloalkyl;

each instance of R$^{4a}$ and R$^{4ab}$ is hydrogen;

R$^5$ is hydrogen, -CN, -OR$^{5a}$, -NHR$^{5a}$, or unsubstituted or substituted C$_{1-6}$alkyl, wherein R$^{5a}$ is unsubstituted or substituted C$_{1-6}$alkyl, unsubstituted or substituted C$_{3-6}$carbocyclyl, unsubstituted or substituted C$_{3-6}$carbocyclylC$_{1-3}$alkyl, unsubstituted or substituted 4- to 6-membered heterocyclyl, or unsubstituted or substituted 4- to 6-membered heterocyclylC$_{1-3}$alkyl;

n is 0 or 1; and each instance of substituted is independent substitution with 1, 2, or 3 substituents selected from the group consisting of halogen, -CN, -OH, C$_{1-3}$alkyl, C$_{1-3}$haloalkyl, -OC$_{1-3}$alkyl, and -OC$_{1-3}$haloalkyl.

Embodiment 76: The compound of Embodiment 74 or 75, or a pharmaceutically acceptable

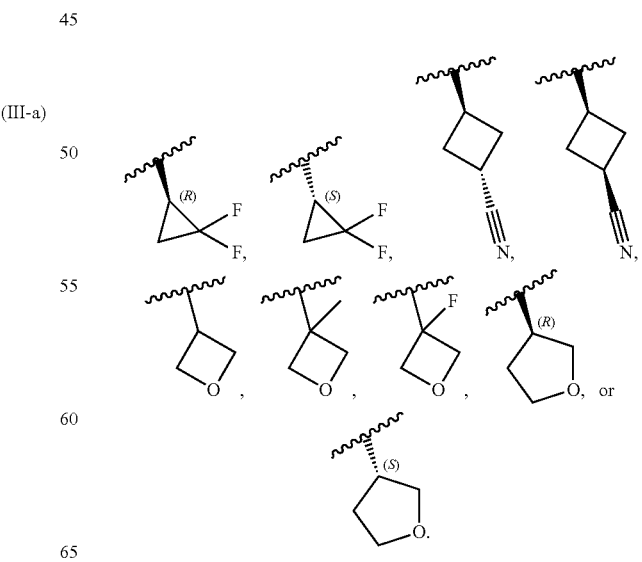

salt thereof, wherein R$^1$ is -CH$_3$, -CH$_2$F, -CHF$_2$, -CF$_3$,

Embodiment 77: The compound of any one of Embodiments 74-76, or a pharmaceutically acceptable salt thereof, wherein $R^2$ is -NH$_2$, -NHCH$_3$, -OCH$_3$, -CH$_3$, or -CH$_2$OH.

Embodiment 78: The compound of any one of Embodiments 74-77, or a pharmaceutically acceptable salt thereof, wherein $R^{1a}$ is hydrogen or -CH$_3$.

Embodiment 79: The compound of any one of Embodiments 74-78, or a pharmaceutically acceptable salt thereof, wherein m is 0.

Embodiment 80: The compound of any one of Embodiments 74-79, or a pharmaceutically acceptable salt thereof, wherein m is 1.

Embodiment 81: The compound of any one of Embodiments 74-80, or a pharmaceutically acceptable salt thereof, wherein each instance of $R^{4a}$ and $R^{4ab}$ is hydrogen.

Embodiment 82: The compound of any one of Embodiments 74-81, or a pharmaceutically acceptable salt thereof, wherein $R^5$ is hydrogen, -CN, -CH$_3$, -CH$_2$F, -CHF$_2$, -CF$_3$, -CH$_2$OCH$_3$, -OCH$_3$,

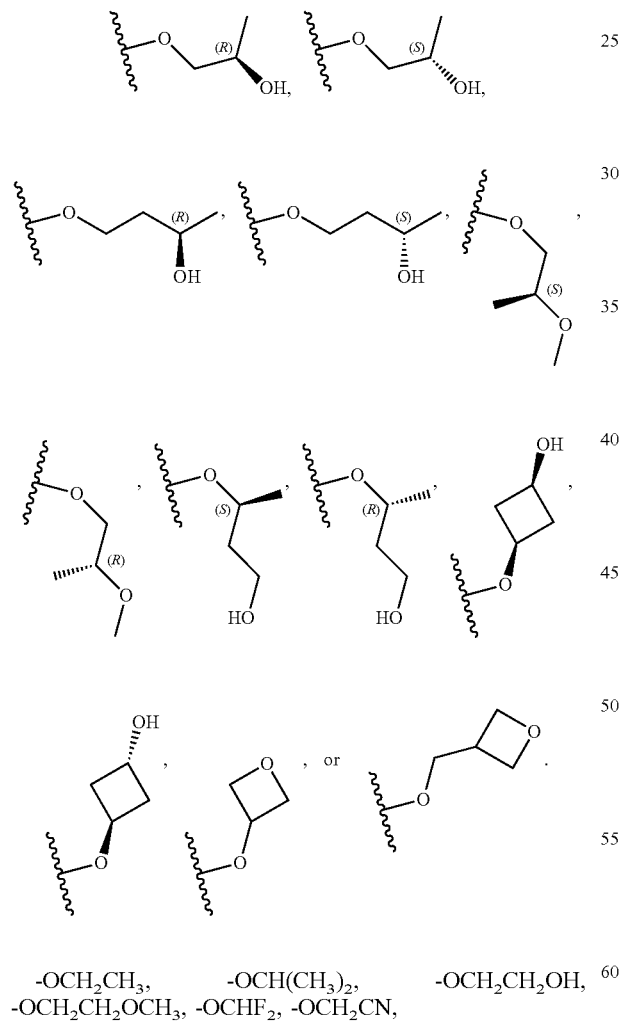

-OCH$_2$CH$_3$, -OCH(CH$_3$)$_2$, -OCH$_2$CH$_2$OH, -OCH$_2$CH$_2$OCH$_3$, -OCHF$_2$, -OCH$_2$CN,

Embodiment 83: The compound of any one of Embodiments 74-82, or a pharmaceutically acceptable salt thereof, wherein n is 1.

Embodiment 84: The compound of Embodiment 1, wherein the compound is of Formula (IV-a):

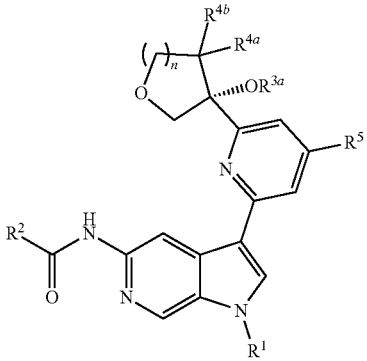

(IV-a)

or a pharmaceutically acceptable salt thereof.

Embodiment 85: The compound of Embodiment 1, wherein the compound is of Formula (IV-a):

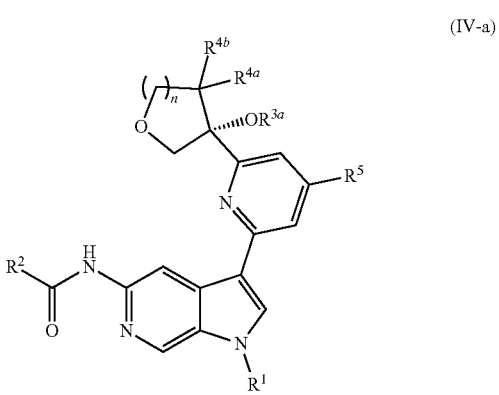

(IV-a)

or a pharmaceutically acceptable salt thereof,
wherein:

$R^1$ is unsubstituted or substituted C$_{1-3}$alkyl, unsubstituted or substituted C$_{3-4}$carbocyclyl, or unsubstituted or substituted 4- to 5-membered heterocyclyl;

$R^2$ is -NH$_2$, -NHR$^{2a}$, unsubstituted or substituted C$_{1-3}$alkyl, and R$^{2a}$ is unsubstituted or substituted C$_{1-3}$alkyl;

$R^{3a}$ is independently hydrogen, C$_{1-3}$alkyl, or C$_{1-3}$haloalkyl; each instance of $R^{4a}$ and $R^{4b}$ is hydrogen;

$R^5$ is hydrogen, -CN, -OR$^5$a, -NHR$^{5a}$, or unsubstituted or substituted C$_{1-6}$alkyl, wherein R$^{5a}$ is unsubstituted or substituted C$_{1-6}$alkyl, unsubstituted or substituted C$_{3-6}$carbocyclyl, unsubstituted or substituted C$_{3-6}$carbocyclylC$_{1-3}$alkyl, unsubstituted or substituted 4- to 6-membered heterocyclyl, or unsubstituted or substituted 4- to 6-membered heterocyclylC$_{1-3}$alkyl;

n is 0 or 1; and each instance of substituted is independent substitution with 1, 2, or 3 substituents selected from the group consisting of halogen, -CN, -OH, C$_{1-3}$alkyl, C$_{1-3}$haloalkyl, -OC$_{1-3}$alkyl, and -OC$_{1-3}$haloalkyl.

Embodiment 86: The compound of Embodiment 84 or 85, or a pharmaceutically acceptable

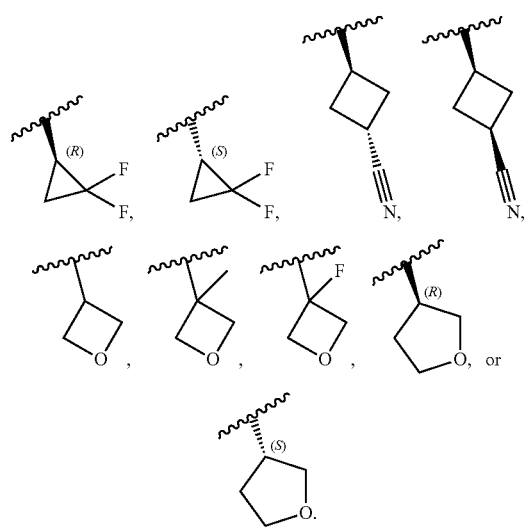

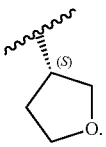

salt thereof, wherein R¹ is -CH₃, -CH₂F, -CHF₂, -CF₃,

Embodiment 87: The compound of any one of Embodiments 84-86, or a pharmaceutically acceptable salt thereof, wherein R² is -NH₂, -NHCH₃, -OCH₃, -CH₃, or -CH₂OH.

Embodiment 88: The compound of any one of Embodiments 84-87, or a pharmaceutically acceptable salt thereof, wherein $R^{3a}$ is hydrogen or -CH₃.

Embodiment 89: The compound of any one of Embodiments 84-88, or a pharmaceutically acceptable salt thereof, wherein each instance of $R^{4a}$ and $R^{4b}$ is hydrogen.

Embodiment 90: The compound of any one of Embodiments 84-89, or a pharmaceutically acceptable salt thereof, wherein R⁵ is hydrogen, -CN, -CH₃, -CH₂F, -CHF₂, -CF₃, -CH₂OCH₃, -OCH₃,

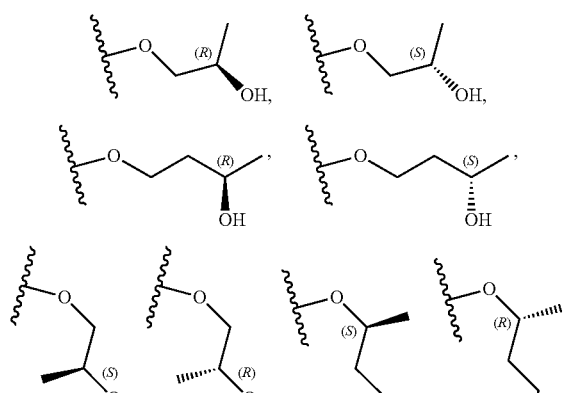

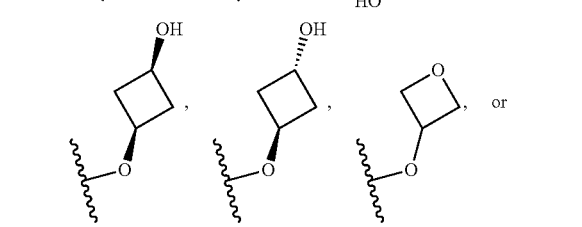

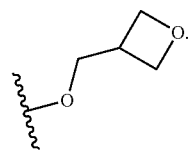

-OCH₂CH₃, -OCH(CH₃)₂, -OCH₂CH₂OH, -OCH₂CH₂OCH₃, -OCHF₂, -OCH₂CN,

Embodiment 91: The compound of any one of Embodiments 84-90, or a pharmaceutically acceptable salt thereof, wherein n is 1.

Embodiment 92: The compound of Embodiment 1, wherein the compound is of Formula (I-i) or (I-iii):

(I-ii)

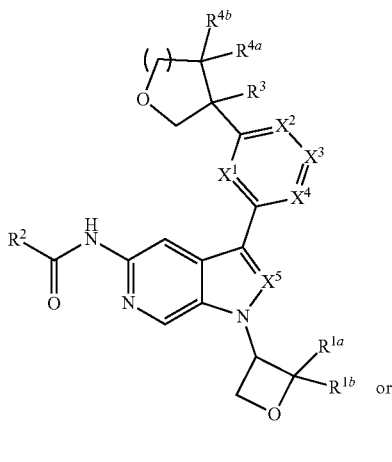

(I-iii)

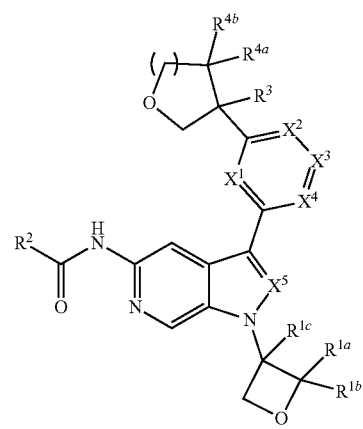

or a pharmaceutically acceptable salt thereof, wherein each of $R^{1a}$ and $R^{1b}$ is independently hydrogen or -CH₃, and $R^{1c}$ is $C_{1-3}$alkyl, $C_{1-3}$haloalkyl, -$OC_{1-3}$alkyl, or -$OC_{1-3}$haloalkyl.

Embodiment 93: The compound of Embodiment 64, or a pharmaceutically acceptable salt thereof, wherein the compound is of Formula (I-ii-II-a) or (I-iii-II-a):

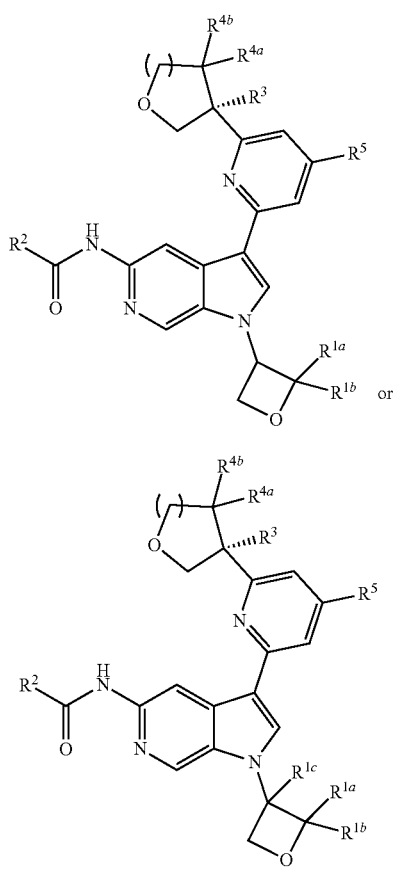

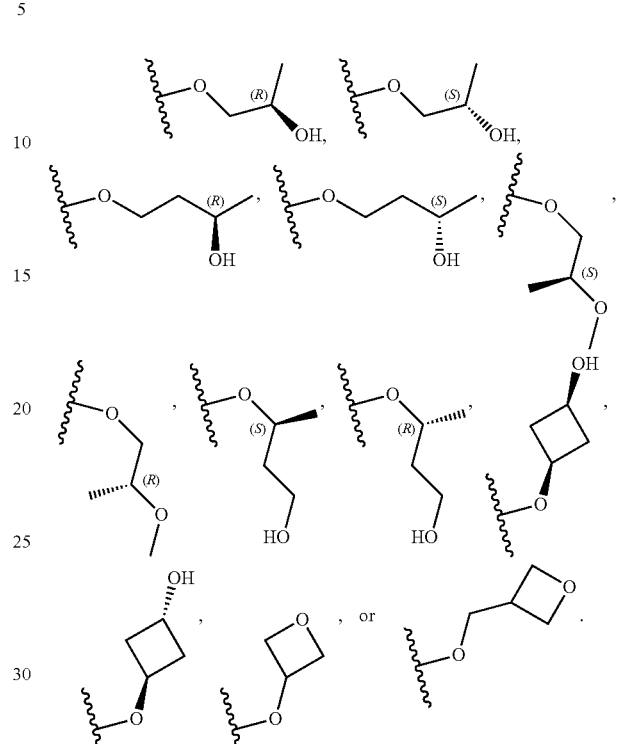

or a pharmaceutically acceptable salt thereof, wherein:

each of $R^{1a}$ and $R^{1b}$ is independently hydrogen or -CH$_3$; $R^{1c}$ is C$_{1-3}$alkyl, C$_{1-3}$haloalkyl, -OC$_{1-3}$alkyl, or -OC$_{1-3}$haloalkyl;

$R^2$ is -NH$_2$, -NHR$^{2a}$, unsubstituted or substituted C$_{1-3}$alkyl, and $R^{2a}$ is unsubstituted or substituted C$_{1-3}$alkyl;

$R^3$ is -(C$_{1-3}$alkylene)$_m$-OR$^{3a}$, -(C$_{1-3}$alkylene)$_m$-N(R$^{3a}$)$_2$, C$_{1-3}$alkyl, or C$_{1-3}$haloalkyl, wherein m is 0 or 1, and each instance of $R^{3a}$ is independently hydrogen, C$_{1-3}$alkyl, or C$_{1-3}$haloalkyl;

each instance of $R^{4a}$ and $R^{4ab}$ is hydrogen;

$R^5$ is hydrogen, -CN, -OR$^{5a}$, -NHR$^{5a}$, or unsubstituted or substituted C$_{1-6}$alkyl, wherein $R^{5a}$ is unsubstituted or substituted C$_{1-6}$alkyl, unsubstituted or substituted C$_{3-6}$carbocyclyl, unsubstituted or substituted C$_{3-6}$carbocyclylC$_{1-3}$alkyl, unsubstituted or substituted 4- to 6-membered heterocyclyl, or unsubstituted or substituted 4- to 6-membered heterocyclylC$_{1-3}$alkyl;

n is 0 or 1; and each instance of substituted is independent substitution with 1, 2, or 3 substituents selected from the group consisting of halogen, -CN, -OH, C$_{1-3}$alkyl, C$_{1-3}$haloalkyl, -OC$_{1-3}$alkyl, and -OC$_{1-3}$haloalkyl.

Embodiment 94: The compound of Embodiment 92 or 93, or a pharmaceutically acceptable salt thereof, wherein $R^2$ is -NH$_2$, -NHCH$_3$, -OCH$_3$, -CH$_3$, or -CH$_2$OH.

Embodiment 95: The compound of any one of Embodiments 92-94, or a pharmaceutically acceptable salt thereof, wherein $R^3$ is -OH, -OCH$_3$, -CH$_2$OH, -CH$_2$NH$_2$, -CH(OH)CH$_3$, -CH$_3$, or CH$_2$CH$_3$.

Embodiment 96: The compound of any one of Embodiments 92-95, or a pharmaceutically acceptable salt thereof, wherein $R^5$ is hydrogen, -CN, -CH$_3$, -CH$_2$F, -CHF$_2$, -CF$_3$, -CH$_2$OCH$_3$, -OCH$_3$, -OCH$_2$CH$_3$, -OCH(CH$_3$)$_2$, -OCH$_2$CH$_2$OH, -OCH$_2$CH$_2$OCH$_3$, -OCHF$_2$, -OCH$_2$CN, Embodiment 97: The compound of any one of Embodiments 92-96, or a pharmaceutically acceptable salt thereof, wherein n is 1.

Embodiment 98: The compound of Embodiment 1 selected from the group consisting of any one of the compounds listed in Tables A1 or A2, or a pharmaceutically acceptable salt thereof.

Embodiment 99: The compound of Embodiment 98 selected from the group consisting of compounds #1, #1.2, #1.3, #1a.2, #1b.2, #2, #2.2, #2.6, #2.8, #2.10, #2a.3, #2a.5, #3, #4, #4.3, #5, #5.2, #6, #6.3, #7, #8, #9, #10, #11, #11.2, #12, #12.3, #12.5, #12.6, #12a.2, #12a.3, #12b.2, #12b.3, #12b.4, #14.4, #14.5, #14.6, #16, #17, #17a, #17.2, #17.3, #17.4, #17.5, #18, #18a, #19, #20, #23, #22.2, #22.10, #24, #25, #26, and pharmaceutically acceptable salts thereof Embodiment 100: The compound of Embodiment 98 selected from the group consisting of compounds #3.2, #3.3, #2.3, #2.3a, #2.11, #1b.5, #1b.6, and pharmaceutically acceptable salts thereof.

Embodiment 101: The compound of Embodiment 98 selected from the group consisting of compounds #21, #21a, #22, #22a, #22.3, #22.4, #22.5, #22.6, #22.7, #22.8, #22.9, and pharmaceutically acceptable salts thereof.

Embodiment 102: The compound of Embodiment 98 selected from the group consisting of compounds #1b.4, #13, #14, #14.2, #14.3, #15, #15.2, and pharmaceutically acceptable salts thereof Embodiment 103: The compound of Embodiment 98 selected from the group consisting of compounds #1, #1.2, #1.3, #1a.2, #1b.2, #2, #2.2, #2.3, #2.6, #2.8, #2.10, #2a.3,

2a.5, #3, #4, #4.3, #5, #5.2, #6, #6.3, #7, #8, #9, #10, #11, #11.2, #12, #12.3, #12.5, #12.6, #12a.2, #12a.3, #12b.2, #12b.3, #12b.4, #14.4, #14.5, #14.6, #16, #17, #17a, #17.2, #17.3, #17.4, #17.5, #18, #18a, #19, #20, #21, #22, #23, #1b.5, #22.2, #22.3, #22.4, #22.5, #22.6, #22.8, #22.10, #24, #25, #26, and pharmaceutically acceptable salts thereof.

Embodiment 104: The compound of Embodiment 1, wherein the compound is selected from the group consisting of any one of the compounds listed in Table B1, or a pharmaceutically acceptable salt thereof.

Embodiment 105: A pharmaceutical composition comprising a compound of any one of Embodiments 1-104, or a pharmaceutically acceptable salt thereof, and a pharmaceutically acceptable excipient.

Embodiment 106: The composition of Embodiment 105 comprising a compound of Formula (I), or pharmaceutically acceptable salt thereof, in >90% amount of stereoisomer (I-a) over the sum total of stereoisomers (I-a) and (I-b) in the composition:

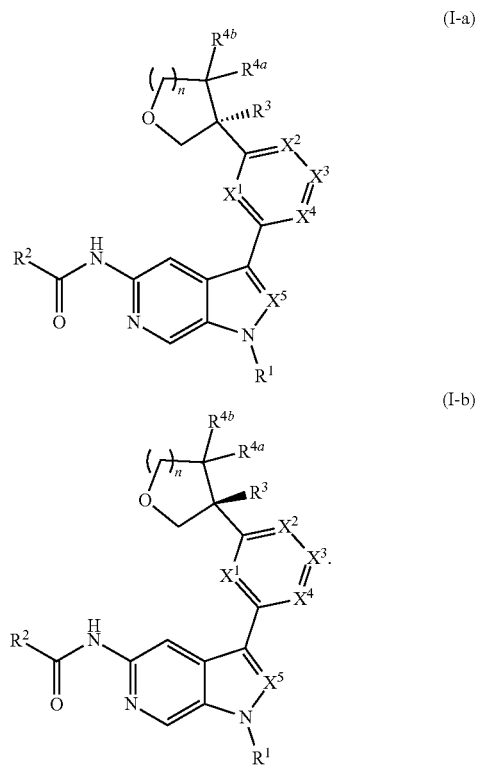

Embodiment 107: A method of treating a disease comprising administering an effective amount of a compound of any one of Embodiments 1-104, or pharmaceutically acceptable salt thereof, or a pharmaceutical composition of any one of Embodiments 105-106, to a subject in need thereof, wherein the disease is inflammatory bowel disease or psoriasis.

Embodiment 108: The method of Embodiment 107, wherein the disease is inflammatory bowel disease.

Embodiment 109: The method of Embodiment 108, wherein the inflammatory bowel disease is Crohn's disease.

Embodiment 110: The method of Embodiment 108, wherein the inflammatory bowel disease is ulcerative colitis.

Embodiment 111: The method of Embodiment 107, wherein the disease is psoriasis.

Embodiment 112: A method of preparing a compound of Formula (I) of Embodiment 1, or salt thereof, from a compound of Formula (D), or salt thereof, or from a compound of Formula (H), or salt thereof:

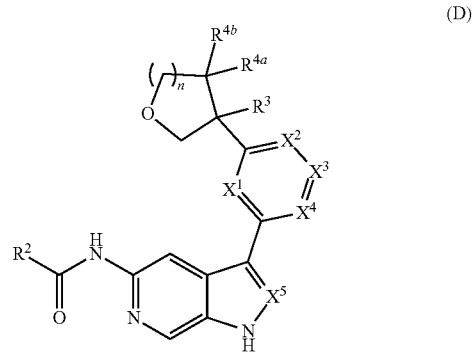

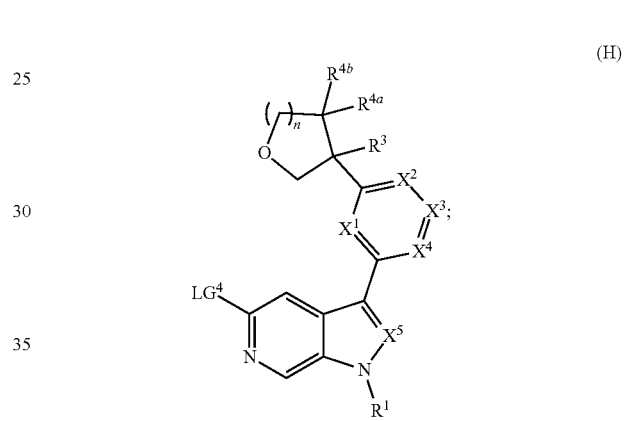

wherein LG$^4$ is a leaving group;

the method comprising treating a compound of Formula (D), or salt thereof, with a compound of formula R$^i$-LG$^3$, wherein R$^1$ is optionally substituted C$_{1-6}$alkyl, optionally substituted C$_{3-6}$carbocyclyl, or optionally substituted 4- to 6-membered heterocyclyl, and LG$^3$ is a leaving group, to provide a compound of Formula (I), or salt thereof; or (ii) the method comprising treating a compound of Formula (D), or salt thereof, with formaldehyde, under reductive amination conditions, to provide a compound of Formula (I), or salt thereof, wherein R$^1$ is -CH$_3$; or (iii) the method comprising treating a compound of Formula (D), or salt thereof,

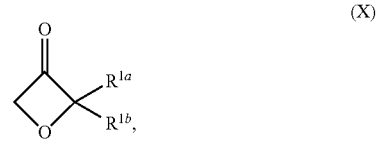

with an oxetan-3-one of Formula wherein each of R$^{1a}$ and R$^{1b}$ is independently hydrogen or -CH$_3$, followed by trapping of the in situ generated hemiaminal by fluorination to provide a fluorinated compound of Formula (I-i):

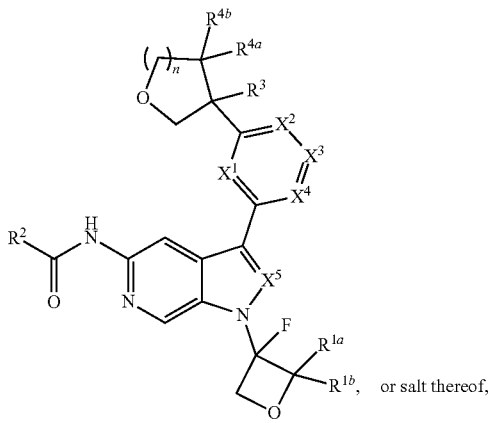

(I-i)

optionally wherein the compound of Formula (I-i), or salt thereof, is treated with a reducing agent to provide a compound of Formula (I-ii):

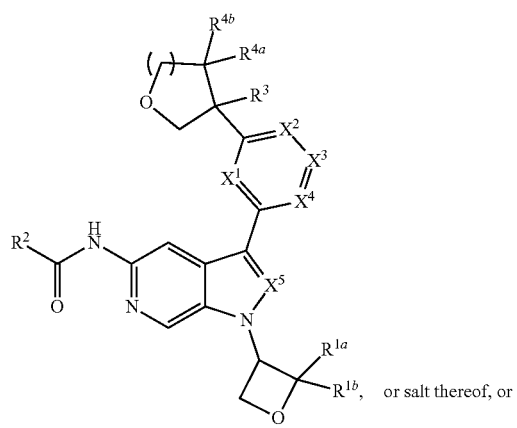

(I-ii)

optionally wherein the fluorine of the compound of Formula (I-i), or salt thereof, is replaced with a group $R^{ic}$, wherein $R^{1c}$ is $C_{1-3}$alkyl, $C_{1-3}$haloalkyl, -O$C_{1-3}$alkyl, or -O$C_{1-3}$haloalkyl to provide a compound of Formula (I-iii):

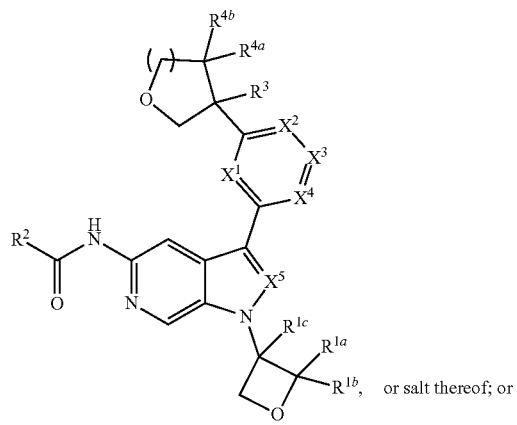

(I-iii)

(iv) the method comprising coupling a compound of Formula (H), or salt thereof, with a compound of Formula $R^2C(\!=\!O)NH_2$, or salt thereof, in the presence of a palladium or copper catalyst, to provide a compound of Formula (I), or salt thereof.

Embodiment 113: The method of Embodiment 112, wherein the compound of Formula (D), or salt thereof, is prepared from a compound of Formula (C):

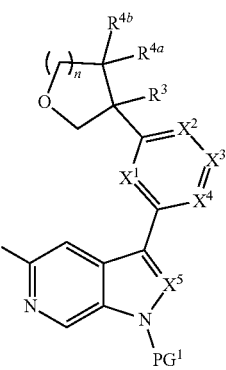

(C)

or salt thereof, by deprotection of an amino protecting group, $PG^1$.

Embodiment 114: The method of Embodiment 113, wherein the compound of Formula (C), or salt thereof, is prepared from cross-coupling of a compound of Formula (A):

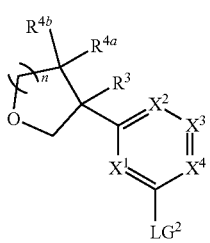

(A)

or salt thereof, with a compound of Formula (B):

(B)

sor salt thereof, wherein $LG^1$ and $LG^2$ are each independently leaving groups.

Embodiment 115: The method of Embodiment 112, wherein the compound of Formula (H), or salt thereof, is prepared from a compound of Formula (G):

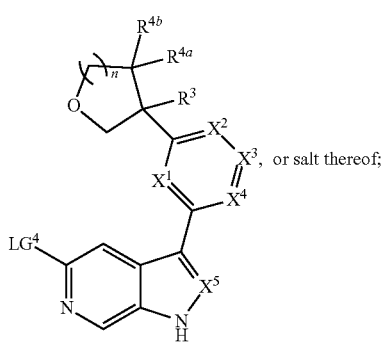

(G)

(i) the method comprising treating a compound of Formula (G), or salt thereof, with a compound of formula $R^1$-$LG^3$, wherein $R^1$ is optionally substituted $C_{1-6}$alkyl, optionally substituted $C_{3-6}$carbocyclyl, or optionally substituted 4- to 6-membered heterocyclyl, and $LG^3$ is a leaving group, to provide a compound of Formula (H), or salt thereof; or (ii) the method comprising treating a compound of Formula (G), or salt thereof, with formaldehyde, under reductive amination conditions, to provide a compound of Formula (H), or salt thereof, wherein $R^1$ is -$CH_3$; or (iii) the method comprising treating a compound of Formula (G), or salt thereof,

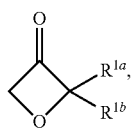

(X)

with an oxetan-3-one of Formula wherein each of $R^{1a}$ and $R^{1b}$ is independently hydrogen or -$CH_3$, followed by trapping of the in situ generated hemiaminal by fluorination to provide a fluorinated compound of Formula (I-iv):

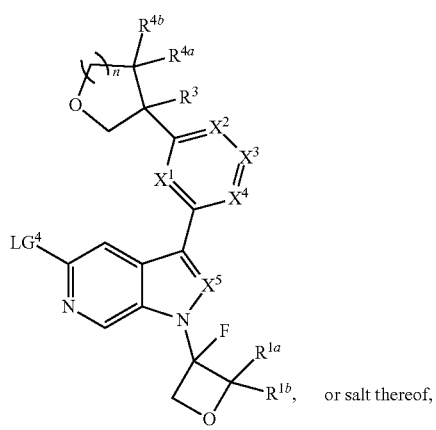

(I-iv)

optionally wherein the compound of Formula (I-iv), or salt thereof, is treated with a reducing agent to provide a compound of Formula (I-v):

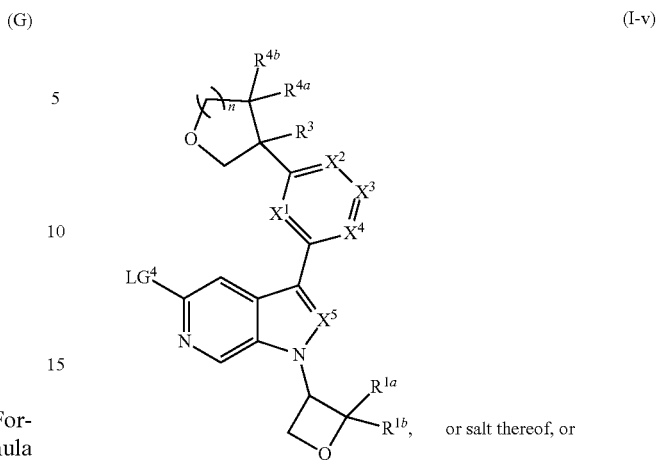

(I-v)

optionally wherein the fluorine of the compound of Formula (I-iv), or salt thereof, is replaced with a group $R^{1c}$, wherein $R^{1c}$ is $C_{1-3}$alkyl, $C_{1-3}$haloalkyl, -$OC_{1-3}$alkyl, or -$OC_{1-3}$haloalkyl, to provide a compound of Formula (I-vi):

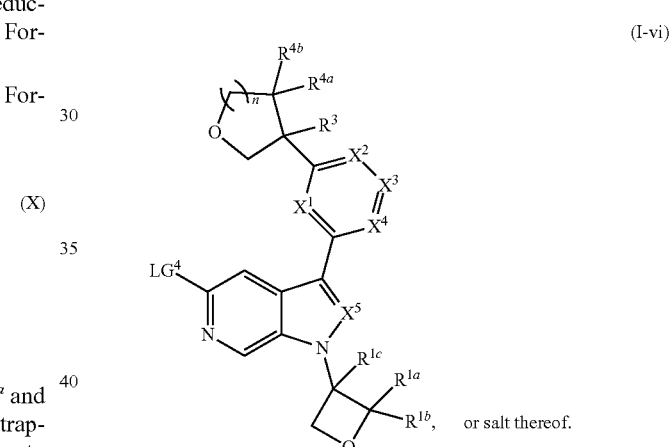

(I-vi)

Embodiment 116: The method of Embodiment 115, wherein the compound of Formula (G), or salt thereof, is prepared from a compound of Formula (F):

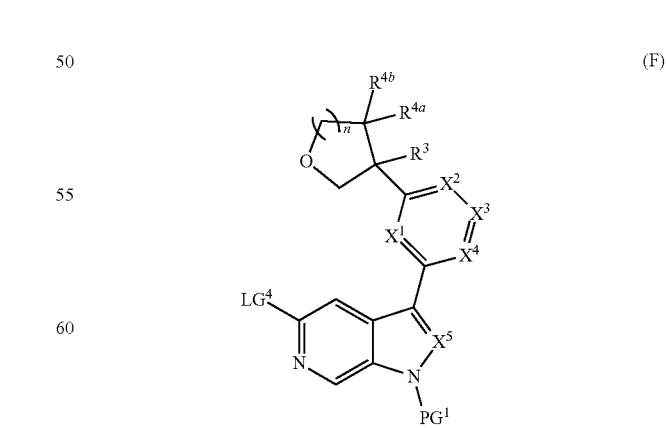

(F)

or salt thereof, by deprotection of an amino protecting group, $PG^1$.

Embodiment 117: The method of Embodiment 116, wherein the compound of Formula (F), or salt thereof, is prepared from the cross-coupling of a compound of Formula (E):

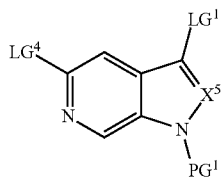
(E)

or salt thereof, with a compound of Formula (B):

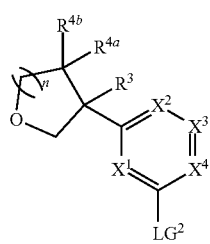
(B)

or salt thereof, wherein $LG^1$ and $LG^2$ are each independently leaving groups.

Embodiment 118: A method of preparing a compound of Formula (II-a) of Embodiment 64 or 66, or salt thereof, from a compound of Formula (D-II-a), or salt thereof, or from a compound of Formula (H-II-a), or salt thereof:

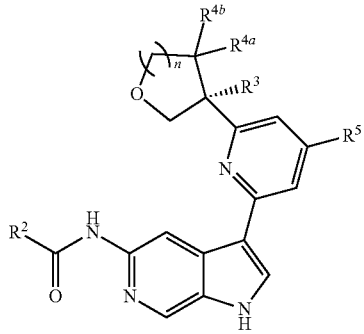
(D-II-a)

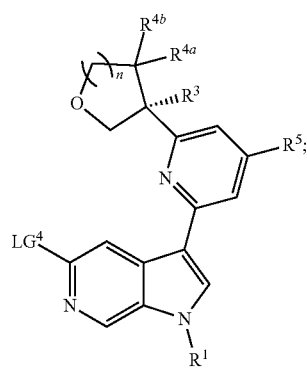
(H-II-a)

wherein $LG^4$ is a leaving group;

(i) the method comprising treating a compound of Formula (D-II-a), or salt thereof, with a compound of formula $R^1$-$LG^3$, wherein $R^1$ is optionally substituted $C_{1-6}$alkyl, optionally substituted $C_{3-6}$carbocyclyl, or optionally substituted 4- to 6-membered heterocyclyl, and $LG^3$ is a leaving group, to provide a compound of Formula (II-a), or salt thereof; or (ii) the method comprising treating a compound of Formula (D-II-a), or salt thereof, with formaldehyde, under reductive amination conditions, to provide a compound of Formula (I), or salt thereof, wherein $R^1$ is -$CH_3$; or (iii) the method comprising treating a compound of Formula (D-II-a), or salt thereof,

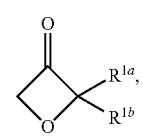
(X)

with an oxetan-3-one of Formula wherein each of $R^{1a}$ and $R^{1b}$ is independently hydrogen or -$CH_3$, followed by trapping of the in situ generated hemiaminal by fluorination to provide a fluorinated compound of Formula (I-i-II-a):

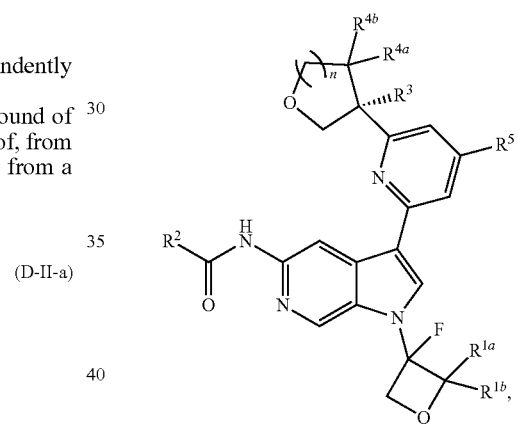
(I-i-II-a)

or salt thereof, optionally wherein the compound of Formula (I-i-II-a), or salt thereof, is treated with a reducing agent to provide a compound of Formula (I-ii-IIa):

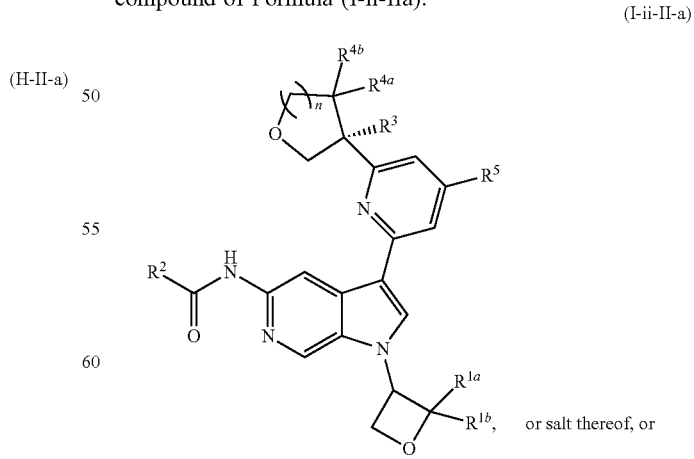
(I-ii-II-a)

or salt thereof, or optionally wherein the fluorine of the compound of Formula (hi-II-a), or salt thereof, is replaced with a group $R^{ic}$, wherein $R^{1c}$ is $C_{1-3}$alkyl, $C_{1-3}$haloalkyl, -$OC_{1-3}$alkyl, or -$OC_{1-3}$haloalkyl, to provide a compound of Formula (I-iii-H-a):

(I-iii-II-a)

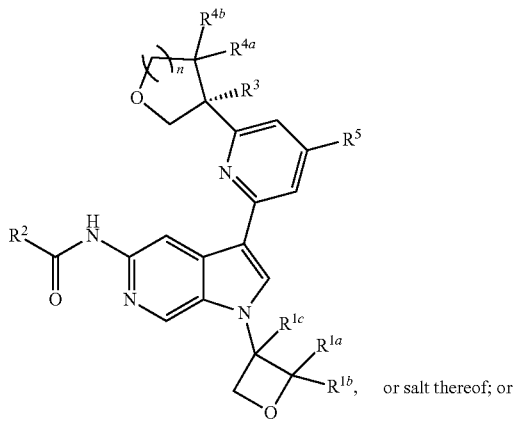

or salt thereof; or (iv) the method comprising coupling a compound of Formula (H-II-a), or salt thereof, with a compound of Formula $R^2C(=O)NH_2$, or salt thereof, in the presence of a palladium or copper catalyst, to provide a compound of Formula (I-II-a), or salt thereof.

Embodiment 119: The method of Embodiment 118, wherein the compound of Formula (D-II-a), or salt thereof, is prepared from a compound of Formula (C-II-a):

(C-II-a)

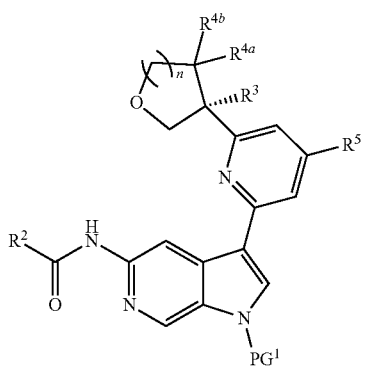

or salt thereof, by deprotection of an amino protecting group, $PG^1$.

Embodiment 120: The method of Embodiment 119, wherein the compound of Formula (C-II-a), or salt thereof, is prepared from cross-coupling of a compound of Formula (A-II-a):

(A-II-a)

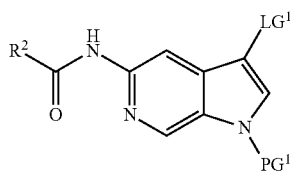

or salt thereof, with a compound of Formula (B-II-a):

(B-II-a)

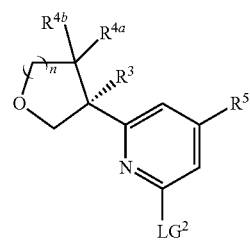

or salt thereof, wherein $LG^1$ and $LG^2$ are each independently leaving groups.

Embodiment 121: The method of Embodiment 118, wherein the compound of Formula (H-II-a), or salt thereof, is prepared from a compound of Formula (G-II-a):

(G-II-a)

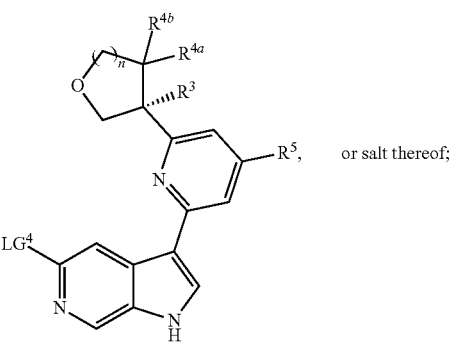

or salt thereof;

(i) the method comprising treating a compound of Formula (G-II-a), or salt thereof, with a compound of formula $R^1$-$LG^3$, wherein $R^1$ is optionally substituted $C_{1-6}$alkyl, optionally substituted $C_{3-6}$carbocyclyl, or optionally substituted 4- to 6-membered heterocyclyl, and $LG^3$ is a leaving group, to provide a compound of Formula (H-II-a), or salt thereof; or (ii) the method comprising treating a compound of Formula (G-II-a), or salt thereof, with formaldehyde, under reductive amination conditions, to provide a compound of Formula (H-II-a), or salt thereof, wherein $R^1$ is -$CH_3$; or (iii) the method comprising treating a compound of Formula (G-II-a), or salt thereof, (X)

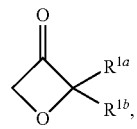

with an oxetan-3-one of Formula wherein each of $R^{1a}$ and $R^{1b}$ is independently hydrogen or -$CH_3$, followed by trapping of the in situ generated hemiaminal by fluorination, to provide a fluorinated compound of Formula (I-iv-II-a):

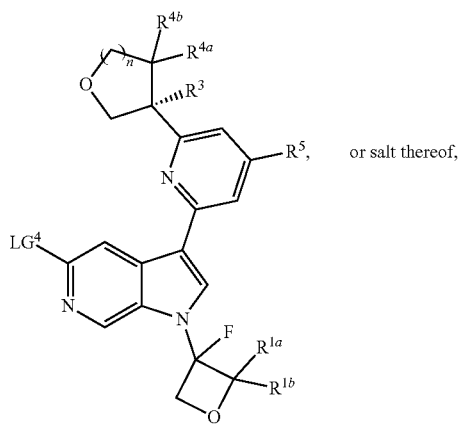

optionally wherein the compound of Formula (I-iv-II-a), or salt thereof, is treated with a reducing agent to provide a compound of Formula (I-v-II-a):

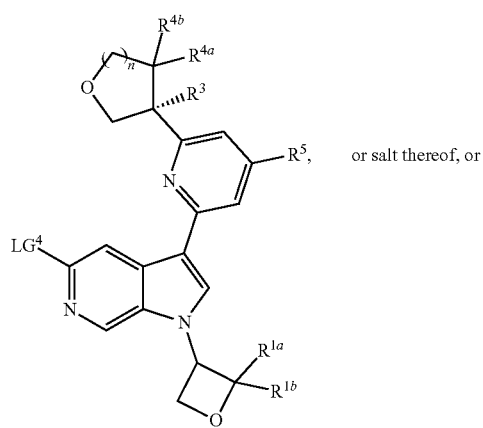

optionally wherein the fluorine of the compound of Formula (I-iv-II-a), or salt thereof, is replaced with a group $R^{1c}$, wherein $R^{1c}$ is $C_{1-3}$alkyl, $C_{1-3}$haloalkyl, -O$C_{1-3}$alkyl, or -O$C_{1-3}$haloalkyl, to provide a compound of Formula (I-vi-II-a):

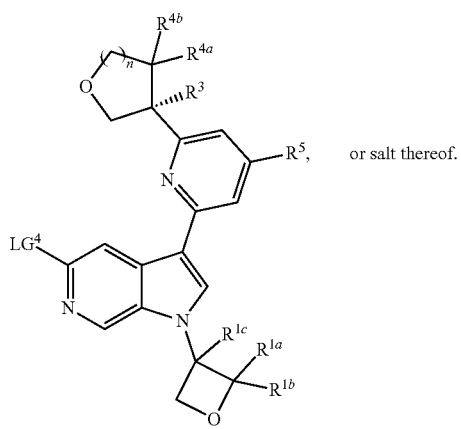

Embodiment 122: The method of Embodiment 121, wherein the compound of Formula (G-II-a), or salt thereof, is prepared from a compound of Formula (F-II-a):

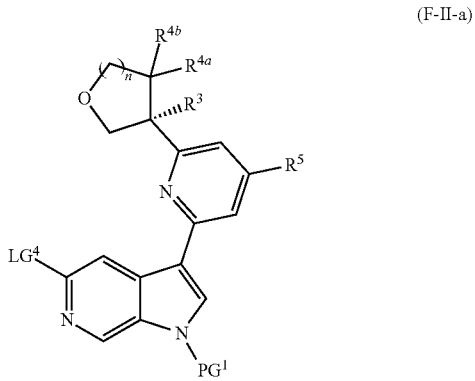

or salt thereof, by deprotection of an amino protecting group, $PG^1$.

Embodiment 123: The method of Embodiment 122, wherein the compound of Formula (F-II-a), or salt thereof, is prepared from the cross-coupling of a compound of Formula (E-II-a):

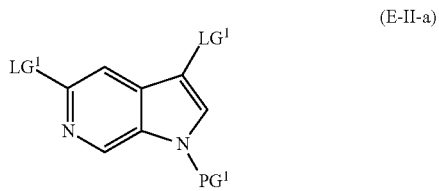

or salt thereof, with a compound of Formula (B-II-a):

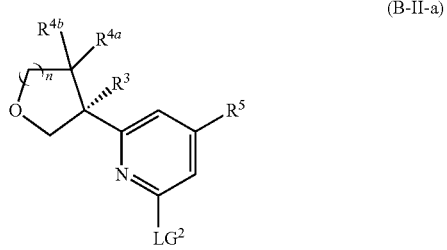

or salt thereof, wherein $LG^1$ and $LG^2$ are each independently leaving groups.

Embodiment 124: a compound selected from the group consisting of

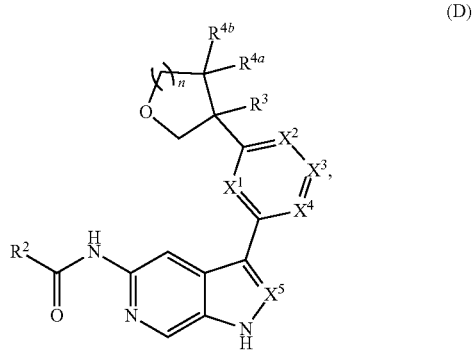

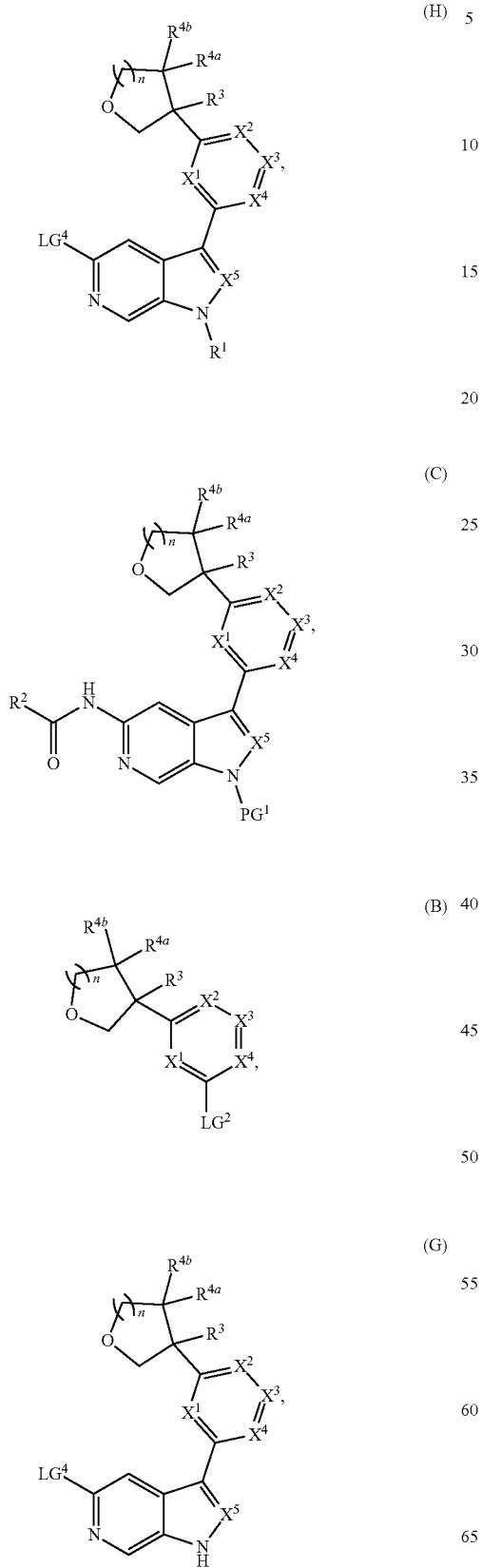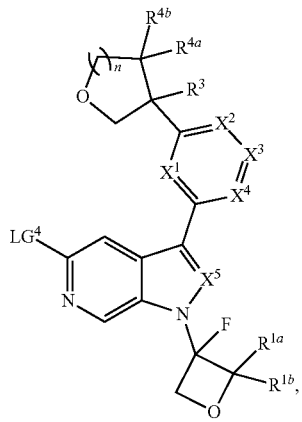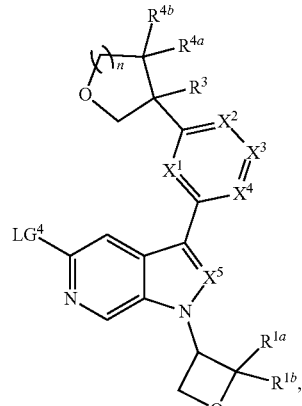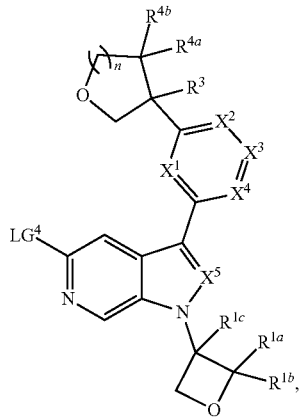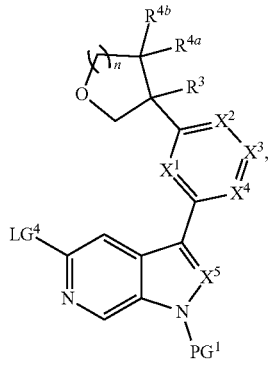

and salts thereof, wherein n, $X^1$, $X_2$, $X^3$, $X^4$, $X^5$, $R^1$, $R^2$, $R^3$, $R^{4a}$, $R^{4b}$, $LG^2$, $LG^4$, $R^{1a}$, $R^{1b}$, $R^{1c}$, and $PG^1$ are as defined in Embodiments 112-117.
Embodiment 125: a compound selected from the group consisting of:
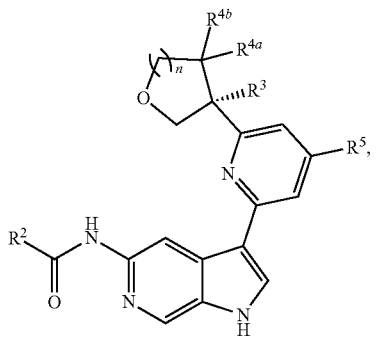
(D-II-a)
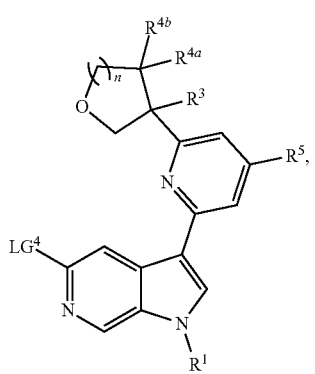
(H-II-a)
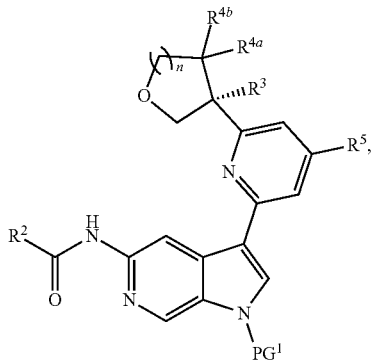
(C-II-a)
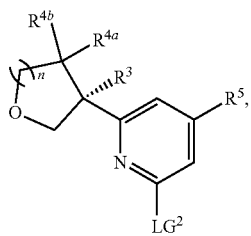
(B-II-a)
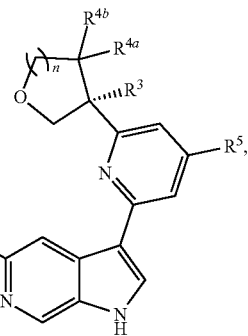
(G-II-a)
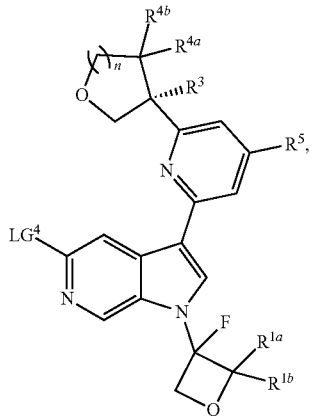
(I-iv-II-a)
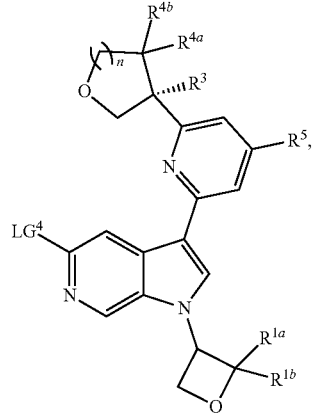
(I-v-II-a)
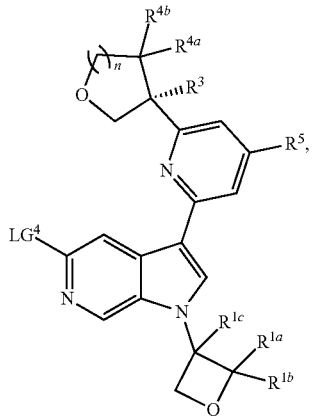
(I-vi-II-a)

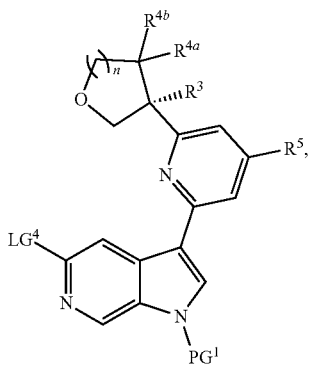

(F-II-a)

and salts thereof, wherein n, $R^1$, $R^2$, $R^3$, $R^{4a}$, $R^{4b}$, $R^5$, $LG^2$, $LG^4$, $R^{1a}$, $R^{1b}$, $R^{1c}$, and $PG^1$ are as defined in Embodiments 118-123.

EXAMPLES

In order that this disclosure may be more fully understood, the following Examples are set forth. It should be understood that these examples are for illustrative purposes only and are not to be construed as limiting this disclosure in any manner.

ANALYTICAL METHODS

Analytical data was included within the procedures below or in the tables of examples. Unless otherwise stated, all $^1$H NMR (proton nuclear magnetic resonance) data were collected on a Varian 400 MHz Mercury Plus, Inova, or 400-MR instrument, and chemical shifts are quoted in parts per million (ppm). LC/MS (liquid chromatography/mass spectrometry) data is referenced to the table of LC/MS conditions using the lower case method letter provided in Table A. Chiral separation methods are referenced using the number provided in Table B. Reverse HPLC (high pressure liquid chromatography) purifications were conducted on a 19×100 mm Atlantis Prep T3 OBD (5 μm particles) column. $R_t$=retention time.

TABLE A

LC/MS methods

| Method | Conditions |
|---|---|
| a | The gradient was 5-60% Mobile phase B in 0.75 minutes then 60-95% Mobile phase B to 1.15 minutes with a hold at 95% Mobile phase B for 0.75 minutes (1.3 mL/minutes flow rate). Mobile phase A was 10 mM ammonium acetate; Mobile phase B was HPLC grade acetonitrile. The column used for the chromatography is a 4.6 × 50 mm MAC-MOD Halo C8 column (2.7 μm particles). Detection methods are diode array (DAD) and evaporative light scattering (ELSD) detection as well as positive/negative electrospray ionization. |
| b | The gradient was 5-60% Mobile phase B in 1.6 minutes then 60-95% Mobile phase B to 2.2 minutes with a hold at 95% Mobile phase B for 0.1 minutes (1.0 mL/minutes flow rate). Mobile phase A was 0.1% Formic acid buffer; Mobile phase B was HPLC grade acetonitrile. The column used for the chromatography is a 2.1 × 30 mm Halo-2 C8 column (2 μm particles). Detection methods are diode array (DAD) and evaporative light scattering (ELSD) detection as well as positive/negative electrospray ionization. |
| c | The gradient was 5-60% Mobile phase B in 1.5 minutes then 60-95% Mobile phase B to 2.5 minutes with a hold at 95% Mobile phase B for 1.2 min (1.3 mL/minutes flow rate). Mobile phase A was 10 mM ammonium acetate; Mobile phase B was HPLC grade acetonitrile. The column used for the chromatography is a 4.6 × 50 mm MAC-MOD Halo C8 column (2.7 μm particles). Detection methods are diode array (DAD) and evaporative light scattering (ELSD) detection as well as positive/negative electrospray ionization. |
| d | The gradient was 5-60% Mobile phase B in 1.6 minutes then 60-95% Mobile phase B to 2.2 minutes with a hold at 95% Mobile phase B for 0.1 minutes (1.0 mL/minutes flow rate). Mobile phase A was 10 mM ammonium acetate; Mobile phase B was HPLC grade acetonitrile. The column used for the chromatography is a 2.1 × 30 mm Waters Cortecs C18 column (1.6 μm particles). Detection methods are diode array (DAD) and evaporative light scattering (ELSD) detection as well as positive/negative electrospray ionization. |
| e | The gradient was 80-65% Mobile phase B in 1.80 minutes then 65-40% Mobile phase B to 2.80 minutes with a hold at 40% for another 1.20 minutes (1.3 mL/minutes flow rate). Mobile phase A was 10 mM ammonium acetate; Mobile phase B was HPLC grade acetonitrile. The column used for the chromatography is a 4.6 × 50 mm X-bridge column (3.5 μm particles). Detection methods are diode array (DAD) and evaporative light scattering (ELSD) detection as well as positive/negative electrospray ionization. |
| f | The gradient was 1-90% Mobile phase B in 3.4 minutes, 90-100% Mobile phase B in 0.45 minutes, 100-1% B in 0.01 minutes, and then held at 0% Mobile phase B for 0.65 minutes (0.8 mL/minutes flow rate). Mobile phase A was 0.0375% trifluoroacetic acid in water; Mobile phase B was 0.018% trifluoroacetic acid in acetonitrile. The column used for the chromatography was a 3.0 × 50 mm Shim-pack XR-ODS column (5 μm particles). Detection methods are diode array (DAD) and evaporative light scattering (ELSD) detection as well as positive/negative electrospray ionization (MS). |
| g | The gradient was 5-95% Mobile phase B in 1.0 minutes, 95-100% Mobile phase B in 0.80 minutes, 100-5% Mobile phase B in 0.01 minutes, and then held at 5% Mobile phase B for 0.39 minutes (1.0 mL/min flow rate). Mobile phase A was 0.0375% |

TABLE A-continued

LC/MS methods

| Method | Conditions |
|---|---|
| | trifluoroacetic acid in water, mobile phase B was 0.018% trifluoroacetic acid in acetonitrile. The column used for the chromatography was a ZORBAX Eclipse XDB-C18 2.1 * 30 mm, 3.5 um. Detection methods are diode array (DAD) and positive electrospray ionization (MS). |

TABLE B

Chiral separation methods

| Method | Conditions |
|---|---|
| 1 | The gradient was 5% Mobile phase B for 9.5 minutes then step to 70% Mobile phase B and hold for 4 minutes (20 mL/minutes flow rate). Mobile phase B was 80:20 HPLC isopropyl alcohol:acetonitrile; Mobile phase A was HPLC grade heptane with 0.2% diethanolamine (DEA) added. The chromatography used a Daicel IG, 20 × 250 mm column (5 μm particles). |
| 2 | The gradient was 8% methanol in $CO_2$ (80 mL/minutes, 100 bar, 45° C.). Cycle time was 3.5 minutes, with single run time of 12.5 minutes. HPLC grade methanol was used with SFC grade $CO_2$. The chromatography used a Daicel IG, 21 × 250 mm column (5 μm particles). |
| 3 | The gradient was 5.5% 80:20 isopropyl alcohol:acetonitrile in $CO_2$ (70 mL/minutes, 100 bar, 35° C.). Cycle time was 2.2 minutes, with single run time of 5 minutes. HPLC grade isopropyl alcohol and acetonitrile was used with SFC grade $CO_2$. The chromatography used a YMC-SB, 30 × 150 mm column (5 μm particles). |
| 4 | The gradient was 6% methanol in $CO_2$ (90 mL/minutes, 90 bar, 25° C.). Cycle time was 2.4 minutes with single run time of 6 minutes. HPLC grade methanol was used with SFC grade $CO_2$. The chromatography used a Daicel IG 21 × 250 mm column (5 μm particles). |
| 5 | The gradient was 5% Mobile phase B for 7 minutes then step to 50% Mobile phase B and hold for 4 minutes (20 mL/min flow rate). Mobile phase B was 80:20 HPLC dichloromethane:ethanol; Mobile phase A was HPLC grade heptane. The chromatography used a Daicel IF 20 × 250 mm column (5 μm particles). |
| 6 | The gradient was 4% Mobile phase B for 15.5 minutes (20 mL/min flow rate). Mobile phase B was 80:20 HPLC grade isopropyl alcohol:acetonitrile; Mobile phase A was HPLC grade heptane. The chromatography used a YMC-SC 20 × 250 mm column (5 μm particles). |
| 7 | The gradient was 4% methanol in $CO_2$ (80 mL/minutes, 100 bar, 40° C.). Cycle time was 4 minutes, with single run time of 6 minutes. HPLC grade methanol was used with SFC grade $CO_2$. The chromatography used a YMC-SA 30 × 150 mm column (5 μm particles). |
| 8 | The gradient was 5% methanol in $CO_2$ (85 mL/minutes, 100 bar, 30° C.). Cycle time was 3 minutes, with single run time of 9 minutes. HPLC grade methanol was used with SFC grade $CO_2$. The chromatography used a Daicel IG 21 × 250 mm column (5 μm particles). |
| 9 | The gradient was 4% ethanol in $CO_2$ (80 mL/minutes, 100 bar, 40° C.). Cycle time was 4 minutes, with single run time of 10 minutes. 200 proof ethanol was used with SFC grade $CO_2$. The chromatography used a YMC-SC 30 × 150 mm column (5 μm particles). |
| 10 | The gradient was 55% Mobile phase B for 15 minutes (20 mL/minutes flow rate). Mobile phase B was 80:20 HPLC grade dichloromethane and isopropanol; Mobile phase A was HPLC grade heptane with 0.2% diethylamine added. The chromatography used a YMC-SA 20 × 250 mm column (5 μm particles). |
| 11 | The gradient was 35% Mobile phase B for 30 minutes (20 mL/minutes flow rate). Mobile phase B was EtOH; Mobile phase A was HPLC grade heptane. The chromatography used a Daicel IF 20 × 250 mm column (5 μm particles). |
| 12 | The gradient was 17% 1:1 dichloromethane:methanol in $CO_2$ with 0.2% diethylamine modifier (90 mL/minutes, 100 bar, 30° C.). Cycle time was 6.5 minutes, with single run time of 9 minutes. HPLC grade methanol and dichloromethane were used with SFC grade $CO_2$. The chromatography used a YMC-SB 30 × 150 mm column (5 μm particles). |
| 13 | The gradient was 50% Mobile phase B for 13 minutes (20 mL/minutes flow rate). Mobile phase B was 80:20 HPLC grade dichloromethane: 200 proof ethanol; Mobile phase A was HPLC grade heptane with 0.2% diethylamine added. The chromatography used a YMC-SA 20 × 250 mm column (5 μm particles). |
| 14 | The gradient was 10% EtOH in $CO_2$ (60 mL/minutes, 100 bar, 30° C.). Cycle time was 3.5 minutes, with single run time of 6 minutes. HPLC grade EtOH was used with SFC grade $CO_2$. The chromatography used a Daicel IF 20 × 250 mm column (5 μm particles). |
| 15 | The gradient was 20% ethanol with 0.2% diethylamine modifier in $CO_2$ (75 mL/minutes, 100 bar, 35° C.). Cycle time was 5 minutes, with single run time of 11 minutes. 200 proof ethanol was used with SFC grade $CO_2$. The chromatography used a YMC-SB 30 × 150 mm column (5 μm particles). |

TABLE B-continued

Chiral separation methods

| Method | Conditions |
|---|---|
| 16 | The gradient was 25% ethanol with 0.2% diethylamine modifier in $CO_2$ (70 mL/minutes, 100 bar, 35° C.). Cycle time was 4.5 minutes, with single run time of 12 minutes. 200 proof ethanol was used with SFC grade $CO_2$. The chromatography used a YMC-SB 30 × 150 mm column (5 μm particles). |
| 17 | The gradient was 4% ethanol with 0.2% diethylamine in $CO_2$ (80 mL/minutes, 100 bar, 40° C.). Cycle time was 4 minutes, with single run time of 10 minutes. 200 proof ethanol with SFC grade $CO_2$. The chromatography used a YMC-SC 30 × 250 mm column (5 μm particles). |
| 18 | The gradient was 28% Mobile phase B for 25 minutes (20 mL/minutes flow rate). Mobile phase B was HPLC grade isopropyl alcohol; Mobile phase A was HPLC grade heptane. The chromatography used a YMC-SB 20 × 250 mm column (5 μm particles). |
| 19 | The gradient was 2% Mobile phase B for 9.5 minutes (20 mL/minutes flow rate). Mobile phase B was 200 proof ethanol; Mobile phase A was HPLC grade heptane. The chromatography used a YMC-SC 20 × 250 mm column (5 μm particles). |
| 20 | The gradient was 40% Mobile phase B for 25 minutes (20 mL/min flow rate). Mobile phase B was HPLC grade 80/20 dichloromethane:isopropyl alcohol with 0.2% diethylamine added; Mobile phase A was HPLC grade heptanes with 0.2% diethylamine added. The chromatography used a YMC-SA 21 × 250 mm column (5 μm particles). |
| 21 | The gradient was 25% Mobile phase B for 25 minutes (20 mL/minutes flow rate). Mobile phase B was HPLC grade Ethanol; Mobile phase A was HPLC grade heptanes. The chromatography used a Daicel IG 20 × 250 mm column (5 μm particles). |
| 22 | The gradient was 25% Mobile phase B for 15 minutes (20 mL/ flow rate). Mobile phase A was Heptane HPLC grade, mobile phase B was 80/20 dichloromethane/isopropyl alcohol HPLC grade. The column used for the chromatography is a 21 × 250 mm Daicel IG (5 μm particles). Detection method was diode array (DAD). |
| 23 | The gradient was 20% Mobile phase B for 16 minutes (20 mL/flow rate). Mobile phase A was Heptane HPLC grade, mobile phase B was 80/20 dichloromethane/isopropyl alcohol HPLC grade. The column used for the chromatography is a 20 × 250 mm YMC-SC (5 μm particles). Detection method was diode array (DAD). |
| 24 | The gradient was 11% methanol in $CO_2$ (70 mL/minutes, 100 bar, 30° C.). Cycle time was 6.5 minutes, with single run time of 10 minutes. HPLC grade methanol was used with SFC grade $CO_2$. The chromatography used a YMC-SA, 30 × 150 mm column (5 μm particles). |
| 25 | The gradient was 30% methanol in $CO_2$ (60 mL/minutes, 100 bar, 55° C.). Cycle time was 4.5 minutes, with single run time of 9 minutes. HPLC grade methanol was used with SFC grade $CO_2$. The chromatography used a YMC-SA, 30 × 150 mm column (5 μm particles). |
| 26 | The gradient was 16% methanol in $CO_2$ (95 mL/minutes, 100 bar, 25° C.). Cycle time was 6 minutes, with single run time of 10 minutes. HPLC grade methanol was used with SFC grade $CO_2$. The chromatography used a YMC-SA, 30 × 150 mm column (5 μm particles). |
| 27 | The gradient was 27% Ethanol in $CO_2$ (80 mL/minutes, 100 bar, 40° C.). Cycle time was 3.15 minutes, with single run time of 6 minutes. HPLC grade Ethanol was used with SFC grade $CO_2$. The chromatography used a Daicel IG, 30 × 150 mm column (5 μm particles). |
| 28 | The gradient was 20% Mobile phase B for 16 minutes (20 mL/minutes flow rate). Mobile phase B was 80:20 HPLC grade dichloromethane:isopropyl alcohol; Mobile phase A was HPLC grade heptane. The chromatography used a YMC-SC, 20 × 250 mm column (5 μm particles). |

SYNTHETIC METHODS

1. Preparation #1: tent-Butyl 5-acetamido-3-bromo-1H-pyrrolo[2,3-c]pyridine-1-carboxylate

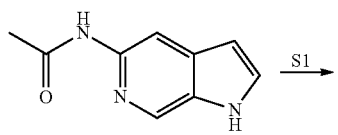

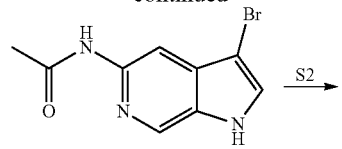

Step 1: N-(3-bromo-1H-pyrrolo[2,3-c]pyridin-5-yl)acetamide. To a suspension of N-(1H-pyrrolo[2,3-c]pyridin-5- ypacetamide (39.9 g, 228 mmol) in dimethyl formamide (227 mL) was added N-bromosuccinimide (40.5 g, 228 mmol) at room temperature. The reaction was stirred for about 20 minutes. A brown precipitate formed, which was collected by filtration and dried in oven overnight to provide the product (46.5 g, 183 mmol, 80% yield). LC/MS (Table A, Method a) $R_f$=0.19 minutes; MS m/z: 254, 256 (M+H)+.

Step 2: tent-butyl 5-acetamido-3-bromo-1H-pyrrolo[2,3-c]pyridine-1-carboxylate. A flask was charged with N-(3-bromo-1H-pyrrolo[2,3-c]pyridin-5-yOacetamide (15 g, 59.0 mmol), di-tert-butyl dicarbonate (16.27 mL, 70.8 mmol), and 4-dimethylamino pyridine (0.721 g, 5.90 mmol) in acetonitrile (295 mL). The mixture stirred at room temperature for about 1 hour, filtered, and the filtered material washed with acetonitrile (50 mL) to provide the product (14.8 g, 71% yield). $^1$H NMR (400 MHz, Dimethyl sulfoxide-$d_6$) δ 10.57 (s, 1H), 8.95 (d, 1H), 8.21 (m, 1H), 8.09 (d, 1H), 2.10 (d, 3H), 1.62 (s, 9H). LC/MS (Table A, Method a) $R_f$=1.51 minutes; MS m/z: 354, 356 (M+H)+. Boc=t-Butoxycarbonyl.

2. Preparation #2: N-(3-Bromo-1-methyl-1H-pyrrolo[2,3-c]pyridin-5-yl)acetamide

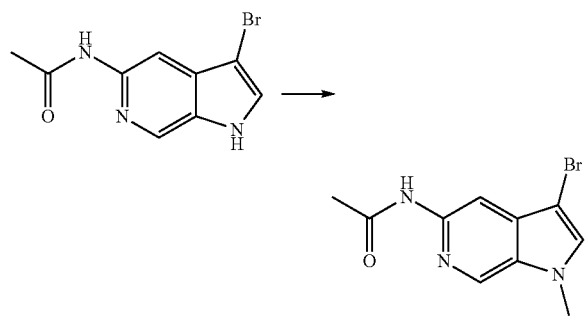

To a solution of N-(3-bromo-1H-pyrrolo[2,3-c]pyridin-5-yOacetamide (19.25 g, 76 mmol) (Preparation #1, Step 1) in acetonitrile (600 mL) was added cesium carbonate (49.4 g, 152 mmol) followed by dimethyl sulfate (7.53 mL, 80 mmol). The reaction stirred with a mechanical stirrer for about 30 minutes at ambient temperature. After 30 minutes, an additional portion of dimethyl sulfate (0.362 mL, 3.79 mmol) was added and stirred for about 10 minutes. The reaction was diluted with water and ethyl acetate, the layers were separated, the aqueous layer was extracted with ethyl acetate three times, the combined organic layers were dried over MgSO$_4$, filtered, and concentrated under reduced pressure to provide the product (19.4 g, 96% yield). LC/MS (Table A, Method b) $R_f$=0.38 minutes; MS m/z: 268, 270 (M+H)+.

3. Preparation #3: 1-(3-Bromo-1-methyl-1H-pyrrolo[2,3-c]pyridin-5-yl)urea

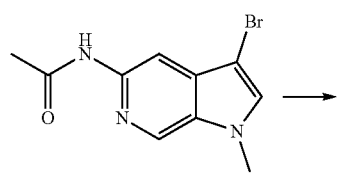

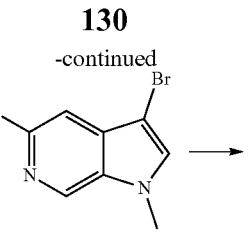

Step 1: 3-bromo-1-methyl-1H-pyrrolo[2,3-c]pyridin-5-amine hydrochloride. N-(3- bromo-1-methyl-1H-pyrrolo[2,3-c]pyridin-5-ypacetamide (8 g, 29.8 mmol) (Preparation #2) in 5N aqueous HC1 (29.8 mL, 149 mmol) and dioxane (99 mL) was heated to 85° C. for 2 hours. The solvent was concentrated under reduced pressure to provide a residue, which was taken up in 10% methanol/dichloromethane, dried over MgSO$_4$, and filtered through a pad of Celite® to provide the product (7.11 g, 83% yield). $^1$H NMR (400 MHz, Dimethyl sulfoxide-$d_6$) 67 8.65 (s, 1H), 8.15 (s, 1H), 6.76 (s, 1H), 3.14 (s, 3H).

Step 2: 1-(3-Bromo-1-methyl-1H-pyrrolo[2,3-c]pyridin-5-yl)urea. 3-Bromo-l-methyl- 1H-pyrrolo[2,3-c]pyridin-5-amine hydrochloride (2.61 g, 9.94 mmol) and N,N-diisopropylethylamine (6.95 mL, 39.8 mmol) in tetrahydrofuran (99 mL) was cooled to −78° C. and phosgene (15 wt % in toluene) (7.84 mL, 10.94 mmol) was added dropwise over 15 minutes. The mixture was allowed to stir for 15 minutes before a 7 M methanolic solution of ammonia (11.36 mL, 80 mmol) was added dropwise via syringe. The solution was then warmed to room temperature and stirred for 1 hour, then quenched with water and brine, and diluted with ethyl acetate. The layers were separated, the aqueous phase was extracted with 10% methanol/ethyl acetate, and the combined organic layers were concentrated to provide a residue, which was triturated using acetonitrile to provide a triturated material. The aqueous phase was also filtered to provide a filtered material. The filtered material and the triturated material were combined to afford the product (1.94 g, 72% yield). $^1$H NMR (400 MHz, Dimethyl sulfoxide-$d_6$) δ 8.81 (s, 1H), 8.53 (d, J =1.1 Hz, 1H), 7.71 (s, 1H), 7.62 (s, 1H), 6.50 (s, 2H), 3.84 (s, 3H).

4. Preparation #4: tent-Butyl 3-bromo-5-ureido-1H-pyrrolo[2,3-c]pyridine-1-carboxylate

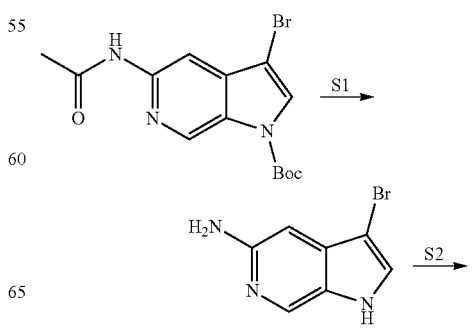

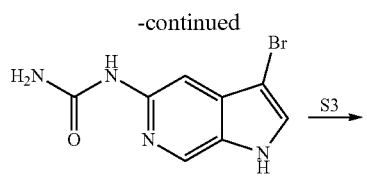

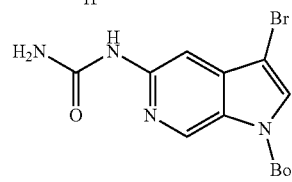

Step 1: 3-bromo-1H-pyrrolo[2,3-c]pyridin-5-amine. tert-Butyl 5-acetamido-3-bromo-1H-pyrrolo[2,3-c]pyridine-1-carboxylate (51 g, 144 mmol) (Preparation #1) in dioxane (600 mL) and 5.0 N aqueous HCl (144 mL, 720 mmol) were heated to 70° C. for 20 hours. The solvents were removed under reduced pressure, the residue partitioned between ethyl acetate and aqueous NaOH/NaHCO$_3$ at pH=10, the organic layer was dried over MgSO$_4$, filtered, and concentrated to provide the product (30.8 g, 100% yield). $^1$H NMR (400 MHz, Dimethyl sulfoxide-d$_6$) δ 11.30 (s, 1H), 8.18 (s, 1H), 7.54 (s, 1H), 6.38 (s, 1H), 5.21 (br, 2H). Boc=t-Butoxycarbonyl.

Step 2: 1-(3-bromo-1H-pyrrolo[2,3-c]pyridin-5-yl)urea. To 3-bromo-1H-pyrrolo[2,3-c]pyridin-5-amine (30 g, 141 mmol) in tetrahydrofuran (707 mL) and 4-dimethylamino pyridine (98 mL, 566 mmol) was added phosgene (15% solution of in toluene) (111 mL, 156 mmol) dropwise via syringe at about −60° C. After the completion of the addition, the mixture stirred for 45 minutes at −78° C. and a solution of 7M ammonia in methanol (162 mL, 1132 mmol) was added at −78° C. The mixture warmed to room temperature over 2 hours, then quenched with 200 mL of 2 M aqueous NaOH, and allowed to stir for 20 minutes, then extracted with ethyl acetate (4×100 mL). The combined organic layers were dried over MgSO$_4$, filtered, and concentrated to provide the product (36 g, 100% yield). $^1$H NMR (400 MHz, Dimethyl sulfoxide-d$_6$) δ 11.67 (s, 1H), 8.74 (s, 1H), 8.40 (d, J =1.1 Hz, 1H), 7.71 (s, 1H), 7.57 (s, 1H), 6.52 (s, 2H).

Step 3: tert-butyl 3-bromo-5-ureido-1H-pyrrolo[2,3-c]pyridine-1-carboxylate. 1-(3- Bromo-1H-pyrrolo[2,3-c]pyridin-5-yl)urea (10.94 g, 42.9 mmol), di-tert-butyl dicarbonate (12.17 g, 55.8 mmol), N,N-diisopropylethylamine (14.84 mL, 86 mmol), and 4-dimethylamino pyridine (0.052 g, 0.429 mmol) in tetrahydrofuran (214 mL) was stirred at room temperature for 48 hours. The reaction was partitioned between ethyl acetate (100 mL) and water (100 mL). A large amount of solid was distributed between the 2 layers. The solids were filtered off, dried under reduced pressure overnight. The combined organic layers were dried over MgSO$_4$, filtered, and concentrated under reduced pressure to provide a residue, which was triturated with acetonitrile (50 mL) at 40° C. for 1 hour, then filtered and dried under reduced pressure to provide the product, which was combined with the previously collected solids to give desired product (8.21 g, 53% yield). $^1$H NMR (400 MHz, Dimethyl sulfoxide-d$_6$) δ 9.05 (s, 1H), 8.85 (d, J=1.0 Hz, 1H), 8.06 (s, 1H), 7.77 (s, 1H), 6.57 (s, 2H), 1.63 (s, 9H). Boc=t-Butoxycarbonyl.

5. Preparation #5 and #5a: (R)-2-Bromo-6-(3-methoxytetrahydrofuran-3-yl)-4-methylpyridine and (S)-2-bromo-6-(3-methoxytetrahydrofuran-3-yl)-4-methylpyridine

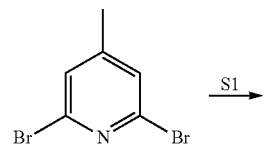

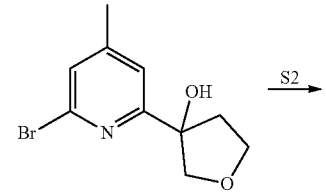

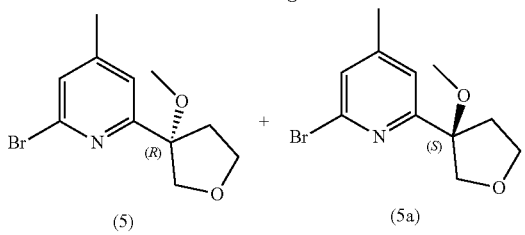

Step 1: 3-(6-bromo-4-methylpyridin-2-yl)tetrahydrofuran-3-ol. 2,6-Dibromo-4-methylpyridine (3.76 g, 14.98 mmol) in dichloromethane (DCM) (80 mL) was cooled to −78° C. under nitrogen. n-Butyl lithium (2.5 M in hexanes) (6.59 mL, 16.48 mmol) was added dropwise, maintaining the internal temperature to less than −70° C. The solution became a suspension after the addition was complete and stirred at −78° C. for 15 minutes. A solution of dihydrofuran-3(2H)-one (1.548 g, 17.98 mmol) in 2 mL of DCM was added over 3 minutes, keeping the internal temperature to less than −60° C. After the addition was complete, the temperature went back down to −78° C. and stirred for 30 minutes. The reaction was quenched with saturated aqueous NH$_4$Cl and extracted with DCM. The organic portion was dried over MgSO$_4$, filtered, and concentrated to provide a residue, which was purified by silica gel column, eluting with 0-50% ethyl acetate/heptanes, to provide the product (2.13 g, 55% yield). LC/MS (Table A, Method b) R$_t$=1.15 minutes; MS m/z: 258, 260 (M+H)$^+$.

Step 2: (R)-2-bromo-6-(3-methoxytetrahydrofuran-3-yl)-4-methylpyridine and (S)-2- bromo-6-(3-methoxytetrahydrofuran-3-yl)-4-methylpyridine. A flask was charged with 3-(6-bromo-4-methylpyridin-2-yl)tetrahydrofuran-3-ol (2.525 g, 9.78 mmol) and was dissolved in tetrahydrofuran (98 mL) and cooled to 0° C. before the addition of NaH (1.1 eq, 60% dispersion in mineral oil). The reaction stirred warming to room temperature for 15 minutes before the addition of iodomethane (0.918 mL, 14.67 mmol). The reaction stirred at room temperature for 1 hour. The reaction was cooled in an ice bath and quenched slowly with sat aq NH$_4$Cl. The reaction was extracted into dichloromethane. The organic portion was dried over MgSO$_4$, filtered, and concentrated under reduced pressure to provide racemic product (2.60 g, 9.55 mmol, 98% yield). The product was further purified via chiral HPLC (Table B, Method 1) to provide the (R) isomer (0.836 g, 32% yield, 99% ee, R$_t$=10.4 minutes, optical rotation =(−)) and to provide the (S) isomer (0.831 g, 31% yield, 99% ee, $R_t$=8.6 minutes, optical rotation =(+)). LC/MS (Table A, Method b) $R_t$=1.33 minutes; MS m/z: 272, 275 (M+H)$^+$.

6. Preparation #6 and #6a: (R)-2-Bromo-4-(methoxymethyl)-6-(3-methoxytetrahydrofuran-3-yl)pyridine and (S)-2-bromo-4-(methoxymethyl)-6-(3-methoxytetrahydrofuran-3-yl)pyridine

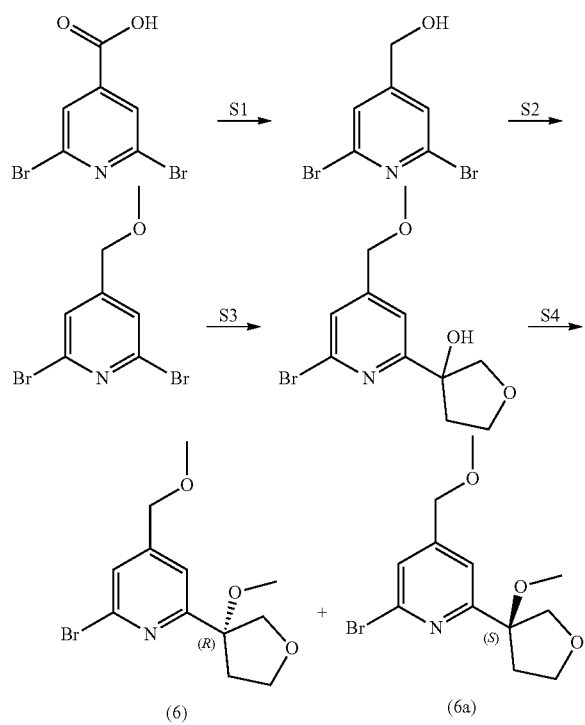

Step 1: (2,6-dibromopyridin-4-yl)methanol. 2,6-Dibromoisonicotinic acid (25 g, 89 mmol) dissolved in tetrahydrofuran (THF) (89 mL) was cooled to 0° C. before the dropwise addition of borane THF-complex, then the mixture was heated at 50° C. for 3 hours. The reaction was cooled, and methanol (MeOH) (30 mL) was added, the reaction was then heated to 50° C. for 10 minutes. The mixture was then concentrated, and chased with an additional 50 mL of MeOH. The residue was partitioned between ethyl acetate and saturated aqueous Na$_2$CO$_3$. The combined organic phase was dried over anhydrous MgSO$_4$, filtered, and concentrated to provide the product (23.26 g, 87 mmol, 98% yield). LC/MS (Table A, Method b) $R_t$=0.86 minutes; MS m/z: 268, 280 (M+H)$^+$.

Step 2: 2,6-dibromo-4-(methoxymethyl)pyridine. A flask was charged with (2,6-dibromopyridin-4-yl)methanol (7.9 g, 29.6 mmol) and dissolved in tetrahydrofuran (118 mL). The reaction was cooled to 0° C. before the addition of NaH (60% dispersion in mineral oil) (1.421 g, 35.5 mmol). The reaction stirred for 15 minutes at 0° C. then, iodomethane (2.0 mL, 32.6 mmol) was added in one portion, and the reaction stirred, warming to room temperature over 30 minutes. The reaction was slowly quenched with water, and NH$_4$Cl and extracted into ethyl acetate. The organic portion was dried over MgSO$_4$, filtered, and concentrated under reduced pressure. The crude product was purified via silica gel chromatography eluting with 0-60% ethyl acetate/heptanes to provide the product (5.09 g, 18.12 mmol, 61.2% yield). LC/MS (Table A, Method b) $R_t$=1.41 minutes; MS m/z: 280, 282(M+H)$^+$.

Step 3: 3-(6-bromo-4-(methoxymethyl)pyridin-2-yl)tetrahydrofuran-3-ol. In a round-bottomed flask, 2,6-dibromo-4-(methoxymethyl)pyridine (10.72 g, 38.2 mmol) was dissolved in dichloromethane (DCM) (127 mL). The solution was stirred over MgSO$_4$ for 10 minutes, and then filtered into the reaction flask. The reaction was cooled to −78° C. under nitrogen before the dropwise addition of n-butyl lithium (2.5 M in hexanes) (16.79 mL, 42.0 mmol), maintaining the internal temperature less than −70° C. The reaction stirred at −78° C. for 50 minutes, then a solution of dihydrofuran-3(2H)-one (3.94 g, 45.8 mmol) in 5 mL of DCM was added, keeping the internal temperature less than −60° C. After addition was complete, the temperature was cooled to −78° C., and stirred at −78° C. for 10 minutes. The reaction was quenched into saturated aqueous NH$_4$Cl and extracted with DCM. The organic portion was dried over MgSO$_4$, filtered, and concentrated to give crude product. The material was purified via silica gel column, eluting with 0-50% ethyl acetate/heptanes to provide the product (5.68 g, 19.71 mmol, 52% yield). LC/MS (Table A, Method b) $R_t$=1.04 minutes; MS m/z: 288, 290 (M+H)$^+$.

Step 4: (R)-2-bromo-4-(methoxymethyl)-6-(3-methoxytetrahydrofuran-3-yl)pyridine and (S)-2-bromo-4-(methoxymethyl)-6-(3-methoxytetrahydrofuran-3-yl)pyridine. A flask was charged with 3-(6-bromo-4-(methoxymethyl)pyridin-2-yl)tetrahydrofuran-3-ol (5.68 g, 19.71 mmol) and was dissolved in tetrahydrofuran (99 mL) and cooled to 0° C. before the addition of NaH (60% dispersion in mineral oil) (1.183 g, 29.6 mmol). The reaction stirred warming to room temperature for 15 minutes before the addition of iodomethane (1.849 mL, 29.6 mmol). The reaction stirred at room temperature for 2 hours. The reaction was cooled in an ice bath and quenched slowly with saturated aqueous NH$_4$Cl. The reaction was extracted into ethyl acetate. The organic portions were dried over MgSO$_4$, filtered, and concentrated under reduced pressure to give crude racemic product, that was purified via chiral SFC (Table B, Method 2) to provide the (R)-isomer (2.3 g, 39% yield, 96% ee, $R_t$=2.9 minutes, optical rotation =(−)) and the (S)-isomer (2.2 g, 37% yield, >99% ee, $R_t$=2.7 minutes, optical rotation =(+)). LC/MS (Table A, Method b) $R_t$=1.25 minutes; MS m/z: 302,304 (M+H)$^+$.

7. Preparation #7:
2,6-Dichloro-4-(1,3-dioxolan-2-yl)pyridine

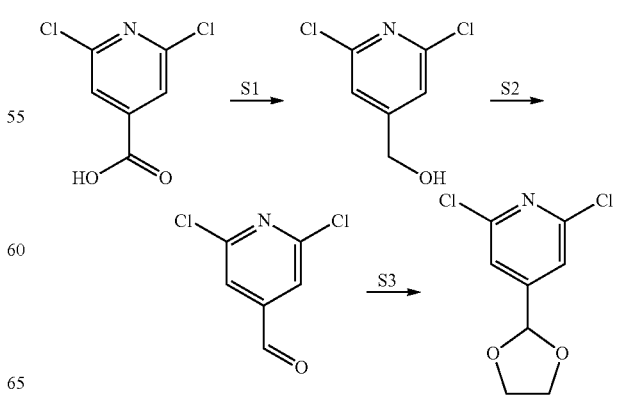

Step 1: (2,6-dichloropyridin-4-yl)methanol. To a solution of 2,6-dichloroisonicotinic acid (100 g, 521 mmol) in tetrahydrofuran (THF) (521 mL) at 0° C. was added borane-THF complex (1M in THF) (781 mL, 781 mmol) dropwise from an addition funnel, keeping the internal temperature around 30° C. After the addition was complete, the mixture was heated at 50° C. for 4 hours. The reaction was cooled, and methanol (MeOH) (100 mL) was added dropwise via addition funnel until the bubbling subsided, then heated to 50° C. for 20 minutes. After that time, the mixture was concentrated to about 500 mL volume, and 100 mL of MeOH was added and rotovaped again to give crude residue, which was then partitioned between ethyl acetate and saturated aqueous NaHCO$_3$. The organic portion was separated, dried over MgSO$_4$, filtered, and concentrated to provide the product (105 g, 92% yield). LC/MS (Table A, Method b) R$_t$=0.84 minutes; MS m/z: 179, 181 (M+H)$^+$.

Step 2: 2,6-dichloroisonicotinaldehyde. To a solution of oxalyl chloride (2.70 mL, 30.9 mmol) in dichloromethane (DCM) (50 mL) was added a solution of dimethyl sulfoxide (4.78 mL, 67.4 mmol) in DCM (50 ml) dropwise at −78° C. under nitrogen. After 10 minutes, a solution of (2,6- dichloropyridin-4-yl)methanol (5 g, 28.1 mmol) in DCM (50 mL) was added dropwise at −78° C. The mixture was stirred for 15 minutes and then triethylamine (19.57 mL, 140 mmol) was added dropwise at −78° C. After the addition, the reaction was stirred at −78° C. for 1 hour. The cooling bath was removed and water (150 mL) was added at 20° C. The mixture was extracted with DCM (3×100 mL). The organic layers were combined, dried over Na$_2$SO$_4$, filtered, and concentrated under reduced pressure to provide the product (4.5 g, 86% yield). $^1$H NMR (400MHz, Chloroform-d) δ =10.01 (s, 1H), 7.68 (s, 2H).

Step 3: 2,6-dichloro-4-(1,3-dioxolan-2-yl)pyridine. To a solution of 2,6- dichloroisonicotinaldehyde (25.3 g, 144 mmol) in toluene (205 mL) and ethylene glycol (12.06 mL, 216 mmol) was added p-toluenesulfonic acid monohydrate (0.54 g, 2.87 mmol) in one portion. The reaction was heated to reflux for 16 hours with Dean-Stark trap apparatus. The reaction cooled to room temperature, and 200 mL of ethyl acetate was added and quenched by addition of aqueous NaHCO$_3$. The layers were separated and the aqueous phase extracted (2×20 mL) with ethyl acetate. The combined organic extracts were then washed once more with NaHCO$_3$, dried over MgSO$_4$, filtered, and concentrated. The product was purified via silica gel chromatography eluting with 5-40% ethyl acetate:heptanes to provide the product (24.8 g, 78% yield). LC/MS (Table A, Method b); R$_t$=1.30 minutes; MS m/z: 219.9, 221.9 (M+H)$^+$.

8. Preparation #8 and #8a: (R)-2-Chloro-6-(3-ethyltetrahydrofuran-3-yl)isonicotinonitrile and (S)-2-chloro-6-(3-ethyltetrahydrofuran-3-yl)isonicotinonitrile

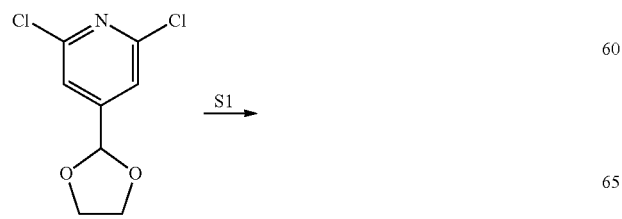

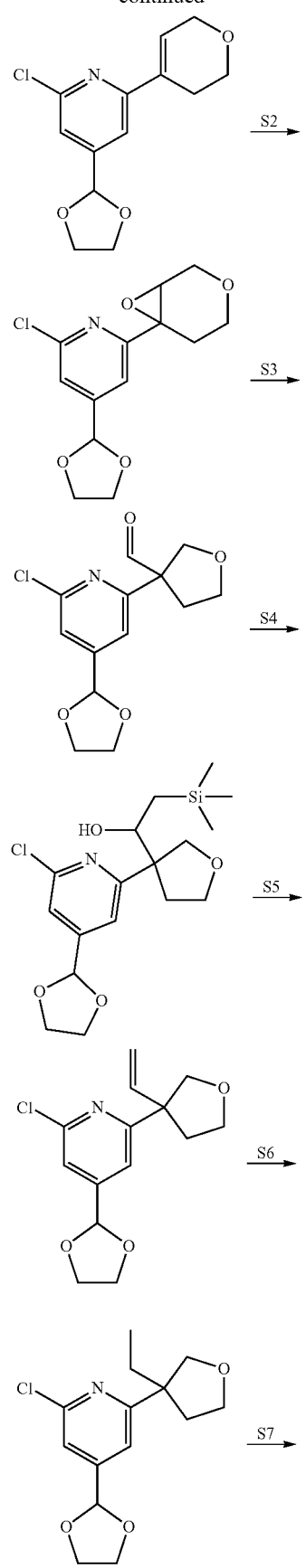

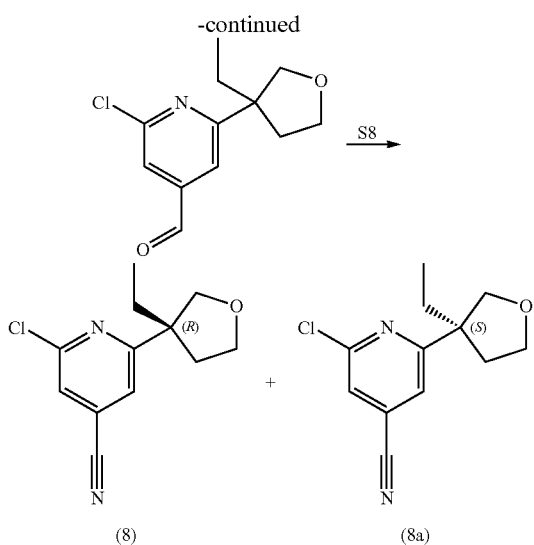

(8)    (8a)

Step 1: 2-chloro-6-(3,6-dihydro-2H-pyran-4-yl)-4-(1,3-dioxolan-2-yl)pyridine. In a 2L 3-neck flask, a mixture of 3,6-dihydro-2H-pyran-4-boronic acid pinacol ester (12.7 g, 60.5 mmol), 2,6-dichloro-4-(1,3-dioxolan-2-yl)pyridine (14.14 g, 64.3 mmol) (Preparation #7) and cesium carbonate (29.5 g, 91 mmol) in dioxane (580 mL) and water (95 mL) was degassed with nitrogen for 40 minutes, then added [1,1'-bis(diphenylphosphino)ferrocene] dichloropalladium (II)-dichloromethane adduct (Pd(dppf)Cl$_2$-DCM adduct) (2.468 g, 3.02 mmol). The reaction was heated at 60° C. for 2 hours. The reaction was removed from heat and allowed to cool to room temperature. Reduced volume of reaction to about 200 mL, then diluted with ethyl acetate (500 mL) and water (300 mL). The organic layers were separated, washed with brine (150 mL), dried over MgSO$_4$, filtered, and concentrated under reduced pressure. The crude material was purified via silica gel chromatography eluting with 0-40% ethyl acetate/heptanes to provide the product (9.23 g, 57% yield). $^1$H NMR (400 MHz, Dimethyl sulfoxide-d$_6$ δ 7.53 (d, J =1.0 Hz, 1H), 7.40-7.34 (m, 1H), 6.86 (tt, J=3.0, 1.6 Hz, 1H), 5.83 (s, 1H), 4.28 (q, J=2.8 Hz, 2H), 4.08-3.95 (m, 4H), 3.81 (t, J=5.4 Hz, 2H), 2.49-2.46 (m, 2H).

Step 2: 2-(3,7-dioxabicyclo[4.1.0]heptan-6-yl)-6-chloro-4-(1,3-dioxolan-2-yl)pyridine. To a solution of 2-chloro-6-(3,6-dihydro-2H-pyran-4-yl)-4-(1,3-dioxolan-2-yl)pyridine (9.23 g, 34.5 mmol) in dichloromethane (DCM) (345 mL), cooled to 0° C., was added meta-chloroperbenzoic acid (m-CPBA) (8.50 g, 37.9 mmol). The reaction was removed from the cooling bath and stirred at room temperature for 16 hours. The reaction was then heated to 35° C. for 2 hours. Additional m-CPBA (0.892 g, 5.17 mmol) was added and the reaction stirred at 35° C. for an additional 2.5 hours. The solution was diluted with DCM (100 mL) and the organic layers were washed with NaHCO$_3$ (2×300 mL), followed by brine (300 mL), then dried over MgSO$_4$, filtered, and concentrated under reduced pressure. The crude material was purified via silica gel chromatography eluting with 0-45% ethyl acetate/heptanes to provide the product (8.8 g, 90% yield). $^1$H NMR (400 MHz, Dimethyl sulfoxide-d$_6$) δ 7.48 (dt, J=1.3, 0.6 Hz, 1H), 7.37 (dt, J=1.2, 0.6 Hz, 1H), 5.84 (d, J=0.6 Hz, 1H), 4.08-3.94 (m, 5H), 3.89 (d, J=13.5 Hz, 1H), 3.62-3.46 (m, 2H), 3.46-3.40 (m, 1H), 2.80-2.65 (m, 1H), 2.00 (dt, J=14.9, 5.4 Hz, 1H).

Step 3: 3-(6-chloro-4-(1,3-dioxolan-2-yl)pyridin-2-yl)tetrahydrofuran-3-carbaldehyde. To a solution of 2-(3,7-dioxabicyclo[4.1.0]heptan-6-yl)-6-chloro-4-(1,3-dioxolan-2-yl)pyridine (2 g, 7.05 mmol) in dioxane (70 mL) was added scandium (II) trifluoromethanesulfonate (0.347 g, 0.705 mmol). The reaction was heated to 80° C. for 8 minutes. The reaction was then cooled to room temperature, and the volume of dioxane was reduced to about 30 mL. The remaining solvent was diluted with ethyl acetate (100 mL) and added aqueous NaHCO$_3$ (50 mL). The organic layers were dried over MgSO$_4$, filtered, and concentrated under reduced pressure. The product was purified via silica gel chromatography eluting with 15-60% ethyl acetate/heptanes to provide the product (1.62 g, 81% yield). $^1$H NMR (400 MHz, Dimethyl sulfoxide-d$_6$) δ 9.69 (s, 1H), 7.48 (dd, J=1.2, 0.5 Hz, 1H), 7.46 (dd, J=1.2, 0.5 Hz, 1H), 5.85 (d, J=0.5 Hz, 1H), 4.41 (d, J=9.2 Hz, 1H), 4.11-3.89 (m, 6H), 3.84 (dd, J=7.3, 6.9 Hz, 2H), 2.65 (dt, J=12.7, 6.8 Hz, 1H), 2.41 (dt, J=12.8, 7.3 Hz, 1H).

Step 4: 1-(3-(6-chloro-4-(1,3-dioxolan-2-yl)pyridin-2-yptetrahydrofuran-3-yl)-2- (trimethylsilypethan-1-ol. To a solution of 3-(6-chloro-4-(1,3-dioxolan-2-yl)pyridin-2-yl)tetrahydrofuran-3-carbaldehyde (1.11 g, 3.91 mmol) in diethyl ether (39 mL) cooled to 0° C. was added trimethylsilylmethyl magnesium chloride (4.7 mL, 4.69 mmol) dropwise. The reaction stirred at 0° C. for 30 minutes, then quenched at this temperature by adding aqueous NH$_4$Cl (50 mL). The reaction was then diluted with diethyl ether (60 mL), and the organic layers were washed with brine (15 mL), dried over MgSO$_4$, filtered, and concentrated under reduced pressure to provide the product (1.35 g, 93% yield). LC/MS (Table A, Method a) R$_t$=1.70 minutes; MS m/z: 354, 372 (M+H)$^+$.

Step 5: 2-chloro-4-(1,3-dioxolan-2-yl)-6-(3-vinyltetrahydrofuran-3-yl)pyridine. To a solution of 1-(3-(6-chloro-4-(1,3-dioxolan-2-yl)pyridin-2-yptetrahydrofuran-3-yl)-2- (trimethylsilypethan-l-ol (1.43 g, 3.84 mmol) in acetonitrile (54.9 mL) at 0° C. was added dropwise boron trifluoride diethyl etherate (0.487 mL, 3.84 mmol). The reaction was removed from cooling bath and heated to 50° C. for 90 minutes. The reaction as then cooled to room temperature and added aqueous NaHCO$_3$ (40 mL). Extracted into ethyl acetate (60 mL), then washed organic layers with brine (20 mL), dried over MgSO$_4$, filtered, and concentrated under reduced pressure to provide crude product that was used in the next step. LC/MS (Table A, Method a) R$_t$=1.32 minutes; MS m/z: 282 (M+H)$^+$.

Step 6: 2-chloro-4-(1,3-dioxolan-2-yl)-6-(3-ethyltetrahydrofuran-3-yl)pyridine. To a nitrogen filled flask was added 10% palladium on carbon (0.355 g, 0.334 mmol) followed by a solution of 2-chloro-4-(1,3-dioxolan-2-yl)-6-(3-vinyltetrahydrofuran-3-yl)pyridine (0.94 g, 3.34 mmol) in ethyl acetate (60 mL). The flask was evacuated and backfilled the flask with hydrogen from balloon. The reaction stirred for 25 minutes at room temperature. The reaction was filtered over a pad of Celite® rinsing with ethyl acetate. The solvent was concentrated under reduced pressure to provide the product (0.93 g, 98% yield). LC/MS (Table A, Method a) R$_t$=1.38 minutes; MS m/z: 284 (M+H)$^+$.

Step 7: 2-chloro-6-(3-ethyltetrahydrofuran-3-yl)isonicotinaldehyde. A solution of 2- chloro-4-(1,3-dioxolan-2-yl)-6-(3-ethyltetrahydrofuran-3-yl)pyridine (0.925 g, 3.26 mmol) in tetrahydrofuran (32 mL) and HCl (5N, aq) (6.52 mL, 32.6 mmol) was heated to 55° C. for 3 hours. The reaction was cooled to room temperature, diluted with water (80 mL) then added solid NaHCO$_3$ until gas evolution ceased. The organic layers were extracted from aqueous layer with ethyl acetate (100 mL), and then the organic layer was washed with brine (40 mL), dried over MgSO$_4$, filtered, and concentrated under reduced pressure. The residue was purified via silica gel chromatography, eluting with 0-40% ethyl acetate/heptanes to provide the product (0.62g, 79% yield). LC/MS (Table A, Method a) R$_f$=1.32 minutes; MS m/z: 240 (M+H)$^+$.

Step 8: (R)-2-chloro-6-(3-ethyltetrahydrofuran-3-yl) isonicotinonitrile and (S)-2- chloro-6-(3-ethyltetrahydrofuran-3-yl)isonicotinonitrile. To a solution of 2-chloro-6-(3-ethyltetrahydrofuran-3-yl)isonicotinaldehyde (0.616 g, 2.57 mmol) dissolved in ethanol (8.57 mL) was added hydroxylamine hydrochloride (0.714 g, 10.28 mmol). The reaction was heated to 75° C. for 70 minutes. The reaction was removed from heat, and then concentrated under reduced pressure. To the mixture was added ethyl acetate (60 mL) and aqueous NaHCO$_3$ (40 mL). The organic portion was separated, dried over MgSO$_4$, and concentrated under reduced pressure. The residue was then dissolved in pyridine (3.7 mL, 46.3 mmol), and mesyl chloride (0.401 mL, 5.14 mmol) was added. The reaction was heated to 75° C. for 15 minutes. The reaction was then removed from heat, diluted with water (20mL), and ethyl acetate (40mL) was added. To this biphasic mixture was added brine (10 mL) to help layer separation. The organic layers were then separated, dried over MgSO$_4$, filtered, and concentrated under reduced pressure. The residue was purified via silica gel chromatography, eluting with 0-100% ethyl acetate/heptanes to give a racemic product, that was further purified via chiral SFC (Table B, Method 3) to provide the (R)-isomer (0.15 g, 25% yield, 96%ee, R$_t$=3.9 minutes) and the (S)-isomer (0.15 g, 25% yield, 99%ee, R$_t$=2.8 minutes). $^1$H NMR (400 MHz, Chloroform-d) δ 8.00 (dd, J=1.1, 0.4 Hz, 1H), 7.96 (dd, J=1.1, 0.4 Hz, 1H), 4.01 (d, J=8.7 Hz, 1H), 3.85 (td, J=8.3, 5.9 Hz, 1H), 3.80 -3.68 (m, 2H), 2.41 (ddd, J=12.6, 8.2, 5.9 Hz, 1H), 2.09 -1.94 (m, 1H), 1.80 (qd, J=7.5, 4.5 Hz, 2H), 0.62 (t, J=7.4 Hz, 3H).

9. Preparation #9 and #9a: (R)-2-Chloro-6-(3-methoxytetrahydrofuran-3- yl)isonicotinonitrile and (S)-2-chloro-6-(3-methoxytetrahydrofuran-3-yl) isonicotinonitrile

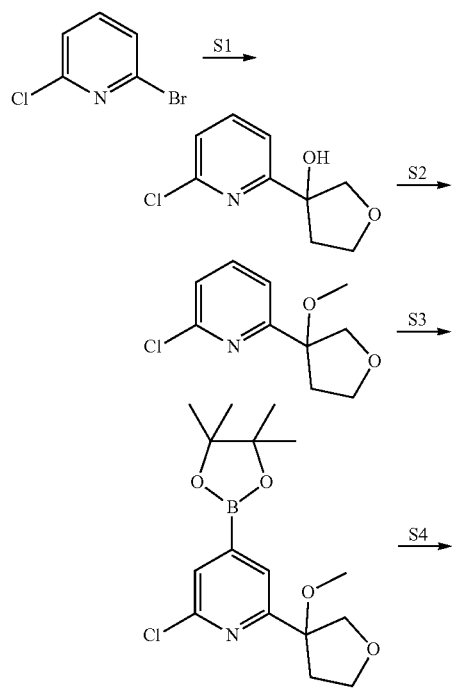

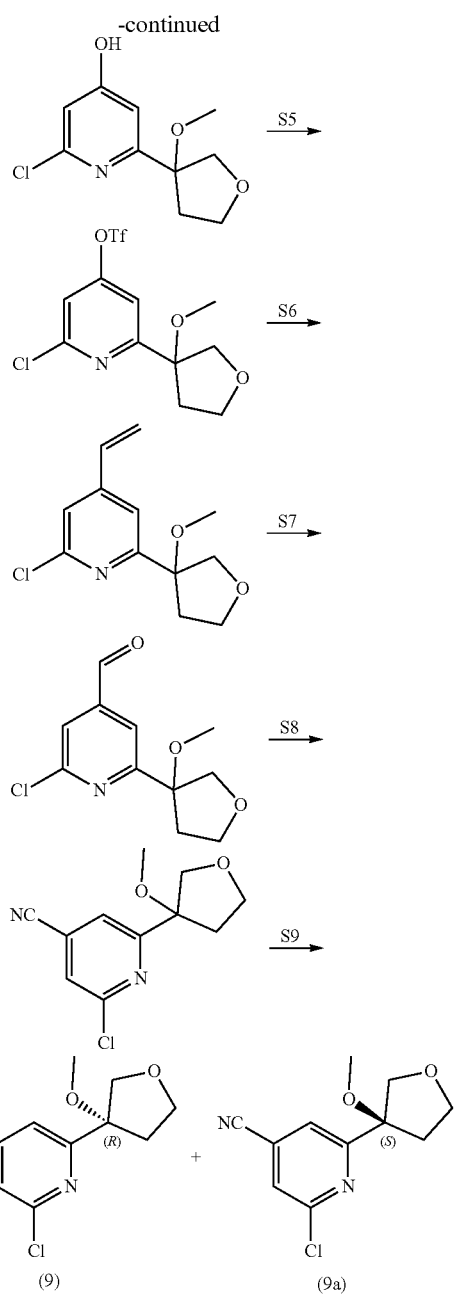

Step 1: 3-(6-chloropyridin-2-yl)tetrahydrofuran-3-ol. 2-Bromo-6-chloropyridine (44.44 g, 231 mmol) was dissolved in dichloromethane (DCM) (770 mL), stirred in a 3 neck 2L reaction flask and then cooled to −78° C. n-Butyllithium (1M in THF) (106 mL, 266 mmol) was cannulated into an addition funnel and then added dropwise into the reaction, maintaining the temperature below −69° C. The reaction was stirred for 20 minutes. Dihydrofuran-3(2H)-one (22.86 g, 266 mmol) was dissolved in minimal DCM and then added into the reaction dropwise. The reaction was allowed to slowly warm to room temperature. After the reaction had reached room temperature, it was quenched with ammonium chloride solution (200 mL) and then the layers were separated. The aqueous layer was extracted with DCM and then the organic layer was washed with brine (200 mL). The organic layer was dried over MgSO$_4$ and then concentrated to dryness. The crude residue was purified by silica gel chromatography eluting with 0%-100% ethyl acetate in heptanes to provide the product (33.5 g, 71% yield). LCMS (Table A, Method a) $R_t$=0.67 minutes; MS m/z: 200, 202 (M+H)$^+$.

Step 2: 2-chloro-6-(3-methoxytetrahydrofuran-3-yl)pyridine. 3-(6-Chloropyridin-2-yl)tetrahydrofuran-3-ol (19.2 g, 96 mmol) was dissolved in tetrahydrofuran (321 mL) and then stirred in a 1L flask at room temperature. NaH (60% dispersion in mineral oil) (7.69 g, 192 mmol) was added and then the reaction was stirred for 10 minutes. After the bubbling ceased, iodomethane (7.82 mL, 125 mmol) was added and then the reaction was allowed to stir for 12 hours at room temperature. Upon conversion of the starting material, the reaction was cooled to room temperature and then reverse quenched into 300 mL aqueous ammonium chloride solution and then extracted (2×200mL) with ethyl acetate. The combined organic layer was washed with brine and then dried over MgSO$_4$ and concentrated to dryness to provide the product (19.7 g, 86% yield). LCMS (Table A, Method a) $R_t$=0.92 minutes; MS m/z: 214, 216 (M+H)$^+$.

Step 3: 2-chloro-6-(3-methoxytetrahydrofuran-3-yl)-4-(4,4,5,5-tetramethyl-1,3,2-dioxaborolan-2-yl)pyridine. 2-Chloro-6-(3-methoxytetrahydrofuran-3-yl)pyridine (19.7 g, 92 mmol) was dissolved in cyclohexane (307 mL), stirred in a 1 L flask and degassed with a stream of nitrogen. Then 4,4'-di-tert-butyl-2,2'-bipyridine (0.495 g, 1.844 mmol), bis(1,5-cyclooctadiene)diiridium(I) dichloride (0.619 g, 0.922 mmol), and 4,4,4',4',5,5,5',5'-octamethyl-2,2'-bi(1,3,2-dioxaborolane) (28.1 g, 111 mmol) were each added to the flask and then the reaction was heated to 75° C. for 1 hour. The reaction was cooled to room temperature. The solvent was concentrated under reduced pressure and then the crude material was triturated with heptanes and filtered to provide a solid. The filtrate was concentrated and then the trituration/filtration was repeated to provide additional solids. The combined solids were dried overnight in a vacuum oven to provide the product (26.2 g, 84% yield). LCMS (Table A, Method a) $R_t$=0.75 minutes; MS m/z: 257, 259 (M+H)$^+$ (boronic acid) $^1$H NMR (400 MHz, Chloroform-d) δ 7.73 (d, J =0.8 Hz, 1H), 7.57 (d, J =0.7 Hz, 1H), 4.17-4.00 (m, 4H), 3.95 (d, J=9.6 Hz, 1H), 3.18 (s, 3H), 2.62 (dt, J=13.2, 8.5 Hz, 1H), 2.36 (dddd, J=13.3, 7.0, 4.4, 1.3 Hz, 1H), 1.34 (s, 13H).

Step 4: 2-chloro-6-(3-methoxytetrahydrofuran-3-yl)pyridin-4-ol. 2-Chloro-6-(3-methoxytetrahydrofuran-3-yl)-4-(4,4,5,5-tetramethyl-1,3,2-dioxaborolan-2-yl)pyridine (26.2 g, 77 mmol) was dissolved in THF (154 mL), stirred in a 1 L flask at 0° C. Potassium peroxomonosulfate (49.8 g, 81 mmol) was dissolved in water (154 mL) and then added to the flask and stirred at room temperature. After 20 minutes, the reaction was complete. The reaction was quenched with 200 mL sodium thiosulfate and then extracted with ethyl acetate (2×100 mL). The combined organic layers were washed with brine (100 mL) and then concentrated to dryness. The crude product was purified via silica gel chromatography eluting with, 10-100% ethyl acetate/heptanes to provide the crude product (21.3 g, 93 mmol) which was used in the next step. LCMS (Table A, Method a) $R_t$=0.79 minutes; MS m/z: 230, 232 (M+H)$^+$.

Step 5: 2-chloro-6-(3-methoxytetrahydrofuran-3-yl)pyridin-4-yl trifluoromethanesulfonate. 2-Chloro-6-(3-methoxytetrahydrofuran-3-yl)pyridin-4-ol (16.0 g, 70 mmol) was dissolved in dichloromethane (DCM) (348 mL), stirred in a 500 mL reaction flask and cooled to 0° C. Triethylamine (12.6 mL, 91 mmol) was added to the reaction, then triflic anhydride (70 mL, 1M solution in DCM) was added dropwise to the reaction while keeping cold. The reaction was stirred at −5° C. in an ice/acetone bath. After 30 minutes, the reaction was quenched with a sodium bicarbonate solution (100 mL). The layers were separated and the organic phase was washed with sodium bicarbonate solution (50 mL) and then brine (50 mL). The organic phase was then dried over MgSO$_4$ and concentrated to dryness to afford a crude residue, which was purified via silica gel chromatography, eluting with 0%- 50% ethyl acetate/heptanes to provide the product (19.0 g, 75% yield). LCMS (Table A, Method a) $R_t$=1.67 minutes; MS m/z: 362, 364 (M+H)$^+$. $^1$H NMR (400 MHz, Chloroform-d) δ 7.43 (s, 1H), 7.18 (s, 1H), 4.18-4.00 (m, 6H), 3.95 (dd, J=9.7, 1.6 Hz, 2H), 3.25 (s, 2H), 2.67-2.52 (m, 2H), 2.38-2.27 (m, 2H), 0.96-0.74 (m, 1H). Tf=-SO$_2$CF$_3$.

Step 6: 2-chloro-6-(3-methoxytetrahydrofuran-3-yl)-4-vinylpyridine. 2-Chloro-6-(3-methoxytetrahydrofuran-3-yl)pyridin-4-yltrifluoromethanesulfonate (15 g, 41.5 mmol) was dissolved in dioxane (173 mL) and water (34.6 mL) and degassed with a stream of nitrogen for 10 minutes. Potassium phosphate (17.60 g, 83 mmol), [1,1'-bis(diphenylphosphino)ferrocene] dichloropalladium(II)- dichloromethane adduct (Pd(dppf)Cl$_2$-DCM adduct) (1.455 g, 2.073 mmol), and 4,4,5,5-tetramethyl-2- vinyl-1,3,2-dioxaborolane (7.74 mL, 45.6 mmol) were each added, and then the reaction was heated to 85° C. After 30 minutes, the reaction was cooled to room temperature and then poured into 5% aqueous cysteine solution (200 mL) and then diluted with ethyl acetate (100 mL) and stirred for 10 minutes. The layers were separated and then the aqueous layer was extracted with ethyl acetate. The combined organic layers were washed with brine and then dried over MgSO$_4$ and concentrated to dryness. The crude material was purified via silica gel chromatography eluting with 0%-50% ethyl acetate/heptanes to provide the product (8.0 g, 80% yield). LCMS (Table A, Method a) $R_t$=1.28 minutes; MS m/z: 240, 242 (M+H)$^+$. $^1$H NMR (400 MHz, Chloroform-d) δ 7.40 (dd, J=1.4, 0.5 Hz, 1H), 7.20 (dd, J=1.4, 0.5 Hz, 1H), 6.63 (dd, J=17.6, 10.9 Hz, 1H), 5.99 (dd, J=17.5, 0.4 Hz, 1H), 5.55 (dd, J =10.9, 0.4 Hz, 1H), 4.16-4.01 (m, 3H), 3.96 (dd, J=9.7, 0.3 Hz, 1H), 3.20 (s, 3H), 2.68-2.56 (m, 1H), 2.33 (dddd, J=13.2, 7.0, 4.4, 1.3 Hz, 1H), 0.91-0.82 (m, 1H).

Step 7: 2-chloro-6-(3-methoxytetrahydrofuran-3-yl)isonicotinaldehyde. 2-Chloro-6-(3- methoxytetrahydrofuran-3-yl)-4-vinylpyridine (6.26 g, 26.1 mmol) was dissolved in dichloromethane (DCM) (34.8 mL), acetonitrile (34.8 mL), and water (60.9 mL) and was vigorously stirred in a reaction flask at 0° C. Ruthenium(III) chloride hydrate (0.118 g, 0.522 mmol) was added and then sodium periodate (22.34 g, 104 mmol) was added batch wise over 5 minutes. The reaction was warmed to room temperature. After one hour, the reaction was quenched with sodium thiosulfate (100 mL) and then extracted with DCM (2×100 mL). The combined organic layers were washed with brine and then dried over MgSO$_4$ and concentrated to dryness. The crude material was purified via silica gel chromatography, eluting with 0%-60% ethyl acetate/heptanes to provide the product (4.02 g, 64% yield). LCMS (Table A, Method a) $R_t$=1.0 minutes; MS m/z: 242, 259 (M+H)$^+$. $^1$H NMR (400 MHz, Dimethyl sulfoxide-d$_6$) δ 10.05 (d, J=0.6 Hz, 1H), 7.88 (dd, J=1.2, 0.6 Hz, 1H), 7.84 (dd, J=1.2, 0.6 Hz, 1H), 4.03 (dt, J=9.7, 0.8 Hz, 1H), 3.96-3.89 (m, 2H), 3.80 (dd, J=9.7, 0.5 Hz, 1H), 3.27 (d, J=0.6 Hz, 1H), 2.45-2.31 (m, 2H).

Step 8: (R)-2-chloro-6-(3-methoxytetrahydrofuran-3-yl) isonicotinonitrile and (S)-2- chloro-6-(3-methoxytetrahydrofuran-3-yl)isonicotinonitrile. To a stirring solution of 2-chloro-6- (3-methoxytetrahydrofuran-3-yl)isonicotinaldehyde (2.5 g, 10.34 mmol) in ethanol (34.5 mL), at room temperature, was added hydroxylamine hydrochloride (2.88 g, 41.4 mmol), and then the reaction was heated to 75° C. for 30 minutes. The reaction was then concentrated and then dissolved in ethyl acetate (50 mL), washed with sodium bicarbonate (10 mL), dried over MgSO$_4$, and concentrated to dryness. The material was dissolved in pyridine (15 mL, 185 mmol) at room temperature and then methanesulfonyl chloride (1.209 mL, 15.52 mmol) was added and the reaction was then heated to 75° C. for 90 minutes. The reaction cooled to room temperature and was diluted with water (100 mL) and then extracted (2×75 mL) with dichloromethane. The combined organic layers were washed with water (50 mL) and brine (50 mL), dried over MgSO$_4$, and then concentrated to dryness. The crude material was purified via silica gel chromatography, eluting with 0-100% ethyl acetate in heptanes to afford racemic product. The racemic product was further purified via chiral SFC (Table B, Method 4) to provide the (R)-isomer (1.2 g, 50% yield, 96% ee, R$_t$=2.6 minutes) and the (S)-isomer (1.107 g, 45% yield, >99% ee, R$_t$=2.4 minutes). LCMS (Table A, Method a) R$_t$=1.18 minutes; MS m/z: 239, 241 (M+H)$^+$. $^1$H NMR (400 MHz, Chloroform-d) δ 7.71 (d, J=1.2 Hz, 1H), 7.45 (d, J=1.2 Hz, 1H), 4.19-4.02 (m, 4H), 3.94 (d, J=9.8 Hz, 1H), 3.26 (s, 3H), 2.58 (ddd, J=13.3, 8.6, 7.7 Hz, 1H), 2.35 (dddd, J=13.3, 7.2, 4.8, 1.2 Hz, 1H).

10. Preparation #10 and #10a: (R)-2-Bromo-6-(3-ethyltetrahydrofuran-3-yl)pyridine and (S)-2-bromo-6-(3-ethyltetrahydrofuran-3-yl)pyridine

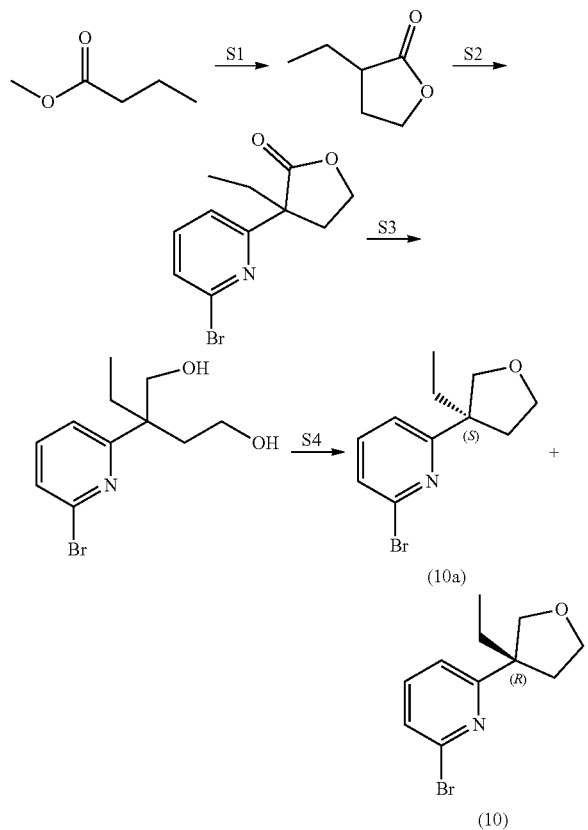

Step 1: 3-ethyldihydrofuran-2(311)-one. A solution of lithium diisopropylamide (1M in THF) (13.00 mL, 26.0 mmol) was added to tetrahydrofuran (THF) (25 mL) at −78° C. in a reaction flask and stirred for 5 minutes. Methyl butyrate (2.84 mL, 25 mmol) was added in THF (12.5 mL) slowly at −78° C. and stirred for 30 minutes. 1,3,2-Dioxathiolane 2,2-dioxide (3.23 g, 26.0 mmol) was added slowly in THF (12.5 mL) and then the reaction was slowly allowed to warm to room temperature over 2 hours.

The reaction was diluted with methanol (15 mL) and then evaporated to remove the volatiles. The crude residue was dissolved in aqueous 20% H$_2$SO$_4$ (6 mL) and toluene (50 mL) and then the biphasic mixture was heated at reflux with vigorous stirring for 6 hours. The organic phase was separated and the aqueous phase was extracted with ethyl acetate (3×50 mL). The combined organic phases were washed with sodium bicarbonate, brine, and dried over MgSO$_4$ and concentrated to dryness to afford crude residue. The residue was purified via silica gel chromatography eluting with 0-50% ethyl acetate/heptanes to provide the product (1.3 g, 46% yield). $^1$H NMR (400 MHz, Chloroform-d) δ 7.80-7.74 (m, 1H), 7.33 (dt, J=8.0, 0.8 Hz, 1H), 4.31 (ddd, J=8.9, 8.5, 3.1 Hz, 1H), 4.21 - 4.13 (m, 1H), 2.49-2.44 (m, 1H), 2.41 - 2.34 (m, 1H), 1.97-1.81 (m, 2H), 1.50 (ddq, J=13.9, 8.6, 7.4 Hz, 1H), 0.99 (t, J=7.5 Hz, 3H).

Step 2: 3-(6-bromopyridin-2-yl)-3-ethyldihydrofuran-2(3H)-one. 3-Ethyldihydrofuran- 2(314)-one (1.0g, 8.76 mmol) and 2-bromo-6-fluoropyridine (1.542 g, 8.76 mmol) were added to a microwave vial and dissolved in toluene (14.6 mL). Lithium bis(trimethylsilyl)amide (1N in tetrahydrofuran) (8.76 mL, 13.14 mmol) was added and then the microwave vial was heated at 120° C. in a microwave for 45 minutes. The reaction was quenched with ammonium chloride and then extracted with ethyl acetate (2×30 mL). The combined organic layers were washed with brine (10 mL) and then dried over MgSO$_4$ and concentrated to dryness. The crude residue was purified via silica gel chromatography, eluting with 0%-50% ethyl acetate/heptanes to provide the product (1.23 g, 52% yield). LCMS (Table A, Method a) R$_t$=1.44 minutes; MS m/z: 270, 272 (M+H)$^+$. $^1$H NMR δ (400 MHz, Dimethyl sulfoxide-d$_6$) δ 7.80 (ddd, J=8.0, 7.4, 0.5 Hz, 1H), 7.61 (dd, J=7.8, 0.5 Hz, 2H), 4.38 (dddd, J =8.8, 8.2, 4.4, 0.4 Hz, 1H), 4.26-4.15 (m, 1H), 2.84 (dddd, J=13.0, 7.4, 4.4, 0.5 Hz, 1H), 2.45-2.36 (m, 1H), 2.12-2.00 (m, 1H), 2.00-1.89 (m, 1H), 0.83-0.77 (m, 3H).

Step 3: 2-(6-bromopyridin-2-yl)-2-ethylbutane-1,4-diol. 3-(6-Bromopyridin-2-yl)-3- ethyldihydrofuran-2(3H)-one (1.26 g, 4.66 mmol) was dissolved in tetrahydrofuran (18 mL) and toluene (4.66 mL) in a reaction flask and lithium borohydride (0.508 g, 23.32 mmol) was added to the flask, which was heated to 60° C. for 2 hours. The reaction was cooled to room temperature and then quenched with aqueous ammonium chloride and acidified with 1M aqueous HCl and then neutralized with aqueous sodium bicarbonate. The mixture was extracted with dichloromethane (2×40 mL), dried over MgSO$_4$, and concentrated to dryness, to provide the crude product which was used in the next step. LCMS (Table A, Method a) R$_t$=0.95 minutes; MS m/z: 274, 276 (M+H)$^+$.

Step 4: (R)-2-bromo-6-(3-ethyltetrahydrofuran-3-yl)pyridine and (S)-2-bromo-6-(3- ethyltetrahydrofuran-3-yl)pyridine. 2(6-Bromopyridin-2-yl)-2-ethylbutane-1,4-diol (1055 mg, 3.85 mmol) was dissolved in tetrahydrofuran (38 mL) and stirred in a reaction flask at 0° C. Triphenylphosphine (1.1 g, 4.24 mmol) was added to the reaction. Diisopropyl azodicarboxylate (749 µl, 3.85 mmol) was added dropwise and then the reaction was slowly warmed to room temperature. After two hours, the reaction was diluted with water (20 mL) and then extracted with ethyl acetate (2×20mL). The combined organic layers were washed with brine, and then dried over MgSO₄ and concentrated to dryness. The crude material was purified via silica gel chromatography, eluting with 0%-50% ethyl acetate/heptanes, and further purified via chiral HPLC (Table B, Method 5) to provide the (R)-isomer (380 mg, 38% yield, >99% ee, $R_t$=7.8 minutes) and the (S)-isomer (340 mg, 34% yield, >99% ee, $R_t$=10.2 minutes) LCMS (Table A, Method a) $R_t$=0.96 minutes; MS m/z: 274, 276 (M+H)⁺.

11. Preparation #11: 4-Nitrophenyl 4-methoxybenzylcarbamate

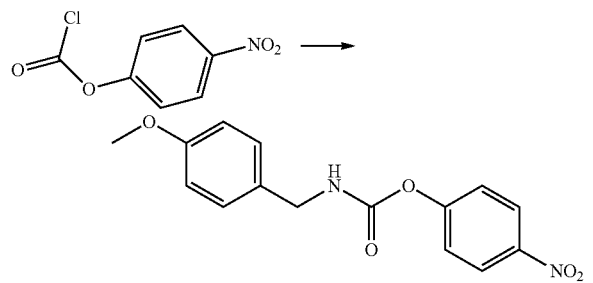

To a solution of 4-nitrophenyl chloroformate (29.4 g, 146 mmol) in acetonitrile (200 mL) was added a solution of (4-methoxyphenyl)methanamine (20 g, 146 mmol) and triethylamine (20 mL, 146 mmol)) in acetonitrile (100 mL) dropwise at 0-5° C. under a nitrogen atmosphere. The mixture was warmed to 25° C. with stirring for 1 hour. Four additional reactions were set up as described above, all five reactions were combined, and the mixture was cooled to 0° C. The suspension was filtered to provide the product (100 g, 50% yield). ¹H NMR (400 MHz, Dimethyl sulfoxide-d₆) δ =3.74 (s, 3H), 4.23 (d, J=6.00 Hz, 2H), 6.91 (d, J=8.80 Hz, 2H), 7.25 (d, J=8.80 Hz, 2H), 7.41 (d, J=9.20 Hz, 2H), 8.26 (d, J=9.20 Hz, 2H), 8.53 (t, J=6.00 Hz, 1H).

12. Preparation #12: tert-Butyl 3-bromo-5-(3-(4-methoxybenzyl)ureido)-1H-pyrrolo[2,3- c]pyridine-1-carboxylate

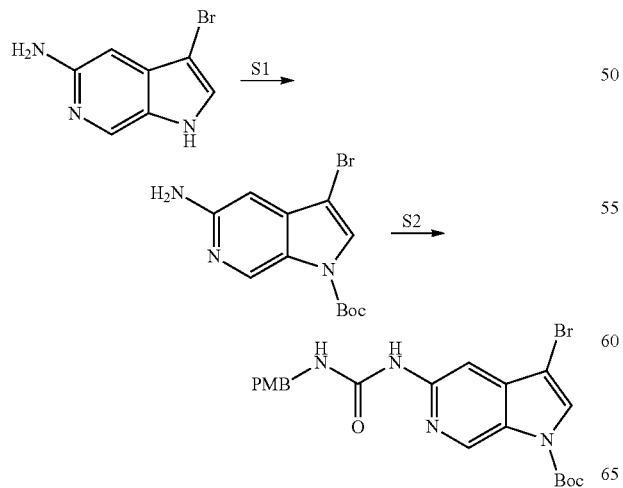

Step 1: tert-butyl 5-amino-3-bromo-1H-pyrrolo[2,3-c]pyridine-1-carboxylate. To a solution of 3-bromo-1H-pyrrolo[2,3-c]pyridin-5-amine (50 g, 236 mmol) (Preparation #4, Step 1) and 4-dimethylamino pyridine (1.4 g, 10 mmol) in acetonitrile (1L) was added a solution of di-tert-butyl dicarbonate (54 g, 248 mmol) in acetonitrile (500 mL) dropwise at 0° C. The reaction mixture was stirred at 0-5° C. for 1 hour. The solvents were concentrated under reduced pressure to give a residue that was triturated with acetonitrile: water (1:10, 500 mL) and dried to provide the product (66 g, 85%yield). ¹H NMR (400 MHz, Dimethyl sulfoxide-d₆) δ=1.60 (s, 9H), 5.86 (br s, 2H), 6.46 (d, J=1.20 Hz, 1H), 7.89 (s, 1H), 8.57-8.68 (m, 1H), 8.63 (s, 1H). Boc=t-Butoxycarbonyl.

Step 2: tert-butyl 3-bromo-5-(3-(4-methoxybenzyl)ureido)-1H-pyrrolo[2,3-c]pyridine- 1-carboxylate. A mixture of tert-butyl 5-amino-3-bromo-1H-pyrrolo[2,3-c]pyridine-1-carboxylate (22 g, 70.5 mmol) and diisopropylethylamine (49 mL, 282 mmol) in toluene (220 mL) was stirred at 25° C. for 10 minutes. A solution of 4-nitrophenyl 4-methoxybenzylcarbamate (32.0 g, 106 mmol) (Preparation #11) in toluene (220 mL) was added dropwise under nitrogen. The resulting mixture was stirred at 110° C. for 5 hours. The reaction was cooled to 25° C. and concentrated on vacuum to get a residue, which was purified via silica gel chromatography eluting with 0-100% dichloromethane:tetrahydrofuran to afford a residue. The residue was triturated with dimethylformamide, then 2-methyltetrahydrofuran, to provide the product (58.8 g, 52% yield). ¹H NMR (400 MHz, Dimethyl sulfoxide-d₆) δ=1.62 (s, 9H), 3.32 (s, 2H), 3.73 (s, 3H), 4.30 (d, J=5.73 Hz, 2H), 6.90 (d, J=8.60 Hz, 2H), 7.25 (d, J=8.60 Hz, 2H), 7.68 (br s, 1H), 7.78 (s, 1H), 8.08 (s, 1H), 8.85 (s, 1H), 9.15 (s, 1H). PMB=4-methoxybenzyl.

13. Preparation #13: 1-(3-Bromo-1-tosyl-1H-pyrrolo[2,3-c]pyridin-5-yl)urea

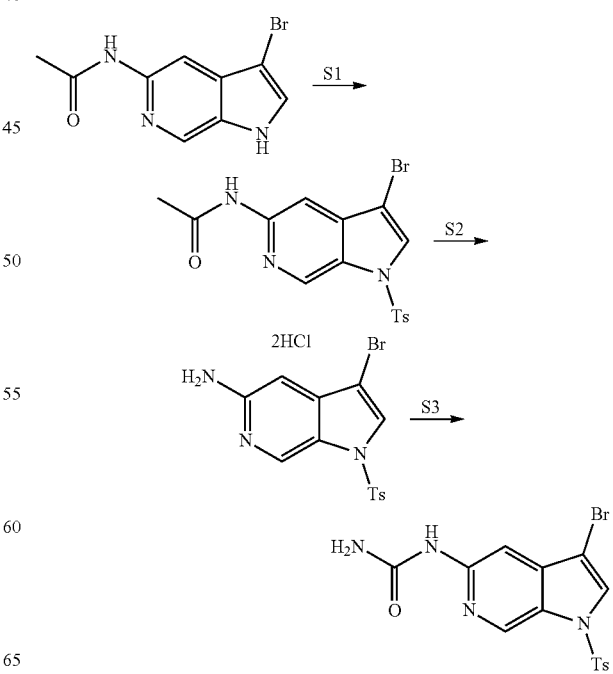

Step 1: N-(3-bromo-1-tosyl-1H-pyrrolo[2,3-c]pyridin-5-yl)acetamide. To a dimethylformamide (265 mL) suspension of N-(3-bromo-1H-pyrrolo[2,3-c]pyridin-5-y)acetamide (40.42 g, 159 mmol) (Preparation #1, Step 1) stirring at about 0° C. was added NaH (60% dispersion in mineral oil) (7.37 g, 175 mmol). After stirring for about 10 minutes, 4-toluenesulfonyl chloride (31.8 g, 167 mmol) was added. The reaction stirred for about 3 hours, then diluted with water (250 mL), and the reaction was filtered. The filtered material was rinsed twice with water before drying in a vacuum oven at about 70° C. to provide the product (64 g, 99% yield). LC/MS (Table A, Method e $R_t$=1.48 minutes; MS m/z: 407.8, 409.9 (M+H)$^+$. Ts=4-toluenesulfonyl.

Step 2: 3-bromo-1-tosyl-1H-pyrrolo[2,3-c]pyridin-5-amine, 2 hydrochloric acid. To a dioxane (448 mL) suspension of N-(3-bromo-1-tosyl-1H-pyrrolo[2,3-c]pyridin-5-ypacetamide (64.02 g, 157 mmol) was added HCl (5M in water) (157 mL, 784 mmol) and the mixture was heated to about 85° C. with stirring. After 4 hours of heating, the reaction was cooled to room temperature. The reaction was filtered, and the filtered product rinsed with diethyl ether, and dried to constant mass in a vacuum oven at about 70° C. to provide the product (63 g, 91% yield). LC/MS (Table A, Method e) $R_t$=1.42 minutes; MS m/z: 365.9, 367.8 (M+H)$^+$.

Step 3: 1-(3-bromo-1-tosyl-1H-pyrrolo[2,3-c]pyridin-5-yOurea. A flask was charged with 3-bromo-1-tosyl-1H-pyrrolo[2,3-c]pyridin-5-amine, 2 hydrochloric acid (30.31 g, 69.0 mmol) as a suspension in tetrahydrofuran (690 mL). To this mixture was added triethylamine (28.9 mL, 207 mmol). After cooling the reaction mixture to an internal temperature of about −75° C., phosgene (15% solution in toluene) (54.2 mL, 76 mmol) was slowly added, then ammonia (7M solution in MeOH) (79 mL, 552 mmol) was slowly added. The reaction was allowed to slowly warm to room temperature. After about 10 minutes, the reaction was quenched by the addition of about 30 mL of water and was allowed to warm to room temperature overnight. The mixture was treated with an additional 120 mL of water, then the reaction was filtered under vacuum, and the filtered material triturated with 5% methanol/ethyl acetate. The filtered material was dried in a vacuum oven at about 70° C. to provide the product (21.6 g, 71% yield). LC/MS (Table A, Method e) $R_t$=1.37 minutes; MS m/z: 408.8, 410.8 (M+H)$^+$. $^1$H NMR (400 MHz, Dimethyl sulfoxide-$d_6$) δ 9.08 (s, 1H), 8.81 (d, J=1.1 Hz, 1H), 8.26 (s, 1H), 7.97-7.89 (m, 2H), 7.72 (d, J=1.1 Hz, 1H), 7.45-7.33 (m, 2H), 6.50 (s, 2H), 2.31 (s, 3H).

14. Preparation #14: 1-(3-Bromo-1-tosyl-1H-pyrrolo[2,3-c]pyridin-5-yl)-3-methylurea

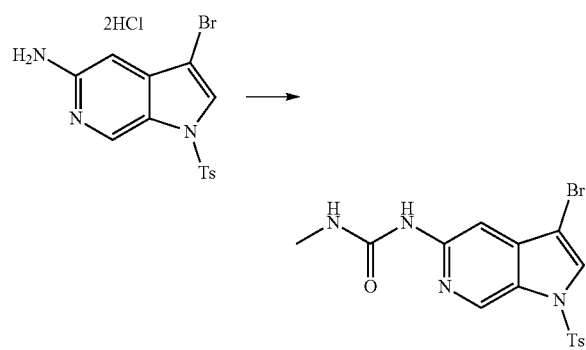

In a round-bottomed flask, 3-bromo-1-tosyl-1H-pyrrolo[2,3-c]pyridin-5-amine 2 hydrochloric acid (32.1 g, 73.1 mmol) (Preparation #13, Step 2) in tetrahydrofuran (700 mL) was added to give a tan suspension. Diisopropylethylamine (50.6 mL, 292 mmol) was added and stirred until dissolution occurred, giving a dark brown solution. The solution was cooled to about −78° C. in a dry ice/acetone bath, and 15% phosgene in toluene (57.4 mL, 80 mmol) was added dropwise via an addition funnel, keeping the temperature less than about −70° C. After the addition was complete, the mixture was stirred for about 30 minutes at about −78° C. Methylamine (2.0 M in tetrahydrofuran, 292 mL, 585 mmol) was then added dropwise via an addition funnel at about −78° C. After the addition was complete, the reaction mixture was allowed to warm to room temperature. The reaction was quenched with water (120 mL) and stirred for about 2 days. The organic layers were removed under reduced pressure to provide a residue, which was filtered, washing with water. The residue was triturated with 5% methanol/ethyl acetate (200 mL) for 1 hour, filtered, washing with ethyl acetate, and then dried under reduced pressure at about 50° C. to provide the product (25.5 g, 79% yield). LC/MS (Table A, Method b) $R_t$=1.47 minutes; MS m/z: 423, 425 (M+H)$^+$. $^1$H NMR (400 MHz, Dimethyl sulfoxide-$d_6$) δ 9.18 (s, 1H), 8.83 (d, J=1.0 Hz, 1H), 8.29 (s, 1H), 7.95 (d, J=8.4 Hz, 2H), 7.67 (d, J=1.0 Hz, 1H), 7.42 (d, J=8.6 Hz, 2H), 7.22 (d, J=5.6 Hz, 1H), 2.70 (d, J=4.7 Hz, 3H), 2.34 (s, 3H). Ts=4-toluenesulfonyl.

15. Preparation #15: 2-Bromo-6-(3-((tert-butyldimethylsilyl)oxy)oxetan-3-yl)pyridine

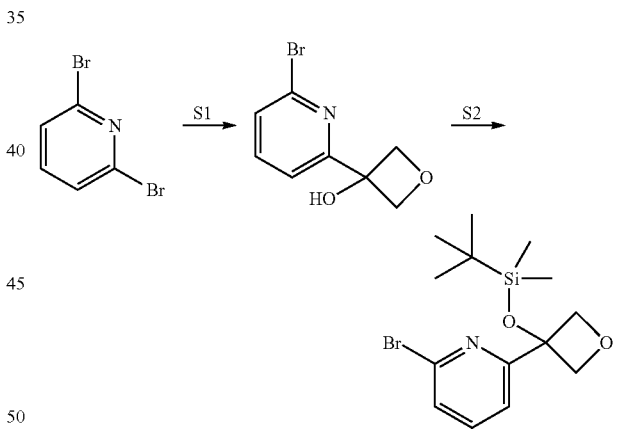

Step 1: 3-(6-bromopyridin-2-yl)oxetan-3-ol. A solution of 2,6-dibromopyridine (10 g, 42.2 mmol) in dichloromethane (DCM) (211 mL) was cooled to about −78° C. and n-butyllithium (2.5M in hexanes, 18.57 mL, 46.4 mmol) was added dropwise, keeping the internal temperature below −68° C. The reaction stirred at about −78° C. for about 15 minutes before adding oxetan-3-one (3.25 mL, 50.7 mmol) as a neat oil slowly. The temperature increased to about −50° C., and the reaction was cooled to about −78° C. and stirred for about 30 minutes before pouring into a vessel with saturated aqueous NH$_4$Cl and DCM. The reaction stirred for 1 hour warming to room temperature. The layers were separated and extracted from the aqueous with DCM three times. The combined organic layers were dried over MgSO$_4$, filtered, concentrated to a residue, which was triturated with diethyl ether to provide the product (7.44 g, 77% yield) LC/MS (Table A, Method a) R$_t$=0.65 minutes; MS m/z: 230, 232 (M+H)$^+$.

Step 2: 2-bromo-6-(3-((tert-butyldimethylsilypoxy)oxetan-3-yl)pyridine. To a solution of 3-(6-bromopyridin-2-yl) oxetan-3-ol (1 g, 4.35 mmol) in dimethylformamide (8.05 mL) was added tert-butyldimethylsilyl chloride (1.179 g, 7.82 mmol), imidazole (0.592 g, 8.69 mmol), and 4- dimethylamino pyridine (0.531 g, 4.35 mmol). The reaction stirred at room temperature for about 16 hours. The reaction was then diluted with water (10 mL) and brine (40 mL), and extracted into diethyl ether (60 mL). The organic layers were dried over MgSO$_4$, filtered and concentrated under reduced pressure to a residue, which was purified via silica gel chromatography, eluting with 0-25% ethyl acetate/heptanes, to provide the product (1.37 g, 92% yield). LC/MS (Table A, Method a) R$_t$=2.10 minutes; MS m/z: 344, 346 (M+H)$^+$. $^1$H NMR (400 MHz, Dimethyl sulfoxide-d$_6$) δ 7.91-7.79 (m, 1H), 7.70-7.56 (m, 2H), 4.97-4.87 (m, 2H), 4.74 (d, J=1.0 Hz, 2H), 0.92-0.85 (m, 9H), -0.00 (d, J=0.4 Hz, 6H).

16. Preparation #16: 2-Bromo-6-(3-((tert-butyldimethylsilypoxy)oxetan-3-yl)-4-methoxypyridine

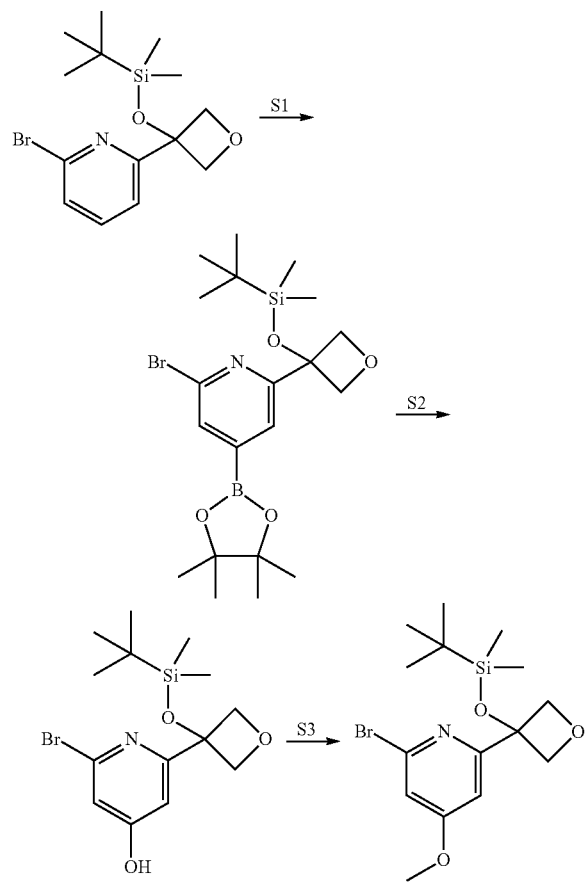

Step 1: 2-bromo-6-(3-((tert-butyldimethylsilypoxy)oxetan-3-yl)-4-(4,4,5,5-tetramethyl- 1,3,2-dioxaborolan-2-yl) pyridine. In a 100 mL flask, (1,5-cyclooctadiene)(methoxy) iridium(I) dimer (0.154 g, 0.232 mmol), 4,4'-di-tert-butyl-2,2'-bipyridine (0.125 g, 0.465 mmol), and bis(pinacolato) diboron (5.90 g, 23.23 mmol) were added under a stream of nitrogen, followed by methyl tert-butyl ether (19.36 mL) ("the catalyst solution") and the reaction was degassed for about 10 minutes. In a separate 250 mL flask, 2-bromo-6-(3-((tert-butyldimethylsilypoxy)oxetan-3-yl)pyridine (4 g, 11.62 mmol) (Preparation #15) and methyl tert-butyl ether (58.1 mL) ("the bromopyridine solution") were degassed with nitrogen. Added 15 mL of the catalyst solution to the bromopyridine solution and heated to about 60° C. under nitrogen for about 1 hour. The reaction was concentrated under reduced pressure to a residue, which was purified via silica gel chromatography, eluting with 0-50% ethyl acetate/ heptanes to provide the product (4.9 g, 90% yield). LC/MS (Table A, Method a) R$_t$=1.76 minutes; MS m/z: 388, 390 (M+H)$^+$. $^1$H NMR (400 MHz, Dimethyl sulfoxide-d$_6$) δ 7.79 (d, J=0.8 Hz, 1H), 7.65 (d, J=0.8 Hz, 1H), 4.88 (d, J=6.7 Hz, 2H), 4.72 (s, 2H), 1.33-1.23 (m, 12H), 0.89 (d, J=0.7 Hz, 9H), -0.03 (d, J=0.7 Hz, 6H).

Step 2: 2-bromo-6-(3-((tert-butyldimethylsilypoxy)oxetan-3-yl)pyridin-4-ol. To a vigorously stirred solution of 2-bromo-6-(3-((tert-butyldimethylsilypoxy)oxetan-3-yl)-4-(4,4,5,5- tetramethyl-1,3,2-dioxaborolan-2-yl)pyridine (4.87 g, 10.36 mmol) in tetrahydrofuran (34.5 mL) was added a solution of Oxone® (7.00 g, 11.39 mmol) in water (34.5 mL). The reaction stirred at room temperature for about 30 minutes. The reaction was quenched with saturated aqueous Na$_2$S$_2$O$_3$ (100 mL) and extracted into ethyl acetate (120 mL). The organic layers were washed with brine (30 mL), dried over MgSO$_4$, filtered and concentrated under reduced pressure to a solid. Triturated the solid with heptanes and filtered, then rinsed with dichloromethane and filtered to provide the product (3.21 g, 86% yield). LC/MS (Table A, Method a) R$_t$=1.84 minutes; MS m/z: 360, 362 (M+H)$^+$. $^1$H NMR (400 MHz, Dimethyl sulfoxide-d$_6$) 6 11.32 (s, 1H), 6.95 (d, J =1.9 Hz, 1H), 6.91 (d, J =1.9 Hz, 1H), 4.92 - 4.81 (m, 2H), 4.65 (d, J=6.7 Hz, 2H), 0.89 (s, 9H), 0.02 (s, 6H).

Step 3: 2-brom o-6-(3-((tert-b utyldimethylsilyl)oxy)oxetan-3-yl)-4-methoxypyridine. To a solution of 2-bromo-6-(3-((tert-butyldimethylsilypoxy)oxetan-3-yl)pyridin-4-ol (1.6 g, 4.44 mmol) in dimethylformamide (44.4 mL) was added iodomethane (0.555 mL, 8.88 mmol) and potassium carbonate (1.227 g, 8.88 mmol). The reaction stirred at room temperature for about 90 minutes. The reaction was quenched with brine (40 mL), ethyl acetate (60 mL) and a little water to help dissolve salts (15 mL). The organic layers were separated and washed again with brine (30 mL), dried over MgSO$_4$, filtered and concentrated under reduced pressure to provide a residue, which was purified via silica gel chromatography, eluting with 0-25% ethyl acetate/heptanes, to provide the product (1.6 g, 96% yield). LC/MS (Table A, Method a) R$_t$=2.15 minutes; MS m/z: 374, 376 (M+H)$^+$. $^1$H NMR (400 MHz, Dimethyl sulfoxide-d$_6$) δ 7.21 (d, J=2.1 Hz, 1H), 7.10 (d, J =2.1 Hz, 1H), 4.95-4.82 (m, 2H), 4.79-4.64 (m, 2H), 3.86 (s, 3H), 0.88 (s, 9H), 0.01 (s, 6H).

17. Preparation #17: 2-Bromo-6-(3-((tert-butyldimethylsilypoxy)oxetan-3-yl)-4-isopropoxypyridine

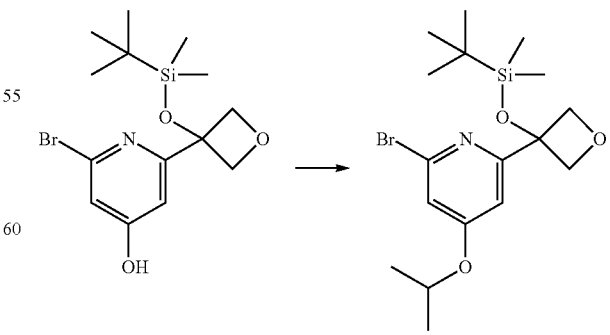

To a solution of 2-bromo-6-(3-((tert-butyldimethylsilypoxy)oxetan-3-yl)pyridin-4-ol (1.6 g, 4.44 mmol) (Preparation #16, Step 2) in dimethylformamide (44.4 mL) was added 2-iodopropane (0.888 mL, 8.88 mmol) and potassium carbonate (1.227 g, 8.88 mmol). The reaction stirred at room temperature for about 16 hours. The reaction was quenched with brine (40 mL), then added ethyl acetate (60 mL) and water (30 mL). The organic layers were separated and washed again with brine (30 mL), dried over MgSO₄, filtered and concentrated under reduced pressure, to provide a residue, which was purified via silica gel chromatography, eluting with 0-20% ethyl acetate/heptanes, to provide the product (1.72 g, 96% yield). LC/MS (Table A, Method a) $R_t$=2.32 minutes; MS m/z: 402, 404 (M+H)⁺. ¹H NMR (400 MHz, Dimethyl sulfoxide-d₆) δ 7.17 (dd, J=2.1, 0.8 Hz, 1H), 7.06 (dd, J=2.1, 0.8 Hz, 1H), 4.92-4.87 (m, 2H), 4.87-4.73 (m, 1H), 4.70-4.61 (m, 2H), 1.27 (dd, J=6.0, 0.8 Hz, 6H), 0.88 (d, J=0.8 Hz, 9H), 0.00 (d, J=0.8 Hz, 6H).

18. Preparation #18 and #18a: (R)-2-Bromo-4-(difluoromethyl)-6-(3- methoxytetrahydrofuran-3-yl) pyridine and (S)-2-bromo-4-(difluoromethyl)-6-(3-methoxytetrahydrofuran-3-yl)pyridine

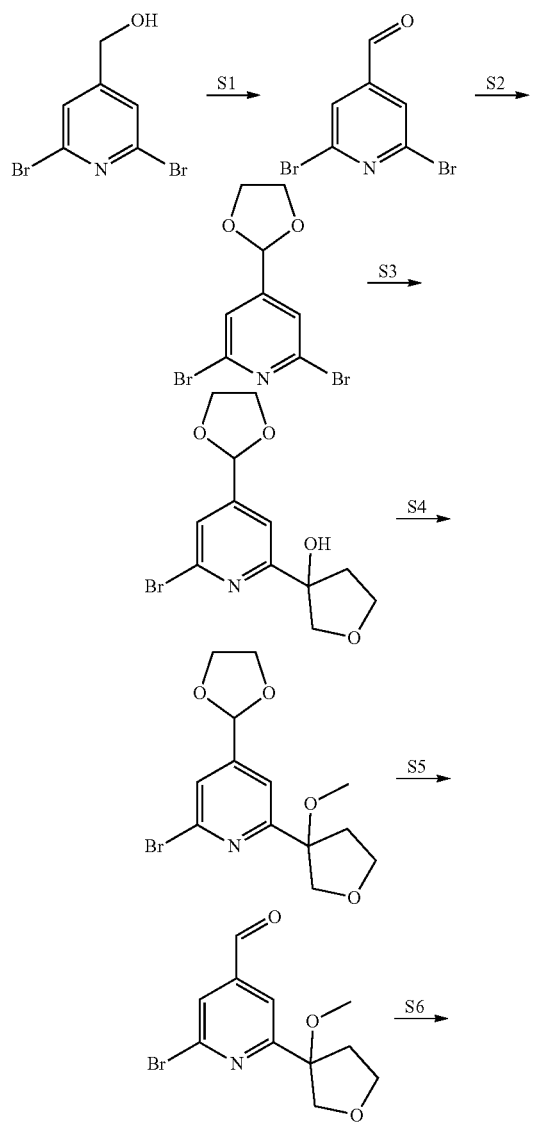

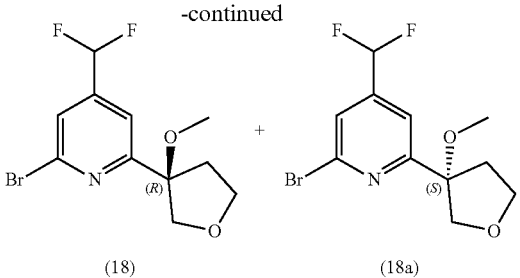

Step 1: 2,6-dibromoisonicotinaldehyde. To a solution of oxalyl chloride (14.43 mL, 165 mmol) in dichloromethane (DCM) (400 mL) was added a solution of dimethyl sulfoxide (25.5 mL, 360 mmol) in DCM (400 mL) dropwise at −78° C. under nitrogen. After 10 minutes, a solution of (2,6-dibromopyridin-4-yl)methanol (40 g, 150 mmol) (Preparation #6, Step 1) in DCM (400 mL) was added dropwise at −78° C. The mixture was stirred for 15 minutes and then triethylamine (104 mL, 749 mmol) was added dropwise at −78° C. After the addition, the reaction was stirred at −78° C. for another 1 hour. The cooling bath was removed, and water (500 mL) was added to the reaction at 20° C. The mixture was extracted with DCM (200 mL), and then the organic layers were combined, dried over Na₂SO₄, filtered and concentrated under reduced pressure to provide the product (30 g, 67% yield). ¹H NMR (400 MHz, chloroform-d) δ 9.97 (s, 1H), 7.86 (s, 2H).

Step 2: 2,6-dibromo-4-(1,3-dioxolan-2-yl)pyridine. A suspension of 2,6- dibromoisonicotinaldehyde (2.313 g, 8.73 mmol) in toluene (29 mL) was treated with ethane-1,2-diol (0.732 mL, 13.10 mmol) and 4-methylbenzenesulfonic acid hydrate (0.332 g, 1.746 mmol) and was refluxed with a Dean Stark trap for 20 hours. The reaction showed complete conversion to the desired product. The reaction was cooled, and quenched with water, and extracted with dichloromethane. The combined organic layers were dried, and concentrated and purified via silica gel chromatography, eluting with 12-100% ethyl acetate/heptanes, to provide the product (1.6 g, 62% yield). LC/MS (Table A, Method a) $R_t$=1.33 minutes; MS m/z: 308, 310 (M+H)⁺.

Step 3: 3-(6-bromo-4-(1,3-dioxolan-2-yl)pyridin-2-yl)tetrahydrofuran-3-ol. To a solution of 2,6-dibromo-4-(1,3-dioxolan-2-yl)pyridine (19 g, 61.5 mmol) in dichloromethane (200 mL) was added n-butyl lithium (1M in hexanes) (54.1 mL, 135 mmol) dropwise with stirring at −78° C. for 15 minutes. Dihydrofuran-3(2H)-one (6.35 g, 73.8 mmol) was added, and the reaction mixture was stirred at the same temperature for 30 minutes. The reaction was then allowed to warm to 20° C. and stirred for 12 hours. This procedure was repeated two more times on same scale, and then combined for workup. The reaction was quenched with saturated aqueous solution NH₄Cl (500 mL) and extracted with dichloromethane (2×250 mL). The organic portion was dried over NaSO₄, filtered, and concentrated to give a residue, which was purified via silica gel chromatography, eluting with 50:1 to 10:1 petroleum ether:ethyl acetate, to provide the product (26 g, 40% yield). LC/MS (Table A, Method f) $R_t$=0.95 minutes; MS m/z: 316, 318 (M+H)⁺.

Step 4: 2-bromo-4-(1,3-dioxolan-2-yl)-6-(3-methoxytetrahydrofuran-3-yl)pyridine. To a solution of 3-(6-bromo-4-(1,3-dioxolan-2-yl)pyridin-2-yl)tetrahydrofuran-3-ol (10 g, 31.6 mmol) in tetrahydrofuran (10 mL) was added NaH (60% dispersion in mineral oil) (1.5 g, 38.0 mmol) at 0° C. The reaction stirred at 0° C. for 30 minutes, before the addition of methyl iodide (2.9 mL, 47.4 mmol). The reaction was stirred at 0° C. for 13 hours. The reaction was extracted with ethyl acetate (20 mL) and NH$_4$Cl (20 mL), then the organic layer was separated, concentrated to provide a residue, which was purified via silica gel chromatography, eluting with 50:1 to 10:1 petroleum ether:ethyl acetate, to provide the product (7 g, 60% yield). LC/MS (Table A, Method f) R$_t$=1.07 minutes; MS m/z: 330, 332 (M+H)$^+$.

Step 5:2-bromo-6-(3-methoxytetrahydrofuran-3-yl)isonicotinaldehyde. To a solution of 2-bromo-4-(1,3-dioxolan-2-yl)-6-(3-methoxytetrahydrofuran-3-yl)pyridine (18 g, 54.5 mmol) in water (180 mL) was added HCl (180 mL, 5924 mmol), and the reaction was stirred at 50° C. for 2 hours. The reaction was then cooled to room temperature, adjusted to pH=7, and extracted with ethyl acetate (200 mL). The organic layer was concentrated and purified via silica gel chromatography, eluting with 50:1 to 1:1 petroleum ether:ethyl acetate, to provide the product (7 g, 43% yield). LC/MS (Table A, Method f) R$_t$=1.03 minutes; MS m/z: 286, 288 (M+H)$^+$.

Step 6: (R)-2-bromo-4-(difluoromethyl)-6-(3-methoxytetrahydrofuran-3-yl)pyridine and (S)-2-bromo-4-(difluoromethyl)-6-(3-methoxytetrahydrofuran-3-yl)pyridine. To a solution of 2-bromo-6-(3-methoxytetrahydrofuran-3-yl)isonicotinaldehyde (7 g, 24.47 mmol) in dichloromethane (DCM) (70 mL) at −78° C. was added diethylaminosulfur trifluoride (16.16 mL, 122 mmol) over a period of 10 minutes. The reaction was warmed to 15° C. and stirred for 2 hours. The reaction mixture was carefully poured into ice water (40 mL) and extracted with DCM (3×80 mL). The combined organic layers were washed with NaHCO$_3$ solution (20 mL), water (30 mL), and brine (30 mL), dried over Na$_2$SO$_4$, and concentrated to give the racemic product (4.9 g). LC/MS (Table A, Method f) R$_t$=3.82 minutes; MS m/z: 310 (M+H)$^+$. The racemate was further purified via chiral HPLC (Table B, Method 6) to provide the (R)-isomer (2.1 g, 42% yield, >99%ee, R$_t$=12.6 minutes, optical rotation=(+)) and the (S)-isomer (2.0 g, 41% yield, >93%ee, R$_t$=14.2 minutes, optical rotation=(−)). $^1$H NMR (400MHz, Chloroform-d) δ=7.62 (s, 1H), 7.54 (s, 1H), 6.78-6.46 (m, 1H), 4.19-4.07 (m, 3H), 3.98 (d, J=9.7 Hz, 1H), 3.25 (s, 3H), 2.64 (td, J=8.4, 13.2 Hz, 1H), 2.37 (dddd, J=1.1, 4.7, 7.1, 13.1 Hz, 1H).

19. Preparation #19 and #19a: (R)-2-Iodo-6-(3-methoxytetrahydrofuran-3-yl)pyrazine and (S)-2-iodo-6-(3-methoxytetrahydrofuran-3-yl)pyrazine dichloromethane (DCM) (150 mL) was added MgSO$_4$, and the solution was stirred for 15 minutes. The solution was then filtered into a heat dried flask and cooled to −78° C. in an acetone/dry ice bath. n-Butyl lithium in hexanes (2.5 mM, 6.24 mL, 15.60 mmol) was added dropwise via a syringe keeping the temperature less than −65° C., and the reaction was stirred for 30 minutes at −78° C. A solution of dihydrofuran-3(2-H)-one (2.56 g, 29.7 mmol) in DCM (150 mL) was added dropwise via syringe and the reaction was allowed to come to room temperature. The reaction stirred at room temperature overnight. The reaction was then quenched with saturated aqueous ammonium chloride (150 mL), the layers were separated and extracted with DCM (2×75 mL), the combined organic extracts were dried over MgSO$_4$, and the solvent was concentrated under reduced pressure to provide a residue. The residue was purified via silica gel chromatography, eluting with 30-100% ethyl acetate:heptanes to provide the product (2.4 g, 56% yield). LC/MS (Table A, Method a) R$_t$=0.70 minutes; MS m/z: 292.91 (M+H)$^+$.

Step 2: (R)-2-iodo-6-(3-methoxytetrahydrofuran-3-yl)pyrazine and (S)-2-iodo-6-(3-methoxytetrahydrofuran-3-yl)pyrazine. A solution of 3-(6-iodopyrazin-2-yl)tetrahydrofuran-3-ol (2.42 g, 8.29 mmol) in tetrahydrofuran (41mL) was cooled to 0° C., and 60% NaH in oil dispersion (0.365 g, 9.11 mmol) was added portionwise. The mixture was stirred for 15 minutes at 0° C., then iodomethane (1.291 mL, 20.71 mmol) was added dropwise via a syringe. After 3 hours, additional NaH (0.099 g, 4.14 mmol) was added, and stirred 15 minutes and additional iodomethane (0.258 mL, 4.14 mmol) was added. The reaction stirred at room temperature for 2 days. The reaction was quenched with saturated aqueous ammonium chloride (100 mL), and ethyl acetate (100 mL) was added. The layers were separated and extracted with ethyl acetate (2×75 mL). The combined organic layers were dried over MgSO$_4$ and the solvent was concentrated under reduced pressure. The crude material was purified via silica gel chromatography, eluting with 0 to 80% ethyl acetate:heptanes to give the crude product (2.0 g), which was further purified by chiral SFC (Table B, Method 7) to provide the (R)-isomer (0.921 g, 36% yield, 95% ee, R$_t$ =2.1 minutes) and the (S)-isomer (0.975 g, 38% yield, >99% ee, R$_t$=2.3minutes). LC/MS (Table A, Method a) R$_t$=0.94 minutes; MS m/z: 306.81 (M+H)$^+$.

20. Preparation #20 and #20a: (R)-2-Bromo-6-(3-methoxytetrahydrofuran-3-yl)pyridine and (S)-2-bromo-6-(3-methoxytetrahydrofuran-3-yl)pyridine

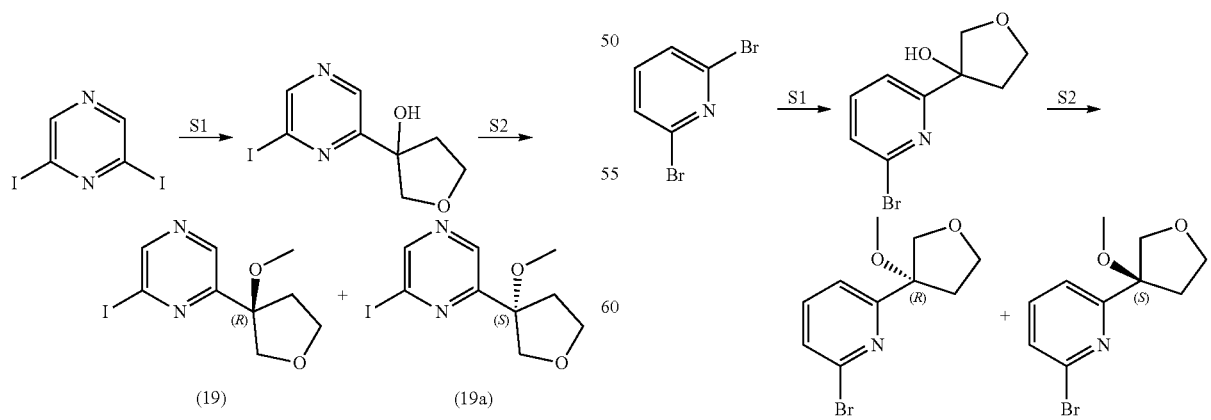

(19)  (19a)  (20)  (20a)

Step 1: 3-(6-iodopyrazin-2-yl)tetrahydrofuran-3-ol. To a solution of 2,6-diiodopyrazine (4.931 g, 14.86 mmol) in Step 1: 3-(6-bromopyridin-2-yl)tetrahydrofuran-3-ol. To a solution of 2,6- dibromopyridine (5 g, 21.11 mmol) in dichloromethane (DCM) (100 mL) cooled to about −78° C. was added n-butyllithium (2.5M in hexanes) (9.29 mL, 23.22 mmol) dropwise, maintaining internal temperature below −74° C. The reaction was stirred at this temperature for 15 minutes, then 3- oxotetrahydrofuran (2.18 g, 25.3 mmol) was added in one portion. The reaction was stirred for about 40 minutes at about −78° C. Poured the reaction into a mixture of saturated aqueous NH$_4$Cl (110 mL) and DCM (80 mL) and stirred for about 30 minutes. Separated the organic layers and dried over MgSO$_4$, filtered, and concentrated under reduced pressure to provide a residue, which was purified via silica gel chromatography, eluting with 0-50% ethyl acetate/heptanes, to provide the product (3.85 g, 75% yield). LC/MS (Table A, Method a) R$_t$=0.75 minutes; MS m/z: 244, 246 (M+H)$^+$.

Step 2: (R)-2-bromo-6-(3-methoxytetrahydrofuran-3-yl) pyridine and (S)-2-bromo-6- (3-methoxytetrahydrofuran-3-yl)pyridine. In a round-bottomed flask, 3-(6-bromopyridin-2- yl)tetrahydrofuran-3-ol (7.20 g, 29.5 mmol) and NaH (60% in oil dispersion) (1.652 g, 41.3 mmol) in tetrahydrofuran (300 mL) were added to give a yellow suspension. The reaction stirred for 15 minutes and then iodomethane (1.8 mL, 29.5 mmol) was added and the mixture was stirred at room temperature overnight. An additional amount of NaH (60% in oil dispersion) (0.472 g, 11.80 mmol) was added and stirred for 15 minutes, then iodomethane (0.735 mL, 11.80 mmol) was added. After 2 hours, the reaction was quenched with saturated aqueous ammonium chloride, extracted with dichloromethane, which was dried over MgSO$_4$, and concentrated to provide the racemic product (6.6 g, 98% yield). LC/MS (Table A, Method a) R$_t$=1.06 minutes; MS m/z: 258, 260 (M+H)$^+$. The racemate was further purified via chiral SFC (Table B, Method 8) to provide the (R)-isomer (3.33 g, 43% yield, >99% ee, R$_t$=1.22 minutes), and the (S)-isomer (3.30 g, 42% yield, >99%ee, R$_t$=1.05 minutes). LC/MS (Table A, Method a) R$_t$=1.06 minutes; MS m/z: 258, 260 (M+H)$^+$.

21. Preparation #21 and #21a: (R)-2-Chloro-6-(3-methoxytetrahydrofuran-3-yl)pyridin-4-ol and (S)-2-chloro-6-(3-methoxytetrahydrofuran-3-yl)pyridin-4-ol

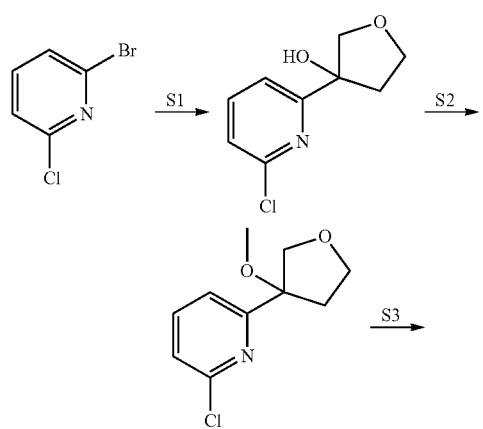

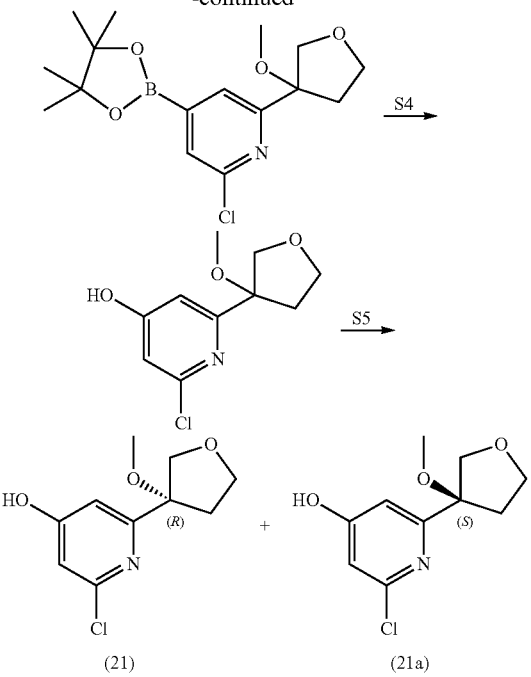

Step 1: 3-(6-chloropyridin-2-yl)tetrahydrofuran-3-ol. 2-Bromo-6-chloropyridine (44.44 g, 231 mmol) was dissolved in dichloromethane (DCM) (770 mL), stirred in a 3 neck 2L reaction flask and then cooled to −78° C. n-Butyl lithium (2.5 M in hexanes) (106 mL, 266 mmol) was cannulated into an addition funnel and then added dropwise into the reaction, maintaining the temperature below −69° C. The reaction was stirred for 20 minutes. Dihydrofuran-3 (2H)-one (22.8 g, 266 mmol) was dissolved in minimal DCM and then added into the reaction dropwise. The reaction stirred, slowly warming to room temperature over 40 minutes. The reaction was quenched with ammonium chloride solution (200mL) and then separated layers, extracting the aqueous with DCM and then washing the organic layer with brine (200mL). The organic layer was dried over MgSO$_4$ and then concentrated to dryness to provide a residue, which was purified via silica gel chromatography, eluting with 0-100% ethyl acetate: heptanes to provide the product (32.7 g, 70% yield). LC/MS (Table A, Method a) R$_t$=0.67 minutes; MS m/z: 200, 202 (M+H)$^+$.

Step 2: 2-chloro-6-(3-methoxytetrahydrofuran-3-yl)pyridine. 3-(6-Chloropyridin-2- yl)tetrahydrofuran-3-ol (13.52 g, 67.7 mmol) was dissolved in tetrahydrofuran (226 mL) and NaH (60% dispersion in oil) (4.88 g, 122 mmol) was added carefully at 0° C. and the reaction was stirred for 10 minutes. Iodomethane (5.51 mL, 88 mmol) was then added and the reaction was allowed to stir overnight at room temperature. The reaction was then quenched into an ammonium chloride solution (300 mL) and diluted with ethyl acetate (100 mL). The layers were separated and the aqueous phase was extracted with ethyl acetate (2×200mL). The combined organic layers were washed with brine, dried over MgSO$_4$, filtered and concentrated to provide the product (14.1g. 98% yield). LC/MS (Table A, Method a) R$_t$=0.95 minutes; MS m/z: 213, 215 (M+H)$^+$.

Substitute Specification (Clean) ABV12402US01 (31247-2221)

Step 3: 2-chloro-6-(3-methoxytetrahydrofuran-3-yl)-4-(4,4,5,5-tetramethyl-1,3,2- dioxaborolan-2-yl)pyridine. A solution of 2-chloro-6-(3-methoxytetrahydrofuran-3-yl)pyridine (42.29 g, 198 mmol) and bis(pinacolato)diboron (60.3 g, 238 mmol) in cyclohexane (660 mL) was sparged with nitrogen for 30 minutes, then chloro (1,5-cyclooctadiene)iridium(I) dimer (1.33 g, 1.979 mmol) and 4,4'-di-tert-butyl -2,2'-bipyridine (1.06 g, 3.96 mmol) were added and the mixture was heated at 75° C. for 1 hour. The reaction was cooled to room temperature and the solvent was concentrated under reduced pressure to provide a residue, which was triturated with heptanes overnight, filtered, and the filtered material washed with heptanes and dried under reduced pressure at 50° C. to provide the product (48 g, 71% yield). LC/MS (Table A, Method a) $R_t$=0.77 minutes; MS m/z: 257.90 (M+H)$^+$(Boronic acid mass). $^1$H NMR (400 MHz, Dimethyl sulfoxide-$d_6$) δ 7.63 (d, J =0.8 Hz, 1H), 7.50 (d, J=0.7 Hz, 1H), 4.04 (dd, J=9.6, 1.1 Hz, 1H), 3.99-3.88 (m, 2H), 3.80 (d, J=9.6 Hz, 1H), 3.08 (s, 3H), 2.43 (dt, J=13.2, 8.4 Hz, 1H), 2.39-2.30 (m, 1H), 1.32 (s, 12H).

Step 4: 2-chloro-6-(3-methoxytetrahydrofuran-3-yl)pyridin-4-ol. A solution of 2- chloro-6-(3-methoxytetrahydrofuran-3-yl)-4-(4,4,5,5-tetramethyl-1,3,2-dioxaborolan-2-yl)pyridine (53.30 g, 157 mmol) in tetrahydrofuran (300 mL) was cooled to 0° C., and a solution of potassium peroxymonosulfate (101 g, 165 mmol) in water (300 mL) was added dropwise via addition funnel, keeping the temperature below 30° C. The reaction was stirred at room temperature for 20 minutes, then quenched with saturated aqueous sodium thiosulfate (400 mL), extracted with ethyl acetate (2×200 mL), dried over MgSO$_4$, filtered and concentrated under reduced pressure to provide a residue, which was purified via silica gel chromatography, eluting with 5-50% ethyl acetate:heptanes, to provide the product (46.2 g, 98% yield). LC/MS (Table A, Method a) $R_t$=0.80 minutes; MS m/z: 230.00 (M+H)$^+$.

Step 5: (R)-2-chloro-6-(3-methoxytetrahydrofuran-3-yl) pyridin-4-ol and (S)-2-chloro- 6-(3-methoxytetrahydrofuran-3-yl)pyridin-4-ol. 2-Chloro-6-(3-methoxytetrahydrofuran-3- yl)pyridine (46.2 g) was further purified via chiral SFC (Table B, Method 9) to provide the (R)-isomer (21.6 g, 49% yield, >99% ee, $R_t$=5.6 minutes) and the (S)-isomer (97% ee, $R_t$=6.1 minutes). LC/MS (Table A, Method a) $R_t$=0.80 minutes; MS m/z: 230.00 (M+H)$^+$.

22. Preparation #22 and #22a: (R)-2-Chloro-4-methoxy-6-(3-methoxytetrahydrofuran-3- yl)pyridine and (S)-2-chloro-4-methoxy-6-(3-methoxytetrahydrofuran-3-yl)pyridine

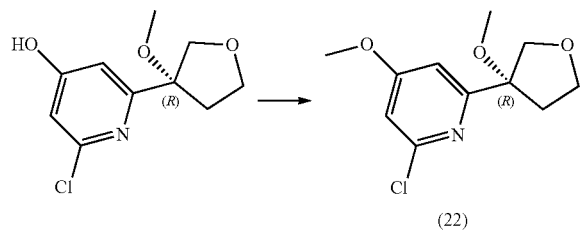

(22)

and

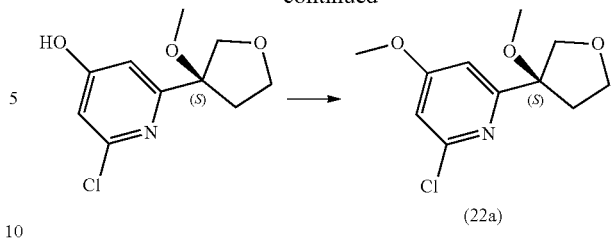

(22a)

The starting material ((R) or (S)-2-chloro-6-(3-methoxytetrahydrofuran-3-yl)pyridin-4-ol) (500mg, 2.177 mmol) (Preparation #21) was dissolved in dimethylformamide (8.7 mL), stirred in a reaction vial at room temperature. Cesium carbonate (1.0 g, 3.27 mmol) and iodomethane (204 µl, 3.27 mmol) were added to the vial and then the reaction was heated at 40° C. for 30 minutes. The reaction was cooled to room temperature and then diluted with 5 mL water and 10 mL ethyl acetate. The mixture stirred for 20 minutes. The layers were separated and extracted with ethyl acetate (2×10mL). Washed and combined the organic portion with brine and then dried over MgSO$_4$ and concentrate to dryness to provide the desired product: the (R)-isomer (410 mg, 77% yield). LC/MS (Table A, Method a) $R_t$=1.08 minutes; MS m/z: 243, 245 (M+H)$^+$; or the (S)-isomer (450 mg, 85% yield). LC/MS (Table A, Method a) $R_t$=1.08 minutes; MS m/z: 243, 245 (M+H)$^+$.

23. Preparation #23: (R)-2-Chloro-6-(3-methoxytetrahydrofuran-3-yl)-4-(oxetan-3-ylmethoxy)pyridine

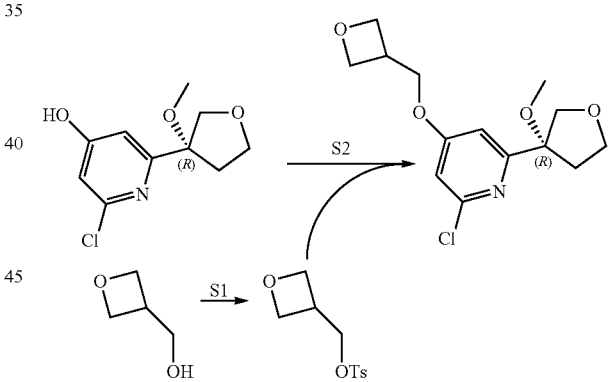

Step 1: oxetan-3-ylmethyl 4-methylbenzenesulfonate. In a round-bottomed flask, 3- oxetane methanol (0.919 g, 10.43 mmol), triethylamine (2.181 mL, 15.65 mmol), and 4-toluenesulfonyl chloride (2.187 g, 11.47 mmol) in dichloromethane (DCM) (25 mL) were added to give a colorless solution. 4-Dimethylamino pyridine (0.064 g, 0.522 mmol) was added and the mixture was stirred at room temperature for about 16 hours. Quenched the reaction with saturated aqueous NH$_4$Cl (10 mL) and separated the layers. Extracted the aqueous layer with DCM (2×10 mL) and the combined organic layers were washed with saturated aqueous NaHCO$_3$ (10 mL) and brine (10 mL). Dried the organic layer over MgSO$_4$ and concentrated under reduced pressure to provide a residue, which was purified via silica gel chromatography, eluting with 10 to 100% ethyl acetate:heptanes, to provide the product (1.71 g, 66% yield). LC/MS (Table A, Method a) $R_t$=1.10 minutes; MS m/z: 243 (M+H)$^+$. $^1$H NMR (400 MHz, Dimethyl sulfoxide-d$_6$) δ 7.87-7.78 (m, 2H), 7.55-7.46 (m, 2H), 4.56 (dd, J=8.0, 6.2 Hz, 2H), 4.24 (d, J=6.6 Hz, 2H), 4.20 (t, J=6.1 Hz, 2H), 3.29 -3.18 (m, 1H), 2.43 (s, 3H).

Step 2: (R)-2-chloro-6-(3-methoxytetrahydrofuran-3-yl)-4-(oxetan-3- ylmethoxy)pyridine. To a solution of (R)-2-chloro-6-(3-methoxytetrahydrofuran-3-yl)pyridin-4-ol (0.909 g, 3.96 mmol) (Preparation #21) in dimethylformamide (DMF) (33.0 mL) cooled to about 0° C. was added NaH (60% dispersion in mineral oil, 0.190 g, 4.75 mmol). The reaction stirred for about 20 minutes, then a solution of oxetan-3-ylmethyl 4-methylbenzenesulfonate (1.15 g, 4.75 mmol) in 1 mL DMF was added slowly. Removed the reaction from ice bath and heated to about 100° C. for about 90 minutes. Continued heating to 100° C. for an additional 1 hour, then left at room temperature for about 2 days. Added brine (80 mL) and ethyl acetate (100 mL) to the reaction mixture, and a little water to clarify the solution. Separated the organic layers, then extracted the aqueous layer again with ethyl acetate (30 mL). Combined the organic layers and washed with brine (50 mL), dried over MgSO$_4$, filtered and concentrated under reduced pressure to provide a residue, which was purified via silica gel chromatography, eluting with 10-70% ethyl acetate/heptanes, to provide the product (0.822 g, 69% yield). LC/MS (Table A, Method a) R$_t$=1.00 minutes; MS m/z: 300 (M+H)$^+$.

24. Preparation #24: (R)-4-((2-Chloro-6-((R)-3-methoxytetrahydrofuran-3-yl)pyridin-4- yl)oxy)butan-2-ol

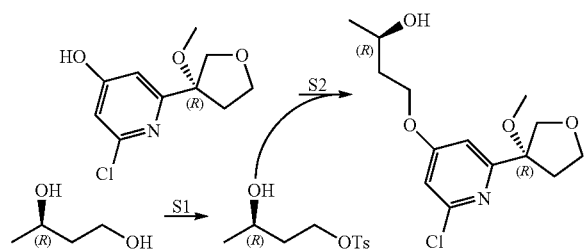

Step 1: (R)-3-hydroxybutyl 4-methylbenzenesulfonate. A flask was charged with (R)-(-)- 1,3-butanediol (1.0 g, 11.10 mmol), 4-dimethylamino pyridine (0.136 g, 1.110 mmol), triethylamine (1.619 mL, 12.21 mmol), and 4-methylbenzene-1-sulfonyl chloride (2.327 g, 12.21 mmol) in dichloromethane (DCM) (27.7 mL), and stirred at room temperature for 1 hour. The reaction was quenched with saturated NH$_4$Cl and extracted with DCM. The organic portion was dried over MgSO$_4$, filtered, and concentrated under reduced pressure to give a residue, which was purified via silica gel chromatography, eluting with 0-50% ethyl acetate/heptanes, to provide the product (1.82 g, 67% yield). $^1$H NMR (400 MHz, Dimethyl sulfoxide-d$_6$) δ 7.78-7.68 (d, 2H), 7.52-7.40 (d, 2H), 4.50 (s, 1H), 4.13-3.96 (m, 2H), 3.65-3.52 (m, 1H), 2.39 (s, 3H), 1.66-1.48 (m, 2H), 1.00 (dd, J=6.1, 0.6 Hz, 1H), 0.98 (s, 3H). (NMR showed 4:1 mixture of isomers). Ts=4-toluenesulfonyl Step 2: (R)-4-((2-chloro-6-((R)-3-methoxytetrahydrofuran-3-yl)pyridin-4- yl)oxy)butan-2-ol. To a solution of (R)-2-chloro-6-(3-methoxytetrahydrofuran-3-yl)pyridin-4-ol (0.270 g, 1.176 mmol) (Preparation #21) in dimethylformamide (DMF) (5.88 mL) cooled to 0° C. was added NaH (60% dispersion in mineral oil) (0.056 g, 1.411 mmol). The reaction stirred for 10 minutes, then a solution of (R)-3-hydroxybutyl 4-methylbenzenesulfonate (0.373 g, 1.528 mmol) in 0.5 mL DMF was slowly added. Allowed the reaction to warm to 50° C. for 1 hour. The reaction was cooled to room temperature and added brine (20 mL) and ethyl acetate (40 mL). The aqueous layer was separated and the organic layer was washed with brine (10 mL). The organic portion was dried over MgSO$_4$, filtered and concentrated under reduced pressure to provide crude product (0.265 g, 75% yield). LC/MS (Table A, Method b) R$_t$ =1.14 minutes; MS m/z: 302, 304 (M+H)$^+$.

25. Preparation #25: (R)-2-Chloro-6-(3-methoxytetrahydrofuran-3-yl)-4-(oxetan-3-yloxy)pyridine

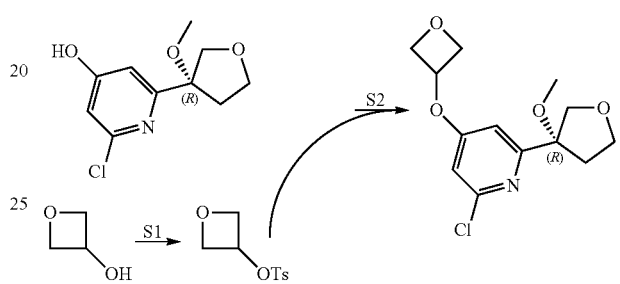

Step 1: oxetan-3-yl 4-methylbenzenesulfonate. In a round-bottomed flask, oxetan-3-ol (3.00 g, 40.5 mmol), triethylamine (8.47 mL, 60.7 mmol), and 4-toluenesulfonyl chloride (8.49 g, 44.5 mmol) in dichloromethane (DCM) (25 mL) were added to give a colorless solution. 4-Dimethylamino pyridine (0.247 g, 2.025 mmol) was added and the mixture was stirred at room temperature for about 16 hours. The reaction was quenched with saturated aqueous NH$_4$Cl (20 mL) and separated layers. Extracted aqueous with DCM (2×20 mL) and the combined organic layers were washed with saturated aqueous NaHCO$_3$ (20 mL) and brine (20 mL). Dried the organic layer over MgSO$_4$ and concentrated under reduced pressure to a residue, which was purified via silica gel chromatography, eluting with 10-100% ethyl acetate/heptanes, to provide the product (7.98 g, 86% yield). LC/MS (Table A, Method a) R$_t$=1.10 minutes; MS m/z: 243 (M+H)$^+$. $^1$H NMR (400 MHz, Dimethyl sulfoxide-d$_6$) δ 7.87-7.78 (m, 2H), 7.55-7.46 (m, 2H), 4.56 (dd, J=8.0, 6.2 Hz, 2H), 4.24 (d, J =6.6 Hz, 2H), 4.20 (t, J=6.1 Hz, 2H), 3.29-3.18 (m, 1H), 2.43 (s, 3H). Ts=4-toluenesulfonyl.

Step 2: (R)-2-chloro-6-(3-methoxytetrahydrofuran-3-yl)-4-(oxetan-3-yloxy)pyridine. To a solution of (R)-2-chloro-6-(3-methoxytetrahydrofuran-3-yl)pyridin-4-ol (0.300 g, 1.306 mmol) (Preparation #21) in dimethylformamide (DMF) (10.89 mL) cooled to about 0° C. was added NaH (60% dispersion in mineral oil) (0.063 g, 1.568 mmol). The reaction stirred for about 10 minutes, then added a solution of oxetan-3-yl 4-methylbenzenesulfonate (0.358 g, 1.568 mmol) in 1 mL DMF slowly. Heated the reaction to about 100° C. for about 16 hours. The temperature was then increased to 115° C. for about 2 hours. The reaction was cooled to room temperature, then brine (30 mL) and ethyl acetate (50 mL) were added. The aqueous layer was separated and organic layers washed with brine (20 mL). The organic layers were dried over MgSO$_4$, filtered and concentrated under reduced pressure to provide a residue, which was purified via silica gel chromatography, eluting with 10-70% ethyl acetate/heptanes, to provide the product (0.325 g, 87% yield). LC/MS (Table A, Method a) R$_t$=0.99 minutes; MS m/z: 286 (M+H)$^+$. $^1$H NMR (400 MHz, Dimethyl sulfoxide-d$_6$) δ 6.93 (d, J =2.1 Hz, 1H), 6.91 (d, J=2.1 Hz, 1H), 5.48 (tt, J=6.0, 4.7 Hz, 1H), 4.95 (ddd, J=7.2, 6.0, 1.0 Hz, 2H), 4.56 (ddt, J =7.4, 4.6, 1.2 Hz, 2H), 3.99 (dd, J=9.6, 1.1 Hz, 1H), 3.96 -3.85 (m, 2H), 3.77 (d, J=9.6 Hz, 1H), 3.08 (s, 3H), 2.45-2.34 (m, 1H), 2.30 (dddd, J=13.2, 6.4, 4.5, 1.1 Hz, 1H).

26. Preparation #26: (S)-4-((2-Chloro-6-((R)-3-methoxytetrahydrofuran-3-yl)pyridin-4-yl)oxy)butan-2-ol

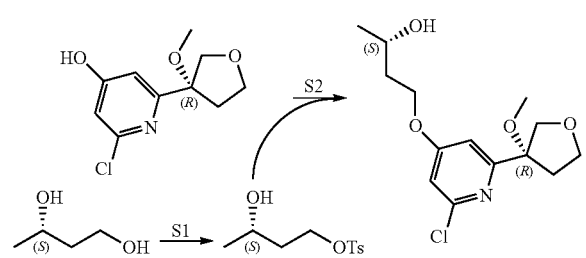

Step 1: (S)-3-hydroxybutyl 4-methylbenzenesulfonate. A flask was charged with (S)- butane-1,3-diol (1.00 g, 11.10 mmol), triethylamine (1.347 g, 13.32 mmol), 4-dimethylamino pyridine (0.136 g, 1.110 mmol), and 4-methylbenzene-1-sulfonyl chloride (2.327 g, 12.21 mmol) in dichloromethane (DCM) (27 mL). The reaction stirred at room temperature for 1 hour. The reaction was quenched with saturated NH$_4$Cl and extracted with DCM. The organic portion was dried over MgSO$_4$, filtered, and concentrated under reduced pressure to give a residue, which was purified via silica gel chromatography, eluting with 0-50% ethyl acetate/heptanes, to provide the product (0.288 g, 1.179 mmol, 10.62% yield). LCMS (Table A, Method b) R$_t$=1.19 minutes; MS m/z: 245 (M+H)$^+$.

Step 2: (S)-4-((2-chloro-6-((R)-3-methoxytetrahydrofuran-3-yl)pyridin-4- yl)oxy)butan-2-ol. To a solution of (R)-2-chloro-6-(3-methoxytetrahydrofuran-3-yl)pyridin-4-ol (0.21 g, 0.914 mmol) (Preparation #21) in dimethylformamide (DMF) (3.6 mL) cooled to 0° C. was added NaH (60% dispersion in mineral oil) (0.044 g, 1.097 mmol). The reaction stirred for 10 minutes at 0° C., then added a solution of (S)-3-hydroxybutyl 4-methylbenzenesulfonate (0.290 g, 1.189 mmol) in 0.5 mL DMF slowly. Allowed the reaction to warm to 50° C. for 2 hours. The reaction was cooled to room temperature and was partitioned between ethyl acetate and water. The organic portion was dried over MgSO$_4$, filtered, and concentrated under reduced pressure to provide the product (0.270 g, 98% yield). LCMS (Table A, Method b) R$_t$=1.13 minutes; MS m/z: 302, 304 (M+H)$^+$.

27. Preparation #27: (R)-2-((2-Chloro-6-(3-methoxytetrahydrofuran-3-yl)pyridin-4-yl)oxy)ethanol

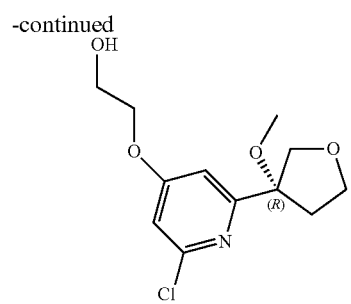

A solution of (R)-2-chloro-6-(3-methoxytetrahydrofuran-3-yl)pyridin-4-ol (0.300 g, 1.306 mmol)(Preparation #21) in dimethylformamide (DMF) (6.5 mL) was treated with NaH (60% dispersion in mineral oil) (0.063 g, 1.568 mmol), and allowed to stir for 30 minutes. The reaction was then treated with 2-bromoethanol (0.326 g, 2.61 mmol) and allowed to stir overnight at 85° C. An additional equivalent of bromoethanol was added. The reaction was quenched with water, and extracted with ethyl acetate, dried over MgSO$_4$, filtered and concentrated to provide the product (0.350 g, 98% yield). LCMS (Table A, Method a) R$_t$=0.77 minutes; MS m/z: 274.2 (M+H)$^+$.

28. Preparation #28: 4-((Trans)-3-(benzyloxy)cyclobutoxy)-2-chloro-6-(3- methoxytetrahydrofuran-3-yl)pyridine Step 1: (cis)-3-(benzyloxy)cyclobutanol. A solution of 3-(benzyloxy)cyclobutanone (0.700 g, 3.97 mmol) in ethanol (50 mL) was cooled to 0° C., and sodium borohydride (0.150 g, 3.97 mmol) was added. The reaction stirred at 0° C. for 1 hour. The reaction was quenched with water (50 mL) and extracted with dichloromethane (2×75 mL). The combined organic layers were washed with brine (75 mL) and dried over MgSO$_4$, filtered and concentrated to provide the product (0.679 g, 96% yield). (95:5 mixture of cis:trans isomers by NMR) $^1$H NMR (400 MHz, Dimethyl sulfoxide-d$_6$) δ 7.37-7.24 (m, 5H), 4.99 (d, J=6.6 Hz, 1H), 4.33 (s, 2H), 3.74-3.62 (m, 1H), 3.54 (ttd, J=7.7, 6.5, 0.5 Hz, 1H), 2.58-2.50 (m, 2H), 1.78 -1.68 (m, 2H). Bn=benzyl.

Step 2: (cis)-3-(benzyloxy)cyclobutyl methanesulfonate. A solution of (cis)-3- (benzyloxy)cyclobutanol (0.679 g, 3.81 mmol) and triethylamine (0.797 mL, 5.71 mmol) in dichloromethane (19 mL) was cooled to 0° C., and methanesulfonyl chloride (0.355 mL, 4.57 mmol) was added dropwise. The reaction stirred warming to room temperature over 2 hours. Added saturated aqueous ammonium chloride (20 mL). Separated the layers and washed with saturated aqueous sodium bicarbonate (20 mL) and brine (20 mL). Dried over MgSO₄ and concentrated under reduced pressure to provide the crude product (0.907 g, 93% yield). LCMS (Table A, Method a) $R_t$=1.30 minutes; MS m/z: 256.93 (M+H)⁺.

Step 3: 4-((trans)-3-(benzyloxy)cyclobutoxy)-2-chloro-6-(3-methoxytetrahydrofuran-3- yl)pyridine. A solution of 2-chloro-6-(3-methoxytetrahydrofuran-3-yl)pyridin-4-ol (0.677 g, 2.95 mmol) (Preparation #21, Step 4) in DMF (29.5 mL) was cooled to 0° C., and NaH (60% in mineral oil dispersion) (0.142 g, 3.54 mmol) was added. The reaction was stirred for 10 minutes, then (cis)-3- (benzyloxy) cyclobutyl methanesulfonate (0.907 g, 3.54 mmol) in dimethylformamide was added. After 15 minutes, the temperature was increased to 50° C. and let stir for 16 hours. The temperature was raised to 80° C. and continued to stir for 16 hours. The temperature was raised to 100° C. and stirred for an additional 16 hours. The reaction cooled to room temperature and added brine (150 mL) and ethyl acetate (300 mL), and water added until solution was clarified. Extracted the aqueous layer with ethyl acetate (100 mL). Dried the organic portion over MgSO₄ and concentrated under reduced pressure to provide a residue, which was purified via silica gel chromatography, eluting 10 to 80% ethyl acetate/heptanes, to provide the product (650 mg, 56% yield). LCMS (Table A, Method a) $R_t$=1.86 minutes; MS m/z: 390.13 (M+H)⁺.

29. Preparation #29: 2-Chloro-6-(oxetan-3-yl)pyridine

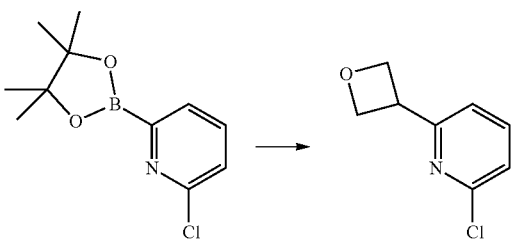 [SMILES: CC1(C)OB(c2cccc(Cl)n2)OC1(C)C ; Clc1cccc(C2COC2)n1]

A solution of nickel(II) iodide (0.522 g, 1.670 mmol) and (1R,2R)-2-aminocyclohexanol hydrochloride (0.253 g, 1.670 mmol) in isopropyl alcohol (IPA) (8.35 mL) was degassed with nitrogen for 10 minutes before adding sodium bis(trimethylsilyl)amide (8.77 mL, 8.77 mmol), and to this solution was added a solution of 2-chloro-6-(4,4,5,5-tetramethyl-1,3,2-dioxaborolan-2-yl)pyridine (2.0 g, 8.35 mmol) and 3-iodooxetane (3.07 g, 16.70 mmol) in degassed IPA (8.35 mL). The reaction was allowed to stir at 120° C. for 1 hour. The reaction mixture cooled to room temperature, and then was partitioned between water/NH₄Cl and ethyl acetate, and separated the phases. Extracted the aqueous layer with ethyl acetate (3×30 mL), dried over MgSO₄, filtered and concentrated to provide a residue, which was purified via silica gel chromatography, eluting with 0-60% ethyl acetate/heptanes, to provide the product (0.50 g, 35% yield). LCMS (Table A, Method a) $R_t$=0.70 minutes; MS m/z: 169.8 (M+H)⁺.

30. Preparation #30: (S)-Tetrahydrofuran-3-yl methanesulfonate

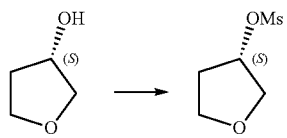

To a solution of (S)-tetrahydrofuran-3-ol (12.71 mL, 159 mmol) in dichloromethane (DCM) (318 mL) at −10° C. in a brine ice bath was added triethylamine (26.6 mL, 191 mmol) followed by dropwise addition of methanesulfonyl chloride (13.64 mL, 175 mmol) via syringe such that the internal temperature did not go above 0° C. The reaction stirred for 4 hours at 0° C. Water (15 mL) was added and the mixture stirred for 5 minutes. Then saturated aqueous sodium bicarbonate was added. The layers were separated and the aqueous phase was extracted with dichloromethane. The combined organic extracts were washed with water, diluted with HCl and then NaHCO₃, dried over MgSO₄, filtered through a pad of silica gel, and the filtrate concentrated to provide the product (22.1 g, 80% yield). ¹H NMR (400 MHz, Dimethyl sulfoxide-d₆) δ 5.31-5.27 (m, 1H), 3.83-3.67 (m, 4H), 3.19 (d, J=0.8 Hz, 3H), 2.19 (dtdd, J=14.4, 8.4, 6.0, 0.7 Hz, 1H), 2.10-2.00 (m, 1H).

31. Preparation #31: 3-Cyanocyclobutyl methanesulfonate

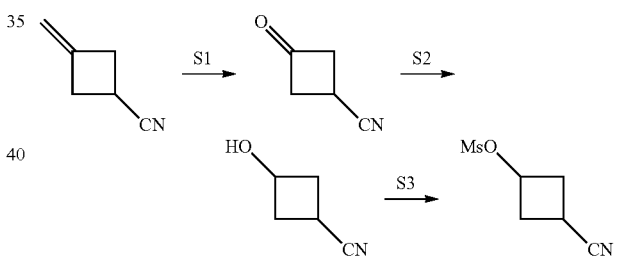

Step 1: 3-oxocyclobutanecarbonitrile. To a mixture of 3-methylenecyclobutanecarbonitrile (10 g, 107 mmol) in dichloromethane (DCM) (200 mL), acetonitrile (200 mL), and water (300 mL) was added ruthenium(III) chloride (0.668 g, 3.22 mmol), followed by small portions of sodium periodate (92 g, 430 mmol) at 0° C. The reaction mixture was stirred at 20° C. for 18 hours. This procedure was repeated 2 other times on same scale. The reaction mixtures were then combined for work up. The mixture was filtered, and the aqueous phase was extracted with DCM (3×1000 mL). The organic phases were combined, dried over MgSO₄, filtered, and concentrated to provide the product (32 g, 75% yield). ¹H NMR (400 MHz, Chloroform-d) δ 3.20-.32 (m, 1H), 3.54 (d, J=8.33 Hz, 4H).

Step 2: 3-hydroxycyclobutanecarbonitrile. A solution of 3-oxocyclobutanecarbonitrile (32 g, 336 mmol) in methanol (330 mL) was cooled to 0° C. before the addition of NaBH₄ (6.37 g, 168 mmol) portionwise. The mixture was stirred at 0° C. for 1 hour. The reaction mixture was quenched by saturated aqueous NaHCO₃ and extracted with ethyl acetate (800 mL). The organic layer was dried over Na₂SO₄, filtered, and concentrated. This procedure was repeated on the same scale two more times and combined for purification via silica gel chromatography, eluting with 10:1 to 1:1 petroleum ether:ethyl acetate, to provide the product (30.3 g, 296 mmol, 70% yield). $^1$H NMR (400 MHz, Chloroform-d) δ 2.22-2.38 (m, 2H), 2.45-2.80 (m, 1H), 2.50-2.80 (m, 2H), 2.95-3.28 (m, 1H), 4.13-4.65 (m, 1H) (a mixture of 8:1 cis:trans products by NMR).

Step 3: 3-cyanocyclobutyl methanesulfonate. To a cooled (0° C.) solution of 3- hydroxycyclobutanecarbonitrile (5 g, 51.5 mmol) in dichloromethane (103 mL) and triethylamine (21.53 mL, 154 mmol) was added methanesulfonyl chloride (4.39 mL, 56.6 mmol) dropwise via syringe, and the mixture was stirred for about 2 hours. The reaction was quenched by addition of NaHCO$_3$ and diethyl ether. The layers were separated and the aqueous phase was extracted with diethyl ether (3×30 mL). The combined organic extracts were washed with brine, dried over MgSO$_4$ and filtered. The solvent was concentrated under reduced pressure to provide the product (8.1 g, 90% yield). $^1$H NMR (400 MHz, Chloroform-d) δ 5.03 -4.83 (m, 1H), 3.03 (d, J=0.8 Hz, 3H), 2.98 -2.85 (m, 2H), 2.85 -2.64 (m, 3H). Ms=-SO$_2$Me.

32. Preparation #32: 2,2-Difluorocyclopropyl 4-methylbenzenesulfonate

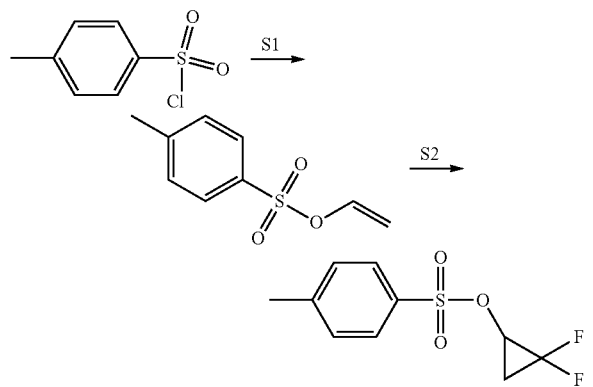

Step 1: vinyl 4-methylbenzenesulfonate. Into a flask containing anhydrous tetrahydrofuran (THF) (120 mL) was added n-butyl lithium (2.5 M in hexanes) (50.4 mL, 126 mmol) under nitrogen, and the mixture was stirred at 35° C. for 4 hours. After being cooled to −78° C., a solution of p-toluenesulfonyl chloride (20 g, 105 mmol) in THF (50 mL) was added dropwise over 30 minutes. The resulting mixture was stirred at −78° C. for 1 hour and warmed to room temperature and stirred for another 1 hour. An additional nine reactions were set up as described above and combined for workup. The reaction mixture was poured into water (800 mL) and extracted with ethyl acetate (3×800 mL). The organic phase was washed with brine (8 L), dried over Na$_2$SO$_4$, filtered, and concentrated under reduced pressure. The residue was purified by column chromatography on silica gel, eluting with 100:1 to 10: 1 petroleum ether/ethyl acetate, to provide the product (105 g, 45% yield). $^1$H NMR (400 MHz, Chloroform-d) δ 7.80 (d, J=8.38 Hz, 2H), 7.36 (d, J=8.16 Hz, 2H), 6.61 (dd, J=13.45, 5.95 Hz, 1H), 4.89 (dd, J=13.67, 2.43 Hz, 1H), 4.69 (dd, J=5.95, 2.43 Hz, 1H).

Step 2: 2,2-difluorocyclopropyl 4-methylbenzenesulfonate. To a solution of vinyl 4- methylbenzenesulfonate (10 g, 45.4 mmol) in xylenes (160 mL) was added NaF (0.212 g, 5.04 mmol) at 20° C. The mixture was heated to 120° C. and trimethylsilyl 2,2-difluoro-2-(fluorosulfonyl)acetate (68.2 g, 272 mmol) was added at 120° C. and stirred for 34 hours. An additional five reactions were set up as described above and combined for workup. After cooling, the reaction mixtures were combined and concentrated to provide a residue, which was purified by column chromatography on silica gel eluting with 100:1 to 30:1 petroleum ether/ethyl acetate, to provide the product (30.2 g, 37.9% yield). $^1$H NMR (400 MHz, Methanol-d$_4$) δ 1.59 (ddt, J=15.93, 10.47, 4.99, 4.99 Hz, 1H) 1.84 (ddd, J=17.53, 14.22, 9.48 Hz, 1H) 2.48 (s, 3H) 4.40 (ddt, J=11.63, 9.21, 2.37, 2.37 Hz, 1H) 7.48 (d, J=8.16 Hz, 2H) 7.80 -7.89 (m, 1H) 7.84 (d, J=8.38 Hz, 1H).

33. Preparation #33: 2-Bromo-6-(3-methoxyoxetan-3-yl)pyridine

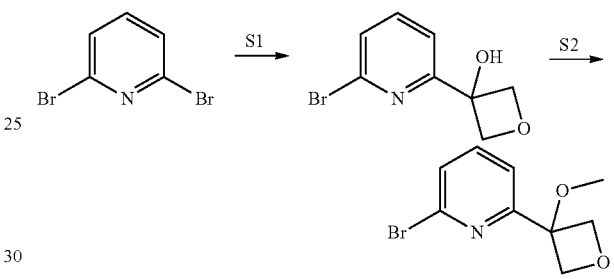

Step 1: 3-(6-bromopyridin-2-yl)oxetan-3-ol. To a solution of 2,6-dibromopyridine (10 g, 42.2 mmol) in dichloromethane (DCM) (211 mL) stirring at −78° C. was added n-butyl lithium (2.5 M in hexanes) (18.58 mL, 46.4 mmol) in a dropwise manner such that the internal temperature did not exceed −67° C. After 20 minutes, 3-oxetanone (3.25 mL, 50.7 mmol) was then added as a neat oil in a dropwise manner. After 1 hour, the reaction was quenched at low temperature by the addition of saturated aqueous ammonium chloride. After warming to room temperature, the mixture was separated and the aqueous portion was extracted with DCM. The combined extracts were dried over anhydrous MgSO$_4$, filtered, and concentrated to provide a residue, which was triturated with diethyl ether to provide the product (6.8g, 68% yield). $^1$HNMR (400 MHz, Dimethyl sulfoxide-d$_6$) δ 7.78 (t, J=7.8 Hz, 1H), 7.60 (dd, J=11.1, 7.6 Hz, 2H), 6.69 (s, 1H), 4.86 (d, J=6.2 Hz, 2H), 4.64 (d, J=6.2 Hz, 2H).

Step 2: 2-bromo-6-(3-methoxyoxetan-3-yl)pyridine. To a solution of 3-(6-bromopyridin- 2-yl)oxetan-3-ol (1.1 g, 4.85 mmol) in tetrahydrofuran (16.15 mL) stirring at 0° C. was added NaH (60% dispersion in mineral oil) (0.22 g, 5.33 mmol). After 5 minutes, iodomethane (0.348 mL, 5.57 mmol) was added as a neat oil in a dropwise manner. The ice bath was removed and the mixture was allowed to warm to room temperature. After 6 hours the reaction was quenched by the addition of saturated aqueous ammonium chloride (20 mL). The mixture was separated and the aqueous portion was extracted with ethyl acetate. The combined extracts were dried over anhydrous MgSO$_4$, filtered, and concentrated to provide a residue, which was purified by silica gel chromatography, eluting with 0-30% ethyl acetate/heptanes, to provide the product (1.08 g, 90% yield). $^1$H NMR (400 MHz, Dimethyl sulfoxide-d$_6$) δ 7.89 -7.81 (m, 1H), 7.65 (dd, J=7.9, 0.8 Hz, 1H), 7.53 (dd, J=7.6, 0.9 Hz, 1H), 4.85 (dd, J=6.9, 0.9 Hz, 2H), 4.73 (dd, J=6.9, 0.9 Hz, 2H), 3.14 (s, 3H).

34. Preparation #34: tert-Butyl 5-bromo-3-(4,4,5,5-tetramethyl-1,3,2-dioxaborolan-2-yl)-1H-pyrrolo[2,3-c]pyridine-1-carboxylate

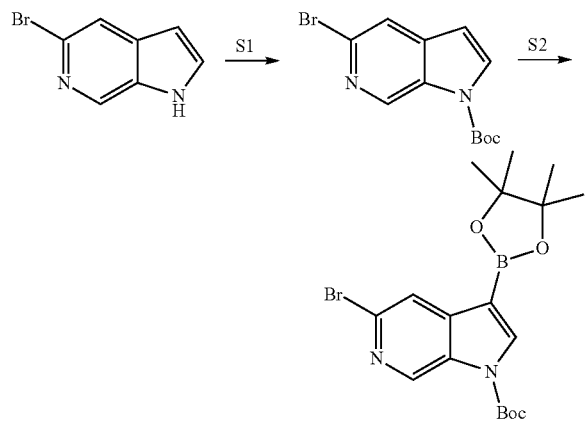

Step 1: tert-butyl 5-bromo-1H-pyrrolo[2,3-c]pyridine-1-carboxylate. To a suspension of 5-bromo-1H-pyrrolo[2,3-c]pyridine (10 g, 50.8 mmol) in acetonitrile (50mL) were added 4- dimethylamino pyridine (0.62 g, 5.08 mmol) and di-tert-butyl dicarbonate (12.9 mL, 55.8 mmol) while stirring at room temperature for 45 minutes. The reaction was diluted with water (40 mL), and the reaction filtered to provide a filtered product, which was rinsed with water, and dried in a vacuum oven at 60° C. to provide the product (12.1g, 80% yield). LC/MS (Table A, Method b) $R_t$=1.73 minutes; MS m/z: 296.73, 298.71 (M+H)$^+$. Boc=t-Butoxycarbonyl.

Step 2: tert-butyl 5-bromo-3-(4,4,5,5-tetramethyl-1,3,2-dioxaborolan-2-0-1H- pyrrolo[2,3-c]pyridine-1-carboxylate. A flask was charged with tert-butyl 5-bromo-1H-pyrrolo[2,3- c]pyridine-1-carboxylate (10 g, 33.7 mmol), 4,4'-di-tert-butyl-2,2'-bipyridine (0.181 g, 0.673 mmol) and cyclohexane (102 mL), degassed with nitrogen for 10 minutes, and bis(pinacolato)diboron (25.6 g, 101 mmol) and bis(1,5-cyclooctadiene)diiridium(I) dichloride (0.226 g, 0.337 mmol) were added. The reaction was sealed and heated to 75° C. for 110 minutes. The reaction was removed from heat, filtered, the filtered product was rinsed with acetonitrile (10 mL), dried in the oven, and then further triturated with heptanes, to provide the product (11.02 g, 77% yield). LC/MS (Table A, Method b) $R_t$=2.23 minutes; MS m/z: 423, 425 (M+H)$^+$.

35. Preparation #35: (R)-Tetrahydrofuran-3-yl methanesulfonate

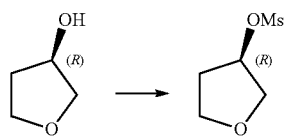

To a solution of (R)-tetrahydrofuran-3-ol (9.1 mL, 114 mmol) in dichloromethane (DCM) (100 mL) at −10° C. in a brine ice bath was added triethylamine (23 mL, 170 mmol) followed by dropwise addition of methanesulfonyl chloride (9.7 mL, 125 mmol) via syringe such that the internal temperature did not go above 0° C. The reaction stirred for 3 hours at 0° C. Water (15 mL) was added and the mixture stirred for 5 minutes. Then saturated aqueous sodium bicarbonate was added. The layers were separated and the aqueous phase was extracted with DCM. The combined organic extracts were washed with water, diluted with HCl and then NaHCO$_3$, dried over MgSO$_4$, filtered through a pad of silica gel, and the filtrate concentrated to provide the product (15.8 g, 84% yield). $^1$H NMR (400 MHz, Dimethyl sulfoxide-d$_6$) δ 5.31 -5.27 (m, 1H), 3.83-3.67 (m, 4H), 3.19 (d, J =0.8 Hz, 3H), 2.19 (dtdd, J =14.4, 8.4, 6.0, 0.7 Hz, 1H), 2.10-2.00 (m, 1H). Ms=-SO$_2$Me.

36. Preparation #36: 2-Chloro-6-(3-methoxytetrahydrofuran-3-yl)pyridin-4-yl acetate

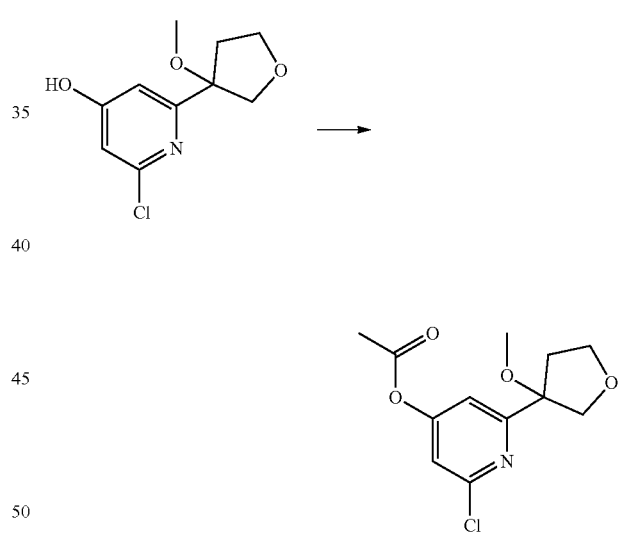

In a round-bottomed flask, 2-chloro-6-(3-methoxytetrahydrofuran-3-yl)pyridin-4-ol (0.677 g, 2.95 mmol) (Preparation #21, Step 4) in acetyl chloride (0.585 mL, 8.23 mmol), and triethylamine (1.434 mL, 10.29 mmol) in tetrahydrofuran (68.6 mL) were added. 4-Dimethylamino pyridine (0.084 g, 0.686 mmol) was added and the mixture was stirred at room temperature for 30 minutes. The reaction was filtered, and the filtrate concentrated to provide a residue, which was purified via silica gel chromatography, eluting with 10 to 100% ethyl acetate:heptanes, to provide the product (1.3 g, 70% yield). LC/MS (Table A, Method a) $R_5$=1.13 minutes; MS m/z: 271.98 (M+H)$^+$.

37. Preparation #37: (S)-2-Chloro-6-(3-methoxytetrahydrofuran-3-yl)-4-(oxetan-3-ylmethoxy)pyridine

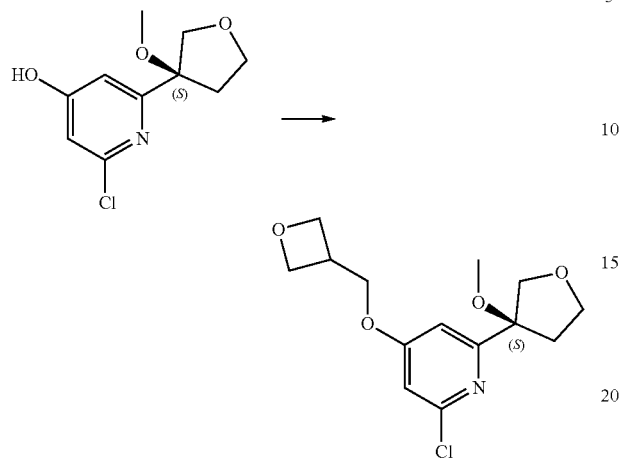

To a solution of (S)-2-chloro-6-(3-methoxytetrahydrofuran-3-yl)pyridin-4-ol (0.178g, 0.775 mmol) (Preparation #21a) in dimethylformamide (DMF) (6 mL) cooled to about 0° C. was added NaH (60% dispersion in mineral oil) (0.037g, 0.93 mmol). The reaction stirred for about 20 minutes, then added a solution of oxetan-3-ylmethyl 4-methylbenzenesulfonate (0.225 g, 0.930 mmol) (Preparation #23, Step 1) in 1 mL DMF slowly. The reaction was removed from the ice bath and heated to about 100° C. for about 90 minutes. The temperature was increased, heating to 100° C. for an additional 1 hour, then left at room temperature for about 2 days. Brine (80 mL) and ethyl acetate (100 mL) were then added to the reaction mixture. The organic layers were separated and the aqueous layer was extracted with ethyl acetate (30 mL). The organic layers were combined and washed with brine (50 mL), dried over MgSO$_4$, filtered and concentrated under reduced pressure to provide a residue, which was purified via silica gel chromatography, eluting with 10-70% ethyl acetate/heptanes to provide the product (0.156g, 67% yield). LC/MS (Table A, Method a) R$_t$=1.01 minutes; MS m/z: 300 (M+H)$^+$.

38. Preparation #38: (R)-2-((2-Chloro-6-(3-methoxytetrahydrofuran-3-yl)pyridin-4-yl)oxy)acetonitrile

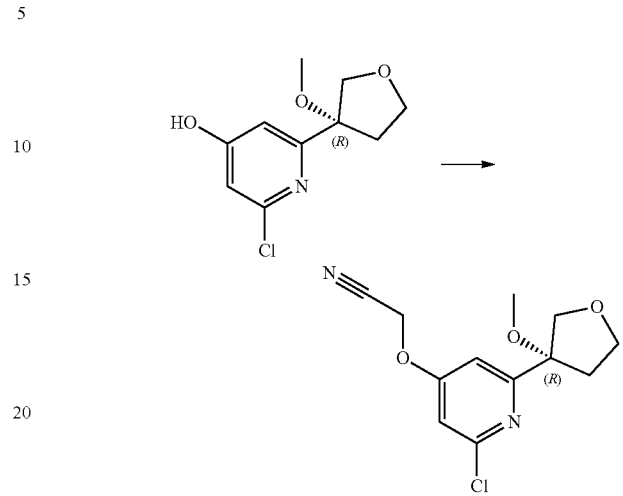

To a solution of (R)-2-chloro-6-(3-methoxytetrahydrofuran-3-yl)pyridin-4-ol (495 mg, 2.155 mmol) (Preparation #21) in dimethylformamide (7 mL) was added cesium carbonate (1053 mg, 3.23 mmol) and bromoacetonitrile (180 μL, 2.59 mmol), and then the reaction was stirred at room temperature for 45 minutes. The reaction was then quenched with water and then extracted with ethyl acetate (2×30 mL). The combined organic layers were washed with water (100 mL) and then brine, dried over MgSO$_4$, filtered, and concentrated to provide a residue, which was purified via silica gel chromatography, eluting with 0-70% ethyl acetate/heptanes, to provide the product (458mg, 79% yield). LC/MS (Table A, Method a) R$_t$ =1.35 min.; MS m/z: 269, 271 (M+H)$^+$.

39. Preparation #39: 4-4(S)-4-((Tert-butyldimethylsilypoxy)butan-2-yl)oxy)-2-chloro-6- ((R)-3-methoxytetrahydrofuran-3-yl)pyridine

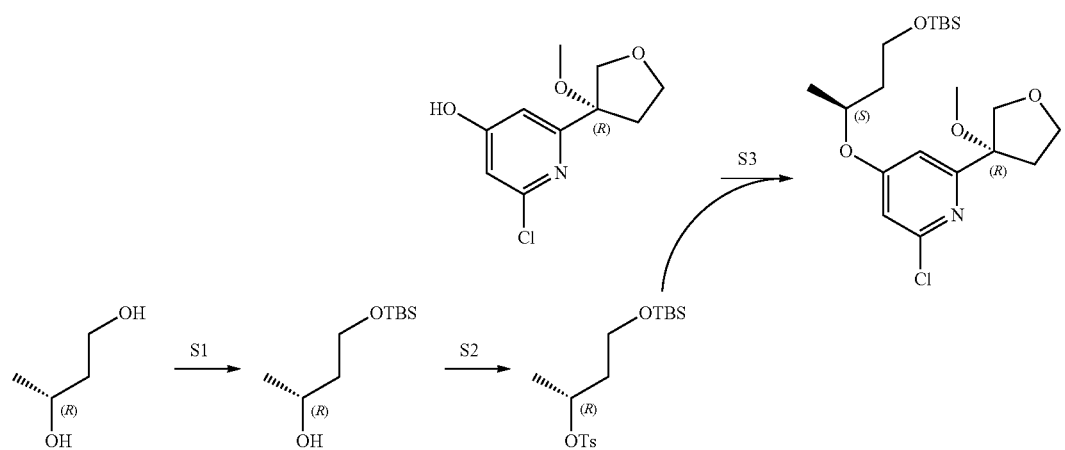

Step 1: (R)-4-((tert-butyldimethylsilyl)oxy)butan-2-ol. A flask was charged with (R)- butane-1,3-diol (1.00 g, 11.10 mmol), imidazole(1.13 g, 16.64 mmol), 4-dimethylamino pyridine (0.136 g, 1.110 mmol), and tert-butyldimethylsilyl chloride (2.00 g, 13.32 mmol) in dichloromethane (37.0 mL) at 0° C. The reaction stirred warming to room temperature. The solvent was concentrated under reduced pressure to provide the product. NMR (400 MHz, Dimethyl sulfoxide-$d_6$) δ 4.25 (d, J=4.8 Hz, 1H), 3.70 -3.64 (m, 1H), 3.64 -3.57 (m, 2H), 1.54 -1.41 (m, 2H), 1.02 (d, J=6.2 Hz, 3H), 0.83 (s, 10H), 0.01 -0.02 (m, 10H). TBS =tert-butyldimethylsilyl.

Step 2: (R)-4-((tert-butyldimethylsilypoxy)butan-2-yl 4-methylbenzenesulfonate. A flask was charged with (R)-4-((tert-butyldimethylsilyl)oxy)butan-2-ol (2.57 g, 12.57 mmol), p- toluenesulfonyl chloride (5.27 g, 27.7 mmol), and 4-dimethylamino pyridine (0.538 g, 4.40 mmol) in pyridine (20 mL) at 0° C. The reaction warmed to room temperature and stirred. Quenched the reaction with water and extracted with diethyl ether (2×30 mL). The organic portion was dried over $MgSO_4$, filtered, and concentrated to give a residue, which was purified via silica gel chromatography, eluting with 0-30% ethyl acetate/heptanes, to provide the product (2.35 g, 52% yield). LC/MS (Table A, Method b) $R_t$=2.27 minutes; MS m/z: 359 $(M+H)^+$.

Step 3: 4-(((S)-4-((tert-butyldimethylsilypoxy)butan-2-yl)oxy)-2-chloro-64(R)-3- methoxytetrahydrofuran-3-yl) pyridine. To a solution of (R)-2-chloro-6-(3- methoxytetrahydrofuran-3-yl)pyridin-4-ol (500 mg, 2.177 mmol) (Preparation #21) in dimethylformamide (DMF) (10.9 mL) was added NaH (60% dispersion in mineral oil) (113 mg, 2.83 mmol), and the reaction was stirred at room temperature for 5 minutes. (R)-4-((tert- butyldimethylsilyl)oxy)butan-2-yl 4-methylbenzenesulfonate (937 mg, 2.61 mmol) was then added in minimal DMF and then the reaction was warmed to 50° C. for 4 hours. The reaction was quenched with water and then extracted with ethyl acetate (2×20 mL). The combined organic portion was washed with water (50 mL) and brine (10 mL), dried over $MgSO_4$, filtered, and concentrated to provide a residue, which was purified via silica gel chromatography, eluting with 0-80% ethyl acetate/heptanes, to provide the product (560 mg, 62% yield). LC/MS (Table A, Method a) $R_t$=2.32 minutes; MS m/z: 416, 418 $(M+H)^+$.

40. Preparation #40: (R)-4-(Methoxymethyl)-2-(3-methoxytetrahydrofuran-3-yl)-6-(tributylstannyl) pyridine

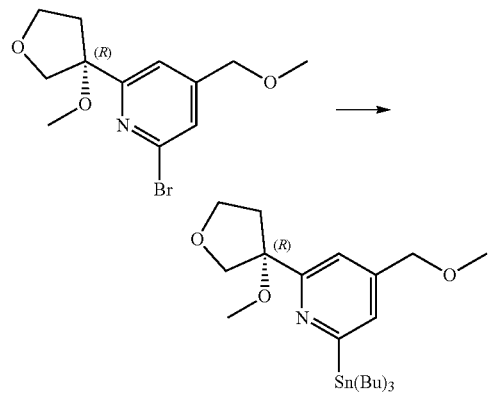

A solution of (R)-2-bromo-4-(methoxymethyl)-6-(3-methoxytetrahydrofuran-3-yl)pyridine (1 g, 3.31 mmol, Preparation #6) in dichloromethane (DCM) (22 mL) was cooled to −78° C. and was treated with 2.5 M butyllithium in tetrahydrofuran (1.45 mL, 3.64 mmol). The reaction stirred for about 20 minutes before adding tributylchlorostannane (1.3 mL, 4.96 mmol) at −78° C. The reaction was warmed to room temperature, and was quenched with ammonium chloride, then extracted with DCM. The combined organic layers were dried over $MgSO_4$, filtered, and concentrated to provide the product. $^1$H NMR (400 MHz, Dimethyl sulfoxide-$d_6$) δ 8.48 (s,1H), 7.45 (s, 1H), 4.49-4.45 (m, 2H), 4.03 -3.94 (m, 1H), 3.94 -3.84 (m, 2H), 3.84 -3.74 (m, 1H), 3.32 (d, J=0.7 Hz, 2H), 3.02 (d, J=2.3 Hz, 2H), 2.29 (dddd, J=13.3, 6.7, 4.4, 1.2 Hz, 1H), 1.62 -1.51 (m, 9H), 1.34 -1.24 (m, 12H), 1.11-1.04 (m, 10H), 0.84 (t, J=7.3 Hz, 17H). Bu=n-butyl.

41. Preparation #41: 4-((cis)-3-(Benzyloxy)cyclobutoxy)-2-chloro-6-((R)-3- methoxytetrahydrofuran-3-yl)pyridine

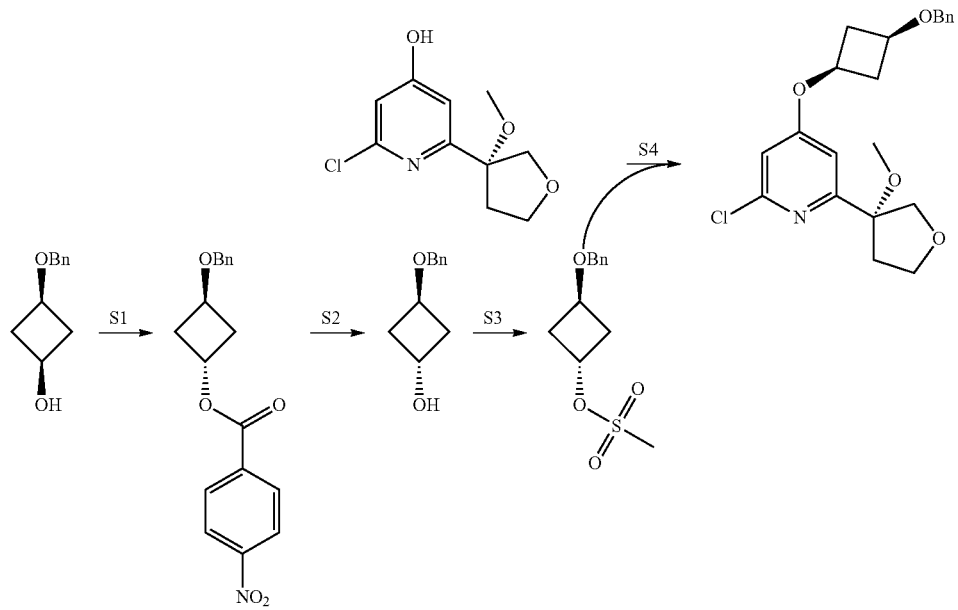

Step 1: trans-3-(benzyloxy)cyclobutyl 4-nitrobenzoate. A solution of (cis)-3- (benzyloxy)cyclobutanol (1.865 g, 10.46 mmol) (Preparation #28, Step 1), 4-nitrobenzoic acid (1.749 g, 10.46 mmol), and triphenylphosphine (3.29 g, 12.56 mmol) in tetrahydrofuran (THF) (100 mL) was cooled to about 0° C., and diisopropyl azodicarboxylate (2.472 mL, 12.56 mmol) was added dropwise. After the addition was complete, the reaction stirred at room temperature for 2 hours. Removed the solvent under reduced pressure to provide a residue, which was then dissolved in a mixture of diethyl ether and heptanes. Filtered the precipitate which formed through Celite® and removed the diethyl ether from the filtrate under reduced pressure. As the diethyl ether was removed, a solid precipitated out. Filtered off the solid and removed the heptanes to provide a residue, which was purified via silica gel chromatography, eluting with 10-60% ethyl acetate/heptanes, to provide the product (2.8 g, 82% yield). $^1$H NMR (400 MHz, Dimethyl sulfoxide-$d_6$) δ 8.40-8.30 (m, 2H), 8.24 -8.15 (m, 2H), 7.40 -7.26 (m, 5H), 5.37 -5.27 (m, 1H), 4.42 (s, 2H), 4.34 (tt, J =6.0, 4.8 Hz, 1H), 2.49 -2.42 (m, 4H). Bn=benzyl.

Step 2: trans-3-(benzyloxy)cyclobutanol. In a round-bottomed flask, trans-3- (benzyloxy)cyclobutyl 4-nitrobenzoate (2.981 g, 9.11 mmol) and potassium carbonate (2.52 g, 18.21 mmol) in methanol (19.51 mL) and water (3.25 mL) were added to give a white suspension. The reaction stirred at room temperature for 16 hours. Filtered off the precipitate that had formed and removed the solvent from filtrate. Added ethyl acetate to the residue, and washed with saturated aqueous sodium bicarbonate and water. Dried the organic portion over $MgSO_4$, filtered, and concentrated under reduced pressure to provide the product (1.7 g, 95% yield). $^1$H NMR (400 MHz, Dimethyl sulfoxide-$d_6$) δ 7.37 - 7.24 (m, 5H), 4.95 (d, J=5.2 Hz, 1H), 4.34 (s, 2H), 4.32 -4.23 (m, 1H), 4.15 (ttd, J=6.8, 4.1, 0.5 Hz, 1H), 2.23 -2.13 (m, 2H), 2.07 -1.96 (m, 2H).

Step 3: trans-3-(benzyloxy)cyclobutyl methanesulfonate. A solution of trans-3- (benzyloxy)cyclobutanol (1.62 g, 9.09 mmol) and triethylamine (1.9 mL, 13.63 mmol) in dichloromethane (DCM) (60 mL) was cooled to 0° C., and methanesulfonyl chloride (0.846 mL, 10.91 mmol) was added dropwise. The reaction stirred warming to room temperature over 36 hours. Saturated aqueous ammonium chloride (50 mL) was added to the reaction mixture. Separated the layers and washed with saturated aqueous sodium bicarbonate (50 mL) and brine (50 mL). The organic portion was dried over $MgSO_4$, filtered, and concentrated to provide the product (1.86, 80%yield). $^1$H NMR (400 MHz, Dimethyl sulfoxide-$d_6$) δ 7.39-7.24 (m, 5H), 5.19 -5.10 (m, 1H), 4.39 (s, 2H), 4.29 -4.21 (m, 1H), 3.15 (s, 3H), 2.45 (dd, J =6.1, 5.4 Hz, 4H).

Step 4: 4-((cis)-3-(benzyloxy)cyclobutoxy)-2-chloro-6-((R)-3-methoxytetrahydrofuran- 3-yl)pyridine. (R)-2-Chloro-6-(3-methoxytetrahydrofuran-3-yl)pyridin-4-ol (0.561 g, 2.443 mmol) (Preparation #21) in dimethylformamide (DMF) (12 mL) was cooled to 0° C. and NaH (60% in oil dispersion) (0.117 g, 2.93 mmol) was added. The reaction stirred for 10 minutes, then trans-3- (benzyloxy)cyclobutyl methanesulfonate (0.751 g, 2.93 mmol) in DMF (12 mL) was added. The reaction was heated to 100° C. for 32 hours. The reaction was cooled to room temperature then added brine (100 mL) and ethyl acetate (150 mL). Added water until salts were solubilized. Separated the layers and extracted the aqueous portion with ethyl acetate (100 mL). Dried the organic portion over $MgSO_4$, filtered and concentrated to provide a residue, which was purified via silica gel chromatography, eluting with 10- 80% ethyl acetate: heptanes, to provide the product (0.717 g, 75% yield). LC/MS (Table A, Method a) $R_t$=1.82 minutes; MS m/z: 390.14 $(M+H)^+$.

42. Preparation #42: 4-((S)-24(Tert-butyldimethylsilypoxy)propoxy)-2-chloro-64(R)-3- methoxytetrahydrofuran-3-yl)pyridine

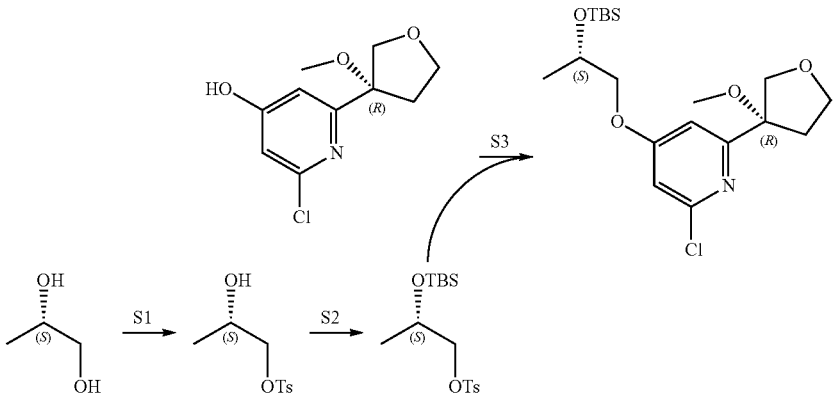

Step 1: (S)-2-hydroxypropyl 4-methylbenzenesulfonate. To a solution of (S)-(+)-1,2- propanediol (2.506 g, 32.9 mmol) and 4-methylbenzene-1-sulfonyl chloride (6.91 g, 36.2 mmol) in dichloromethane (DCM) (80 mL) was added triethylamine (6.89 mL, 49.4 mmol), followed by 4- dimethylamino pyridine (0.201 g, 1.647 mmol). The reaction stirred at room temperature for 16 hours. Quenched the reaction with saturated aqueous ammonium chloride (20 mL) and separated the layers. Extracted the aqueous portion with DCM (2×20 mL) and the combined organic layers were washed with saturated aqueous sodium bicarbonate (20 mL) and brine (20 mL). Dried the organic portion over $MgSO_4$, filtered, and concentrated under reduced pressure to provide a residue, which was purified via silica gel chromatography, eluting with 10 to 100% ethyl acetate: heptanes to provide the product (4.56 g, 60% yield). $^1$H NMR (400 MHz, Dimethyl sulfoxide-$d_6$) δ 7.82-7.75 (m, 2H), 7.51 -7.44 (m, 2H), 4.96 (d, J =4.6 Hz, 1H), 3.85 -3.72 (m, 3H), 2.42 (s, 3H), 0.98 (d, J =6.1 Hz, 3H). Ts =4-toluenesulfonyl.

Step 2: (S)-2-((tert-butyldimethylsilyl)oxy)propyl 4-methylbenzenesulfonate. To a cooled (0° C.) solution of (S)-2-hydroxypropyl 4-methylbenzenesulfonate (1.50 g, 6.51 mmol), tert-butyldimethylsilyl chloride (1.080 g, 7.17 mmol), and imidazole (0.665 g, 9.77 mmol) in dichloromethane (DCM) (50 mL), was added 4-dimethylamino pyridine (0.080 g, 0.651 mmol), and the mixture stirred warming to room temperature over 36 hours. Filtered off the precipitate that had formed and removed the solvent under reduced pressure from the filtrate to provide a residue, which was purified via silica gel chromatography, eluting with 0 to 100% ethyl acetate/heptanes, to provide the product (2.08 g, 92% yield). LC/MS (Table A, Method a) $R_t$=2.22 minutes; MS m/z: 345.10 (M+H)$^+$. TBS =tert-butyldimethylsilyl.

Step 3: 44(S)-2-((tert-butyldimethylsilypoxy)propoxy)-2-chloro-64(R)-3-methoxytetrahydrofuran-3-yl)pyridine. To a cooled (0° C.) solution of (R)-2-chloro-6-(3-methoxytetrahydrofuran-3-yl)pyridin-4-ol (0.500 g, 2.177 mmol) (Preparation #21) in dimethylformamide (DMF) (10.89 mL) was added NaH (60% in oil dispersion) (0.104 g, 2.61 mmol). The reaction stirred for 10 minutes, then (S)-2-((tert-butyldimethylsilypoxy)propyl 4-methylbenzenesulfonate (0.900 g, 2.61 mmol) in DMF (10.89 mL) was added. The reaction was heated to 100° C. for 16 hours. The reaction cooled to room temperature, and the solvent was concentrated. Added water (25 mL) and extracted the aqueous portion with dichloromethane (2×50 mL). Dried the combined organic layers over MgSO$_4$ and concentrated under reduced pressure to provide a residue, which was purified via silica gel chromatography, eluting with 0-60% ethyl acetate/heptanes to provide the product (0.51 g, 58% yield). LC/MS (Table A, Method a) $R_t$=2.26 minutes; MS m/z: 402.18(M+H)$^+$.

43. Preparation #43: 4-((R)-24(Tert-butyldimethylsilypoxy)propoxy)-2-chloro-64(R)-3-methoxytetrahydrofuran-3-yl)pyridine with DCM (2×20 mL) and the combined organic layers were washed with saturated aqueous sodium bicarbonate (20 mL) and brine (20 mL). Dried the organic portion over MgSO$_4$, filtered, and concentrated under reduced pressure to provide a residue, which was purified via silica gel chromatography, eluting with 10 to 100% ethyl acetate:heptanes, to provide the product (4.8 g, 63% yield). $^1$H NMR (400 MHz, Dimethyl sulfoxide-d$_6$) δ7.82 -7.75 (m, 2H), 7.51-7.44 (m, 2H), 4.96 (d, J =4.6 Hz, 1H), 3.85-3.72 (m, 3H), 2.42 (s, 3H), 0.98 (d, J=6.1 Hz, 3H).

Step 2: (R)-2-((tert-butyldimethylsilyl)oxy)propyl 4-methylbenzenesulfonate. To a cooled (0° C.) solution of (R)-2-hydroxypropyl 4-methylbenzenesulfonate (1.50 g, 6.51 mmol), tert-butyldimethylsilyl chloride (1.080 g, 7.17 mmol), and imidazole (0.665 g, 9.77 mmol) in dichloromethane (DCM) (50 mL) was added 4-dimethylamino pyridine (0.080 g, 0.651 mmol), and the mixture stirred warming to room temperature over 36 hours. Filtered off the precipitate that had formed and removed the solvent under reduced pressure from the filtrate to provide a residue, which was purified via silica gel chromatography, eluting with 0 to 100% ethyl acetate/heptanes, to provide the product (1.7 g, 75% yield). LC/MS (Table A, Method a) $R_t$=2.22 minutes; MS m/z: 345.10 (M+H)$^+$. TBS=tert-butyldimethylsilyl. Ts=4-toluenesulfonyl.

Step 3: 44(R)-2-((tert-butyldimethylsilypoxy)propoxy)-2-chloro-64(R)-3-methoxytetrahydrofuran-3-yl)pyridine. A solution of (R)-2-chloro-6-(3-methoxytetrahydrofuran-3-yl)pyridin-4-ol (0.524 g, 2.2 mmol) (Preparation #21) in dimethylformamide (DMF) (11 mL) was cooled to 0° C. and NaH (60% in oil dispersion) (0.1 g, 2.7 mmol) was added. The reaction stirred for 10 minutes, then (R)-2-((tert-butyldimethylsilyl)oxy)propyl 4-methylbenzenesulfonate (0.94g, 2.7 mmol) in DMF (10.89 mL) was added. The reaction was heated to 100° C. for 16 hours. The reaction

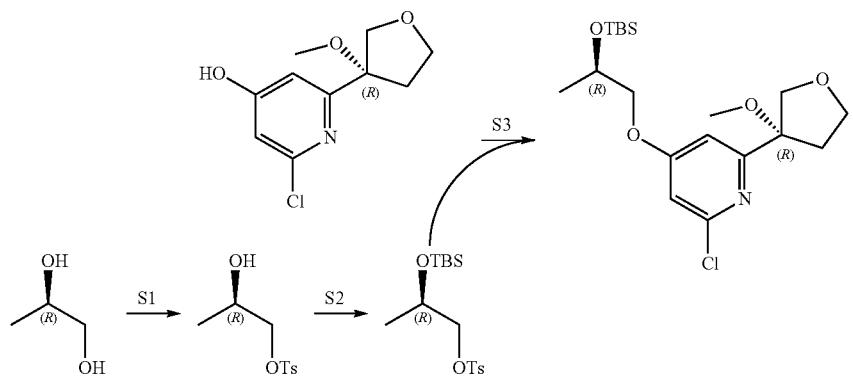

Step 1: (R)-2-hydroxypropyl 4-methylbenzenesulfonate. To a solution of (R)-(+)-1,2-propanediol (2.506 g, 32.9 mmol) and 4-methylbenzene-1-sulfonyl chloride (6.91 g, 36.2 mmol) in dichloromethane (DCM) (80 mL) was added triethylamine (6.89 mL, 49.4 mmol), followed by 4-dimethylamino pyridine (DMAP) (0.201 g, 1.647 mmol). The reaction stirred at room temperature for 16 hours. Quenched the reaction with saturated aqueous ammonium chloride (20 mL) and separated the layers. Extracted the aqueous portion cooled to room temperature, and the solvent was concentrated. Added water (25 mL) and extracted the aqueous portion with dichloromethane (2×50 mL). Dried the combined organic layers over MgSO$_4$ and concentrated under reduced pressure to provide a residue, which was purified via silica gel chromatography, eluting with 0-60% ethyl acetate/heptanes to provide the product (0.555 g, 58% yield). LC/MS (Table A, Method a) $R_t$=2.26 minutes; MS m/z: 402.18(M+H)$^+$.

44. Preparation #44: (3-(6-Chloropyridin-2-yl)tetrahydrofuran-3-yl)methanol

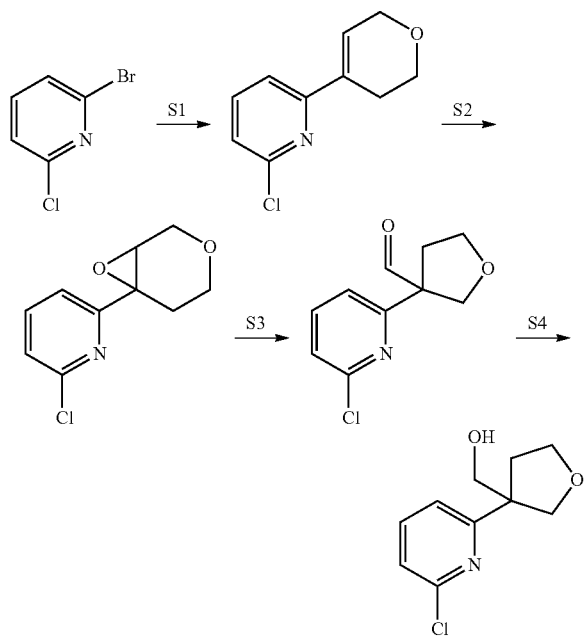

Step 1: 2-chloro-6-(3,6-dihydro-2H-pyran-4-yl)pyridine. 2-Bromo-6-chloropyridine (9.62 g, 50.0 mmol), 2-(3,6-dihydro-2H-pyran-4-yl)-4,4,5,5-tetramethyl-1,3,2-dioxaborolane (10.0 g, 47.6 mmol), and cesium carbonate (23.26 g, 71.4 mmol) were each added sequentially to a 500 mL reaction flask and then dissolved in dioxane (204 mL) and water (34.0 mL). The mixture was degassed with a stream of nitrogen for 10 minutes, before the addition of [1,1'- bis(diphenylphosphino)ferrocene]dichloropalladium(II)-dichloromethane adduct (Pd(dppf)Cl$_2$-DCM adduct) (1.944 g, 2.380 mmol). The reaction was heated at 65° C. for 4 hours. The reaction was cooled to room temperature, and poured into 200 mL of water with cysteine and stirred overnight with 100 mL ethyl acetate. The reaction mixture was extracted with ethyl acetate and the combined organic layer was washed with brine, dried over MgSO$_4$, and concentrated to dryness. The residue was purified via silica gel chromatography, eluting with 0-40% ethyl acetate in heptanes, to provide the product (7.1 g, 76% yield). $^1$H NMR (400 MHz, Dimethyl sulfoxide-d$_6$) δ 7.81 (t, J =7.8 Hz, 1H), 7.51 (dd, J=7.8, 0.7 Hz, 1H), 7.33 (dd, J=7.9, 0.7 Hz, 1H), 6.78 (tt, J=3.1, 1.6 Hz, 1H), 4.24 (q, J=2.9 Hz, 3H), 3.78 (t, J=5.5 Hz, 3H), 2.45 -2.43 (m, 1H).

Step 2: 2-(3,7-dioxabicyclo[4.1.0]heptan-6-yl)-6-chloropyridine. 2-Chloro-6-(3,6- dihydro-2H-pyran-4-yl)pyridine (3.0 g, 15.33 mmol) was dissolved in dichloromethane (DCM) (153 mL), and stirred in a 500 mL flask cooled to 0° C. in an ice bath. meta-Chloroperoxybenzoic acid (4.47 g, 19.93 mmol) was added and the bath was removed and the reaction was stirred at room temperature overnight. The reaction was quenched with sodium bicarbonate and then extracted with DCM. The organic layer was washed with brine, dried over MgSO$_4$, and concentrated to dryness. The residue was redissolved in ethyl ether and washed with bicarbonate, and then dried over MgSO$_4$, and concentrated to provide a residue, which was purified via silica gel chromatography, eluting with 0-50% ethyl acetate/heptanes, to provide the product (4 g, 95% yield, 85% purity). LC/MS (Table A, Method a) R$_t$=0.94 minutes; MS m/z: 212, 214 (M+H)$^+$.

Step 3: 3-(6-chloropyridin-2-yl)tetrahydrofuran-3-carbaldehyde. 2-(3,7- Dioxabicyclo[4.1.0]heptan-6-yl)-6-chloropyridine (2.15 g, 10.16 mmol) was dissolved in dioxane (50 mL) before the addition of scandium(III) triflate (Sc(OTf)$_3$). The reaction mixture was heated to 80° C. for 20 minutes, then cooled to room temperature and concentrated to dryness to provide a residue, which was purified via silica gel chromatography, eluting with 0-40% ethyl acetate/heptanes, to provide the product (1.3 g, 60% yield). $^1$H NMR (400 MHz, Dimethyl sulfoxide-d$_6$) δ 9.66 (s, 1H), 7.93 -7.84 (m, 1H), 7.47 -7.40 (m, 2H), 4.38 (d, J=9.2 Hz, 1H), 3.91 (d, J =9.3 Hz, 1H), 3.81 (t, J=7.1 Hz, 2H), 2.64 -2.56 (m, 1H), 2.36 (dt, J=12.9, 7.4 Hz, 1H).

Step 4: (3-(6-chloropyridin-2-yl)tetrahydrofuran-3-yl)methanol. 3-(6-Chloropyridin-2- yl)tetrahydrofuran-3-carbaldehyde (1.1 g, 5.20 mmol) was dissolved in ethanol (EtOH) (26 mL) before the addition of NaBH$_4$ (0.197 g, 5.20 mmol). The reaction was stirred at room temperature for 30 minutes, then the EtOH was concentrated off and the remaining residue was dissolved in ethyl acetate, and washed with sodium bicarbonate until the pH=7. The organic portion was then washed with brine, dried over MgSO$_4$, filtered, and concentrated to provide the product (1.1 g, 99% yield). LC/MS (Table A, Method a) R$_t$=0.69minutes; MS m/z: 241, 216 (M+H)$^+$.

45. Preparation #45 and #45a: (R)-(3-(6-Bromo-4-(methoxymethyl)pyridin-2- yl)tetrahydrofuran-3-yl)methanol and (S)-(3-(6-bromo-4-(methoxymethyl)pyridin-2- yl)tetrahydrofuran-3-yl)methanol

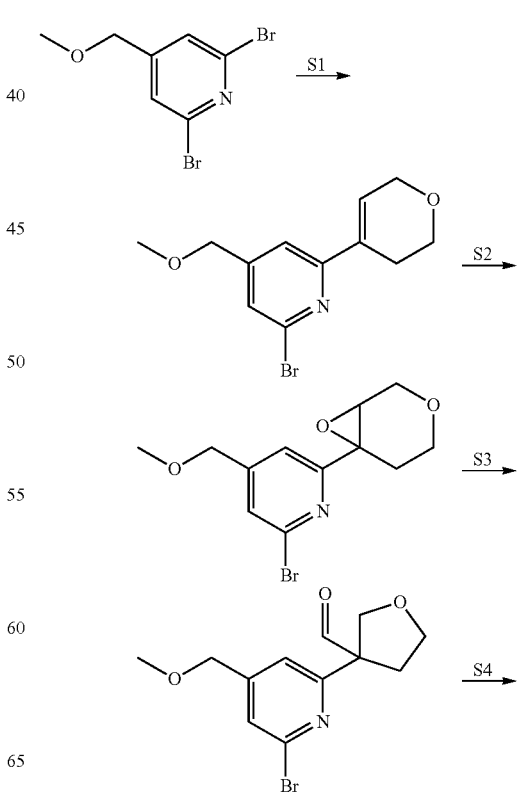

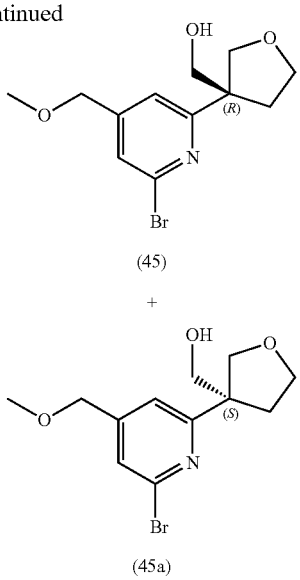

(45)

+

(45a)

Step 1: 2-bromo-6-(3,6-dihydro-2H-pyran-4-yl)-4-(methoxymethyl)pyridine. 2,6- Dibromo-4-(methoxymethyl)pyridine (2.79 g, 9.93 mmol, Preparation #6, Step 2), 2-(3,6-dihydro-2H- pyran-4-yl)-4,4,5,5-tetramethyl-1,3,2-dioxaborolane (2.191 g, 10.43 mmol) and potassium phosphate (4.22 g, 19.86 mmol) were dissolved in dioxane (40 mL) and water (8mL) and degassed with a stream of nitrogen. Tris(dibenzylideneacetone)dipalladium(0) (Pd$_2$(dba)$_3$) (0.227 g, 0.248 mmol) and 1S,3R,5R,7S)-1,3,5,7-tetramethyl-8-phenyl-2,4,6-trioxa-8-phosphaadamantane (PaPH) (0.145 g, 0.497 mmol) were added to the flask and was heated to 80° C. for 20 minutes. The reaction was cooled to room temperature and then poured into a 5% aqueous cysteine solution (100 mL) and diluted with 50 mL of ethyl acetate. The mixture was stirred for 10 minutes and the layers were then separated. The aqueous layer was extracted with ethyl acetate. The combined organic layers were washed with 50 mL of brine, dried over MgSO$_4$ and concentrated to dryness to provide a residue, which was purified by silica gel chromatography, eluting with 0-50% ethyl acetate: heptanes, to provide the product (1.70 g, 60% yield), LC/MS (Table A, Method a) R$_f$=1.34 minutes; MS m/z: 284, 286 (M+H)$^+$.

Step 2: 2-(3,7-dioxabicyclo[4.1.0]heptan-6-yl)-6-bromo-4-(methoxymethyppyridine. A solution of bromo-6-(3,6-dihydro-2H-pyran-4-yl)-4-(methoxymethyl)pyridine (1.7 g, 5.98 mmol) in dichloromethane (DCM) (59 mL) was cooled in an ice bath for 10 minutes before the addition of meta-chloroperoxybenzoic acid (2.011 g, 8.97 mmol). The reaction stirred overnight at room temperature, then quenched with 20 mL of aqueous sodium bicarbonate. The organic layer was separated and then concentrated to dryness, and the residue was redissolved in 50 mL ethyl ether and washed with aqueous sodium bicarbonate, 20 mL brine, then dried over MgSO$_4$, and concentrated to dryness to provide a residue, which was purified via silica gel chromatography, eluting with 0-70% ethyl acetate:heptanes, to provide the product (1.45 g, 81% yield), LC/MS (Table A, Method a) R$_f$=1.16 minutes; MS m/z: 301, 303 (M+H)$^+$.

Step 3: 3-(6-bromo-4-(methoxymethyl)pyridin-2-yl)tetrahydrofuran-3-carbaldehyde. A solution of 2-(3,7-dioxabicyclo[4.1.0]heptan-6-yl)-6-bromo-4-(methoxymethyppyridine (1.45 g, 4.83 mmol) in dioxane (24 mL) was stirred at room temperature before the addition of scandium(III) triflate (Sc(OTf)$_3$) (0.071 g, 0.145 mmol). The reaction was heated to 80° C. for 20 minutes. The reaction was then concentrated to dryness to provide a residue, which was purified via silica gel chromatography, eluting with 0-75% ethyl acetate:heptanes, to provide the product (1.13 g, 78% yield), LC/MS (Table A, Method a) R$_f$=1.19 minutes; MS m/z: 300, 302 (M+H)$^+$.

Step 4: (R)-(3-(6-bromo-4-(methoxymethyl)pyridin-2-yl)tetrahydrofuran-3- yl)methanol and (S)-(3-(6-bromo-4-(methoxymethyppyridin-2-yptetrahydrofuran-3- yl)methanol. A solution of 3-(6-bromo-4-(methoxymethyppyridin-2-yptetrahydrofuran-3- carbaldehyde (1.13 g, 3.76 mmol) in ethanol (19 mL) was cooled to 0° C. before the addition of NaBH$_4$ (0.142 g, 3.76 mmol). The reaction stirred warming to room temperature over 20 minutes. The solvent was concentrated under reduced pressure and the residue was diluted with 50 mL ethyl acetate and washed with ammonium chloride. The organic layer was washed with brine, dried over MgSO$_4$ and concentrated to dryness. The residue was purified via silica gel chromatography, eluting with 10-100% ethyl acetate:heptanes, to provide the racemic product. The product was further purified via chiral HPLC (Table B, Method 21) to provide the (R)-isomer (0.346 g, 31% yield, >99%ee, R$_t$=12.52 minutes) and the (S)-isomer (0.342 g, 30% yield, >99%ee, R$_t$=14.62 minutes). LC/MS (Table A, Method a) R$_f$=1.19 minutes; MS m/z: 300, 302 (M+H)$^+$.

46. Preparation #46 and #46a: (S)-2-chloro-6-(3-methyltetrahydrofuran-3-yl)pyrazine and (R)-2-chloro-6-(3-methyltetrahydrofuran-3-yl)pyrazine

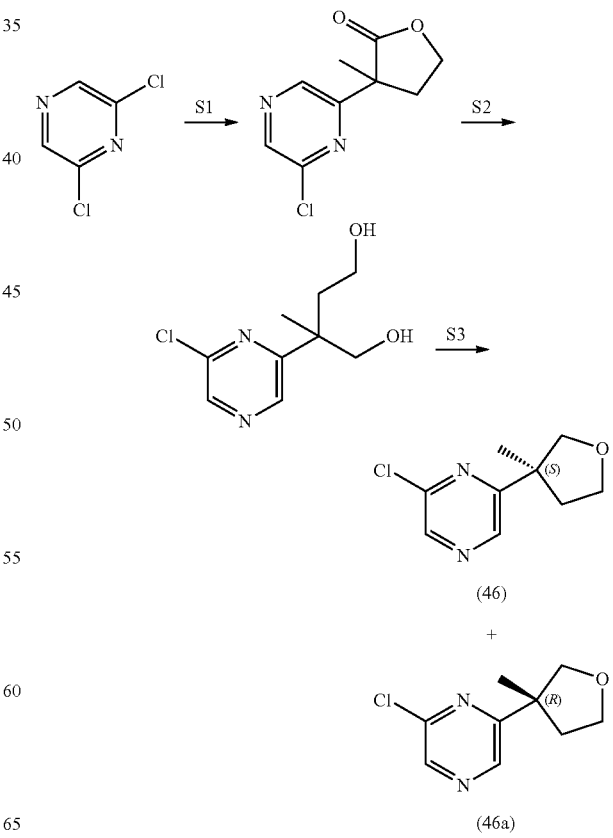

(46)

+

(46a)

Step 1: 3-(6-chloropyrazin-2-yl)-3-methyldihydrofuran-2 (3H)-one. To a tetrahydrofuran (THF) (37 mL) solution of diisopropylamine (2.3 mL, 16.16 mmol) was added n-butyl lithium (2.5 M in hexanes, 5.92 mL, 14.81 mmol) while stirring at −78° C. After stirring for 5 minutes, alpha-methyl-gamma-butyrolactone (1.416 mL, 14.81 mmol) was added in a dropwise manner. After stirring at 0° C. for 15 minutes, the reaction mixture was cooled to −75° C., and 2,6-dichloropyrazine (2.0059 g, 13.46 mmol) was added in a dropwise manner as a solution in THF (7.5 mL). The mixture stirred warming to room temperature overnight. The reaction mixture was dilluted with saturated aqueous sodium bicarbonate solution and was extracted with dichloromethane (2×10 mL). The combined extracts were dried over anhydrous sodium sulfate, filtered and concentrated under reduced pressure. The product was purified via silica gel chromatography eluting with 0-40% ethylacetate/heptanes to give the desired product (2.5 g, 76% yield). LC/MS (Table A, Method d) $R_t$=0.75 minutes; MS m/z: 213, 215 (M+H)$^+$.

Step 2: 2-(6-chloropyrazin-2-yl)-2-methylbutane-1,4-diol. A solution of 3-(6- chloropyrazin-2-yl)-3-methyldihydrofuran-2(3H)-one (2.5 g, 11.95 mmol) in methanol (MeOH) (40 mL) was treated with NaBH$_4$ (1.3 g, 35.9 mmol) and stirred at 25° C. overnight. The reaction mixture was quenched with saturated aqueous sodium chloride and extracted with dichloromethane (DCM). The DCM layer was dried over anhydrous sodium sulfate, filtered and concentrated under reduced pressure. The product was purified via silica gel chromatography eluting with 100% ethylacetate to give the desired product (1.8 g, 64% yield). LC/MS (Table A, Method d) $R_t$=0.40 minutes; MS m/z: 217, 219 (M+H)$^+$.

Step 3: (S)-2-chloro-6-(3-methyltetrahydrofuran-3-yl) pyrazine and (R)-2-chloro-6-(3- methyltetrahydrofuran-3-yl)pyrazine. A solution of 2-(6-chloropyrazin-2-yl)-2-methylbutane-1,4- diol (5.5 g, 25.6 mmol) in tetrahydrofuran (THF) (256 mL) was treated with sodium hydride (NaH) (60% dispersion in mineral oil) (2.4 g, 56.3 mmol) while stirring at −35° C. After stirring for 5 minutes, p- toluenesulfonyl chloride (5.4 g, 28.1 mmol) was added to the reaction mixture. The reaction was heated at reflux for 4 hours. The reaction mixture was quenched with saturated aqueous sodium chloride and extracted with ethyl acetate (EtOAc). The organic layer was dried over anhydrous magnesium sulfate, filtered and concentrated under reduced pressure. The residue was purified via silica gel chromatography eluting with 0-60% EtOAc in n-heptanes to give racemic product. The product was further purified via chiral HPLC (Table B, Method 22) to provide the (S)-2-chloro-6-(3-methyltetrahydrofuran-3- yl)pyrazine (0.78 g, 15% yield, >99% ee, $R_t$=9.35 minutes) and (R)-2-chloro-6-(3- methyltetrahydrofuran-3-yl)pyrazine (0.82 g, 16% yield, >99% ee, rt =6.44 minutes). LC/MS (Table A, Method d) $R_t$=0.87 minutes; MS m/z: 199, 201 (M+H)$^+$.

47. Preparation #47: (R)-2-chloro-4-(difluoromethoxy)-6-(3-methoxytetrahydrofuran-3-yl)pyridine

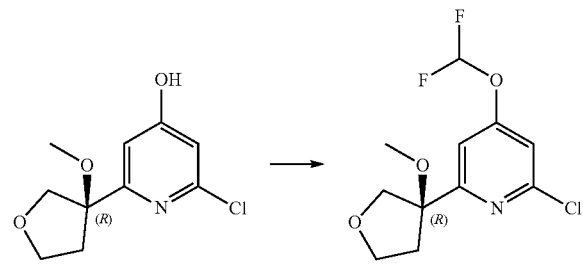

To a suspension of (R)-2-chloro-6-(3-methoxytetrahydrofuran-3-yl)pyridin-4-ol (150 mg, 0.653 mmol, Preparation #21) in dichloromethane (DCM) (3.2 mL) and potassium hydroxide (aqueous, 20% w/w) (1.0 g, 3.92 mmol) at 0° C., bromodifluoromethyl trimethylsilane (0.2 mL, 0.30 mmol) was added. The reaction mixture was allowed to stir vigorously at 0° C. for 30 minutes before diluting with water and extracting with DCM (3 times). The combined organic extracts were washed with brine, dried over magnesium sulfate, filtered, and concentrated under reduced pressure. The residue was purified by silica gel chromatography, eluting with 4 to 40% ethyl acetate in heptanes, to afford the desired product (0.16 g, 89% yield). $^1$H NMR (400 MHz, Dimethyl sulfoxide-d$_6$) δ 7.58 (t, J =72.3 Hz, 1H), 7.38 (d, J =2.1 Hz, 1H), 7.28 (d, J =2.1 Hz, 1H), 4.02 (dd, J=9.6, 1.1 Hz, 1H), 3.98 3.88 (m, 2H), 3.80 (d, J=9.6 Hz, 1H), 3.10 (s, 3H), 2.47 2.27 (m, 2H).

48. Preparation #48: (R)-2-chloro-4-(2-methoxyethoxy)-6-(3-methoxytetrahydrofuran-3-yl)pyridine

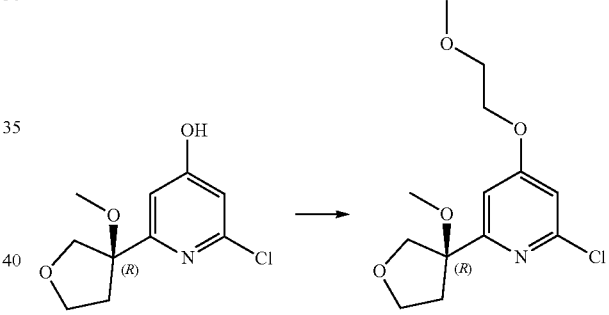

A flask was charged with (R)-2-chloro-6-(3-methoxytetrahydrofuran-3-yl)pyridin-4-ol (15 g, 65.3 mmol, Preparation #21) and dimethylformamide (DMF) (218 mL). To the mixture was added sodium hydride (60% dispersion in mineral oil) (3.13 g, 78 mmol) portionwise. The reaction mixture was stirred at room temperature. After 30 minutes, 1-bromo-2-methoxyethane (12.3 mL, 131 mmol) was added and the reaction was heated to 80° C. for 90 minutes. The reaction mixture was cooled to room temperature, quenched with 400 mL of water and extracted into ethyl acetate (EtOAc). The combined organic fractions were dried over MgSO$_4$, filtered and concentrated under reduced pressure. The crude residue was purified via silica gel chromatography, eluting with 0-50% EtOAc in heptanes, to provide the desired product (17.1 g, 91% yield). $^1$H NMR (400 MHz, Dimethyl sulfoxide-d$_6$) δ 7.06 (d, J=2.1 Hz, 1H), 7.01 (d, J=2.0 Hz, 1H), 4.27-4.22 (m, 2H), 3.97 (d, J=9.7 Hz, 1H), 3.89 (ddd, J=8.1, 5.4, 2.4 Hz, 2H), 3.76 (d, J =9.5 Hz, 1H), 3.67 -3.61 (m, 2H), 3.28 (s, 2H), 3.06 (s, 3H), 2.39 (dt, J =13.3, 8.6 Hz, 1H), 2.33 -2.22 (m, 1H).

49. Preparation #49 and #49a : (S)-1-((R)-3-(6-chloro-4-(methoxymethyl)pyridin-2- yl)tetrahydrofuran-3-yl)ethan-1-ol and (R)-1-((R)-3-(6-chloro-4-(methoxymethyl)pyridin-2- yl)tetrahydrofuran-3-yl) ethan-1-ol

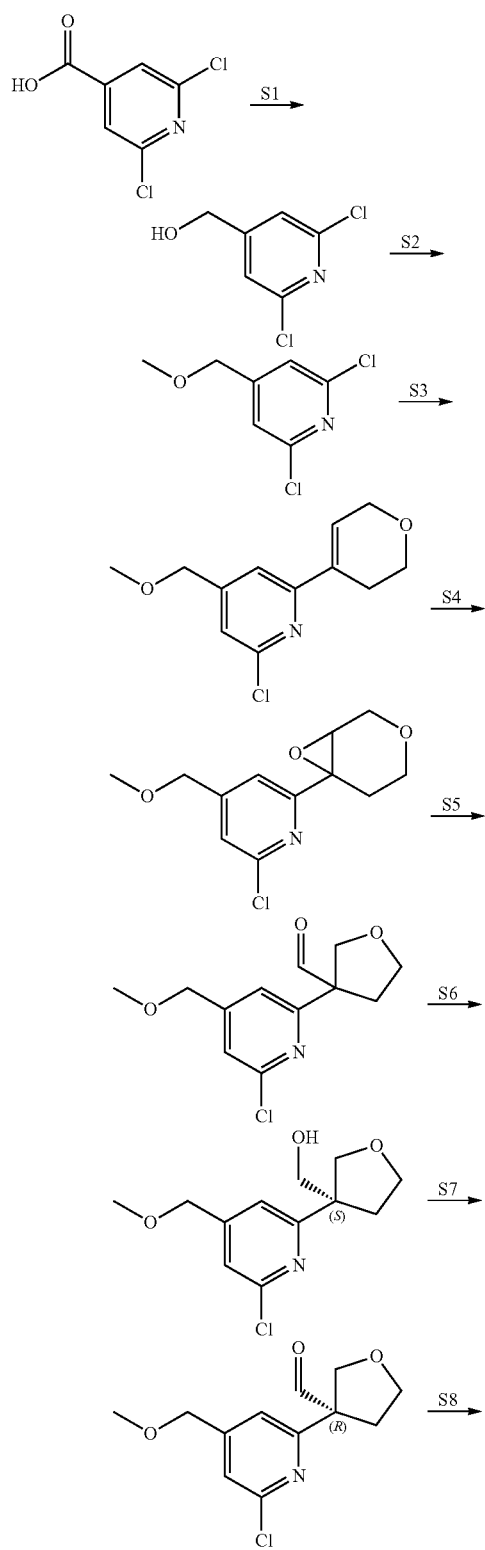

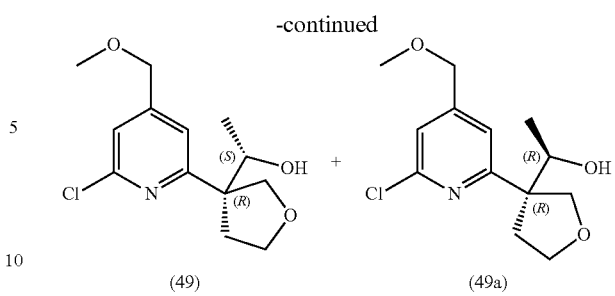

(49)  (49a)

Step 1: (2,6-dichloropyridin-4-yl)methanol. To a solution of 2,6-dichloroisonicotinic acid (29.12 g, 152 mmol) in tetrahydrofuran (THF) (146 mL) was added boranetetrahydrofuran complex (228 mL, 228 mmol, 1M in THF). The mixture was heated at 50° C. for 4 hours. The reaction was cooled, and methanol (MeOH) (10 mL) was added dropwise. The reaction was heated to 50° C. for 10 minutes.

The mixture was then concentrated, and partitioned between ethyl acetate (EtOAc) and saturated aqueous $Na_2CO_3$. The combined organic phase was dried over anhydrous $MgSO_4$, filtered, and concentrated to give desired product (20 g, 75% yield). LC/MS (Table A, Method b) $R_t$ =0.83 minutes; MS m/z: 178, 180 $(M+H)^+$.

Step 2: 2,6-dichloro-4-(methoxymethyl)pyridine. A flask was charged with (2,6- dichloropyridin-4-yl)methanol (12 g, 67.4 mmol) and dissolved in dimethyl formamide (DMF) (169 mL) before the addition of cesium carbonate (35.1 g, 108 mmol) and iodomethane (5.90 mL, 94 mmol) dropwise. The reaction stirred at 45° C. for 4 hours. The reaction was quenched with 150 mL of water and extracted with ethyl acetate (EtOAc) (2 x 200 mL). The organic portion was dried over $MgSO_4$, filtered and concentrated under reduced pressure to give crude product. The crude material was run through a pad of silica gel washing with 200 mL of 30% EtOAc/heptanes to give 2,6-dichloro-4- (methoxymethyl)pyridine (7.4 g, 57% yield). LC/MS (Table A, Method b) $R_t$ =1.30 minutes; MS m/z: 191, 193 $(M+H)^+$.

Step 3: 2-chloro-6-(3,6-dihydro-2H-pyran-4-yl)-4-(methoxymethyl)pyridine. A solution of 2,6-dichloro-4-(methoxymethyl)pyridine (15.3 g, 80 mmol), 2-(3,6-dihydro-2H-pyran-4-yl)-4,4,5,5- tetramethyl-1,3,2-dioxaborolane (17.63 g, 84 mmol) and potassium phosphate (34 g, 160 mmol) in a mixture of dioxane (333 ml) and water (66.6 ml) was purged with nitrogen for 30 minutes before adding (tris(dibenzylideneacetone)dipalladium(0)) (1.8 g, 1.99 mmol) and (1S,3R,5R,7S)-1,3,5,7-tetramethyl-8- phenyl-2,4,6-trioxa-8-phosphaadamantane (1.12 g, 4.00 mmol). The reaction was heated to 45° C. for 3 hours. The reaction was cooled and quenched with 5% aqueous $Na_2CO_3$ and cysteine and stirred for 1 hour at ambient temperature before separating the layers and extracting with ethyl acetate. The combined organics were dried over $MgSO_4$, filtered and concentrated. The crude material was purified via silica gel chromatography, eluting with 0 to 50% EtOAc/heptanes to give desired product (9.5 g, 50% yield). LC/MS (Table A, Method b) $R_t$ =2.32 minutes; MS m/z: 298, 300 $(M+H)^+$.

Step 4: 2-(3,7-dioxabicyclo[4.1.0]heptan-6-yl)-6-chloro-4-(methoxymethyppyridine. A solution of 2-chloro-6-(3,6-dihydro-2H-pyran-4-yl)-4-(methoxymethyl)pyridine (9.5 g, 39.5 mmol) in dichloromethane (DCM) (395 mL) was treated with 3-chlorobenzoperoxoic acid (9.73 g, 43.4 mmol) and allowed to stir at room temperature overnight. The reaction showed incomplete conversion, and additional 3-chlorobenzoperoxoic acid (2.2 g, 9.87 mmol) was added.

The reaction stirred an additional 4 hours and was quenched with saturated aqueous Na$_2$CO$_3$. The layers were separated and the aqueous portion was extracted three times with DCM. The crude material was purified via silica gel chromatography eluting with 0 to 50% EtOAc/heptanes to give the desired product (8.2g, 81% yield). LC/MS (Table A, Method b) R$_t$ =1.07 minutes; MS m/z: 256, 258 (M+H)$^+$.

Step 5: 3-(6-chloro-4-(methoxymethyl)pyridin-2-yl)tetrahydrofuran-3-carbaldehyde. A solution of 2-(3,7-dioxabicyclo[4.1.0]heptan-6-yl)-6-chloro-4-(methoxymethyl)pyridine (8.16 g, 31.9 mmol) in dioxane (160 mL) at ambient temperature was treated with scandium(III) trifluoromethanesulfonate (0.39 g, 0.79 mmol) and heated to 50° C. for 20 minutes. The reaction mixture was concentrated under reduced pressure to give crude material that was used directly in the next step.

Step 6: (S)-(3-(6-chloro-4-(methoxymethyl)pyridin-2-yl)tetrahydrofuran-3-yl)methanol and (R)-(3-(6-chloro-4-(methoxymethyl)pyridin-2-yl)tetrahydrofuran-3-yl)methanol. A solution of 3-(6-chloro-4-(methoxymethyl)pyridin-2-yl)tetrahydrofuran-3-carbaldehyde (8.2 g, 31.9 mmol) in ethanol (160 mL) was treated with sodium borohydride (1.2 g, 31.9 mmol) at ambient temperature. The reaction stirred at room temperature for 30 minutes. The reaction was quenched with saturated ammonium chloride, and the product was extracted with ethyl acetate (EtOAc). The combined organics were dried over MgSO$_4$, filtered and concentrated to yield crude racemic product. The product was purified via chiral SFC using (Table B, Method 27) to yield the desired products; (S)-(3-(6-chloro-4-(methoxymethyl)pyridin-2-yl)tetrahydrofuran-3-yl)methanol (3.4g, 41% yield over 2 steps,>99% ee, R$_1$=2.41) and (R)-(3-(6-chloro-4-(methoxymethyl)pyridin-2-yl)tetrahydrofuran-3-yl)methanol (not collected, R$_t$ =3.03). LC/MS (Table A, Method b) R$_t$ =0.83 minutes; MS m/z: 258, 260 (M+H).

Step 7: (R)-3-(6-chloro-4-(methoxymethyl)pyridin-2-yl)tetrahydrofuran-3- carbaldehyde. A flask was charged with (S)-(3-(6-chloro-4-(methoxymethyl)pyridin-2- yl)tetrahydrofuran-3-yl)methanol (1.05 g, 4.07 mmol) and Dess-Martin periodinane (2 g, 4.89 mmol) in dichloromethane (DCM) (20 mL). The reaction mixture was stirred at room temperature for 1 hour. The reaction was quenched with the addition of saturated aqueous sodium thiosulfate and extracted with DCM. The organic portion was washed with brine, dried over MgSO$_4$, filtered and concentrated. The crude material was purified via silica gel chromatography eluting with 10-70% ethyl acetate in heptanes to give desired product (1.0 g, 86% yield). LC/MS (Table A, Method b) R$_t$ =1.11 minutes; MS m/z: 256, 258 (M+H)$^+$.

Step 8: (S)-14(R)-3-(6-chloro-4-(methoxymethyppyridin-2-yptetrahydrofuran-3- ypethan-1-ol and (R)-14(R)-3-(6-chloro-4-(methoxymethyppyridin-2-yptetrahydrofuran-3-ypethan-1-ol. (R)-3-(6-Chloro-4-(methoxymethyl)pyridin-2-yl)tetrahydrofuran-3-carbaldehyde (1.0 g, 3.91 mmol) was dissolved in tetrahydrofuran (THF) (20 mL) and cooled to −5° C. before the addition of methyl magnesium bromide (2.61 mL, 7.82 mmol, 3M in THF). The reaction mixture was stirred at 0° C. for 30 minutes. The reaction was quenched with saturated aqueous ammonium chloride and the mixture was extracted into ethyl acetate (EtOAc). The organic portion was washed with brine, dried over MgSO$_4$, filtered, and concentrated. The crude material was purified via silica gel chromatography eluting with 10- 100% EtOAc in heptanes to give racemic product. The material was further purified via chiral HPLC (Table B, Method 28) to give (S)-14(R)-3-(6-chloro-4-(methoxymethyppyridin-2-yptetrahydrofuran-3- ypethan-l-ol (0.316 g, 30% yield, >99%de, R$_t$ =11.1 minutes) and (R)-1-((R)-3-(6-chloro-4-(methoxymethyl)pyridin-2-yl)tetrahydrofuran-3-ypethan-l-ol (0.342 g, 32% yield, >99%de, R$_t$ =13.7 minutes). LC/MS (Table A, Method b) R$_t$ =0.95 minutes; MS m/z: 272, 274 (M+H)$^+$.

50. Preparation #50 and #50a. (S)-(3-(6-chloro-4-(difluoromethyppyridin-2- yptetrahydrofuran-3-yl)methanol and (R)-(3-(6-chloro-4-(difluoromethyppyridin-2- yptetrahydrofuran-3-yl)methanol

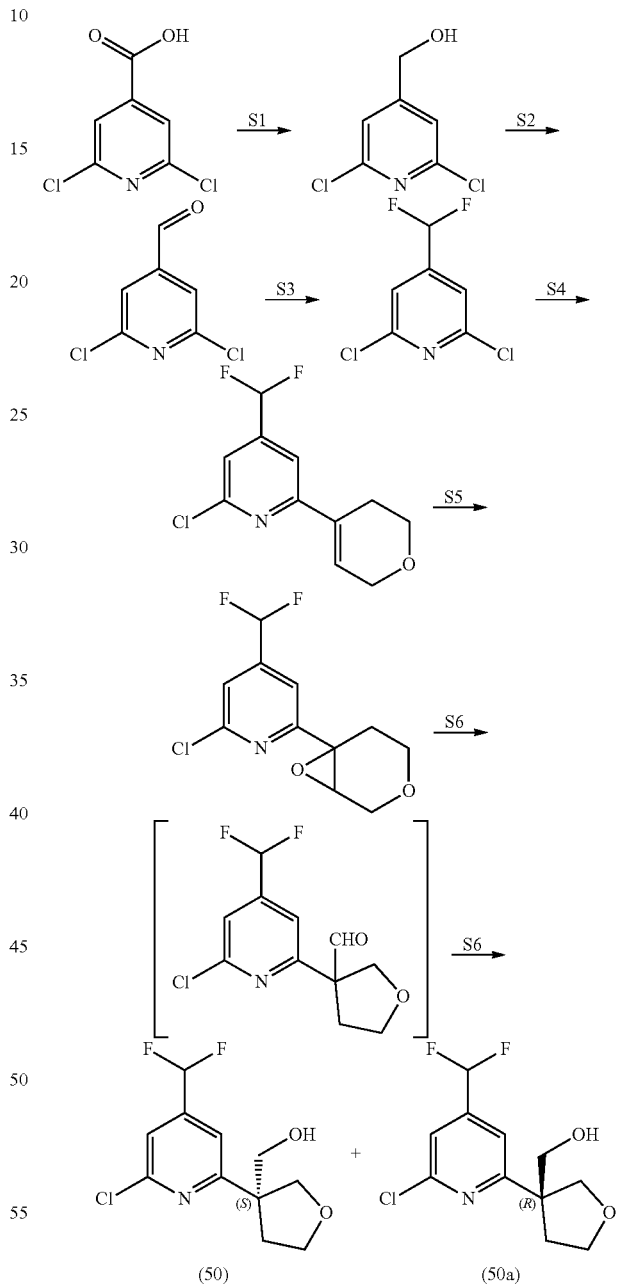

Step 1: (2,6-dichloropyridin-4-yl)methanol. A solution of 2,6-dichloroisonicotinic acid (100 g, 521 mmol) in tetrahydrofuran (1 L) was cooled to 0° C. and 10 M BH$_3$-Me$_2$S (156 mL, 1.56 mol) was slowly added. After the addition, the cooling bath was removed and the mixture was stirred at 20° C. for 12 h. Methanol (400 mL) was carefully added dropwise at 0° C. to quench the reaction until gas evolution ceased. Four additional vials were set up as described above.

All five reaction mixtures were combined. The solution was concentrated under reduced pressure to give a residue. The residue was diluted with water (500 mL) and extracted with ethyl acetate (3 x 500 mL). The combined organic layers were dried over Na$_2$SO$_4$, filtered and concentrated to give desired product (300 g, 62% yield). NMR (400 MHz, chloroform-d) δ 7.39 (s, 2H), 4.64 (s, 2H).

Step 2: 2,6-dichloroisonicotinaldehyde. To a solution of oxalyl chloride (21.6 mL, 247 mmol) in dichloromethane (500 mL) was added a solution of dimethyl sulfoxide (38.3 mL, 539 mmol) in dichloromethane (500 mL) dropwise at −78° C. After 10 minutes, a solution of (2,6-dichloropyridin-4-yl)methanol (40 g, 225 mmol) in dichloromethane (500 mL) was added dropwise at −78° C. The mixture was stirred for 15 minutes, then triethylamine (157 mL, 1.12 mol) was added dropwise at −78° C. After the addition, the reaction mixture was stirred at −78° C. for 1 hour. Four additional vials were set up as described above. All five reaction mixtures were combined. The cooling bath was removed and water (150 mL) was added at 20° C. The organic layer was separated and the aqueous layer was further extracted with dichloromethane (3×500 mL). The organic layers were combined and then dried over Na$_2$SO$_4$, filtered and concentrated under reduced pressure to give the desired product (140 g, 68% yield).¹H NMR (400 MHz, chloroform-d) δ 10.01 (s, 1H), 7.68 (s, 2H).

Step 3: 2,6-dichloro-4-(difluoromethyl)pyridine. To a solution of 2,6- dichloroisonicotinaldehyde (30 g, 170 mmol) in dichloromethane (450 mL) was added diethylaminosulfur trifluoride (90 mL, 682 mmol) in dichloromethane (200 mL) over a period of 10 minutes at -78° C. The reaction mixture was warmed to 25° C. and stirred for 2 hours. The reaction mixture was quenched with ice water (500 mL) and extracted with dichloromethane (3 x 300 mL). The combined organic layers were washed with NaHCO$_3$ (sat.aq, 200 mL), water (200 mL), and brine (200 mL), dried over Na$_2$SO$_4$, filtered and concentrated to give the desired product (20 g, 57% yield). ¹H NMR: (400 MHz, chloroform-d) 7.41 (s, 2H), 6.77 -6.45 (m, 1H).

Step 4: 2-chloro-4-(difluoromethyl)-6-(3,6-dihydro-2H-pyran-4-yl)pyridine. A slurry of 2,6-dichloro-4-(difluoromethyl)pyridine (10.5 g, 53.0 mmol), 2-(3,6-dihydro-2H-pyran-4-yl)-4,4,5,5- tetramethyl-1,3,2-dioxaborolane (14.48 g, 68.9 mmol) and potassium phosphate (22.51 g, 106 mmol) in tetrahydrofuran (THF) (147 mL) and water (30 mL) was degassed with a stream of nitrogen for about 15 minutes before the addition of Pd(OAc)$_2$ (0.23 g, 1.06 mmol) and (1S,3R,5R,7S)-1,3,5,7-tetramethyl-8- phenyl-2,4,6-trioxa-8-phosphaadamantane (0.620 g, 2.121 mmol). The reaction mixture was heated to 60 ° C. for 2 hours. The reaction mixture was cooled to room temperature and quenched by addition of water (150 mL) and tert-butyl methyl ether (TBME) (200 mL). The mixture was stirred for 5 minutes and then the layers were separated. The aqueous layer was extracted 2 x 100 mL with TBME. The combined organic portions were dried over MgSO$_4$, filtered and concentrated. The residue was purified via silica gel chromatography, eluting with 15-20% ethyl acetate/heptanes to give desired product. (9.9 g, 71% yield). LC/MS (Table A, Method b) R$_t$ =1.50 minutes; MS m/z: 246, 248 (M+H)$^+$.

Step 5: 2-(3,7-dioxabicyclo[4.1.0]heptan-6-yl)-6-chloro-4-(difluoromethyppyridine. A flask was charged with 2-chloro-4-(difluoromethyl)-6-(3,6-dihydro-2H-pyran-4-yl) pyridine (9.91 g, 40.3 mmol) in dichloromethane (DCM) (202 mL) and cooled to 0° C. before the addition of meta-chloroperoxybenzoic acid (m-CPBA) (10.94 g, 44.4 mmol). The reaction mixture was stirred with gradual warming to room temperature overnight. Upon completion of the reaction, some of the DCM was removed under reduced pressure with a water bath set to 30° C. Then, the residue was partitioned between saturated aqueous NaHCO$_3$ (200 mL), 50 mL of 1 M aqueous NaOH and 200 mL of diethyl ether (Et$_2$O). The layers were separated and the aqueous phase was extracted with Et$_2$O and ethyl acetate (EtOAc). The combined organic extracts were then washed with 1 M NaOH/NaHCO$_3$. The organic phase was dried over MgSO$_4$, filtered and concentrated under reduced pressure to give crude product (10.9 g). LC/MS (Table A, Method b) R$_t$ =1.32 minutes; MS m/z: 262, 264 (M+H)$^+$.

Step 6: (S)-(3-(6-chloro-4-(difluoromethyppyridin-2-yptetrahydrofuran-3-yl)methanol. To a solution of 2-(3,7-dioxabicyclo[4.1.0]heptan-6-yl)-6-chloro-4-(difluoromethyppyridine (10.9 g, 41.7 mmol) in tetrahydrofuran (THF) (208 mL) was added scandium (III) triflate (Sc(OTf)$_3$) (0.513 g, 1.041 mmol) in one portion and the reaction mixture was heated to 50° C. and stirred for about 2 hours. The reaction had gone to completion to the desired aldehyde. Ethanol (93 mL) was added to the crude reaction mixture followed by cooling to 0° C. NaBH$_4$ (2.366 g, 62.6 mmol) was added in one portion and the reaction mixture was stirred for about 1 hour. The volatiles were removed under reduced pressure and then the reaction was quenched with saturated aqueous NH$_4$Cl. The product was extracted into ethyl acetate (EtOAc). The combined organic portions were washed with brine, dried over MgSO$_4$, filtered and concentrated. The crude material was purified via silica gel chromatography eluting with 50% EtOAc in heptanes to give the desired racemic product. The product was further purified using chiral SFC (Table B, Method 24) to give (S)-(3-(6-chloro-4-(difluoromethyppyridin-2-yOtetrahydrofuran-3-yl)methanol (4.2 g, 47% yield, >99%ee, R$_t$=2.5 minutes) and (R)-(3-(6-chloro-4-(difluoromethyppyridin-2- yptetrahydrofuran-3-yl)methanol (not collected: R$_t$ 3.3 minutes); LC/MS (Table A, Method b) R$_t$ =1.1 minutes; MS m/z: 264, 266 (M+H)$^+$.

51. Preparation #51 and #51a: (S)-(3-(6-bromo-4-methoxypyridin-2-yl)tetrahydrofuran-3- yl)methanol and (R)-(3-(6-bromo-4-methoxypyridin-2-yl)tetrahydrofuran-3-yl)methanol

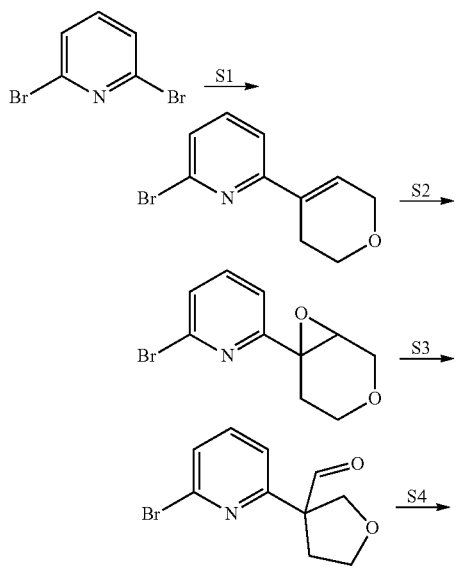

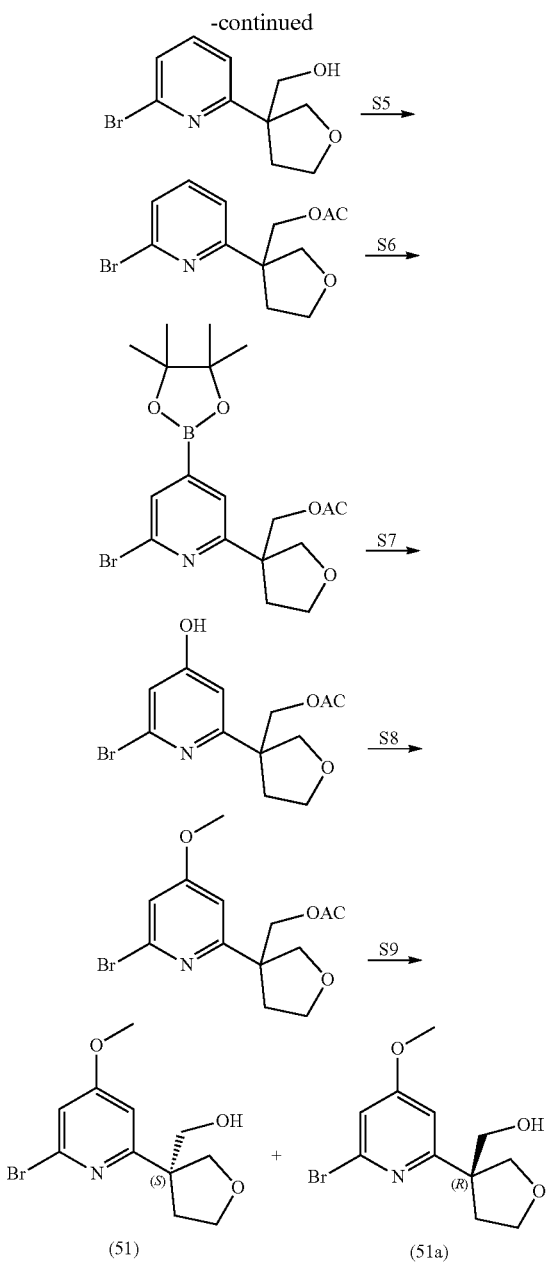

Step 1: 2-bromo-6-(3,6-dihydro-2H-pyran-4-yl)pyridine. To a solution of 2,6- dibromopyridine (58.6 g, 248 mmol) and 2-(3,6-dihydro-2H-pyran-4-yl)-4,4,5,5-tetramethyl-1,3,2- dioxaborolane (40 g, 190 mmol) in 1,4-dioxane (800 mL) and water (200 mL) was added anhydrous sodium carbonate (40.4 g, 381 mmol) and 1,1'-bis(diphenylphosphino) ferrocenedichloro palladium(II) dichloromethane complex (23.3 g, 28.6 mmol) at 20° C. The reaction mixture was stirred at 100° C. for 12 hours. Another four additional vials were set up as described above. All five reaction mixtures were combined. The combined reaction mixtures were cooled to room temperature and were quenched with water (2 L) and extracted with ethyl acetate (3 x 2 L). The combined organic fractions were washed with brine (1 L), dried over anhydrous sodium sulfate and filtered. The filtrate was concentrated and the residue was purified via silica gel chromatography, eluting with 100:1 to 10:1 petroleum ether in ethyl acetate to give the desired product (120 g, 50% yield). $^1$H NMR:(400 MHz, chloroform-d) δ 7.53 -7.47 (m, 1H), 7.27 (s, 2H), 6.76 (br s, 1H), 4.36 (q, J =2.6 Hz, 2H), 3.92 (t, J =5.4 Hz, 2H), 2.58 (td, J =2.5, 4.6 Hz, 2H).

Step 2: 2-(3,7-dioxabicyclo[4.1.0]heptan-6-yl)-6-bromopyridine To a solution of 2-bromo-6- (3,6-dihydro-2H-pyran-4-yl)pyridine (20 g, 83 mmol) in dichloromethane (600 mL) was added 3- chloroperoxybenzoic acid (21.5 g, 100 mmol) at 0° C. The reaction mixture was stirred at 30° C. for 12 hours. Another five additional vials were set up as described above. All six reaction mixtures were combined. The reaction mixture was poured into saturated aqueous sodium bicarbonate solution (2 L) and extracted with ethyl acetate (3 x 1 L), washed with aqueous sodium sulfite solution (15%, 1 L), and brine (1 L), dried over anhydrous sodium sulfate and filtered. The organic filtrate was concentrated under reduced pressure to give crude product (120 g, 70% yield). LC/MS (Table A, Method g) R$_t$ =0.99 minutes; MS m/z: 258, 260 (M+H)$^+$.

Step 3: 3-(6-bromopyridin-2-yl)tetrahydrofuran-3-carbaldehyde. To a solution of 243,7- dioxabicyclo[4.1.0]heptan-6-yl)-6-bromopyridine (30 g, 88 mmol) in dichloromethane (600 mL) was added boron trifluoride diethyl etherate (33.4 mL, 264 mmol) at 0° C. The reaction mixture was stirred at 20° C. for 12 hours. Another three additional vials were set up as described above. All four reaction mixtures were combined. The reaction mixture was poured into saturated aqueous sodium bicarbonate solution (2 L) and extracted with ethyl acetate (3 x 1 L) The combined organic fractions were washed with brine. The organic fraction was dried with anhydrous sodium sulfate and filtered. The organic filtrate was concentrated under reduced pressure to give desired crude product (100 g, yield 78%). NMR: (400 MHz, chloroform-d) δ 9.73 (s, 1H), 7.58 -7.52 (m, 1H), 7.40 (d, J =7.9 Hz, 1H), 7.17 (d, J =7.5 Hz, 1H), 4.48 (d, J =9.3 Hz, 1H), 4.04 (d, J =9.3 Hz, 1H), 3.98 -3.92 (m, 2H), 2.77 -2.66 (m, 1H), 2.41 (td, J =7.5, 12.8 Hz, 1H).

Step 4: (3-(6-bromopyridin-2-yl)tetrahydrofuran-3-yl) methanol. To a solution of (3-(6- bromopyridin-2-yl)tetrahydrofuran-3-carbaldehyde (25 g, 68.3 mmol) in methanol (600 mL) was added NaBH$_4$ (2.8 g, 75 mmol) at 0° C. The reaction mixture was stirred at 20° C. for 5 hours. Another three additional vials were set up as described above. All four reaction mixtures were combined. The reaction mixture was poured into saturated aqueous ammonium chloride solution (1 L) and concentrated to remove excess methanol. The mixture was extracted with ethyl acetate (3×800 mL) and the organic fractions were combined and washed with brine, dried with anhydrous sodium sulfate, filtered and concentrated under reduced pressure. The crude material was purified via silica gel chromatography eluting with 100:1 to 1:1 petroleum ether:ethyl acetate to give desired product (50 g, 69% yield). $^1$H NMR: (400 MHz, chloroform-d) δ 7.58 -7.52 (m, 1H), 7.38 (d, J=7.7 Hz, 1H), 7.32 (d, J=7.7 Hz, 1H), 4.05 -4.01 (m, 2H), 4.01 -3.94 (m, 2H), 3.94-3.84 (m, 2H), 3.78 -3.29 (m, 1H), 2.29 -2.15 (m, 2H).

Step 5: (3-(6-bromopyridin-2-yl)tetrahydrofuran-3-yl) methyl acetate. To a solution of (3- (6-bromopyridin-2-yl) tetrahydrofuran-3-yl)methanol (17.5 g, 67.8 mmol) and triethylamine (18.9 mL, 136 mmol) in dichloromethane (400 mL) was added acetyl chloride (6.4 g, 81 mmol) at 0° C. The reaction mixture was stirred at 20° C. for 2 hours. Another additional vial was set up as described above. The two reaction mixtures were combined. The reaction mixture was treated with water (200 mL) and extracted with ethyl acetate (3×400 mL), washed with aqueous hydrochloric acid solution (1 M, 300 mL) and brine (300 mL), dried over anhydrous sodium sulfate, filtered and concentrated under reduced pressure to give desired product (40 g, 93% yield). $^1$H NMR: (400 MHz, chloroform-d) δ 7.53 -7.43 (m, 1H), 7.32 (d, J=7.9 Hz, 1H), 7.19 (d, J=7.7 Hz, 1H), 4.43 -4.34 (m, 1H), 4.31 -4.23 (m, 1H), 4.06 - 4.00 (m, 2H), 3.99 -3.85 (m, 2H), 2.36 (ddd, J=6.7, 8.3, 13.0 Hz, 1H), 2.20-2.13 (m, 1H), 1.98-1.90 (m, 3H).

Step 6: (3-(6-bromo-4-(4,4,5,5-tetramethyl-1,3,2-dioxaborolan-2-yl)pyridin-2- yptetrahydrofuran-3-yl)methyl acetate. To a solution of (3-(6-bromopyridin-2-yl)tetrahydrofuran-3- yl)methyl acetate (22.5 g, 75.0 mmol) in cyclohexane (1 L) was added 4,4,4',4',5,5,5',5'-octamethyl-2,2'-bi(1,3,2-dioxaborolane) (B$_2$pin$_2$) (22.8 g, 90 mmol) and 4,4'-di-tert-butyl-2,2'-bipyridine (2 g, 7.50 mmol). The reaction mixture was sparged with N$_2$ for 30 minutes. Then chloro(1,5-cyclooctadiene) iridium(I) dimer (5 g, 7.50 mmol) was added to the reaction and the mixture was heated to 70° C. for 1 hour. An additional vial was set up as described above. Both reaction mixtures were combined. The reaction mixture was concentrated to give crude residue, which was washed with n-heptanes (500 mL) and filtered to give the desired product (60 g, 89% yield). $^1$H NMR: (400 MHz, chloroform-d) δ 7.70 (s, 1H), 7.51 (s, 1H), 4.46-4.40 (m, 1H), 4.33-4.28 (m, 1H), 4.13-4.06 (m, 2H), 4.06-3.93 (m, 2H), 2.45 (ddd, J=6.6, 8.3, 12.9 Hz, 1H), 2.28-2.16 (m, 1H), 1.99 (s, 3H), 1.35 (s, 12H).

Step 7: (3-(6-bromo-4-hydroxypyridin-2-yl)tetrahydrofuran-3-yl)methyl acetate. To a solution of (3-(6-bromo-4-(4,4,5,5-tetramethyl-1,3,2-dioxaborolan-2-yl)pyridin-2-yl)tetrahydrofuran-3- yl)methyl acetate (15 g, 35.2 mmol) in tetrahydrofuran (THF) (200 mL) was added a solution of potassium peroxomonosulfate (24 g, 38.7 mmol) in water (200 mL) at 0° C. The reaction mixture was stirred at 20° C. for 1 hour. The reaction mixture was treated with water (300 mL) and extracted with ethyl acetate (3×500 mL). The combined organic fractions were washed with saturated aqueous sodium sulfite (300 mL) and brine (300 mL). The organic portion was dried over anhydrous sodium sulfate, filtered and concentrated under reduced pressure. The crude material was purified via silica gel chromatography eluting with 100/1 to 0/1 petroleum ether/ethyl acetate to give the desired product (35 g, 77% yield). NMR: (400 MHz, chloroform-d) δ 8.77 (br s, 1H), 6.85 (d, J=1.5 Hz, 1H), 6.70 (d, J=1.5 Hz, 1H), 4.46 (d, J=11.0 Hz, 1H), 4.30 (d, J=11.0 Hz, 1H), 4.14-4.04 (m, 2H), 4.04-3.94 (m, 2H), 2.46-2.31 (m, 1H), 2.27-2.14 (m, 1H), 2.03 (s, 3H).

Step 8: (3-(6-bromo-4-methoxypyridin-2-yl)tetrahydrofuran-3-yl)methyl acetate. A solution of (3-(6-bromo-4-hydroxypyridin-2-yl)tetrahydrofuran-3-yl)methyl acetate (1 g, 3.16 mmol) in dimethylformamide (DMF) (10 mL) was treated with cesium carbonate (1.5 g, 4.7 mmol) and iodomethane (0.29 mL, 4.74 mmol). The reaction mixture was heated to 40° C. for 1 hour. The reaction was quenched with saturated aqueous ammonium chloride. The reaction mixture was diluted with ethyl acetate and water. The layers were separated and the aqueous solution was extracted 3 times with ethyl acetate. The combined organic fractions were dried over MgSO$_4$, filtered and concentrated under reduced pressure to give crude product. LC/MS (Table A, Method a) R$_t$=1.21 minutes; MS m/z: 330, 332 (M+H)$^+$.

Step 9: (S)-(3-(6-bromo-4-methoxypyridin-2-yl)tetrahydrofuran-3-yl)methanol and (R)-(3- (6-br omo-4 -methoxy py ridin-2-yl)tetrahydrofuran-3-yl)methanol. A solution of (3-(6-bromo-4- methoxypyridin-2-yOtetrahydrofuran-3-yl) methyl acetate (1.0 g, 3.1 mmol) in methanol (31.5 mL) was treated with solid sodium methanolate (0.85 g, 15.7 mmol) at ambient temperature. The reaction mixture was stirred for 10 minutes at room temperature. The reaction was quenched with saturated aqueous ammonium chloride, extracted with ethyl acetate, dried and concentrated, and purified via silica gel chromatography, eluting with 30 to 100% ethyl acetate/heptanes to give racemic product (0.78 g, 87% yield). The racemic material was further purified via chiral SFC using (Table B, Method 25) to provide (S)-(3-(6-bromo-4-methoxypyridin-2-yl)tetrahydrofuran-3-yl)methanol (0.37 g, 41% yield, >99% ee, R$_s$=2.5 minutes, optical rotation=(-)) and (R)-(3-(6-bromo-4-methoxypyridin-2-yptetrahydrofuran-3- yl)methanol (0.37 g, 41% yield, >99% ee, R$_t$=3.3 minutes, optical rotation=(+)). LC/MS (Table A, Method d) R$_t$=0.95 minutes; MS m/z: 368 (M+H)$^+$.

52. Preparation #52 and #52a: (S)-(3-(6-bromo-4-(2-methoxyethoxy)pyridin-2- yl)tetrahydrofuran-3-yl)methanol and (R)-(3-(6-bromo-4-(2-methoxyethoxy)pyridin-2- yl)tetrahydrofuran-3-yl)methanol.

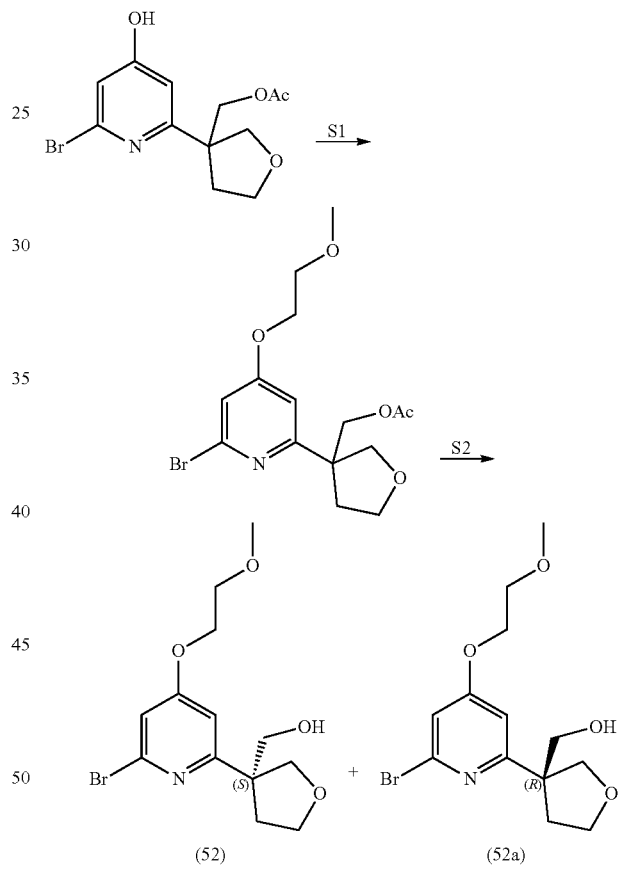

Step 1: (3-(6-bromo-4-(2-methoxyethoxy)pyridin-2-yl) tetrahydrofuran-3-yl)methyl acetate. A solution of (3-(6-bromo-4-hydroxypyridin-2-yl)tetrahydrofuran-3-yl)methyl acetate (1 g, 3.16 mmol, Preparation #51 step 7) in dimethylformamide (DMF) (10 mL) at ambient temperature was treated with cesium carbonate (1.5 g, 4.74 mmol) and 1-bromo-2-methoxyethane (0.659 g, 4.74 mmol). The reaction mixture was heated to 40° C. for 1hour. The reaction was quenched with saturated aqueous ammonium chloride. The reaction mixture was diluted with ethyl acetate and water. The layers were separated and the aqueous solution was extracted three times with ethyl acetate. The combined organic fractions were dried over MgSO₄, filtered and concentrated to give crude product (1.21 g, 100% yield).

Step 2: (S)-(3-(6-bromo-4-(2-methoxyethoxy)pyridin-2-yl)tetrahydrofuran-3-yl)methanol and (R)-(3-(6-bromo-4-(2-methoxyethoxy)pyridin-2-yl)tetrahydrofuran-3-yl) methanol. A solution of (3-(6-bromo-4-(2-methoxyethoxy)pyridin-2-yl)tetrahydrofuran-3-yl)methyl acetate (1.21 g, 3.23 mmol) in methanol (MeOH) (32 mL) was treated with solid sodium methanolate (0.87 g, 16.2 mmol) at ambient temperature. The reaction mixture was stirred for 10 minutes at room temperature. The reaction was quenched with saturated aqueous ammonium chloride and the product was extracted with ethyl acetate. The organic portion was dried over MgSO₄, filtered and concentrated. The racemic product was purified via silica gel chromatography, eluting with 30-100% ethyl acetate/heptanes. The product was further purified via chiral SFC using (Table B, Method 26) to give (S)-(3-(6-bromo-4-(2- methoxyethoxy)pyridin-2-yptetrahydrofuran-3-yl)methanol (0.429 g, 40%yield, >99%ee, R$_t$=2.5 minutes, optical rotation=(−)) and (R)-(3-(6-bromo-4-(2-methoxyethoxy)pyridin-2-yl)tetrahydrofuran-3-yl)methanol (0.435 g, 41% yield, >99%ee, R$_t$=4.2 minutes; optical rotation =(+)).

53. Preparation #53: 2-chloro-4-((R)-2-methoxypropoxy)-6-((R)-3-methoxytetrahydrofuran-3-yl) pyridine.

Step 2: 2-chloro-4-((R)-2-methoxypropoxy)-6-((R)-3-methoxytetrahydrofuran-3- yl)pyridine.To a solution of crude (R)-1-((2-chloro-6-((R)-3-methoxytetrahydrofuran-3-yl)pyridin-4- yl)oxy)propan-2-ol (215 mg, 0.746 mmol,) in tetrahydrofuran (THF) (10 mL) in an ice-water bath was added sodium hydride (60% in mineral oil) (60 mg, 1.49 mmol). After stirring for 10 minutes, dimethyl sulfate (0.143 mL, 1.49 mmol) was added to the mixture. After 1 hour, the mixture was quenched with saturated aqueous NH₄Cl solution and extracted with dichloromethane (DCM). After concentration of the organic fraction, the crude product was purified by silica gel chromatography to give the desired product (0.22 g, 98% yield). ¹H NMR (400 MHz, Dimethyl sulfoxide-d₆) δ 7.09 (s, 1H), 7.03 (s, 1H), 4.13-4.07 (dd, 2H), 4.00 (dd, 2H), 3.91 (m, 2H), 3.77 (d, 1H), 3.67 (m, 1H), 3.30 (s, 3H), 3.08 (s, 3H), 2.41-2.31 (m, 2H), 1.17 (s, 3H).

54. Example #1 and #1a: (R)-1-(3-(6-(3-Methoxytetrahydrofuran-3-yl)pyridin-2-yl)-1-methyl-1H-pyrrolo[2,3-c]pyridin-5-yl)urea and (S)-1-(3-(6-(3-methoxytetrahydrofuran-3- yl)pyridin-2-yl)-1-methyl-1H-pyrrolo[2,3-c]pyridin-5-yl)urea

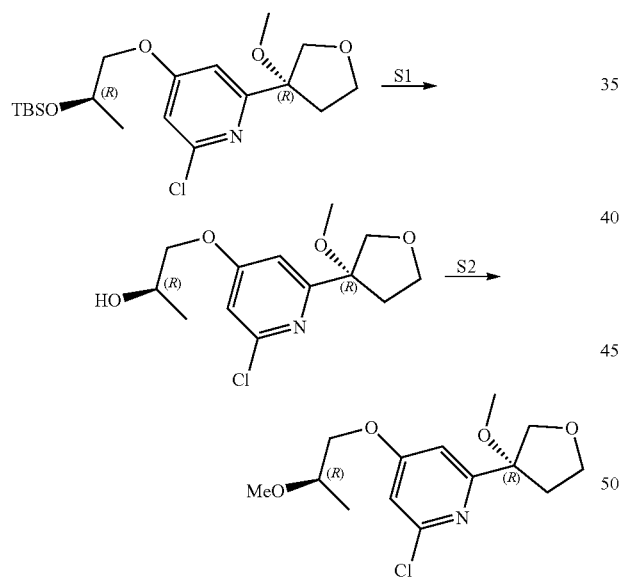

Step 1: (R)-1-((2-chloro-6-((R)-3-methoxytetrahydrofuran-3-yl)pyridin-4-yl)oxy)propan-2- ol. To a solution of 44(R)-2-((tert-butyldimethylsilypoxy)propoxy)-2-chloro-6-4R)-3- methoxytetrahydrofuran-3-yppyridine (300 mg, 0.746 mmol, Preparation #43) in tetrahydrofuran (THF) (3 mL) was added hydrogen chloride (aq. 3 M) (2.5 mL, 7.46 mmol) at room temperature. The mixture was stirred for 1 hour. To the mixture was added solid NaHCO₃ until no gas evolution was observed. The product was extracted into dichloromethane (DCM). The organic portion was dried over MgSO₄, filtered and concentrated to give a crude product that was used directly in the next step.

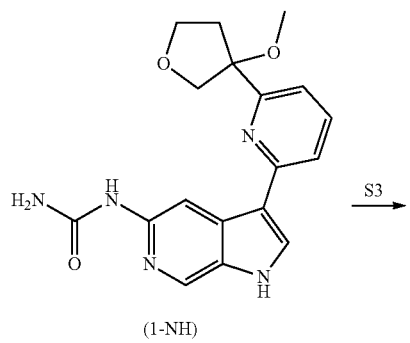

(1-NH)

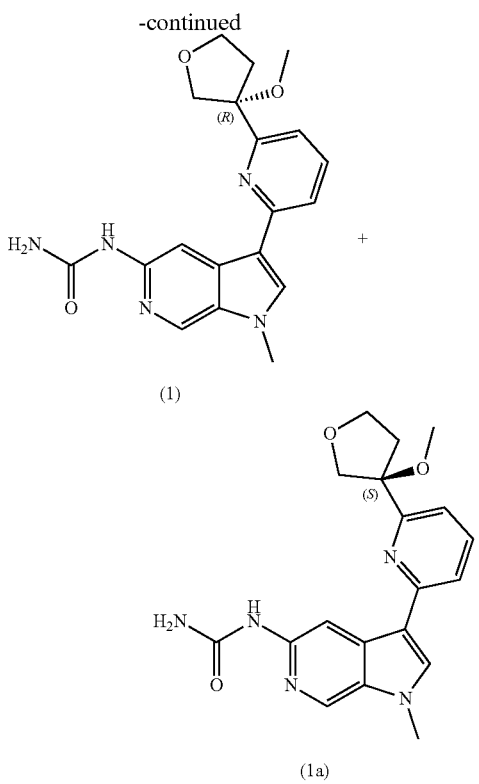

Step 1: 1-(3-(6-(3-methoxytetrahydrofuran-3-yl)pyridin-2-yl)-1-tosyl-1H-pyrrolo[2,3- c]pyridin-5-yl)urea. To a white suspension of 1-(3-bromo-1-tosyl-1H-pyrrolo[2,3-c]pyridin-5- yl)urea (0.920 g, 2.248 mmol) (Preparation #13), bis(pinacolato)diboron (0.856 g, 3.37 mmol), potassium acetate (0.441 g, 4.50 mmol) and 4Å molecular sieves in dioxane (22 mL) degassed with nitrogen for about 10 minutes, was added [1,1'-bis(diphenylphosphino)ferrocene] dichloropallalium(II)- dichloromethane adduct (Pd(dppf)Cl$_2$-DCM adduct) (0.184 g, 0.225 mmol). Sealed the reaction vessel and heated to about 105° C. for about 3 hours. Filtered the reaction mixture over Celite® as a hot solution, and concentrated the filtrate to provide a residue, which was then dissolved in dioxane (19 mL), to which was added 2-bromo-6-(3-methoxytetrahydrofuran-3-yl)pyridine (0.550 g, 2.131 mmol)(Preparation #20, Step 1), potassium phosphate (1.357 g, 6.39 mmol), and water (1.937 mL). Degassed the reaction mixture for about 10 minutes with nitrogen, then added (1S,3R,5R,7S)-1,3,5,7- tetramethyl-8-phenyl-2,4,6-trioxa-8-phosphaadamantane) (PaPH) (0.062 g, 0.213 mmol) and tris(dibenzylideneacetone)dipalladium (0) (Pd$_2$(dba)$_3$) (0.098 g, 0.107 mmol) and degassed for another 2 minutes. The reaction was heated to about 85° C. for about 1 hour. Filtered the hot mixture over Celite®. Suspended the Celite® filter cake in 100 mL 10% methanol/dichloromethane (MeOH/DCM) and heated to reflux. Filtered the mixture. Took up the Celite® and solids in another 100 mL of 10% MeOH/DCM and heated mixture until reflux, and then filtered. The filtrates were combined and concentrated under reduced pressure. With the filtrate of the reaction solution, diluted with ethyl acetate (100 mL) and stirred with 80 mL of 5% cysteine/NaHCO$_3$ aqueous solution, then separated organic layer and dried over MgSO$_4$, filtered, and concentrated under reduced pressure to provide a residue, which was triturated with DCM and filtered to provide a filtered material, rinsing with DCM, to give 274 mg of the first crop of product. The filtrates were combined with the crude product material isolated from the Celite® rinses and concentrated under reduced pressure to provide a residue, which was triturated with DCM and filtered to provide a filtered material, rinsing with DCM, to give 472 mg as the second crop of product. Concentrated filtrate under reduced pressure to provide a residue, which was purified via silica gel chromatography, eluting with 0-10% MeOH/DCM, to provide a purified material, which was further triturated with acetone and filtered to provide a filtered product, rinsing with acetone to give a third crop of product, 78 mg. Combined all 3 crops to provide the product (0.746 g, 69% yield). LC/MS (Table A, Method a) R$_t$=1.47 minutes; MS m/z: 508 (M+H)$^+$. Ts=4-toluenesulfonyl.

Step 2: 1-(3-(6-(3-methoxytetrahydrofuran-3-yl)pyridin-2-yl)-1H-pyrrolo[2,3- c]pyridin-5-yl)urea. To a mixture of 1-(3-(6-(3-methoxytetrahydrofuran-3-yl)pyridin-2-yl)-1-tosyl- 1H-pyrrolo[2,3-c]pyridin-5-yl)urea (0.824 g, 1.623 mmol) in tetrahydrofuran (12 mL) and water (4.06 mL) was added LiOH (0.176 g, 7.35 mmol). Stirred at about 60° C. for about 3 hours, and then left at room temperature for about 2 days. Heated reaction to about 60° C. for an additional 3 hours. Added more LiOH (0.070 g, 2.92 mmol) and 1 mL of water and stirred for about 6 hours. Added additional LiOH (0.078 g, 3.25 mmol) and left to stir at about 60° C. for about 16 hours. Removed from heat and neutralized with 1N aqueous HCl. Removed the organic layers under reduced pressure and filtered resulting solid rinsing with water. Dried solid in vacuum oven for about 16 hours to provide the product (0.645 g, 100% yield). LC/MS (Table A, Method a) R$_t$=0.71 minutes; MS m/z: 354 (M+H)$^+$.

Step 3: (R)-1-(3-(6-(3-methoxytetrahydrofuran-3-yl)pyridin-2-yl)-1-methyl-1H- pyrrolo[2,3-c]pyridin-5-yl)urea and (S)-1-(3-(6-(3-methoxytetrahydrofuran-3-yl)pyridin-2-yl)-1-methyl-1H-pyrrolo[2,3-c]pyridin-5-yl)urea. To a mixture of 1-(3-(6-(3-methoxytetrahydrofuran- 3-yl)pyridin-2-yl)-1H-pyrrolo[2,3-c]pyridin-5-yl)urea (0.574 g, 1.623 mmol) and cesium carbonate (1.058 g, 3.25 mmol) in acetonitrile (16 mL) was added dimethyl sulfate (0.17 mL, 1.785 mmol). The reaction stirred at room temperature for 22 hours. Added 20 mL of water and filtered the solution to provide a filtered material, which was dried in a vacuum oven (460 mg). Re-extracted the water filtrate with ethyl acetate (40 mL), dried organic layer over MgSO$_4$, filtered and concentrated under reduced pressure to provide a residue, which was triturated with water, filtered to provide a filtered material, which was dried in a vacuum oven (100 mg). The dried filtered materials were combined and further purified via chiral HPLC (Table B, Method 10) to provide the R-isomer (0.146 g, 24% yield, 99% ee, R$_t$=6.9 minutes) and the S-isomer (0.155 g, 26% yield, 99% ee, R$_t$=7.2 minutes). LC/MS (Table A, Method d) R$_t$=0.95 minutes; MS m/z: 368 (M+H)$^+$. $^1$H NMR (400 MHz, Dimethyl sulfoxide-d$_6$) δ 8.85 (s, 1H), 8.53 (d, J=1.0 Hz, 1H), 8.47 (s, 1H), 8.25 (s, 1H), 7.81 (t, J=7.8 Hz, 1H), 7.65 (dd, J=8.0, 0.9 Hz, 1H), 7.25 (dd, J=7.6, 0.9 Hz, 1H), 6.58 (s, 2H), 4.22 (dd, J=9.7, 1.2 Hz, 1H), 4.09-3.97 (m, 2H), 3.94 (d, J=9.6 Hz, 1H), 3.91 (s, 3H), 3.11 (s, 3H), 2.71 (dt, J=13.2, 8.8 Hz, 1H), 2.49-2.40 (m, 1H).

The compounds shown in Table 1a were synthesized in a manner similar to Example #1 from 1-(3-bromo-1-tosyl-1H-pyrrolo[2,3-c]pyridin-5-yl)urea (Preparation #13) and the corresponding aromatic halide followed by Example #1, Step 2, and Example #1, Step 3 using 2,2-difluorocyclopropyl 4-methylbenzenesulfonate (Preparation #32). The product was purified via chiral SFC using Table B, Method 14.

TABLE 1a

| Ex | Aromatic Halide | Product | $R_t$ min (Method) | m/z (M + H)$^+$ |
|---|---|---|---|---|
| 1.2 | (R)-2-bromo-6-(3-methoxytetrahydrofuran-3-yl)pyridine (Preparation #20) | 1-(1-((R)-2,2-difluorocyclopropyl)-3-(6-((R)-3-methoxytetrahydrofuran-3-yl)pyridin-2-yl)-1H-pyrrolo[2,3-c]pyridin-5-yl)urea | 1.10 (d) 6.25 (14) | 430 |
| 1.3 | (R)-2-bromo-6-(3-methoxytetrahydrofuran-3-yl)pyridine (Preparation #20) | 1-(1-((S)-2,2-difluorocyclopropyl)-3-(6-((R)-3-methoxytetrahydrofuran-3-yl)pyridin-2-yl)-1H-pyrrolo[2,3-c]pyridin-5-yl)urea | 1.10 (d) 6.80 (14) | 430 |

The compound shown in Table 1b was synthesized in a manner similar to Example #1 from 1- (3-bromo-1-tosyl-1H-pyrrolo[2,3-c]pyridin-5-yl)-3-methylurea (Preparation #14) and the corresponding aromatic halide followed by Example #1, Step 2, and Example #1, Step 3.

TABLE 1b

| Ex | Aromatic Halide | Product | $R_t$ min (Method) | m/z (M + H)$^+$ |
|---|---|---|---|---|
| 1a.2 | (R)-2-bromo-6-(3-methoxytetrahydrofuran-3-yl)pyridine (Preparation #20) | (R)-1-(3-(6-(3-methoxytetrahydrofuran-3-yl)pyridin-2-yl)-1-methyl-1H-pyrrolo[2,3-c]pyridin-5-yl)-3-methylurea | 0.92 (a) | 382 |

The compounds shown in Table 1c were synthesized in a manner similar to Example #1 from 1-(3-bromo-1-tosyl-1H-pyrrolo[2,3-c]pyridin-5-yl)urea (Preparation #13) and the corresponding aromatic halide followed by Example #1, Step 2, and Example #1, Step 3.

TABLE 1c

| Ex | Aromatic Halide | Product | $R_t$ min (Method) | m/z (M + H)$^+$ |
|---|---|---|---|---|
| 1b.2 | (R)-2-bromo-6-(3-methoxytetrahydrofuran-3-yl)-4-methylpyridine (Preparation #5) | (R)-1-(3-(6-(3-methoxytetrahydrofuran-3-yl)-4-methylpyridin-2-yl)-1-methyl-1H-pyrrolo[2,3-c]pyridin-5-yl)urea | 0.98 (d) | 382 |
| 1b.3 | (S)-2-bromo-6-(3-methoxytetrahydrofuran-3-yl)-4-methylpyridine (Preparation #5a) | (S)-1-(3-(6-(3-methoxytetrahydrofuran-3-yl)-4-methylpyridin-2-yl)-1-methyl-1H-pyrrolo[2,3-c]pyridin-5-yl)urea | 0.98 (d) | 382 |
| 1b.4 | 2-bromo-6-(3-methoxyoxetan-3-yl)pyridine (Preparation #33) | 1-(3-(6-(3-methoxyoxetan-3-yl)pyridin-2-yl)-1-methyl-1H-pyrrolo[2,3-c]pyridin-5-yl)urea | 0.86 (d) | 354 |
| 1b.5 | (S)-2-chloro-6-(3-methyltetrahydrofuran-3-yl)pyrazine (Preparation #46) | (S)-1-(1-methyl-3-(6-(3-methyltetrahydrofuran-3-yl)pyrazin-2-yl)-1H-pyrrolo[2,3-c]pyridin-5-yl)urea | 0.80 (d) | 353 |
| 1b.6 | (R)-2-chloro-6-(3-methyltetrahydrofuran-3-yl)pyrazine (Preparation #46a) | (R)-1-(1-methyl-3-(6-(3-methyltetrahydrofuran-3-yl)pyrazin-2-yl)-1H-pyrrolo[2,3-c]pyridin-5-yl)urea | 0.80 (d) | 353 |

55. Example #2: (R)-N-(3-(4-(Methoxymethyl)-6-(3-methoxytetrahydrofuran-3-yl)pyridin- 2-yl)-1-methyl-1H-pyrrolo[2,3-c]pyridin-5-yl)acetamide

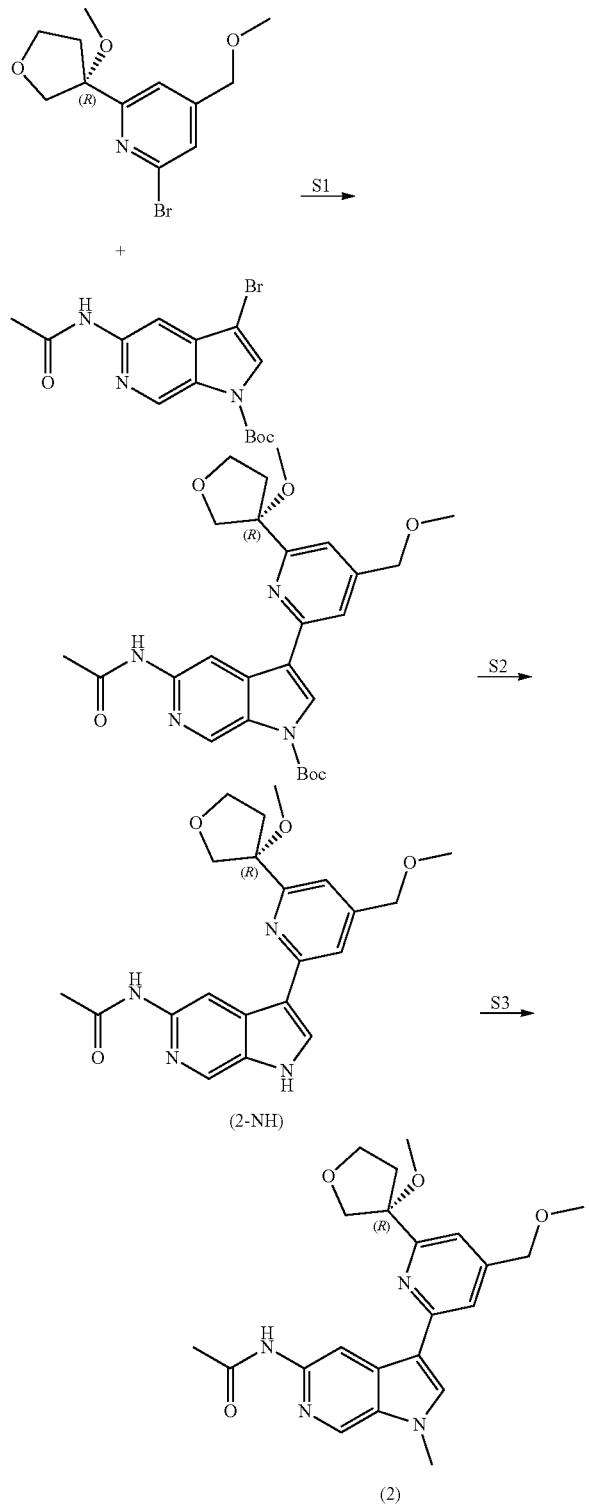

Step 1: (R)-tert-butyl 5-acetamido-3-(4-(methoxymethyl)-6-(3- methoxytetrahydrofuran-3-yl)pyridin-2-yl)-1H-pyrrolo[2,3-c]pyridine-1-carboxylate. A vial was charged with tert-butyl 5-acetamido-3-bromo-1H-pyrrolo[2,3-c]pyridine-1-carboxylate (2.13g, 6.02 mmol) (Preparation #1), bis(pinacolato)diboron (3.06 g, 12.03 mmol), and potassium acetate (1.181 g, 12.03 mmol) in dioxane (18 mL) with 4 Å molecular sieves. The reaction was degassed with nitrogen for 5 minutes before the addition of [1,1'-bis(diphenylphosphino)ferrocene] dichloropalladium(II)- dichloromethane adduct (Pd(dppf)Cl$_2$-DCM adduct) (0.369 g, 0.451 mmol). The reaction was heated to 90° C. for 2 hours. The reaction was cooled to room temperature. In a separate vial (R)-2-bromo-4- (methoxymethyl)-6-(3-methoxytetrahydrofuran-3-yl)pyridine (2 g, 6.62 mmol) (Preparation #6) and potassium phosphate (2.55 g, 12.03 mmol) was dissolved in dioxane (18.23 mL) and water (3.65 mL) and degassed with nitrogen for 5 minutes before the addition of the filtered solution of boronate. The reaction was sealed and heated to 75° C. for 25 minutes. The reaction cooled to room temperature, and was partitioned between water and ethyl acetate. The organic portion was dried over MgSO$_4$, filtered, and concentrated under reduced pressured to provide a residue, which was purified via silica gel chromatography, eluting with 0-100% heptanes:ethyl acetate, to provide the product (2.17 g, 73% yield). LC/MS (Table A, Method b) R$_f$=1.47 minutes; MS m/z: 497 (M+H)$^+$. Boc=t-Butoxycarbonyl.

Step 2: (R)-N-(3-(4-(methoxymethyl)-6-(3-methoxytetrahydrofuran-3-yOpyridin-2- yl)-1H-pyrrolo[2,3-c]pyridin-5-yl)acetamide. A large microwave vial was charged with (R)-tert- butyl 5-acetamido-3-(4-(methoxymethyl)-6-(3-methoxytetrahydrofuran-3-yl)pyridin-2-yl)-1H- pyrrolo[2,3-c]pyridine-1-carboxylate (2.16 g, 4.35 mmol) and dissolved in ethanol (14 mL). The reaction was heated in a Biotage® microwave to 150° C. for 20 minutes. The solvent was concentrated to give crude residue, which was triturated with acetonitrile to provide the product (1.18 g, 69% yield). LC/MS (Table A, Method b) R$_f$=0.74 minutes; MS m/z: 397 (M+H)$^+$.

Step 3: (R)-N-(3-(4-(methoxymethyl)-6-(3-methoxytetrahydrofuran-3-yOpyridin-2- yl)-1-methyl-1H-pyrrolo[2,3-c]pyridin-5-yl)acetamide. A flask was charged with (R)-N-(3-(4- (methoxymethyl)-6-(3-methoxytetrahydrofuran-3-yl)pyridin-2-yl)-1H-pyrrolo[2,3-c]pyridin-5- ypacetamide (0.740 g, 1.867 mmol), cesium carbonate (1.216 g, 3.73 mmol), and methyl iodide (0.128 mL, 2.053 mmol) in acetonitrile (18.6 mL). The reaction stirred at room temperature for 30 minutes. Water was then added, the solution was extracted into ethyl acetate, and the organic layer was dried over MgSO$_4$, filtered, and concentrated under reduced pressure to provide the product (0.621 g, 81% yield, 96% ee). LC/MS (Table A, Method d) R$_f$=0.94 minutes; MS m/z: 411 (M+H)$^+$. $^1$H NMR (400 MHz, Dimethyl sulfoxide-d$_6$) δ 10.16 (s, 1H), 9.04 (s, 1H), 8.58 (d, J=0.9 Hz, 1H), 8.28 (s, 1H), 7.58 (t, J 32 1.0 Hz, 1H), 7.20-7.12 (m, 1H), 4.52-4.45 (m, 2H), 4.16 (d, J=9.5 Hz, 1H), 4.05-3.96 (m, 1H), 3.90 (t, J=1.4 Hz, 3H), 3.36 (d, J=0.8 Hz, 3H), 3.09 (d, J=0.7 Hz, 3H), 2.75 (dt, J=13.2, 8.6 Hz, 1H), 2.45- 2.35 (m, 1H), 2.06 (d, J=0.7 Hz, 3H).

The compounds shown in Table 2a were synthesized in a manner similar to Example #2 using tert-butyl 5-acetamido-3-bromo-1H-pyrrolo[2,3-c]pyridine-1-carboxylate (Preparation #1) and the corresponding aromatic halide followed by Example #2, Step 2, and Example #2, Step 3.

TABLE 2a

| Ex | Aromatic Halide | Product | $R_t$ min (Method) | m/z $(M + H)^+$ |
|---|---|---|---|---|
| 2.2 | (R)-2-bromo-6-(3-methoxytetrahydrofuran-3-yl)-4-methylpyridine (Preparation #5) | (R)-N-(3-(6-(3-methoxytetrahydrofuran-3-yl)-4-methylpyridin-2-yl)-1-methyl-1H-pyrrolo[2,3-c]pyridin-5-yl)acetamide | 0.98 (d) | 381 |
| 2.3 | (S)-2-bromo-6-(3-ethyltetrahydrofuran-3-yl)pyridine (Preparation #10a) | (S)-N-(3-(6-(3-ethyltetrahydrofuran-3-yl)pyridin-2-yl)-1-methyl-1H-pyrrolo[2,3-c]pyridin-5-yl)acetamide | 1.12 (d) | 365 |
| 2.3a | (R)-2-bromo-6-(3-ethyltetrahydrofuran-3-yl)pyridine (Preparation #10) | (R)-N-(3-(6-(3-ethyltetrahydrofuran-3-yl)pyridin-2-yl)-1-methyl-1H-pyrrolo[2,3-c]pyridin-5-yl)acetamide | 1.12 (d) | 365 |
| 2.4 | (S)-2-bromo-4-(methoxymethyl)-6-(3-methoxytetrahydrofuran-3-yl)pyridine (Preparation #6a) | (S)-N-(3-(4-(methoxymethyl)-6-(3-methoxytetrahydrofuran-3-yl)pyridin-2-yl)-1-methyl-1H-pyrrolo[2,3-c]pyridin-5-yl)acetamide | 0.94 (d) | 411 |
| 2.5 | (S)-2-chloro-6-(3-methoxytetrahydrofuran-3-yl)isonicotinonitrile (Preparation #9a) | (S)-N-(3-(4-cyano-6-(3-methoxytetrahydrofuran-3-yl)pyridin-2-yl)-1-methyl-1H-pyrrolo[2,3-c]pyridin-5-yl)acetamide | 1.02 (d) | 392 |
| 2.6 | (R)-2-chloro-6-(3-methoxytetrahydrofuran-3-yl)isonicotinonitrile (Preparation #9) | (R)-N-(3-(4-cyano-6-(3-methoxytetrahydrofuran-3-yl)pyridin-2-yl)-1-methyl-1H-pyrrolo[2,3-c]pyridin-5-yl)acetamide | 1.02 (d) | 392 |
| 2.7 | (S)-2-bromo-4-(difluoromethyl)-6-(3-methoxytetrahydrofuran-3-yl)pyridine (Preparation #18a) | (S)-N-(3-(4-(difluoromethyl)-6-(3-methoxytetrahydrofuran-3-yl)pyridin-2-yl)-1-methyl-1H-pyrrolo[2,3-c]pyridin-5-yl)acetamide | 1.08 (d) | 417 |
| 2.8 | (R)-2-bromo-4-(difluoromethyl)-6-(3-methoxytetrahydrofuran-3-yl)pyridine (Preparation #18) | (R)-N-(3-(4-(difluoromethyl)-6-(3-methoxytetrahydrofuran-3-yl)pyridin-2-yl)-1-methyl-1H-pyrrolo[2,3-c]pyridin-5-yl)acetamide | 1.08 (d) | 417 |
| 2.9 | (S)-2-iodo-6-(3-methoxytetrahydrofuran-3-yl)pyrazine (Preparation #19a) | (S)-N-(3-(6-(3-methoxytetrahydrofuran-3-yl)pyrazin-2-yl)-1-methyl-1H-pyrrolo[2,3-c]pyridin-5-yl)acetamide | 0.77 (d) | 368 |
| 2.10 | (R)-2-iodo-6-(3-methoxytetrahydrofuran-3-yl)pyrazine (Preparation #19) | (R)-N-(3-(6-(3-methoxytetrahydrofuran-3-yl)pyrazin-2-yl)-1-methyl-1H-pyrrolo[2,3-c]pyridin-5-yl)acetamide | 0.77 (d) | 368 |
| 2.11 | (R)-2-chloro-6-(3-ethyltetrahydrofuran-3-yl)isonicotinonitrile (Preparation #8) | (R)-N-(3-(4-cyano-6-(3-ethyltetrahydrofuran-3-yl)pyridin-2-yl)-1-methyl-1H-pyrrolo[2,3-c]pyridin-5-yl)acetamide | 1.22 (d) | 390 |

The compounds shown in Table 2b were synthesized in a manner similar to Example #2 using tert-butyl 5-acetamido-3-bromo-1H-pyrrolo[2,3-c]pyridine-1-carboxylate (Preparation #1) and the corresponding aromatic halide followed by Example #2, Steps 2, and Example #2, Step 3 using 2,2-difluorocyclopropyl 4-methylbenzenesulfonate (Preparation #32). The product was purified via chiral SFC (Table B, Method used, as indicated).

TABLE 2b

| Ex | Aromatic Halide | Product | $R_t$ min (Method) | m/z $(M + H)^+$ |
|---|---|---|---|---|
| 2a.2 | (S)-2-chloro-6-(3-methoxytetrahydrofuran-3-yl)isonicotinonitrile (Preparation #9a) | N-(3-(4-cyano-6-((S)-3-methoxytetrahydrofuran-3-yl)pyridin-2-yl)-1-((R)-2,2-difluorocyclopropyl)-1H-pyrrolo[2,3-c]pyridin-5-yl)acetamide | 1.23 (d) 4.4 (15) | 454 |
| 2a.4 | (S)-2-chloro-6-(3-methoxytetrahydrofuran-3-yl)isonicotinonitrile (Preparation #9a) | N-(3-(4-cyano-6-((S)-3-methoxytetrahydrofuran-3-yl)pyridin-2-yl)-1-((S)-2,2-difluorocyclopropyl)-1H-pyrrolo[2,3-c]pyridin-5-yl)acetamide | 1.23 (d) 4.6 (15) | 454 |

TABLE 2b-continued

| Ex | Aromatic Halide | Product | R, min (Method) | m/z (M + H)+ |
|---|---|---|---|---|
| 2a.3 | (R)-2-chloro-6-(3-methoxytetrahydrofuran-3-yl)isonicotinonitrile (Preparation #9) | N-(3-(4-cyano-6-((R)-3-methoxytetrahydrofuran-3-yl)pyridin-2-yl)-1-((R)-2,2-difluorocyclopropyl)-1H-pyrrolo[2,3-c]pyridin-5-yl)acetamide | 1.23 (d) 4.6 (16) | 454 |
| 2a.5 | (R)-2-chloro-6-(3-methoxytetrahydrofuran-3-yl)isonicotinonitrile (Preparation #9) | N-(3-(4-cyano-6-((R)-3-methoxytetrahydrofuran-3-yl)pyridin-2-yl)-1-((S)-2,2-difluorocyclopropyl)-1H-pyrrolo[2,3-c]pyridin-5-yl)acetamide | 1.23 (d) 4.8 (16) | 454 |

56. Example #3: (R)-1-(3-(4-(Methoxymethyl)-6-(3-methoxytetrahydrofuran-3-yl)pyridin-2-yl)-1-methyl-1H-pyrrolo[2,3-c]pyridin-5-yl)urea

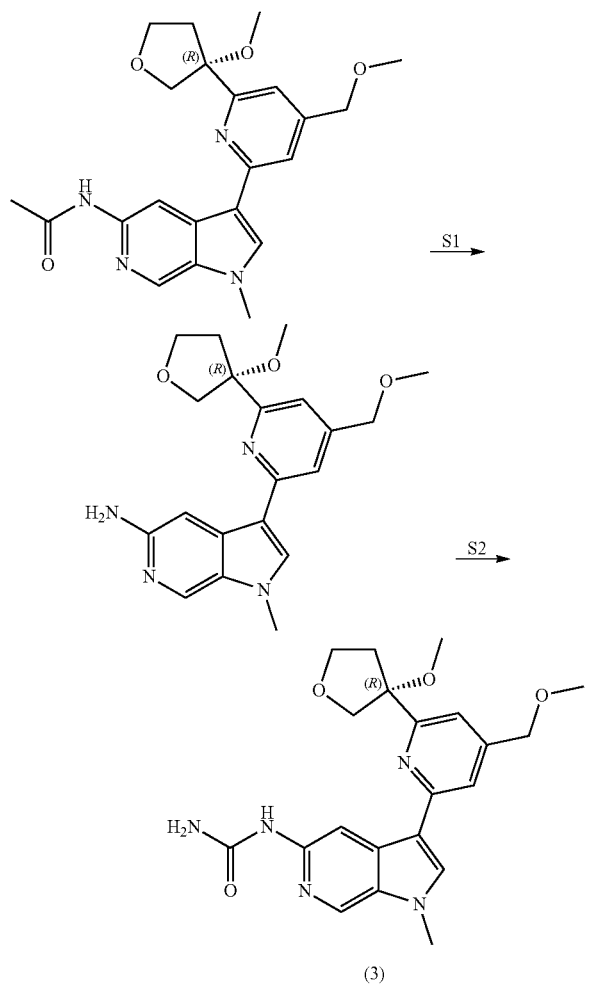

(3)

Step 1: (R)-3-(4-(methoxymethyl)-6-(3-methoxytetrahydrofuran-3-yl)pyridin-2-yl)-1-methyl-1H-pyrrolo[2,3-c]pyridin-5-amine, Hydrochloric Acid. A flask was charged with (R)-N-(3-(4-(methoxymethyl)-6-(3-methoxytetrahydrofuran-3-yOpyridin-2-yl)-1-methyl-1H-pyrrolo[2,3-c]pyridin-5-ypacetamide (0.525 g, 1.279 mmol) (Example #2, Step 3) and HCl (5N, aqueous) (1.279 mL, 6.40 mmol). The reaction was heated to 80° C. for 1 hour. The reaction cooled to room temperature, and the solvent was concentrated and dried in vacuum oven to provide the product (0.540 g, 100% yield). LC/MS (Table A, Method b) $R_t$=0.89 minutes; MS m/z: 369 (M+H)+.

Step 2: (R)-1-(3-(4-(methoxymethyl)-6-(3-methoxytetrahydrofuran-3-yl)pyridin-2-yl)-1-methyl-1H-pyrrolo[2,3-c]pyridin-5-yOurea. (R)-3-(4-(methoxymethyl)-6-(3-methoxytetrahydrofuran-3-yl)pyridin-2-yl)-1-methyl-1H-pyrrolo[2,3-c]pyridin-5-amine, hydrochloric acid (0.515 g, 1.272 mmol) was dissolved in tetrahydrofuran (12 mL) and stirred in a 100 mL reaction flask under nitrogen. N,N-diisopropylethylamine (0.889 mL, 5.09 mmol) was added and the flask was cooled to −78° C. Phosgene (1M in toluene) (1.1 mL, 1.526 mmol) was added slowly and then stirred for 5 minutes before the addition of ammonia (7M in methanol) (1.454 mL, 10.18 mmol). The reaction warmed to room temperature slowly. The reaction was quenched into water and filtered to provide a filtered material, which was purified on reverse HPLC, eluting with 20-65% 0.1% ammonium acetate in acetonitrile over 15 minutes, to provide the product (0.115 g, 22% yield, 96% ee). LC/MS (Table A, Method d) $R_t$=0.89 minutes; MS m/z: 369 (M+H)+. $^1$H NMR (400 MHz, Dimethyl sulfoxide- $d_6$) δ 8.82 (s, 1H), 8.49 (d, J=1.0 Hz, 1H), 8.43 (s, 1H), 8.24 (d, J=0.9 Hz, 1H), 7.55 (dq, J=1.5, 0.9 Hz, 1H), 7.16 (dq, J=1.4, 0.8 Hz, 1H), 6.56 (s, 2H), 4.49 (t, J=0.8 Hz, 2H), 4.18 (dt, J=9.6, 1.1 Hz, 1H), 4.05-3.94 (m, 2H), 3.91 (d, J=0.9 Hz, 1H), 3.87 (d, J=0.9 Hz, 3H), 3.36 (d, J=1.0 Hz, 3H), 3.08 (d, J=0.9 Hz, 3H), 2.69 (ddd, J=13.2, 9.2, 8.3 Hz, 1H), 2.41 (dddd, J=13.1, 6.7, 4.0, 1.2 Hz, 1H).

The compounds shown in Table 3 were synthesized in a manner similar to Example #2 using tert-butyl 5-acetamido-3-bromo-1H-pyrrolo[2,3-c]pyridine-1-carboxylate (Preparation #1) and the corresponding aromatic halide followed by Example #3, Step 1, and Example #3, Step 2.

TABLE 3

| Ex | Aromatic Halide | Product | R, min (Method) | m/z (M + H)+ |
|---|---|---|---|---|
| 3.2 | (S)-3-(3-bromo-5-methylphenyl)-3-ethyltetrahydrofuran (Preparation #10a) | (S)-1-(3-(6-(3-ethyltetrahydrofuran-3-yl)pyridin-2-yl)-1-methyl-1H-pyrrolo[2,3-c]pyridin-5-yl)urea | 1.05 (d) | 366 |
| 3.3 | (R)-3-(3-bromo-5-methylphenyl)-3-ethyltetrahydrofuran (Preparation #10) | (R)-1-(3-(6-(3-ethyltetrahydrofuran-3-yl)pyridin-2-yl)-1-methyl-1H-pyrrolo[2,3-c]pyridin-5-yl)urea | 1.05 (d) | 366 |

57. Example #4: (R)-N-(3-(4-(methoxymethyl)-6-(3-methoxytetrahydrofuran-3-yl)pyridin-2-yl)-1-(oxetan-3-yl)-1H-pyrrolo[2,3-c]pyridin-5-yl)acetamide

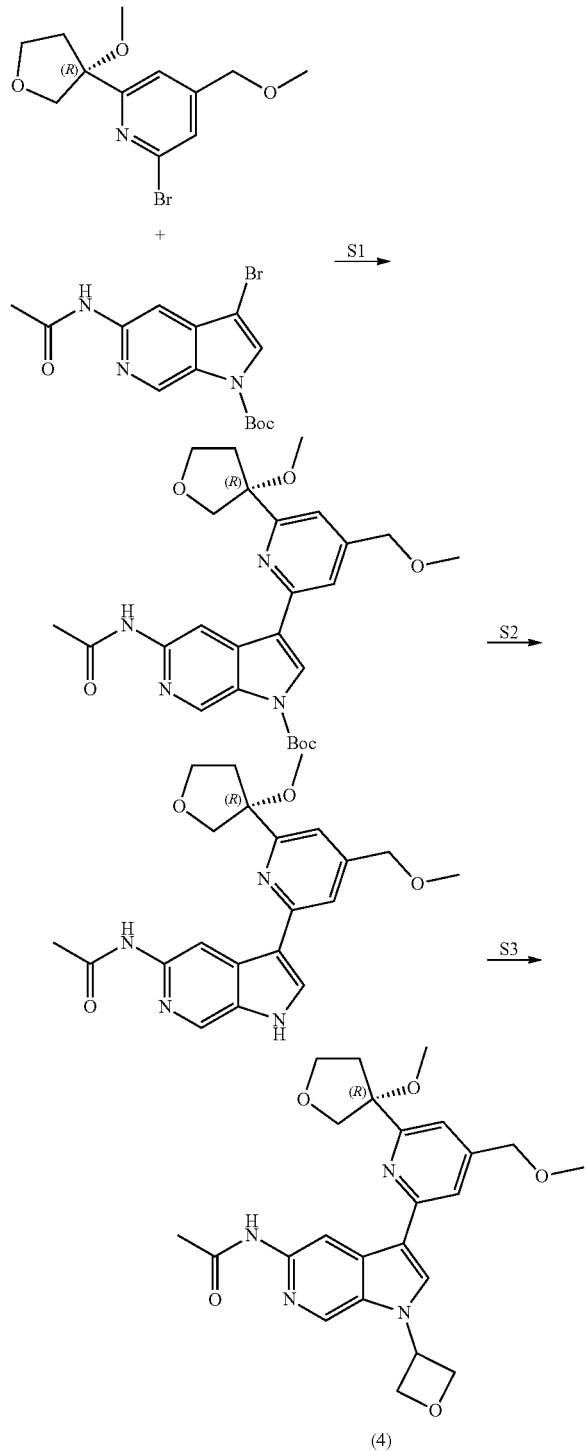

(4)

Step 1: (R)-tert-butyl 5-acetamido-3-(4-(methoxymethyl)-6-(3-methoxytetrahydrofuran-3-yl)pyridin-2-yl)-1H-pyrrolo[2,3-c]pyridine-1-carboxylate. A flask was charged with tert-butyl 5-acetamido-3-bromo-1H-pyrrolo[2,3-c]pyridine-1-carboxylate (2.1 g, 6.02 mmol) (Preparation #1), bis(pinocalato)diboron (3.06 g, 12 mmol), potassium acetate (1.1 g, 12 mmol) in dioxane (18 mL). The reaction was degassed with nitrogen for 5-10 minutes before the addition of [1,1'-bis(diphenylphosphino)ferrocene] dichloropalladium(II)-dichloromethane adduct (Pd(dppf)Cl$_2$-DCM adduct) (0.369 g, 0.45 mmol). The reaction was heated to 90° C. for 2 hours, then the reaction was cooled to room temperature, and filtered through a pad of Celite®, washing with 1,4-dioxane to provide a filtered solution of boronate. In a separate vial, a mixture of (R)-2-bromo-4-(methoxymethyl)-6-(3-methoxytetrahydrofuran-3-yl)pyridine (2.2 g, 4.37 mmol) (Preparation #6), potassium phosphate (2.5g, 12 mmol), 1,4-dioxane (18.2 mL), and water (3.6 mL) was degassed for 5 minutes. The filtered solution of boronate was then added to this mixture, and the vial was sealed and heated to 75° C. for about 25 minutes. The reaction was cooled to room temperature, and partitioned between water and ethyl acetate. The combined organic extracts were dried over MgSO$_4$, filtered, and concentrated under reduced pressure to provide a residue, which was purified via silica gel chromatography, eluting with 0-100% ethyl acetate/heptanes, to provide the product (2.2 g, 73% yield). LC/MS (Table A, Method b) R$_t$=1.47 minutes; MS m/z: 497(M+H)$^+$.

Step 2: (R)-N-(3-(4-(methoxymethyl)-6-(3-methoxytetrahydrofuran-3-yl)pyridin-2-yl)-1H-pyrrolo[2,3-c]pyridin-5-yl)acetamide. A slurry of (R)-tert-butyl 5-acetamido-3-(4-(methoxymethyl)-6-(3-methoxytetrahydrofuran-3-yl)pyridin-2-yl)-1H-pyrrolo[2,3-c]pyridine-1-carboxylate (2.16 g, 4.4 mmol) in ethanol (15 mL) was heated to 150° C. for 20 minutes in a Biotage® microwave. The solvent was concentrated under reduced pressure and the remaining solids were triturated with 3 mL of acetonitrile to provide the product. The filtrate was also concentrated and combined with the filtered solids to give additional product (1.2 g, 69% yield). LC/MS (Table A, Method b) R$_t$=0.74 minutes; MS m/z: 397(M+H)$^+$.

Step 3: (R)-N-(3-(4-(methoxymethyl)-6-(3-methoxytetrahydrofuran-3-yl)pyridin-2-yl)-1-(oxetan-3-yl)-1H-pyrrolo[2,3-c]pyridin-5-yl)acetamide. To a slurry of (R)-N-(3-(4-(methoxymethyl)-6-(3-methoxytetrahydrofuran-3-yl)pyridin-2-yl)-1H-pyrrolo[2,3-c]pyridin-5-yl)acetamide (200 mg, 0.52 mmol)) in acetonitrile (2.6 mL) was added cesium carbonate (0.34 g, 1.05 mmol) and 3-iodooxetane (0.15 g, 0.79 mmol), and the mixture was heated to 75° C. for 16 hours. Additional 3-iodooxetane (0.15 g, 0.79 mmol) was added and the reaction was heated to 75° C. for 5 hours. The reaction was cooled to room temperature, and quenched by the addition of water. The aqueous phase was extracted with 10% methanol/dichloromethane (2×10 mL) and the combined organic extracts were dried over MgSO$_4$, filtered, and concentrated to a residue, which was purified via silica gel chromatography, eluting with 0-10% methanol/ethyl acetate, to provide the product (0.13 g, 55% yield). LC/MS (Table A, Method d) R$_t$=0.94 minutes; MS m/z: 453 (M+H)$^+$. $^1$H NMR (400 MHz, Dimethyl sulfoxide-d$_6$) δ 10.24 (s, 1H), 9.11 (s, 1H), 8.79 (s, 1H), 8.71 (d, J=1.0 Hz, 1H), 7.81 (dt, J=1.3, 0.7 Hz, 1H), 7.25 (d, J =1.3 Hz, 1H), 6.00-5.82 (m, 1H), 5.09 (t, J=7.3 Hz, 2H), 5.04 (td, J=6.7, 2.4 Hz, 2H), 4.54 (d, J=0.8 Hz, 2H), 4.22 (dd, J=9.7, 1.2 Hz, 1H), 4.11 -3.96 (m, 2H), 3.93 (d, J=9.7 Hz, 1H), 3.40 (s, 3H), 3.13 (s, 3H), 2.79 (dt, J=13.2, 8.7 Hz, 1H), 2.49-2.38 (m, 1H), 2.10 (s, 3H).

The compounds shown in Table 4 were synthesized in a manner similar to Example #4 using tert-butyl 5-acetamido-3-bromo-1H-pyrrolo[2,3-c]pyridine-1-carboxylate (Preparation #1) and the corresponding aromatic halide followed by Example #4, Step 2, and Example #4, Step 3.

TABLE 4

| Ex | Aromatic Halide | Product | R, min (Method) | m/z (M + H)+ |
|---|---|---|---|---|
| 4.2 | (S)-2-bromo-4-(difluoromethyl)-6-(3-methoxytetrahydrofuran-3-yl)pyridine (Preparation #18a) | (S)-N-(3-(4-(difluoromethyl)-6-(3-methoxytetrahydrofuran-3-yl)pyridin-2-yl)-1-(oxetan-3-yl)-1H-pyrrolo[2,3-c]pyridin-5-yl)acetamide | 1.00 (d) | 459 |
| 4.3 | (R)-2-bromo-4-(difluoroymethyl)-6-(3-methoxytetrahydrofuran-3-yl)pyridine (Preparation #18) | (R)-N-(3-(4-(difluoromethyl)-6-(3-methoxytetrahydrofuran-3-yl)pyridin-2-yl)-1-(oxetan-3-yl)-1H-pyrrolo[2,3-c]pyridin-5-yl)acetamide | 1.07 (d) | 459 |
| 4.4 | (S)-2-chloro-4-methoxy-6-(3-methoxytetrahydrofuran-3-yl)pyridine (Preparation #22a) | (S)-N-(3-(4-methoxy-6-(3-methoxytetrahydrofuran-3-yl)pyridin-2-yl)-1-(oxetan-3-yl)-1H-pyrrolo[2,3-c]pyridin-5-yl)acetamide | 0.97 (d) | 439 |

58. Example #5: (R)-N-(3-(4-methoxy-6-(3-methoxytetrahydrofuran-3-yl)pyridin-2-yl)-1-(oxetan-3-yl)-1H-pyrrolo[2,3-c]pyridin-5-yl)acetamide

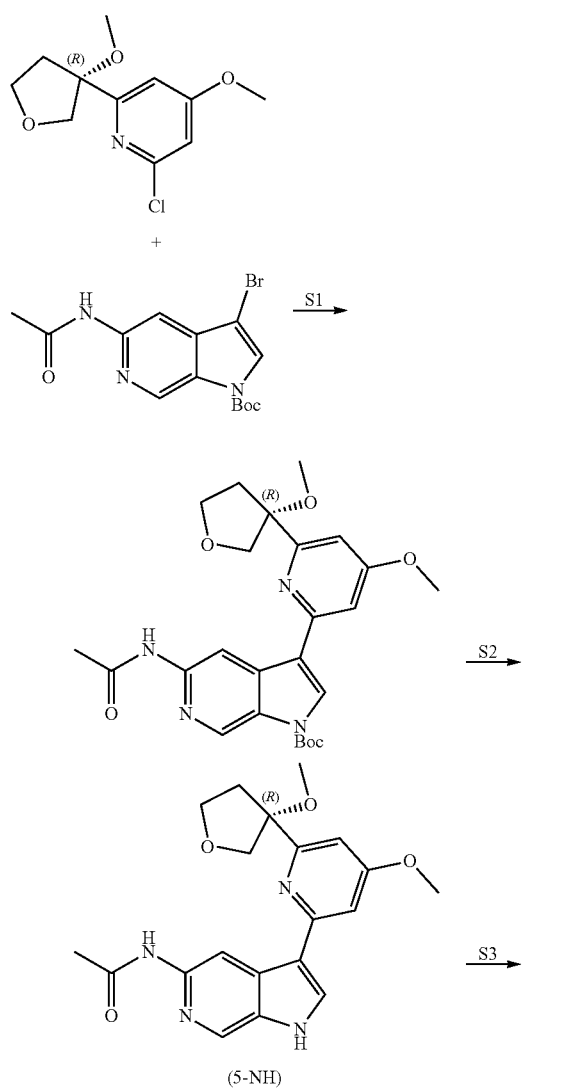

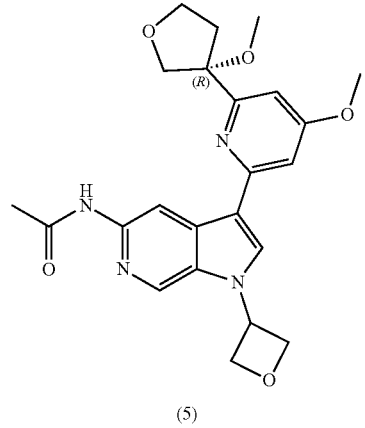

Step 1: (R)-tert-butyl 5-acetamido-3-(4-methoxy-6-(3-methoxytetrahydrofuran-3-yl)pyridin-2-yl)-1H-pyrrolo[2,3-c]pyridine-1-carboxylate. Dioxane (5.9 mL) was degassed in a separate vial with a stream of nitrogen. In a reaction vial containing 4Å molecular sieves, tert-butyl 5-acetamido-3-bromo-1H-pyrrolo[2,3-c]pyridine-1-carboxylate (529 mg, 1.492 mmol) (Preparation #1), potassium acetate (293 mg, 2.98 mmol), bis(pinacolato)diboron (758 mg, 2.98 mmol) and [1,1'-bis(diphenylphosphino)ferrocene]dichloropalladium(II)-dichloromethane adduct (Pd(dppf)Cl$_2$-DCM adduct) (91 mg, 0.112 mmol) were each added and then the vial was purged three times with an atmosphere of nitrogen. The dioxane was added to the vial and then it was heated to 95° C. for 2 hours, then the vial was cooled to room temperature. (R)-2-chloro-4-methoxy-6-(3-methoxytetrahydrofuran-3-yl)pyridine (400 mg, 1.641 mmol) (Preparation #22) was dissolved in dioxane (5.9 mL) and degassed under a stream of nitrogen. Potassium phosphate (633 mg, 2.98 mmol), tris(dibenzylideneacetone)dipalladium(0) (Pd$_2$(dba)$_3$) (13.66 mg, 0.015 mmol), 1S,3R,5R,7S)-1,3,5,7-tetramethyl-8-phenyl-2,4,6-trioxa-8-phosphaadamantane (PaPH) (8.72 mg, 0.030 mmol), and water (2984 µl) were added to the reaction flask, along with the solution of boronate in dioxane, and the final mixture was degassed for 5 minutes and then heated to 80° C. for 2 hours. Upon conversion to the Suzuki product, the reaction was cooled to room temperature and then 5% aqueous cysteine solution (20 mL) and dichloromethane (DCM) (30 mL) were added, and then mixture was stirred for 30 minutes. The layers were separated, and the aqueous layer was extracted with more DCM. The combined organic layers were washed with water, brine, dried over MgSO$_4$, and concentrated to provide a residue, which was purified via silica gel chromatography, eluting with 0-10% methanol/DCM, to provide the product (400 mg, 56% yield). LC/MS (Table A, Method a) R$_t$=1.53 minutes; MS m/z: 483 (M+H)$^+$.

Step 2: (R)-N-(3-(4-methoxy-6-(3-methoxytetrahydrofuran-3-yl)pyridin-2-yl)-1H- pyrrolo[2,3-c]pyridin-5-yl)acetamide. (R)-tert-butyl 5-acetamido-3-(4-methoxy-6-(3-methoxytetrahydrofuran-3-yl)pyridin-2-yl)-1H-pyrrolo[2,3-c]pyridine-1-carboxylate (400mg, 0.829 mmol) was dissolved in ethanol (2.7 mL) in a microwave vial and heated to 135° C. for 45 minutes. The solvent was concentrated under reduced pressure to provide a residue, which was purified via silica gel chromatography, eluting with 0-20% methanol/dichloromethane, to provide the product (277 mg, 44% yield). LC/MS (Table A, Method a). R$_t$=0.86 minutes; MS m/z: 383 (M+H)$^+$.

Step 3: (R)-N-(3-(4-methoxy-6-(3-methoxytetrahydrofuran-3-yl)pyridin-2-yl)-1- (oxetan-3-yl)-1H-pyrrolo[2,3-c]pyridin-5-yl)acetamide. (R)-N-(3-(4-methoxy-6-(3-methoxytetrahydrofuran-3-yl)pyridin-2-yl)-1H-pyrrolo[2,3-c]pyridin-5-yl)acetamide (277mg, 0.724 mmol) was dissolved in dimethylformamide (3.6 mL), stirred in a reaction vial. Cesium carbonate (590 mg, 1.811 mmol) and 3-iodooxetane (176 µL, 2.173 mmol) were added and the reaction was heated to 50° C. for 5 hours. The reaction was then cooled to room temperature, the reaction solution was filtered through a flitted funnel, and filtered again through a syringe filter, rinsing with MeOH. The filtrate was concentrated to provide a residue, which was purified via reverse HPLC, eluting with 25-75% acetonitrile:0.1% ammonium acetate: water, to provide the product (89 mg, 28% yield). LC/MS (Table A, Method a) R$_t$=0.97 minutes; MS m/z: 439 (M+H)$^+$. $^1$H NMR (400 MHz, Dimethyl sulfoxide-d$_6$) δ 10.18 (s, 1H), 9.09 (s, 1H), 8.79 (s, 1H), 8.66 (d, J=1.0 Hz, 1H), 7.43 (d, J=2.2 Hz, 1H), 6.82 (d, J=2.2 Hz, 1H), 5.88 (t, J=7.0 Hz, 1H), 5.06 (t, J=7.3 Hz, 2H), 4.99 (td, J=6.6, 3.0 Hz, 2H), 4.14 (d, J=9.7 Hz, 1H), 4.05-3.97 (m, 1H), 3.95 (d, J=7.5 Hz, 1H), 3.90 (s, 3H), 3.87 (d, J=9.7 Hz, 1H), 3.10 (s, 3H), 2.76 (dt, J=13.0, 8.6 Hz, 1H), 2.06 (s, 3H).

The compounds shown in Table 5 were synthesized in a manner similar to Example #5 from tert-butyl 5-acetamido-3-bromo-1H-pyrrolo[2,3-c]pyridine-1-carboxylate (Preparation #1) and the corresponding aromatic halide followed by Example #5, Step 2 and Step 3 using (S)-tetrahydrofuran-3- yl methanesulfonate (Preparation #30).

59. Example #6: (R)-N-(3-(6-(3-Methoxytetrahydrofuran-3-yl)-4-(oxetan-3- ylmethoxy)pyridin-2-yl)-1-methyl-1H-pyrrolo[2,3-c]pyridin-5-yl)acetamide

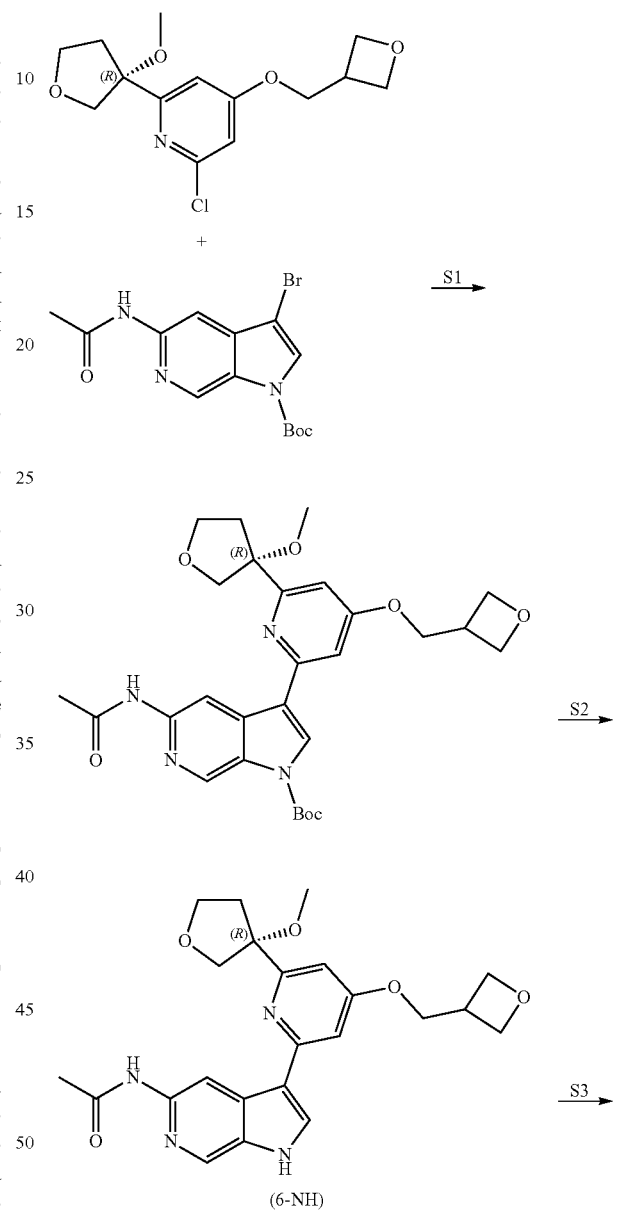

TABLE 5

| Ex | Aromatic Halide | Product | R$_t$ min (Method) | m/z (M + H)$^+$ |
|---|---|---|---|---|
| 5.2 | (R)-2-chloro-4-methoxy-6-(3-methoxytetrahydrofuran-3-yl)pyridine (Preparation #22) | N-(3-(4-methoxy-6-((R)-3-methoxytetrahydrofuran-3-yl)pyridin-2-yl)-1-((R)-tetrahydrofuran-3-yl)-1H-pyrrolo[2,3-c]pyridin-5-yl)acetamide | 1.03 (d) | 453 |
| 5.3 | (S)-2-chloro-4-methoxy-6-(3-methoxytetrahydrofuran-3-yl)pyridine (Preparation #22a) | N-(3-(4-methoxy-6-((S)-3-methoxytetrahydrofuran-3-yl)pyridin-2-yl)-1-((R)-tetrahydrofuran-3-yl)-1H-pyrrolo[2,3-c]pyridin-5-yl)acetamide | 1.03 (d) | 453 |

-continued

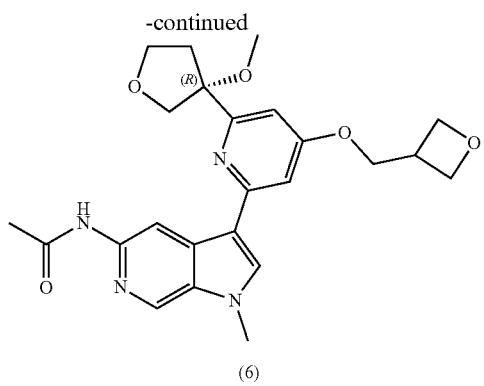

(6)

Step 1: (R)-tert-butyl 5-acetamido-3-(6-(3-methoxytetrahydrofuran-3-yl)-4-(oxetan-3- ylmethoxy)pyridin-2-yl)-1H-pyrrolo[2,3-c]pyridine-1-carboxylate. A mixture of tert-butyl 5- acetamido-3-bromo-1H-pyrrolo[2,3-c]pyridine-1-carboxylate (0.970 g, 2.74 mmol) (Preparation #1), bis (pinacolato)diboron (1.182 g, 4.66 mmol), and potassium acetate (0.538 g, 5.48 mmol) in dioxane (8.30 mL) with 4Å molecular sieves was purged with nitrogen for about 15 minutes. [1,1'- Bis(diphenylphosphino)ferrocene]dichloropalladium(II)-dichloromethane adduct (Pd(dppf)Cl$_2$-DCM adduct) (0.168 g, 0.205 mmol) was added to the reaction, and then the reaction was heated at about 100° C. for about 90 minutes. The reaction was removed from heat and filtered over Celite® into flask containing (R)-2-chloro-6-(3-methoxytetrahydrofuran-3-yl)-4-(oxetan-3-ylmethoxy)pyridine (0.821 g, 2.74 mmol) (Preparation #23). The filter cake was rinsed with dioxane (8.30 mL). To the filtrate was added potassium phosphate (1.163 g, 5.48 mmol) and water (1.660 mL), and the reaction solution was degassed with nitrogen. Tris(dibenzylideneacetone)dipalladium(0) (Pd$_2$(dba)$_3$) (0.100 g, 0.110 mmol) and (1S,3R,5R,7S)-1,3,5,7-tetramethyl-8-phenyl-2,4,6-trioxa-8-phosphaadamantane (PaPH) (0.064 g, 0.219 mmol) were added, and the reaction mixture stirred at about 85° C. for about 30 minutes. The reaction was then removed from heat and left at room temperature for 16 hours. Ethyl acetate (130 mL) and a 5% aqueous cysteine/NaHCO$_3$ solution (100 mL) were added to the reaction mixture, and stirred for about 10 minutes. The reaction mixture was filtered over Celite®, and the organic layers were separated, dried over MgSO$_4$, filtered, and concentrated under reduced pressure to provide a residue, which was purified via silica gel chromatography, eluting with 0-100% ethyl acetate/heptanes then increased to 10% methanol/dichloromethane, to provide the product (0.559 g, 38% yield). LC/MS (Table A, Method a) R$_t$=1.41 minutes; MS m/z: 539 (M+H)$^+$.

Step 2: (R)-N-(3-(6-(3-methoxytetrahydrofuran-3-yl)-4-(oxetan-3-ylmethoxy)pyridin- 2-yl)-1H-pyrrolo[2,3-c]pyridin-5-yl)acetamide. A mixture of (R)-tert-butyl 5-acetamido-3-(6-(3- methoxytetrahydrofuran-3-yl)-4-(oxetan-3-ylmethoxy)pyridin-2-yl)-1H-pyrrolo[2,3-c]pyridine-1-carboxylate (Step 1, 0.559 g, 1.038 mmol) in ethanol (10.38 mL) in a microwave vial was heated in Biotage® microwave at about 150° C. for about 20 minutes. Concentrated the reaction mixture under reduced pressure to provide a residue, triturated and filtered with ethanol (EtOH), rinsing with EtOH, to provide a filtered material, which was dried in vacuum oven at 60° C. for about 4 hours to provide the product (0.432 g, 95% yield). LC/MS (Table A, Method a) R$_t$=0.83 minutes; MS m/z: 439 (M+H)$^+$.

Step 3: (R)-N-(3-(6-(3-methoxytetrahydrofuran-3-yl)-4-(oxetan-3-ylmethoxy)pyridin- 2-yl)-1-methyl-1H-pyrrolo[2,3-c]pyridin-5-yl)acetamide. To a suspension of (R)-N-(3-(6-(3- methoxytetrahydrofuran-3-yl)-4-(oxetan-3-ylmethoxy) pyridin-2-yl)-1H-pyrrolo[2,3-c]pyridin-5- ypacetamide (0.400 g, 0.912 mmol) and cesium carbonate (0.594 g, 1.824 mmol) in acetonitrile (9.12 mL) at room temperature was added iodomethane (0.063 mL, 1.003 mmol). The reaction stirred at room temperature for about 16 hours. Concentrated the reaction under reduced pressure to provide a residue, which was taken up in 10% methanol/dichloromethane (MeOH/DCM) and filtered, rinsing with MeOH. The filtrate was then concentrated under reduced pressure to provide a residue which was purified via silica gel chromatography, eluting with 0-10% MeOH/DCM, to provide the product (0.2978 g, 71% yield). LC/MS (Table A, Method d) R$_t$=0.93 minutes; MS m/z: 453 (M+H)$^+$. $^1$H NMR (400 MHz, Dimethyl sulfoxide-d$_6$) δ 10.17 (s, 1H), 9.05 (s, 1H), 8.61 (d, J=1.0 Hz, 1H), 8.34 (s, 1H), 7.30 (d, J =2.2 Hz, 1H), 6.85 (d, J=2.2 Hz, 1H), 4.75 (dd, J =7.9, 6.1 Hz, 2H), 4.47 (t, J=6.0 Hz, 2H), 4.40 (d, J=6.7 Hz, 2H), 4.17 (dd, J=9.6, 1.2 Hz, 1H), 4.08-3.95 (m, 2H), 3.95 -3.84 (m, 4H), 3.45 (ddd, J=13.7, 7.6, 6.0 Hz, 1H), 3.14 (s, 3H), 2.78 (dt, J=13.1, 8.7 Hz, 1H), 2.47-2.36 (m, 1H), 2.10 (s, 3H).

The compounds shown in Table 6 were synthesized in a manner similar to Example #6 from tert-butyl 5-acetamido-3-bromo-1H-pyrrolo[2,3-c]pyridine-1-carboxylate (Preparation #1) and the corresponding aromatic halide.

TABLE 6

| Ex | Aromatic Halide | Product | R$_t$ min (Method) | m/z (M + H)$^+$ |
|---|---|---|---|---|
| 6.2 | (S)-2-chloro-6-(3-methoxytetrahydrofuran-3-yl)-4-(oxetan-3-ylmethoxy)pyridine (Preparation #37) | (S)-N-(3-(6-(3-methoxytetrahydrofuran-3-yl)-4-(oxetan-3-ylmethoxy)pyridin-2-yl)-1-methyl-1H-pyrrolo[2,3-c]pyridin-5-yl)acetamide | 0.93 (d) | 453 |
| 6.3 | (R)-2-((2-chloro-6-(3-methoxytetrahydrofuran-3-yl)pyridin-4-yl)oxy)acetonitrile (Preparation #38) | (R)-N-(3-(4-(cyanomethoxy)-6-(3-methoxytetrahydrofuran-3-yl)pyridin-2-yl)-1-methyl-1H-pyrrolo[2,3-c]pyridin-5-yl)acetamide | 0.97 (d) | 422 |

60. Example #7: N-(3-(44(R)-3-Hydroxybutoxy)-64 (R)-3-methoxytetrahydrofuran-3- yl)pyridin-2-yl)-1-methyl-1H-pyrrolo[2,3-c]pyridin-5-ypacetamide

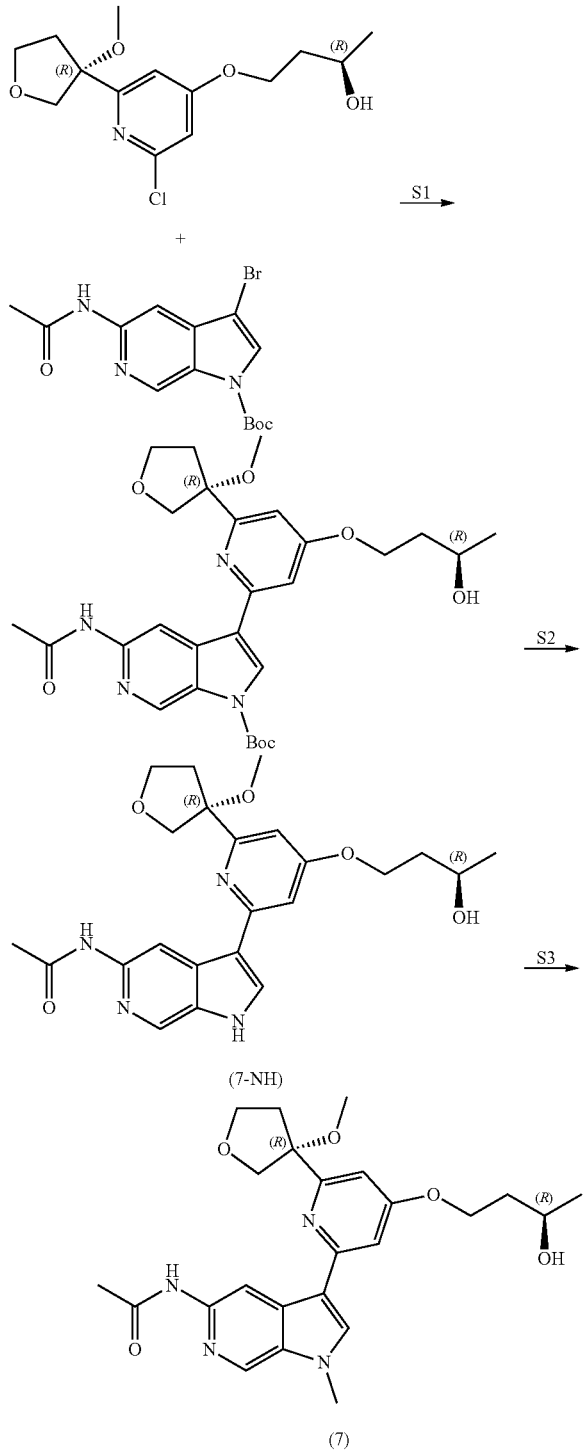

Step 1: tert-butyl 5-acetamido-3-(4-((R)-3-hydroxybutoxy)-6-((R)-3- methoxytetrahydrofuran-3-yl)pyridin-2-yl)-1H-pyrrolo[2,3-c]pyridine-1-carboxylate. A vial was charged with tert-butyl 5-acetamido-3-bromo-1H-pyrrolo[2,3-c]pyridine-1-carboxylate (0.25 g, 0.706 mmol) (Preparation #1), bis(pinocalato)diboron (0.358 g, 1.412 mmol), potassium acetate (0.139 g, 1.412 mmol), in dioxane (1.694 mL) with 4 Å molecular sieves. The reaction was degassed with nitrogen for 10 minutes before the addition of [1,1'-bis(diphenylphosphino)ferrocene]dichloropalladium(II)-dichloromethane adduct (Pd(dppf)Cl$_2$-DCM adduct) (0.043 g, 0.053 mmol). The reaction was heated to 90° C. for 1 hour. The reaction was cooled to room temperature, and filtered over a pad of Celite® into a flask containing (R)-4-42-chloro-6-((R)-3-methoxytetrahydrofuran-3-yl)pyridin-4-yl)oxy)butan-2-ol (0.250 g, 0.828 mmol) (Preparation #24), potassium phosphate (0.440 g, 2.071 mmol), dioxane (2.371 mL), and water (0.474 mL). The reaction was degassed with nitrogen for 5 minutes before the addition of (1S,3R,5R,7S)-1,3,5,7-tetramethyl-8-phenyl-2,4,6-trioxa-8-phosphaadamantane (PaPH) (0.012 g, 0.041 mmol) and tris(dibenzylideneacetone)dipalladium(0) (Pd$_2$(dba)$_3$) (0.019 g, 0.021 mmol). The reaction was sealed and heated to 75° C. for 1 hour. The reaction cooled to room temperature, and was partitioned between aqueous 5% cysteine and 10% methanol/dichloromethane (MeOH/DCM). The organic portion was dried over MgSO$_4$, filtered and concentrated under reduced pressure to provide a residue which was purified via silica gel chromatography, eluting with 0-10% MeOH/ethyl acetate, to provide the product (0.135 g, 33% yield). LC/MS (Table A, Method b) R$_t$=1.38 minutes; MS m/z: 541 (M+H)$^+$.

Step 2: N-(3-(44(R)-3-hydroxybutoxy)-64(R)-3-methoxytetrahydrofuran-3- yl)pyridin-2-yl)-1H-pyrrolo[2,3-c]pyridin-5-yl)acetamide. A microwave vial was charged with tert-butyl 5-acetamido-3-(44(R)-3-hydroxybutoxy)-6(R)-3-methoxytetrahydrofuran-3-yl)pyridin- 2-yl)-1H-pyrrolo[2,3-c]pyridine-1-carboxylate (0.127 g, 0.211 mmol) in ethanol (2 mL). The reaction was heated to 150° C. for 20 minutes, then cooled to room temperature, and the solvent removed under reduced pressure to provide the product (0.087 g, 84% yield). LC/MS (Table A, Method b) R$_t$=0.85 minutes; MS m/z: 441 (M+H)$^+$.

Step 3: N-(3-(44(R)-3-hydroxybutoxy)-6(R)-3-methoxytetrahydrofuran-3- yl)pyridin-2-yl)-1-methyl-1H-pyrrolo[2,3-c]pyridin-5-yl)acetamide. A vial was charged with N- (3-(4-((R)-3-hydroxybutoxy)-6-((R)-3-methoxytetrahydrofuran-3-yl)pyridin-2-yl)-1H-pyrrolo[2,3- c]pyridin-5-ypacetamide(0.085 g, 0.174 mmol), cesium carbonate (0.113 g, 0.347 mmol), and iodomethane (0.012 mL, 0.191 mmol) in acetonitrile (1.9 mL). The reaction was stirred at room temperature for 1 hour. The reaction was quenched with water and extracted three times with 10% methanol/dichloromethane (MeOH/DCM). The organic portion was dried over MgSO$_4$, filtered, and concentrated under reduced pressure to provide a residue, which was purified via silica gel chromatography, eluting with 0-10% MeOH/ethyl acetate, to provide the product (0.045 g, 57% yield). LC/MS (Table A, Method d) R$_t$=0.94 minutes; MS m/z: 455 (M+H)$^+$. $^1$H NMR (400 MHz, Dimethyl sulfoxide-d$_6$) δ 10.13 (s, 1H), 9.01 (s, 1H), 8.57 (d, J=1.0 Hz, 1H), 8.30 (s, 1H), 7.22 (d, J=2.3 Hz, 1H), 6.78 (d, J=2.2 Hz, 1H), 4.57 (d, J=4.9 Hz, 1H), 4.23 -4.09 (m, 3H), 4.06-3.93 (m, 2H), 3.89 (d, J=4.6 Hz, 3H), 3.84 (d, J=13.1 Hz, 1H), 3.10 (s, 3H), 2.74 (dt, J=13.2, 8.6 Hz, 1H), 2.44-2.35 (m, 1H), 2.06 (s, 3H), 1.92-1.70 (m, 2H), 1.12 (d, J=6.1 Hz, 3H).

61. Example #8: (R)-N-(3-(6-(3-Methoxytetrahydrofuran-3-yl)-4-(oxetan-3-yloxy)pyridin-2-yl)-1-methyl-1H-pyrrolo[2,3-c]pyridin-5-yl)acetamide

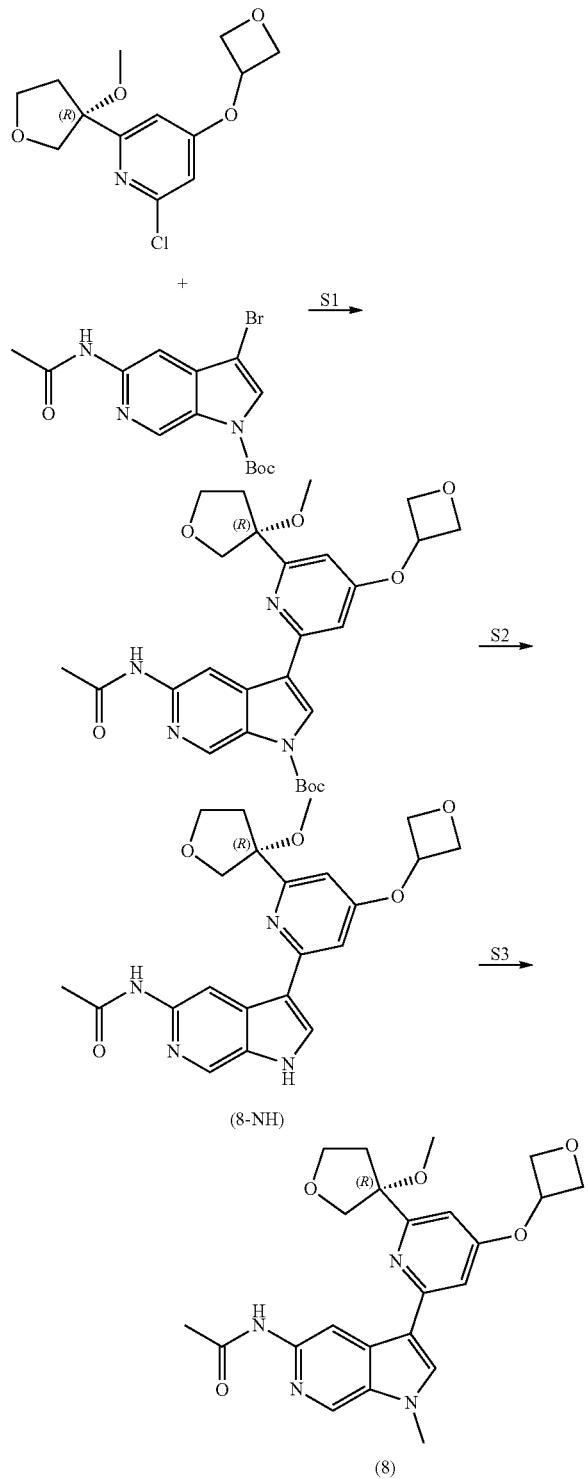

Step 1: (R)-tert-butyl 5-acetamido-3-(6-(3-methoxytetrahydrofuran-3-yl)-4-(oxetan-3-yloxy)pyridin-2-yl)-1H-pyrrolo[2,3-c]pyridine-l-carboxylate. A solution of tert-butyl 5-acetamido-3-bromo-1H-pyrrolo[2,3-c]pyridine-l-carboxylate (0.425 g, 1.2 mmol) (Preparation #1), bis(pinacolato)diboron (0.457 g, 1.800 mmol), and potassium acetate (0.353 g, 3.60 mmol) in dioxane (10.00 mL) with 4Å molecular sieves was purged with nitrogen for about 15 minutes. Added [1, F- Bis(diphenylphosphino)ferrocene]dichloropalladium(II)-dichloromethane adduct (Pd(dppf)Cl$_2$-DCM adduct) (0.098 g, 0.120 mmol), then heated in sealed vial at about 110° C. for about 90 minutes. Removed the reaction from heat, and filtered over Celite® into new reaction vial, rinsing with 4 mL dioxane. To the filtrate was added (R)-2-chloro-6-(3-methoxytetrahydrofuran-3-yl)-4-(oxetan-3- yloxy)pyridine (0.327 g, 1.143 mmol) (Preparation #25), potassium phosphate (0.728 g, 3.43 mmol), and water (2 mL). Degassed with nitrogen for about 10 minutes, then added (1S,3R,5R,7S)-1,3,5,7- tetramethyl-8-phenyl-2,4,6-trioxa-8-phosphaadamantane (PaPH) (0.033 g, 0.114 mmol) and tris(dibenzylideneacetone)dipalladium(0) (Pd$_2$(dba)$_3$) (0.052 g, 0.057 mmol) and degassed for another 2 minutes. Heated the reaction to about 80° C. for about 25 minutes. The reaction was then cooled to room temperature, diluted with 5% aqueous cysteine/NaHCO$_3$ aqueous solution (30 mL) and ethyl acetate (50 mL), and filtered over Celite®, rinsing with ethyl acetate. The organic layers were separated, dried over MgSO$_4$, filtered and concentrated under reduced pressure to provide a residue, which was purified via silica gel chromatography, eluting with 0-10% methanol/dichloromethane, to provide the product (0.659 g, 100% yield). LC/MS (Table A, Method a) R$_t$=1.42 minutes; MS m/z: 525 (M+H)$^+$.

Step 2: (R)-N-(3-(6-(3-methoxytetrahydrofuran-3-yl)-4-(oxetan-3-yloxy)pyridin-2- yl)-1H-pyrrolo[2,3-c]pyridin-5-yl)acetamide. A solution of (R)-tert-butyl 5-acetamido-3-(6-(3- methoxytetrahydrofuran-3-yl)-4-(oxetan-3-yloxy)pyridin-2-yl)-1H-pyrrolo[2,3-c]pyridine-1- carboxylate (0.600 g, 1.143 mmol) in ethanol (4 mL) was heated in Biotage® microwave to about 150° C. for about 20 minutes. Concentrated the reaction mixture under reduced pressure to provide a residue, which was then purified via silica gel chromatography, eluting with 0-10% methanol/dichloromethane, provide the product (0.276 g, 57% yield). LC/MS (Table A, Method a) R$_t$=0.83 minutes; MS m/z: 425 (M+H)$^+$.

Step 3: (R)-N-(3-(6-(3-methoxytetrahydrofuran-3-yl)-4-(oxetan-3-yloxy)pyridin-2- yl)-1-methyl-1H-pyrrolo[2,3-c]pyridin-5-yl)acetamide. To a solution of (R)-N-(3-(6-(3-methoxytetrahydrofuran-3-yl)-4-(oxetan-3-yloxy)pyridin-2-yl)-1H-pyrrolo[2,3-c]pyridin-5- yl)acetamide (0.276 g, 0.650 mmol) and cesium carbonate (0.424 g, 1.301 mmol) in acetonitrile (6.50 mL) at room temperature was added iodomethane (0.045 mL, 0.715 mmol). The reaction stirred at room temperature for 16 hours. Quenched the reaction with water and removed organic layers under reduced pressure to provide a residue and minimal water, which was triturated with water, and filtered, rinsing with water to provide a filtered material. The filtered material was then dissolved in dimethyl sulfoxide and purified via reverse HPLC, eluting with 20-75% acetonitrile/water with 10 mM ammonium acetate buffer, to provide the product (0.150g, 50% yield). LC/MS (Table A, Method d) R$_t$=0.94 minutes; MS m/z: 439 (M+H)$^+$. $^1$H NMR (400 MHz, Dimethyl sulfoxide-d$_6$) δ 10.20 (s, 1H), 9.00 (s, 1H), 8.62 (d, J=1.0 Hz, 1H), 8.33 (s, 1H), 7.03 (d, J=2.2 Hz, 1H), 6.71 (d, J=2.2 Hz, 1H), 5.50 (tt, J=6.0, 4.9 Hz, 1H), 5.15-4.92 (m, 2H), 4.62 (ddt, J=7.2, 4.8, 1.1 Hz, 2H), 4.15 (dd, J=9.6, 1.2 Hz, 1H), 4.09-3.96 (m, 2H), 3.93 (s, 3H), 3.90 (d, J=9.6 Hz, 1H), 3.13 (s, 3H), 2.75 (dt, J=13.1, 8.6 Hz, 1H), 2.41 (dddd, J=13.1, 6.8, 4.0, 1.2 Hz, 1H), 2.10 (s, 3H).

62. Example #9: N-(3-(4-((S)-3-Hydroxybutoxy)-6-((R)-3-methoxytetrahydrofuran-3- yl)pyridin-2-yl)-1-methyl-1H-pyrrolo[2,3-c]pyridin-5-yl)acetamide

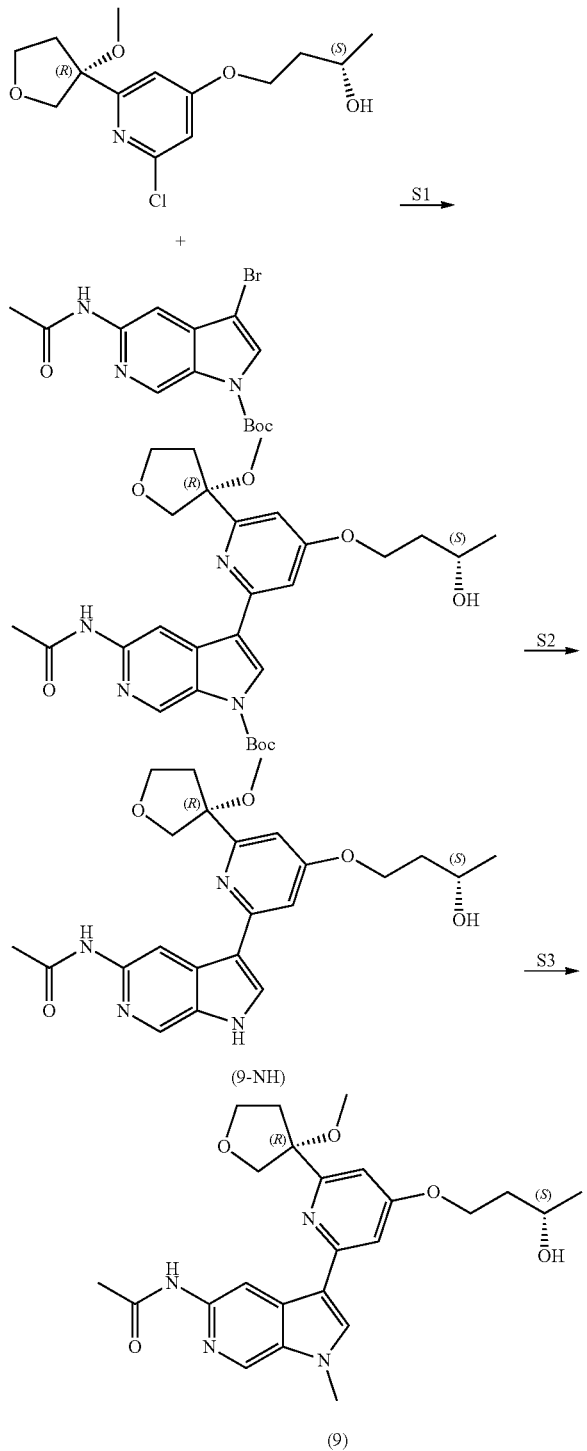

Step 1: tert-butyl 5-acetamido-3-(4-((S)-3-hydroxybutoxy)-6-((R)-3- methoxytetrahydrofuran-3-yl)pyridin-2-yl)-1H-pyrrolo[2,3-c]pyridine-1-carboxylate. Dioxane (1.9 mL) was degassed in a separate vial with a stream of nitrogen. In a reaction vial containing 4A molecular sieves, tert-butyl 5-acetamido-3-bromo-1H-pyrrolo[2,3-c]pyridine-1-carboxylate (269 mg, 0.759 mmol) (Preparation #1), potassium acetate (149 mg, 1.519 mmol), bis(pinacolato)diboron (386 mg, 1.519 mmol), and [1,1'-bis(diphenylphosphino)ferrocene]dichloropalladium(II)-dichloromethane adduct (Pd (dppf)Cl$_2$-DCM adduct) (46.5 mg, 0.057 mmol) were each added and then the vial was purged three times with an atmosphere of nitrogen. The dioxane was added to the vial and then it was heated to 95° C. for 2 hours. After conversion of the bromide to the boronate, the vial was cooled to room temperature. (S)-4-42-chloro-6(R)-3-methoxytetrahydrofuran-3-yl)pyridin-4-ypoxy)butan-2-ol (275 mg, 0.911 mmol) (Preparation#26) was dissolved in dioxane (1.3 mL) and degassed under a stream of nitrogen. Potassium phosphate (322 mg, 1.519 mmol), tris(dibenzylideneacetone) dipalladium(0) (Pd$_2$(dba)$_3$) (20.86 mg, 0.023 mmol), (1S, 3R,5R,7S)-1,3,5,7-tetramethyl-8-phenyl-2,4,6-trioxa-8-phosphaadamantane (PaPH) (13. mg, 0.046 mmol), and water (524 µl) were added to the reaction flask, along with the solution of pyridine boronate in dioxane, the final mixture was degassed for 5 minutes and then heated to 80° C. for 1 hour. Upon conversion to the Suzuki product, the reaction was cooled to room temperature and then 5% aqueous cysteine solution (20 mL) and dichloromethane (DCM) (30 mL) were added and then the mixture was stirred for 30 minutes. Separated the layers and extracted the aqueous layer one more time with DCM. The combined organic layers were washed with water, brine, and dried over MgSO$_4$ and concentrated to provide a residue, which was purified via silica gel chromatography, eluting with 0-100% ethyl acetate:DCM, to provide the product (180 mg, 44% yield). LCMS (Table A, Method a) R$_t$=2.35 minutes; MS m/z: 655 (M+H)$^+$. $^1$H NMR (400 MHz, Dimethyl sulfoxide-d$_6$) δ 10.36 (s, $^1$H), 9.14 (s, 1H), 8.97 (d, J=1.2 Hz, 1H), 8.58 (d, J=1.5 Hz, 1H), 7.52 (d, J=2.1 Hz, 1H), 6.93 (d, J=2.1 Hz, 1H), 4.57 (d, J=4.9 Hz, 1H), 4.28-4.13 (m, 3H), 3.95-3.92 (m, 1H), 3.90-3.85 (m, 1H), 3.85- 3.78 (m, 0H), 3.10 (d, J=1.5 Hz, 3H), 2.77-2.65 (m, 2H), 2.45-2.38 (m, 2H), 2.08 (d, J=1.4 Hz, 3H), 1.65 (d, J=1.4 Hz, 9H), 1.12 (d, J=4.5 Hz, 2H).

Step 2: N-(3-(4-((S)-3-hydroxybutoxy)-6-((R)-3-methoxytetrahydrofuran-3- yl)pyridin-2-yl)-1H-pyrrolo[2,3-c]pyridin-5-yl)acetamide. tert-Butyl 5-acetamido-3-(4-(S)-3- hydroxybutoxy)-6-((R)-3-methoxytetrahydrofuran-3-yl)pyridin-2-yl)-1H-pyrrolo[2,3-c]pyridine-1- carboxylate (180 mg, 0.333 mmol) was dissolved in ethanol (1.6 mL), stirred and heated to about 130° C. for about 30 minutes in a microwave vial. The reaction was then concentrated to dryness to provide the product (145mg, 99% yield) LCMS (Table A, Method b) R$_t$=0.86 minutes; MS m/z: 441 (M+H)$^+$.

Step 3: N-(3-(4-((S)-3-hydroxybutoxy)-6-((R)-3-methoxytetrahydrofuran-3- yl)pyridin-2-yl)-1-methyl-1H-pyrrolo[2,3-c]pyridin-5-yl)acetamide. Cesium carbonate (161 mg, 0.494 mmol) and iodomethane (22.64 µl, 362 mmol) were added to a reaction vial containing N-(3-(4-((S)-3-hydroxybutoxy)-6-4R)-3-methoxytetrahydrofuran-3-yppyridin-2-yl)-1H-pyrrolo[2,3- c]pyridin-5-ypacetamide (145mg, 0.329 mmol) dissolved in acetonitrile (3.3 mL), and the reaction was stirred at room temperature for 2 hours. The reaction was diluted with water and then extracted two times with 10% methanol/dichloromethane (MeOH/DCM) solution. The organic layers were dried over MgSO$_4$ and concentrated to dryness to provide a residue, which was purified via silica gel chromatography, eluting with 0-10% MeOH/DCM, to provide the product (45mg, 30% yield) LC/MS (Table A, Method d) R$_t$=0.95 minutes;

MS m/z: 455 (M+H)+. 1H NMR (400 MHz, Dimethyl sulfoxide-d6) δ 10.13 (s, 1H), 9.01 (s, 1H), 8.57 (d, J=1.0 Hz, 1H), 8.29 (d, J=0.7 Hz, 1H), 7.22 (dd, J=2.2, 0.8 Hz, 1H), 6.78 (dd, J =2.2, 0.8 Hz, 1H), 4.57 (dd, J=4.9, 0.8 Hz, 1H), 4.26-4.08 (m, 4H), 4.07-3.92 (m, 2H), 3.89 (d, J=0.8 Hz, 4H), 3.89-3.85 (m, 2H), 3.10 (d, J=0.8 Hz, 4H), 2.74 (dt, J=13.2, 8.7 Hz, 1H), 2.39 (dd, J=12.4, 6.1 Hz, 1H), 2.06 (d, J=0.8 Hz, 4H), 1.87-1.71 (m, 2H), 1.12 (dd, J=6.2, 0.8 Hz, 3H).

63. Example #10: (R)-N-(3-(4-(2-Hydroxyethoxy)-6-(3-methoxytetrahydrofuran-3- yl)pyridin-2-yl)-1-methyl-1H-pyrrolo[2,3-c]pyridin-5-yl)acetamide

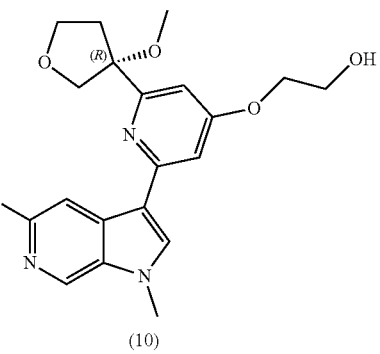

(10)

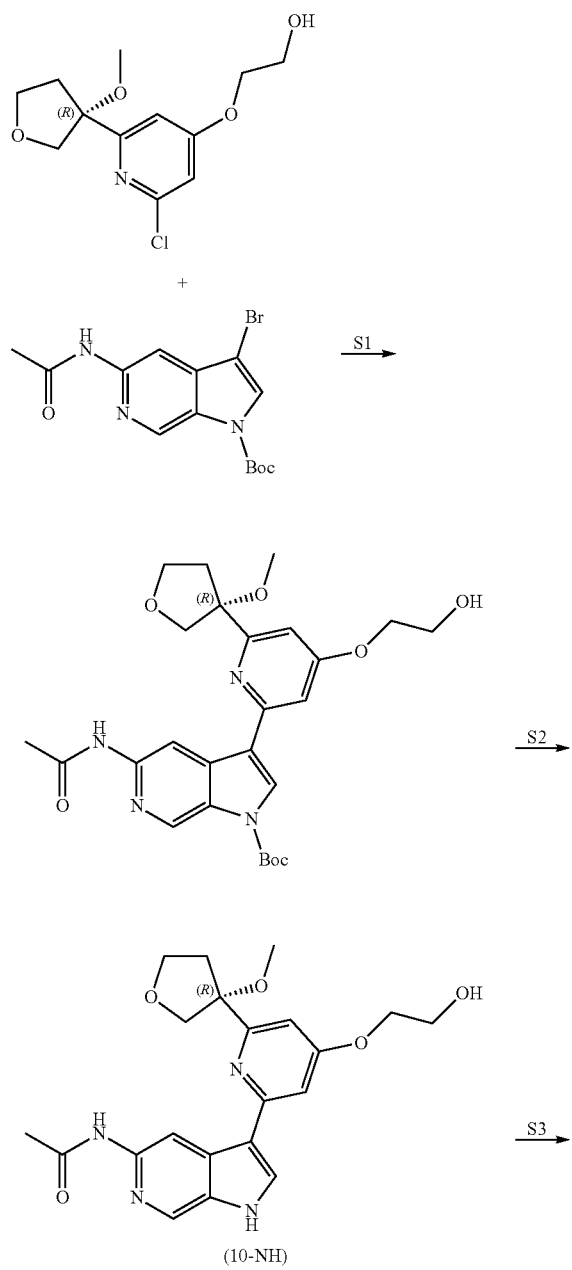

Step 1: (R)-tert-butyl 5-acetamido-3-(4-(2-hydroxyethoxy)-6-(3- methoxytetrahydrofuran-3-yl)pyridin-2-yl)-1H-pyrrolo[2,3-c]pyridine-1-carboxylate. A solution of tert-butyl 5-acetamido-3-bromo-1H-pyrrolo[2,3-c]pyridine-1-carboxylate (0.571 g, 1.611 mmol) (Preparation #1), bis(pinacolato)diboron (0.584 g, 2.302 mmol), potassium acetate (0.376 g, 3.84 mmol), and 4 Å molecular sieves in dioxane (13 mL) was sparged with nitrogen for 30 minutes before adding [1,1'-bis(diphenylphosphino)ferrocene]dichloropalladium(II)-dichloromethane adduct (Pd(dppf)Cl₂- DCM adduct) (0.125 g, 0.153 mmol). The reaction was heated to 95° C. for 2 hours and was filtered through a pad of Celite®, and rinsed with dioxane. To this dioxane solution was added (R)-2-42-chloro- 6-(3-methoxytetrahydrofuran-3-yl)pyridin-4-yl)oxy)ethanol (0.420 g, 1.534 mmol) (Preparation #27), potassium phosphate (0.977 g, 4.60 mmol), and water (1.534 mL). The mixture was sparged for 30 minutes with nitrogen before adding (1S,3R,5R,7S)-1,3,5,7-tetramethyl-8-phenyl-2,4,6-trioxa-8- phosphaadamantane (PaPH) (0.027 g, 0.092 mmol) and tris(dibenzylideneacetone)dipalladium(0) (Pd₂(dba)₃) (0.042 g, 0.046 mmol). The reaction was sealed and heated to 80° C. for 2 hours. The reaction was cooled and filtered through a pad of Celite®, washed with water, and extracted with ethyl acetate. The combined organic layers were dried and concentrated under reduced pressure to provide a residue, which was purified via silica gel chromatography, eluting with 0-15% methanol/dichloromethane, to provide the product (0.513g, 65% yield). LCMS (Table A, Method a) R$_t$=1.23 minutes; MS m/z: 513.3 (M+H)+.

Step 2: (R)-N-(3-(4-(2-hydroxyethoxy)-6-(3-methoxytetrahydrofuran-3-yl)pyridin-2- yl)-1H-pyrrolo[2,3-c]pyridin-5-yl)acetamide. A solution of (R)-tert-butyl 5-acetamido-3-(4-(2- hydroxyethoxy)-6-(3-methoxytetrahydrofuran-3-yl)pyridin-2-yl)-1H-pyrrolo[2,3-c]pyridine-1- carboxylate (0.514 g, 1.003 mmol) in ethanol (3.3 mL) was heated in the microwave for 20 minutes at 150° C. The reaction was then concentrated under reduced pressure to provide the product (0.415 g, 100% yield). LCMS (Table A, Method a) R$_t$=0.67 minutes; MS m/z: 413.3 (M+H)+.

Step 3: (R)-N-(3-(4-(2-hydroxyethoxy)-6-(3-methoxytetrahydrofuran-3-yl)pyridin-2- yl)-1-methyl-1H-pyrrolo[2,3-c]pyridin-5-yl)acetamide. A solution of (R)-N-(3-(4-(2-hydroxyethoxy)-6-(3-methoxytetrahydrofuran-3-yl)pyridin-2-yl)-1H-pyrrolo [2,3-c]pyridin-5- yl)acetamide (0.415 g, 1.005 mmol) in acetonitrile (10.05 mL) was treated with cesium carbonate (0.491 g, 1.508 mmol) followed by iodomethane (0.069 mL, 1.106 mmol). The reaction was allowed to stir at room temperature for 2 hours. The reaction was quenched with water, extracted with ethyl acetate, dried, and concentrated to provide a residue, which was purified via silica gel chromatography, eluting with 0 to 15% methanol/dichloromethane, to provide the product (0.198 g, 46% yield). LCMS (Table A, Method c) $R_f$=0.81 minutes; MS m/z: 427.3 (M+H)$^+$. $^1$H NMR (400 MHz, Dimethyl sulfoxide-d$_6$) δ 10.17 (s, 1H), 9.04 (s, 1H), 8.61 (d, J=1.0 Hz, 1H), 8.32 (s, 1H), 7.26 (d, J =2.2 Hz, 1H), 6.83 (d, J=2.2 Hz, 1H), 4.95-4.88 (m, 1H), 4.20-4.11 (m, 3H), 4.07-4.01 (m, 1H), 3.98 (td, J=8.2, 6.9 Hz, 1H), 3.93 (s, 3H), 3.91 (d, J=9.6 Hz, 1H), 3.78 (q, J=5.3 Hz, 2H), 3.13 (s, 3H), 2.77 (dt, J=13.1, 8.6 Hz, 1H), 2.47-2.37 (m, 1H), 2.09 (s, 3H).

64. Example #11 and #11a : N-(3-(4-((trans)-3-Hydroxycyclobutoxy)-6-((R)-3- methoxytetrahydrofuran-3-yl)pyridin-2-yl)-1-methyl-1H-pyrrolo[2,3-c] pyridin-5-yl)acetamide and N-(3-(4-((trans)-3-hydroxycyclobutoxy)-6((S)-3-methoxytetrahydrofuran-3-yl)pyridin-2- yl)-1-methyl-1H-pyrrolo[2,3-c]pyridin-5-yl)acetamide

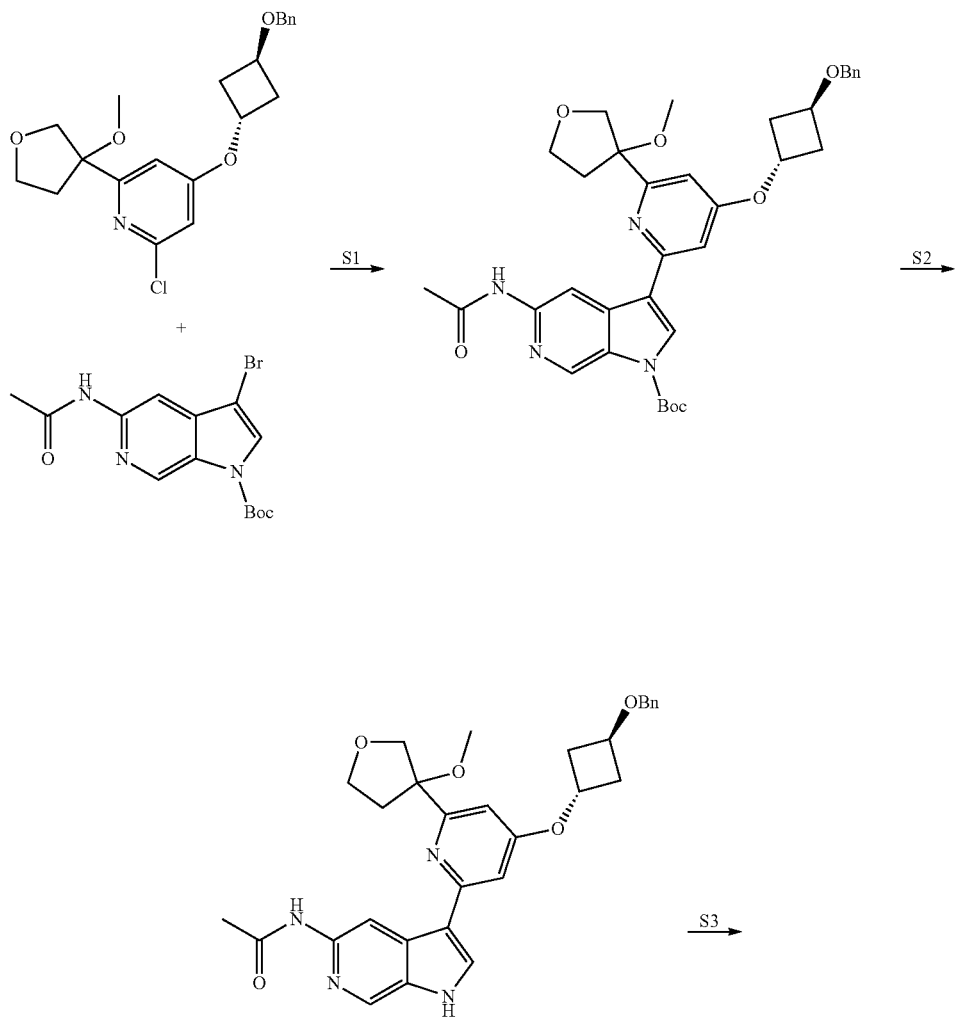

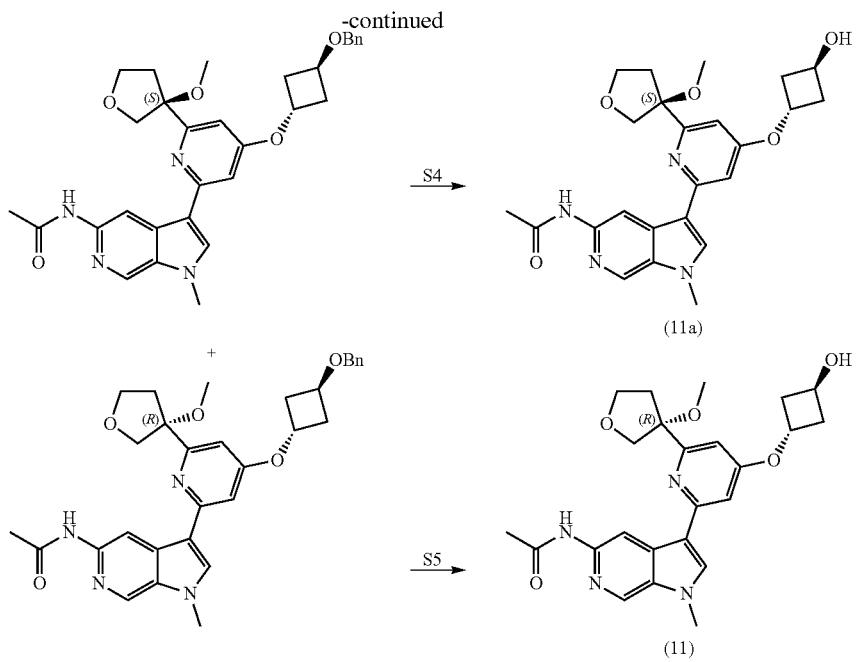

Step 1: tert-butyl 5-acetamido-3-(4-((trans)-3-(benzyloxy)cyclobutoxy)-6-(3-methoxytetrahydrofuran-3-yl)pyridin-2-yl)-1H-pyrrolo[2,3-c]pyridine-1-carboxylate. In a reaction vial, tert-butyl 5-acetamido-3-bromo-1H-pyrrolo[2,3-c]pyridine-1-carboxylate (0.492 g, 1.389 mmol) (Preparation #1), B$_2$(Pin)$_2$ (bis(pinacolato)diboron) (0.529 g, 2.084 mmol), and potassium acetate (0.273 g, 2.78 mmol) in dioxane (12 mL) were added to give a brown solution. Added 4 Å molecular sieves and sparged with nitrogen for 30 minutes, then [1,1'-bis(diphenylphosphino)ferrocene]dichloropalladium(II)-dichloromethane adduct (Pd(dppf)Cl$_2$-DCM adduct) (0.170 g, 0.208 mmol) was added and mixture was heated at 95° C. for 7 hours. The mixture was cooled to room temperature and was filtered through a pad of Celite®, washing with dioxane. 4-((trans)-3-(Benzyloxy)cyclobutoxy)-2-chloro-6-(3-methoxytetrahydrofuran-3-yl)pyridine (0.650 g, 1.667 mmol) (Preparation #28), potassium phosphate (0.295 g, 1.389 mmol) and water (1.2 mL) were added, and the mixture was sparged with nitrogen for 15 minutes. (1S,3R,5R,7 S)-1,3,5,7-tetramethyl-8-phenyl-2,4,6-trioxa-8-phosphaadamantane (PaPH) (0.041 g, 0.139 mmol) and tris(dibenzylideneacetone)dipalladium(0) (Pd$_2$(dba)$_3$) (0.064 g, 0.069 mmol) were added and the mixture was heated at 75° C. for 90 minutes. The reaction cooled to room temperature and was filtered through a pad of Celite®, washing with ethyl acetate. The filtrate was partitioned between water (30 mL) and ethyl acetate (50 mL), and the water layer was separated and further extracted with ethyl acetate (10 mL). Dried the combined organic layers over MgSO$_4$ and concentrated under reduced pressure to provide a residue, which was purified via silica gel chromatography, eluting with 10 to 100% ethyl acetate: heptanes, to provide the product (370 mg, 42% yield). LCMS (Table A, Method a) R$_t$=2.00 minutes; MS m/z: 629.32 (M+H)$^+$.

Step 2: N-(3-(4-((trans)-3-(benzyloxy)cyclobutoxy)-6-(3-methoxytetrahydrofuran-3-yl)pyridin-2-yl)-1H-pyrrolo[2,3-c]pyridin-5-yl)acetamide. In a round-bottomed flask tert-butyl 5-acetamido-3-(4-((trans)-3-(benzyloxy)cyclobutoxy)-6-(3-methoxytetrahydrofuran-3-yl)pyridin-2-yl)-1H-pyrrolo[2,3-c]pyridine-1-carboxylate (0.872 g, 1.708 mmol) in n-propanol (50 mL) was added to give a brown solution. The reaction was heated to 100° C. for 36 hours, which was then cooled to room temperature, and concentrated under reduced pressure to provide the product (296 mg, 87% yield). LCMS (Table A, Method a) R$_t$=1.45 minutes; MS m/z: 529.16 (M+H)$^+$.

Step 3: N-(3-(4-((trans)-3-(benzyloxy)cyclobutoxy)-6-((R)-3-methoxytetrahydrofuran-3-yl)pyridin-2-yl)-1-methyl-1H-pyrrolo[2,3-c]pyridin-5-yl)acetamide and N-(3-(4-((trans)-3-(benzyloxy)cyclobutoxy)-6-((S)-3-methoxytetrahydrofuran-3-yOpyridin-2-yl)-1-methyl-1H-pyrrolo[2,3-c]pyridin-5-yl)acetamide. In a reaction vial, N-(3-(4-((trans)-3-(benzyloxy)cyclobutoxy)-6-(3-methoxytetrahy dr ofuran-3-yOpyridin-2-yl)-1H-pyrrolo[2,3-c]pyridin-5-yl)acetamide (0.296 g, 0.560 mmol), cesium carbonate (0.049 mL, 0.616 mmol), and iodomethane (0.070 mL, 1.120 mmol) in acetonitrile (10 mL) were added to give a brown solution. The reaction stirred at room temperature for 16 hours. The reaction mixture was partitioned between water and ethyl acetate. Separated the layers and extracted with ethyl acetate. Dried the combined organic layers over MgSO$_4$, filtered, and concentrated to provide a residue, which was purified via silica gel chromatography, eluting 10 to 100% ethyl acetate/heptanes then increased to 10% methanol/dichloromethane, to give a racemic product (0.255 g). The product was further purified via chiral HPLC (Table 2, Method 11) to provide the R-isomer (0.069 g, 23% yield, >99%ee, R$_t$=20.48 minutes) and the S-isomer (0.070 g, 22% yield, >99%ee, R$_t$ =16.45 minutes). LCMS (Table A, Method a) R$_t$=1.56 minutes; MS m/z: 543.16 (M+H)$^+$.

Step 4: N-(3-(4-((trans)-3-hydroxycyclobutoxy)-6-((S)-3-methoxytetrahydrofuran-3-yl)pyridin-2-yl)-1-methyl-1H-pyrrolo[2,3-c]pyridin-5-ypacetamide. In a stainless steel hydrogenation vessel purged with nitrogen, palladium hydroxide (0.014 g, 0.013 mmol) was added followed by a solution of N-(3-(4-((trans)-3-(benzyloxy)cyclobutoxy)-6-((S)-3-methoxytetrahydrofuran-3-yl)pyridin-2-yl)-1-methyl-1H-pyrrolo[2,3-c]pyridin-5-ypacetamide (0.070 g, 0.129 mmol) in methanol (25 mL) and the mixture was hydrogenated at 60 psi (H₂ gas) at 80° C. for 5 hours. The reaction mixture was filtered through a pad of Celite® over nitrogen, washing with methanol, and the solvent was concentrated to provide the S-isomeric product (0.028 g, 45% yield). LCMS (Table A, Method d) R$_t$=0.90 minutes; MS m/z: 453.23 (M+H)⁺. ¹H NMR (400 MHz, Dimethyl sulfoxide-d₆) δ 10.18 (s, 1H), 9.01 (s, 1H), 8.61 (d, J=1.1 Hz, 1H), 8.31 (s, 1H), 7.08 (d, J=2.2 Hz, 1H), 6.70 (d, J=2.2 Hz, 1H), 5.22 (d, J=5.3 Hz, 1H), 5.02 (p, J=5.5 Hz, 1H), 4.41 (q, J=6.1 Hz, 1H), 4.14 (dd, J=9.7, 1.2 Hz, 1H), 4.07 -3.94 (m, 2H), 3.93 (s, 3H), 3.90 (d, J =9.6 Hz, 1H), 3.13 (s, 3H), 2.77 (dt, J =13.3, 8.7 Hz, 1H), 2.47-2.32 (m, 6H), 2.10 (s, 3H).

Step 5: N-(3-(4-((trans)-3-hydroxycyclobutoxy)-6-((R)-3-methoxytetrahydrofuran-3-yl)pyridin-2-yl)-1-methyl-1H-pyrrolo[2,3-c]pyridin-5-yl)acetamide. In a stainless steel hydrogenation vessel purged with nitrogen, palladium hydroxide (9.06 mg, 0.013 mmol) was added followed by a solution of N-(3-(4-((trans)-3-(benzyloxy)cyclobutoxy)-6 (R)-3-methoxytetrahydrofuran-3-yl)pyridin-2-yl)-1-methyl-1H-pyrrolo[2,3-c]pyridin-5-yl)acetamide (0.070 g, 0.129 mmol) in methanol (25 mL) and the mixture was hydrogenated at 60 psi (H₂ gas) at 80° C. for 5 hours. The reaction mixture was then filtered through a pad of Celite® over nitrogen, washing with methanol, and the solvent was concentrated to provide the R-isomeric product (0.037 g, 61% yield). LCMS (Table A, Method d) R$_t$=0.90 minutes; MS m/z: 453.23 (M+H)⁺. ¹H NMR (400 MHz, Dimethyl sulfoxide-d₆) δ 10.18 (s, 1H), 9.01 (s, 1H), 8.61 (d, J=1.1 Hz, 1H), 8.31 (s, 1H), 7.08 (d, J=2.2 Hz, 1H), 6.70 (d, J=2.2 Hz, 1H), 5.22 (d, J=5.3 Hz, 1H), 5.02 (p, J=5.5 Hz, 1H), 4.41 (q, J=6.1 Hz, 1H), 4.14 (dd, J=9.7, 1.2 Hz, 1H), 4.07-3.94 (m, 2H), 3.93 (s, 3H), 3.90 (d, J=9.6 Hz, 1H), 3.13 (s, 3H), 2.77 (dt, J =13.3, 8.7 Hz, 1H), 2.47-2.32 (m, 6H), 2.10 (s, 3H).

The compound shown in Table 11 were synthesized in a manner similar to Example #11 from tert-butyl 5-acetamido-3-bromo-1H-pyrrolo[2,3-c]pyridine-l-carboxylate (Preparation #1) and the corresponding aromatic halide followed by Example #11 Steps 2-5.

TABLE 11

| Ex | Aromatic Halide | Product | R$_t$, min (Method) | m/z (M + H)⁺ |
|---|---|---|---|---|
| 11.2 | 4-((cis)-3-(benzyloxy)cyclobutoxy)-2-chloro-6-((R)-3-methoxytetrahydrofuran-3-yl)pyridine (Preparation #41) | N-(3-(4-((cis)-3-hydroxycyclobutoxy)-6-((R)-3-methoxytetrahydrofuran-3-yl)pyridin-2-yl)-1-methyl-1H-pyrrolo[2,3-c]pyridin-5-yl)acetamide | 0.88 (d) | 453 |

65. Example #12: (R)-1-(3-(6-(3-Methoxytetrahydrofuran-3-yl)pyrazin-2-yl)-1-methyl-1H- pyrrolo[2,3-c]pyridin-5-yl)urea

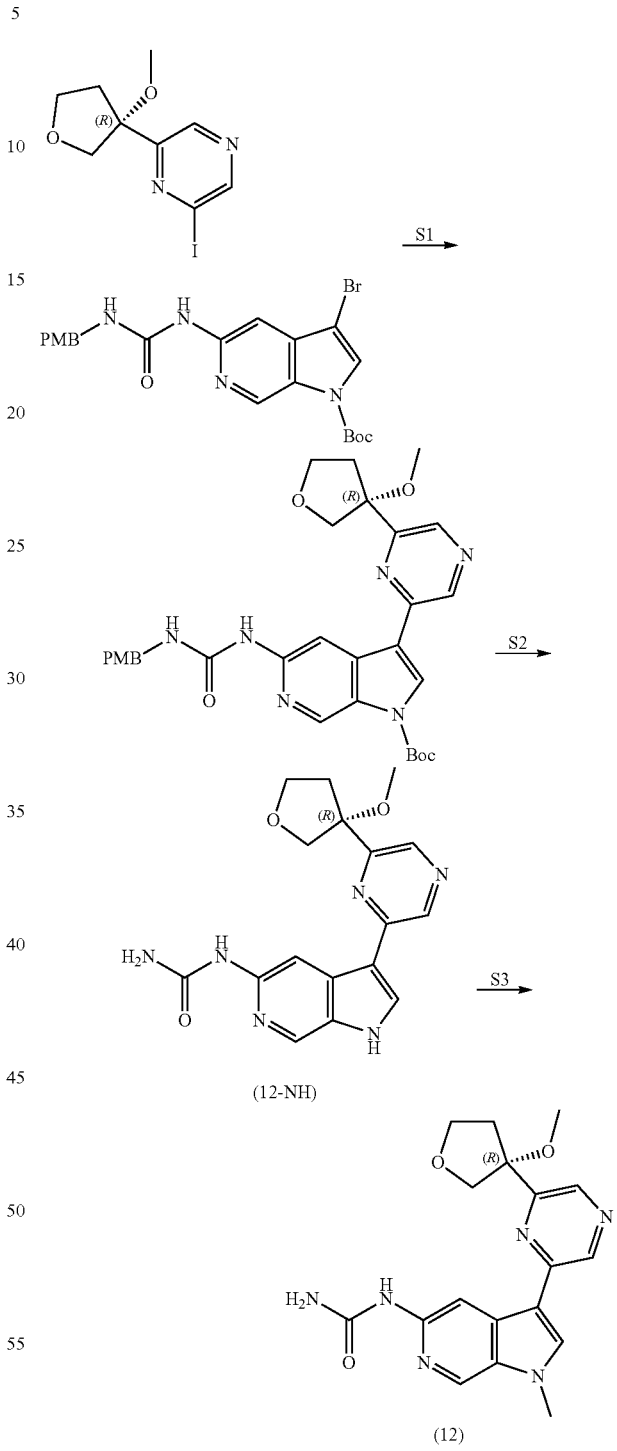

Step 1: (R)-tert-butyl 5-(3-(4-methoxybenzyl)ureido)-3-(6-(3-methoxytetrahydrofuran- 3-yl)pyrazin-2-yl)-1H-pyrrolo[2,3-c]pyridine-1-carboxylate. A mixture of tert-butyl 3-bromo-5- (3-(4-methoxybenzyl)ureido)-1H-pyrrolo[2,3-c]pyridine-1-carboxylate (0.625 g, 1.315 mmol) (Preparation #12), bis(pinacolato)diboron (0.501 g, 1.972 mmol), and potassium acetate (0.258 g, 2.63 mmol) in dioxane (4.98 mL) with 4Å molecular sieves was purged with nitrogen for about 15 minutes. Added [1,1/-Bis(diphenylphosphino)ferrocene]dichloropalladium(II)-dichloromethane adduct (Pd(dppf)Cl$_2$-DCM adduct) (0.081 g, 0.099 mmol), then heated at about 95° C. for about 2 hours. The reaction mixture was filtered over Celite® into new flask and rinsed with dioxane (4.98 mL). To the filtrate was added (R)-2-iodo-6-(3-methoxytetrahydrofuran-3-yl)pyrazine (0.443 g, 1.446 mmol) (Preparation #19), potassium phosphate (0.558 g, 2.63 mmol), and water (0.996 mL). Degassed the mixture for about 20 minutes then added [1,1'-bis(diphenylphosphino)ferrocene] dichloropalladium(II)- dichloromethane adduct (Pd(dppf)Cl$_2$-DCM adduct) (0.081 g, 0.099 mmol). The reaction was heated to about 85° C. for about 20 minutes. Cooled the reaction to room temperature, degassed with nitrogen and added tris(dibenzylideneacetone)dipalladium(0) (Pd$_2$(dba)$_3$) (0.036 g, 0.039 mmol) and (1S,3R,5R,7S)- 1,3,5,7-tetramethyl-8-phenyl-2,4,6-trioxa-8-phosphaadamantane (PaPH) (0.023 g, 0.079 mmol). Heated the reaction to about 85° C. for about 15 minutes. Added an additional 150 mg more of (R)-2- iodo-6-(3-methoxytetrahydrofuran-3-yl)pyrazine and continued heating at about 85° C. for 1 hour. Removed the reaction from heat and cooled to room temperature. Added 80 mL of 5% aqueous cysteine/NaHCO$_3$ solution and extracted into 10% methanol/dichloromethane (MeOH/DCM) (120 mL). Separated the organic layers, dried over MgSO$_4$, filtered and concentrated under reduced pressure to provide a residue, which was purified via silica gel chromatography, eluting with 0-5% MeOH/DCM then increased gradient to 5-10% MeOH/DCM, to provide the product (0.970 g, 89% yield). LC/MS (Table A, Method a) R$_t$=1.72 minutes; MS m/z: 575 (M+H)$^+$. PMB =4-methoxybenzyl; Boc=t-Butoxycarbonyl.

Step 2: (R)-1-(3-(6-(3-methoxytetrahydrofuran-3-yl)pyrazin-2-yl)-1H-pyrrolo[2,3- c]pyridin-5-yOurea. To a solution of (R)-tert-butyl 5-(3-(4-methoxybenzypureido)-3-(6-(3- methoxytetrahydrofuran-3-yl)pyrazin-2-yl)-1H-pyrrolo[2,3-c]pyridine-1-carboxylate (0.970 g, 1.165 mmol) in dichloroethane (3.88 mL) was added trifluoroacetic acid (TFA) (1.346 mL, 17.47 mmol). Heated the reaction to about 75° C. for about 23 hours. Added more TFA (0.449 mL, 5.82 mmol) and heated to about 75° C. for an additional 2 hours. Quenched the reaction with saturated aqueous NaHCO$_3$ until aqueous solution was slightly basic and extracted with a 10% methanol/dichloromethane solution. Dried the organic layers over MgSO$_4$, and filtered to provide a filtrate. Dissolved the MgSO$_4$ in water and filtered to get more filtrate. Combined the two filtrates and reduced volume down to provide a residue in about a 25 mL solution, which was then purified via reverse HPLC, eluting with 10-50% acetonitrile/water (10mM ammonium acetate buffer), to provide the product (0.124 g, 30% yield). LC/MS (Table A, Method a) R$_t$=0.63 minutes; MS m/z: 355 (M+H)$^+$.

Step 3: (R)-1-(3-(6-(3-methoxytetrahydrofuran-3-yl)pyrazin-2-yl))-1-methyl-1H- pyrrolo[2,3-c]pyridin-5-yl)urea. To a mixture of (R)-1-(3-(6-(3-methoxytetrahydrofuran-3- yl)pyrazin-2-yl))-1H-pyrrolo[2,3-c]pyridin-5-yOurea (0.064 g, 0.181 mmol) and cesium carbonate (0.118 g, 0.361 mmol) in acetonitrile (2.258 mL) was added iodomethane (0.012 mL, 0.199 mmol). The reaction stirred at room temperature for about 3.5 hours. Added more iodomethane (4.52 µL, 0.072 mmol) and continued stirring at room temperature for about 16 hours. The reaction was quenched with water, ethyl acetate was added, and the organic layers were removed under reduced pressure, to provide a residue, which was then purified via reverse HPLC, eluting with 10-65% acetonitrile/water (10mM ammonium acetate buffer), to provide the product (0.045 g, 61% yield). LC/MS (Table A, Method d) R$_t$=0.74 minutes; MS m/z: 369 (M+H)$^+$. $^1$H NMR (400 MHz, Dimethyl sulfoxide-d$_6$) δ 8.98 (s, 1H), 8.91 (s, 1H), 8.57 (d, J=1.1 Hz, 1H), 8.51 (s, 1H), 8.46 (s, 2H), 6.58 (s, 2H), 4.28 (dd, J=9.8, 1.3 Hz, 1H), 4.13-3.98 (m, 2H), 3.98-3.87 (m, 4H), 3.16 (s, 3H), 2.71 (dt, J=13.2, 8.6 Hz, 1H), 2.62-2.51 (m, 1H).

The compounds shown in Table 12a were synthesized in a manner similar to Example #12 from tert-butyl 3-bromo-5-(3-(4-methoxybenzyl)ureido)-1H-pyrrolo[2,3-c]pyridine-1-carboxylate (Preparation #12) and the corresponding aromatic halide followed by Example #12, Step 2 and Step 3.

TABLE 12a

| Ex | Aromatic Halide | Product | R$_t$ min (Method) | m/z (M + H)$^+$ |
|---|---|---|---|---|
| 12.2 | (S)-2-chloro-6-(3-methoxytetrahydrofuran-3-yl)isonicotinonitrile (Preparation #9a) | (S)-1-(3-(4-cyano-6-(3-methoxytetrahydrofuran-3-yl)pyridin-2-yl)-1-methyl-1H-pyrrolo[2,3-c]pyridin-5-yl)urea | 0.96 (d) | 393 |
| 12.3 | (R)-2-chloro-6-(3-methoxytetrahydrofuran-3-yl)isonicotinonitrile (Preparation #9) | (R)-1-(3-(4-cyano-6-(3-methoxytetrahydrofuran-3-yl)pyridin-2-yl)-1-methyl-1H-pyrrolo[2,3-c]pyridin-5-yl)urea | 0.96 (d) | 393 |
| 12.4 | (S)-2-bromo-4-(methoxymethyl)-6-(3-methoxytetrahydrofuran-3-yl)pyridine (Preparation #6a) | (S)-1-(3-(4-(methoxymethyl)-6-(3-methoxytetrahydrofuran-3-yl)pyridin-2-yl)-1-methyl-1H-pyrrolo[2,3-c]pyridin-5-yl)urea | 0.89 (d) | 412 |
| 12.5 | (R)-2-bromo-4-(difluoromethyl)-6-(3-methoxytetrahydrofuran-3-yl)pyridine (Preparation #18) | (R)-1-(3-(4-(difluoromethyl)-6-(3-methoxytetrahydrofuran-3-yl)pyridin-2-yl)-1-methyl-1H-pyrrolo[2,3-c]pyridin-5-yl)urea | 1.04 (d) | 418 |
| 12.6 | (R)-2-chloro-4-methoxy-6-(3-methoxytetrahydrofuran-3-yl)pyridine (Preparation #22) | (R)-1-(3-(4-methoxy-6-(3-methoxytetrahydrofuran-3-yl)pyridin-2-yl)-1-methyl-1H-pyrrolo[2,3-c]pyridin-5-yl)urea | 0.93 (d) | 398 |
| 12.7 | (S)-2-chloro-4-methoxy-6-(3-methoxytetrahydrofuran-3-yl)pyridine (Preparation #22a) | (S)-1-(3-(4-methoxy-6-(3-methoxytetrahydrofuran-3-yl)pyridin-2-yl)-1-methyl-1H-pyrrolo[2,3-c]pyridin-5-yl)urea | 0.93 (d) | 398 |

The compounds shown in Table 12b were synthesized in a manner similar to Example #12 from tert-butyl 3-bromo-5-(3-(4-methoxybenzyl)ureido)-1H-pyrrolo[2,3-c]pyridine-1-carboxylate (Preparation #12) and the corresponding aromatic halide followed by Example #12, Step 2 and Step 3 using 2,2-difluorocyclopropyl 4-methylbenzenesulfonate (Preparation #32). The product was purified via chiral SFC using Table 2, Method 17.

TABLE 12b

| Ex | Aromatic Halide | Product | R$_t$ min (Method) | m/z (M + H)$^+$ |
|---|---|---|---|---|
| 12a.2 | (R)-2-chloro-6-(3-methoxytetrahydrofuran-3-yl)isonicotinonitrile (Preparation #9) | 1-(3-(4-cyano-6-((R)-3-methoxytetrahydrofuran-3-yl)pyridin-2-yl)-1-((S)-2,2-difluorocyclopropyl)-1H-pyrrolo[2,3-c]pyridin-5-yl)urea | 1.19 (d) 5.9 (17) | 455 |
| 12a.3 | (R)-2-chloro-6-(3-methoxytetrahydrofuran-3-yl)isonicotinonitrile (Preparation #9) | 1-(3-(4-cyano-6-((R)-3-methoxytetrahydrofuran-3-yl)pyridin-2-yl)-1-((R)-2,2-difluorocyclopropyl)-1H-pyrrolo[2,3-c]pyridin-5-yl)urea | 1.19 (d) 5.6 (17) | 455 |

The compounds shown in Table 12c were synthesized in a manner similar to Example #12 from tert-butyl 3-bromo-5-(3-(4-methoxybenzyl)ureido)-1H-pyrrolo[2,3-c]pyridine-1-carboxylate (Preparation #12) and the corresponding aromatic halide followed by Example #12, Step 2 and Step 3 using either (S)-tetrahydrofuran-3-yl methanesulfonate (Preparation #30), (R)-tetrahydrofuran-3-yl methanesulfonate (Preparation #35), or 3-iodooxetane.

TABLE 12c

| Ex | Aromatic Halide | Product | R$_t$ min (Method) | m/z (M + H)$^+$ |
|---|---|---|---|---|
| 12b.2 | (R)-2-bromo-4-(difluoromethyl)-6-(3-methoxytetrahydrofuran-3-yl)pyridine (Preparation #18) | 1-(3-(4-(difluoromethyl)-6-((R)-3-methoxytetrahydrofuran-3-yl)pyridin-2-yl)-1-((R)-tetrahydrofuran-3-yl)-1H-pyrrolo[2,3-c]pyridin-5-yl)urea | 1.08 (d) | 474 |
| 12b.3 | (R)-2-bromo-4-(difluoromethyl)-6-(3-methoxytetrahydrofuran-3-yl)pyridine (Preparation #18) | 1-(3-(4-(difluoromethyl)-6-((R)-3-methoxytetrahydrofuran-3-yl)pyridin-2-yl)-1-((S)-tetrahydrofuran-3-yl)-1H-pyrrolo[2,3-c]pyridin-5-yl)urea | 1.08 (d) | 474 |
| 12b.4 | (R)-2-bromo-4-(difluoromethyl)-6-(3-methoxytetrahydrofuran-3-yl)pyridine (Preparation #18) | (R)-1-(3-(4-(difluoromethyl)-6-(3-methoxytetrahydrofuran-3-yl)pyridin-2-yl)-1-(oxetan-3-yl)-1H-pyrrolo[2,3-c]pyridin-5-yl)urea | 1.02 (d) | 460 |

66. Example #13: 1-(1-methyl-3-(6-(oxetan-3-yl)pyridin-2-yl)-1H-pyrrolo[2,3-c]pyridin-5-yl)urea

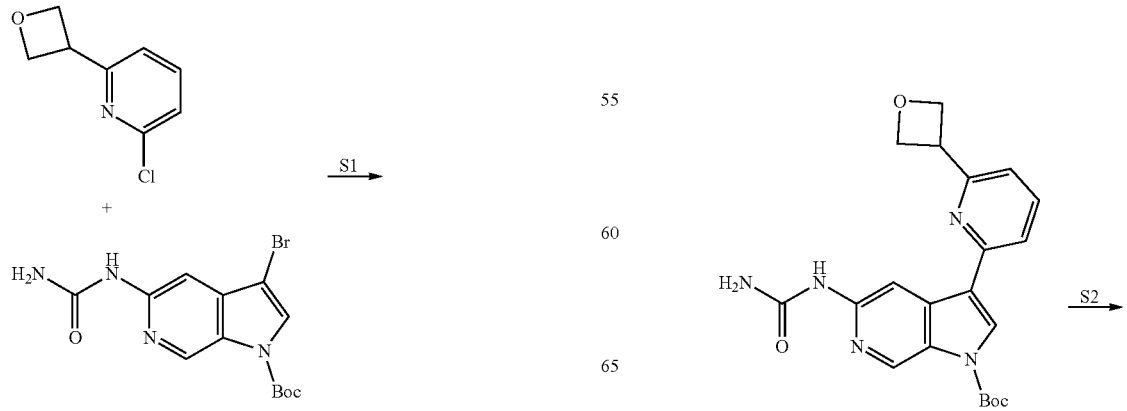

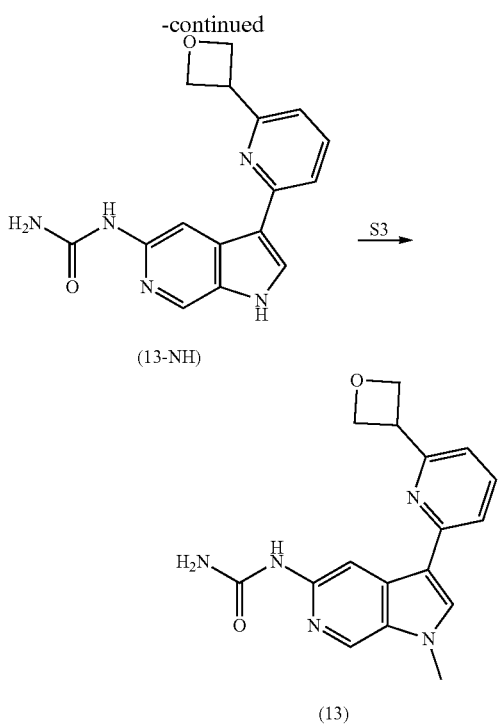

Step 1: tert-butyl 3-(6-(oxetan-3-yl)pyridin-2-yl)-5-ureido-1H-pyrrolo[2,3-c]pyridine-1-carboxylate. A solution of tert-butyl 3-bromo-5-ureido-1H-pyrrolo[2,3-c]pyridine-1-carboxylate (0.5 g, 1.408 mmol) (Preparation #4), bis(pinacolato)diboron (0.536 g, 2.112 mmol), and potassium acetate (0.414 g, 4.22 mmol) in dioxane (14.0 mL) with 4 Å molecular sieves was purged with nitrogen for 15 minutes before adding [1,1¹-bis(diphenylphosphino)ferrocene]dichloropalladium(II)-dichloromethane adduct (Pd(dppf)Cl₂-DCM adduct) (0.115 g, 0.141 mmol). The reaction was sealed and heated to 100° C. for 4 hours. The heat was increased to 115° C., and stirred for 5 hours. The reaction was cooled, filtered over Celite®, and concentrated. The material was dissolved in dioxane (12.80 mL) and to this was added 2-chloro-6-(oxetan-3-yl)pyridine (0.299 g, 1.760 mmol) (Preparation #29), cesium carbonate (1.376 g, 4.22 mmol), and water (1.2 mL). The resulting solution was purged with nitrogen for 15 minutes before adding additional PdCl₂(dppf)-DCM adduct (0.115 g, 0.141 mmol). The reaction vessel was sealed and heated to 70° C. for 1 hour. The reaction was cooled to room temperature, and filtered over Celite®, rinsing with ethyl acetate, and stirred with 5% aqueous cysteine solution for 30 minutes before separating the layers, and then extracting the aqueous with ethyl acetate. The combined organic layers were dried over MgSO₄, filtered, and concentrated. The product was purified via silica gel chromatography, eluting with 0 to 25% methanol/ethyl acetate to provide the product (0.197 g, 34% yield). LC/MS (Table A, Method a) R$_t$=1.36 minutes; MS m/z: 409.9 (M+H)⁺.

Step 2: 1-(3-(6-(oxetan-3-yl)pyridin-2-yl)-1H-pyrrolo[2,3-c]pyridin-5-yl)urea. A solution of tert-butyl 3-(6-(oxetan-3-yl)pyridin-2-yl)-5-ureido-1H-pyrrolo[2,3]-dpyridine-1-carboxylate (0.190 g, 0.464 mmol) in dichloromethane (4.6 mL) at room temperature was treated with trifluoroacetic acid (0.358 mL, 4.64 mmol) and stirred for 3 hours at 40° C. The reaction was concentrated under reduced pressure to provide a residue, which was then sonicated with ethanol and concentrated to provide the product (0.1 g, 69% yield). LC/MS (Table A, Method a) R$_t$=0.67 minutes; MS m/z: 309.8 (M+H)⁺.

Step 3: 1-(1-methyl-3-(6-(oxetan-3-yl)pyridin-2-yl)-1H-pyrrolo[2,3-c]pyridin-5-yl)urea. A suspension of 1-(3-(6-(oxetan-3-yOpyridin-2-yl)-1H-pyrrolo[2,3-c]pyridin-5-yl)urea (0.096 g, 0.310 mmol) in acetonitrile (3.1 mL) was treated with cesium carbonate (0.202 g, 0.621 mmol), and dimethyl sulfate (0.029 mL, 0.310 mmol). The reaction was allowed to stir at 40° C. for 2 hours before a second addition of dimethyl sulfate and base was added. The reaction stirred another hour, and another portion of reagents was added, and the reaction was then heated to 50° C. for 16 hours. The reaction was quenched with water and extracted with 10% isopropyl alcohol/dichloromethane and the combined organic layers were dried over MgSO₄, and concentrated to provide a residue, which was purified via reverse HPLC, eluting with 0-95% of 0.1% aqueous ammonium acetate: acetonitrile, to provide the product (0.017g, 16% yield). LC/MS (Table A, Method d) R$_t$=0.77 minutes; MS m/z: 323.75 (M+H)⁺. ¹H NMR (400 MHz, Dimethyl sulfoxide-d₆) δ 8.83 (s, 1H), 8.53 (d, J=1.1 Hz, 1H), 8.46 (s, 1H), 8.24 (s, 1H), 7.76 (t, J=7.8 Hz, 1H), 7.59 (d, J=7.8 Hz, 1H), 7.09 (d, J=7.5 Hz, 1H), 6.61 (d, J=45.3 Hz, 2H), 5.02-4.88 (m, 4H), 4.46 (p, J=7.7 Hz, 1H), 3.91 (s, 3H).

67. Example #14: 1-(3-(6-(3-hydroxyoxetan-3-yl)pyridin-2-yl)-1-methyl-1H-pyrrolo[2,3-c]pyridin-5-yl)urea

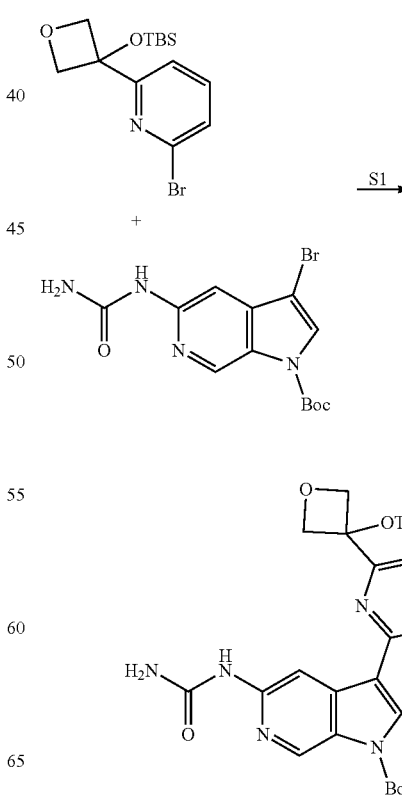

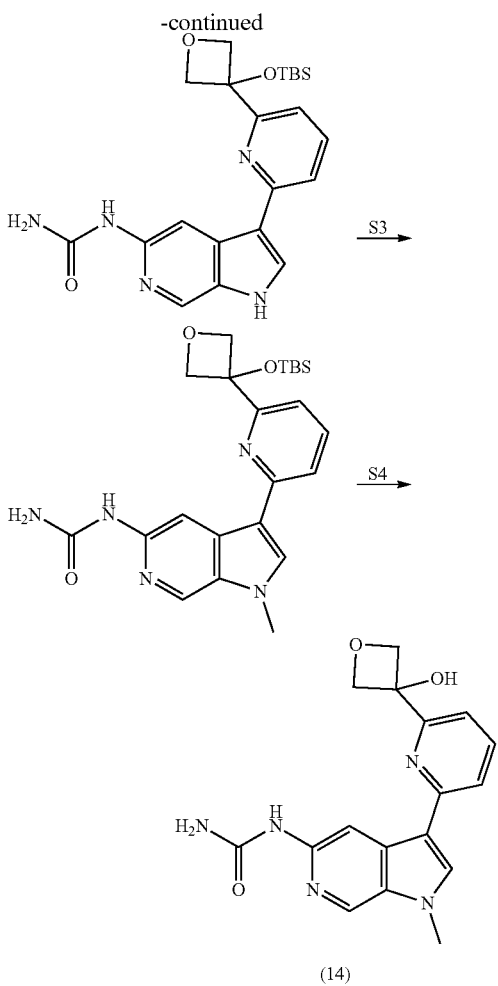

(14)

Step 1: tert-butyl 3-(6-(3-((tert-butyldimethylsilypoxy)oxetan-3-yl)pyridin-2-yl)-5- ureido-1H-pyrrolo[2,3-c]pyridine-1-carboxylate. The product was prepared as described in Example #13 Step 1, using tert-Butyl 3-bromo-5-ureido-1H-pyrrolo[2,3-c]pyridine-1-carboxylate (Preparation #4) and 2-bromo-6-(3-((tert-butyldimethylsilypoxy)oxetan-3-yl)pyridine (Preparation #15) (0.77 g, 57% yield). LC/MS (Table A, Method a) R$_t$=2.13 minutes; MS m/z: 540 (M+H)$^+$. TBS=tert-butyldimethylsilyl. Boc =t-Butoxycarbonyl.

Step 2: 1-(3-(6-(3-((tert-butyldimethylsilyl)oxy)oxetan-3-yOpyridin-2-yl))-1H- pyrrolo[2,3-c]pyridin-5-yl)urea. A microwave vial containing a mixture of tert-butyl 3-(6-(3-((tert- butyldimethylsilyl)oxy)oxetan-3-yl)pyridin-2-yl))-5- ureido-1H-pyrrolo[2,3-c]pyridine-1-carboxylate (0.769 g, 1.425 mmol) in ethanol (EtOH) (12 mL) with ammonia (2M in EtOH) (2.85 mL, 5.70 mmol) was heated in Biotage® microwave at 130° C. for 20 minutes. The reaction was then heated again at 130° C. for 16 minutes. The solvent was concentrated under reduced pressure. The product was purified via silica gel chromatography, eluting with 0-10% methanol/dichloromethane, to provide the product (0.342 g, 55% yield). LC/MS (Table A, Method a) R$_t$=1.56 minutes; MS m/z: 440 (M+H)$^+$.

Step 3: 1-(3-(6-(3-((tert-butyldimethylsilyl)oxy)oxetan-3-yOpyridin-2-yl))-1-methyl- 1H-pyrrolo[2,3-c]pyridin-5-yl)urea. The product was prepared as described in Example #13 Step 3, using 1-(3-(6-(3-((tert-butyldimethylsilypoxy)oxetan-3-yl)pyridin-2-yl))-1H-pyrrolo [2,3-c]pyridin- 5-yl)urea (0.159 g, 96% yield) LC/MS (Table A, Method a) R$_t$=1.69 minutes; MS m/z: 454 (M+H)$^+$.

Step 4: 1-(3-(6-(3-hydroxyoxetan-3-yl)pyridin-2-yl))-1-methyl-1H-pyrrolo[2,3- c]pyridin-5-yl)urea. To a solution of 1-(3-(6-(3-((tert-butyldimethylsilypoxy)oxetan-3-yl)pyridin- 2-yl))-1-methyl-1H-pyrrolo[2,3-c]pyridin-5-yl)urea (0.130 g, 0.287 mmol) in tetrahydrofuran (THF) (2.87 mL) was added tetra-n-butylammonium fluoride (1M in THF) (0.315 mL, 0.315 mmol). The reaction stirred at room temperature for 10 minutes. The reaction was concentrated under reduced pressure to provide a residue, which was dissolved in dimethyl sulfoxide and purified via reverse HPLC, eluting with 5-75% acetonitrile/water (10mM ammonium acetate buffer), to provide product fractions, which were concentrated and lyophilized to provide a crude product. The crude product was dissolved in water. After 5 minutes, a precipitate formed, which was then filtered, rinsed with water, and dried in a vacuum oven at 60° C. After about 3 hours, additional precipitate had formed in the filtrate. The water volume of the filtrate was reduced under reduced pressure, and the additional precipitate was collected via filtration, rinsed with water, and dried in vacuum oven at 60° C. The filtered precipitates were then combined to provide the product (0.06 g, 68% yield). LC/MS (Table A, Method d) R$_t$=0.67 minutes; MS m/z: 340 (M+H)$^+$. $^1$H NMR (400 MHz, Dimethyl sulfoxide-d$_6$) δ 8.77 (s, 1H), 8.53 (d, J=1.1 Hz, 1H), 8.39 (s, 1H), 8.24 (s, 1H), 7.81 (t, J=7.8 Hz, 1H), 7.61 (dd, J=7.9, 0.9 Hz, 1H), 7.35 (dd, J=7.7, 0.9 Hz, 1H), 6.61 (s, 2H), 6.36 (s, 1H), 5.19 -5.04 (m, 2H), 4.83-4.58 (m, 2H), 3.90 (s, 3H).

The compounds shown in Table 14 were synthesized in a manner similar to Example #14 from tert-butyl 5-acetamido-3-bromo-1H-pyrrolo[2,3-c]pyridine-1-carboxylate (Preparation #1) and the corresponding aromatic halide followed Example #14, Steps 2-4. Additional synthetic protocol and characterization of the compound of Example #14.6 is also provided following Table 14.

TABLE 14

| Ex | Aromatic Halide | Product | R$_t$ min (Method) | m/z (M + H)$^+$ |
|---|---|---|---|---|
| 14.2 | 2-bromo-6-(3-((tert-butyldimethylsilyl)oxy)oxetan-3-yl)-4-methoxypyridine (Preparation #16) | N-(3-(6-(3-hydroxyoxetan-3-yl)-4-methoxypyridin-2-yl)-1-methyl-1H-pyrrolo[2,3-c]pyridin-5-yl)acetamide | 0.79 (d) | 369 |
| 14.3 | 2-bromo-6-(3-((tert-butyldimethylsilyl)oxy)oxetan-3-yl)-4-isopropoxypyridine (Preparation #17) | N-(3-(6-(3-hydroxyoxetan-3-yl)-4-isopropoxypyridin-2-yl)-1-methyl-1H-pyrrolo [2,3-c]pyridin-5-yl)acetamide | 1.01 (d) | 397 |

TABLE 14-continued

| Ex | Aromatic Halide | Product | R, min (Method) | m/z (M + H)+ |
|---|---|---|---|---|
| 14.4 | 4-(((S)-4-((tert-butyldimethylsilyl)oxy)butan-2-yl)oxy)-2-chloro-6-((R)-3-methoxytetrahydrofuran-3-yl)pyridine (Preparation #39) | N-(3-(4-(((S)-4-hydroxybutan-2-yl)oxy)-6-((R)-3-methoxytetrahydrofuran-3-yl)pyridin-2-yl)-1-methyl-1H-pyrrolo[2,3-c]pyridin-5-yl)acetamide | 0.95 (d) | 455 |
| 14.5 | 4-((S)-2-((tert-butyldimethylsilyl)oxy)propoxy)-2-chloro-6-((R)-3-methoxytetrahydrofuran-3-yl)pyridine (Preparation #42) | N-(3-(4-((S)-2-hydroxypropoxy)-6-((R)-3-methoxytetrahydrofuran-3-yl)pyridin-2-yl)-1-methyl-1H-pyrrolo[2,3-c]pyridin-5-yl)acetamide | 0.86 (d) | 441 |
| 14.6 | 4-((R)-2-((tert-butyldimethylsilyl)oxy)propoxy)-2-chloro-6-((R)-3-methoxytetrahydrofuran-3-yl)pyridine (Preparation #43) | N-(3-(4-((R)-2-hydroxypropoxy)-6-((R)-3-methoxytetrahydrofuran-3-yl)pyridin-2-yl)-1-methyl-1H-pyrrolo[2,3-c]pyridin-5-yl)acetamide | 0.86 (d) | 441 |

68. Example #14.6: N-(3-(4-((R)-2-hydroxypropoxy)-6-((R)-3-methoxytetrahydrofuran-3-yl)pyridin-2-yl)-1-methyl-1H-pyrrolo[2,3-c]pyridin-5-yl)acetamide

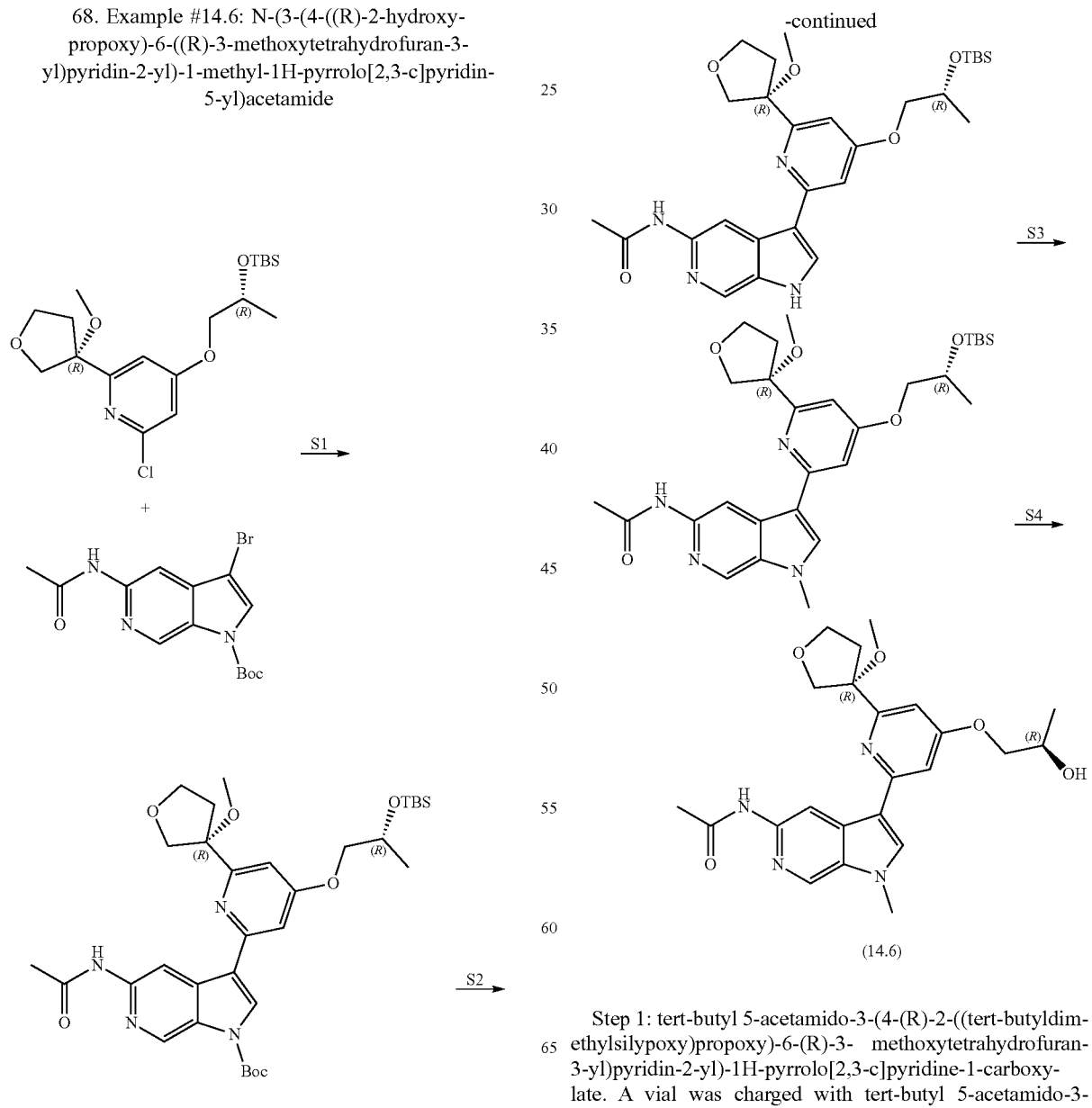

Step 1: tert-butyl 5-acetamido-3-(4-(R)-2-((tert-butyldimethylsilypoxy)propoxy)-6-(R)-3- methoxytetrahydrofuran-3-yl)pyridin-2-yl)-1H-pyrrolo[2,3-c]pyridine-1-carboxylate. A vial was charged with tert-butyl 5-acetamido-3- bromo-1H-pyrrolo[2,3-c]pyridine-1-carboxylate (0.25 g, 0.709 mmol) (Preparation #1), bis(pinocalato)diboron (0.27 g, 1.06 mmol), and potassium acetate (0.139 g, 1.41 mmol) in dioxane (10 mL) with 4 Å molecular sieves. The reaction was degassed with nitrogen for 5 minutes before the addition of [1,1'-bis(diphenylphosphino)ferrocene]dichloropalladium(II)- dichloromethane adduct (Pd(dppf)Cl$_2$-DCM adduct) (0.0.087 g, 0.106 mmol). The reaction mixture was heated to 100° C. for 2 hours. The mixture was cooled to room temperature. In a separate vial 4-(R)-2- ((tert-butyldimethylsilypoxy)propoxy)-2-chloro-6-((R)-3-methoxytetrahydrofuran-3-yl)pyridine (0.285 g, 0.709 mmol) (Preparation #43) and potassium phosphate (0.15 g, 0.709 mmol) were dissolved in dioxane (10 mL) and water (2.0 mL) and degassed with nitrogen for 5 minutes before the addition of the filtered solution of boronate. The reaction mixture was sealed and heated to 75° C. for 1 hour. The mixture was cooled to room temperature, and was partitioned between water and ethyl acetate. The organic portion was dried over MgSO$_4$, filtered, and concentrated under reduced pressured to provide a residue, which was purified via silica gel chromatography, eluting with 0-100% heptanes:ethyl acetate, to provide the product (0.113 g, 25% yield). LC/MS (Table A, Method b) R$_t$=2.33 minutes; MS m/z: 641 (M+H)$^+$.

Step 2: N-(3-(4-(R)-2-((tert-butyldimethylsilypoxy)propoxy)-6-(R)-3- methoxytetrahydrofuran-3-yl)pyridin-2-yl)-1H-pyrrolo[2,3-c]pyridin-5-yl)acetamide. A large microwave vial was charged with tert-butyl 5-acetamido-3-(44 (R)-2-((tert- butyldimethylsilypoxy)propoxy)-6-((R)-3-methoxytetrahydrofuran-3-yl)pyridin-2-yl)-1H-pyrrolo[2,3-c]pyridine-1-carboxylate (0.113 g, 0.176 mmol) dissolved in ethanol (15 mL). The reaction was heated in a Biotage® microwave to 140° C. for 45 minutes. The solvent was concentrated to give crude residue, which was triturated with acetonitrile to provide the product (0.095 g, 92% yield). LC/MS (Table A, Method b) R$_t$=1.83 minutes; MS m/z: 541 (M+H)$^+$.

Step 3: N-(3-(4-((R)-2-((tert-butyldimethylsilypoxy)propoxy)-6-((R)-3- methoxytetrahydrofuran-3-yl)pyridin-2-yl)-1-methyl-1H-pyrrolo[2,3-c]pyridin-5-yl)acetamide. In a round-bottomed flask, N-(3-(4-((R)-2-((tert-butyldimethylsilypoxy)propoxy)-64(R)-3- methoxytetrahydrofuran-3-yl)pyridin-2-yl)-1H-pyrrolo[2,3-c]pyridin-5-yl)acetamide (0.095 g, 0.176 mmol) and cesium carbonate (0.063 g, 0.193 mmol) in acetonitrile (15 mL) were combined to give a yellow solution. A solution of 2.0 M iodomethane in methyl tert-butyl ether (MTBE) (0.176 mL, 0.351 mmol) was added and the mixture was stirred at ambient temperature overnight. The mixture was concentrated under reduced pressure and the residue was partitioned between water and ethyl acetate. The combined organic portion was dried over MgSO$_4$, filtered and concentrated to give crude product (0.089 g, 91% yield). LC/MS (Table A, Method d) R$_t$=1.95 minutes; MS m/z: 555 (M+H)$^+$.

Step 4: N-(3-(4-((R)-2-hydroxypropoxy)-6-((R)-3-methoxytetrahydrofuran-3-yl)pyridin-2- yl)-1-methyl-1H-pyrrolo[2,3-c]pyridin-5-ypacetamide. A round-bottomed flask was charged with N- (3 -(4-( (R)-2-((tert-butyldimethylsilypoxy)propoxy)-6-((R)-3-methoxytetrahydrofuran-3-yl) pyridin-2-yl)- 1-methyl-1H-pyrrolo[2,3-c]pyridin-5-yl)acetamide (0.089 g, 0.160 mmol) and tetrahydrofuran (THF) (20 mL). Tetra-n-butylammonium fluoride (TBAF) (0.209 mL, 0.209 mmol, 1 M in THF) was added and the mixture stirred at ambient temperature for 2 hours. The solvent was removed to give product residue. The residue was purified via reverse HPLC eluting with 20-55% acetonitrile:aqueous ammonium acetate buffer (10 mM) to give desired product (0.04 g, 55% yield, >99% ee). LC/MS (Table A, Method d) R$_t$=0.86 minutes; MS m/z: 441 (M+H)$^+$. $^1$H NMR (400 MHz, Dimethyl sulfoxide-d$_6$) δ 10.17 (s, 1H), 9.05 (s, 1H), 8.61 (d, J=1.1 Hz, 1H), 8.34 (s, 1H), 7.26 (d, J=2.2 Hz, 1H), 6.82 (d, J=2.2 Hz, 1H), 4.94 (s, 1H), 4.16 (dd, J=9.7, 1.2 Hz, 1H), 4.08-3.95 (m, 5H), 3.93 (s, 3H), 3.90 (d, J=9.6 Hz, 1H), 3.13 (s, 3H), 2.78 (dt, J=13.2, 8.7 Hz, 1H), 2.45-2.37 (m, 1H), 2.09 (s, 3H), 1.20 (d, J=5.9 Hz, 3H).

69. Example #15: (R)-1-(3-(6-(3-Hydroxyoxetan-3-yl)pyridin-2-yl)-1-(tetrahydrofuran-3- yl)-1H-pyrrolo[2,3-c]pyridin-5-yl)urea

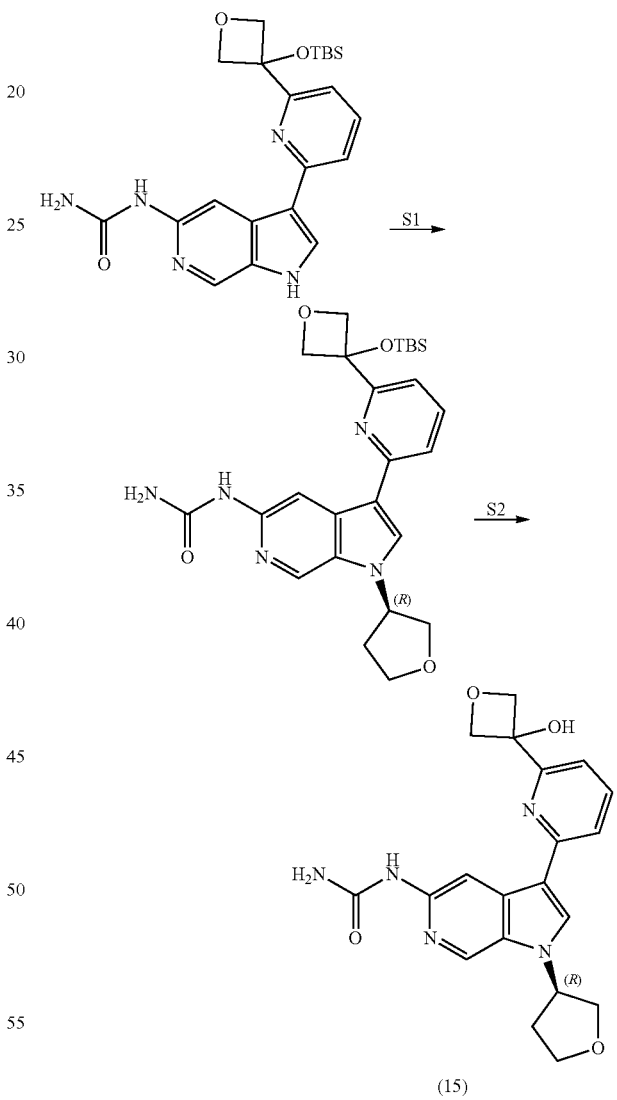

(15)

Step 1: (R)-1-(3-(6-(3-((tert-butyldimethylsilypoxy)oxetan-3-yl)pyridin-2-yl)-1- (tetrahydrofuran-3-yl)-1H-pyrrolo[2,3-c]pyridin-5-yl)urea. To a flask containing 1434643-((tert-butyldimethylsilypoxy)oxetan-3-yl)pyridin-2-yl))-1H-pyrrolo[2,3-c]pyridin-5-yl)urea (Example #14, Step 2) and cesium carbonate (0.267 g, 0.819 mmol) was added dimethylformamide (DMF) (4.09 mL) and (S)-tetrahydrofuran-3-yl methanesulfonate (0.135 g, 0.812 mmol) (Preparation #30). The reaction stirred at 80° C. for about 4 hours. The reaction mixture was concentrated under reduced pressure to provide a residue, which was taken up in ethyl acetate (40mL) and washed with water (15 mL). The organic layer was separated, and the aqueous layer again was washed with ethyl acetate (10 mL). The combined organic layers were dried over MgSO$_4$, filtered, and concentrated to provide the product (0.230 g, 82% yield). LC/MS (Table A, Method a) R$_t$=1.70 minutes; MS m/z: 510 (M+H)$^+$. TBS=tert-butyldimethylsilyl.

Step 2: (R)-1-(3-(6-(3-hydroxyoxetan-3-yl)pyridin-2-yl)-1-(tetrahydrofuran-3-yl)- 1H-pyrrolo[2,3-c]pyridin-5-yl) urea. The product was prepared as described in Example #14, Step 4, using (R)-1-(3-(6-(3-((tert-butyldimethylsilypoxy)oxetan-3-yl)pyridin-2-yl)-1-(tetrahydrofuran-3- yl)-1H-pyrrolo[2,3-c]pyridin-5-yl)urea (0.075 g, 55% yield). LC/MS (Table A, Method d) R$_t$=0.74 minutes; MS m/z: 396 (M+H)$^+$. $^1$H NMR (400 MHz, Dimethyl sulfoxide-d$_6$) δ 8.78 (s, 1H), 8.64 (d, J=1.0 Hz, 1H), 8.43 (s, 1H), 8.27 (s, 1H), 7.80 (t, J=7.8 Hz, 1H), 7.70 (dd, J=7.9, 1.0 Hz, 1H), 7.36 (dd, J =7.7, 0.9 Hz, 1H), 6.60 (s, 2H), 6.37 (s, 1H), 5.34 (dq, J=8.4, 4.2 Hz, 1H), 5.11 (dd, J=6.3, 2.4 Hz, 2H), 4.66 (d, J=6.3 Hz, 2H), 4.13 (td, J=8.3, 6.0 Hz, 1H), 4.07 -3.91 (m, 2H), 3.83 (td, J=8.5, 6.3 Hz, 1H), 2.61-2.50 (m, 1H), 2.40-2.14 (m, 1H).

The compound shown in Table 15 was synthesized in a manner similar to Example #15 from 1- (3-(6-(3-((tert-butyldimethylsilypoxy)oxetan-3-yl)pyridin-2-yl)-1H-pyrrolo[2,3-c]pyridin-5-yl)urea (Example #14, Step 2) and the corresponding alkylating agent.

TABLE 15

| Ex | Alkylating Agent | Product | R$_t$ min (Method) | m/z (M + H)$^+$ |
|---|---|---|---|---|
| 15.2 | (R)-tetrahydrofuran-3-yl methanesulfonate (Preparation #35) | (S)-1-(3-(6-(3-hydroxyoxetan-3-yl)pyridin-2-yl)-1-(tetrahydrofuran-3-yl)-1H-pyrrolo[2,3-c]pyridin-5-yl)urea | 0.78 (d) | 396 |

70. Example #16 and #16a: (R)-N-(3-(6-(3-Methoxytetrahydrofuran-3-yl)pyridin-2-yl)-1- methyl-1H-pyrrolo[2,3-c]pyridin-5-yl)acetamide and (S)-N-(3-(6-(3-methoxytetrahydrofuran- 3-yl)pyridin-2-yl)-1-methyl-1H-pyrrolo [2,3-c] pyridin-5-yl)acetamide

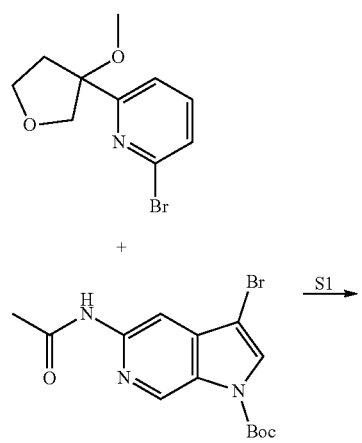

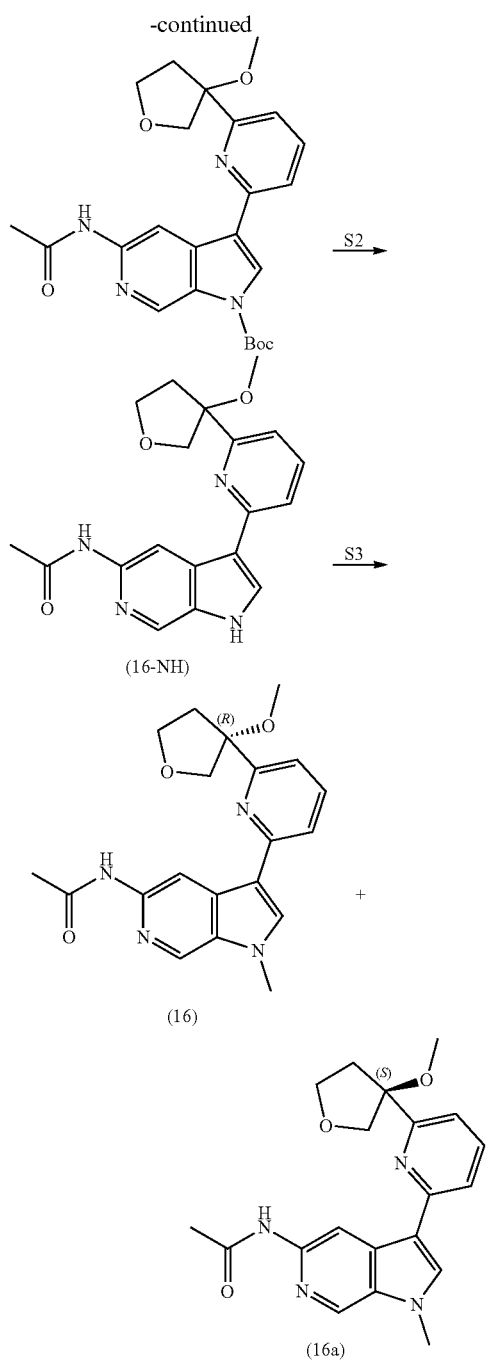

Step 1: tert-butyl 5-acetamido-3-(6-(3-methoxytetrahydrofuran-3-yl)pyridin-2-yl)- 1H-pyrrolo[2,3-c]pyridine-1-carboxylate. The product was prepared as described in Example #2, Step 1 using tert-butyl 5-acetamido-3-bromo-1H-pyrrolo[2,3-c]pyridine-1-carboxylate (Preparation #1) and 2-bromo-6-(3-methoxytetrahydrofuran-3-yl)pyridine (Preparation #20, Step 1) (0.55 g, 79% yield). LC/MS (Table A, Method a) R$_t$=1.45 minutes; MS m/z: 453 (M+H)$^+$.

Step 2: N-(3-(6-(3-methoxytetrahydrofuran-3-yl)pyridin-2-yl)-1H-pyrrolo[2,3- c]pyridin-5-yl)acetamide. The product was prepared as described in Example #2, Step 2, using tert- butyl 5-acetamido-3-(6-(3-methoxytetrahydrofuran-3-yl)pyridin-2-yl))-1H-pyrrolo[2,3-c]pyridine-1- carboxylate (0.35 g, 81% yield). LC/MS (Table A, Method d) R$_t$=0.83 minutes; MS m/z: 353 (M+H)$^+$.

Step 3: (R)-N-(3-(6-(3-methoxytetrahydrofuran-3-yl)pyridin-2-yl)-1-methyl-1H- pyrrolo[2,3-c]pyridin-5-yl)acetamide and (S)-N-(3-(6-(3-methoxytetrahydrofuran-3-yl)pyridin-2-yl)-1-methyl-1H-pyrrolo[2,3-c]pyridin-5-yl) acetamide. The product was prepared as described in Example #2, Step 3, using N-(3-(6-(3-methoxytetrahydrofuran-3-yl)pyridin-2-yl)-1H-pyrrolo[2,3- c]pyridin-5-ypacetamide. The product was further purified via chiral SFC (Table 2, Method 12) to provide the R-isomer (0.127g, 36% yield, >99%ee, R$_t$=2.78 minutes) and the S-isomer (0.132 g, 37% yield, 99%ee, R$_t$=2.71 minutes). LC/MS (Table A, Method d) R$_t$=1.45 minutes; MS m/z: 453 (M+H)$^+$. $^1$H NMR (400 MHz, Dimethyl sulfoxide-d$_6$) δ 10.21 (s, 1H), 9.06 (s, 1H), 8.63 (d, J=1.1 Hz, 1H), 8.30 (s, 1H), 7.82 (t, J=7.8 Hz, 1H), 7.68 (dd, J=8.0, 0.9 Hz, 1H), 7.27 (dd, J=7.7, 0.9 Hz, 1H), 4.20 (dd, J =9.7, 1.3 Hz, 1H), 4.09-3.96 (m, 2H), 3.93 (d, J=10.1 Hz, 4H), 3.12 (s, 3H), 2.77 (dt, J=13.1, 8.7 Hz, 1H), 2.49-2.39 (m, 1H), 2.10 (s, 3H).

71. Example #17 and #17a: N-(1-((trans)-3-Cyano-cyclobutyl)-3-(6-((R)-3- methoxytetrahydrofuran-3-yl)pyridin-2-yl)-1H-pyrrolo[2,3-c]pyridin-5-yl)acetamide and N-(1- ((cis)-3-cyanocyclobutyl)-3-(6-((R)-3-methoxytetrahydrofuran-3-yl)pyridin-2-yl)-1H- pyrrolo[2,3-c]pyridin-5-yl)acetamide

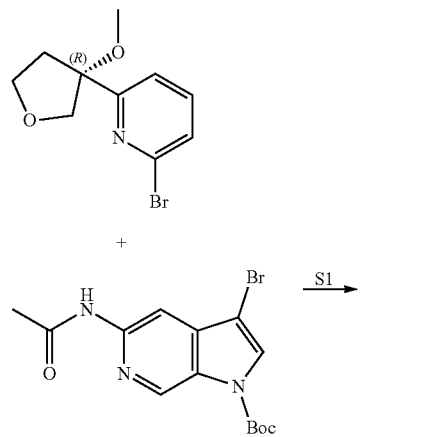

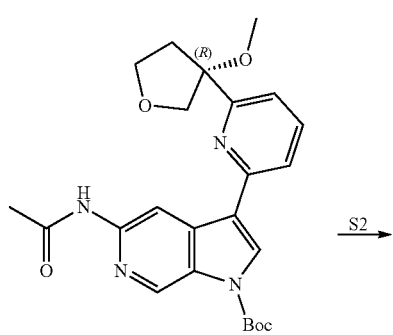

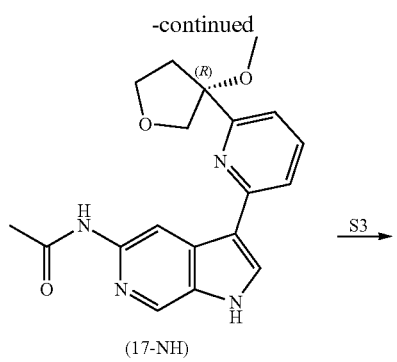

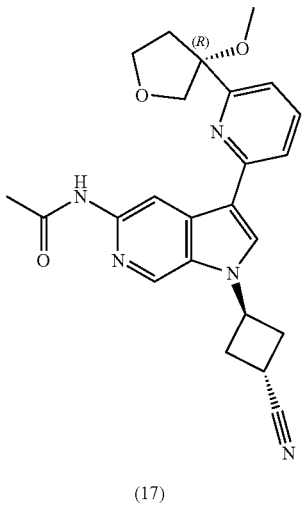

Step 1: (R)-tert-butyl 5-acetamido-3-(6-(3-methoxytetrahydrofuran-3-yl)pyridin-2- yl)-1H-pyrrolo[2,3-c]pyridine-1-carboxylate. The product was prepared as described in Example #2, Step 1, using tert-butyl 5-acetamido-3-bromo-1H-pyrrolo[2,3-c]pyridine-1-carboxylate (Preparation #1) and (R)-2-bromo-6-(3-methoxytetrahydrofuran-3-yl)pyridine (Preparation #20) (1.02 g, 80% yield). LC/MS (Table A, Method a) R$_t$=1.46 minutes; MS m/z: 453.16 (M+H)$^+$. Boc=t-Butoxycarbonyl.

Step 2: (R)-N-(3-(6-(3-methoxytetrahydrofuran-3-yl)pyridin-2-yl))-1H-pyrrolo[2,3- c]pyridin-5-ypacetamide. The product was prepared as described in Example #11, Step 2, using (R)- tert-butyl 5-acetamido-3-(6-(3-methoxytetrahydrofuran-3-yl)pyridin-2-yl)-1H-pyrrolo[2,3- c]pyridine- 1-carboxylate (0.516 g, 56% yield). LC/MS (Table A, Method a) R$_t$=0.80 minutes; MS m/z: 353.09 (M+H)$^+$.

Step 3: N-(1-((trans)-3-cyanocyclobutyl)-3-(6-((R)-3-methoxytetrahydrofuran-3- yl)pyridin-2-yl))-1H-pyrrolo[2,3-c]pyridin-5-yl)acetamide and N-(1-((cis)-3-cyanocyclobutyl)-3- (6-((R)-3-methoxytetrahydrofuran-3-yl) pyridin-2-yl)-1H-pyrrolo[2,3-c]pyridin-5-ypacetamide. In a reaction vial, (R)-N-(3-(6-(3-methoxytetrahydrofuran-3-yl) pyridin-2-yl)-1H-pyrrolo[2,3- c]pyridin-5-yl)acetamide (0.516 g, 1.464 mmol) in dimethylformamide (5 mL) was added. Cesium carbonate (1.431 g, 4.39 mmol) and 3-cyanocyclobutyl methanesulfonate (0.513 g, 2.93 mmol) (Preparation #31) were added and the mixture was heated at 85° C. for 16 hours. The reaction was cooled to room temperature, and was then diluted with water (20 mL) and dichloromethane (DCM) (40 mL). Separated the layers and extracted aqueous layer with DCM (20 mL). The combined organic layers were dried over MgSO$_4$ and concentrated under reduced pressure to provide a residue, which was purified via chiral HPLC (Table 2, Method 13) to provide the trans-isomeric product (0.162 g, 24% yield, >99% ee, R$_t$=8.2 minutes) LC/MS (Table A, Method d) R$_t$=1.09 minutes; MS m/z: 432.17 (M+H)$^+$, and the cis- isomeric product (0.1 g, 15% yield, >99%ee, R$_t$=10.9 minutes). LC/MS (Table A, Method d) R$_t$=1.09 minutes; MS m/z: 432.17 (M+H)$^+$. $^1$H NMR (400 MHz, Dimethyl sulfoxide-d$_6$) δ 10.21 (s, 1H), 9.09 (s, 1H), 8.73 (d, J=1.0 Hz, 1H), 8.60 (s, 1H), 7.85 (dd, J=8.0, 7.4 Hz, 1H), 7.79 (dd, J=8.0, 1.2 Hz, 1H), 7.29 (dd, J=7.4, 1.2 Hz, 1H), 5.58-5.46 (m, 1H), 4.21 (dd, J=9.6, 1.2 Hz, 1H), 4.09-3.96 (m, 2H), 3.92 (d, J=9.6 Hz, 1H), 3.59-3.49 (m, 1H), 3.12 (s, 3H), 3.08-2.88 (m, 4H), 2.78 (dt, J=13.1, 8.7 Hz, 1H), 2.48-2.42 (m, 1H), 2.10 (s, 3H).

The compounds shown in Table 17 were synthesized in a manner similar to Example #17 from tert-butyl 5-acetamido-3-bromo-1H-pyrrolo[2,3-c]pyridine-1-carboxylate (Preparation #1) and the corresponding aromatic halide followed by Example #17, Step 2 and Step3.

72. Example #18 and #18a: (R)-N-(3-(6-(3-Methoxytetrahydrofuran-3-yl)pyridin-2-yl)-1-(3-methyloxetan-3-yl)-1H-pyrrolo[2,3-c]pyridin-5-yl)acetamide and (R)-N-(1-(3-fluorooxetan- 3-yl)-3-(6-(3-methoxytetrahydrofuran-3-yl)pyridin-2-yl)-1H-pyrrolo[2,3-c]pyridin-5-yl)acetamide

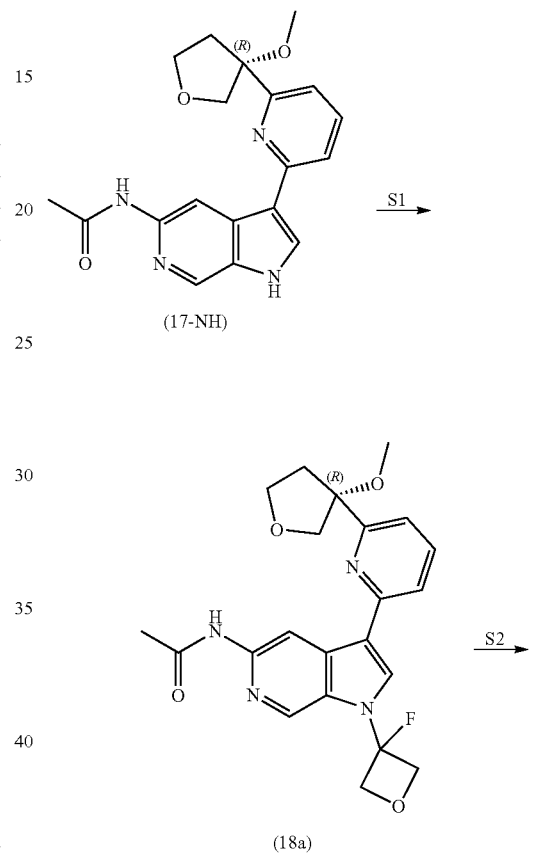

TABLE 17

| Ex | Aromatic Halide | Product | R$_t$ min (Method) | m/z (M + H)$^+$ |
|---|---|---|---|---|
| 17.2 | (R)-2-bromo-4-(difluoromethyl)-6-(3-methoxytetrahydrofuran-3-yl)pyridine (Preparation #18) | N-(1-((trans)-3-cyanocyclobutyl)-3-(4-(difluoromethyl)-6-((R)-3-methoxytetrahydrofuran-3-yl)pyridin-2-yl)-1H-pyrrolo[2,3-c]pyridin-5-yl)acetamide | 1.22 (d) | 482 |
| 17.3 | (R)-2-bromo-4-(difluoromethyl)-6-(3-methoxytetrahydrofuran-3-yl)pyridine (Preparation #18) | N-(1-((cis)-3-cyanocyclobutyl)-3-(4-(difluoromethyl)-6-((R)-3-methoxytetrahydrofuran-3-yl)pyridin-2-yl)-1H-pyrrolo[2,3-c]pyridin-5-yl)acetamide | 1.23 (d) | 482 |
| 17.4 | (R)-2-bromo-6-(3-methoxytetrahydrofuran-3-yl)-4-methylpyridine (Preparation #5) | N-(1-((trans)-3-cyanocyclobutyl)-3-(6-((R)-3-methoxytetrahydrofuran-3-yl)-4-methylpyridin-2-yl)-1H-pyrrolo[2,3-c]pyridin-5-yl)acetamide | 1.15 (d) | 446 |
| 17.5 | (R)-2-bromo-6-(3-methoxytetrahydrofuran-3-yl)-4-methylpyridine (Preparation #5) | N-(1-((cis)-3-cyanocyclobutyl)-3-(6-((R)-3-methoxytetrahydrofuran-3-yl)-4-methylpyridin-2-yl)-1H-pyrrolo [2,3-c]pyridin-5-yl)acetamide | 1.16 (d) | 446 |

245
-continued

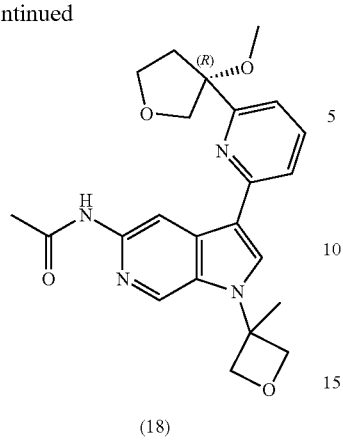

(18)

Step 1: (R)-N-(1-(3-fluorooxetan-3-yl)-3-(6-(3-methoxytetrahydrofuran-3-yl)pyridin-2-yl)-1H-pyrrolo[2,3-c]pyridin-5-yl)acetamide. A solution of (R)-N-(3-(6-(3-methoxytetrahydrofuran-3-yl)pyridin-2-yl)-1H-pyrrolo[2,3-c]pyridin-5-yl)acetamide (0.500 g, 1.419 mmol) (Example #17, Step 2) in dimethylacetamide (4.73 mL) was treated with oxetan-3-one (0.204 g, 2.84 mmol) and bis(2-methoxyethyl)aminosulfur trifluoride (0.576 mL, 3.12 mmol). The reaction was allowed to stir at room temperature for 1 hour. The reaction was quenched with water and extracted with ethyl acetate. The combined organic layers were dried over MgSO$_4$, filtered, and concentrated to provide a residue, which was purified via silica gel chromatography, eluting with 0-10% methanol/dichloromethane, to provide the product (0.252 g, 41% yield). LC/MS (Table A, Method d) R$_t$=1.05 minutes; MS m/z: 427.3 (M+H)$^+$. $^1$H NMR (400 MHz, Dimethyl sulfoxide-d$_6$) δ 10.36 (s, 1H), 9.19 (s, 1H), 8.65 (s, 1H), 8.42 (d, J=1.0 Hz, 1H), 7.93-7.88 (m, 1H), 7.85 (dd, J=7.9, 1.1 Hz, 1H), 7.38 (dd, J=7.5, 1.1 Hz, 1H), 5.52-5.38 (m, 2H), 5.30 (dd, J=15.1, 8.8 Hz, 2H), 4.23 (dd, J=9.6, 1.2 Hz, 1H), 4.10 -3.97 (m, 2H), 3.93 (d, J=9.7 Hz, 1H), 3.13 (s, 3H), 2.12 (s, 3H).

Step 2: (R)-N-(3-(6-(3-methoxytetrahydrofuran-3-yl)pyridin-2-yl)-1-(3-methyloxetan-3-yl)-1H-pyrrolo[2,3-c]pyridin-5-yl)acetamide. A solution of (R)-N-(1-(3-fluorooxetan-3-yl)-3- (6-(3-methoxytetrahydrofuran-3-yl)pyridin-2-yl)-1H-pyrrolo[2,3-c]pyridin-5-yl)acetamide (0.100 g, 0.234 mmol) in tetrahydrofuran (THF) (2.345 mL) was cooled to −78° C. and treated with methylmagnesium bromide (3M in THF) (0.391 mL, 1.172 mmol). The reaction stirred warming to room temperature for 2 hours. The reaction was quenched with methanol and purified using reverse HPLC, eluting with 5-95% acetonitrile/water (5 mM ammonium chloride), and the product fractions were combined, concentrated, and lyophilized to provide the product (0.051g, 48% yield). LC/MS (Table A, Method d) R$_t$=0.98 minutes; MS m/z: 423.2 (M+H)$^+$. $^1$H NMR (400 MHz, Dimethyl sulfoxide-d$_6$) δ 10.22 (s, 1H), 9.14 (s, 1H), 8.38-8.33 (m, 2H), 7.87-7.80 (m, 1H), 7.78 (dd, J=8.0, 1.1 Hz, 1H), 7.29 (dd, J=7.5, 1.1 Hz, 1H), 5.20 (d, J=6.6 Hz, 2H), 4.86 (d, J=6.7 Hz, 2H), 4.22 (dd, J=9.7, 1.3 Hz, 1H), 4.10-3.96 (m, 3H), 3.92 (d, J=9.6 Hz, 1H), 3.12 (s, 3H), 2.11 (s, 3H), 1.89 (s, 3H).

73. Example #19: (R)-1-(3-(6-(3-methoxytetrahydrofuran-3-yl)pyridin-2-yl)-1-(3- methyloxetan-3-yl)-1H-pyrrolo[2,3-c]pyridin-5-yl)urea

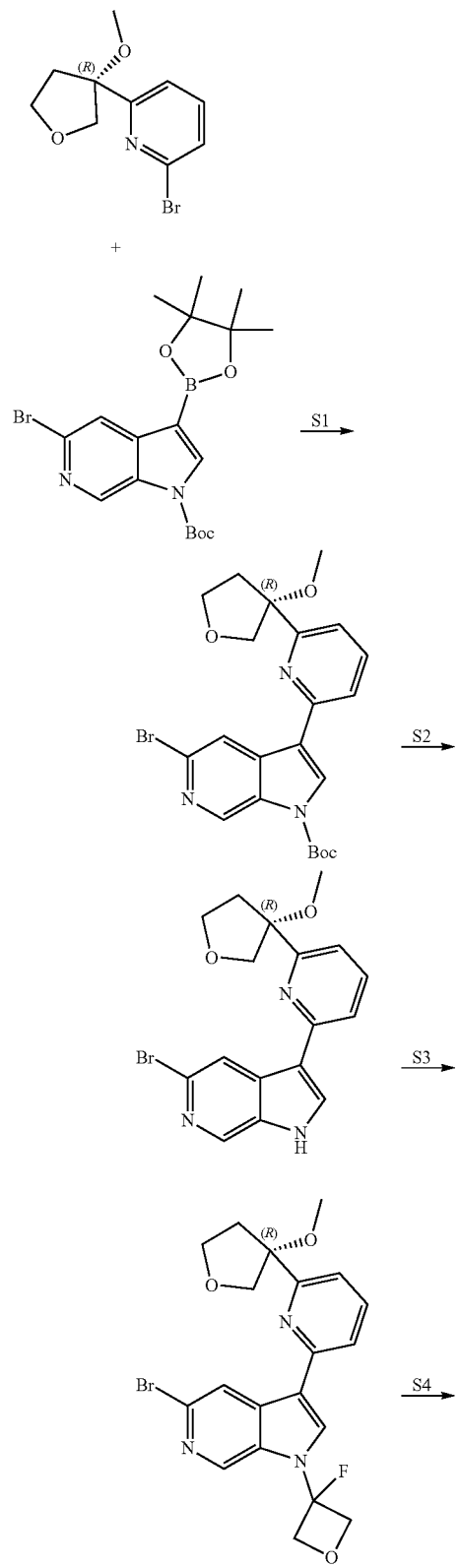

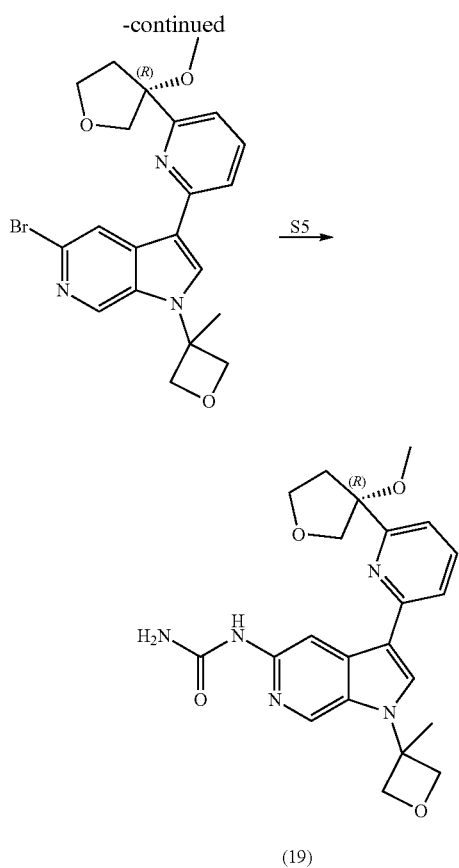

(19)

Step 1: (R)-tert-butyl 5-bromo-3-(6-(3-methoxytetrahydrofuran-3-yl)pyridin-2-yl)-1H-pyrrolo[2,3-c]pyridine-1-carboxylate. A flask was charged with(R)-2-bromo-6-(3-methoxytetrahydrofuran-3-yl)pyridine (1.00 g, 3.87 mmol) (Preparation #20), tert-butyl 5-bromo-3- (4,4,5,5-tetramethyl-1,3,2-dioxaborolan-2-yl)-1H-pyrrolo[2,3-c]pyridine-1-carboxylate (2.459 g, 5.81 mmol) (Preparation #34), and sodium carbonate (1.23 g, 11.62 mmol) in a mixture of dioxane (12.91 mL) and water (3.23 mL). The reaction was degassed with a stream of nitrogen for 10 minutes before the addition of [1,1'-bis(diphenylphosphino)ferrocene]dichloropalladium(II)-dichloromethane adduct (Pd(dppf)Cl$_2$-DCM adduct) (0.158 g, 0.194 mmol). The reaction was heated to 80° C. for 30 minutes. The reaction was then cooled to room temperature, poured into 5% aqueous cysteine, and extracted with ethyl acetate. The organic portion was dried over MgSO$_4$, filtered, and concentrated under reduced pressure to provide a residue, which was purified via silica gel chromatography, eluting with 0-50% ethyl acetate/heptanes, to provide the product (0.955 g, 36% yield, 60% purity). LC/MS (Table A, Method b) R$_t$=1.97 minutes; MS m/z: 474, 476 (M+H)$^+$.

Step 2: (R)-5-bromo-3-(6-(3-methoxytetrahydrofuran-3-yl)pyridin-2-yl)-1H- pyrrolo[2,3-c]pyridine. A microwave vial was charged with (R)-tert-butyl 5-bromo-3-(6-(3-methoxytetrahydrofuran-3-yl)pyridin-2-yl)-1H-pyrrolo[2,3-c]pyridine-1-carboxylate (0.900 g, 1.233 mmol) (60% purity) in ethanol (6.17 mL). The reaction was heated in a Biotage® microwave at 150° C. for 20 minutes. The ethanol was concentrated under reduced pressure to provide a residue, which was purified via silica gel chromatography, eluting with 0-10% methanol/dichloromethane, to provide the product (0.305 g, 66% yield). LC/MS (Table A, Method b) R$_t$=1.26 minutes; MS m/z: 374, 376 (M+H)$^+$.

Step 3: (R)-5-bromo-1-(3-fluorooxetan-3-yl)-3-(6-(3-methoxytetrahydrofuran-3- yl)pyridin-2-yl)-1H-pyrrolo[2,3-c]pyridine. A vial was charged with (R)-5-bromo-3-(6-(3-methoxytetrahydrofuran-3-yl)pyridin-2-yl)-1H-pyrrolo[2,3-c]pyridine (0.3 g, 0.802 mmol) and dissolved in dimethylacetamide (2.67 mL) before the addition of oxetan-3-one (0.094 mL, 1.603 mmol) and bis(2-methoxyethyl)aminosulfur trifluoride (0.325 mL, 1.764 mmol). The reaction stirred at room temperature for 1 hour. The reaction was cooled to 0° C. then slowly quenched with water and extracted with ethyl acetate. The organic portion was dried over MgSO$_4$, filtered, and concentrated under reduced pressure to provide a residue, which was purified via silica gel chromatography, eluting with 0-10% methanol/dichloromethane, to provide the product (0.215 g, 60% yield). LC/MS (Table A, Method b) R$_t$=1.50 minutes; MS m/z: 48, 450 (M+H)$^+$.

Step 4: (R)-5-bromo-3-(6-(3-methoxytetrahydrofuran-3-yl)pyridin-2-yl)-1-(3- methyloxetan-3-yl)-1H-pyrrolo[2,3-c]pyridine. A vial was charged with (R)-5-bromo-1-(3- fluorooxetan-3-yl)-3-(6-(3-methoxytetrahydrofuran-3-yl) pyridin-2-yl))-1H-pyrrolo[2,3-c]pyridine (0.165 g, 0.368 mmol) and dissolved in tetrahydrofuran (THF) (1.4 mL). The reaction was cooled to 0° C. before the dropwise addition of methylmagnesium bromide (3M in THF) (0.368 mL, 1.104 mmol). The reaction stirred warming to room temperature over 30 minutes. The reaction was quenched with methanol, and concentrated to provide a residue, which was purified via silica gel chromatography, eluting with 0-100% ethyl acetate/heptanes, to provide the product (0.076 g, 47% yield). LC/MS (Table A, Method b) R$_t$=1.44 minutes; MS m/z: 444, 446 (M+H)$^+$.

Step 5: (R)-1-(3-(6-(3-methoxytetrahydrofuran-3-yl)pyridin-2-yl)-1-(3-methyloxetan- 3-yl)-1H-pyrrolo[2,3-c]pyridin-5-yl)urea. A vial was charged with (R)-5-bromo-3-(6-(3-methoxytetrahydrofuran-3-yl)pyridin-2-yl)-1-(3-methyloxetan-3-yl)-1H-pyrrolo[2,3-c]pyridine (0.075 g, 0.169 mmol), urea (0.020 g, 0.338 mmol), potassium 2-methylpropan-2-olate (0.047 g, 0.422 mmol) in dioxane (1.6 mL). The reaction was degassed for 10 minutes, then [(2-Dicyclohexylphosphino-3,6-dimethoxy-2',4',6'-triisopropyl-1,1'-biphenyl)-2-(2'-amino-1,1'- biphenyl)]palladium(II) methanesulfonate (BrettPhos Pd G3) (7.66 mg, 8.44 μmol) was added and the reaction was heated to 85° C. for 1 hour. The reaction was cooled to room temperature, quenched with water, concentrated to a residue, which was then purified purified via reverse HPLC, eluting with 30-75% 0.1% ammonium acetate in acetonitrile, to provide the product (0.010 g, 14% yield). LC/MS (Table A, Method d) R$_t$=0.94 minutes; MS m/z: 424 (M+H)$^+$. $^1$H NMR (400 MHz, Dimethyl sulfoxide-d$_6$) δ 8.86 (s, 1H), 8.54 (s, 1H), 8.27 (s, 1H), 8.23 (d, J=1.0 Hz, 1H), 7.79 (s, 1H), 7.72 (d, J=7.8 Hz, 1H), 7.25 (d, J=7.5 Hz, 1H), 5.15 (d, J=6.4 Hz, 2H), 4.81 (d, J=6.6 Hz, 2H), 4.26-4.15 (m, 1H), 3.90 (d, J=9.7 Hz, 1H), 2.72-2.61 (m, 2H), 1.84 (s, 3H), 1.60 (s, 7H).

74. Example #20 and #20a: (R)-N-(3-(4-Methoxy-6-(3-methoxytetrahydrofuran-3-yl)pyridin-2-yl)-1-methyl-1H-pyrrolo[2,3-c]pyridin-5-yl)acetamide and (S)-N-(3-(4-methoxy-6-(3-methoxytetrahydrofuran-3-yl)pyridin-2-yl)-1-methyl-1H-pyrrolo[2,3-c]pyridin-5-yl)acetamide

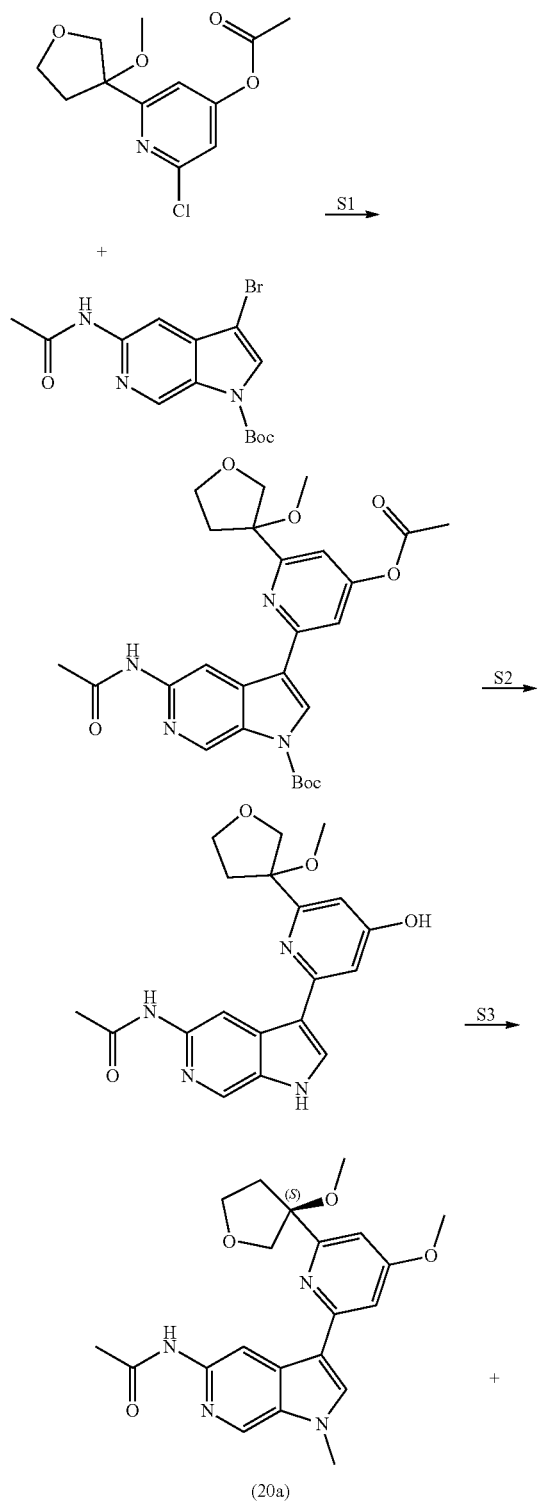

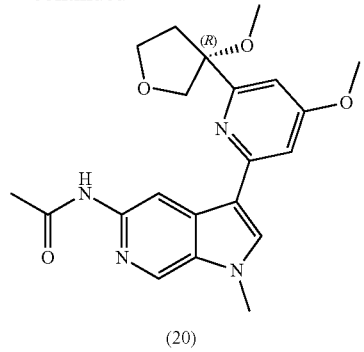

(20)

Step 1: tert-butyl 5-acetamido-3-(4-acetoxy-6-(3-methoxytetrahydrofuran-3-yl)pyridin-2-yl)-1H-pyrrolo[2,3-c]pyridine-1-carboxylate. The product was prepared as described in Example #2, Step1, using tert-butyl 5-acetamido-3-bromo-1H-pyrrolo[2,3-c]pyridine-1-carboxylate (Preparation #1) and 2-chloro-6-(3-methoxytetrahydrofuran-3-yl)pyridin-4-yl acetate (Preparation #36) (0.87 g, 43% yield). LC/MS (Table A, Method a) R$_t$=1.46 minutes; MS m/z: 511.19 (M+H)$^+$.

Step 2: N-(3-(4-hydroxy-6-(3-methoxytetrahydrofuran-3-yl)pyridin-2-yl)-1H-pyrrolo[2,3-c]pyridin-5-yl)acetamide. The product was prepared as described in Example #11, Step 2, using tert-butyl 5-acetamido-3-(4-acetoxy-6-(3-methoxytetrahydrofuran-3-yl)pyridin-2-yl)-1H-pyrrolo[2,3-c]pyridine-1-carboxylate (0.396 g, 60% yield). LC/MS (Table A, Method a) R$_t$=0.51 minutes; MS m/z: 369.16 (M+H)$^+$.

Step 3: (R)-N-(3-(4-methoxy-6-(3-methoxytetrahydrofuran-3-yl)pyridin-2-yl)-1-methyl-1H-pyrrolo[2,3-c]pyridin-5-yl)acetamide and (S)-N-(3-(4-methoxy-6-(3-methoxytetrahydrofuran-3-yl)pyridin-2-yl)-1-methyl-1H-pyrrolo[2,3-c]pyridin-5-yl)acetamide. In a reaction vial, N-(3-(4-hydroxy-6-(3-methoxytetrahydrofuran-3-yl)pyridin-2-yl)-1H-pyrrolo[2,3-c]pyridin-5-yl)acetamide (0.396 g, 1.075 mmol), iodomethane (0.067 mL, 1.075 mmol), and cesium carbonate (0.350 g, 1.075 mmol) in acetonitrile (10.75 mL) were added to give a suspension. The reaction stirred at room temperature for 6 hours, filtered, and concentrated under reduced pressure. The product was purified via silica gel chromatography, eluting with 0-50% methanol/dichloromethane, to give a racemic material, which was further purified via chiral HPLC (Table 2, Method 18) to provide the R- isomer (0.003g, 1% yield, >99%ee, R$_t$=16.41 minutes), and the S-isomer (0.040 g, 9% yield, >99%ee, R$_t$=19.48 minutes). LC/MS (Table A, Method a) R$_t$=0.98 minutes; MS m/z: 397 (M+H)$^+$. $^1$H NMR (400 MHz, Dimethyl sulfoxide-d$_6$) δ 10.19 (s, 1H), 9.05 (s, 1H), 8.61 (d, J=1.1 Hz, 1H), 8.33 (s, 1H), 7.26 (d, J=2.1 Hz, 1H), 6.83 (d, J=2.1 Hz, 1H), 4.16 (d, J=9.5 Hz, 1H), 4.10-3.87 (m, 3H), 3.93 (s, 3H), 3.91 (s. 3H), 3.14 (s, 3H), 2.78 (dt, J=13.3, 8.7 Hz, 1H), 2.41 (dd, J=12.8, 6.0 Hz, 1H), 2.09 (s, 3H).

75. Example #21 and #21a: (S)-N-(3-(6-(3-(Hydroxymethyl)tetrahydrofuran-3-yl)pyridin-2-yl)-1-methyl-1H-pyrrolo[2,3-c]pyridin-5-yl)acetamide and (R)-N-(3-(6-(3-(hydroxymethyl)tetrahydrofuran-3-yl)pyridin-2-yl)-1-methyl-1H-pyrrolo[2,3-c]pyridin-5-yl)acetamide Step 1: tert-butyl 5-acetamido-3-(6-(3-(hydroxymethyltetrahydrofuran-3-yl)pyridin-2-yl)-1H-pyrrolo[2,3-c]

pyridine-1-carboxylate. A vial was charged with tert-butyl 5-acetamido-3-bromo-1H-pyrrolo[2,3-c]pyridine-1-carboxylate (1.7 g, 4.84 mmol) (Preparation #1), bis(pinacolato)diboron (2.2 g, 8.8 mmol), potassium acetate (0.864g, 8.8 mmol) in dioxane (19 mL) with 4 Å mol sieves. The reaction was degassed with nitrogen for 5 minutes before the addition of [1,1'-bis(diphenylphosphino)ferrocene] dichloropalladium(II)-dichloromethane adduct (Pd(dppf)Cl$_2$-DCM adduct) (0.269g, 0.33 mmol). The reaction was heated to 95° C. for 2 hours. The reaction was cooled to room temperature and filtered. In a separate vial, (3-(6-chloropyridin-2-yl)tetrahydrofuran-3-yl)methanol (0.94 g, 4.4 mmol) (Preparation #44) and potassium phosphate (1.8 g, 8.8 mmol) was dissolved in dioxane (19 mL) and water (6 mL) and degassed with nitrogen for 5 minutes before the addition of the filtered solution of boronate, tris(dibenzylideneacetone)dipalladium(0) (Pd$_2$(dba)$_3$) (0.121 g, 0.132 mmol), and 1S,3R,5R,7S)-1,3,5,7-tetramethyl-8-phenyl-2,4,6-trioxa-8-phosphaadamantane (PaPH) (0.077 g, 0.264 mmol). The reaction was sealed and heated to 80° C. for 2 hours. The reaction cooled to room temperature, and was partitioned between water and ethyl acetate. The organic portion was dried over MgSO$_4$, filtered, and concentrated under reduced pressure to provide a residue, which was purified via silica gel chromatography, eluting with 0-100% ethyl acetate:heptanes then flushed with 7% methanol:dichloromethane, to provide the product (0.76 g, 38% yield). LC/MS (Table A, Method a) R$_t$=1.30 minutes; MS m/z: 453 (M+H)$^+$.

Step 2: N-(3-(6-(3-(hydroxymethyptetrahydrofuran-3-yl)pyridin-2-yl)-1H-pyrrolo[2,3-c]pyridin-5-ypacetamide. A microwave vial was charged with tert-butyl 5-acetamido-3-(643-(hydroxymethyptetrahydrofuran-3-yl)pyridin-2-yl)-1H-pyrrolo[2,3-c]pyridine-1-carboxylate (760mg, 1.680 mmol) and ethanol (6 mL). The reaction was heated to 130° C. for about 30 minutes. The reaction was cooled to room temperature, and concentrated under reduced pressure to provide the product (0.61 g, 100% yield). LC/MS (Table A, Method a) R$_t$=0.70 minutes; MS m/z: 353 (M+H)$^+$.

Step 3: ((R)-N-(3-(6-(3-(hydroxymethyptetrahydrofuran-3-yl)pyridin-2-yl)-1-methyl-1H-pyrrolo[2,3-c]pyridin-5-ypacetamide and ((S)-N-(3-(6-(3-(hydroxymethyl)tetrahydrofuran-3-yl)pyridin-2-yl)-1-methyl-1H-pyrrolo[2,3-c]pyridin-5-yl)acetamide . A vial was charged with N-(3-(6-(3-(hydroxymethyptetrahydrofuran-3-yl)pyridin-2-yl)-1H-pyrrolo[2,3-c]pyridin-5-ypacetamide (340 mg, 0.965 mmol) and acetonitrile (6 mL), before the addition of cesium carbonate (472 mg, 1.44 mmol) and iodomethane (30.2 µl, 0.482 mmol). The reaction stirred at room temperature for 1 hour. The reaction was quenched with water and extracted with dichloromethane. The organic layer was washed with brine and dried over MgSO$_4$, and concentrated to dryness to provide the racemic product (0.315 g). The racemate was further purified via chiral HPLC (Table B, Method 20) to provide the R-isomer (0.107g, 30% yield, >97%ee, R$_t$=13.44 minutes), and the S-isomer (0.0.108 g, 30%y, >97%ee, R$_t$=15.88 minutes). LC/MS (Table A, Method b) R$_t$=0.77 minutes; MS m/z: 367 (M+H)$^+$. $^1$H NMR (400 MHz, Dimethyl sulfoxide-d$_6$) δ 10.13 (s, 1H), 9.04 (s, 1H), 8.57 (d, J=1.1 Hz, 1H), 8.20 (s, 1H), 7.67 (t, J=7.8 Hz, 1H), 7.53 (dd, J=7.9, 0.9 Hz, 1H), 7.06 (dd, J=7.7, 0.9 Hz, 1H), 4.74-4.69 (m, 1H), 4.09 (d, J=8.7 Hz, 1H), 3.95 (d, J=8.8 Hz, 1H), 3.90 (s, 3H), 3.88-3.76 (m, 2H), 3.73-3.64 (m, 2H), 2.41-2.19 (m, 3H), 2.06 (s, 3H).

76. Example #22: (S)-N-(3-(6-(3-(Hydroxymethyl)tetrahydrofuran-3-yl)-4-(methoxymethyl)pyridin-2-yl)-1-methyl-1H-pyrrolo[2,3-c]pyridin-5-yl)acetamide

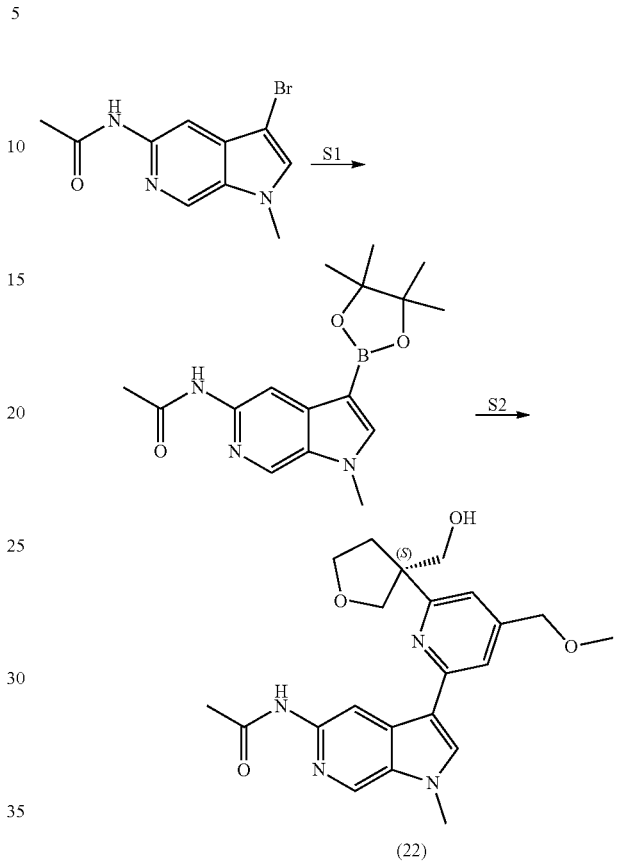

Step 1: N-(1-methyl-3-(4,4,5,5-tetramethyl-1,3,2-dioxaborolan-2-yl)-1H-pyrrolo[2,3-c]pyridin-5-yl)acetamide. A slurry of N-(3-bromo-1-methyl-1H-pyrrolo[2,3-c]pyridin-5-yl)acetamide (10 g, 37.3 mmol, Preparation #2), 4 Å molecular sieves, potassium acetate (12.81 g, 131 mmol) and bis(pinacolato)diboron (28.4 g, 112 mmol)) in dioxane (186 mL) was degassed for 10 minutes before the addition of dicyclohexyl(2',4',6'-triisopropyl-[1,1'-biphenyl]-2-yl)phosphine (1.778 g, 3.73 mmol) and tris(dibenzylideneacetone)dipalladium(0) (Pd$_2$(dba)$_3$) (1.708 g, 1.865 mmol). The mixture was heated to 90° C. for 16 hours. The solvent was concentrated to provide a residue, which was reslurried using diethyl ether for about 1 hour, then collected via filtration to provide the product (2.7 g, 23% yield). LC/MS (Table A, Method a) R$_t$=0.76 minutes; MS m/z: 316 (M+H)$^+$.

Step 2: (S)-N-(3-(6-(3-(hydroxymethyl)tetrahydrofuran-3-yl)-4-(methoxymethyl)pyridin-2-yl)-1-methyl-1H-pyrrolo[2,3-c]pyridin-5-ypacetamide . A flask was charged with (S)-(3-(6-bromo-4-(methoxymethyppyridin-2-yptetrahydrofuran-3-yl)methanol (350mg, 1.15 mmol, Preparation #45a), N-(1-methyl-3-(4,4,5,5-tetramethyl-1,3,2-dioxaborolan-2-yl)-1H-pyrrolo[2,3-c]pyridin-5-ypacetamide (402 mg, 1.2 mmol), and cesium carbonate (755 mg, 2.3 mmol) in dioxane (4.8 mL) and water (1 mL), and degassed for 10 minutes with a stream of nitrogen before the addition of (2-dicyclohexylphosphino-2',4',6'-triisopropyl-1,1'-biphenyl)[2,-(2'-amino-1,1'-biphenyl)]palladium(II) methanesulfonate (XPhos Pd G3) (49 mg, 0.058 mmol). The reaction was heated to 85° C. for 30 minutes, then cooled to room temperature and poured into 5% aqueous cysteine solution. The mixture was diluted with 50 mL ethyl acetate, and the organic portion was separated, washed with brine, dried over MgSO₄ and concentrated to dryness to provide a residue, which was purified via silica gel chromatography, eluting with 0-15% methanol: dichloromethane, to provide the product (0.272 g, 57% yield). LC/MS (Table A, Method b) R$_f$=0.83 minutes; MS m/z: 411 (M+H)⁺. ¹H NMR (400 MHz, Dimethyl sulfoxide-d₆) δ 10.12 (s, 1H), 9.05 (s, 1H), 8.57 (d, J=1.0 Hz, 1H), 8.23 (s, 1H), 7.48 (d, J=1.2 Hz, 1H), 6.98 (d, J=1.2 Hz, 1H), 4.72 (t, J=5.3 Hz, 1H), 4.45 (s, 2H), 4.10 (d, J=8.8 Hz, 1H), 3.93 (d, J=8.8 Hz, 1H), 3.90 (s, 3H), 3.88-3.77 (m, 2H), 3.73-3.65 (m, 2H), 3.36 (s, 3H), 2.35 (ddd, J=12.6, 8.5, 7.1 Hz, 1H), 2.25 (ddd, J=12.8, 7.6, 5.6 Hz, 1H), 2.06 (s, 3H).

The compounds shown in Tables 22a and 22b were synthesized in a manner similar to Example #22 from N-(1-methyl-3-(4,4,5,5-tetramethyl-1,3,2-dioxaborolan-2-yl)-1H-pyrrolo [2,3-c]pyridin-5-ypacetamide (Example #22, Step 1) and the corresponding aromatic halide.

TABLE 22a

| Ex | Aromatic Halide | Product | R$_t$ min (Method) | m/z (M + H)⁺ |
|---|---|---|---|---|
| 22a | (R)-(3-(6-bromo-4-(methoxymethyl)pyridin-2-yl)tetrahydrofuran-3-yl)methanol (Preparation #45) | (R)-N-(3-(6-(3-(hydroxymethyl)tetrahydrofuran-3-yl)-4-(methoxymethyl)pyridin-2-yl)-1-methyl-1H-pyrrolo[2,3-c]pyridin-5-yl)acetamide | 0.83 (b) | 411 |
| 22.3 | (S)-1-((R)-3-(6-chloro-4-(methoxymethyl)pyridin-2-yl)tetrahydrofuran-3-yl)ethan-1-ol (Preparation #49) | N-(3-(6-((R)-3-((S)-1-hydroxyethyl)tetrahydrofuran-3-yl)-4-(methoxymethyl)pyridin-2-yl)-1-methyl-1H-pyrrolo[2,3-c]pyridin-5-yl)acetamide | 0.87 (d) | 425 |
| 22.4 | (R)-1-((R)-3-(6-chloro-4-(methoxymethyl)pyridin-2-yl)tetrahydrofuran-3-yl)ethan-1-ol (Preparation #49a) | N-(3-(6-((R)-3-((R)-1-hydroxyethyl)tetrahydrofuran-3-yl)-4-(methoxymethyl)pyridin-2-yl)-1-methyl-1H-pyrrolo[2,3-c]pyridin-5-yl)acetamide | 0.87 (d) | 425 |
| 22.5 | (S)-(3-(6-chloro-4-(difluoromethyl)pyridin-2-yl)tetrahydrofuran-3-yl)methanol (Preparation #50) | (S)-N-(3-(4-(difluoromethyl)-6-(3-(hydroxymethyl)tetrahydrofuran-3-yl)pyridin-2-yl)-1-methyl-1H-pyrrolo[2,3-c]pyridin-5-yl)acetamide | 0.94 (d) | 417 |
| 22.6 | (S)-(3-(6-bromo-4-methoxypyridin-2-yl)tetrahydrofuran-3-yl)methanol (Preparation #51) | (S)-N-(3-(6-(3-(hydroxymethyl)tetrahydrofuran-3-yl)-4-methoxypyridin-2-yl)-1-methyl-1H-pyrrolo[2,3-c]pyridin-5-yl)acetamide | 0.82 (d) | 397 |
| 22.7 | (R)-(3-(6-bromo-4-methoxypyridin-2-yl)tetrahydrofuran-3-yl)methanol (Preparation #51a) | (R)-N-(3-(6-(3-(hydroxymethyl)tetrahydrofuran-3-yl)-4-methoxypyridin-2-yl)-1-methyl-1H-pyrrolo[2,3-c]pyridin-5-yl)acetamide | 0.82 (d) | 397 |
| 22.8 | (S)-(3-(6-bromo-4-(2-methoxyethoxy)pyridin-2-yl)tetrahydrofuran-3-yl)methanol (Preparation #52) | (S)-N-(3-(6-(3-(hydroxymethyl)tetrahydrofuran-3-yl)-4-(2-methoxyethoxy)pyridin-2-yl)-1-methyl-1H-pyrrolo[2,3-c]pyridin-5-yl)acetamide | 0.87 (d) | 441 |
| 22.9 | (R)-(3-(6-bromo-4-(2-methoxyethoxy)pyridin-2-yl)tetrahydrofuran-3-yl)methanol (Preparation #52a) | (R)-N-(3-(6-(3-(hydroxymethyl)tetrahydrofuran-3-yl)-4-(2-methoxyethoxy)pyridin-2-yl)- 1-methyl- 1H-pyrrolo[2,3-c]pyridin-5-yl)acetamide | 0.87 (d) | 441 |

TABLE 22b

| Ex | Aromatic Halide | Product | HRMS (+ESI) |
|---|---|---|---|
| 22.2 | (R)-2-chloro-4-(difluoromethoxy)-6-(3-methoxytetrahydrofuran-3-yl)pyridine (Preparation #47) | (R)-N-(3-(4-(difluoromethoxy)-6-(3-methoxytetrahydrofuran-3-yl)pyridin-2-yl)-1-methyl-1H-pyrrolo[2,3-c]pyridin-5-yl)acetamide | 433 |
| 22.10 | 2-chloro-4-((R)-2-methoxypropoxy)-6-((R)-3-methoxytetrahydrofuran-3-yl)pyridine (Preparation #53) | N-(3-(4-((R)-2-methoxypropoxy)-6-((R)-3-methoxytetrahydrofuran-3-yl)pyridin-2-yl)-1-methyl-1H-pyrrolo[2,3-c]pyridin-5-yl)acetamide | 455 |

77. Example #23: (R)-N-(3-(4-(Methoxymethyl)-6-(3-methoxytetrahydrofuran-3-yl)pyridin-2-yl)-1-methyl-1H-pyrazolo[3,4-c]pyridin-5-yl)acetamide

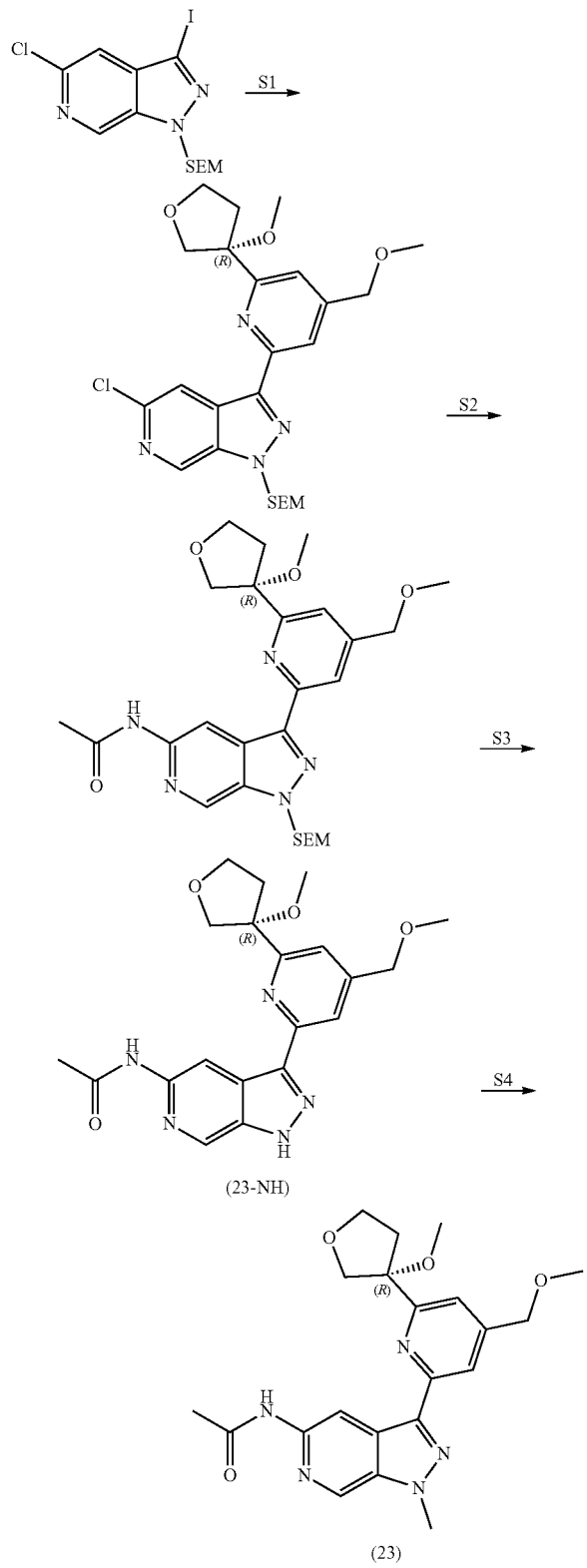

Step 1: (R)-5-chloro-3-(4-(methoxymethyl)-6-(3-methoxytetrahydrofuran-3-yl)pyridin-2-yl)-1-O2-(trimethylsilyethoxy)methyl)-1H-pyrazolo[3,4-c]pyridine. A solution of (R)-4-(methoxymethyl)-2-(3-methoxytetrahydrofuran-3-yl)-6-(tributylstannyOpyridine (1.695 g, 3.31 mmol, Preparation #40), and 5-chloro-3-iodo-1-((2-(trimethylsilyethoxy)methyl)-1H-pyrazolo[3,4-c]pyridine (1.232 g, 3.01 mmol; See PCT Publication No. WO 2015026683) with copper (I) iodide (0.069 g, 0.361 mmol) was stirred in toluene (15 mL) while sparging with nitrogen for about 20 minutes.

Tetrakis(triphenylphosphine)palladium (0) (0.348 g, 0.301 mmol) was added to the reaction mixture, and the reaction was heated to 100° C. overnight. The reaction cooled to room temperature and was quenched with water and extracted with dichloromethane. The combined organic layers were dried over MgSO$_4$, filtered, and concentrated to provide a residue, which was purified via silica gel chromatography, eluting with 0-100% ethyl acetate:heptanes, to provide the product (0.45 g, 30% yield). LC/MS (Table A, Method a) R, =2.09 minutes; MS m/z: 505, 507 (M+H)$^+$. SEM=2-(trimethylsilyl)ethoxy)methyl.

Step 2: (R)-N-(3-(4-(methoxymethyl)-6-(3-methoxytetrahydrofuran-3-yl)pyridin-2-yl)-14(2-(trimethylsilyethoxy)methyl)-1H-pyrazolo[3,4-c]pyridin-5-yl)acetamide. A solution of (R)-5-chloro-3-(4-(methoxymethyl)-6-(3-methoxytetrahydrofuran-3-yl)pyridin-2-yl)-1-((2-(trimethylsilyl)ethoxy)methyl)-1H-pyrazolo[3,4-c]pyridine (0.458 g, 0.907 mmol), acetamide (0.107 g, 1.814 mmol), and cesium carbonate (0.886 g, 2.72 mmol) in dimethylamine (3.0 mL) was sparged with nitrogen for 30 minutes before adding [(2-Di-cyclohexylphosphino-3,6-dimethoxy-2',4',6'- triisopropyl-1,1'-biphenyl)-2-(2'-amino-1,1'-biphenyl)]palladium(II) methanesulfonate (BrettPhos Pd G3) (0.082 g, 0.091 mmol). The reaction was heated to 120° C. for 40 minutes. The reaction cooled to room temperature and was filtered through a pad of Celite®, rinsing with ethyl acetate. The filtrate was diluted with water, and the layers were separated, and the aqueous layer was extracted three times with ethyl acetate. The combined organic layers were washed successively with water and brine, dried over MgSO4, filtered, and concentrated to provide the product (0.47 g, 100% yield). LC/MS (Table A, Method a) R$_t$=1.75 minutes; MS m/z: 528 (M+H)$^+$.

Step 3: (R)-N-(3-(4-(methoxymethyl)-6-(3-methoxytetrahydrofuran-3-yl)pyridin-2-yl)-1H-pyrazolo[3,4-c]pyridin-5-yl)acetamide. A flask was charged with (R)-N-(3-(4-(methoxymethyl)-6-(3-methoxytetrahydrofuran-3-yl)pyridin-2-yl)-1-((2-(trimethylsilyl)ethoxy)methyl)-1H-pyrazolo[3,4-c]pyridin-5-yl)acetamide (0.47 g, 0.907 mmol) and 1M solution of tetrabutylammonium fluoride in tetrahydrofuran (4.5 mL, 4.54 mmol). The reaction was heated in a Biotage® microwave to 100° C. for 1 hour. The reaction was quenched with water, extracted with ethyl acetate and the combined organic layers were dried over MgSO$_4$, filtered, and concentrated to provide the product (0.36 g, 100% yield). LC/MS (Table A, Method a) R$_t$=0.90 minutes; MS m/z: 398 (M+H)$^+$.

Step 4: (R)-N-(3-(4-(methoxymethyl)-6-(3-methoxytetrahydrofuran-3-yl)pyridin-2-yl)-1-methyl-1H-pyrazolo[3,4-c]pyridin-5-yl)acetamide. A solution of (R)-N-(3-(4-(methoxymethyl)-6-(3-methoxytetrahydrofuran-3-yl)pyridin-2-yl)-1H-pyrazolo[3,4-c]pyridin-5-ypacetamide (0.360 g, 0.907 mmol) in acetonitrile (9.0 mL) was treated with cesium carbonate (0.591 g, 1.814 mmol) and dimethyl sulfate (0.095 mL, 0.998 mmol). The reaction stirred at room temperature for 1 hour. The reaction was quenched with water, extracted with ethyl acetate, filtered, and concentrated to provide a residue, which was purified by silica gel chromatography, eluting with 0 to 15% methanol:dichloromethane, then further purified by reverse phase HPLC, eluting with 25 to 75% aqueous 10 mM ammonium acetate: acetonitrile, to provide the product (0.05 g, 13% yield). LC/MS (Table A, Method d) R$_f$=1.05 minutes; MS m/z: 412 (M+H)$^+$. $^1$H NMR (400 MHz, Dimethyl sulfoxide-d$_6$) δ 10.45 (s, 1H), 9.17 (s, 1H), 8.98 (t, J=1.0 Hz, 1H), 8.03-7.96 (m, 1H), 7.40 (dd, J=1.6, 0.7 Hz, 1H), 4.59 (d, J=0.9 Hz, 2H), 4.25-4.20 (m, 4H), 4.09 (td, J=8.3, 4.2 Hz, 1H), 4.06-3.99 (m, 1H), 3.92 (d, J=9.5 Hz, 1H), 3.41 (d, J=0.6 Hz, 3H), 3.13 (d, J=0.6 Hz, 3H), 2.81 (dt, J=13.2, 8.6 Hz, 1H), 2.52 (s, 9H), 2.50 (s, 6H), 2.46 (s, 1H), 2.13 (d, J=0.7 Hz, 3H).

78. Example #24: (R)-2-hydroxy-N-(3-(4-(methoxymethyl)-6-(3-methoxytetrahydrofuran-3-yl)pyridin-2-yl)-1-methyl-1H-pyrrolo[2,3-c]pyridin-5-yl)acetamide

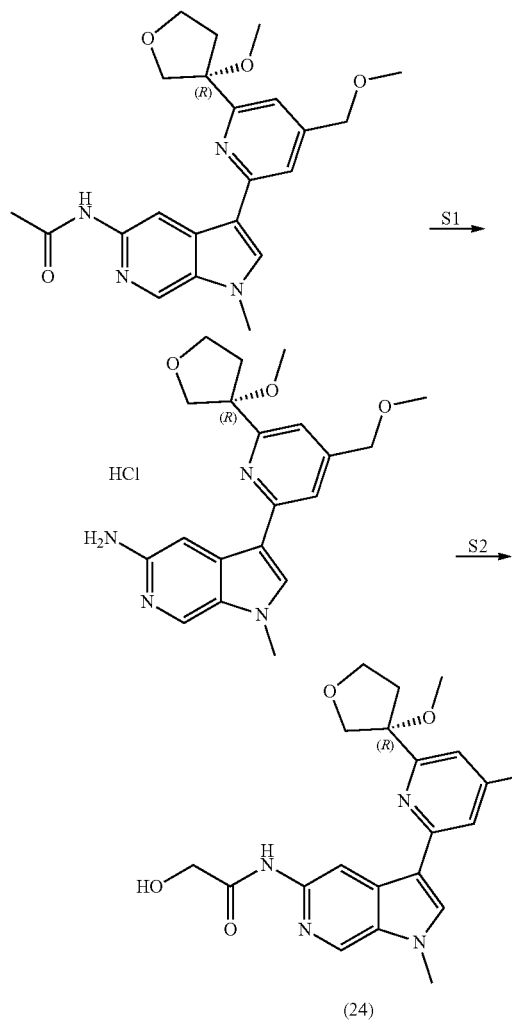

Step 1: (R) 3-(4-(methoxymethyl)-6-(3-methoxytetrahydrofuran-3-yl)pyridin-2-yl)-1-methyl-1H-pyrrolo[2,3-c]pyridin-5-amine, Hydrochloric Acid salt. A solution of (R)-N-(3-(4-(methoxymethyl)-6-(3-methoxytetrahydrofuran-3-yl)pyridin-2-yl)-1-methyl-1H-pyrrolo[2,3-c]pyridin-5-yl)acetamide (1.0 g, 2.43 mmol, Example #2), and aqueous HCl (2.4 mL, 12.2 mmol, 5 N) in dioxane (12 mL) was heated to 80° C. for 1 hour. The reaction mixture was cooled to room temperature and concentrated under reduced pressure. The remaining residue was azeotroped with ethanol and dried in a vacuum oven to give product (0.98 g, 99% yield). LC/MS (Table A, Method a) R$_f$=0.77 minutes; MS m/z: 369 (M+H)$^+$.

Step 2: (R)-2-hydroxy-N-(3-(4-(methoxymethyl)-6-(3-methoxytetrahydrofuran-3-yl)pyridin-2-yl)-1-methyl-1H-pyrrolo[2,3-c]pyridin-5-yl)acetamide. A solution of (R)-3-(4-(methoxymethyl)-6-(3-methoxytetrahydrofuran-3-yl)pyridin-2-yl)-1-methyl-1H-pyrrolo[2,3-c]pyridin-5- amine, HCl salt was dissolved in a mixture of dichloromethane (DCM) (8 mL) and pyridine (2 mL). Acetoxylacetyl chloride (0.54 mL, 5.08 mmol) was added and the reaction mixture was stirred for 3 hours at room temperature. The reaction mixture was concentrated under reduced pressure and taken back up in methanol (MeOH) (12 mL) before the addition of potassium carbonate (1.1 g, 2.4 mmol). The mixture was stirred at room temperature for 15 minutes. The excess salts were filtered off, and the remaining filtrate was concentrated under reduced pressure. The residue was then dissolved in DCM and washed with water. The organic portion was dried over MgSO$_4$, filtered and concentrated under reduced pressure to give crude material. The crude material was purified via silica gel chromatography, eluting with 0-10% MeOH in ethyl acetate to give desired product (0.78 g, 77% yield). LC/MS (Table A, Method d) R$_f$=0.93 minutes; MS m/z: 427(M+H)$^+$. $^1$H NMR (400 MHz, Dimethyl sulfoxide-d$_6$) δ 9.32 (s, 1H), 9.08 (s, 1H), 8.61 (d, J=1.0 Hz, 1H), 8.32 (s, 1H), 7.60 (d, J=1.2 Hz, 1H), 7.18 (d, J=1.2 Hz, 1H), 5.82 (t, J=5.9 Hz, 1H), 4.50 (s, 2H), 4.17 (dd, J=9.7, 1.2 Hz, 1H), 4.06 -3.95 (m, 4H), 3.91 (s, 3H), 3.89 (d, J=9.6 Hz, 1H), 3.37 (s, 3H), 3.09 (s, 3H), 2.77 (dt, J=13.2, 8.7 Hz, 1H), 2.44-2.37 (m, 1H).

79. Example #25: (R)-N-(3-(4-(2-methoxyethoxy)-6-(3-methoxytetrahydrofuran-3- yl)pyridin-2-yl)-1-methyl-1H-pyrrolo[2,3-c]pyridin-5-yl)acetamide

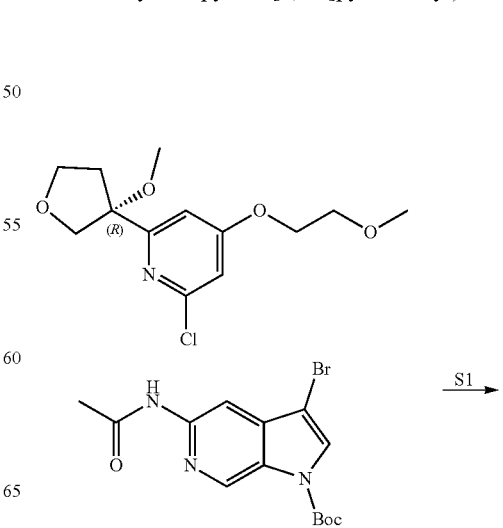

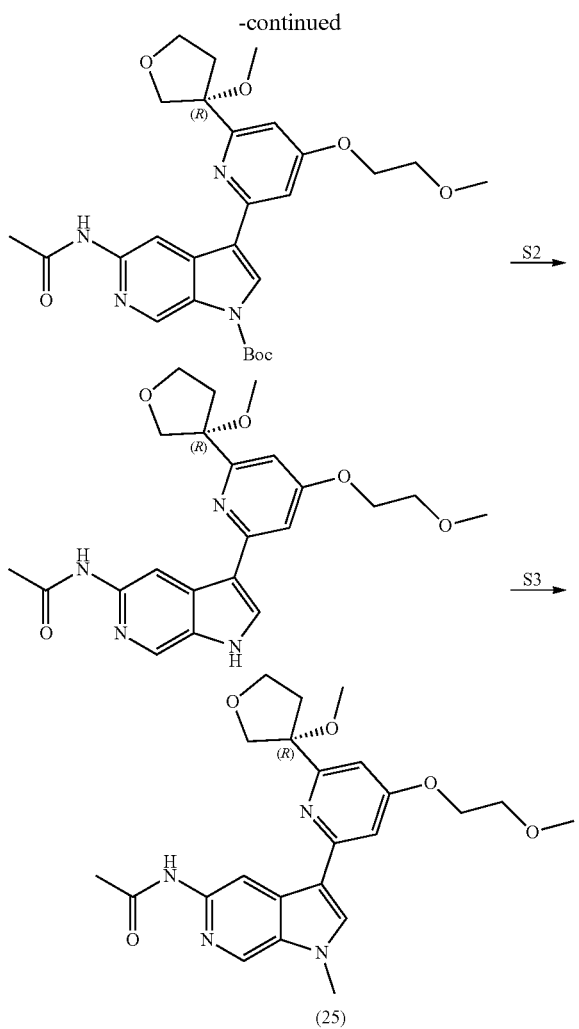

(25)

Step 1: tert-butyl (R)-5-acetamido-3-(4-(2-methoxyethoxy)-6-(3-methoxytetrahydrofuran-3-yl)pyridin-2-yl)-1H-pyrrolo[2,3-c]pyridine-1-carboxylate. A vial was charged with tert-butyl 5- acetamido-3-bromo-1H-pyrrolo[2,3-c]pyridine-1-carboxylate (7.5 g, 21.2 mmol) (Preparation #1), bis(pinocalato)diboron (7.7 g, 30.3 mmol), and potassium acetate (4.9 g, 50.5 mmol) in dioxane (180 mL) with 4 Å molecular sieves. The mixture was degassed with nitrogen for 5 minutes before the addition of 1,3,5,7-tetramethyl-6-phenyl-2,4,8-trixa-6-phosphadamantane (0.41 g, 0.451 mmol) and $Pd_2(dba)_3$ (0.64 g, 0.70 mmol). The reaction was heated to 85° C. for about 5 hours. The mixture was cooled to room temperature. In a separate vial (R)-2-chloro-4-(2-methoxyethoxy)-6-(3-methoxytetrahydrofuran-3-yl)pyridine (5.81 g, 20.19 mmol) (Preparation #48) and potassium phosphate (12.8 g, 60.6 mmol) were dissolved in water (20 mL) and the mixture was degassed with nitrogen for 5 minutes before the addition of the filtered solution of boronate. The mixture was sealed and heated to 70° C. for 90 minutes. The mixture was cooled to room temperature, and was washed with 5% aqueous solution of sodium bicarbonate/L-cysteine (200 mL). The mixture was stirred vigorously. After stirring overnight a tan precipitate had formed. The solid was isolated by vacuum filtration, rinsed with deionized water, rinsed with acetonitrile, and dried in a vacuum oven at 60° C. to give desired product (5.75 g, 53% yield). $^1$H NMR (400 MHz, Dimethyl sulfoxide-$d_6$) δ 10.39 (s, 1H), 9.18 (s, 1H), 9.01 (d, J=1.0 Hz, 1H), 8.62 (s, 1H), 7.59 (d, J=2.2 Hz, 1H), 6.98 (d, J=2.2 Hz, 1H), 4.40-4.26 (m, 2H), 4.20 (dd, J=9.7, 1.2 Hz, 1H), 4.08-3.94 (m, 2H), 3.91 (d, J=9.6 Hz, 1H), 3.76-3.65 (m, 2H), 3.34 (s, 3H), 3.13 (s, 3H), 2.75 (dt, J=13.2, 8.7 Hz, 1H), 2.11 (s, 3H), 1.69 (s, 10H).

Step 2: (R)-N-(3-(4-(2-methoxyethoxy)-6-(3-methoxytetrahydrofuran-3-yl)pyridin-2-yl)- 1H-pyrrolo[2,3-c]pyridin-5-yl)acetamide. A large microwave vial was charged with tert-butyl (R)-5 - acetamido-3 -(4 -(2-methoxy ethoxy)-6-(3 -methoxytetrahy drofuran-3-yl)pyridin-2-yl)-1H-pyrrolo[2,3- c]pyridine-1-carboxylate (2.00 g, 3.81 mmol) dissolved in ethanol (15 mL). The mixture was heated in a Biotage® microwave to 150° C. for 20 minutes. The reaction mixture was cooled to room temperature and then cooled in an ice bath. The precipitate that formed was isolated by vacuum filtration and rinsed with acetonitrile to give the product (1.15 g, 69% yield). LC/MS (Table A, Method b) $R_t$=0.85 minutes; MS m/z: 427 (M+H)$^+$.

Step 3: (R)-N-(3-(4-(2-methoxyethoxy)-6-(3-methoxytetrahydrofuran-3-yl)pyridin-2-yl)- 1-methyl-1H-pyrrolo[2,3-c]pyridin-5-yl)acetamide. A flask was charged (R)-N -(3 -(4 -(2- methoxy ethoxy)-6-(3 -methoxytetrahy drofuran-3-yl)pyridin-2-yl)-1H-pyrrolo[2,3-c]pyridin-5- yl)acetamide (2.0 g, 4.8mmo1), cesium carbonate (4.78 g, 14.6 mmol), and methyl iodide (0.321 mL, 5.13 mmol) in acetonitrile (44 mL). The reaction mixture was stirred at room temperature for 3 hours. The reaction mixture was diluted with 100 mL of 10% methanol (MeOH) in dichloromethane (DCM) and filtered. After rinsing the solids with additional 10% MeOH in DCM, the filtrate was dried over $MgSO_4$, filtered and concentrated, then purified via silica gel chromatography, eluting with 0-10% MeOH in DCM to give the desired product (1.9 g, 90% yield, 94% ee). LC/MS (Table A, Method d) $R_t$=0.97 minutes; MS m/z: 441 (M+H). $^1$H NMR (400 MHz, Dimethyl sulfoxide-$d_6$) δ 10.17 (s, 1H), 9.04 (s, 1H), 8.61 (d, J =1.0 Hz, 1H), 8.32 (s, 1H), 7.27 (d, J=2.2 Hz, 1H), 6.83 (d, J=2.1 Hz, 1H), 4.34-4.23 (m, 2H), 4.16 (dd, J=9.6, 1.2 Hz, 1H), 4.07-3.95 (m, 2H), 3.93 (s, 3H), 3.90 (d, J=9.6 Hz, 1H), 3.76-3.67 (m, 2H), 3.34 (s, 3H), 3.13 (s, 3H), 2.77 (dt, J=13.1, 8.7 Hz, 1H), 2.46-2.38 (m, 1H), 2.09 (s, 3H).

80. Example #26: (R)-N-(3-(4-(difluoromethyl)-6-(3-methoxytetrahydrofuran-3-yl)pyridin- 2-yl)-1-methyl-1H-pyrrolo[2,3-c]pyridin-5-yl)-2-hydroxyacetamide

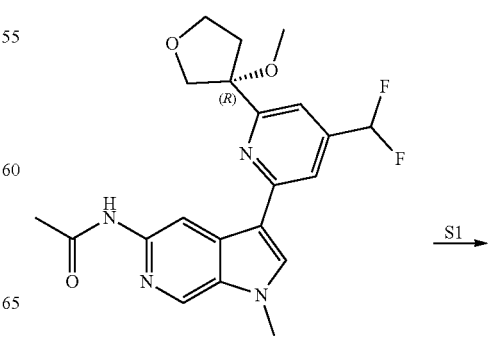

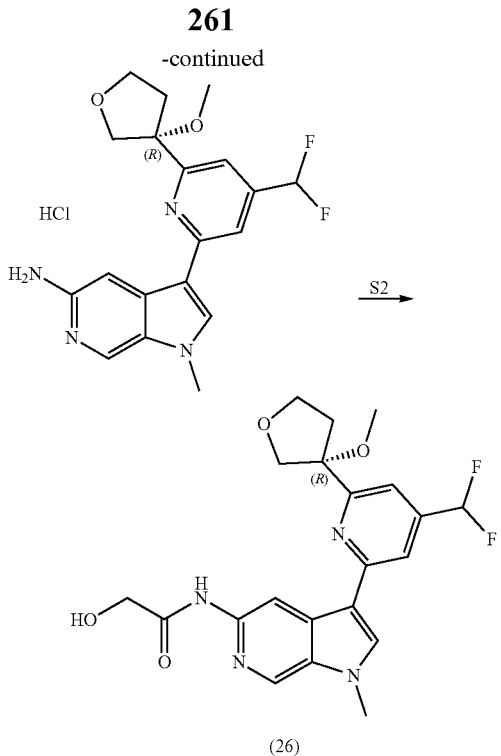

Step 1: (R)-3-(4-(difluoromethyl)-6-(3-methoxytetrahydrofuran-3-yl)pyridin-2-yl)-1-methyl-1H-pyrrolo[2,3-c]pyridin-5-amine, Hydrochloride. A solution of (R)-N-(3-(4-(difluoromethyl)-6-(3-methoxytetrahydrofuran-3-yl)pyridin-2-yl)-1-methyl-1H-pyrrolo[2,3-c]pyridin-5-yl)acetamide (0.280 g, 0.67 mmol, Example #2.8) and aqueous HCl (1 mL, 5.4 mmol, 5 N) in dioxane (6 mL) was heated to 70° C. for 1 hour. The reaction mixture was cooled to room temperature and concentrated under reduced pressure to give desired crude product (0.25 g, 99% yield). LC/MS (Table A, Method a) $R_t$=1.05 minutes; MS m/z: 375 (M+H)$^+$.

Step 2: (R)-N-(3-(4-(difluoromethyl)-6-(3-methoxytetrahydrofuran-3-yl)pyridin-2-yl)-1-methyl-1H-pyrrolo[2,3-c]pyridin-5-yl)-2-hydroxyacetamide. To a solution of (R)-3-(4-(difluoromethyl)-6-(3-methoxytetrahydrofuran-3-yl)pyridin-2-yl)-1-methyl-1H-pyrrolo[2,3-c]pyridin-5-amine hydrochloride (0.276 g, 0.67 mmol) in dichloromethane (DCM) (3.3 mL) was added pyridine (0.43 mL, 5.3 mmol) and acetoxyacetyl chloride (0.18 mL, 1.68 mmol). The reaction mixture was stirred for about 16 hours. Additional pyridine (0.43 mL, 5.38 mmol)) and acetoxyacetyl chloride (0.181 ml, 1.680 mmol) were added and the reaction mixture was stirred for 24 hours at room temperature. The reaction was quenched by addition of NH$_4$Cl and the mixture was extracted into ethyl acetate (EtOAc). The combined organic extracts were washed with NaHCO$_4$ and brine, dried over MgSO$_4$, filtered, and concentrated to give crude residue. The residue was taken up in methanol (MeOH) (3.3 mL) and potassium carbonate (0.27 g, 2.01 mmol) was added. The reaction mixture was stirred at room temperature for about 2 hours. The reaction mixture was quenched with saturated aqueous NH$_4$Cl and the mixture was extracted with EtOAc. The organic portion was dried over MgSO$_4$, filtered and concentrated under reduced pressure. The crude material was purified via silica gel chromatography, eluting with 0-8% MeOH/DCM to give desired product (0.14 g, 46% yield). LC/MS (Table A, Method d) $R_t$=1.02 minutes; MS m/z: 433 (M+H)$^+$. $^1$H NMR (400 MHz, Dimethyl sulfoxide-d$_6$) δ 9.43 -9.32 (m, 1H), 9.13 (s, 1H), 8.67 (d, J=1.0 Hz, 1H), 8.50 (s, 1H), 7.87 (qd, J=0.8 Hz, 1H), 7.41 (dt, J=1.8, 0.9 Hz, 1H), 7.31-6.95 (m, 1H), 5.85 (t, J=5.9 Hz, 1H), 4.23 (dd, J=9.6, 1.3 Hz, 1H), 4.14-3.98 (m, 4H), 3.97 - 3.91 (m, 4H), 3.16 (s, 3H), 2.83 (dt, J=13.2, 8.6 Hz, 1H), 2.49-2.43 (m, 1H).

ASSAY METHODS

1. TYK2 (TYK2/JAK2 PSTAT4 T-BLAST) ALPHA SCREEN ASSAY

IL-12 is known to transduce its signal through IL-12 receptor via Jak2 and/or Tyk2. For that reason, the activity against Tyk2/Jak2 was measured by determining the inhibition of IL-12 induced phosphorylation of STAT4 in T-blast cells. From these tests, the EC$_{50}$ (effective concentration for 50% maximal response) values were determined in uM for the test compounds. If the compounds showed minimal activity in the Jak2 (PTATS UT7) alpha screen assay (e.g., >25 μM activity), then it was stipulated that the activity from the Tyk2 (Tyk2/Jak2 T-Blast) alpha screen assay is driven by inhibition of Tyk2. See, e.g., Sohn et al., J. Immunology (2013) 2205-2216.

a. Materials

Cell Type: Frozen primary phytohemagglutinin (PHA) T-Blasts; Culture Medium: Roswell Park Memorial Institute (RPMI) 1640 Medium, 10% heat-inactivated fetal bovine serum (FBS), 1% penicillin/streptomycin (Pen-Strep), 10 mM hydroxyethyl piperazineethanesulfonic acid (HEPES), 10 ng/mL recombinant human interleukin-12 (rhIL-12); Assay Medium: Hank's Balanced Salt Solution (HBSS), no phenol red.

b. Plate Preparation

Compound dilutions:

i. Automated 11-point 1:3 dilution curve: 2.5 mM top concentration dispensed in column 1 of a Corning 96-well polypropylene plate. Dimethyl sulfoxide (DMSO) was added to column 12 for high and low controls. Compounds were serially diluted 1:3 by adding 20 uL stock to 40 μL DMSO across the plate via Hamilton Microlab Star instrument.

ii. Media dilution of compounds: Serially diluted compounds were diluted 1:50 in assay medium by adding 4 μL compound to 196 μL assay medium in a Corning 96-well polypropylene plate (now 2% DMSO).

iii. Plating on assay plates: 2.5 μL of serially diluted compounds in media were plated in duplicate on a 384-well gray Alphaplate (PerkinElmer). Technical replicates were plated horizontally so that each row contains an 11-point compound curve.

Primary T-Blasts from overnight culture were centrifuged, washed once in assay medium, and pelleted. T-Blasts were counted and resuspended at 12,500,000 cells/mL. 5μL of T-Blast suspension was added to each well of 384-well Alphaplate with compounds for a volume of 7.5 μL. Final DMSO: 0.5%. Top final compound concentration: 12.5 μM. Cells and compounds were pre-incubated for 30 minutes at 37° C. and 5% CO$_2$.

c. IL-12 Stimulation 4X working stock of recombinant human interleukin-12 (rhIL-12) was prepared by adding 484 5μg/mL rhIL-12 to 4.95 mL assay medium. 2.5 μL of 4X working dilution rhIL-12 was added to columns 1-23 of assay plate for a final rhIL-12 concentration of 12ng/mL. 2.5 μL of assay medium was added to column 24 for the low control wells. Final reaction volume was 10 µL. Plates were incubated for 20 minutes at 37° C. and 5% $CO_2$.

d. Cell Lysis 2.5 µL 5X lysis buffer (PerkinElmer) was added to each well of the Alphaplate. Plates were incubated at room temperature on orbital shaker for 30 minutes.

e. Protein (A) Acceptor Beads Preparation:

Phosphorylated Signal Transducer and Activator of Transcription 4 (pSTAT4) was quantified using the PerkinElmer SureFire Ultra pSTAT4 (Tyrosine 693) Assay. Make master mix of Protein A acceptor beads using the following volumes per well: 2.82 µL Reaction Buffer 1; 2.82 µL Reaction Buffer 2; 0.48 µLActivation Buffer (warmed to 37° C. prior to use); and 0.12 µL Acceptor Beads. Added 6 µL to each well and covered with foil. Final volume was 16 µL. Shaked on orbital shaker at room temperature for 2 hours at 500 rpm (revolutions per minute).

f. Streptavidin Donor Beads Preparation:

Make master mix of Protein A donor beads using the following volumes per well: 5.88 µL Dilution Buffer and 0.12 µL Acceptor Beads. Added 6 µL to each well and covered with foil. Final volume was 24 µL. Shaked on orbital shaker at room temperature overnight at 500 rpm. Read plate on Perkin Elmer Envision. Raw data was entered into Assay Explorer and dose-response curves were generated to report $EC_{50}$ data based on percent activity from high controls (column 23) and low controls (column 24).

2. JAK1 (PSTAT3 TF1) ALPHA SCREEN ASSAY

IL-6 is known to transduce its signal through IL-6 receptor via Jak1. Activity against Jak1 was therefore measured by determining inhibition of IL-6 induced phosphorylation of STAT3 in TF1 cells.

From these tests, the $EC_{50}$ (effective concentration for 50% maximal response) values were determined in uM for the test compounds.

a. Materials

Cell Type: TF1 Cells; Culture Medium: RPMI 1640 Medium, 2mM L-glutamine, 10% heat- inactivated fetal bovine serum (FBS), 10 mM hydroxyethyl piperazineethanesulfonic acid (HEPES), and 2 ng/mL recombinant human interleukin-6(IL-6); Assay Medium: Dulbecco's Modified Eagle Medium (DMEM) medium with 2 mM L-glutamine, 10 mM HEPES, 100 U/mL penicillin/streptomycin, 1.5 g/L sodium bicarbonate, 4.5 g/L glucose, 1 mM sodium pyruvate, 10% heat-inactivated FBS; Compound Preparation: Compounds are dissolved in 100% dimethyl sulfoxide (DMSO).

b. Plate Preparation

Day One—Starve Cells: 4 Flasks for one 384 plate (spin down @1000 rpm for 10 minutes and add RPMI 1640 Medium, 2 mM L-glutamine, 10% FBS, 10 mM HEPES with no IL-6 -incubate overnight).

Day Two—Compound Dilutions:

i. Manual 8-point 1:5 dilution curve: 5 mM top concentration dispensed in row A of a Corning 96-well polypropylene plate, columns 2-12. DMSO dispensed in position A01 for low and high controls. Compounds were serially diluted 1:5 by adding 10 µL stock to 404 µL DMSO down the plate.

ii. Media dilution of compounds: Serially diluted compounds were further diluted 1:12.5 in assay medium by adding 4 µL compound to 46 µL assay medium in a Corning 96-well polypropylene plate.

384 Alpha Screen Plate Set up: Transfer 2.5 µL/well of compound solution from assay media dilution plate. Replicates were vertical, one column of the 96-well dilution plate goes into one column on the 384-well plate twice. Plated $1 \times 10^5$ starved cells/well in 5 µL. Washed cells in 10 mL DMEM medium after spinning down. Brought cell pellet up in assay media. Counted live cells. Multiplied by dilution factor and 10,000 (constant) to get the concentration of viable cells. Multiplied by volume of assay media used to bring up cells to get the total number of live cells. Divided by 20,000,000 cells/mL to get the volume needed. Cells were plated at 5 µL/well in gray Alpha Screen 384-well plate. Spinned the plate to bring the contents to the bottom of the wells at 300 rpm for 60 seconds. Top final compound concentration: 25 µM. Sealed with adhesive and tapped gently. Incubated plate at 37° C. for 30 minutes. c. IL-6 Stimulation (pSTAT3)

Once cells were in incubator, immediately prepared working stock of IL-6 (100 ng/mL final concentration). IL-6 stock=10 µg/mL of IL-6 in phosphate buffered saline with 0.1% bovine serum albumin. Diluted 1:25 by adding 60 µL stock IL-6 to 1440 µL assay media. Added 2.5 µL IL-6 to each well. Spinned plate at 300 rpm briefly; tapped the plate gently before covering with an adhesive seal. Incubated plate at 37° C. for 30 minutes.

d. Cell Lysis

Added 2.5 µL of 5X Lysis buffer to each well. Incubated at room temperature on orbital shaker for 10 minutes.

e. Protein (A) Acceptor Beads Preparation:

Phosphorylated Signal Transducer and Activator of Transcription 3 (pSTAT3) was quantified using the PerkinElmer SureFire pSTAT3 (Tyrosine 705) Assay. Calculated total volume needed (wells×154 µL×25%). Divided total volume by 5 to get volume of activation buffer. Subtracted volume of activation buffer from total volume and divide by 40 to get volume of acceptor beads (add last). Total volume–acceptor bead volume–activation buffer=volume of reaction buffer. Added 15 µL to each well and covered with foil. Shaked on orbital shaker for 2 hours at 500 rpm.

f. Streptavidin Donor Beads Preparation:

Calculated total volume needed (wells×6 ∞L×25%). Divided total volume by 20 to get volume of donor beads (add last). Subtracted volume of donor beads from total volume to get volume of dilution buffer. Added 6 µL to each well and covered with foil. Shaked on orbital shaker overnight at 500 rpm.

Read plate on a Perkin Elmer Envision. Raw data was entered into Assay Explorer and dose- response curves were generated to report $EC_{50}$ data based on percent activity.

3. JAK2 (PSTATS UT7) ALPHA SCREEN ASSAY

Erythropoietin (EPO) is known to transduce its signal through EPO receptor via Jak2. Activity against Jak2 was therefore measured by determining inhibition of EPO induced phosphorylation of STATS in UT7 cells. From these tests, the $EC_{50}$ (effective concentration for 50% maximal response) values were determined in uM for the test compounds. a. Materials Cell Type: UT7 cells engineered to express the erythropoietin (EPO) receptor; Culture Medium: Dulbecco's Modified Eagle Medium (DMEM) with 2 mM L-glutamine, 10 mM hydroxyethyl piperazineethanesulfonic acid (HEPES), 10% heat-inactivated fetal bovine serum (FBS) and Stock EPO (5000U in 250 uL, need 5U/mL, so add 250 µL to 1L of media); Assay Medium: 5% FBS ultra-low IgG and 1% Pen/Strep. Compounds were made-up in 100% dimethyl sulfoxide (DMSO).

b. Plate Preparation

Day One - Starve Cells: 4 Flasks for one 384 plate (spin down @1000 rpm for 10 minutes and add DMEM with no EPO).

Day Two—Compound Dilutions:

i. Manual 8-point 1:3 dilution curve: 5 mM top concentration dispensed in row A of a Corning 96-well polypropylene plate, columns 2-12. DMSO dispensed in position A01 for low and high controls. Compounds were serially diluted 1:3 by adding 10 μL stock to 20 μL DMSO down the plate.

ii. Media dilution of compounds: Serially diluted compounds were diluted 1:50 in assay medium by adding 4 μL compound to 196 μL assay medium in a Corning 96-well polypropylene plate.

384 Alpha Screen Plate Set up: Transferred 2.5 μL/well of compound solution from last dilution plate. Replicates were vertical, so that one column of the 96-well dilution plate goes into one column on the 384-well plate twice. Plated $1 \times 10^5$ starved cells/well in 5μL. Washed cells in 10 mL Hank's balanced salt solution (HBSS) after spinning down. Counted live cells. Multiplied by dilution factor and 10,000 (constant) to get the concentration of viable cells. Multiplied by volume of cells to get the total number of live cells. Divided by 20,000,000 cells/mL to get the volume needed. Subtracted the original volume to get the volume to be added to get the final concentration of cells. Mixed in reservoir if needed, ensuring that all cell clumps are broken up (if not broken up, they were removed from the suspension). Cells were plated at 5 μL/well in gray Alpha Screen 384-well plate. Spinned the plate to bring the contents to the bottom of the wells at 400 rpm for 2 minutes. Top final compound concentration: 25 μM. Sealed with adhesive and tapped gently. Incubated cells at 37° C. for 30 minutes.

c. EPO Stimulation (p STATS)

Once cells were in incubator, immediately prepared working stock of EPO (1 nM final assay concentration). EPO stock=2860 nM of sterile filtered liquid in sodium citrate buffer (1 liter of ddH2O containing 5.9 g of sodium citrate, 5.8 g of sodium chloride and 0.06 g of citric acid). Diluted 1:22.72 by adding 4.44 stock EPO to 95.6 pi assay media, then dilute again 1:250 depending on how much volume is needed for the assay plates. Used assay medium to bring to volume. Added 2.5 μL EPO to each well. Spinned plate at 400 rpm briefly; tap the plate gently before covering with an adhesive seal. Cells were incubated at 37° C. for 20 minutes.

d. Cell Lysis

Added 2.5 μL of 5X Lysis buffer to each well. Spinned plate at 400 rpm briefly. Incubated at room temperature (on orbital shaker) for 10 minutes.

e. Protein (A) Acceptor Beads Preparation: (Light sensitive)

Phosphorylated Signal Transducer and Activator of Transcription 5 (pSTAT5) was quantified using the PerkinElmer SureFire pSTATS (Tyrosine 694/699) Assay. Calculated total volume needed (wells×15 μL×30%). Divided total volume by 5 to get volume of activation buffer. Subtracted volume of activation buffer from total volume and divide by 40 to get volume of acceptor beads (add last). Total volume - acceptor bead volume - activation buffer to get volume of reaction buffer. Added 15 μL to each well and covered with foil. Shaked on orbital shaker for 2 hours at 500 rpm.

f. Streptavidin Donor Beads Preparation:

Calculated total volume needed (wells×6μL×30%). Divided total volume by 20 to get volume of donor beads (add last). Subtracted volume of donor beads from total volume to get volume of dilution buffer. Added 6μL to each well and covered with foil. Shaked on orbital shaker overnight at 500 rpm.

Read plate on Perkin Elmer Envision. Raw data was entered into Assay Explorer and dose-response curves were generated to report $EC_{50}$ data based on percent activity.

4. ACTIVITY AND SELECTIVITY DATA

Certain compounds listed in Table C were tested for Tyk2 activity following the aforementioned Tyk2 (Tyk2/Jak2 PSTAT4 T-Blast) alpha screen assay and Jak2 (PTATS UT7) alpha screen assay. If the compounds showed minimal activity in the Jak2 (PTATS UT7) alpha screen assay (e.g., >25 μM activity), then it was stipulated that the activity from the Tyk2 (Tyk2/Jak2 T-Blast) alpha screen assay is driven by inhibition of Tyk2. Certain compounds were also tested for Jak1 activity following the aforementioned Jak1 (PTAT3 TF1) alpha screen assay. Selectivity for Tyk2 over Jak1, and Tyk2 over Jak2, are calculated from the tabulated activity data.

TABLE C

| Ex# | Tyk2 alpha screen (Tyk2/Jak2 PSTAT4 T-Blast) $EC_{50}$ (μM) | Jak1 alpha screen (PSTAT3 TF1) $EC_{50}$ (μM) | Tyk2 selectivity over Jak1 | Jak2 alpha screen (PSTAT5 UT7) $EC_{50}$ (μM) | Tyk2 selectivity over Jak2 |
|---|---|---|---|---|---|
| 1 | 0.059 | 5.45 | 92-fold | >25 | >424-fold |
| 1a | 0.468 | — | — | — | — |
| 1.2 | 0.045 | 13.5 | 300-fold | >25 | >556-fold |
| 1.3 | 2.03 | —Table 1x | — | — | — |
| 1a.2 | 0.288 | — | — | — | — |
| 1b.2 | 0.025 | 21 | 840-fold | >25 | >1000-fold |
| 1b.3 | 0.445 | 4.46 | 10-fold | — | — |
| 1b.4 | 0.142 | 7.6 | 54-fold | >25 | >176-fold |
| 1b.5 | 0.018 | 1.5 | 83-fold | >25 | >1389-fold |
| 1b.6 | 0.195 | 4.2 | 22-fold | >25 | >128-fold |
| 2 | 0.126 | >40 | >317-fold | >25 | >198-fold |
| 2-NH | 0.31 | — | — | — | — |
| 2.2 | 0.198 | 41 | 207-fold | >25 | >126-fold |
| 2.3 | 0.096 | 18 | 188-fold | — | — |
| 2.3a | 2.22 | — | — | — | — |
| 2.4 | 0.699 | — | — | — | — |
| 2.5 | 0.694 | — | — | — | — |
| 2.6 | 0.268 | — | — | — | — |
| 2.7 | 0.254 | — | — | — | — |
| 2.8 | 0.042 | 17 | 405-fold | >25 | >595-fold |
| 2.9 | 0.716 | — | — | — | — |
| 2.10 | 0.368 | — | — | — | — |
| 2.11 | 0.104 | 7.5 | 72-fold | >25 | >240-fold |

TABLE C-continued

| Ex# | Tyk2 alpha screen (Tyk2/Jak2 PSTAT4 T-Blast) EC$_{50}$ (μM) | Jak1 alpha screen (PSTAT3 TF1) EC$_{50}$ (μM) | Tyk2 selectivity over Jak1 | Jak2 alpha screen (PSTAT5 UT7) EC$_{50}$ (μM) | Tyk2 selectivity over Jak2 |
|---|---|---|---|---|---|
| 2a.2 | 0.749 | — | — | — | — |
| 2a.4 | 2.36 | — | — | — | — |
| 2a.3 | 0.127 | 56 | 440-fold | >25 | >197-fold |
| 2a.5 | 1.59 | — | — | — | — |
| 3 | 0.035 | 18 | 514-fold | >25 | >714-fold |
| 3.2 | 0.014 | 3.4 | 243-fold | >25 | >1786-fold |
| 3.3 | 0.388 | — | — | — | — |
| 4 | 0.137 | >100 | >730-fold | >25 | >182-fold |
| 4.2 | 0.616 | — | — | — | — |
| 4.3 | 0.174 | 54 | 310-fold | >25 | >144-fold |
| 4.4 | 0.353 | — | — | — | — |
| 5 | 0.111 | >100 | >901-fold | — | — |
| 5.2 | 0.156 | >100 | >641-fold | — | — |
| 5.3 | 0.561 | — | — | — | — |
| 6 | 0.050 | 21 | 420-fold | >25 | >500-fold |
| 6.2 | 0.103 | 5.2 | 50-fold | — | — |
| 6.3 | 0.352 | — | — | — | — |
| 7 | 0.878 | 34 | 39-fold | >25 | >28-fold |
| 8 | 0.090 | 22 | 244-fold | — | — |
| 9 | 0.085 | 42 | 494-fold | >25 | >294-fold |
| 10 | 0.091 | 27 | 297-fold | >25 | >275-fold |
| 11 | 0.052 | 23 | 442-fold | >25 | >481-fold |
| 11a | 0.496 | — | — | — | — |
| 11.2 | 0.124 | — | — | — | — |
| 12 | 0.244 | 16.2 | 66-fold | >25 | >102-fold |
| 12.2 | 0.551 | — | — | — | — |
| 12.3 | 0.094 | 13 | 138-fold | >25 | >266-fold |
| 12.4 | 0.319 | — | — | — | — |
| 12.5 | 0.022 | 20 | 909-fold | — | — |
| 12.6 | 0.039 | 15 | 385-fold | >25 | >641-fold |
| 12.7 | 0.185 | 15 | 81-fold | — | — |
| 12a.2 | 0.578 | — | — | — | — |
| 12a.3 | 0.066 | >100 | >1515-fold | — | — |
| 12b.2 | 0.015 | 40 | 2667-fold | — | — |
| 12b.3 | 0.056 | 68 | 1214-fold | — | — |
| 12b.4 | 0.045 | 40 | 889-fold | — | — |
| 13 | 0.492 | — | — | — | — |
| 14 | 0.563 | 11.1 | 20-fold | — | — |
| 14.2 | 0.673 | — | — | — | — |
| 14.3 | 0.339 | — | — | — | — |
| 14.4 | 0.134 | 63 | 470-fold | >25 | >187-fold |
| 14.5 | 0.146 | 71 | 486-fold | >25 | >171-fold |
| 14.6 | 0.087 | 49 | 563-fold | >25 | >287-fold |
| 15 | 0.908 | 73 | 80-fold | — | — |
| 15.2 | 1.84 | — | — | — | — |
| 16 | 0.310 | — | — | — | — |
| 16-NH | 3.14 | — | — | — | — |
| 16a | 1.59 | — | — | — | — |
| 17 | 0.031 | 27 | 871-fold | >25 | >806-fold |
| 17-NH | 1.52 | — | — | — | — |
| 17a | 0.477 | — | — | — | — |
| 17.2 | 0.144 | 35 | 243-fold | >25 | >174-fold |
| 17.3 | 0.008 | — | — | — | — |
| 17.4 | 0.127 | 20 | 157-fold | — | — |
| 17.5 | 0.005 | 32 | 6400-fold | — | — |
| 18 | 0.494 | — | — | — | — |
| 18a | 0.537 | — | — | — | — |
| 19 | 0.198 | — | — | — | — |
| 20 | 0.137 | 45 | 328-fold | — | — |
| 20a | 0.906 | — | — | — | — |
| 21 | 0.08 | 2.8 | 35-fold | >25 | >313-fold |
| 21a | 1.31 | — | — | — | — |
| 21-NH (R-isomer) | 0.54 | — | — | — | — |
| 22 | 0.146 | 10.5 | 72-fold | >25 | >171-fold |
| 22a | 1.2 | — | — | >25 | >21-fold |
| 22.2 | 0.089 | 35 | 393-fold | >25 | >281-fold |
| 22.3 | 0.147 | 12.9 | 88-fold | >25 | >170-fold |
| 22.4 | 0.112 | 27.2 | 243-fold | >25 | >223-fold |
| 22.5 | 0.072 | 7.05 | 98-fold | >25 | >347-fold |
| 22.6 | 0.13 | 11.1 | 85-fold | >25 | >192-fold |
| 22.7 | 3.1 | — | — | — | — |
| 22.8 | 0.184 | 18.9 | 103-fold | >25 | >136-fold |
| 22.9 | 1.32 | — | — | — | — |
| 22.10 | 0.092 | >25 | >272-fold | >25 | >272-fold |

TABLE C-continued

| Ex# | Tyk2 alpha screen (Tyk2/Jak2 PSTAT4 T-Blast) $EC_{50}$ (μM) | Jak1 alpha screen (PSTAT3 TF1) $EC_{50}$ (μM) | Tyk2 selectivity over Jak1 | Jak2 alpha screen (PSTAT5 UT7) $EC_{50}$ (μM) | Tyk2 selectivity over Jak2 |
|---|---|---|---|---|---|
| 23 | 0.33 | — | — | — | — |
| 24 | 0.092 | >100 | >1087-fold | >25 | >272-fold |
| 25 | 0.025 | 49 | 1960-fold | >25 | >1000-fold |
| 26 | 0.050 | >25 | >500-fold | >25 | >500-fold |

OTHER EMBODIMENTS

This application refers to various issued patent, published patent applications, journal articles, and other publications, each of which is incorporated herein by reference.

The foregoing has been described of certain non-limiting embodiments of the present disclosure. Those of ordinary skill in the art will appreciate that various changes and modifications to this description may be made without departing from the spirit or scope of the present disclosure, as defined in the following claims.

What is claimed is:

1. A compound of Formula (II-a):

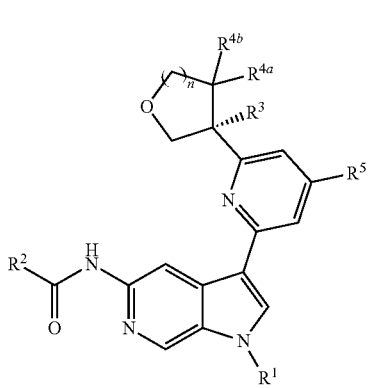

(II-a)

or a pharmaceutically acceptable salt thereof;
wherein:
$R^1$ is unsubstituted or substituted $C_{1-3}$alkyl, unsubstituted or substituted $C_{3-4}$carbocyclyl, or unsubstituted or substituted 4- to 5-membered heterocyclyl;
$R^2$ is $-NH_2$, $-NHR^{2a}$, unsubstituted or substituted $C_{1-3}$alkyl, and $R^{2a}$ is unsubstituted or substituted $C_{1-3}$alkyl;
$R^3$ is $-(C_{1-3}$alkylene$)_m$-$OR^{3a}$, $-(C_{1-3}$alkylene$)_m$-$N(R^{3a})_2$, $C_{1-3}$alkyl, or $C_{1-3}$haloalkyl, wherein m is 0 or 1, and each instance of $R^{3a}$ is independently hydrogen, $C_{1-3}$alkyl, or $C_{1-3}$haloalkyl;
each instance of $R^{4a}$ and $R^{4ab}$ is hydrogen;
$R^5$ is hydrogen, -CN, $-OR^{5a}$, $-NHR^{5a}$, or unsubstituted or substituted $C_{1-6}$alkyl, wherein $R^{5a}$ is unsubstituted or substituted $C_{1-6}$alkyl, unsubstituted or substituted $C_{3-6}$carbocyclyl, unsubstituted or substituted $C_{3-6}$carbocyclyl$C_{1-3}$alkyl, unsubstituted or substituted 4- to 6-membered heterocyclyl, or unsubstituted or substituted 4- to 6-membered heterocyclyl$C_{1-3}$alkyl;
n is 1; and
each instance of substituted is independent substitution with 1, 2, or 3 substituents selected from the group consisting of halogen, -CN, -OH, $C_{1-3}$alkyl, $C_{1-3}$haloalkyl, $-OC_{1-3}$alkyl, and $-OC_{1-3}$haloalkyl.

2. The compound of claim 1, or a pharmaceutically acceptable salt thereof, wherein $R^1$ is $-CH_3$, $-CH_2F$, $-CHF_2$, $-CF_3$

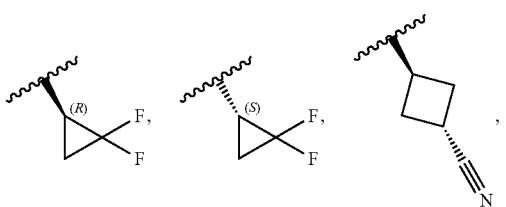

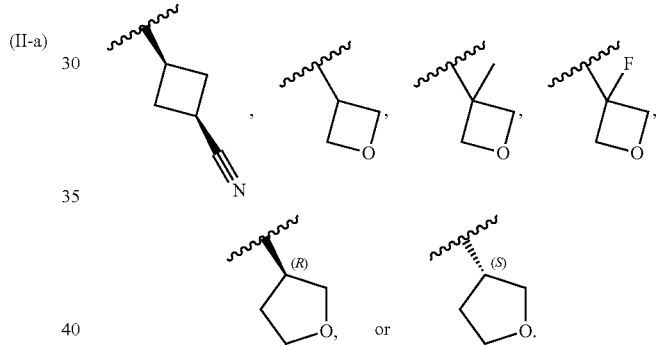

3. The compound of claim 2, or a pharmaceutically acceptable salt thereof, wherein $R^2$ is $-NH_2$, $-NHCH_3$, $-CH_3$, or $-CH_2OH$.

4. The compound of claim 3, or a pharmaceutically acceptable salt thereof, wherein $R^3$ is -OH, $-OCH_3$, $-CH_2OH$, $-CH_2NH_2$, $-CH(OH)CH_3$, $-CH_3$, or $CH_2CH_3$.

5. The compound of claim 4, or a pharmaceutically acceptable salt thereof, wherein $R^5$ is hydrogen, -CN, $-CH_3$, $-CH_2F$, $-CHF_2$, $-CF_3$, $-CH_2OCH_3$, $-OCH_3$, $-OCH_2CH_3$, $-OCH(CH_3)_2$, $-OCH_2CH_2OH$, -

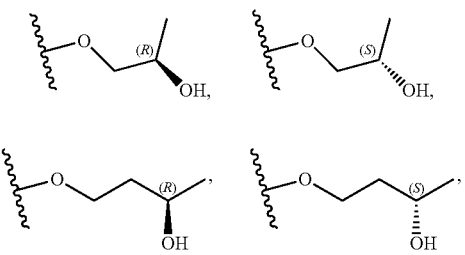

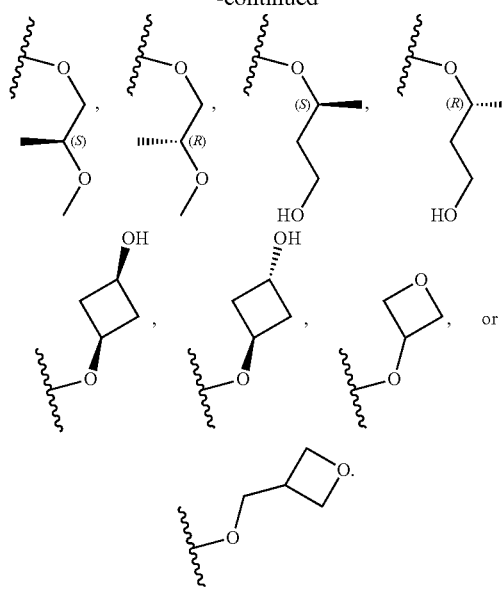

OCH$_2$CH$_2$OCH$_3$, -OCHF$_2$, -OCH$_2$CN.

6. The compound of claim 1, wherein the compound is of Formula (III-a):

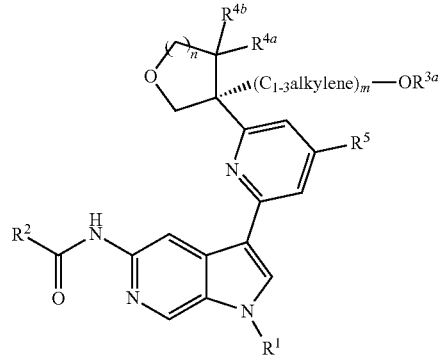

or a pharmaceutically acceptable salt thereof.

7. The compound of claim 6, or a pharmaceutically acceptable salt thereof, wherein R$^1$ is -CH$_3$, -CH$_2$F, -CHF$_2$, -CF$_3$.

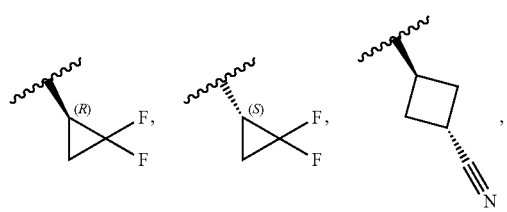

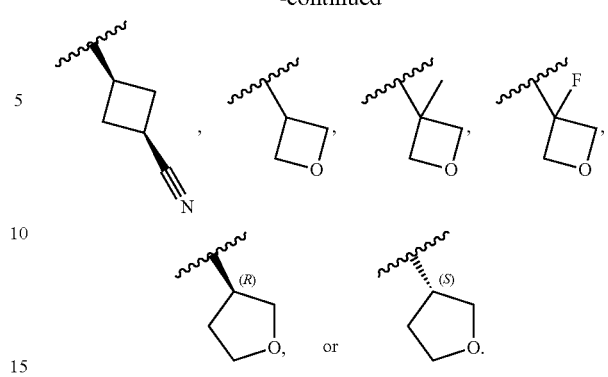

8. The compound of claim 7, or a pharmaceutically acceptable salt thereof, wherein R$^2$ is -NH$_2$, -NHCH$_3$, -CH$_3$, or -CH$_2$OH.

9. The compound of claim 8, or a pharmaceutically acceptable salt thereof, wherein R$^{3a}$ is hydrogen or -CH$_3$.

10. The compound of claim 9, or a pharmaceutically acceptable salt thereof, wherein m is 1.

11. The compound of claim 10, or a pharmaceutically acceptable salt thereof, wherein R$^5$ is hydrogen, -CN, -CH$_3$, -CH$_2$F, -CHF$_2$, -CF$_3$, -CH$_2$OCH$_3$, -OCH$_3$, -OCH$_2$CH$_3$, -OCH(CH$_3$)$_2$, -

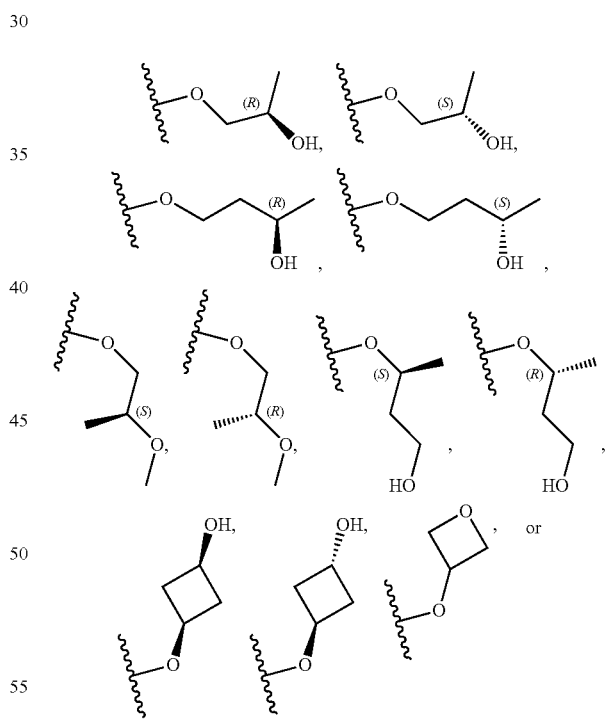

OCH$_2$CH$_2$OH, -OCH$_2$CH$_2$OCH$_3$, -OCHF$_2$, -OCH$_2$CN.

12. The compound of claim 1, wherein the compound is of Formula (IV-a):

(IV-a)

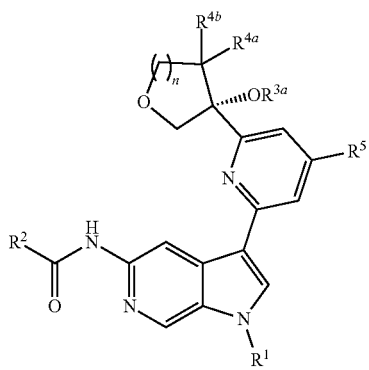

or a pharmaceutically acceptable salt thereof.

13. The compound of claim 12, or a pharmaceutically acceptable salt thereof, wherein $R^1$ is -CH$_3$, -CH$_2$F, -CHF$_2$, -CF$_3$.

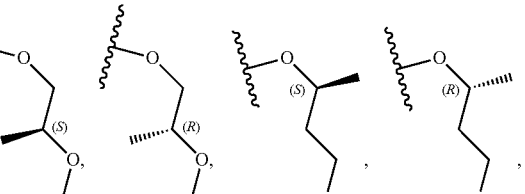

-continued

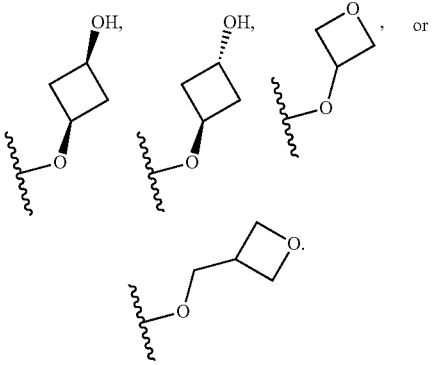

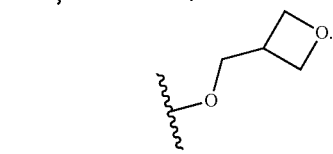

17. The compound of claim 1, wherein the compound is of Formula (I-ii-II-a):

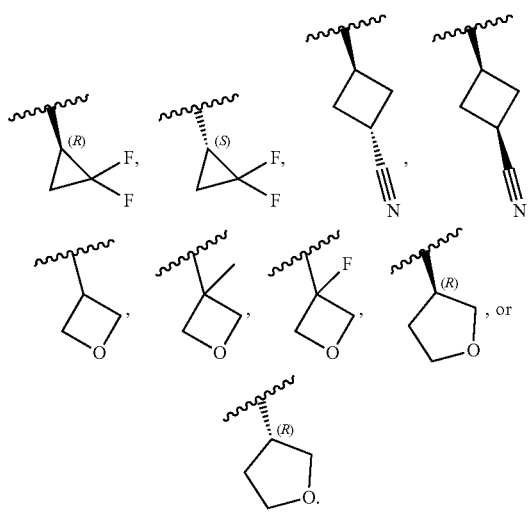

(I-ii-II-a)

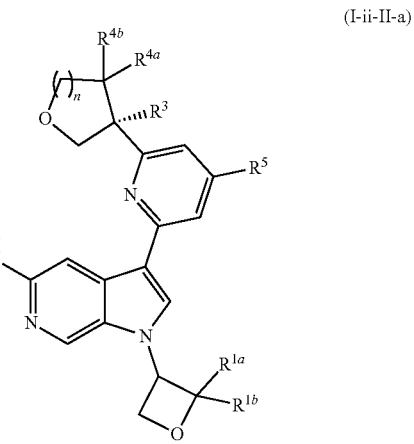

or a pharmaceutically acceptable salt thereof, wherein each of $R^{1a}$ and $R^{1b}$ is independently hydrogen or -CH$_3$.

14. The compound of claim 13, or a pharmaceutically acceptable salt thereof, wherein $R^2$ is -NH$_2$, -NHCH$_3$, -CH$_3$, or -CH$_2$OH.

15. The compound of claim 14, or a pharmaceutically acceptable salt thereof, wherein $R^{3a}$ is hydrogen or -CH$_3$.

16. The compound of claim 15, or a pharmaceutically acceptable salt thereof, wherein $R^5$ is hydrogen, -CN, -CH$_3$, -CH$_2$F, -CHF$_2$, -CF$_3$, -CH$_2$OCH$_3$, -OCH$_3$, -OCH$_2$CH$_3$, -OCH(CH$_3$)$_2$, -OCH$_2$CH$_2$OH, -OCH$_2$CH$_2$OCH$_3$, -OCHF$_2$, -OCH$_2$CN.

18. The compound of claim 17, or a pharmaceutically acceptable salt thereof, wherein $R^2$ is -NH$_2$, -NHCH$_3$, -CH$_3$, or -CH$_2$OH.

19. The compound of claim 18, or a pharmaceutically acceptable salt thereof, wherein $R^3$ is -OH, -OCH$_3$, -CH$_2$OH, -CH$_2$NH$_2$, -CH(OH)CH$_3$, -CH$_3$, or CH$_2$CH$_3$.

20. The compound of claim 19, or a pharmaceutically acceptable salt thereof, wherein $R^5$ is hydrogen, -CN, -CH$_3$, -CH$_2$F, -CF$_3$, -CH$_2$OCH$_3$, -OCH$_3$, -OCH$_2$CH$_3$, -OCH(CH$_3$)$_2$, -OCH$_2$CH$_2$OH, -OCH$_2$CH$_2$OCH$_3$, -OCHF$_2$, -OCH$_2$CN.

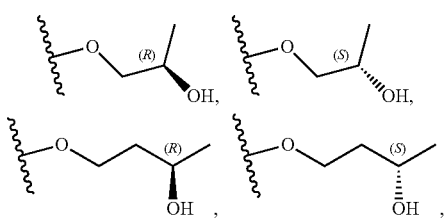

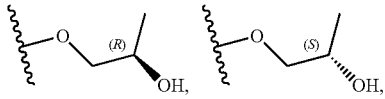

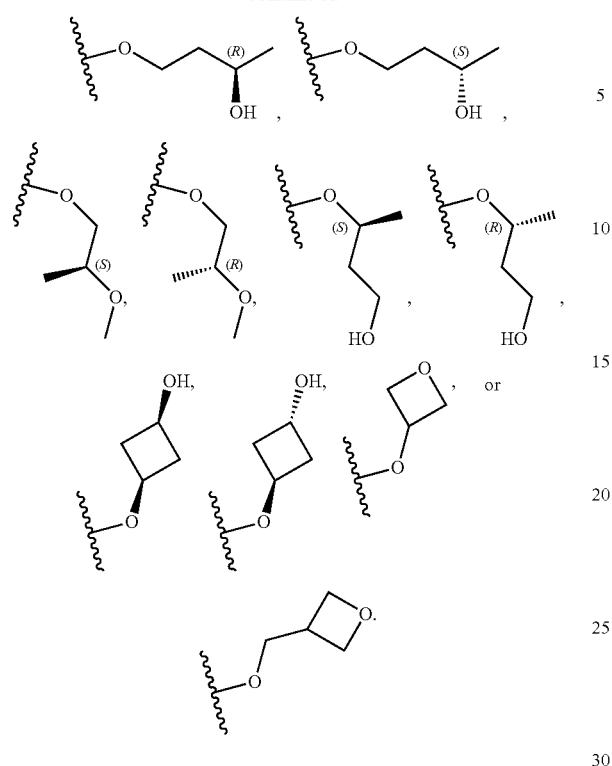
21. The compound of claim 1 selected from the group consisting of:
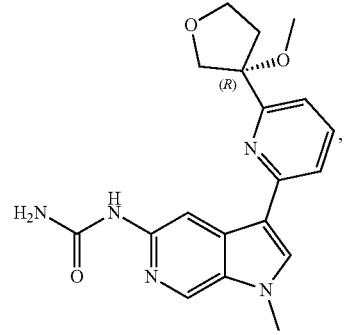
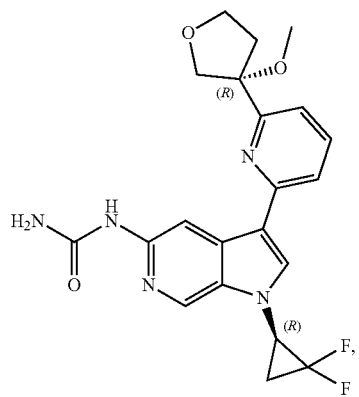
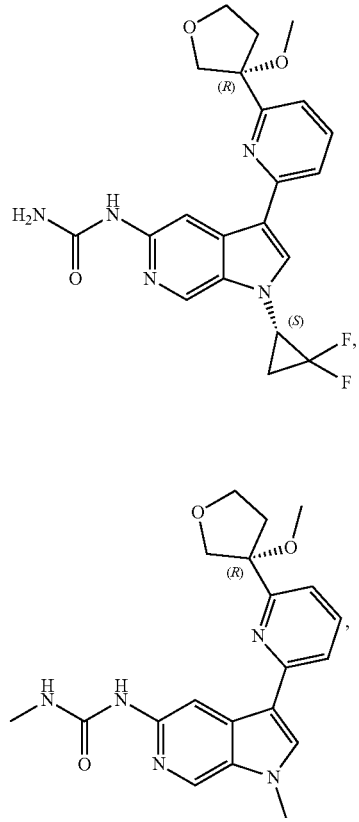
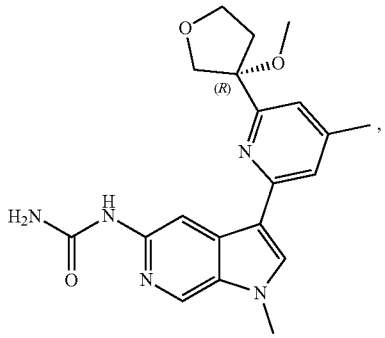
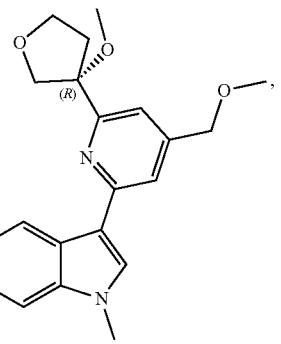

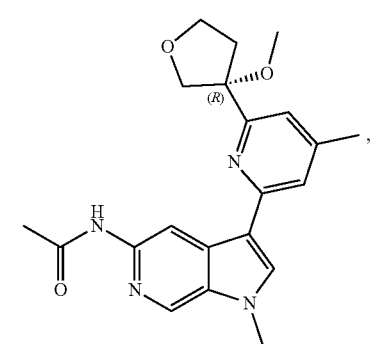
(2.2)
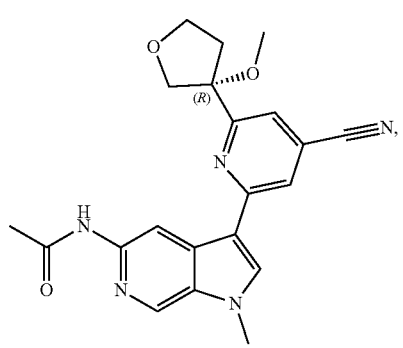
(2.6)
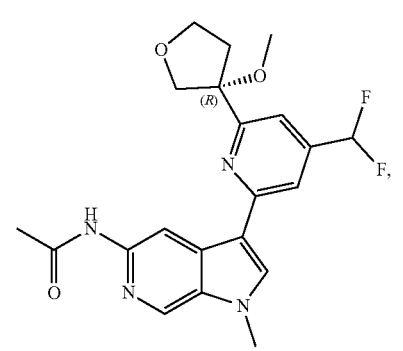
(2.8)
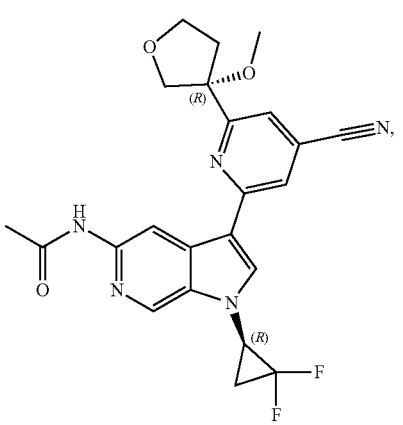
(2a.3)
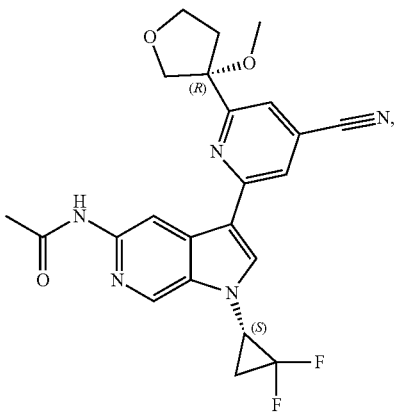
(2a.5)
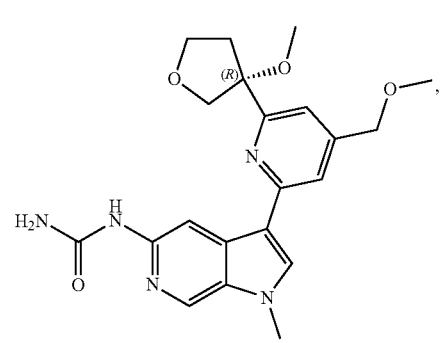
(3)
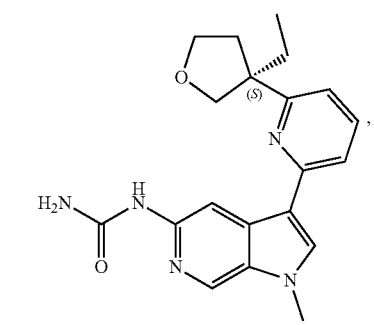
(3.2)
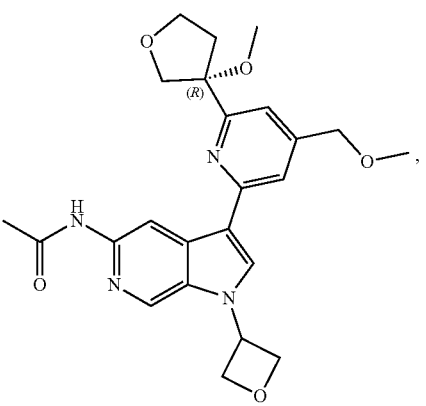
(4)

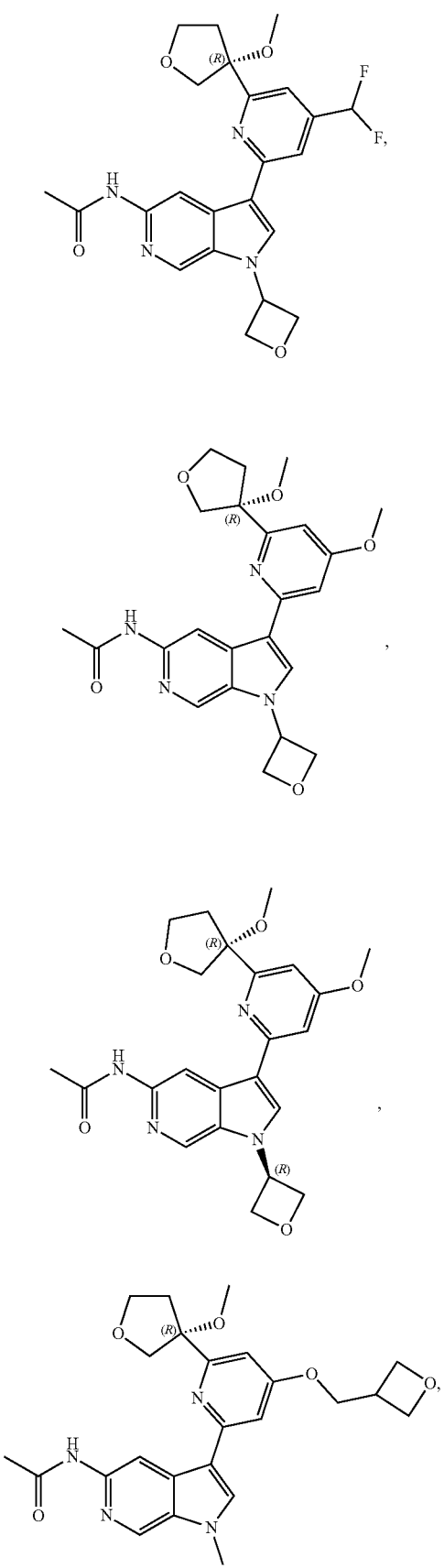
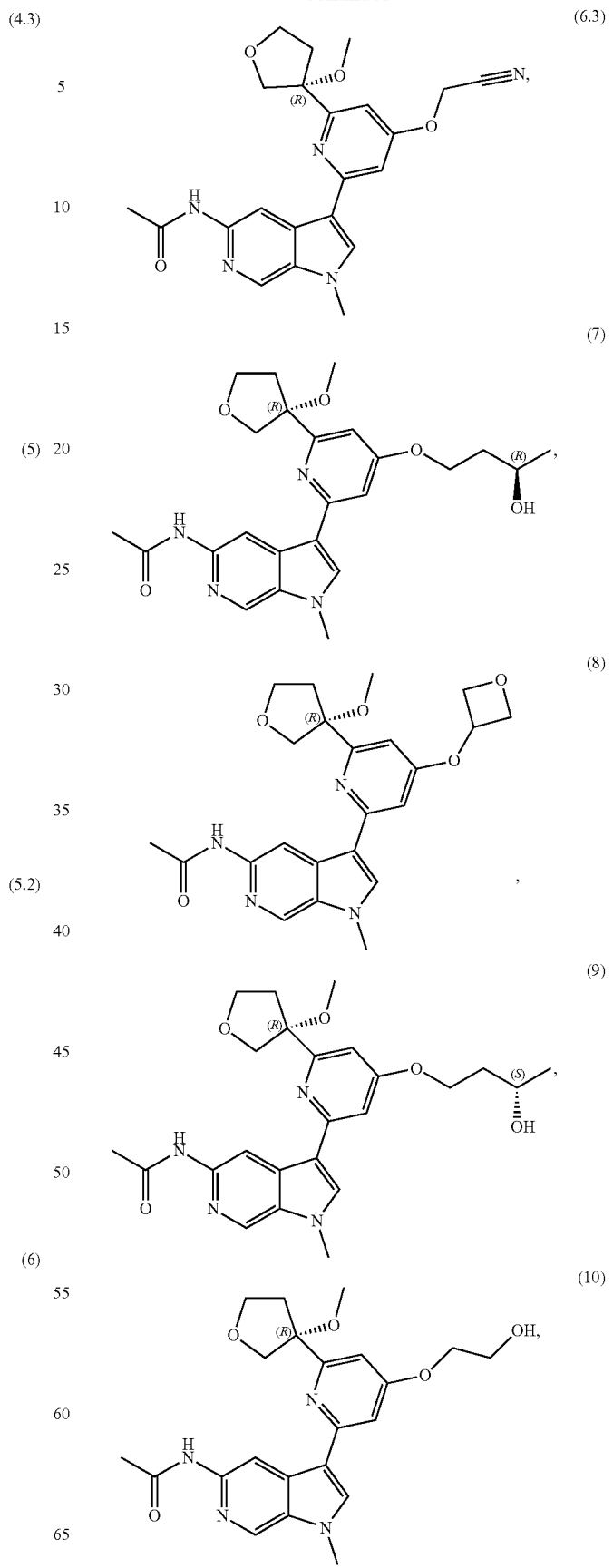

281
-continued
(11)
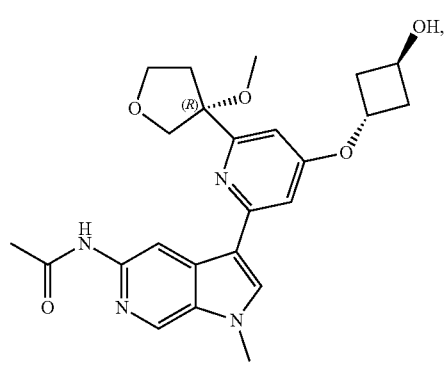
(11.2)
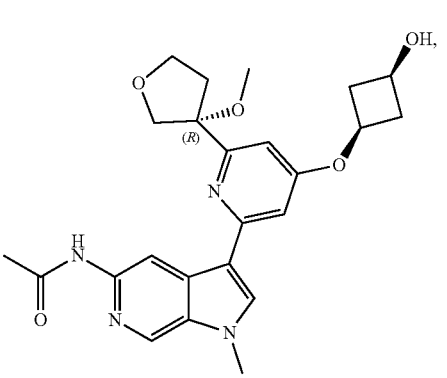
(12.3)
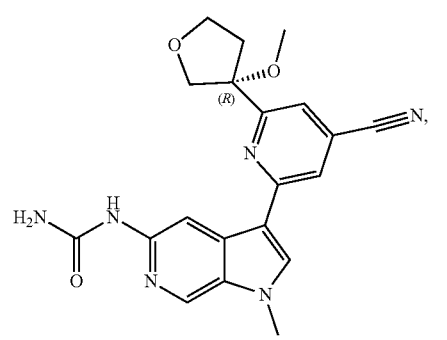
(12.5)
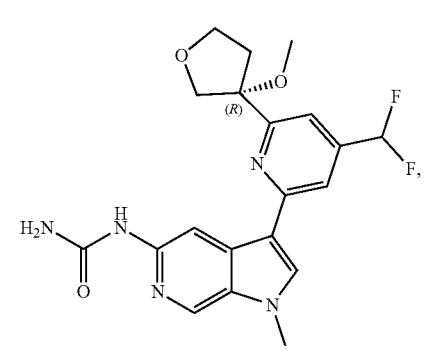
282
-continued
(12.6)
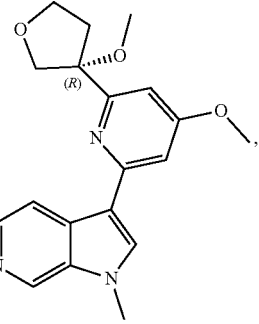
(12a.2)
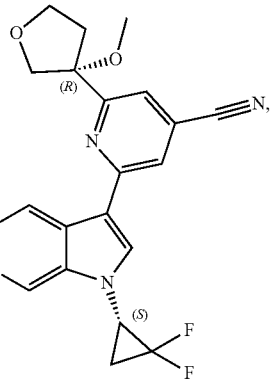
(12a.3)
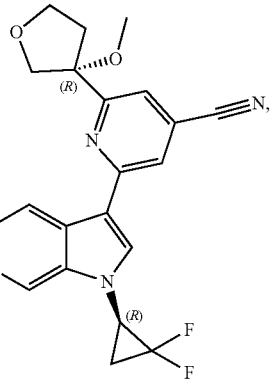
(12b.2)
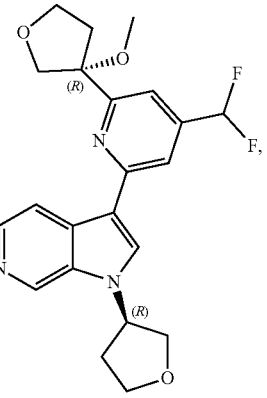

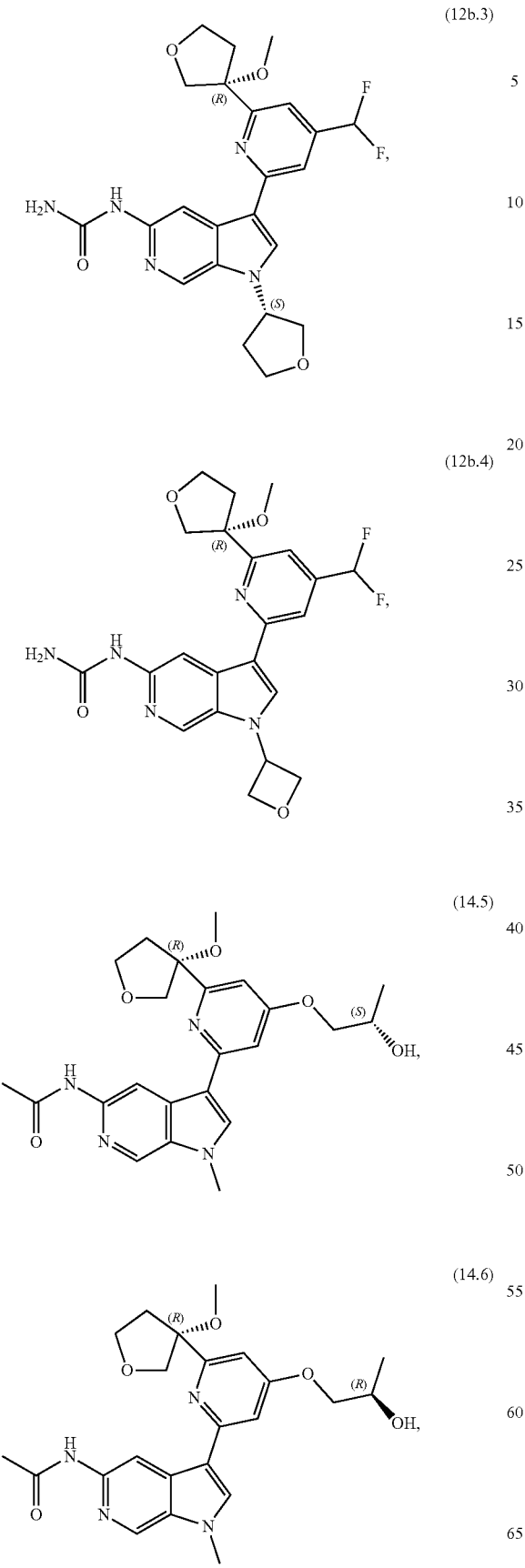
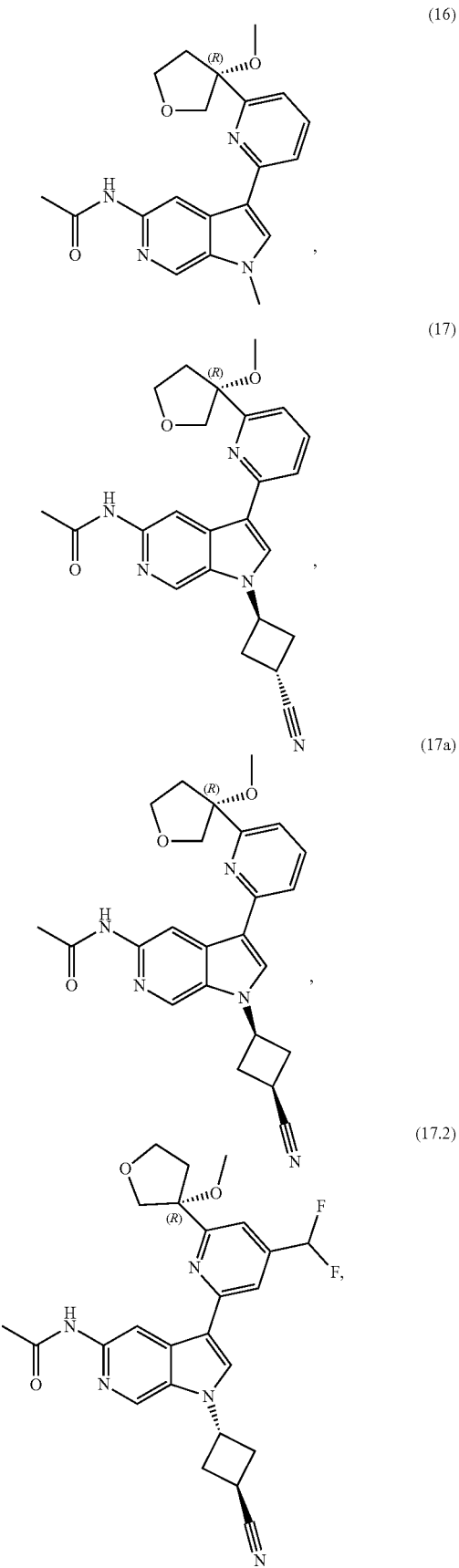

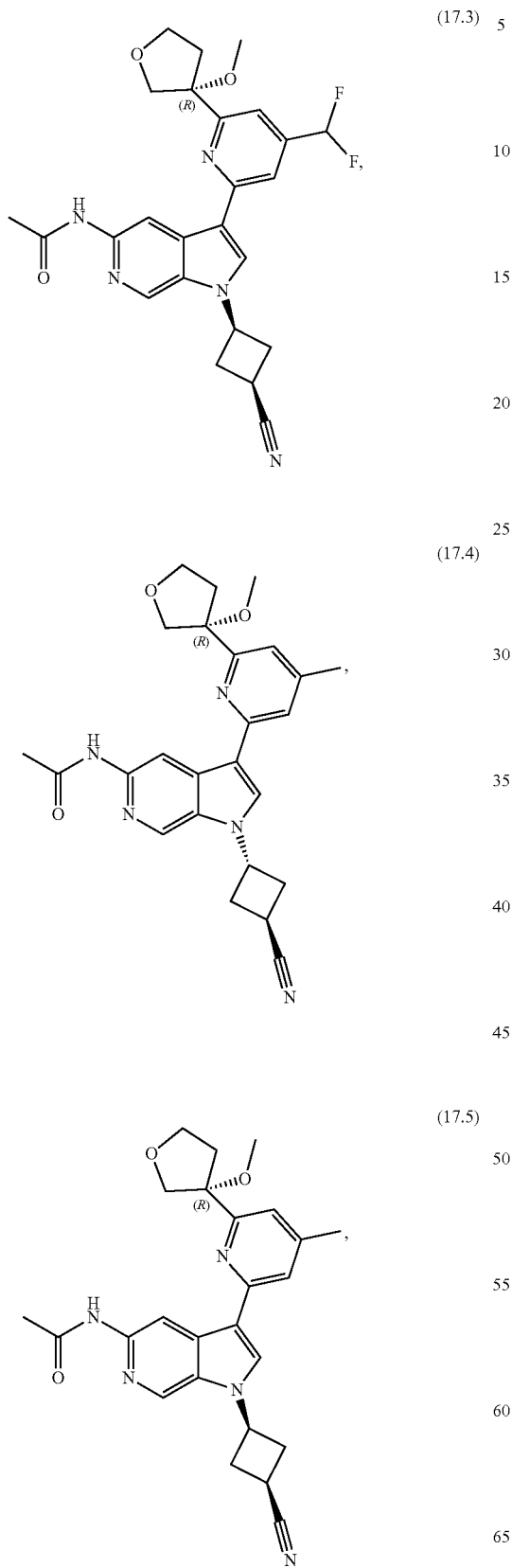
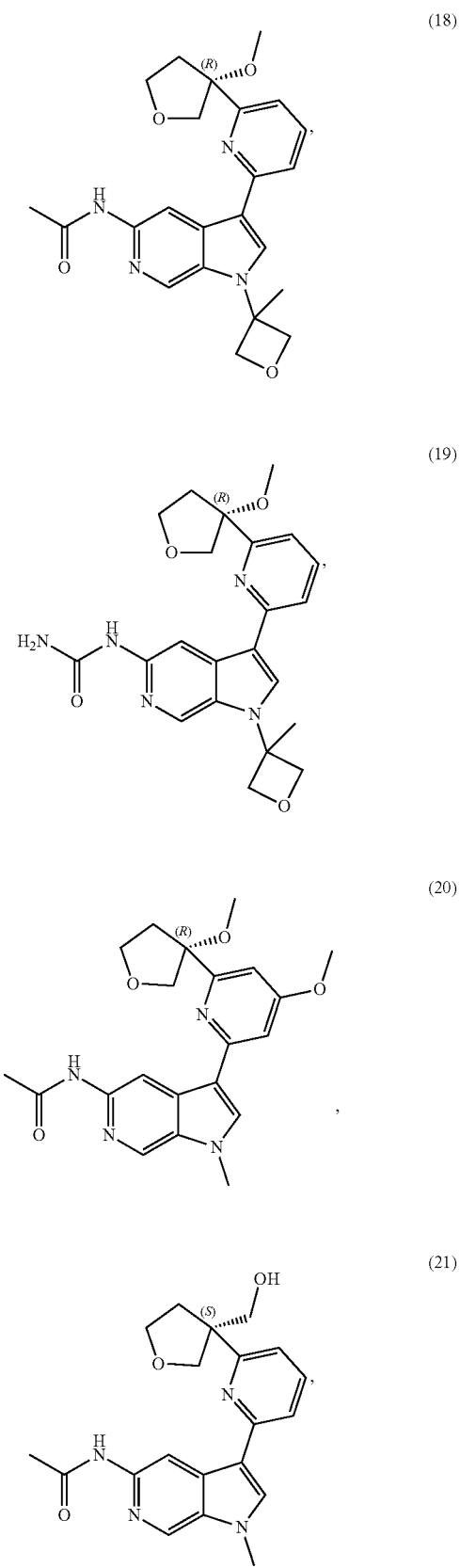

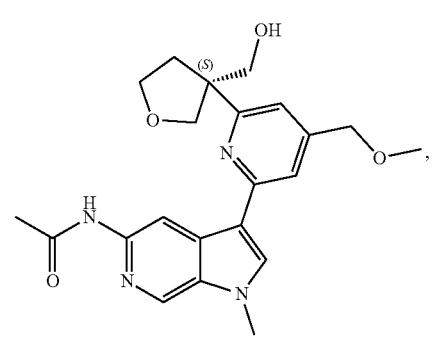
(22)
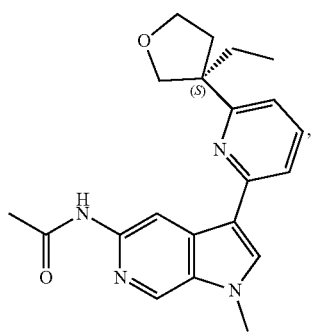
(2.3)
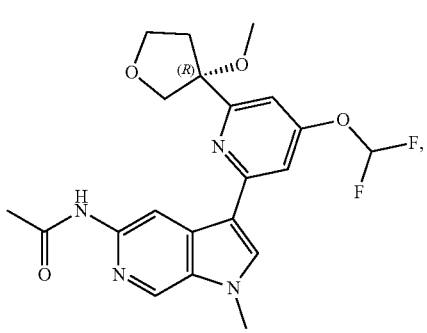
(22.2)
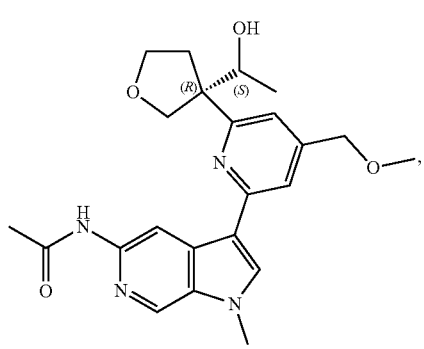
(22.3)
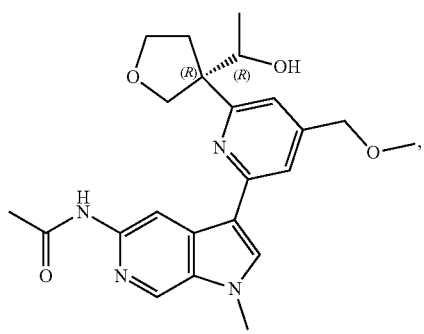
(22.4)
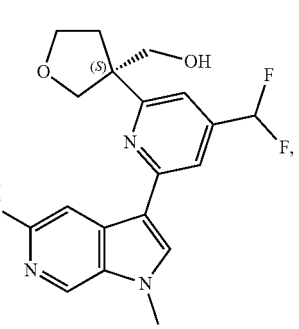
(22.5)
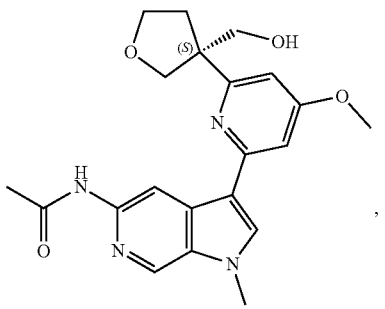
(22.6)
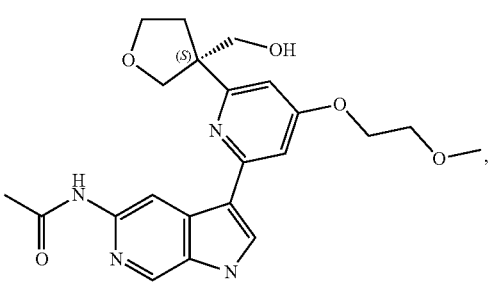
(22.8)
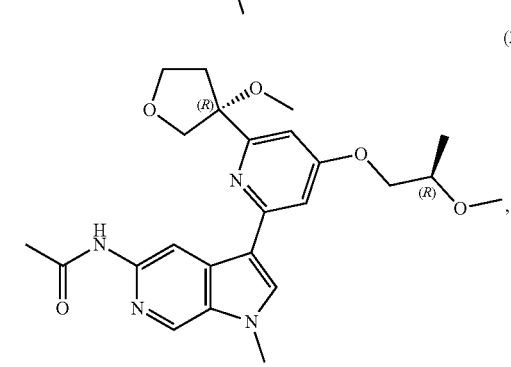
(22.10)
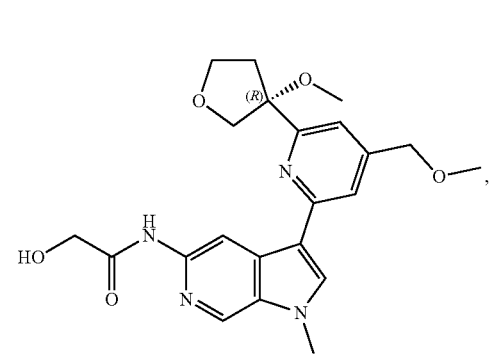
(24)

289
-continued
(25)
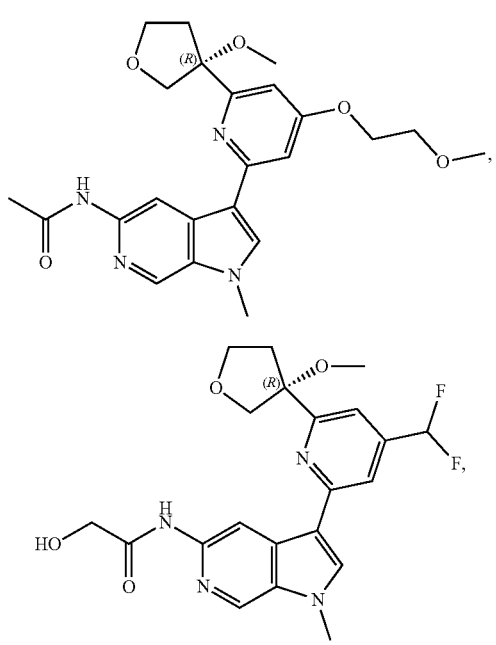
(26)
and pharmaceutically acceptable salts thereof.
22. A compound of formula:
(4)
24. The pharmaceutically acceptable salt of the compound of claim 22:
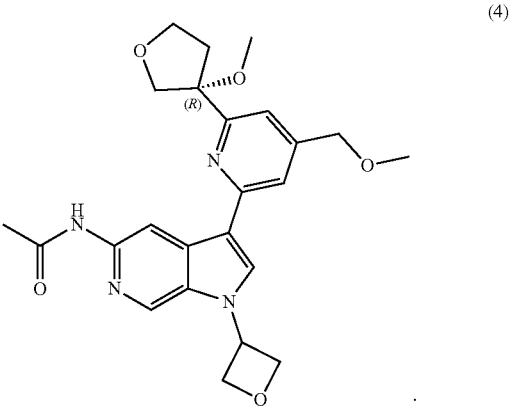
(4)
25. A compound of formula:
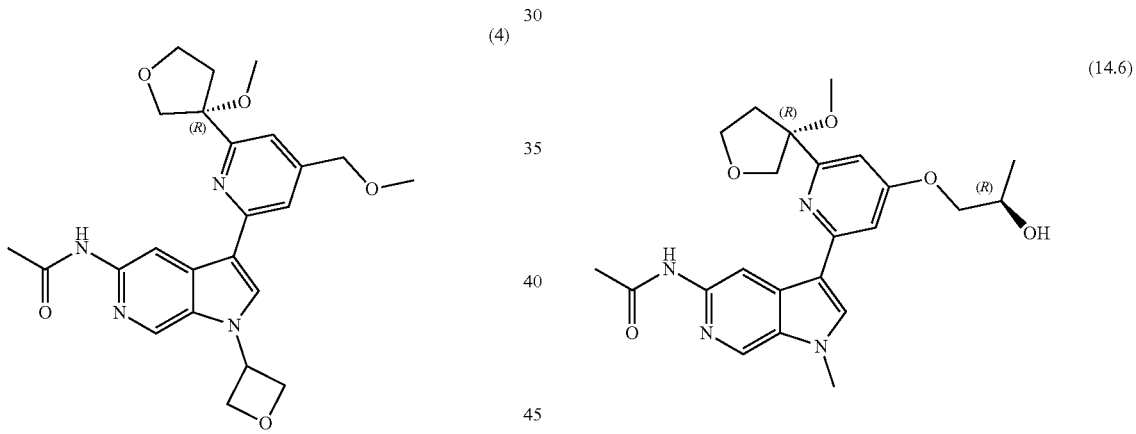
(14.6)
or a pharmaceutically acceptable salt thereof.
26. The compound of claim 25:
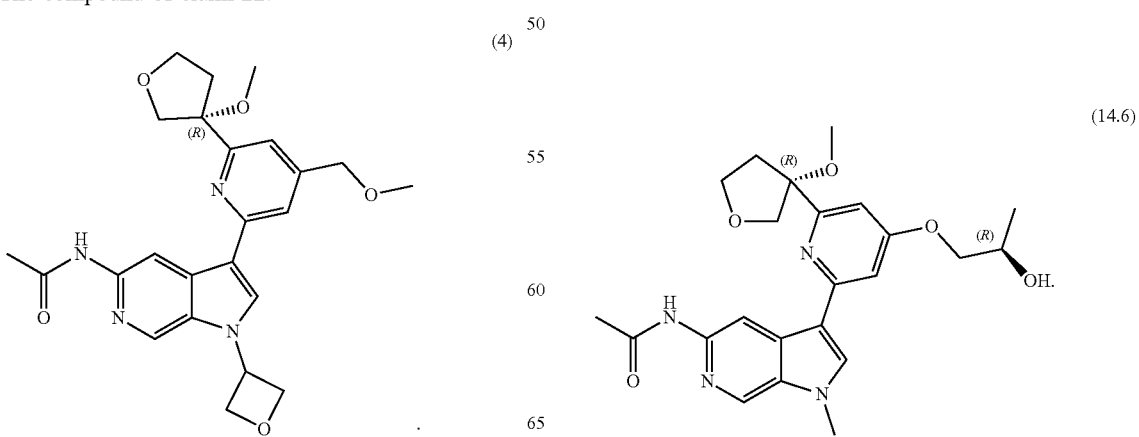
(14.6)
or a pharmaceutically acceptable salt thereof.
23. The compound of claim 22:
(4)

27. The pharmaceutically acceptable salt of the compound of claim 25:
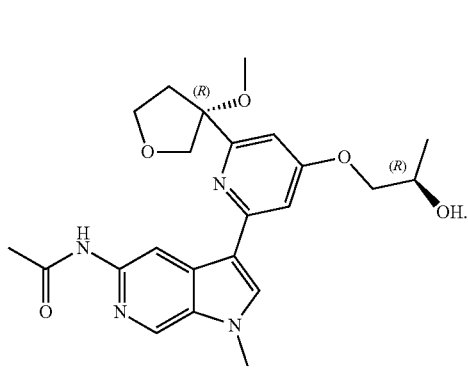
(14.6)
28. A compound of formula:
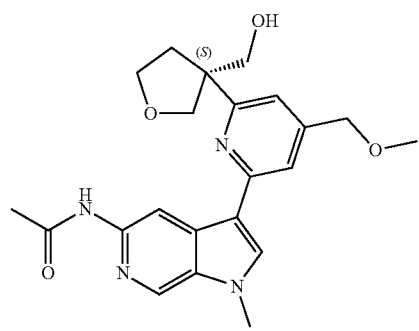
(22)
or a pharmaceutically acceptable salt thereof.
29. The compound of claim 28:
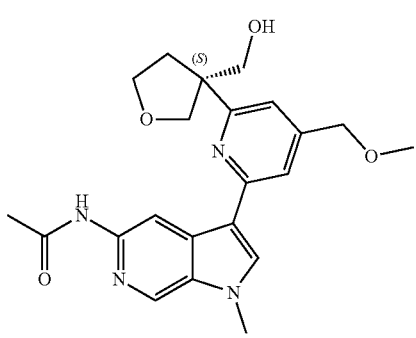
(22)
30. The pharmaceutically acceptable salt of the compound of claim 28:
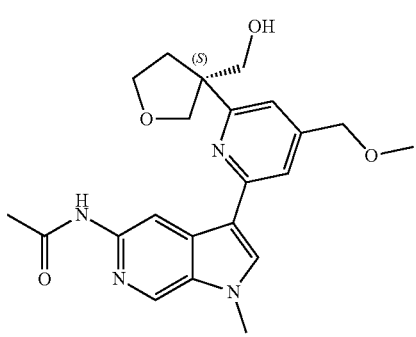
(22)
* * * * *

UNITED STATES PATENT AND TRADEMARK OFFICE
CERTIFICATE OF CORRECTION

PATENT NO. : 10,508,113 B2
APPLICATION NO. : 16/299485
DATED : December 17, 2019
INVENTOR(S) : Maria A. Argiriadi et al.

It is certified that error appears in the above-identified patent and that said Letters Patent is hereby corrected as shown below:

On the Title Page

Item (57) In the Abstract, in Column 2, Line 2-3, delete "$R_1$, R2, $R_3$, $R_{4a}$, $R_{4b}$," and insert --$R^1$, $R^2$, $R^3$, $R^{4a}$, $R^{4b}$,--.

Item (57) In the Abstract, in Column 2, Line 3, delete "nad" and insert --and--.

Item (57) In the Abstract, in Column 2, Lines 3-6, delete "n are as defined herein, pharmaeceutical compositions 2C $X^5$, and n are as defined herein, pharmaceutical compositions comprising same, and methods of preparation and use." and insert --n are as defined herein, pharmaceutical compositions comprising same, and methods of preparation and use.--.

In the Specification

In Column 156, Lines 64-65, delete "Substitute Specification (clean) ABV12402US01 (31247-2221)".

In the Claims

In Claim 1, Column 269, Line 57, delete "$R^{4ab}$" and insert --$R^{4b}$--.

In Claim 5, Column 270, Line 53, delete "–$OCH(CH_3)_2$, –$OCH_2CH_2OH$, –" and insert -- –$OCH(CH_3)_2$, –$OCH_2CH_2OH$, –$OCH_2CH_2OCH_3$, –$OCHF_2$, –$OCH_2CN$,--.

In Claim 5, Column 271, Line 25, delete "$OCH_2CH_2OCH_3$, –$OCHF_2$, –$OCH_2CN$".

In Claim 7, Column 271, Line 53, delete "–$CF_3$." and insert -- –$CF_3$,--.

In Claim 11, Column 272, Line 29, delete "–$OCH(CH_3)_2$, -" and insert -- –$OCH(CH_3)_2$, –$OCH_2CH_2OH$, –$OCH_2CH_2OCH_3$, –$OCHF_2$, –$OCH_2CN$,--.

Signed and Sealed this
Fifth Day of January, 2021

Andrei Iancu
*Director of the United States Patent and Trademark Office*

CERTIFICATE OF CORRECTION (continued)
U.S. Pat. No. 10,508,113 B2

In Claim 11, Column 272, Line 65, delete "OCH₂CH₂OH, –OCH₂CH₂OCH₃, –OCHF₂, –OCH₂CN".

In Claim 13, Column 273, Line 22, delete "–CF₃." and insert -- –CF₃,--.

In Claim 13, Column 273, Line 40, replace:

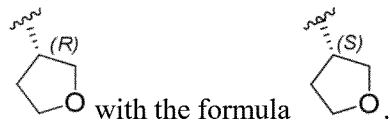 with the formula .

In Claim 16, Column 273, Line 56, delete "–OCH₂CN." and insert -- –OCH₂CN,--.

In Claim 17, Column 274, Line 26, delete "Formula (I-ii-I1-a):" and insert --Formula (I-ii-II-a):--.

In Claim 17, Column 274, Line 30, replace formula:

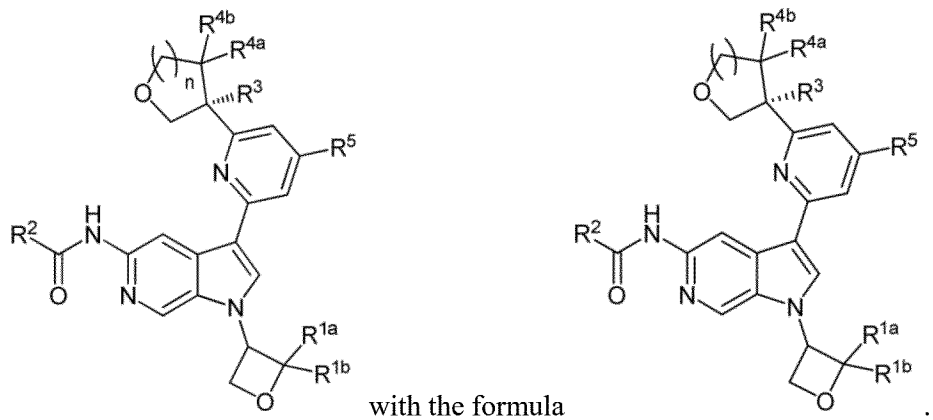 with the formula .

In Claim 18, Column 274, Line 51, delete "NH₂" and insert -- –NH₂--.

In Claim 20, Column 274, Line 58, delete "–CH₂F, –CF₃" and insert -- –CH₂F, –CHF₂, –CF₃,--.

In Claim 20, Column 274, Line 60, delete "–OCH₂CN." and insert -- –OCH₂CN,--.

In Claim 21, Column 279, Line 38, replace:

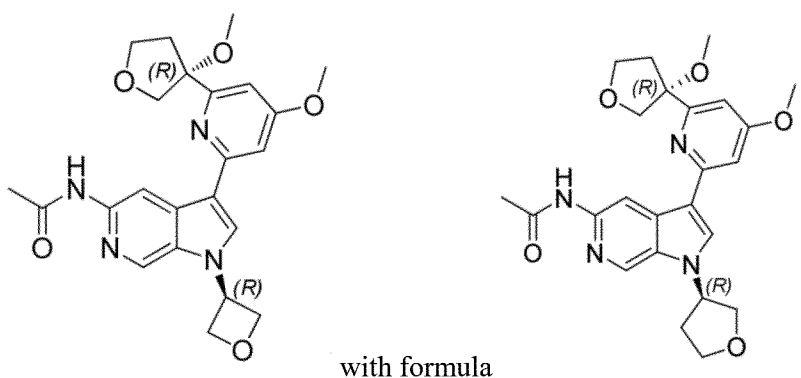 with formula .